(12) United States Patent
Burns et al.

(10) Patent No.: US 9,926,336 B2
(45) Date of Patent: *Mar. 27, 2018

(54) BETA-LACTAMASE INHIBITORS

(71) Applicant: VenatoRx Pharmaceuticals, Inc., Malvern, PA (US)

(72) Inventors: Christopher J. Burns, Malvern, PA (US); Denis Daigle, Street, MD (US); Bin Liu, Plainsboro, NJ (US); Randy W. Jackson, Livingston, MT (US); Jodie Hamrick, New Holland, PA (US); Daniel McGarry, Malvern, PA (US); Daniel C. Pevear, Downingtown, PA (US); Robert E. Lee Trout, Collegeville, PA (US)

(73) Assignee: VENATORX PHARMACEUTICALS, Malvern, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/675,253

(22) Filed: Aug. 11, 2017

(65) Prior Publication Data

US 2017/0342092 A1 Nov. 30, 2017

Related U.S. Application Data

(63) Continuation of application No. 15/435,097, filed on Feb. 16, 2017, now Pat. No. 9,783,555, which is a continuation of application No. 15/162,395, filed on May 23, 2016, now Pat. No. 9,637,504, which is a continuation of application No. PCT/US2015/035407, filed on Jun. 11, 2015.

(60) Provisional application No. 62/118,227, filed on Feb. 19, 2015, provisional application No. 62/010,968, filed on Jun. 11, 2014, provisional application No. 62/010,969, filed on Jun. 11, 2014, provisional application No. 62/010,940, filed on Jun. 11, 2014.

(51) Int. Cl.
*C07F 5/05* (2006.01)
*A61K 31/69* (2006.01)
*A61K 45/06* (2006.01)
*C07F 5/02* (2006.01)

(52) U.S. Cl.
CPC .............. *C07F 5/025* (2013.01); *A61K 31/69* (2013.01); *A61K 45/06* (2013.01)

(58) Field of Classification Search
CPC ............ C07F 5/05; A61K 31/69; A61K 45/06
See application file for complete search history.

(56) References Cited

U.S. PATENT DOCUMENTS

| 4,427,690 | A | 1/1984 | Cole et al. |
|---|---|---|---|
| 7,271,186 | B1 | 9/2007 | Shoichet et al. |
| 8,680,136 | B2 | 3/2014 | Hirst et al. |
| 8,912,169 | B2 | 12/2014 | Burns et al. |
| 9,040,504 | B2 | 5/2015 | Burns et al. |
| 9,101,638 | B2 | 8/2015 | Reddy et al. |
| 9,376,454 | B2 | 6/2016 | Burns et al. |
| 9,403,850 | B2 | 8/2016 | Burns et al. |
| 9,422,314 | B2 | 8/2016 | Burns et al. |
| 9,511,142 | B2 | 12/2016 | Burns et al. |
| 9,637,504 | B2 * | 5/2017 | Burns ............... C07F 5/025 |
| 2010/0056478 | A1 | 3/2010 | Desarbre et al. |
| 2010/0120715 | A1 | 5/2010 | Burns et al. |
| 2010/0286092 | A1 | 11/2010 | Burns et al. |
| 2010/0292185 | A1 | 11/2010 | Burns et al. |
| 2010/0317621 | A1 | 12/2010 | Burns et al. |
| 2011/0294777 | A1 | 12/2011 | Blizzard et al. |
| 2015/0361107 | A1 | 12/2015 | Trout |
| 2015/0361108 | A1 | 12/2015 | Burns et al. |
| 2016/0024121 | A1 | 1/2016 | Burns et al. |
| 2016/0304539 | A1 | 10/2016 | Burns et al. |
| 2016/0326189 | A1 | 11/2016 | Burns et al. |
| 2017/0073360 | A1 | 3/2017 | Burns et al. |
| 2017/0107239 | A1 | 4/2017 | Burns et al. |
| 2017/0145037 | A1 | 5/2017 | Burns et al. |
| 2017/0226135 | A1 | 8/2017 | Burns et al. |

FOREIGN PATENT DOCUMENTS

| WO | WO-2005004799 A2 | 1/2005 |
|---|---|---|
| WO | WO-2009064413 A1 | 5/2009 |
| WO | WO-2009064414 A1 | 5/2009 |
| WO | WO-2010056827 A1 | 5/2010 |
| WO | WO-2010130708 A1 | 11/2010 |
| WO | WO-2012021455 A1 | 2/2012 |
| WO | WO-2013053372 A1 | 4/2013 |
| WO | WO-2013092979 A1 | 6/2013 |
| WO | WO-2013122888 A2 | 8/2013 |
| WO | WO-2014089365 A1 | 6/2014 |
| WO | WO-2014107535 A1 | 7/2014 |
| WO | WO-2014107536 A1 | 7/2014 |
| WO | WO-2014110442 A1 | 7/2014 |
| WO | WO-2014151958 A1 | 9/2014 |
| WO | WO-2015171398 A1 | 11/2015 |
| WO | WO-2015171430 A1 | 11/2015 |
| WO | WO-2015179308 A1 | 11/2015 |
| WO | WO-2016003929 A1 | 1/2016 |
| WO | WO-2017100537 A1 | 6/2017 |

OTHER PUBLICATIONS

Bacterial Infection 101. Available at http://www.onhealth.com/content/l/bacterial_infections (34 pgs) (2017).
Bodner Research Web. The Chemistry of the Halogens. Available from http://web.archive.org/web/20090414155348/http://chemechem/topicreview/bp/ch10/group3.php (2009).

(Continued)

Primary Examiner — Timothy R Rozof
(74) Attorney, Agent, or Firm — Wilson Sonsini Goodrich & Rosati

(57) ABSTRACT

Described herein are compounds and compositions that modulate the activity of beta-lactamases. In some embodiments, the compounds described herein inhibit beta-lactamase. In certain embodiments, the compounds described herein are useful in the treatment of bacterial infections.

20 Claims, No Drawings

(56) References Cited

OTHER PUBLICATIONS

Bundgaard. Design of Prodrugs. Elsevier. Chapter 1. pp. 1-3 (1985).
Co-pending U.S. Appl. No. 15/675,262, filed Aug. 11, 2017.
Definition of Quinoxaline from PubChem. http://pubchem.ncbi.nlm.nih.gov/compund/quinoxaline#section=information-sources. (24 pgs) (2005).
Definition of Quinoxaline from Wikipedia. http://en.wikipedia.org/wiki/Quinoxaline (3 pgs.) (2016).
Eidam et al. Design, synthesis, crystal structures, and antimicrobial activity of sulfonamide boronic acids as β-lactamase inhibitors. J. Med. Chem. 53(21):7852-7863 (2010).
Ettmayer et al. Lessons Learned from Marketed and Investigational Prodrugs. J Medicinal Chem 47(10):2393-2404 (2004).
Han. Targeted Prodrug Design to Optimize Drug Delivery. AAPS Pharmsci. 2(1)Article 6:1-11 (2000).
Ishikawa et al. Synthesis and antimicrobial activity of 2,3-bis(bromomethyl)quinoxaline derivatives. Bioorg Chem 41-42:1-5 (2012).
Isomer. https://en.wikipedia.org/wiki/Isomer (2015).
Isomer. https://en.wikipedia.org/wiki/Isomer (5 pgs) (2017).
Lima et al. Bioisosterism: A Useful Strategy for Molecular Modification and Drug Design. Current Medicinal Chemistry 12:23-49 (2005).
Morandi et al. Structure-based optimization of cephalothin-analogue boronic acids as β-lactamase inhibitors. Bioorg. Med. Chem. 16(3):1195-1205 (2008) (Epub: Nov. 7, 2007).
Ness et al. Structure-based design guides the improved efficacy of deacylation transition state analogue inhibitors of TEM-1 β-lactamase. Biochemistry 39(18):5312-5321 (2000).
Patani et al. Bioisosterism: A Rational Approach in Drug Design. Chemical Reviews 96:3147-3176 (1996).
PCT/US2013/073428 International Preliminary Report on Patentability dated Jun. 18, 2015.
PCT/US2013/073428 International Search Report dated Apr. 25, 2014.
PCT/US2014/011144 International Preliminary Report on Patentability dated Jul. 23, 2015.
PCT/US2014/011144 International Search Report dated May 12, 2014.
PCT/US2014/026727 International Preliminary Report on Patentability dated Sep. 24, 2015.
PCT/US2014/026727 International Search Report and Written Opinion dated Jul. 25, 2014.
PCT/US2015/035407 International Preliminary Report on Patentability dated Dec. 22, 2016.
PCT/US2015/035407 International Search Report and Written Opinion dated Oct. 20, 2015.
PCT/US2016/065771 International Search Report and Written Opinion dated Apr. 21, 2017.
Powers et al. Structure-based approach for binding site identification on AmpC β-lactamase. J. Med. Chem. 45(15):3222-3234 (2002).
Powers et al. Structures of ceftazidime and its transition-state analogue in complex with AmpC β-lactamase: implications for resistance mutations and inhibitor design. Biochemistry 40(31):9207-9214 (2001).
Testa. Prodrug research: futile or fertile? Biochem. Pharm. 68:2097-2106 (2004).
U.S. Appl. No. 14/152,916 Office Action dated Aug. 29, 2014.
U.S. Appl. No. 14/649,527 Office Action dated Nov. 9, 2015.
U.S. Appl. No. 14/693,318 Office Action dated Sep. 1, 2015.
U.S. Appl. No. 14/736,921 Office Action dated Jun. 23, 2017.
U.S. Appl. No. 14/737,156 Office Action dated Jun. 1, 2016.
U.S. Appl. No. 14/759,853 Office Action dated Dec. 11, 2015.
U.S. Appl. No. 14/773,717 Office Action dated Feb. 27, 2017.
U.S. Appl. No. 14/773,717 Office Action dated Jun. 8, 2017.
U.S. Appl. No. 15/162,395 Office Action dated Oct. 5, 2016.
U.S. Appl. No. 15/194,433 Office Action dated Feb. 9, 2017.
U.S. Appl. No. 15/212,959 Office Action dated Mar. 23, 2017.
U.S. Appl. No. 90/013,866 Ex Parte Reexam Office Action dated Apr. 20, 2017.
Weston et al. Structure-based enhancement of boronic acid-based inhibitors of AmpC β-lactamase. J. Med. Chem. 41(23):4577-4586 (1998).
Co-pending U.S. Appl. No. 15/715,705, filed Sep. 26, 2017.
U.S. Appl. No. 15/675,262 Office Action dated Sep. 18, 2017.

* cited by examiner

BETA-LACTAMASE INHIBITORS

CROSS REFERENCE

This application is a continuation of U.S. patent application Ser. No. 15/435,097, filed Feb. 16, 2017, which is a continuation of U.S. patent application Ser. No. 15/162,395, filed May 23, 2016, now U.S. Pat. No. 9,637,504, which is a continuation of PCT International Application No. PCT/US2015/035407 filed Jun. 11, 2015 which claims the benefit of U.S. Provisional Application No. 62/118,227 filed Feb. 19, 2015, U.S. Provisional Application No. 62/010,968 filed Jun. 11, 2014, U.S. Provisional Application No. 62/010,969 filed Jun. 11, 2014, and U.S. Provisional Application Ser. No. 62/010,940, filed Jun. 11, 2014, the contents of which are hereby incorporated by reference in their entireties.

STATEMENT AS TO FEDERALLY SPONSORED RESEARCH

This invention was made with government support under Grant No. R01AI111539 and Grant No. R43AI109879 awarded by the National Institutes of Health. The government has certain rights in the invention.

FIELD OF INVENTION

The present invention relates to boron-containing compounds, compositions, preparations and their use as inhibitors of beta-lactamase enzymes and as antibacterial agents. The present invention also relates to orally bioavailable boron-containing compounds, compositions, preparations and their use as inhibitors of beta-lactamase enzymes and as antibacterial agents

BACKGROUND OF THE INVENTION

Antibiotics are the most effective drugs for curing bacteria-infectious diseases clinically. They have a wide market due to their advantages of good antibacterial effect with limited side effects. Among them, the beta-lactam class of antibiotics (for example, penicillins, cephalosporins, and carbapenems) is widely used because they have a strong bactericidal effect and low toxicity.

To counter the efficacy of the various beta-lactams, bacteria have evolved to produce variants of beta-lactam deactivating enzymes called beta-lactamases, and in the ability to share this tool inter- and intra-species. These beta-lactamases are categorized as "serine" or "metallo" based, respectively, on presence of a key serine or zinc in the enzyme active site. The rapid spread of this mechanism of bacterial resistance can severely limit beta-lactam treatment options in the hospital and in the community.

SUMMARY OF THE INVENTION

Described herein are compounds that modulate the activity of beta-lactamases. In some embodiments, the compounds described herein inhibit beta-lactamases. In certain embodiments, the compounds described herein are useful in the treatment of bacterial infections. In other embodiments, the compounds described herein are esters designed to deliver the corresponding carboxylic acid compounds.

One aspect provides a compound of Formula (II) or pharmaceutically acceptable salts, tautomers, or N-oxides thereof:

Formula (II)

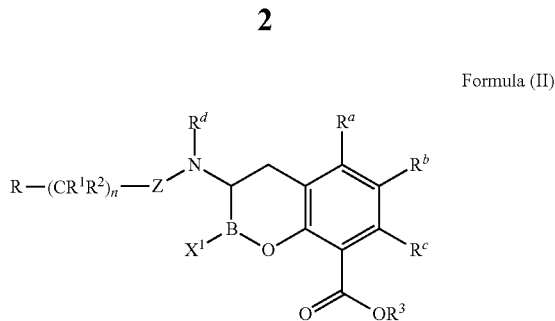

wherein:

M is hydrogen, fluoro, chloro, bromo, —$CF_3$, —CN, —$OR^4$, —$SR^4$, —S(O)—$R^4$, —$SO_2$—$R^4$, —$SO_2$—N($R^4R^5$), —N($R^4R^5$), —N($R^4$)—C(O)$R^5$, —N($R^4$)—C(O)—N($R^4R^5$), —N($R^4$)—$SO_2$—$R^5$, —N($R^4$)Heteroaryl, —C(O)—$R^4$, —C(O)—N($R^4R^5$), —C(O)($C_1$-$C_3$alkyl)C(O)$R^5$, optionally substituted oxyimino, optionally substituted alkenyl, optionally substituted alkynyl, heteroaryl, or heretocycloalkyl;

each $R^1$ and $R^2$ is independently hydrogen, fluoro, chloro, bromo, optionally substituted $C_1$-$C_6$ alkyl, optionally substituted aryl, —$OR^4$, —$SR^4$, or —$NR^4R^5$; or $R^1$ and $R^2$ are taken together with the carbon to which they are attached to form an optionally substituted $C_3$-$C_8$ cycloalkyl; or when n is at least 2, two $R^1$ on adjacent carbons are taken together to form a double bond; or two $R^1$ and two $R^2$ on adjacent carbons are taken together to form a triple bond;

each n is independently 0, 1, 2, 3, 4, 5, or 6;

$X^1$ is independently —$OR^4$, or F;

Z is >C=O, >C=S, or >$SO_2$;

$R^3$ is $R^{31}$, —$(R^{30})_q OR^{31}$, —$(R^{30})_q O(R^{30})_q OR^{31}$, —$R^{30}OC(O)R^{31}$, —$R^{30}OC(O)OR^{31}$, —$R^{30}OC(O)NHR^{31}$, —$R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one;

each q is independently 2, 3, 4, 5, or 6;

each $R^{30}$ is independently —$CH_2$—, —$CH(CH_3)$—, —$C(CH_3)_2$—, or optionally substituted 1,1'-cyclopropylene;

each $R^{31}$ is independently optionally substituted $C_1$-$C_{12}$ alkyl, optionally substituted alkoxyalkyl, optionally substituted $C_1$-$C_{12}$ alkenyl, optionally substituted $C_1$-$C_{12}$ alkynyl, optionally substituted $C_3$-$C_8$ cycloalkyl, optionally substituted $C_3$-$C_8$ heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl; or two $R^{31}$ are taken together with the Nitrogen to which they are attached to form a $C_3$-$C_8$ heterocycloalkyl;

$R^a$, $R^b$, and $R^c$ are independently hydrogen, fluoro, chloro, bromo, optionally substituted $C_1$-$C_6$ alkyl, optionally substituted $C_3$-$C_6$ cycloalkyl, optionally substituted heretocycloalkyl, optionally substituted aryl, optionally substituted heteroaryl, —$OR^4$, —$NR^4R^5$, or —$SR^4$;

$R^d$, $R^4$ and $R^5$ are independently hydrogen, —OH, —CN, —CF$_3$, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heretocycloalkyl, optionally substituted aryl, optionally substituted heteroaryl, optionally substituted cycloalkylalkyl, optionally substituted heretocycloalkylalkyl, optionally substituted aralkyl, optionally substituted heteroaralkyl, (poly-ethylene-glycol)-ethyl, or an optionally substituted saccharide;

or $R^4$ and $R^5$ taken together form an optionally substituted heterocycle with the nitrogen to which they are attached.

In some embodiments, $R^a$, $R^b$, and $R^c$ are independently hydrogen, fluoro, optionally substituted $C_1$-$C_6$ alkyl, —OR$^4$, —NR$^4$R$^5$, or —SR$^4$. In some embodiments, $R^a$, $R^b$, and $R^c$ are independently hydrogen, fluoro, chloro, —OH, or —OCH$_3$. In some embodiments, $R^a$, $R^b$, and $R^c$ are hydrogen.

In some embodiments, $X^1$ is —OH.

In some embodiments, $R^d$ is hydrogen or $C_1$-$C_4$ alkyl. In some embodiments, $R^d$ is hydrogen.

In some embodiments, Z is >C=O.

In some embodiments, n is 0, 1, 2, or 3. In some embodiments, n is 2. In some embodiments, n is 1.

In some embodiments, each $R^1$ and $R^2$ are independently hydrogen, fluoro, chloro, optionally substituted $C_1$-$C_6$ alkyl, and —CF$_3$. In some embodiments, each $R^1$ and $R^2$ are hydrogen.

In some embodiments, M is hydrogen, —CN, or optionally substituted alkynyl. In some embodiments, M is —C(O)—R$^4$. In some embodiments, M is —C(O)—R$^4$; and $R^4$ is optionally substituted $C_1$-$C_6$ alkyl.

In some embodiments, $R^3$ is $R^{31}$. In some embodiments, $R^3$ is $R^{31}$; and $R^{31}$ is $C_1$-$C_{12}$ alkyl or $C_3$-$C_8$ heterocycloalkyl. In some embodiments, $R^3$ is —R$^{30}$OC(O)R$^{31}$ or —R$^{30}$OC(O)OR$^{31}$.

In some embodiments, $R^3$ is —R$^{30}$OC(O)R$^{31}$ or —R$^{30}$OC(O)OR$^{31}$; and $R^{30}$ is independently —CH$_2$— or —CH(CH$_3$)—; and each $R^{31}$ is independently optionally substituted $C_1$-$C_{12}$ alkyl, aryl, $C_3$-$C_8$ cycloalkyl; or $C_3$-$C_8$ heterocycloalkyl.

Another aspect provides a pharmaceutical composition comprising at least one compound of Formula (II), or a pharmaceutically acceptable salt, N-oxide, or isomer thereof, and a pharmaceutically acceptable excipient.

In some embodiments, the pharmaceutical composition further comprises a beta-lactam antibiotic.

In some embodiments, the pharmaceutical composition further comprises a beta-lactam antibiotic, wherein the beta-lactam antibiotic is a penicillin, cephalosporin, carbapenem, monobactam, bridged monobactam, or a combination thereof.

Another aspect provides a method of treating a bacterial infection in a subject, comprising administering to the subject a compound of Formula (II) in combination with a therapeutically effective amount of beta-lactam antibiotic.

The compounds of Formula (I) and (II) disclosed herein are present in a closed, cyclic form as shown in the structures above, or an open, acyclic form of Formula (I-1) and (II-1), or mixtures thereof.

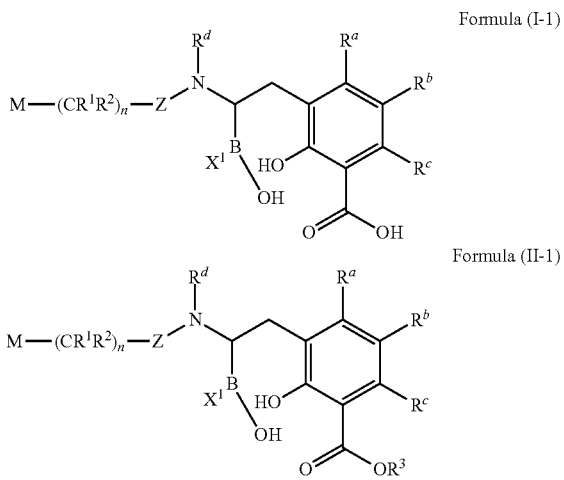

Formula (I-1)

Formula (II-1)

Accordingly, the compounds described herein may exist in an equilibrium between the "closed" cyclic form shown in Formula (I) and (II) and the "open" acyclic form shown in Formula (I-1) and (II-1). In addition the compounds described herein may associate into intramolecular dimers, trimers, and related combinations.

In another aspect, provided herein are pharmaceutical compositions comprising a compound Formula (I) or Formula (II) as described herein, or a pharmaceutically acceptable salt, N-oxide, or isomer thereof, and a pharmaceutically acceptable excipient. In some embodiments, the pharmaceutical composition further comprises a beta-lactam antibiotic. In certain embodiments, the beta-lactam antibiotic is a penicillin, cephalosporin, carbapenem, monobactam, bridged monobactam, or a combination thereof.

In a further aspect, provided herein are methods of treating a bacterial infection in a subject, comprising administering to the subject a pharmaceutical composition as described herein, optionally in combination with a beta-lactam antibiotic.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Beta-lactamases are typically grouped into 4 classes: Ambler classes A, B, C, and D, based on their amino acid sequences. Enzymes in classes A, C, and D are active-site serine beta-lactamases, while class B enzymes are Zn-dependent. Newer generation cephalosporins and carbapenems were developed partly based on their ability to evade the deactivating effect of the early serine-based beta-lactamase variants. However, a recent surge in new versions of serine-based beta-lactamases—for example Class A Extended-Spectrum Beta-Lactamase (ESBL) enzymes, Class A carbapenemases (e.g. KPC-2), chromosomal and plasmid mediated Class C cephalosporinases (AmpC, CMY, etc.), and Class D oxacillinases—as well as Class B metallo-beta-lactamases (e.g. VIM, NDM) has begun to diminish the utility of the beta-lactam antibiotic family, including the more recent generation beta-lactam drugs, leading to a serious medical problem. Indeed the number of catalogued serine-based beta-lactamases has exploded from less than ten in the 1970s to over 750 variants (see, e.g., Jacoby & Bush, "Amino Acid Sequences for TEM, SHV and OXA Extended-Spectrum and Inhibitor Resistant β-Lactamases", on the Lahey Clinic website).

The commercially available beta-lactamase inhibitors (clavulanic acid, sulbactam, tazobactam) were developed to address the beta-lactamases that were clinically relevant in the 1970s and 1980s (e.g. penicillinases). These enzyme inhibitors are available only as fixed combinations with penicillin derivatives. No combinations with cephalosporins (or carbapenems) are clinically available. This fact, combined with the increased use of newer generation cephalosporins and carbapenems, is driving the selection and spread of the new beta-lactamase variants (ESBLs, carbapenemases, chromosomal and plasmid-mediated Class C, Class D oxacillinases, etc.). While maintaining good inhibitory activity against ESBLs, the legacy beta-lactamase inhibitors are largely ineffective against the new Class A and Class B carbapenemases, against the chromosomal and plasmid-mediated Class C cephalosporinases and against many of the Class D oxacillinases. To address this growing therapeutic vulnerability, a new generation of beta-lactamase inhibitors must be developed with broad spectrum functionality.

Use of a boronic acid compound to inhibit a beta-lactamase enzyme has been limited. For example, U.S. Pat. No. 7,271,186 discloses beta-lactamase inhibitors that target AmpC (from class C). Ness et al. (Biochemistry (2000) 39:5312-21) discloses beta-lactamase inhibitors that target TEM-1 (a non-ESBL TEM variant from class A; one of approximately 140 known TEM-type beta-lactamase variants). Because there are four major molecular classes of serine-based beta-lactamases, and each of these classes contains significant numbers of beta-lactamase variants, inhibition of one or a small number of beta-lactamases is unlikely to be of therapeutic value. Therefore, there is an imperative need to develop novel beta-lactamase inhibitors with broad spectrum functionality. In particular, there is a need for compounds that are active against both serine- and metallo-based beta-lactamase enzymes.

Moreover, these beta-lactamase inhibitor boronic acid compounds are typically not highly absorbed when orally administered. Thus, higher drug dosages may be required for oral administration in order to obtain a therapeutically effective plasma level of the beta-lactamase inhibitors. Since these beta-lactamase inhibitors are usually administered in combination with an oral antibiotic, there is a need to develop novel beta-lactamase inhibitors with oral bioavailability and activity. The novel boronic acid based inhibitors described herein address this medical need.

The present invention is directed to certain boron-based compounds (boronic acids and cyclic boronic acid esters) which are beta-lactamase inhibitors and antibacterial compounds. The present invention is also directed to certain orally bioavailable boron-based compounds (boronic acids and cyclic boronic acid esters) which are beta-lactamase inhibitors and antibacterial compounds. The compounds and their pharmaceutically acceptable salts are useful alone and in combination with beta-lactam antibiotics for the treatment of bacterial infections, particularly antibiotic resistant bacterial infections. Some embodiments include compounds, compositions, pharmaceutical compositions, use and preparation thereof.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" or "some embodiments" means that a particular feature, structure or characteristic described in connection with the embodiment is included in at least one embodiment. Thus, the appearances of the phrases "in one embodiment" or "in an embodiment" or "some embodiments" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics suitable for use with respect to the present invention include penicillins, cephalosporins and carbapenems.

The term "β-lactam antibiotic" refers to a compound with antibiotic properties that contains a β-lactam functionality. Non-limiting examples of β-lactam antibiotics useful with respect to the invention include penicillins, cephalosporins, penems, carbapenems, and monobactams.

The term "β-lactamase" denotes a protein capable of inactivating a β-lactam antibiotic. The β-lactamase can be an enzyme which catalyzes the hydrolysis of the β-lactam ring of a β-lactam antibiotic. Of particular interest herein are microbial β-lactamases. The β-lactamase may be, for example, a serine β-lactamase or a metallo-β-lactamase. β-Lactamases of interest include those disclosed in an ongoing website that monitors beta-lactamase nomenclature (www.lahey.org) and in Bush, K. and G. A. Jacoby. 2010. An updated functional classification of β-lactamases. Antimicrob. Agents Chemother. 54:969-976. β-Lactamases of particular interest herein include β-lactamases found in bacteria such as class A β-lactamases including the SHV, CTX-M and KPC subclasses, class B β-lactamases such as VIM, class C β-lactamases (both chromosomal and plasmid-mediated), and class D β-lactamases. The term "β-lactamase inhibitor" refers to a compound which is capable of inhibiting β-lactamase activity. Inhibiting β-lactamase activity means inhibiting the activity of a class A, B, C, or D β-lactamase. For antimicrobial applications inhibition at a 50% inhibitory concentration is preferably achieved at or below about 100 micrograms/mL, or at or below about 50 micrograms/mL, or at or below about 25 micrograms/mL. The terms "class A", "class B", "class C", and "class D" β-lactamases are understood by those skilled in the art and are described in Bush, K. and G. A. Jacoby. 2010. An updated functional classification of β-lactamases. Antimicrob. Agents Chemother. 54:969-976.

The term "oral bioavailability" (F %) denotes the fraction of an oral administered drug that reaches systemic circulation. After intravenous administration, a drug is directly and fully available in the bloodstream and can be distributed via systemic circulation to the point where a pharmacological effect takes place. If a drug is administered orally, it has to cross further barriers to reach the systemic circulation, which can significantly reduce the final extent of a drug in the bloodstream. Oral bioavailability is one of the most important properties in drug design and development. A high oral bioavailability reduces the amount of an administered drug necessary to achieve a desired pharmacological effect and therefore could reduce the risk of side-effects and toxicity. A poor oral bioavailability can result in low efficacy and higher inter-individual variability and therefore can lead to unpredictable response to a drug. In some embodiments the F % is greater than about 5%, greater than about 10%, greater than about 15%, greater than about 20%, greater than about 25%, greater than about 30%, greater than about 35%, greater than about 40%, greater than about 50%, greater than about 55%, greater than about 60%, greater than about 65%, greater than about 70%, greater than about 75%, greater than about 80%, greater than about 85%, greater than about 90%, or greater than about 95%.

A compound of Formula (I), as described herein, includes a compound of a compound of Formula (I-1), Formula (Ia), a compound of Formula (Ib), a compound of Formula (Ic), a compound of Formula (Id), a compound of Formula (Ie), a compound of Formula (If), a compound of Formula (Ig), a compound of Formula (Ih), or a compound of Formula (Ii).

A compound of Formula (II), as described herein, includes a compound of Formula (II-1), a compound of Formula (IIa), a compound of Formula (IIb), a compound of Formula (IIc), a compound of Formula (IId), a compound of Formula (IIe), a compound of Formula (IIf), a compound of Formula (IIg), a compound of Formula (IIh), or a compound of Formula (IIi).

The terms below, as used herein, have the following meanings, unless indicated otherwise:

"Amino" refers to the —$NH_2$ radical.
"Cyano" or "nitrile" refers to the —CN radical.
"Hydroxy" or "hydroxyl" refers to the —OH radical.
"Nitro" refers to the —$NO_2$ radical.
"Oxo" refers to the =O substituent.
"Oxime" refers to the =N—OH substituent.
"Thioxo" refers to the =S substituent.

"Alkyl" refers to a straight or branched hydrocarbon chain radical, which is fully saturated or comprises unsaturations, has from one to thirty carbon atoms, and is attached to the rest of the molecule by a single bond. Alkyls comprising any number of carbon atoms from 1 to 30 are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (isopropyl), n-butyl, i-butyl, s-butyl, n-pentyl, 1,1-dimethylethyl (t-butyl), 2-ethylpropyl, 3-methylhexyl, 2-methylhexyl, vinyl, allyl, propynyl, and the like. Alkyl comprising unsaturations include alkenyl and alkynyl groups. Unless stated otherwise specifically in the specification, an alkyl group may be optionally substituted as described below.

"Alkylene" or "alkylene chain" refers to a straight or branched divalent hydrocarbon chain, as described for alkyl above. Unless stated otherwise specifically in the specification, an alkylene group may be optionally substituted as described below.

"Alkoxy" refers to a radical of the formula —ORa where Ra is an alkyl radical as defined. Unless stated otherwise specifically in the specification, an alkoxy group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Cycloalkyl" or "carbocycle" refers to a stable, non-aromatic, monocyclic or polycyclic carbocyclic ring, which may include fused or bridged ring systems, which is saturated or unsaturated. Representative cycloalkyls or carbocycles include, but are not limited to, cycloalkyls having from three to fifteen carbon atoms, from three to ten carbon atoms, from three to eight carbon atoms, from three to six carbon atoms, from three to five carbon atoms, or three to four carbon atoms. Monocyclic cycloalkyls or carbocycles include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Unless otherwise stated specifically in the specification, a cycloalkyl or carbocycle group may be optionally substituted. Illustrative examples of cycloalkyl groups include, but are not limited to, the following moieties:

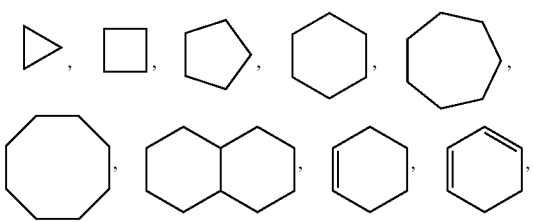

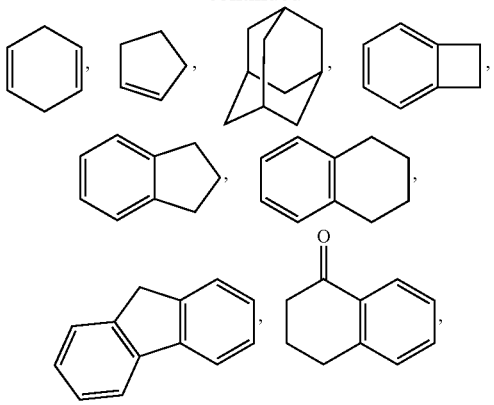

and the like.

"Fused" refers to any ring structure described herein which is fused to an existing ring structure. When the fused ring is a heretocycloalkyl ring or a heteroaryl ring, any carbon atom on the existing ring structure which becomes part of the fused heretocycloalkyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" similarly refers to a radical of the formula —ORa where Ra is a haloalkyl radical as defined. Unless stated otherwise specifically in the specification, a haloalkoxy group may be optionally substituted as described below.

"Heterocycloalkyl" or "heterocyclyl" or "heterocyclic ring" or "heterocycle" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocycloalkyl radical may be a monocyclic, bicyclic, tricyclic or tetracyclic ring system, which may include fused or bridged ring systems; and the nitrogen, carbon or sulfur atoms in the heterocycloalkyl radical may be optionally oxidized; the nitrogen atom may be optionally quaternized; and the heterocycloalkyl radical may be partially or fully saturated. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocycloalkyl group may be optionally substituted. Illustrative examples of heterocycloalkyl groups, also referred to as non-aromatic heterocycles, include:

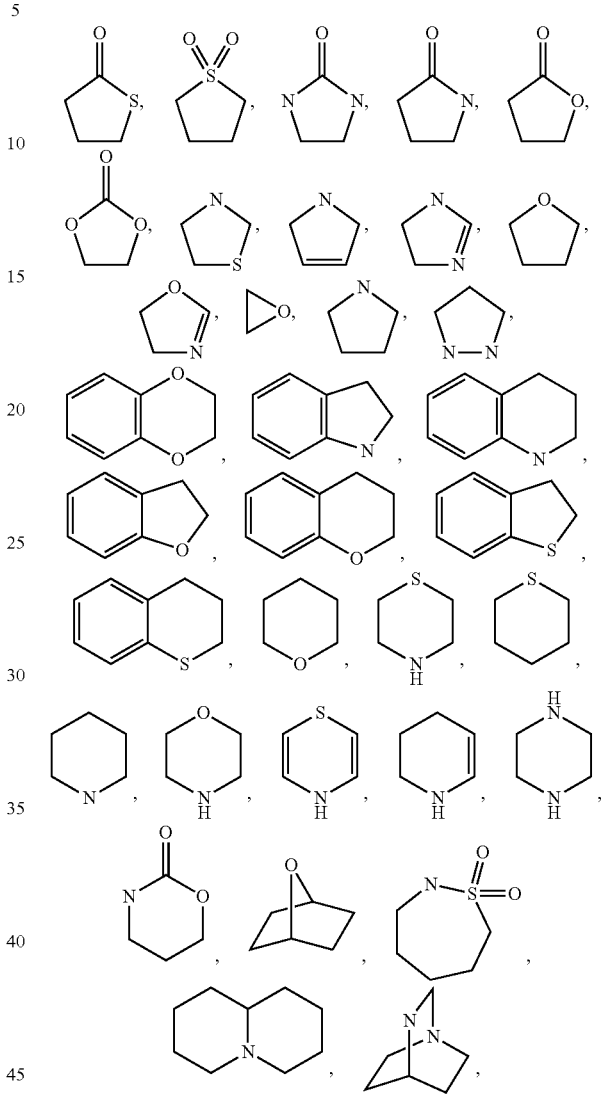

and the like. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo [1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups (e.g, alkyl, alkenyl, alkynyl, alkylene, alkoxy, aryl, cycloalkyl, haloalkyl, heterocycloalkyl and/or heteroaryl) may be further functionalized wherein at least one hydrogen atom is replaced by a bond to a non-hydrogen atom substituent. Unless stated specifically in the specification, a substituted group may include one or more substituents selected from: oxo, amino, —$CO_2H$, nitrile, nitro, hydroxyl, thiooxy, alkyl, alkylene, alkoxy, aryl, cycloalkyl, heterocycloalkyl, heteroaryl, dialkylamines, arylamines, alkylarylamines, diarylamines, trialkylammonium (—$N^+R_3$), N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NH_2$, —$NR_gC(\!=\!O)NR_gR_h$, —$NR_gC(\!=\!O)OR_h$, —$NR_gSO_2R_h$, —$OC(\!=\!O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocycloalkyl, N-heterocycloalkyl, heterocycloalkylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen, sulfur, or nitrogen atoms. For example, an alkyl group may be substituted with one or more internal oxygen atoms to form an ether or polyether group. Similarly, an alkyl group may be substituted with one or more internal sulfur atoms to form a thioether, disulfide, etc.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —$CH_2CH_2$), fully substituted (e.g., —$CF_2CF_3$), mono-substituted (e.g., —$CH_2CH_2F$) or substituted at a level anywhere in-between fully substituted and mono-substituted (e.g., —$CH_2CHF_2$, —$CH_2CF_3$, —$CF_2CH_3$, —$CFHCHF_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition. In other embodiments, treatment also includes prophylactic treatment (e.g., administration of a composition described herein when an individual is suspected to be suffering from a bacterial infection).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

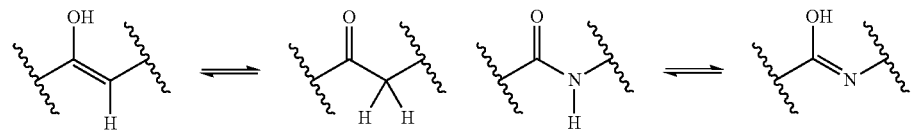

-continued

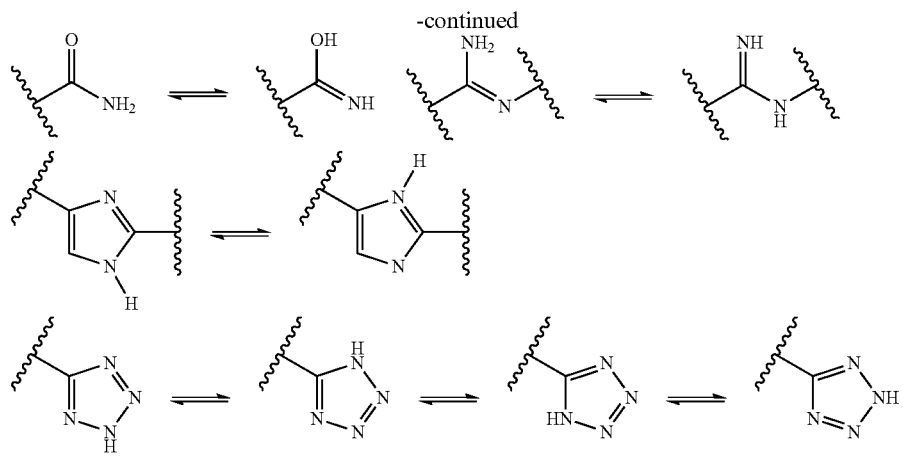

Compounds

Described herein are compounds that modulate the activity of beta-lactamase. In some embodiments, the compounds described herein inhibit beta-lactamase. In certain embodiments, the compounds described herein are orally bioavailable. In certain embodiments, the compounds described herein are useful in the treatment of bacterial infections. In some embodiments, the bacterial infection is an upper or lower respiratory tract infection, a urinary tract infection, an intra-abdominal infection, or a skin infection.

In one aspect, provided herein are compounds of Formula (I) or Formula (II), or pharmaceutically acceptable salts, tautomers, or N-oxides thereof:

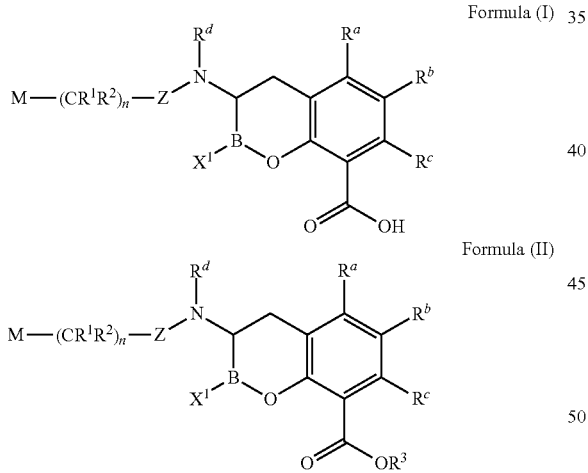

wherein:
M is H, fluoro, chloro, bromo, $(CR^1)(Cl)_2$, $(CR^1)(F)_2$, —$CF_3$, —CN, —OH, —$OR^4$, —$SR^4$, —S(O)—$R^4$, —$SO_2$—$R^4$, $SO_2$—$N(R^4R^5)$, —$N(R^4R^5)$, —$N(R^4)$—C(O)$R^5$, —$N(R^4)$—C(O)—$N(R^4R^5)$, —$N(R^4)$—$SO_2$—$R^5$, —$N(R^4)$Heteroaryl, —C(O)—$R^4$, —C(O)—N($R^4R^5$), —C(O)($C_1$-$C_3$alkyl)C(O)$R^5$, optionally substituted oxyimino, optionally substituted alkenyl, optionally substituted alkynyl, heteroaryl, or heterocycloalkyl;

each $R^1$ and $R^2$ are independently hydrogen, fluoro, chloro, bromo, optionally substituted $C_1$-$C_6$ alkyl, —OH, —$OR^4$, —$SR^4$, optionally substituted aryl, or —$NR^4R^5$; or $R^1$ and $R^2$ are taken together with the carbon to which they are attached to form an optionally substituted $C_3$-$C_8$ cycloalkyl; or when n is at least 2, two $R^1$ on adjacent carbons are taken together to form a double bond; or two $R^1$ and two $R^2$ on adjacent carbons are taken together to form a triple bond;

each n is independently 0, 1, 2, 3, 4, 5, or 6;

$X^1$ is independently —OH, —$OR^4$, or F;

Z is >C=O, >C=S, or >$SO_2$;

$R^3$ is $R^{31}$, —$(R^{30})_q OR^{31}$, —$(R^{30})_q O(R^{30})_q OR^{31}$, —$R^{30}OC(O)R^{31}$, —$R^{30}OC(O)OR^{31}$, —$R^{30}OC(O)NHR^{31}$, —$R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each q is independently 2, 3, 4, 5, or 6;

each $R^{30}$ is independently —$CH_2$—, —$CH(CH_3)$—, —$C(CH_3)_2$—, or optionally substituted 1,1'-cyclopropylene;

$R^{31}$ is optionally substituted $C_1$-$C_{12}$ alkyl, optionally substituted $C_1$-$C_{12}$ alkenyl, optionally substituted $C_1$-$C_{12}$ alkynyl, $C_3$-$C_8$ cycloalkyl, $C_3$-$C_8$ heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl; or two $R^{31}$ are taken together with the Nitrogen to which they are attached to form a $C_3$-$C_8$ heterocycloalkyl;

$R^a$, $R^b$, and $R^c$ are independently hydrogen, fluoro, chloro, bromo, optionally substituted $C_1$-$C_6$ alkyl, optionally substituted $C_3$-$C_6$ cycloalkyl, optionally substituted heterocycloalkyl, optionally substituted aryl, optionally substituted heteroaryl, —OH, —$OR^4$, —$NR^4R^5$, or —$SR^4$;

$R^d$, $R^4$ and $R^5$ are independently hydrogen, —OH, —CN, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;

or $R^4$ and $R^5$ taken together form an optionally substituted heterocycle with the nitrogen to which they are attached.

In some embodiments of the compounds of Formula (I) or Formula (II),

M is H, fluoro, $(CR^1)(F)_2$, —$CF_3$, —CN, —OH, —$OR^4$, —$N(R^4R^5)$, —$N(R^4)$—$SO_2$—$R^5$, —C(O)—$R^4$, —C(O)—$N(R^4R^5)$, heteroaryl;

n is 1, 2, 3;

$X^1$ is independently —OH, or —$OR^4$;

Z is >C=O;

$R^3$ when present is alkyl, or acyloxyalkyl;

$R^a$, $R^b$, and $R^c$ are independently hydrogen, fluoro, optionally substituted $C_1$-$C_6$ alkyl, —OH, —$OR^4$, —$NR^4R^5$, or —$SR^4$;

$R^1$ and $R^2$ are independently hydrogen, fluoro, chloro, or optionally substituted $C_1$-$C_6$ alkyl;

$R^d$ is hydrogen $R^4$ and $R^5$ are independently hydrogen, or optionally substituted $C_1$-$C_6$ alkyl.

In some embodiments of the compounds of Formula (II),

M is H, —CN, —$N(R^4)$—$SO_2$—$R^5$, —C(O)—$R^4$, —C(O)—$N(R^4R^5)$, heteroaryl;

n is 1, 2, 3;

$X^1$ is independently —OH, or —$OR^4$;

Z is >C=O;

$R^3$ when present is methyl, ethyl, butyl, pivaloyloxymethyl, acetoxymethyl, ethoxycarbonyloxymethyl, 1-(acetoxy)ethyl, 1-(pivaloyloxy)ethyl, 1-(isopropoxycarbonyoxy)ethyl, and 1-cyclohexyloxycarbonyloxymethyl;

$R^a$, $R^b$, $R^c$, and $R^d$ are hydrogen;

each $R^1$ and $R^2$ are independently hydrogen, methyl, ethyl, propyl, isopropyl, butyl, isobutyl, sec-butyl or tert-butyl;

each $R^4$ and $R^5$ are independently hydrogen, methyl, ethyl, propyl, isopropyl, butyl, isobutyl, sec-butyl or tert-butyl.

In some embodiments of the compounds of Formula (I) or Formula (II), M-$(CR^1R^2)_n$— is unsubstituted alkyl. In some embodiments, M-$(CR^1R^2)_n$— is propyl or isobutyl.

In other embodiments of the compounds of Formula (I) or Formula (II), M-$(CR^1R^2)_n$— is a substituted alkyl group. In some embodiments, M-$(CR^1R^2)_n$— comprises at least one cyano group. In some embodiments of the compounds of Formula (I) or Formula (II), M-$(CR^1R^2)_n$—Z— is —C(O)$(CR^1R^2)_n$CN, for example —$CH_2$—$CH_2$—CN.

In some embodiments, the compound comprises at least 2 halogen atoms selected from fluorine or chlorine atoms. In some embodiments, the compound comprises at least 3 halogen atoms selected from fluorine or chlorine atoms.

In some embodiments of the compounds of Formula (I) or Formula (II), M-$(CR^1R^2)_n$—Z is —$C(O)(CR^1R^2)$ $C(O)CH_3$ for example —$C(O)CH_2$—$CH_2$—$C(O)CH_3$.

One aspect provides a compound of Formula (I) or pharmaceutically acceptable salts, tautomers, or N-oxides thereof:

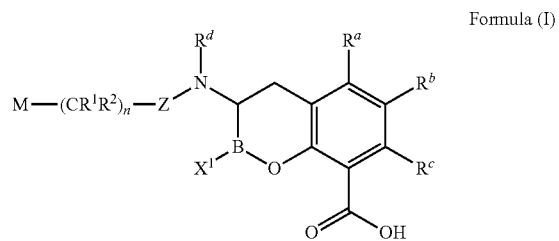

Formula (I)

wherein:

M is fluoro, chloro, bromo, —$CF_3$, —CN, —$OR^6$, —$SR^4$, —S(O)—$R^4$, —$SO_2$—$R^4$, —$SO_2$—$N(R^4R^5)$, —$N(R^4)$—C(O)—$O(R^4)$, —$N(R^4)$—C(O)—$N(R^4R^5)$, —$N(R^4)$—$SO_2$—$R^5$, —$N(R^4)$Heteroaryl, —C(O)—$R^4$, —C(O)—$N(R^4R^5)$, —$C(O)(C_1-C_3 alkyl)C(O)R^5$, optionally substituted oxyimino, optionally substituted alkenyl, optionally substituted alkynyl, heteroaryl, or heretocycloalkyl;

with the proviso that when M is heteroaryl, then n is 2, 3, 4, 5, or 6;

each $R^1$ and $R^2$ are independently hydrogen, fluoro, chloro, bromo, optionally substituted $C_1$-$C_6$ alkyl, —$CF_3$, optionally substituted aryl, —$OR^4$, —$SR^4$, or —$NR^4R^5$; or $R^1$ and $R^2$ are taken together with the carbon to which they are attached to form an optionally substituted $C_3$-$C_8$ cycloalkyl; or when n is at least 2, two $R^1$ on adjacent carbons are taken together to form a double bond; or two $R^1$ and two $R^2$ on adjacent carbons are taken together to form a triple bond;

each n is independently 1, 2, 3, 4, 5, or 6;

$X^1$ is independently —$OR^4$ or F;

Z is >C=O, >C=S, or >$SO_2$;

$R^a$, $R^b$, and $R^c$ are hydrogen, fluoro, chloro, bromo, optionally substituted $C_1$-$C_6$ alkyl, optionally substituted $C_3$-$C_6$ cycloalkyl, optionally substituted heterocycloalkyl, optionally substituted aryl, optionally substituted heteroaryl, —$OR^4$, —$NR^4R^5$, or —$SR^4$;

$R^d$, $R^4$ and $R^5$ are independently hydrogen, —OH, —CN, —$CF_3$, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;

or $R^4$ and $R^5$ taken together form an optionally substituted heterocycle with the nitrogen to which they are attached; and $R^6$ is optionally substituted —CN, —$CF_3$, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted heteroaralkyl, (poly-ethylene-glycol)-ethyl, or an optionally substituted saccharide;

with the proviso that the compound of Formula (I) is not 3-(2-(1,3-dioxoisoindolin-2-yl)acetamido)-2-hydroxy-3,4-dihydro-2H-benzo[e][1,2]oxaborinine-8-carboxylic acid or 3-(2-borono-2-(4-oxo-4-(thiophen-2-yl)butanamido)ethyl)-2-hydroxybenzoic acid.

In some embodiments of a compound of Formula (I), Z is >C=S. In some embodiments of a compound of Formula (I), Z is >SO$_2$. In some embodiments of a compound of Formula (I), Z is >C=O.

In some embodiments of a compound of Formula (I) is a compound of Formula (Ia) or pharmaceutically acceptable salts, tautomers, or N-oxides thereof:

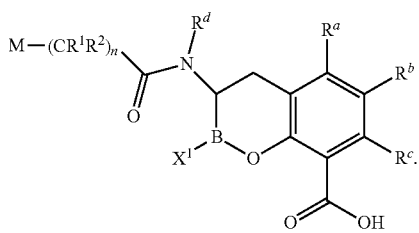

Formula (Ia)

In some embodiments of a compound of Formula (I), $R^a$, $R^b$, and $R^c$ are independently hydrogen, fluoro, optionally substituted $C_1$-$C_6$ alkyl, —OR$^4$, —NR$^4$R$^5$, or —SR$^4$. In some embodiments of a compound of Formula (I), $R^a$, $R^b$, and $R^c$ are independently methyl, ethyl, propyl, isopropyl, 2-ethylpropyl, butyl, tert-butyl, pentyl, isobutyl or isopentyl. In some embodiments of a compound of Formula (I), $R^a$, $R^b$, and $R^c$ are independently hydrogen, fluoro, chloro, —OH, or —OCH$_3$. In some embodiments of a compound of Formula (I), $R^a$, $R^b$, and $R^c$ are hydrogen. In some embodiments of a compound of Formula (I), at least one of $R^a$, $R^b$, and $R^c$ is not hydrogen.

In some embodiments of a compound of Formula (I), $X^1$ is —OR$^4$. In some embodiments of a compound of Formula (I), $X^1$ is —OH. In some embodiments of a compound of Formula (I), $X^1$ is F.

In some embodiments of a compound of Formula (I), $R^a$ is hydrogen or $C_1$-$C_4$ alkyl. In some embodiments of a compound of Formula (I), $R^a$ is hydrogen. In some embodiments, $R^a$ is methyl, ethyl, or propyl. In some embodiments, $R^d$ is methyl.

In some embodiments of a compound of Formula (I) is a compound of Formula (Ib) or pharmaceutically acceptable salts, tautomers, or N-oxides thereof:

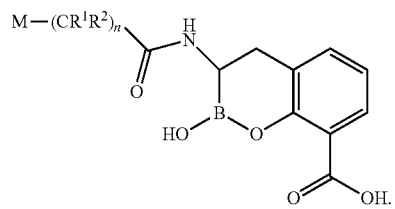

Formula (Ib)

In some embodiments of a compound of Formula (I), n is 0, 1, 2, 3, 4, 5, or 6. In some embodiments of a compound of Formula (I), n is 0. In some embodiments of a compound of Formula (I), n is 1. In some embodiments of a compound of Formula (I), n is 2. In some embodiments of a compound of Formula (I), n is 3. In some embodiments of a compound of Formula (I), n is 4. In some embodiments of a compound of Formula (I), n is 5. In some embodiments of a compound of Formula (I), n is 6. In some embodiments of a compound of Formula (I), n is 0, 1, 2, or 3.

In some embodiments of a compound of Formula (I) is a compound of Formula (Ic), (Id), or (Ie) or pharmaceutically acceptable salts, tautomers, or N-oxides thereof:

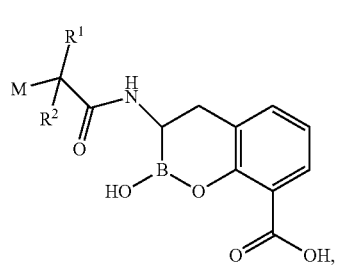

Formula (Ic)

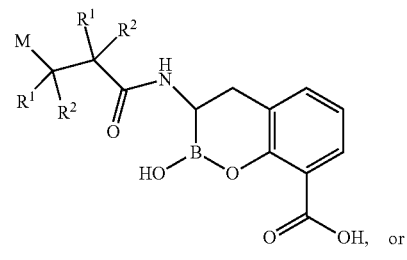

Formula (Id)

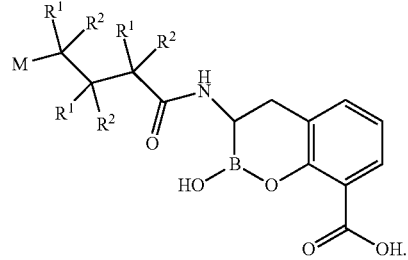

Formula (Ie)

In some embodiments of a compound of Formula (I), each $R^1$ and $R^2$ are independently hydrogen, fluoro, chloro, bromo, optionally substituted $C_1$-$C_6$ alkyl, —CF$_3$, optionally substituted aryl, —OR$^4$, —SR$^4$, or —NR$^4$R$^5$. In some embodiments of a compound of Formula (I), each $R^1$ and $R^2$ are independently hydrogen, optionally substituted aryl, —OR$^4$, —SR$^4$, or —NR$^4$R$^5$. In some embodiments of a compound of Formula (I), each $R^1$ and $R^2$ are independently hydrogen, fluoro, chloro, optionally substituted $C_1$-$C_6$ alkyl, or —CF$_3$. In some embodiments of a compound of Formula (I), each $R^1$ and $R^2$ are independently hydrogen or $C_1$-$C_6$ alkyl. In some embodiments of a compound of Formula (I), each $R^1$ and $R^2$ are independently hydrogen or methyl. In some embodiments of a compound of Formula (I), each $R^1$ and $R^2$ are hydrogen. In some embodiments of a compound of Formula (I), each $R^1$ and $R^2$ are independently hydrogen, fluoro and chloro. In some embodiments of a compound of Formula (I), each $R^1$ and $R^2$ are independently hydrogen and —CF$_3$. In some embodiments of a compound of Formula (I), $R^1$ and $R^2$ are taken together with the carbon to which they are attached to form an optionally substituted $C_3$-$C_8$ cycloalkyl. In some embodiments of a compound of Formula (I), $R^1$ and $R^2$ are taken together with the carbon to which they are attached to form a cyclopropyl, cyclobutyl, cyclopentyl, or cyclohexyl. In some embodiments of a compound of Formula (I), when n is at least 2, two $R^1$ on adjacent carbons are taken together to form a double bond. In some embodiments of a compound of Formula (I), two $R^1$ and two $R^2$ on adjacent carbons are taken together to form a triple bond.

In some embodiments of a compound of Formula (I) is a compound of Formula (If), (Ig), or (Ih) or pharmaceutically acceptable salts, tautomers, or N-oxides thereof:

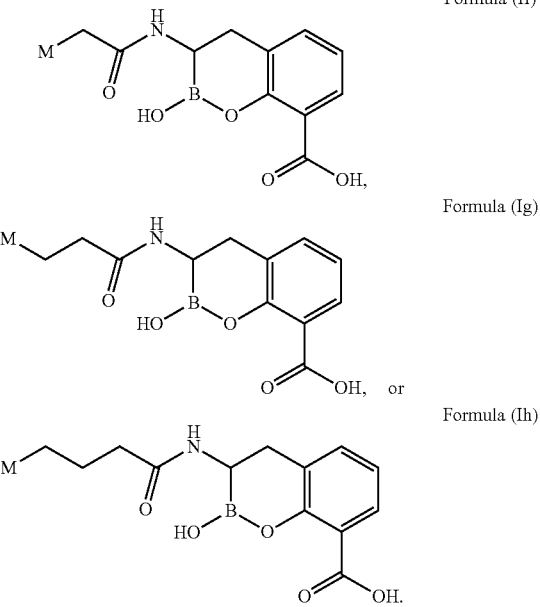

In some embodiments of a compound of Formula (I), M is fluoro, chloro, bromo, —$CF_3$, —CN, —$OR^6$, —$SR^4$, —S(O)—$R^4$, —$SO_2$—$R^4$, —$SO_2$—N($R^4R^5$), —N($R^4$)—C(O)—O($R^4$), —N($R^4$)—C(O)—N($R^4R^5$), —N($R^4$)—$SO_2$—$R^5$, —N($R^4$)Heteroaryl, —C(O)—$R^4$, —C(O)—N($R^4R^5$), —C(O)($C_1$-$C_3$alkyl)C(O)$R^5$, optionally substituted oxyimino, optionally substituted alkenyl, optionally substituted alkynyl, heteroaryl, or heterocycloalkyl.

In some embodiments of a compound of Formula (I), M is —$CF_3$, —CN, —$OR^6$, —N($R^4$)—$SO_2$—$R^5$, —C(O)—$R^4$, —C(O)—N($R^4R^5$), optionally substituted alkynyl, heteroaryl, or heterocycloalkyl.

In some embodiments of a compound of Formula (I), M is —$CF_3$.

In some embodiments of a compound of Formula (I), M is —CN.

In some embodiments of a compound of Formula (I), M is —$OR^6$. In some embodiments of a compound of Formula (I), M is —$OR^6$ and $R^6$ is —$CF_3$, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted heteroaralkyl, (poly-ethylene-glycol)-ethyl, or an optionally substituted saccharide. In some embodiments of a compound of Formula (I), M is —$OR^6$ and $R^6$ is optionally substituted $C_1$-$C_6$ alkyl or optionally substituted alkoxyalky. In some embodiments of a compound of Formula (I), M is —$OR^6$ and $R^6$ is $C_1$-$C_6$ alkyl or alkoxyalkyl. In some embodiments of a compound of Formula (I), M is —$OR^6$ and $R^6$ is methyl, ethyl, propyl, isopropyl, 2-ethylpropyl, butyl, tert-butyl, pentyl, isobutyl or isopentyl. In some embodiments of a compound of Formula (I), M is —$OR^6$ and $R^6$ is methyl.

In some embodiments of a compound of Formula (I), M is —N($R^4$)—$SO_2$—$R^5$, —C(O)—$R^4$, or —C(O)—N($R^4R^5$).

In some embodiments of a compound of Formula (I), M is —N($R^4$)—$SO_2$—$R^5$; and $R^4$ and $R^5$ are independently hydrogen or optionally substituted $C_1$-$C_6$ alkyl. In some embodiments of a compound of Formula (I), M is —N($R^4$)—$SO_2$—$R^5$ and $R^4$ and $R^5$ are independently hydrogen or $C_1$-$C_6$ alkyl. In some embodiments of a compound of Formula (I), M is —N($R^4$)—$SO_2$—$R^5$, $R^4$ is hydrogen, and $R^5$ is $C_1$-$C_6$ alkyl. In some embodiments of a compound of Formula (I), M is —N($R^4$)—$SO_2$—$R^5$, $R^4$ is hydrogen, and $R^5$ is methyl, ethyl, propyl, isopropyl, 2-ethylpropyl, butyl, tert-butyl, pentyl, isobutyl, or isopentyl. In some embodiments of a compound of Formula (I), M is —N($R^4$)—$SO_2$—$R^5$, $R^4$ is hydrogen, and $R^5$ is methyl. In some embodiments of a compound of Formula (I), M is —N($R^4$)—$SO_2$—$R^5$ and $R^4$ and $R^5$ are independently hydrogen or —$CF_3$. In some embodiments of a compound of Formula (I), M is —N($R^4$)—$SO_2$—$R^5$ and $R^4$ is hydrogen and $R^5$ is —$CF_3$.

In some embodiments of a compound of Formula (I), M is —C(O)—$R^4$ and $R^4$ is optionally substituted $C_1$-$C_6$ alkyl. In some embodiments of a compound of Formula (I), M is —C(O)—$R^4$ and $R^4$ is $C_1$-$C_6$ alkyl. In some embodiments of a compound of Formula (I), M is —C(O)—$R^4$ and $R^4$ is methyl, ethyl, propyl, isopropyl, 2-ethylpropyl, butyl, tert-butyl, pentyl, isobutyl, or isopentyl. In some embodiments of a compound of Formula (I), M is —C(O)—$R^4$ and $R^4$ is methyl.

In some embodiments of a compound of Formula (I), M is —C(O)—N($R^4R^5$) and $R^4$ and $R^5$ are independently hydrogen or optionally substituted $C_1$-$C_6$ alkyl. In some embodiments of a compound of Formula (I), M is —C(O)—N($R^4R^5$) and $R^4$ and $R^5$ are independently hydrogen or $C_1$-$C_6$ alkyl. In some embodiments of a compound of Formula (I), M is —C(O)—N($R^4R^5$) and $R^4$ is hydrogen and $R^5$ is $C_1$-$C_6$ alkyl. In some embodiments of a compound of Formula (I), M is —C(O)—N($R^4R^5$) and $R^4$ is hydrogen and $R^5$ is methyl, ethyl, propyl, isopropyl, 2-ethylpropyl, butyl, tert-butyl, pentyl, isobutyl, or isopentyl. In some embodiments of a compound of Formula (I), M is —C(O)—N($R^4R^5$) and R is hydrogen and $R^5$ is methyl. In some embodiments of a compound of Formula (I), M is —C(O)—N($R^4R^5$) and each R and $R^5$ are independently $C_1$-$C_6$ alkyl. In some embodiments of a compound of Formula (I), M is —C(O)—N($R^4R^5$) and each R and $R^5$ are independently methyl, ethyl, propyl, isopropyl, 2-ethylpropyl, butyl, tert-butyl, pentyl, isobutyl, or isopentyl. In some embodiments of a compound of Formula (I), M is —C(O)—N($R^4R^5$) and each R and $R^5$ are methyl. In some embodiments of a compound of Formula (I), M is —C(O)—N($R^4R^5$) and each R and $R^5$ are hydrogen.

In some embodiments of a compound of Formula (I), M is optionally substituted alkynyl. In some embodiments of a compound of Formula (I), M is alkynyl.

In some embodiments of a compound of Formula (I), M is heteroaryl, or heterocycloalkyl. In some embodiments of a compound of Formula (I), M is heteroaryl. In some embodiments of a compound of Formula (I), M is pyridinyl, pyrimidinyl, pyridazinyl, pyrazinyl, imidazolyl, pyrrazolyl, thiazolyl, or oxazolyl. In some embodiments of a compound of Formula (I), M is imidazolyl, pyrrazolyl, thiazolyl, or oxazolyl. In some embodiments of a compound of Formula (I), M is heterocycloalkyl. In some embodiments of a compound of Formula (I), M is pyrrolidinone or pyrrolidine-2,5-dione.

In some embodiments of a compound of Formula (I), M is fluoro.

In some embodiments of a compound of Formula (I), M is chloro.

In some embodiments of a compound of Formula (I), M is bromo.

In some embodiments of a compound of Formula (I), M is optionally substituted oxyimino.

In some embodiments of a compound of Formula (I), M is optionally substituted alkenyl. In some embodiments of a compound of Formula (I), M is alkenyl.

In some embodiments of a compound of Formula (I), M is —SR$^4$, —S(O)—R$^4$, or —SO$_2$—R$^4$. In some embodiments of a compound of Formula (I), M is —SR$^4$, —S(O)—R$^4$, or —SO$_2$—R$^4$; and each R$^4$ is independently optionally substituted C$_1$-C$_6$ alkyl. In some embodiments of a compound of Formula (I), M is —SR$^4$, —S(O)—R$^4$, or —SO$_2$—R$^4$; and each R$^4$ is independently C$_1$-C$_6$ alkyl. In some embodiments of a compound of Formula (I), M is —SR$^4$, —S(O)—R$^4$, or —SO$_2$—R$^4$ and each R$^4$ is independently methyl, ethyl, propyl, isopropyl, 2-ethylpropyl, butyl, tert-butyl, pentyl, isobutyl, or isopentyl. In some embodiments of a compound of Formula (I), M is —SR$^4$, —S(O)—R$^4$, or —SO$_2$—R$^4$ and each R$^4$ is methyl.

In some embodiments of a compound of Formula (I), M is —SO$_2$—N(R$^4$R$^5$), —N(R$^4$)—C(O)—O(R$^4$), —N(R$^4$)—C(O)—N(R$^4$R$^5$), —N(R$^4$)heteroaryl, or —C(O)(C$_1$-C$_3$alkyl)C(O)R$^5$. In some embodiments of a compound of Formula (I), M is —SO$_2$—N(R$^4$R$^5$), —N(R$^4$)—C(O)—O(R$^4$), —N(R$^4$)—C(O)—N(R$^4$R$^5$), —N(R$^4$)heteroaryl, or —C(O)(C$_1$-C$_3$alkyl)C(O)R$^5$ and each R$^4$ and R$^5$ are independently hydrogen or optionally substituted C$_1$-C$_6$ alkyl. In some embodiments of a compound of Formula (I), M is —SO$_2$—N(R$^4$R$^5$), —N(R$^4$)—C(O)—O(R$^4$), —N(R$^4$)—C(O)—N(R$^4$R$^5$), —N(R$^4$)heteroaryl, or —C(O)(C$_1$-C$_3$alkyl)C(O)R$^5$. In some embodiments of a compound of Formula (I), M is —SO$_2$—N(R$^4$R$^5$), —N(R$^4$)—C(O)—O(R$^4$), —N(R$^4$)—C(O)—N(R$^4$R$^5$), —N(R$^4$)heteroaryl, or —C(O)(C$_1$-C$_3$alkyl)C(O)R$^5$ and each R$^4$ and R$^5$ are independently hydrogen or C$_1$-C$_6$ alkyl.

In some embodiments of a compound of Formula (I), M is:

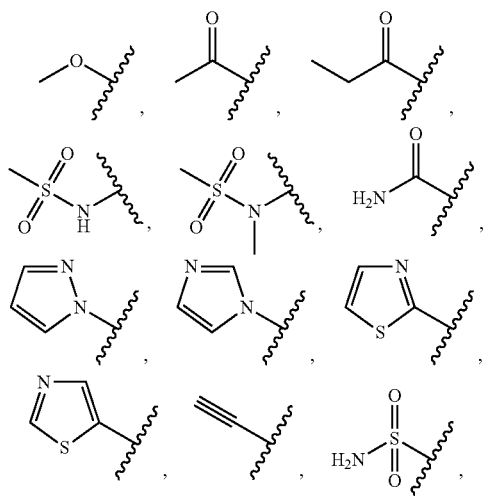

-continued

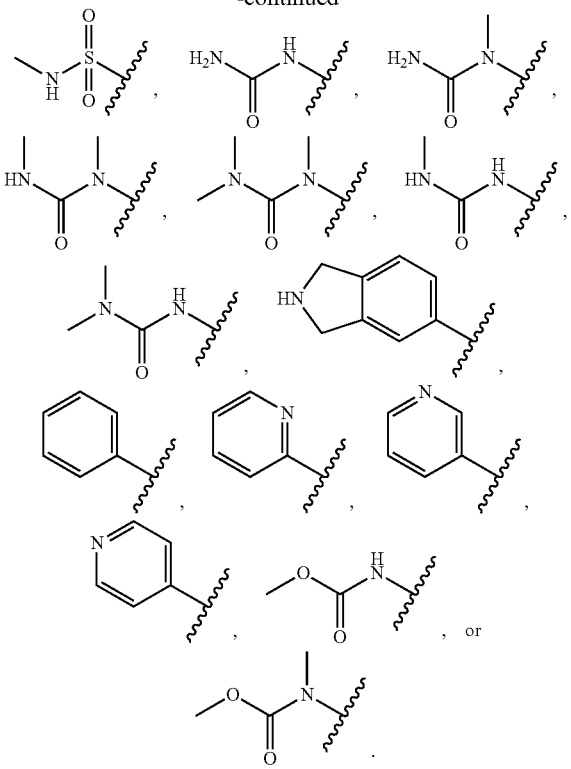

, or

In some embodiments of a compound of Formula (Ii), at least 1 on R$^a$, R$^b$ or R$^c$ is not hydrogen and M is H. In some embodiments of a compound of Formula (Ii), at least 1 on R$^a$, R$^b$ or R$^c$ is not hydrogen and M is —N(R$^4$R$^5$). In some embodiments of a compound of Formula (Ii), at least 1 on R$^a$, R$^b$ or R$^c$ is not hydrogen, M is —N(R$^4$R$^5$) and each R$^4$ and R$^5$ are independently hydrogen or optionally substituted C$_1$-C$_6$ alkyl. In some embodiments of a compound of Formula (Ii), at least 1 on R$^a$, R$^b$ or R$^c$ is not hydrogen, M is —N(R$^4$R$^5$), R$^4$ is hydrogen, and R$^5$ is hydrogen or optionally substituted C$_1$-C$_6$ alkyl. In some embodiments of a compound of Formula (Ii), at least 1 on R$^a$, R$^b$ or R$^c$ is not hydrogen, M is —N(R$^4$R$^5$), R$^4$ is optionally substituted C$_1$-C$_6$ alkyl, and R$^5$ is hydrogen or optionally substituted C$_1$-C$_6$ alkyl.

In some embodiments of a compound of Formula (I) is a compound of Formula (Ii) or pharmaceutically acceptable salts, tautomers, or N-oxides thereof:

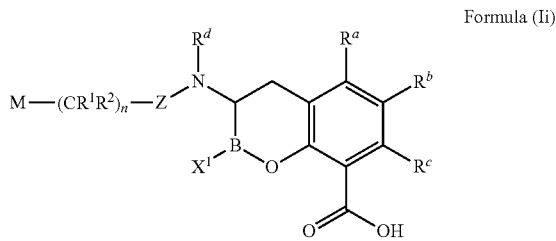

Formula (Ii)

wherein:
M is fluoro, chloro, bromo, —CF$_3$, —CN, —OR$^6$, —SR$^4$, —S(O)—R$^4$, —SO$_2$—R$^4$, —SO$_2$—N(R$^4$R$^5$), —N(R$^4$)—C(O)—O(R$^4$), —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, or optionally substituted alkynyl;

each R$^1$ and R$^2$ are independently hydrogen, fluoro, chloro, bromo, optionally substituted C$_1$-C$_6$ alkyl, —CF$_3$, optionally substituted aryl, —OR$^4$, —SR$^4$, or —NR$^4$R$^5$; or R$^1$ and R$^2$ are taken together with the carbon to which they are attached to form an optionally substituted C$_3$-C$_8$ cycloalkyl; or when n is at least 2, two R$^1$ on adjacent carbons are taken together to form a double bond; or two R$^1$ and two R$^2$ on adjacent carbons are taken together to form a triple bond;

each n is independently 1, 2, 3, 4, 5, or 6;

X$^1$ is independently —OR$^4$ or F;

Z is >C=O, >C=S, or >SO$_2$;

R$^a$, R$^b$, and R$^c$ are independently hydrogen, fluoro, chloro, bromo, optionally substituted C$_1$-C$_6$ alkyl, optionally substituted C$_3$-C$_6$ cycloalkyl, optionally substituted heretocycloalkyl, optionally substituted aryl, optionally substituted heteroaryl, —OR$^4$, —NR$^4$R$^5$, or —SR$^4$;

R$^d$, R$^4$ and R$^5$ are independently hydrogen, —OH, —CN, —CF$_3$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heretocycloalkyl, optionally substituted aryl, optionally substituted cycloalkylalkyl, optionally substituted heretocycloalkylalkyl, optionally substituted aralkyl, optionally substituted heteroaralkyl, (poly-ethylene-glycol)-ethyl, or an optionally substituted saccharide;

or R$^4$ and R$^5$ taken together form an optionally substituted heterocycle with the nitrogen to which they are attached; and R$^6$ is optionally substituted —CN, —CF$_3$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heretocycloalkyl, optionally substituted aryl, optionally substituted heteroaryl, optionally substituted cycloalkylalkyl, optionally substituted heretocycloalkylalkyl, optionally substituted heteroaralkyl, (poly-ethylene-glycol)-ethyl, or an optionally substituted saccharide.

Another aspect provides a compound of Formula (IX) or pharmaceutically acceptable salts, tautomers, or N-oxides thereof:

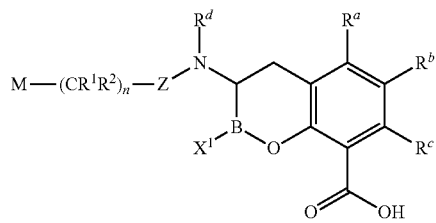

Formula (IX)

wherein:

M is hydrogen, fluoro, chloro, bromo, —CF$_3$, —CN, —N(R$^4$R$^5$), —N(R$^4$)C(O)R$^5$, —OR$^4$, —SR$^4$, —S(O)—R$^4$, —SO$_2$—R$^4$, —SO$_2$—N(R$^4$R$^5$), —N(R$^4$)—C(O)—O(R$^4$), —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, optionally substituted alkynyl, heteroaryl, or heterocycloalkyl;

each R$^1$ and R$^2$ are independently hydrogen, fluoro, chloro, bromo, optionally substituted C$_1$-C$_6$ alkyl, —CF$_3$, optionally substituted aryl, —OR$^4$, —SR$^4$, or —NR$^4$R$^5$; or R$^1$ and R$^2$ are taken together with the carbon to which they are attached to form an optionally substituted C$_3$-C$_8$ cycloalkyl; or when n is at least 2, two R$^1$ on adjacent carbons are taken together to form a double bond; or two R$^1$ and two R$^2$ on adjacent carbons are taken together to form a triple bond;

each n is independently 1, 2, 3, 4, 5, or 6;

X$^1$ is independently —OR$^4$ or F;

Z is >C=O, >C=S, or >SO$_2$;

R$^a$, R$^b$, and R$^c$ are independently hydrogen, fluoro, chloro, bromo, optionally substituted C$_1$-C$_6$ alkyl, optionally substituted C$_3$-C$_6$ cycloalkyl, optionally substituted heterocycloalkyl, optionally substituted aryl, optionally substituted heteroaryl, —OR$^4$, —NR$^4$R$^5$, or —SR$^4$, with the proviso that at least one of R$^a$, R$^b$, and R$^c$ is not hydrogen;

R$^d$, R$^4$ and R$^5$ are independently hydrogen, —OH, —CN, —CF$_3$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide; and or R$^4$ and R$^5$ taken together form an optionally substituted heterocycle with the nitrogen to which they are attached.

In some embodiments of a compound of Formula (IX), at least 1 on R$^a$, R$^b$ or R$^c$ is not hydrogen; and M is hydrogen. In some embodiments of a compound of Formula (IX), at least 1 on R$^a$, R$^b$ or R$^c$ is not hydrogen; and M is —N(R$^4$)C(O)R$^5$. In some embodiments of a compound of Formula (IX), at least 1 on R$^a$, R$^b$ or R$^c$ is not hydrogen; M is —N(R$^4$)C(O)R$^5$; and each R$^4$ and R$^5$ are independently hydrogen or optionally substituted C$_1$-C$_6$ alkyl. In some embodiments of a compound of Formula (IX), at least 1 on R$^a$, R$^b$ or R$^c$ is not hydrogen; M is —N(R$^4$)C(O)R$^5$, R$^4$ is hydrogen; and R$^5$ is optionally substituted C$_1$-C$_6$ alkyl. In some embodiments of a compound of Formula (IX), at least 1 on R$^a$, R$^b$ or R$^c$ is not hydrogen; M is —N(R$^4$)C(O)R$^5$; R$^4$ is optionally substituted C$_1$-C$_6$ alkyl; and R$^5$ or optionally substituted C$_1$-C$_6$ alkyl. In some embodiments of a compound of Formula (IX), at least 1 on R$^a$, R$^b$ or R$^c$ is not hydrogen; and M is —OR$^4$. In some embodiments of a compound of Formula (IX), at least 1 on R$^a$, R$^b$ or R$^c$ is not hydrogen; and M is —OR$^4$ and R$^4$ is hydrogen, optionally substituted C$_1$-C$_6$ alkyl, optionally substituted cycloalkyl, optionally substituted aryl, optionally substituted heteroaryl, or optionally substituted aralkyl.

In some embodiments, the compound of Formula (I) or Formula (IX) is:
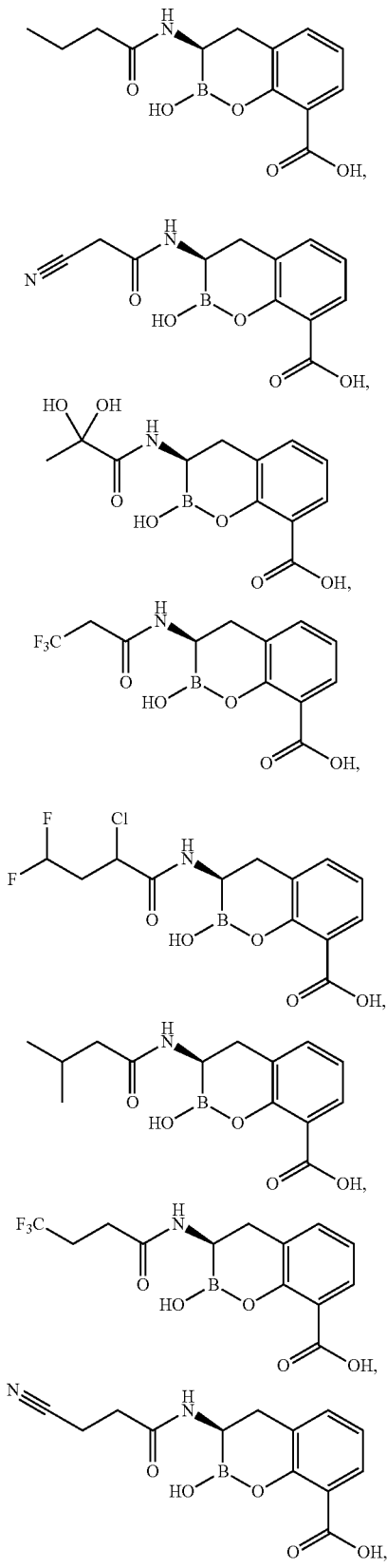
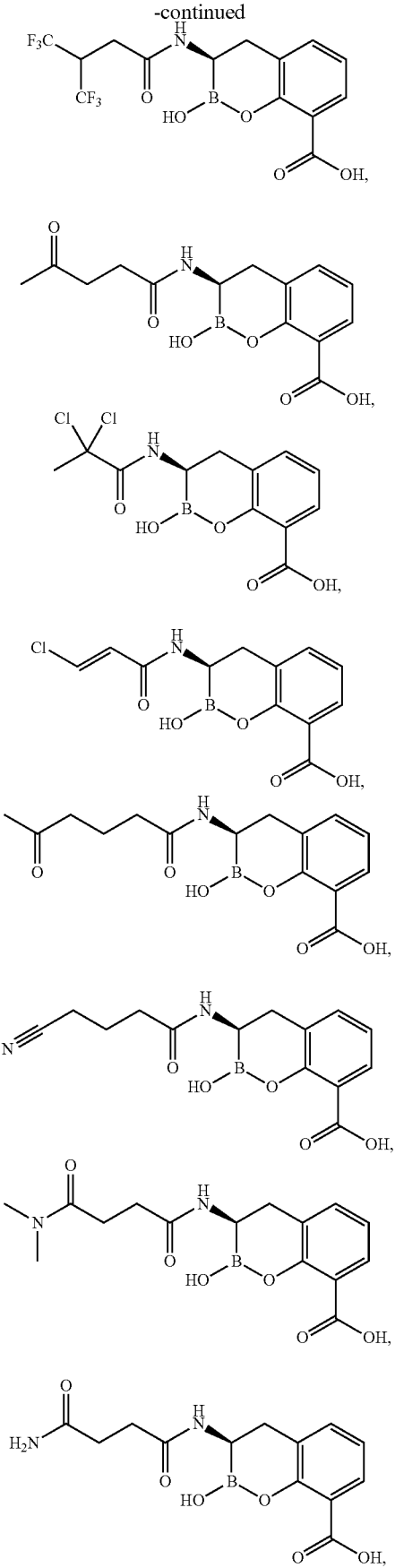

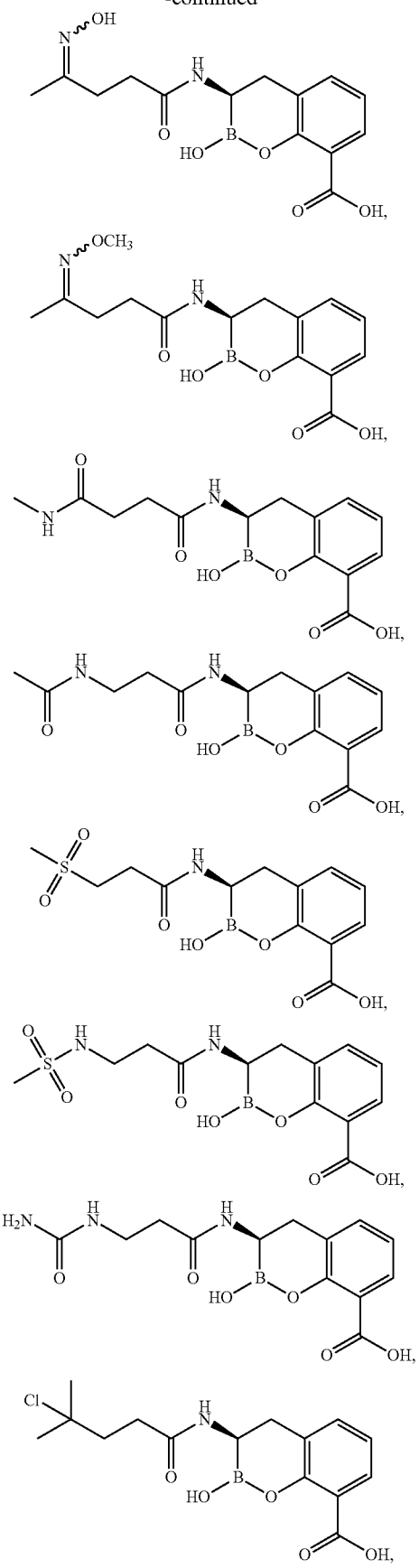
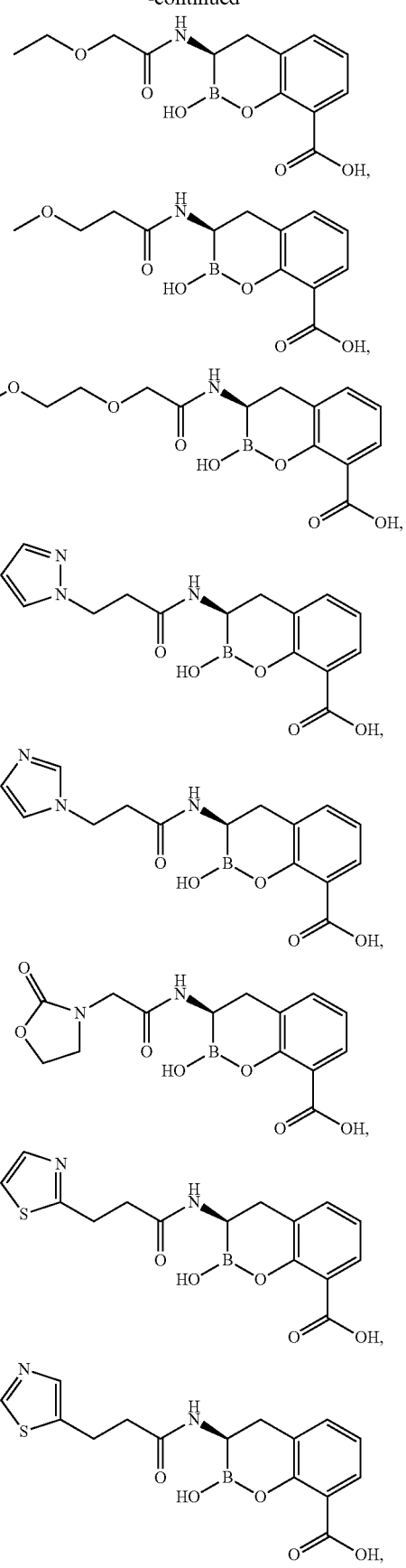

29
-continued
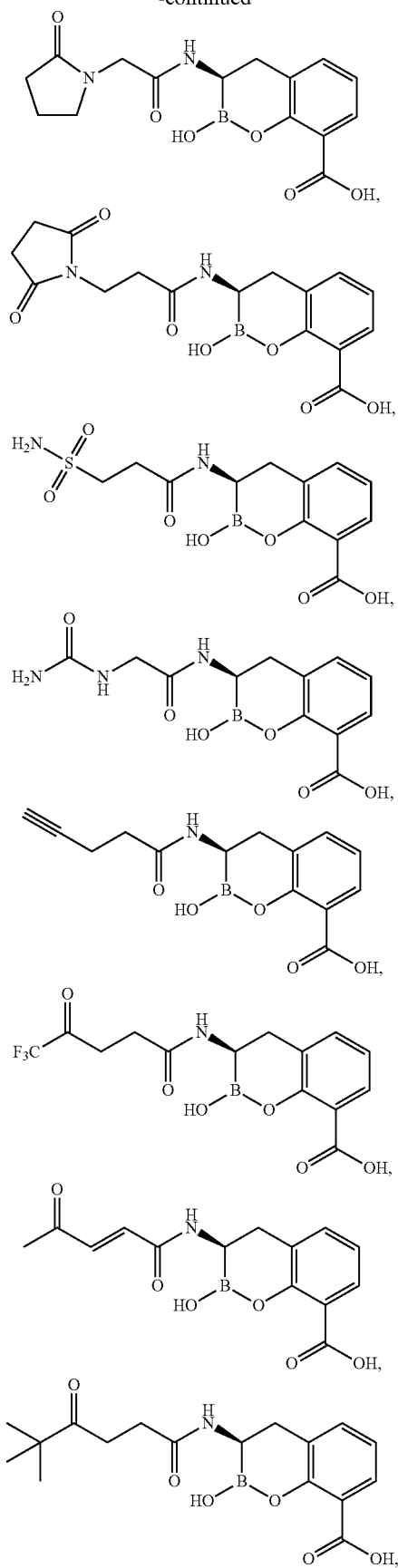
30
-continued
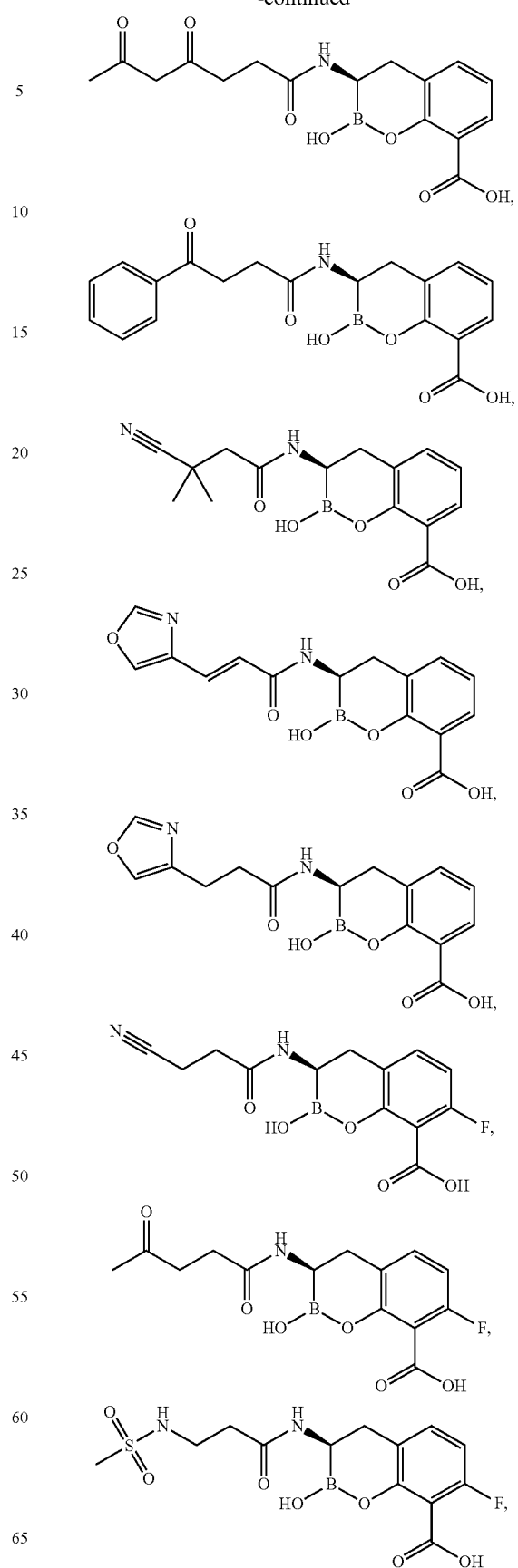

31
-continued
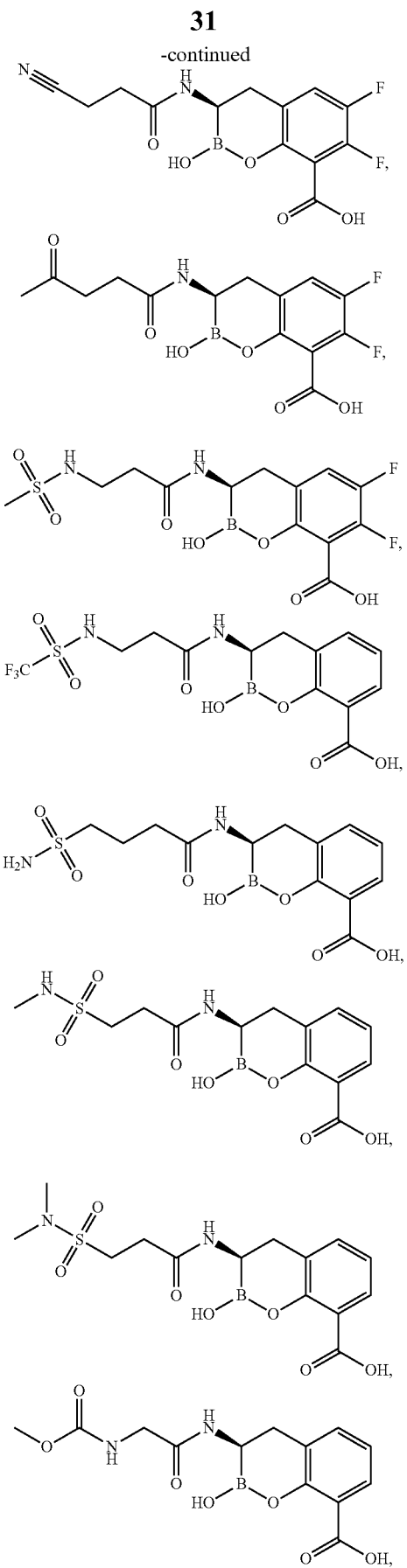
32
-continued
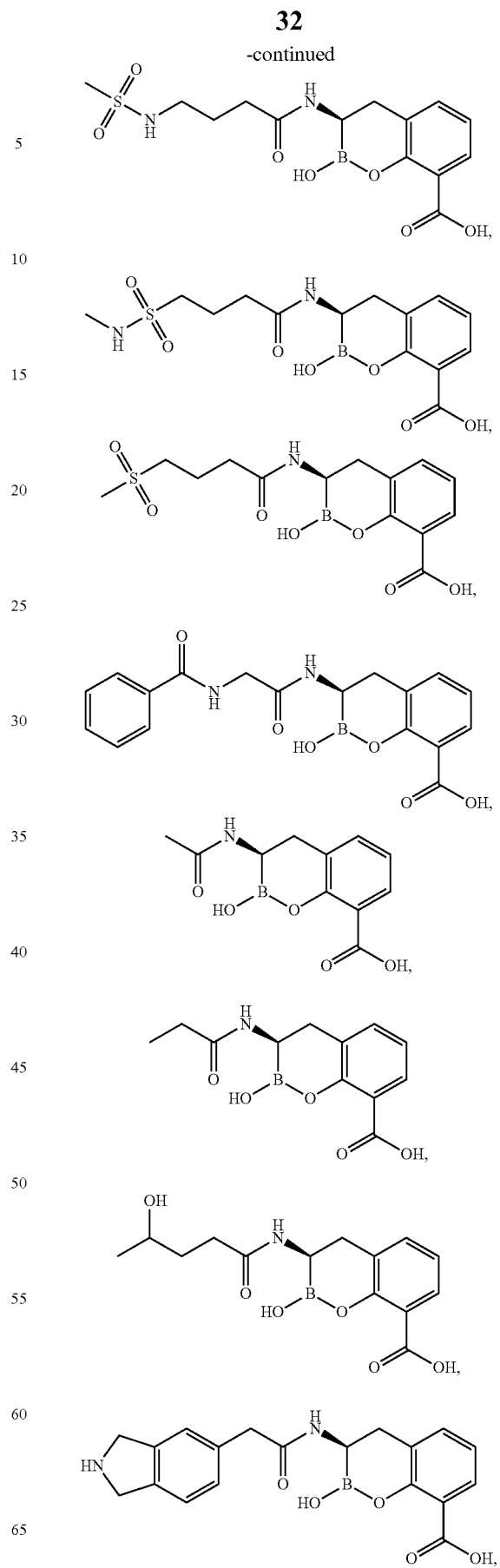

-continued
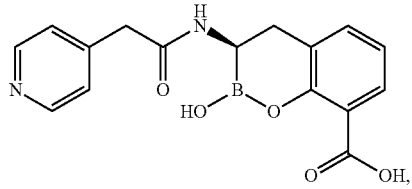
a pharmaceutically acceptable salt, N-oxide, or isomer thereof.
In some embodiments, the compound of Formula (I) or Formula (IX) is:
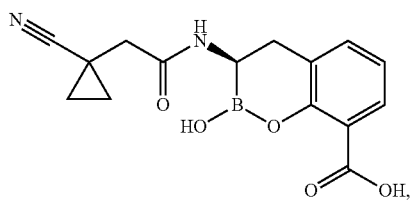
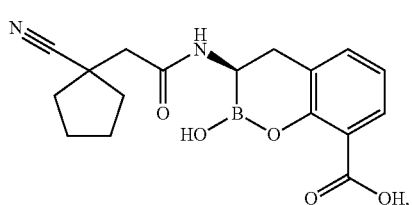
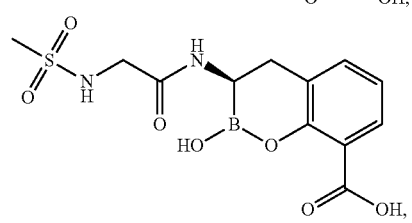
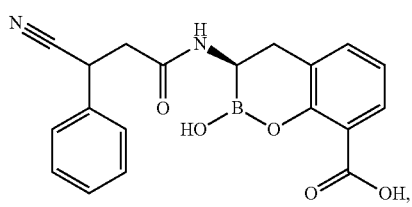
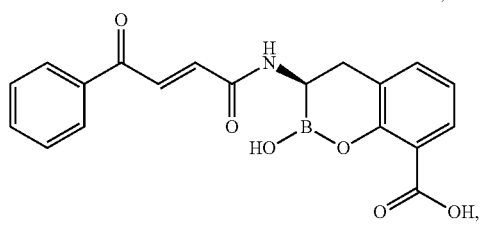
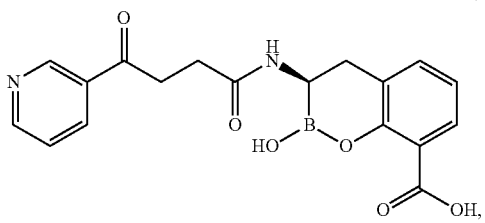
-continued
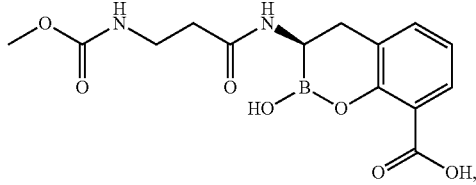
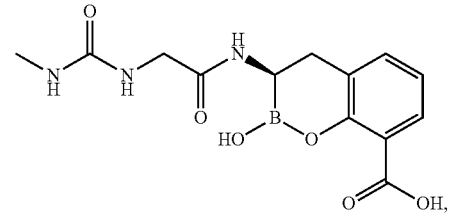
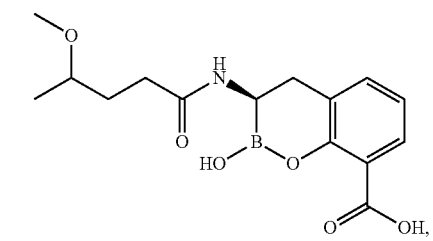
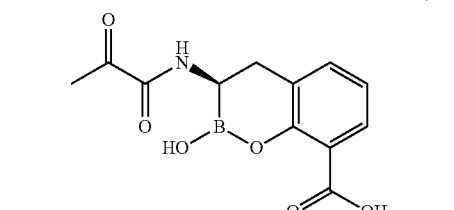
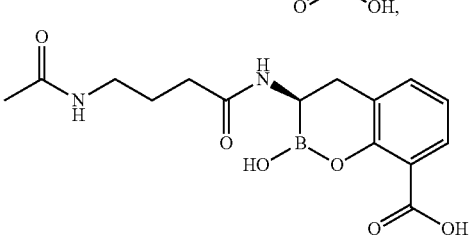
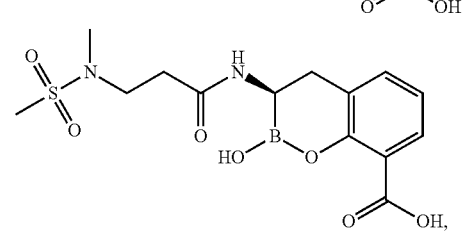
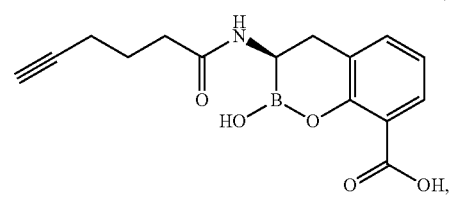
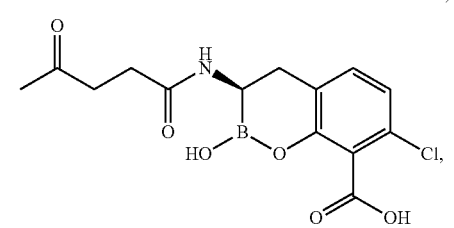

35
-continued
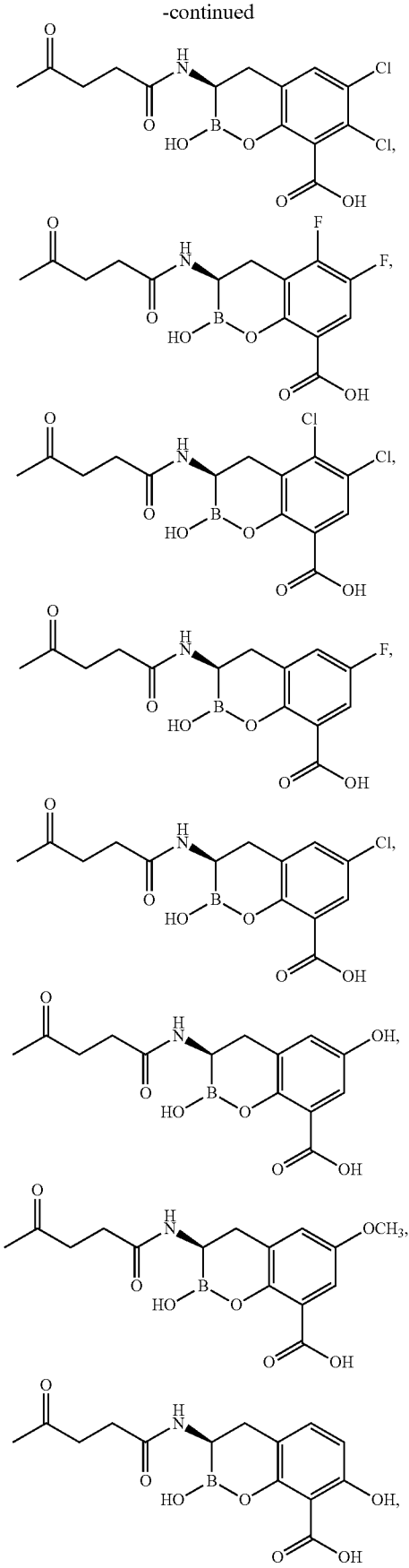
36
-continued
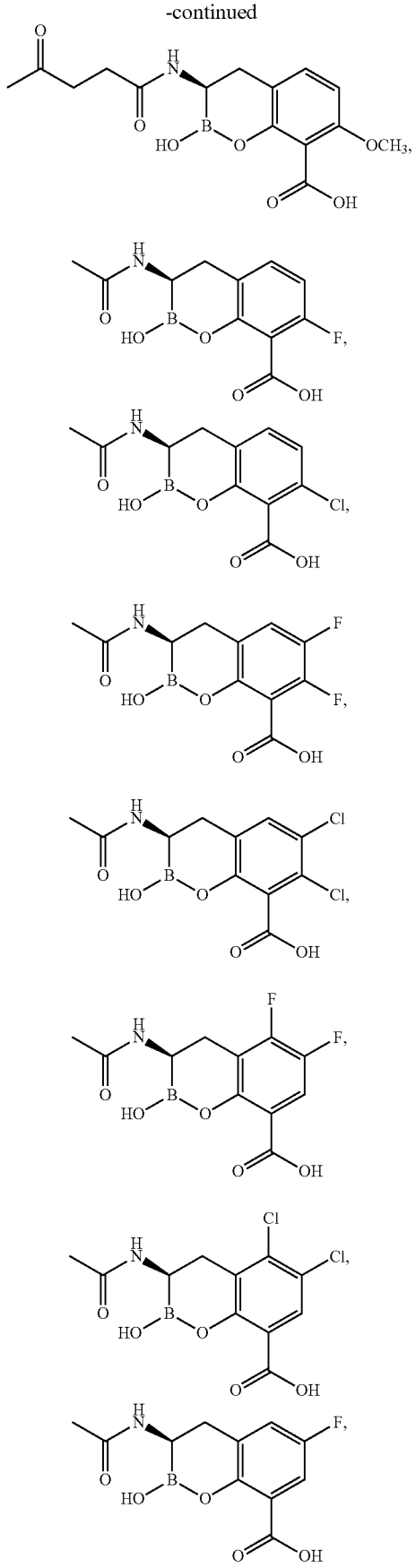

37
-continued
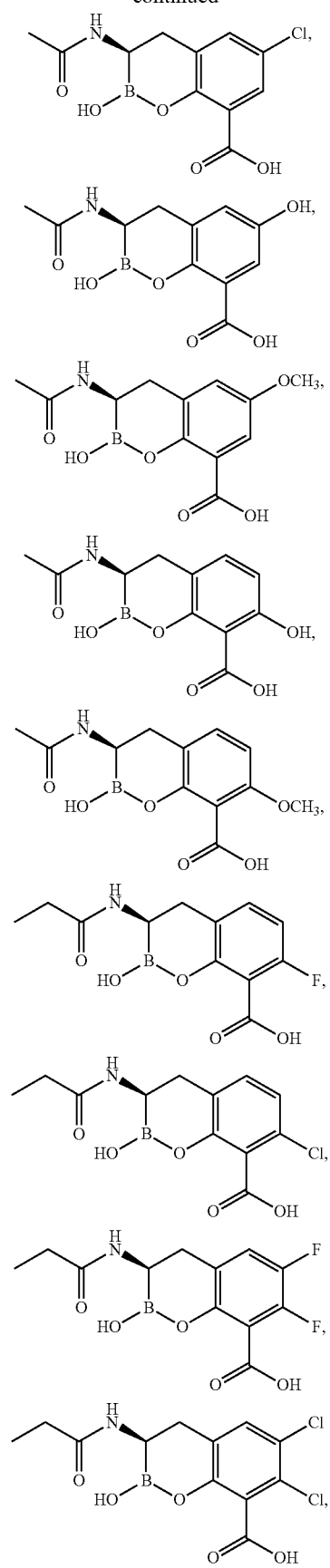
38
-continued
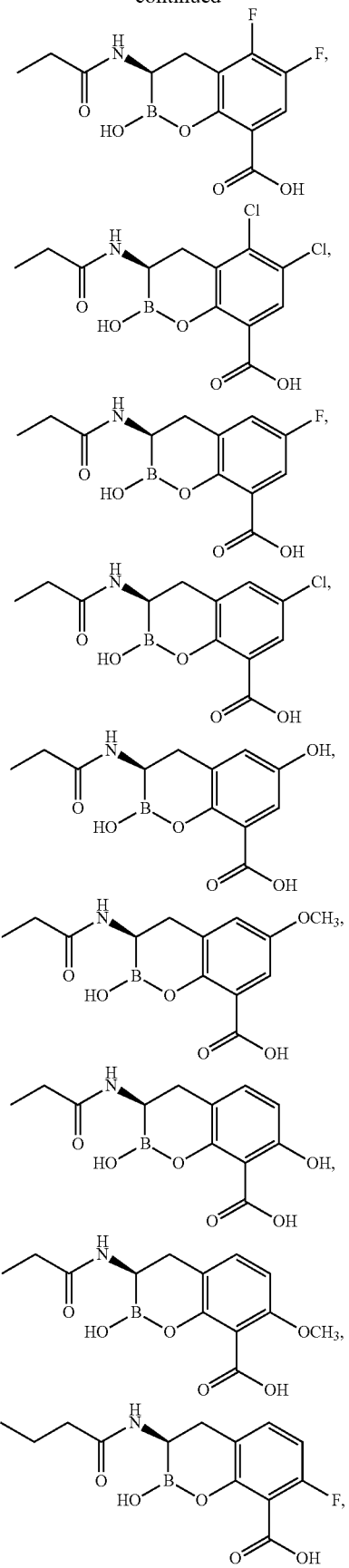

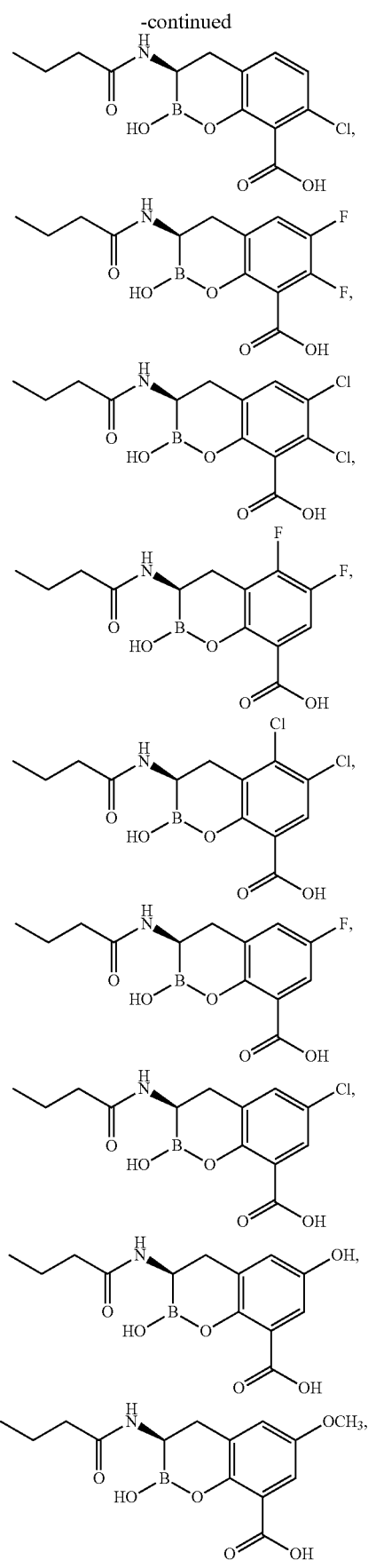

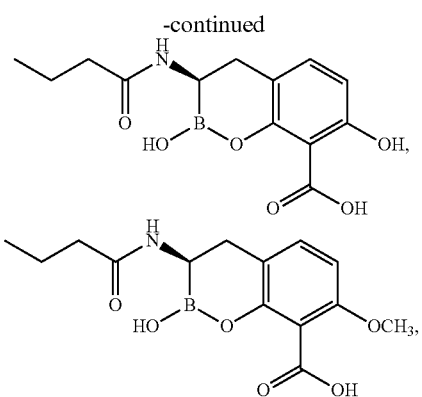

or a pharmaceutically acceptable salt, N-oxide, or isomer thereof.

One aspect provides a compound of Formula (II) or pharmaceutically acceptable salts, tautomers, or N-oxides thereof:

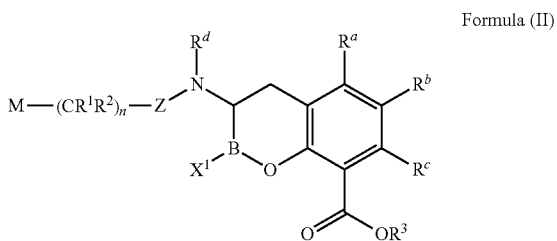

Formula (II)

wherein:

M is hydrogen, fluoro, chloro, bromo, —$CF_3$, —CN, —$OR^4$, —$SR^4$, —S(O)—$R^4$, —$SO_2$—$R^4$, —$SO_2$—N($R^4R^5$), —N($R^4R^5$), —N($R^4$)—C(O)$R^5$, —N($R^4$)—C(O)—N($R^4R^5$), —N($R^4$)—$SO_2$—$R^5$, —N($R^4$)heteroaryl, —C(O)—$R^4$, —C(O)—N($R^4R^5$), —C(O)($C_1$-$C_3$alkyl)C(O)$R^5$, optionally substituted oxyimino, optionally substituted alkenyl, optionally substituted alkynyl, heteroaryl, or heterocycloalkyl;

each $R^1$ and $R^2$ is independently hydrogen, fluoro, chloro, bromo, optionally substituted $C_1$-$C_6$ alkyl, —$CF_3$, optionally substituted aryl, —$OR^4$, —$SR^4$, or —$NR^4R^5$; or $R^1$ and $R^2$ are taken together with the carbon to which they are attached to form an optionally substituted $C_3$-$C_8$ cycloalkyl; or when n is at least 2, two $R^1$ on adjacent carbons are taken together to form a double bond; or two $R^1$ and two $R^2$ on adjacent carbons are taken together to form a triple bond;

each n is independently 0, 1, 2, 3, 4, 5, or 6;

$X^1$ is independently —$OR^4$, or F;

Z is >C=O, >C=S, or >$SO_2$;

$R^3$ is $R^{31}$, —($R^{30}$)$_q$$OR^{31}$, ($R^{30}$)$_q$O($R^{30}$)$_q$$OR^{31}$, $R^{30}$OC(O)$R^{31}$, —$R^{30}$OC(O)$OR^{31}$, —$R^{30}$OC(O)NHR$^{31}$, $R^{30}$OC(O)N($R^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one;

each q is independently 2, 3, 4, 5, or 6;

each $R^{30}$ is independently —$CH_2$—, —$CH(CH_3)$—, —$C(CH_3)_2$—, or optionally substituted 1,1'-cyclopropylene;

each $R^{31}$ is independently optionally substituted $C_1$-$C_{12}$ alkyl, optionally substituted $C_1$-$C_{12}$ alkenyl, optionally substituted alkoxyalkyl, optionally substituted $C_1$-$C_{12}$ alkynyl, optionally substituted $C_3$-$C_8$ cycloalkyl, optionally substituted $C_3$-$C_8$ heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl; or two $R^{31}$ are taken together with the nitrogen to which they are attached to form a $C_3$-$C_8$ heterocycloalkyl;

$R^a$, $R^b$, and $R^c$ are independently hydrogen, fluoro, chloro, bromo, optionally substituted $C_1$-$C_6$ alkyl, optionally substituted $C_3$-$C_6$ cycloalkyl, optionally substituted heterocycloalkyl, optionally substituted aryl, optionally substituted heteroaryl, —$OR^4$, —$NR^4R^5$, or —$SR$;

$R^d$, $R^4$ and $R^5$ are independently hydrogen, —OH, —CN, —$CF_3$, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;

or $R^4$ and $R^5$ taken together form an optionally substituted heterocycle with the nitrogen to which they are attached.

In some embodiments of a compound of Formula (II), Z is >C=S. In some embodiments of a compound of Formula (II), Z is >$SO_2$. In some embodiments of a compound of Formula (II), Z is >C=O.

In some embodiments of a compound of Formula (II) is a compound of Formula (IIa) or pharmaceutically acceptable salts, tautomers, or N-oxides thereof:

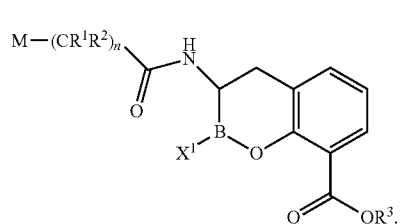

Formula (IIa)

In some embodiments of a compound of Formula (II), $R^a$, $R^b$, and $R^c$ are independently hydrogen, fluoro, optionally substituted $C_1$-$C_6$ alkyl, —$OR^4$, —$NR^4R^5$, or —$SR^4$. In some embodiments of a compound of Formula (II), $R^a$, $R^b$, and $R^c$ are independently $C_1$-$C_6$ alkyl. In some embodiments of a compound of Formula (II), $R^a$, $R^b$, and $R^c$ are independently hydrogen, fluoro, chloro, —OH, or —$OCH_3$. In some embodiments of a compound of Formula (II), $R^a$, $R^b$, and $R^c$ are hydrogen. In some embodiments of a compound of Formula (II), at least one of $R^a$, $R^b$, and $R^c$ is not hydrogen.

In some embodiments of a compound of Formula (II), $X^1$ is —$OR^4$. In some embodiments of a compound of Formula (II), $X^1$ is —OH. In some embodiments of a compound of Formula (II), $X^1$ is F.

In some embodiments of a compound of Formula (II), $R^d$ is hydrogen or $C_1$-$C_4$ alkyl. In some embodiments of a compound of Formula (II), $R^d$ is hydrogen. In some embodiments of a compound of Formula (II), $R^d$ is methyl, ethyl, or propyl. In some embodiments, $R^d$ is methyl.

In some embodiments of a compound of Formula (II) is a compound of Formula (IIb) or pharmaceutically acceptable salts, tautomers, or N-oxides thereof:

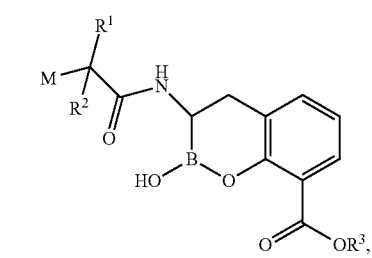

Formula (IIb)

In some embodiments of a compound of Formula (II), n is 0, 1, 2, 3, 4, 5, or 6. In some embodiments of a compound of Formula (II), n is 0. In some embodiments of a compound of Formula (II), n is 1. In some embodiments of a compound of Formula (II), n is 2. In some embodiments of a compound of Formula (II), n is 3. In some embodiments of a compound of Formula (II), n is 4. In some embodiments of a compound of Formula (II), n is 5. In some embodiments of a compound of Formula (II), n is 6. In some embodiments of a compound of Formula (II), n is 0, 1, 2, or 3.

In some embodiments of a compound of Formula (II) is a compound of Formula (IIc), (IId), or (IIe) or pharmaceutically acceptable salts, tautomers, or N-oxides thereof:

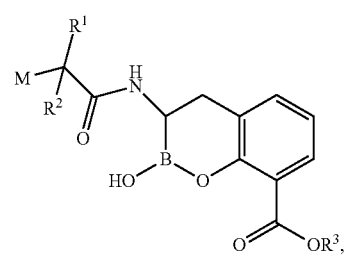

Formula (IIc)

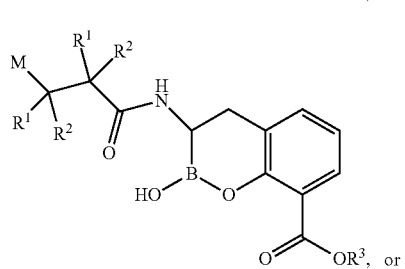

Formula (IId)

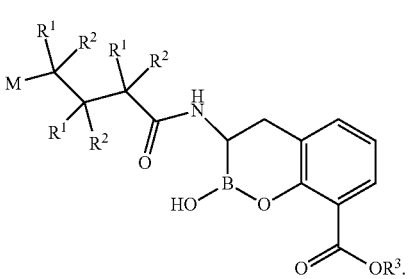

Formula (IIe)

In some embodiments of a compound of Formula (II), each $R^1$ and $R^2$ are independently hydrogen, fluoro, chloro, bromo, optionally substituted $C_1$-$C_6$ alkyl, —$CF_3$, optionally substituted aryl, —$OR^4$, —$SR^4$, or —$NR^4R^5$. In some embodiments of a compound of Formula (II), each $R^1$ and $R^2$ are independently hydrogen, optionally substituted aryl, —$OR^4$, —$SR^4$, or —$NR^4R^5$. In some embodiments of a compound of Formula (II), each $R^1$ and $R^2$ are independently hydrogen, fluoro, chloro, optionally substituted $C_1$-$C_6$ alkyl, or —$CF_3$. In some embodiments of a compound of Formula (II), each $R^1$ and $R^2$ are independently hydrogen or $C_1$-$C_6$ alkyl. In some embodiments of a compound of Formula (II), each $R^1$ and $R^2$ are independently hydrogen or methyl. In some embodiments of a compound of Formula (II), each $R^1$ and $R^2$ are hydrogen. In some embodiments of a compound of Formula (II), each $R^1$ and $R^2$ are independently hydrogen, fluoro and chloro. In some embodiments of a compound of Formula (II), each $R^1$ and $R^2$ are independently hydrogen and —$CF_3$. In some embodiments of a compound of Formula (II), $R^1$ and $R^2$ are taken together with the carbon to which they are attached to form an optionally substituted $C_3$-$C_8$ cycloalkyl. In some embodiments of a compound of Formula (II), $R^1$ and $R^2$ are taken together with the carbon to which they are attached to form a cyclopropyl, cyclobutyl, cyclopentyl, or cyclohexyl. In some embodiments of a compound of Formula (II), when n is at least 2, two $R^1$ on adjacent carbons are taken together to form a double bond. In some embodiments of a compound of Formula (II), two $R^1$ and two $R^2$ on adjacent carbons are taken together to form a triple bond.

In some embodiments of a compound of Formula (II) is a compound of Formula (IIf), (IIg), or (IIh) or pharmaceutically acceptable salts, tautomers, or N-oxides thereof:

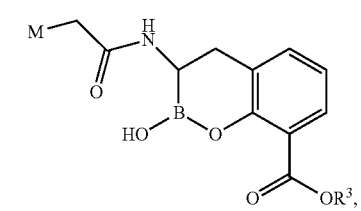

Formula (IIf)

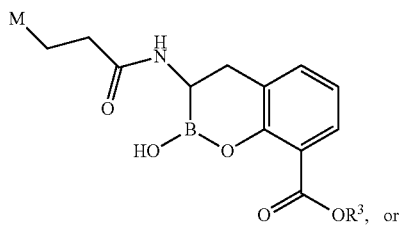

Formula (IIg)

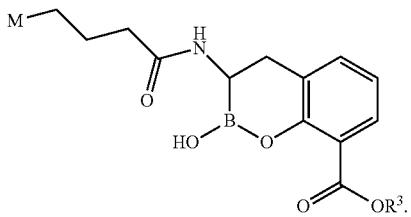

Formula (IIh)

In some embodiments of a compound of Formula (II), M is hydrogen, fluoro, chloro, bromo, —$CF_3$, —CN, —$OR^4$, —$SR^4$, —S(O)—$R^4$, —$SO_2$—$R^4$, —$SO_2$—$N(R^4R^5)$, —$N(R^4R^5)$, —$N(R^4)$—C(O)$R^5$, —$N(R^4)$—C(O)—$N(R^4R^5)$, —$N(R^4)$—$SO_2$—$R^5$, —$N(R^4)$heteroaryl, —C(O)—$R^4$, —C(O)—$N(R^4R^5)$, —C(O)($C_1$-$C_3$alkyl)C(O)$R^5$, optionally substituted oxyimino, optionally substituted alkenyl, optionally substituted alkynyl, heteroaryl, or heterocycloalkyl; and $R^3$ is $R^{31}$, —$(R^{30})_qOR^{31}$, —$(R^{30})_qO(R^{30})_qOR^{31}$, —$R^{30}OC(O)R^{31}$, —$R^{30}OC(O)OR^{31}$, —$R^{30}OC(O)NHR^{31}$, —$R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one.

In some embodiments of a compound of Formula (II), M is hydrogen, —CN, —$SO_2$—$N(R^4R^5)$, —$N(R^4)$—C(O)—$N(R^4R^5)$, —$N(R^4)$—$SO_2$—$R^5$, —C(O)—$R^4$, —C(O)—$N(R^4R^5)$, optionally substituted alkynyl, heteroaryl, or heterocycloalkyl; and $R^3$ is $R^{31}$, —$(R^{30})_qOR^{31}$, —$(R^{30})_qO(R^{30})_qOR^{31}$, —$R^{30}OC(O)R^{31}$, —$R^{30}OC(O)OR^{31}$, $R^{30}OC(O)NHR^{31}$, —$R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one.

In some embodiments of a compound of Formula (II), M is hydrogen, —CN, —$SO_2$—$N(R^4R^5)$, —$N(R^4)$—C(O)—$N(R^4R^5)$, —$N(R^4)$—$SO_2$—$R^5$, —C(O)—$R^4$, —C(O)—$N(R^4R^5)$, optionally substituted alkynyl, heteroaryl, or heterocycloalkyl; each $R^4$ and $R^5$ are independently hydrogen or optionally substituted $C_1$-$C_6$ alkyl; and $R^3$ is $R^{31}$, —$(R^{30})_qOR^{31}$, —$(R^{30})_qO(R^{30})_qOR^{31}$, —$R^{30}OC(O)R^{31}$, —$R^{30}OC(O)OR^{31}$, —$R^{30}OC(O)NHR^{31}$, —$R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one.

In some embodiments of a compound of Formula (II), M is —$SO_2$—$N(R^4R^5)$, —$N(R^4)$—C(O)—$N(R^4R^5)$, —$N(R^4)$—$SO_2$—$R^5$, —C(O)—$N(R^4R^5)$; each $R^4$ and $R^5$ are independently hydrogen or $C_1$-$C_6$ alkyl; and $R^3$ is $R^{31}$, —$(R^{30})_qOR^{31}$, —$(R^{30})_qO(R^{30})_qOR^{31}$, —$R^{30}OC(O)R^{31}$, —$R^{30}OC(O)OR^{31}$, —$R^{30}OC(O)NHR^{31}$, —$R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one.

In some embodiments of a compound of Formula (II), M is —$SO_2$—$N(R^4R^5)$, —$N(R^4)$—C(O)—$N(R^4R^5)$, —$N(R^4)$—$SO_2$—$R^5$, —C(O)—$N(R^4R^5)$; each $R^4$ and $R^5$ are independently hydrogen, methyl, ethyl, propyl, isopropyl, 2-ethylpropyl, butyl, tert-butyl, pentyl, isobutyl, isopentyl; and $R^3$ is $R^{31}$, —$(R^{30})_qOR^{31}$, —$(R^{30})_qO(R^{30})_qOR^{31}$, —$R^{30}OC(O)R^{31}$, —$R^{30}OC(O)OR^{31}$, —$R^{30}OC(O)NHR^{31}$, —$R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one.

In some embodiments of a compound of Formula (II), M is —$SO_2$—$N(R^4R^5)$, —$N(R^4)$—C(O)—$N(R^4R^5)$, —$N(R^4)$—$SO_2$—$R^5$, —C(O)—$N(R^4R^5)$; each $R^4$ and $R^5$ are independently hydrogen or methyl; and $R^3$ is $R^{31}$, $(R^{30})_qOR^{31}$, —$(R^{30})_qO(R^{30})_qOR^{31}$, —$R^{30}OC(O)R^{31}$, —$R^{30}OC(O)OR^{31}$, —$R^{30}OC(O)NHR^{31}$, —$R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one.

In some embodiments of a compound of Formula (II), M is optionally substituted alkynyl; and $R^3$ is $R^{31}$, $-(R^{30})_qOR^{31}$, $-(R^{30})_qO(R^{30})_qOR^{31}$, $-R^{30}OC(O)R^{31}$, $-R^{30}OC(O)OR^{31}$, $-R^{30}OC(O)NHR^{31}$, $-R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one.

In some embodiments of a compound of Formula (II), M is heteroaryl or heterocycloalkyl; each $R^4$ and $R^5$ are independently hydrogen or optionally substituted $C_1$-$C_6$ alkyl; and $R^3$ is $R^{31}$, $-(R^{30})_qOR^{31}$, $-(R^{30})_qO(R^{30})_qOR^{31}$, $-R^{30}OC(O)R^{31}$, $-R^{30}OC(O)OR^{31}$, $-R^{30}OC(O)NHR^{31}$, $-R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one.

In some embodiments of a compound of Formula (II), M is pyridinyl, pyrimidinyl, pyridazinyl, pyrazinyl, imidazolyl, pyrrazolyl, thiazolyl, oxazolyl, aziridinyl, azetidinyl, pyrrolidinyl, piperidinyl, pyperazinyl, pyrrolidinone or pyrrolidine-2,5-dione; and $R^3$ is $R^{31}$, $-(R^{30})_qOR^{31}$, $-(R^{30})_qO(R^{30})_qOR^{31}$, $-R^{30}OC(O)R^{31}$, $-R^{30}OC(O)OR^{31}$, $-R^{30}OC(O)NHR^{31}$, $-R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one.

In some embodiments of a compound of Formula (II), M is pyridinyl, imidazolyl, pyrrazolyl, thiazolyl, or oxazolyl; and $R^3$ is $R^{31}$, $-(R^{30})_qOR^{31}$, $-(R^{30})_qO(R^{30})_qOR^{31}$, $-R^{30}OC(O)R^{31}$, $-R^{30}OC(O)OR^{31}$, $-R^{30}OC(O)NHR^{31}$, $-R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one.

In some embodiments of a compound of Formula (II), M is hydrogen, $-CN$, $-C(O)-R^4$, or alkynyl; and $R^3$ is $R^{31}$, $-(R^{30})_qOR^{31}$, $-(R^{30})_qO(R^{30})_qOR^{31}$, $-R^{30}OC(O)R^{31}$, $-R^{30}OC(O)OR^{31}$, $-R^{30}OC(O)NHR^{31}$, $-R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one.

In some embodiments of a compound of Formula (II), M is hydrogen, $-CN$, $-C(O)-R^4$, or alkynyl; $R^4$ is optionally substituted $C_1$-$C_6$ alkyl; and $R^3$ is $R^{31}$, $-(R^{30})_qOR^{31}$, $-(R^{30})_qO(R^{30})_qOR^{31}$, $-R^{30}OC(O)R^{31}$, $-R^{30}OC(O)OR^{31}$, $-R^{30}OC(O)NHR^{31}$, $-R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one.

In some embodiments of a compound of Formula (II), M is hydrogen; and $R^3$ is $R^{31}$, $-(R^{30})_qOR^{31}$, $-(R^{30})_qO(R^{30})_qOR^{31}$, $-R^{30}OC(O)R^{31}$, $-R^{30}OC(O)OR^{31}$, $-R^{30}OC(O)NHR^{31}$, $-R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one.

In some embodiments of a compound of Formula (II), M is $-CN$; and $R^3$ is $R^{31}$, $-(R^{30})_qOR^{31}$, $(R^{30})_qO(R^{30})_qOR^{31}$, $-R^{30}OC(O)R^{31}$, $-R^{30}OC(O)OR^{31}$, $-R^{30}OC(O)NHR^{31}$, $-R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one.

In some embodiments of a compound of Formula (II), M is $-C(O)-R^4$; $R^4$ is optionally substituted $C_1$-$C_6$ alkyl; and $R^3$ is $R^{31}$, $-(R^{30})_qOR^{31}$, $-(R^{30})_qO(R^{30})_qOR^{31}$, $-R^{30}OC(O)R^{31}$, $-R^{30}OC(O)OR^{31}$, $-R^{30}OC(O)NHR^{31}$, $-R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one.

In some embodiments of a compound of Formula (II), M is $-C(O)-R^4$; $R^4$ is methyl, ethyl, propyl, isopropyl, 2-ethylpropyl, butyl, tert-butyl, pentyl, isobutyl, isopentyl; and $R^3$ is $R^{31}$, $-(R^{30})_qOR^{31}$, $-(R^{30})_qO(R^{30})_qOR^{31}$, $-R^{30}OC(O)R^{31}$, $-R^{30}OC(O)OR^{31}$, $-R^{30}OC(O)NHR^{31}$, $-R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one.

In some embodiments of a compound of Formula (II), M is $-C(O)-R^4$; $R^4$ is methyl; and $R^3$ is $R^{31}$, $-(R^{30})_qOR^{31}$, $-(R^{30})_qO(R^{30})_qOR^{31}$, $-R^{30}OC(O)R^{31}$, $-R^{30}OC(O)OR^{31}$, $-R^{30}OC(O)NHR^{31}$, $-R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one.

In some embodiments of a compound of Formula (II), M is alkynyl; and $R^3$ is $R^{31}$, $-(R^{30})_qOR^{31}$, $-(R^{30})_qO(R^{30})_qOR^{31}$, $-R^{30}OC(O)R^{31}$, $-R^{30}OC(O)OR^{31}$, $-R^{30}OC(O)NHR^{31}$, $-R^{30}OC(O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one.

In some embodiments of a compound of Formula (II), M is hydrogen, fluoro, chloro, bromo, $-CF_3$, $-CN$, $-OR^4$, $-SR^4$, $-S(O)-R^4$, $-SO_2-R^4$, $-SO_2-N(R^4R^5)$, $-N(R^4R^5)$, $-N(R^4)-C(O)R^5$, $-N(R^4)-C(O)-N(R^4R^5)$, $-N(R^4)-SO_2-R^5$, $-N(R^4)$heteroaryl, $-C(O)-R^4$, $-C(O)-N(R^4R^5)$, $-C(O)(C_1$-$C_3$alkyl)$C(O)R^5$, optionally substituted oxyimino, optionally substituted alkenyl, optionally substituted alkynyl, heteroaryl, or heterocycloalkyl; $R^3$ is $R^{31}$, $-R^{30}OC(O)R^{31}$ or $-R^{30}OC(O)OR^{31}$; $R^{30}$ is $-CH_2-$, $-CH(CH_3)-$, $-C(CH_3)_2-$, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is hydrogen, fluoro, chloro, bromo, —$CF_3$, —CN, —$OR^4$, —$SR^4$, —S(O)—$R^4$, —$SO_2$—$R^4$, —$SO_2$—N($R^4R^5$), —N($R^4R^5$), —N($R^4$)—C(O)$R^5$, —N($R^4$)—C(O)—N($R^4R^5$), —N($R^4$)—$SO_2$—$R^5$, —N($R^4$)heteroaryl, —C(O)—$R^4$, —C(O)—N($R^4R^5$), —C(O)($C_1$-$C_3$alkyl)C(O)$R^5$, optionally substituted oxyimino, optionally substituted alkenyl, optionally substituted alkynyl, heteroaryl, or heterocycloalkyl; $R^3$ is $R^{31}$; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is hydrogen, fluoro, chloro, bromo, —$CF_3$, —CN, —$OR^4$, —$SR^4$, —S(O)—$R^4$, —$SO_2$—$R^4$, —$SO_2$—N($R^4R^5$), —N($R^4R^5$), —N($R^4$)—C(O)$R^5$, —N($R^4$)—C(O)—N($R^4R^5$), —N($R^4$)—$SO_2$—$R^5$, —N($R^4$)heteroaryl, —C(O)—$R^4$, —C(O)—N($R^4R^5$), —C(O)($C_1$-$C_3$alkyl)C(O)$R^5$, optionally substituted oxyimino, optionally substituted alkenyl, optionally substituted alkynyl, heteroaryl, or heterocycloalkyl; $R^3$ is $R^{31}$; and $R^{31}$ is $C_1$-$C_{12}$ alkyl, alkoxyalkyl, or $C_3$-$C_8$ heterocycloalkyl.

In some embodiments of a compound of Formula (II), M is hydrogen, fluoro, chloro, bromo, —$CF_3$, —CN, —$OR^4$, —$SR^4$, —S(O)—$R^4$, —$SO_2$—$R^4$, —$SO_2$—N($R^4R^5$), —N($R^4R^5$), —N($R^4$)—C(O)$R^5$, —N($R^4$)—C(O)—N($R^4R^5$), —N($R^4$)—$SO_2$—$R^5$, —N($R^4$)heteroaryl, —C(O)—$R^4$, —C(O)—N($R^4R^5$), —C(O)($C_1$-$C_3$alkyl)C(O)$R^5$, optionally substituted oxyimino, optionally substituted alkenyl, optionally substituted alkynyl, heteroaryl, or heterocycloalkyl; $R^3$ is $R^{31}$; and $R^{31}$ is methyl, ethyl, propyl, isopropyl, 2-ethylpropyl, butyl, tert-butyl, pentyl, isobutyl, isopentyl, methoxyethyl, or an isobenzofuran-1(3H)-one ring.

In some embodiments of a compound of Formula (II), M is hydrogen, fluoro, chloro, bromo, —$CF_3$, —CN, —$OR^4$, —$SR^4$, —S(O)—$R^4$, —$SO_2$—$R^4$, —$SO_2$—N($R^4R^5$), —N($R^4R^5$), —N($R^4$)—C(O)$R^5$, —N($R^4$)—C(O)—N($R^4R^5$), —N($R^4$)—$SO_2$—$R^5$, —N($R^4$)heteroaryl, —C(O)—$R^4$, —C(O)—N($R^4R^5$), —C(O)($C_1$-$C_3$alkyl)C(O)$R^5$, optionally substituted oxyimino, optionally substituted alkenyl, optionally substituted alkynyl, heteroaryl, or heterocycloalkyl; $R^3$ is —$R^{30}$OC(O)$R^{31}$; $R^{30}$ is —$CH_2$—, —CH($CH_3$)—, —C($CH_3$)$_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is hydrogen, fluoro, chloro, bromo, —$CF_3$, —CN, —$OR^4$, —$SR^4$, —S(O)—$R^4$, —$SO_2$—$R^4$, —$SO_2$—N($R^4R^5$), —N($R^4R^5$), —N($R^4$)—C(O)$R^5$, —N($R^4$)—C(O)—N($R^4R^5$), —N($R^4$)—$SO_2$—$R^5$, —N($R^4$)heteroaryl, —C(O)—$R^4$, —C(O)—N($R^4R^5$), —C(O)($C_1$-$C_3$alkyl)C(O)$R^5$, optionally substituted oxyimino, optionally substituted alkenyl, optionally substituted alkynyl, heteroaryl, or heterocycloalkyl; $R^3$ is —$R^{30}$OC(O)$R^{31}$; $R^{30}$ is —$CH_2$—, —CH($CH_3$)—; and $R^{31}$ is optionally substituted $C_1$-$C_{12}$ alkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is hydrogen, fluoro, chloro, bromo, —$CF_3$, —CN, —$OR^4$, —$SR^4$, —S(O)—$R^4$, —$SO_2$—$R^4$, —$SO_2$—N($R^4R^5$), —N($R^4R^5$), —N($R^4$)—C(O)$R^5$, —N($R^4$)—C(O)—N($R^4R^5$), —N($R^4$)—$SO_2$—$R^5$, —N($R^4$)heteroaryl, —C(O)—$R^4$, —C(O)—N($R^4R^5$), —C(O)($C_1$-$C_3$alkyl)C(O)$R^5$, optionally substituted oxyimino, optionally substituted alkenyl, optionally substituted alkynyl, heteroaryl, or heterocycloalkyl; $R^3$ is —$R^{30}$OC(O)$R^{31}$; $R^{30}$ is —$CH_2$—, —CH($CH_3$)—; and $R^{31}$ is $C_1$-$C_{12}$ alkyl, $C_3$-$C_8$ cycloalkyl, $C_3$-$C_8$ heterocycloalkyl, aryl, or alkylcycloalkyl.

In some embodiments of a compound of Formula (II), M is hydrogen, fluoro, chloro, bromo, —$CF_3$, —CN, —$OR^4$, —$SR^4$, —S(O)—$R^4$, —$SO_2$—$R^4$, —$SO_2$—N($R^4R^5$), —N($R^4R^5$), —N($R^4$)—C(O)$R^5$, —N($R^4$)—C(O)—N($R^4R^5$), —N($R^4$)—$SO_2$—$R^5$, —N($R^4$)heteroaryl, —C(O)—$R^4$, —C(O)—N($R^4R^5$), —C(O)($C_1$-$C_3$alkyl)C(O)$R^5$, optionally substituted oxyimino, optionally substituted alkenyl, optionally substituted alkynyl, heteroaryl, or heterocycloalkyl; $R^3$ is —$R^{30}$OC(O)$R^{31}$; $R^{30}$ is —$CH_2$—, —CH($CH_3$)—; and $R^{31}$ is methyl, ethyl, propyl, isopropyl, 2-ethylpropyl, butyl, tert-butyl, pentyl, isobutyl, isopentyl, cyclopropyl, cyclobutyl, cyclopentyl, cyclohexyl, cyclohexylmethyl, piperidinyl, phenyl, or 4-fluorophenyl.

In some embodiments of a compound of Formula (II), M is hydrogen, fluoro, chloro, bromo, —$CF_3$, —CN, —$OR^4$, —$SR^4$, —S(O)—$R^4$, —$SO_2$—$R^4$, —$SO_2$—N($R^4R^5$), —N($R^4R^5$), —N($R^4$)—C(O)$R^5$, —N($R^4$)—C(O)—N($R^4R^5$), —N($R^4$)—$SO_2$—$R^5$, —N($R^4$)heteroaryl, —C(O)—$R^4$, —C(O)—N($R^4R^5$), —C(O)($C_1$-$C_3$alkyl)C(O)$R^5$, optionally substituted oxyimino, optionally substituted alkenyl, optionally substituted alkynyl, heteroaryl, or heterocycloalkyl; $R^3$ is —$R^{30}$OC(O)$R^{31}$; $R^{30}$ is —$CH_2$—, —CH($CH_3$)—; and $R^{31}$ is methyl, ethyl, propyl, isopropyl, 2-ethylpropyl, butyl, tert-butyl, pentyl, isobutyl, cyclohexyl, cyclohexylmethyl, piperidinyl, phenyl, or 4-fluorophenyl.

In some embodiments of a compound of Formula (II), M is hydrogen, fluoro, chloro, bromo, —$CF_3$, —CN, —$OR^4$, —$SR^4$, —S(O)—$R^4$, —$SO_2$—$R^4$, —$SO_2$—N($R^4R^5$), —N($R^4R^5$), —N($R^4$)—C(O)$R^5$, —N($R^4$)—C(O)—N($R^4R^5$), —N($R^4$)—$SO_2$—$R^5$, —N($R^4$)heteroaryl, —C(O)—$R^4$, —C(O)—N($R^4R^5$), —C(O)($C_1$-$C_3$alkyl)C(O)$R^5$, optionally substituted oxyimino, optionally substituted alkenyl, optionally substituted alkynyl, heteroaryl, or heterocycloalkyl; $R^3$ is —$R^{30}$OC(O)O$R^{31}$; $R^{30}$ is —$CH_2$—, —CH($CH_3$)—, —C($CH_3$)$_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is hydrogen, fluoro, chloro, bromo, —CF$_3$, —CN, —OR$^4$, —SR$^4$, —S(O)—R$^4$, —SO$_2$—R$^4$, —SO$_2$—N(R$^4$R$^5$), —N(R$^4$R$^5$), —N(R$^4$)—C(O)R$^5$, —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, optionally substituted alkynyl, heteroaryl, or heterocycloalkyl; R$^3$ is —R$^{30}$OC(O)OR$^{31}$; R$^{30}$ is —CH$_2$—, —CH(CH$_3$)—; and R$^{31}$ is optionally substituted C$_1$-C$_{12}$ alkyl, optionally substituted alkoxyalkyl, optionally substituted C$_3$-C$_8$ cycloalkyl, optionally substituted C$_3$-C$_8$ heterocycloalkyl, optionally substituted aryl, or optionally substituted alkylcycloalkyl.

In some embodiments of a compound of Formula (II), M is hydrogen, fluoro, chloro, bromo, —CF$_3$, —CN, —OR$^4$, —SR$^4$, —S(O)—R$^4$, —SO$_2$—R$^4$, —SO$_2$—N(R$^4$R$^5$), —N(R$^4$R$^5$), —N(R$^4$)—C(O)R$^5$, —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, optionally substituted alkynyl, heteroaryl, or heterocycloalkyl; R$^3$ is —R$^{30}$OC(O)OR$^{31}$; R$^{30}$ is —CH$_2$—, —CH(CH$_3$)—; and R$^{31}$ is optionally substituted C$_3$-C$_8$ cycloalkyl, optionally substituted C$_3$-C$_8$ heterocycloalkyl, or optionally substituted alkylcycloalkyl.

In some embodiments of a compound of Formula (II), M is hydrogen, fluoro, chloro, bromo, —CF$_3$, —CN, —OR$^4$, —SR$^4$, —S(O)—R$^4$, —SO$_2$—R$^4$, —SO$_2$—N(R$^4$R$^5$), —N(R$^4$R$^5$), —N(R$^4$)—C(O)R$^5$, —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, optionally substituted alkynyl, heteroaryl, or heterocycloalkyl; R$^3$ is —R$^{30}$OC(O)OR$^{31}$; R$^{30}$ is —CH$_2$—, —CH(CH$_3$)—; and R$^{31}$ is C$_1$-C$_{12}$ alkyl, C$_3$-C$_8$ cycloalkyl, C$_3$-C$_8$ heterocycloalkyl, or alkylcycloalkyl.

In some embodiments of a compound of Formula (II), M is hydrogen, fluoro, chloro, bromo, —CF$_3$, —CN, —OR$^4$, —SR$^4$, —S(O)—R$^4$, —SO$_2$—R$^4$, —SO$_2$—N(R$^4$R$^5$), —N(R$^4$R$^5$), —N(R$^4$)—C(O)R$^5$, —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, optionally substituted alkynyl, heteroaryl, or heterocycloalkyl; R$^3$ is —R$^{30}$OC(O)OR$^{31}$; R$^{30}$ is —CH$_2$—, —CH(CH$_3$)—; and R$^{31}$ is methyl, ethyl, propyl, isopropyl, 2-ethylpropyl, butyl, tert-butyl, pentyl, isobutyl, isopentyl, cyclopropyl, cyclobutyl, cyclopentyl, cyclohexyl, cyclohexylmethyl, or tetrahydropyranyl.

In some embodiments of a compound of Formula (II), M is hydrogen, fluoro, chloro, bromo, —CF$_3$, —CN, —OR$^4$, —SR$^4$, —S(O)—R$^4$, —SO$_2$—R$^4$, —SO$_2$—N(R$^4$R$^5$), —N(R$^4$R$^5$), —N(R$^4$)—C(O)R$^5$, —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, optionally substituted alkynyl, heteroaryl, or heterocycloalkyl; R$^3$ is —R$^{30}$OC(O)OR$^{31}$; R$^{30}$ is —CH$_2$—, —CH(CH$_3$)—; and R$^{31}$ is methyl, ethyl, propyl, isopropyl, butyl, cyclohexyl, cyclohexylmethyl, or tetrahydropyranyl.

In some embodiments of a compound of Formula (II), M is hydrogen, fluoro, chloro, bromo, —CF$_3$, —CN, —OR$^4$, —SR$^4$, —S(O)—R$^4$, —SO$_2$—R$^4$, —SO$_2$—N(R$^4$R$^5$), —N(R$^4$R$^5$), —N(R$^4$)—C(O)R$^5$, —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, optionally substituted alkynyl, heteroaryl, or heterocycloalkyl; R$^3$ is R$^{31}$, —R$^{30}$OC(O)R$^{31}$, or —R$^{30}$OC(O)OR$^{31}$; R$^{30}$ is —CH$_2$—, —CH(CH$_3$)—, —C(CH$_3$)$_2$—, or optionally substituted 1,1'-cyclopropylene; and R$^{31}$ is optionally substituted C$_1$-C$_{12}$ alkyl, optionally substituted C$_3$-C$_8$ cycloalkyl, optionally substituted C$_3$-C$_8$ heterocycloalkyl, or optionally substituted aryl.

In some embodiments of a compound of Formula (II), M is hydrogen, fluoro, chloro, bromo, —CF$_3$, —CN, —OR$^4$, —SR$^4$, —S(O)—R$^4$, —SO$_2$—R$^4$, —SO$_2$—N(R$^4$R$^5$), —N(R$^4$R$^5$), —N(R$^4$)—C(O)R$^5$, —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, optionally substituted alkynyl, heteroaryl, or heterocycloalkyl; R$^3$ is R$^{31}$, —R$^{30}$OC(O)R$^{31}$, or —R$^{30}$OC(O)OR$^{31}$; R$^{30}$ is —CH$_2$—; and R$^{31}$ is optionally substituted C$_1$-C$_{12}$ alkyl, optionally substituted C$_3$-C$_8$ cycloalkyl, optionally substituted C$_3$-C$_8$ heterocycloalkyl, or optionally substituted aryl.

In some embodiments of a compound of Formula (II), M is hydrogen, fluoro, chloro, bromo, —CF$_3$, —CN, —OR$^4$, —SR$^4$, —S(O)—R$^4$, —SO$_2$—R$^4$, —SO$_2$—N(R$^4$R$^5$), —N(R$^4$R$^5$), —N(R$^4$)—C(O)R$^5$, —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, optionally substituted alkynyl, heteroaryl, or heterocycloalkyl; R$^3$ is R$^{31}$, —R$^{30}$OC(O)R$^{31}$, or —R$^{30}$OC(O)OR$^{31}$; R$^{30}$ is —CH$_2$—; and R$^{31}$ is C$_1$-C$_{12}$ alkyl, C$_3$-C$_8$ cycloalkyl, C$_3$-C$_8$ heterocycloalkyl, or aryl.

In some embodiments of a compound of Formula (II), M is hydrogen, fluoro, chloro, bromo, —CF$_3$, —CN, —OR$^4$, —SR$^4$, —S(O)—R$^4$, —SO$_2$—R$^4$, —SO$_2$—N(R$^4$R$^5$), —N(R$^4$R$^5$), —N(R$^4$)—C(O)R$^5$, —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, optionally substituted alkynyl, heteroaryl, or heterocycloalkyl; R$^3$ is R$^{31}$, —R$^{30}$OC(O)R$^{31}$, or —R$^{30}$OC(O)OR$^{31}$; R$^{30}$ is —CH$_2$—; and R$^{31}$ is methyl, ethyl, propyl, isopropyl, 2-ethylpropyl, butyl, tert-butyl, isobutyl, cyclohexyl, an isobenzofuran-1(3H)-one ring, or phenyl.

In some embodiments of a compound of Formula (II), M is hydrogen, fluoro, chloro, bromo, —CF$_3$, —CN, —OR$^4$, —SR$^4$, —S(O)—R$^4$, —SO$_2$—R$^4$, —SO$_2$—N(R$^4$R$^5$), —N(R$^4$R$^5$), —N(R$^4$)—C(O)R$^5$, —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, optionally substituted alkynyl, heteroaryl, or heterocycloalkyl; R$^3$ is R$^{31}$, —R$^{30}$OC(O)R$^{31}$, or —R$^{30}$OC(O)OR$^{31}$; R$^{30}$ is —CH(CH$_3$)—; and R$^{31}$ is optionally substituted C$_1$-C$_{12}$ alkyl, optionally substituted C$_3$-C$_8$ cycloalkyl, optionally substituted C$_3$-C$_8$ heterocycloalkyl, or optionally substituted aryl.

In some embodiments of a compound of Formula (II), M is hydrogen, fluoro, chloro, bromo, —CF$_3$, —CN, —OR$^4$, —SR$^4$, —S(O)—R$^4$, —SO$_2$—R$^4$, —SO$_2$—N(R$^4$R$^5$), —N(R$^4$R$^5$), —N(R$^4$)—C(O)R$^5$, —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, optionally substituted alkynyl, heteroaryl, or heterocycloalkyl; R$^3$ is R$^{31}$, —R$^{30}$OC(O)R$^{31}$, or —R$^{30}$OC(O)

$OR^{31}$; $R^{30}$ is —CH(CH$_3$)—; and $R^{31}$ is $C_1$-$C_{12}$ alkyl, $C_3$-$C_8$ cycloalkyl, $C_3$-$C_8$ heterocycloalkyl, or aryl.

In some embodiments of a compound of Formula (II), M is hydrogen, fluoro, chloro, bromo, —CF$_3$, —CN, —OR$^4$, —SR$^4$, —S(O)—R$^4$, —SO$_2$—R$^4$, —SO$_2$—N(R$^4$R$^5$), —N(R$^4$R$^5$), —N(R$^4$)—C(O)R$^5$, —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, optionally substituted alkynyl, heteroaryl, or heterocycloalkyl; R$^3$ is R$^{31}$, —R$^{30}$OC(O)R$^{31}$, or —R$^{30}$OC(O)OR$^{31}$; R$^{30}$ is —CH(CH$_3$)—; and R$^{31}$ is methyl, ethyl, propyl, isopropyl, 2-ethylpropyl, butyl, tert-butyl, isobutyl, cyclohexyl, an isobenzofuran-1(3H)-one ring, or phenyl.

In some embodiments of a compound of Formula (II), M is hydrogen, fluoro, chloro, bromo, —CF$_3$, —CN, —OR$^4$, —SR$^4$, —S(O)—R$^4$, —SO$_2$—R$^4$, —SO$_2$—N(R$^4$R$^5$), —N(R$^4$R$^5$), —N(R$^4$)—C(O)R$^5$, —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, optionally substituted alkynyl, heteroaryl, or heterocycloalkyl; R$^3$ is R$^{31}$, —R$^{30}$OC(O)R$^{31}$, or —R$^{30}$OC(O)OR$^{31}$; R$^{30}$ is —C(CH$_3$)$_2$—; and R$^{31}$ is optionally substituted C$_1$-C$_{12}$ alkyl, optionally substituted C$_3$-C$_8$ cycloalkyl, optionally substituted C$_3$-C$_8$ heterocycloalkyl, or optionally substituted aryl.

In some embodiments of a compound of Formula (II), M is hydrogen, fluoro, chloro, bromo, —CF$_3$, —CN, —OR$^4$, —SR$^4$, —S(O)—R$^4$, —SO$_2$—R$^4$, —SO$_2$—N(R$^4$R$^5$), —N(R$^4$R$^5$), —N(R$^4$)—C(O)R$^5$, —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, optionally substituted alkynyl, heteroaryl, or heterocycloalkyl; R$^3$ is R$^{31}$, —R$^{30}$OC(O)R$^{31}$, or —R$^{30}$OC(O)OR$^{31}$; R$^{30}$ is —C(CH$_3$)$_2$—; and R$^{31}$ is C$_1$-C$_{12}$ alkyl, C$_3$-C$_8$ cycloalkyl, C$_3$-C$_8$ heterocycloalkyl, or aryl.

In some embodiments of a compound of Formula (II), M is hydrogen, fluoro, chloro, bromo, —CF$_3$, —CN, —OR$^4$, —SR$^4$, —S(O)—R$^4$, —SO$_2$—R$^4$, —SO$_2$—N(R$^4$R$^5$), —N(R$^4$R$^5$), —N(R$^4$)—C(O)R$^5$, —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, optionally substituted alkynyl, heteroaryl, or heterocycloalkyl; R$^3$ is R$^{31}$, —R$^{30}$OC(O)R$^{31}$, or —R$^{30}$OC(O)OR$^{31}$; R$^{30}$ is —C(CH$_3$)$_2$—; and R$^{31}$ is methyl, ethyl, propyl, isopropyl, 2-ethylpropyl, butyl, tert-butyl, isobutyl, cyclohexyl, an isobenzofuran-1(3H)-one ring, or phenyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; R$^3$ is R$^{31}$, —R$^{30}$OC(O)R$^{31}$ or —R$^{30}$OC(O)OR$^{31}$; R$^{30}$ is —CH$_2$—, —CH(CH$_3$)—, —C(CH$_3$)$_2$—, or optionally substituted 1,1'-cyclopropylene; and R$^{31}$ is optionally substituted C$_1$-C$_{12}$ alkyl, optionally substituted alkoxyalkyl, optionally substituted C$_3$-C$_8$ cycloalkyl, optionally substituted C$_3$-C$_8$ heterocycloalkyl, optionally substituted aryl, or optionally substituted alkylcycloalkyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; R$^3$ is —R$^{30}$OC(O)R$^{31}$ or —R$^{30}$OC(O)OR$^{31}$; R$^{30}$ is —CH$_2$—, —CH(CH$_3$)—, —C(CH$_3$)$_2$—, or optionally substituted 1,1'-cyclopropylene; and R$^{31}$ is optionally substituted C$_1$-C$_{12}$ alkyl, optionally substituted alkoxyalkyl, optionally substituted C$_3$-C$_8$ cycloalkyl, optionally substituted C$_3$-C$_8$ heterocycloalkyl, optionally substituted aryl, or optionally substituted alkylcycloalkyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; each R$^4$ and R$^5$ are independently hydrogen or optionally substituted C$_1$-C$_6$ alkyl; R$^3$ is R$^{31}$; and R$^{31}$ is optionally substituted C$_1$-C$_{12}$ alkyl, optionally substituted alkoxyalkyl, optionally substituted C$_3$-C$_8$ cycloalkyl, optionally substituted C$_3$-C$_8$ heterocycloalkyl, optionally substituted aryl, or optionally substituted alkylcycloalkyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; each R$^4$ and R$^5$ are independently hydrogen or optionally substituted C$_1$-C$_6$ alkyl; R$^3$ is R$^{31}$; and R$^{31}$ is C$_1$-C$_{12}$ alkyl, alkoxyalkyl, or C$_3$-C$_8$ heterocycloalkyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; each R$^4$ and R$^5$ are independently hydrogen or optionally substituted C$_1$-C$_6$ alkyl; R$^3$ is R$^{31}$; and R$^{31}$ is methyl, ethyl, propyl, isopropyl, 2-ethylpropyl, butyl, tert-butyl, pentyl, isobutyl, isopentyl, methoxyethyl, or an isobenzofuran-1(3H)-one ring.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; each R$^4$ and R$^5$ are independently hydrogen or optionally substituted C$_1$-C$_6$ alkyl; R$^3$ is R$^{31}$; and R$^{31}$ is methyl, ethyl, propyl, butyl, isobutyl, methoxyethyl, or an isobenzofuran-1(3H)-one ring.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; each R$^4$ and R$^5$ are independently hydrogen or optionally substituted C$_1$-C$_6$ alkyl; R$^3$ is —R$^{30}$OC(O)R$^{31}$; R$^{30}$ is —CH$_2$—, —CH(CH$_3$)—, —C(CH$_3$)$_2$—, or optionally substituted 1,1'-cyclopropylene; and R$^{31}$ is optionally substituted C$_1$-C$_{12}$ alkyl, optionally substituted alkoxyalkyl, optionally substituted C$_3$-C$_8$ cycloalkyl, optionally substituted C$_3$-C$_8$ heterocycloalkyl, optionally substituted aryl, or optionally substituted alkylcycloalkyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; each R$^4$ and R$^5$ are independently hydrogen or optionally substituted C$_1$-C$_6$ alkyl; R$^3$ is —R$^{30}$OC(O)R$^{31}$; R$^{30}$ is —CH$_2$—, —CH(CH$_3$)—; and R$^{31}$ is optionally substituted C$_1$-C$_{12}$ alkyl, optionally substituted alkoxyalkyl, optionally substituted C$_3$-C$_8$ cycloalkyl, optionally substituted C$_3$-C$_8$ heterocycloalkyl, optionally substituted aryl, or optionally substituted alkylcycloalkyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N ($R^4R^5$), optionally substituted alkynyl, heteroaryl, or heterocycloalkyl; each $R^4$ and $R^5$ are independently hydrogen or optionally substituted $C_1$-$C_6$ alkyl; $R^3$ is —$R^{30}$OC(O)$R^{31}$; $R^{30}$ is —$CH_2$—, —$CH(CH_3)$—; and $R^{31}$ is optionally substituted $C_1$-$C_{12}$ alkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is hydrogen, —CN, —$SO_2$—$N(R^4R^5)$, —$N(R^4)$—C(O)—N($R^4R^5$), —$N(R^4)$—$SO_2$—$R^5$, —C(O)—$R^4$, —C(O)—N($R^4R^5$), optionally substituted alkynyl, heteroaryl, or heterocycloalkyl; each $R^4$ and $R^5$ are independently hydrogen or optionally substituted $C_1$-$C_6$ alkyl; $R^3$ is —$R^{30}$OC(O)$R^{31}$; $R^{30}$ is —$CH_2$—, —$CH(CH_3)$—; and $R^{31}$ is $C_1$-$C_{12}$ alkyl, $C_3$-$C_8$ cycloalkyl, $C_3$-$C_8$ heterocycloalkyl, aryl, or alkylcycloalkyl.

In some embodiments of a compound of Formula (II), M is hydrogen, —CN, —$SO_2$—$N(R^4R^5)$, —$N(R^4)$—C(O)—N($R^4R^5$), —$N(R^4)$—$SO_2$—$R^5$, —C(O)—$R^4$, —C(O)—N($R^4R^5$), optionally substituted alkynyl, heteroaryl, or heterocycloalkyl; each $R^4$ and $R^5$ are independently hydrogen or optionally substituted $C_1$-$C_6$ alkyl; $R^3$ is —$R^{30}$OC(O)$R^{31}$; $R^{30}$ is —$CH_2$—, —$CH(CH_3)$—; and $R^{31}$ is methyl, ethyl, propyl, isopropyl, 2-ethylpropyl, butyl, tert-butyl, pentyl, isobutyl, isopentyl, cyclopropyl, cyclobutyl, cyclopentyl, cyclohexyl, cyclohexylmethyl, piperidinyl, phenyl, or 4-fluorophenyl.

In some embodiments of a compound of Formula (II), M is hydrogen, —CN, —$SO_2$—$N(R^4R^5)$, —$N(R^4)$—C(O)—N($R^4R^5$), —$N(R^4)$—$SO_2$—$R^5$, —C(O)—$R^4$, —C(O)—N($R^4R^5$), optionally substituted alkynyl, heteroaryl, or heterocycloalkyl; each $R^4$ and $R^5$ are independently hydrogen or optionally substituted $C_1$-$C_6$ alkyl; $R^3$ is —$R^{30}$OC(O)$R^{31}$; $R^{30}$ is —$CH_2$—, —$CH(CH_3)$—; and $R^{31}$ is methyl, ethyl, propyl, isopropyl, 2-ethylpropyl, butyl, tert-butyl, pentyl, isobutyl, cyclohexyl, cyclohexylmethyl, piperidinyl, phenyl, or 4-fluorophenyl.

In some embodiments of a compound of Formula (II), M is hydrogen, —CN, —$SO_2$—$N(R^4R^5)$, —$N(R^4)$—C(O)—N($R^4R^5$), —$N(R^4)$—$SO_2$—$R^5$, —C(O)—$R^4$, —C(O)—N($R^4R^5$), optionally substituted alkynyl, heteroaryl, or heterocycloalkyl; each $R^4$ and $R^5$ are independently hydrogen or optionally substituted $C_1$-$C_6$ alkyl; $R^3$ is —$R^{30}$OC(O)O$R^{31}$; $R^{30}$ is —$CH_2$—, —$CH(CH_3)$—, —$C(CH_3)_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is hydrogen, —CN, —$SO_2$—$N(R^4R^5)$, —$N(R^4)$—C(O)—N($R^4R^5$), —$N(R^4)$—$SO_2$—$R^5$, —C(O)—$R^4$, —C(O)—N($R^4R^5$), optionally substituted alkynyl, heteroaryl, or heterocycloalkyl; each $R^4$ and $R^5$ are independently hydrogen or optionally substituted $C_1$-$C_6$ alkyl; $R^3$ is —$R^{30}$OC(O)O$R^{31}$; $R^{30}$ is —$CH_2$—, —$CH(CH_3)$—; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is hydrogen, —CN, —$SO_2$—$N(R^4R^5)$, —$N(R^4)$—C(O)—N($R^4R^5$), —$N(R^4)$—$SO_2$—$R^5$, —C(O)—$R^4$, —C(O)—N($R^4R^5$), optionally substituted alkynyl, heteroaryl, or heterocycloalkyl; each $R^4$ and $R^5$ are independently hydrogen or optionally substituted $C_1$-$C_6$ alkyl; $R^3$ is —$R^{30}$OC(O)O$R^{31}$; $R^{30}$ is —$CH_2$—, —$CH(CH_3)$—; and $R^{31}$ is optionally substituted $C_1$-$C_{12}$ alkyl, optionally substituted $C_3$-$C_8$ cycloalkyl, optionally substituted $C_3$-$C_8$ heterocycloalkyl, or optionally substituted alkylcycloalkyl.

In some embodiments of a compound of Formula (II), M is hydrogen, —CN, —$SO_2$—$N(R^4R^5)$, —$N(R^4)$—C(O)—N($R^4R^5$), —$N(R^4)$—$SO_2$—$R^5$, —C(O)—$R^4$, —C(O)—N($R^4R^5$), optionally substituted alkynyl, heteroaryl, or heterocycloalkyl; each $R^4$ and $R^5$ are independently hydrogen or optionally substituted $C_1$-$C_6$ alkyl; $R^3$ is —$R^{30}$OC(O)O$R^{31}$; $R^{30}$ is —$CH_2$—, —$CH(CH_3)$—; and $R^{31}$ is $C_1$-$C_{12}$ alkyl, $C_3$-$C_8$ cycloalkyl, $C_3$-$C_8$ heterocycloalkyl, or alkylcycloalkyl.

In some embodiments of a compound of Formula (II), M is hydrogen, —CN, —$SO_2$—$N(R^4R^5)$, —$N(R^4)$—C(O)—N($R^4R^5$), —$N(R^4)$—$SO_2$—$R^5$, —C(O)—$R^4$, —C(O)—N($R^4R^5$), optionally substituted alkynyl, heteroaryl, or heterocycloalkyl; each $R^4$ and $R^5$ are independently hydrogen or optionally substituted $C_1$-$C_6$ alkyl; $R^3$ is —$R^{30}$OC(O)O$R^{31}$; $R^{30}$ is —$CH_2$—, —$CH(CH_3)$—; and $R^{31}$ is methyl, ethyl, propyl, isopropyl, 2-ethylpropyl, butyl, tert-butyl, pentyl, isobutyl, isopentyl, cyclopropyl, cyclobutyl, cyclopentyl, cyclohexyl, cyclohexylmethyl, or tetrahydropyranyl.

In some embodiments of a compound of Formula (II), M is hydrogen, —CN, —$SO_2$—$N(R^4R^5)$, —$N(R^4)$—C(O)—N($R^4R^5$), —$N(R^4)$—$SO_2$—$R^5$, —C(O)—$R^4$, —C(O)—N($R^4R^5$), optionally substituted alkynyl, heteroaryl, or heterocycloalkyl; each $R^4$ and $R^5$ are independently hydrogen or optionally substituted $C_1$-$C_6$ alkyl; $R^3$ is —$R^{30}$OC(O)O$R^{31}$; $R^{30}$ is —$CH_2$—, —$CH(CH_3)$—; and $R^{31}$ is methyl, ethyl, propyl, isopropyl, butyl, cyclohexyl, cyclohexylmethyl, or tetrahydropyranyl.

In some embodiments of a compound of Formula (II), M is —$SO_2$—$N(R^4R^5)$, —$N(R^4)$—C(O)—N($R^4R^5$), —$N(R^4)$—$SO_2$—$R^5$, —C(O)—N($R^4R^5$); each $R^4$ and $R^5$ are independently hydrogen or $C_1$-$C_6$ alkyl; and $R^3$ is $R^{31}$, —$R^{30}$OC(O)$R^{31}$ or —$R^{30}$OC(O)O$R^{31}$; $R^{30}$ is —$CH_2$—, —$CH(CH_3)$—, —$C(CH_3)_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is —$SO_2$—$N(R^4R^5)$, —$N(R^4)$—C(O)—N($R^4R^5$), —$N(R^4)$—$SO_2$—$R^5$, —C(O)—N($R^4R^5$); each $R^4$ and $R^5$ are independently hydrogen, methyl, ethyl, propyl, isopropyl, 2-ethylpropyl, butyl, tert-butyl, pentyl, isobutyl, isopentyl; and $R^3$ is $R^{31}$, —$R^{30}$OC(O)$R^{31}$ or —$R^{30}$OC(O)O$R^{31}$; $R^{30}$ is —$CH_2$—, —$CH(CH_3)$—, —$C(CH_3)_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is —$SO_2$—$N(R^4R^5)$, —$N(R^4)$—C(O)—N($R^4R^5$), —$N(R^4)$—$SO_2$—$R^5$, —C(O)—N($R^4R^5$); each $R^4$ and $R^5$ are independently hydrogen or methyl; and $R^3$ is $R^{31}$, $R^{30}$OC(O)$R^{31}$ or —$R^{30}$OC(O)O$R^{31}$; $R^{30}$ is —$CH_2$—, —$CH(CH_3)$—, —$C(CH_3)_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is optionally substituted alkynyl; and $R^3$ is $R^{31}$, —$R^{30}$OC(O)$R^{31}$ or —$R^{30}$OC(O)O$R^{31}$; $R^{30}$ is —$CH_2$—, —CH($CH_3$)—, —C($CH_3$)$_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is heteroaryl or heterocycloalkyl; each $R^4$ and $R^5$ are independently hydrogen or optionally substituted $C_1$-$C_6$ alkyl; and $R^3$ is $R^{31}$, —$R^{30}$OC(O)$R^{31}$ or —$R^{30}$OC(O)O$R^{31}$; $R^{30}$ is —$CH_2$—, —CH($CH_3$)—, —C($CH_3$)$_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is pyridinyl, pyrimidinyl, pyridazinyl, pyrazinyl, imidazolyl, pyrrazolyl, thiazolyl, oxazolyl, aziridinyl, azetidinyl, pyrrolidinyl, piperidinyl, pyperazinyl, pyrrolidinone or pyrrolidine-2,5-dione; and $R^3$ is $R^{31}$, —$R^{30}$OC(O)$R^{31}$ or —$R^{30}$OC(O)O$R^{31}$; $R^{30}$ is —$CH_2$—, —CH($CH_3$)—, —C($CH_3$)$_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is pyridinyl, imidazolyl, pyrrazolyl, thiazolyl, or oxazolyl; and $R^3$ is $R^{31}$, —$R^{30}$OC(O)$R^{31}$ or —$R^{30}$OC(O)O$R^{31}$; $R^{30}$ is —$CH_2$—, —CH($CH_3$)—, —C($CH_3$)$_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is:

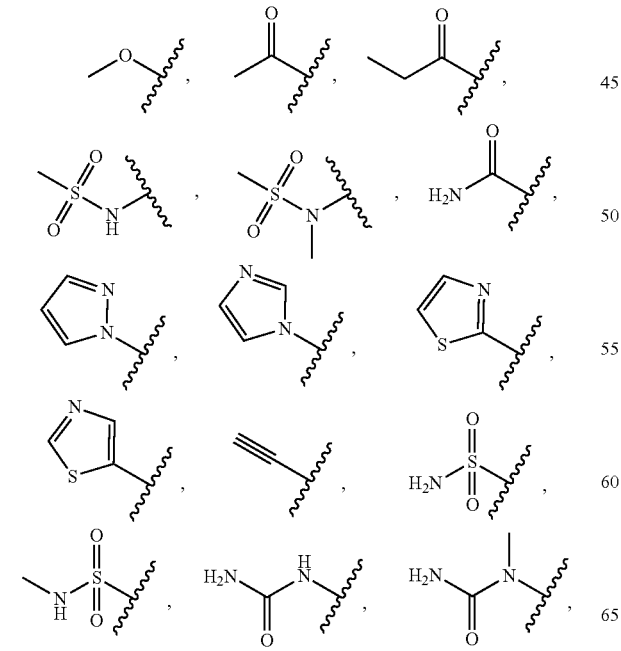

$R^3$ is:

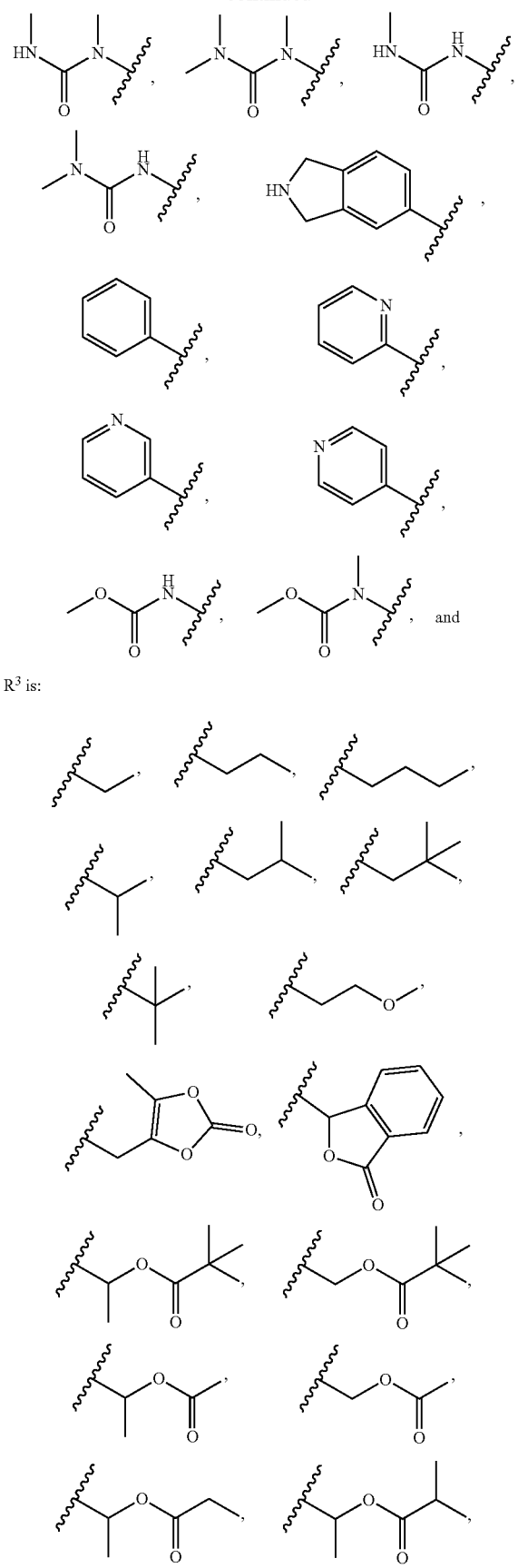

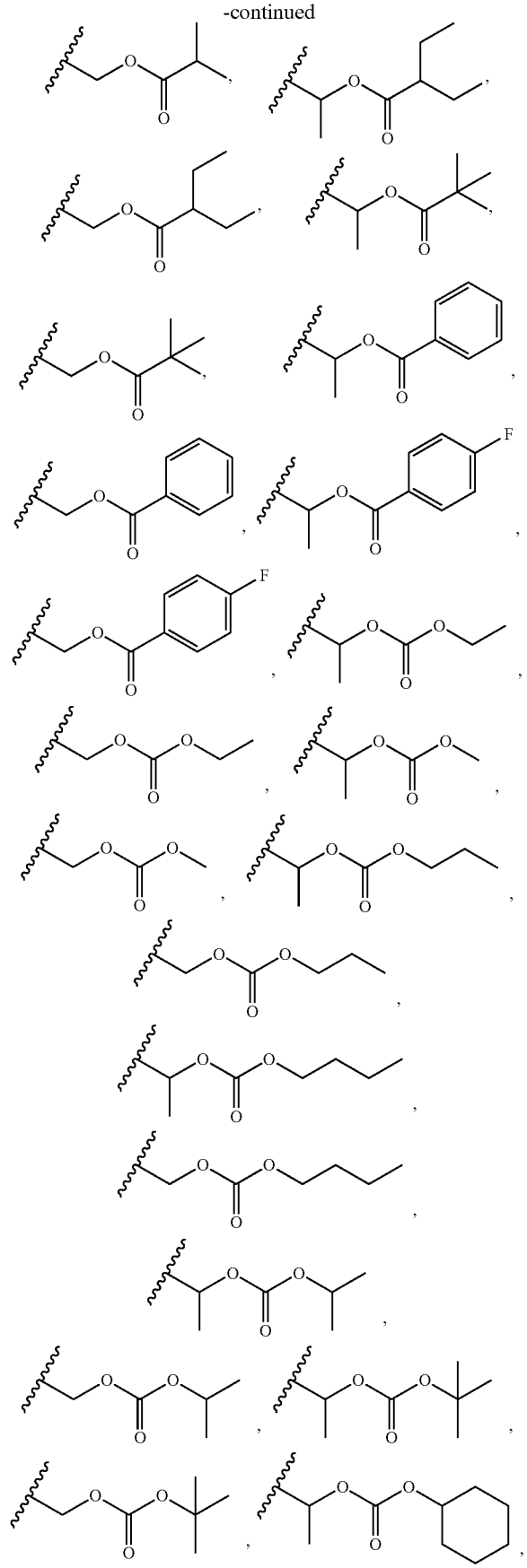

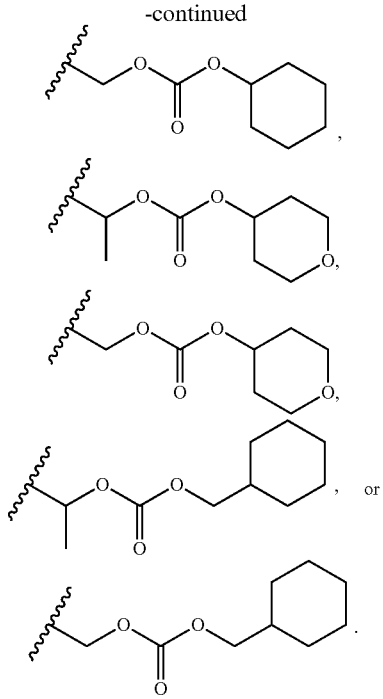

In some embodiments of a compound of Formula (II), M is hydrogen, —CN, —C(O)—$R^4$, optionally substituted alkynyl; $R^3$ is $R^{31}$, —$R^{30}$OC(O)$R^{31}$ or —$R^{30}$OC(O)O$R^{31}$; $R^{30}$ is —$CH_2$—, —CH($CH_3$)—, —C($CH_3$)$_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is $R^{31}$, —$R^{30}$OC(O)$R^{31}$ or —$R^{30}$OC(O)O$R^{31}$; $R^{30}$ is —$CH_2$—, —CH($CH_3$)—, —C($CH_3$)$_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is hydrogen; and $R^3$ is $R^{31}$, —$R^{30}$OC(O)$R^{31}$ or —$R^{30}$OC(O)O$R^{31}$; $R^{30}$ is —$CH_2$—, —CH($CH_3$)—, —C($CH_3$)$_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is —CN; and $R^3$ is $R^{31}$, —$R^{30}$OC(O)$R^{31}$ or —$R^{30}$OC(O)O$R^{31}$; $R^{30}$ is —$CH_2$—, —CH($CH_3$)—, —C($CH_3$)$_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is —C(O)—$R^4$; $R^4$ is optionally substituted $C_1$-$C_6$ alkyl; and $R^3$ is $R^{31}$, —$R^{30}$OC(O)$R^{31}$ or —$R^{30}$OC(O)O$R^{31}$; $R^{30}$ is —$CH_2$—, —CH($CH_3$)—, —C($CH_3$)$_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is —C(O)—$R^4$; $R^4$ is methyl, ethyl, propyl, isopropyl, 2-ethylpropyl, butyl, tert-butyl, pentyl, isobutyl, isopentyl; and $R^3$ is $R^{31}$, —$R^{30}$OC(O)$R^{31}$ or —$R^{30}$OC(O)O$R^{31}$; $R^{30}$ is —CH$_2$—, —CH(CH$_3$)—, —C(CH$_3$)$_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is —C(O)—$R^4$; $R^4$ is methyl; and $R^3$ is $R^{31}$, —$R^{30}$OC(O)$R^{31}$ or —$R^{30}$OC(O)O$R^{31}$; $R^{30}$ is —CH$_2$—, —CH(CH$_3$)—, —C(CH$_3$)$_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is alkynyl; and $R^3$ is $R^{31}$, —$R^{30}$OC(O)$R^{31}$ or —$R^{30}$OC(O)O$R^{31}$; $R^{30}$ is —CH$_2$—, —CH(CH$_3$)—, —C(CH$_3$)$_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is $R^{31}$; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is $R^{31}$; and $R^{31}$ is $C_1$-$C_{12}$ alkyl, alkoxyalkyl, or $C_3$-$C_8$ heterocycloalkyl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is $R^{31}$; and $R^{31}$ is methyl, ethyl, propyl, isopropyl, 2-ethylpropyl, butyl, tert-butyl, pentyl, isobutyl, isopentyl, methoxyethyl, or an isobenzofuran-1(3H)-one ring.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is $R^{31}$; and $R^{31}$ is methyl, ethyl, propyl, butyl, isobutyl, methoxyethyl, or an isobenzofuran-1(3H)-one ring.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is —$R^{30}$OC(O)$R^{31}$; $R^{30}$ is —CH$_2$—, —CH(CH$_3$)—, —C(CH$_3$)$_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is —$R^{30}$OC(O)$R^{31}$; $R^{30}$ is —CH$_2$—, —CH(CH$_3$)—; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is hydrogen, —CN, —C(O)—$R^4$, optionally substituted alkynyl; $R^4$ is or optionally substituted $C_1$-$C_6$ alkyl; $R^3$ is —$R^{30}$OC(O)$R^{31}$; $R^{30}$ is —CH$_2$—, —CH(CH$_3$)— and $R^{31}$ is optionally substituted $C_1$-$C_{12}$ alkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is hydrogen, —CN, —C(O)—$R^4$, optionally substituted alkynyl; $R^4$ is optionally substituted $C_1$-$C_6$ alkyl; $R^4$ is optionally substituted $C_1$-$C_6$ alkyl; $R^3$ is —$R^{30}$OC(O)$R^{31}$; $R^{30}$ is —CH$_2$—, —CH(CH$_3$)—; and $R^{31}$ is $C_1$-$C_{12}$ alkyl, $C_3$-$C_8$ cycloalkyl, $C_3$-$C_8$ heterocycloalkyl, aryl, or alkylcycloalkyl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is —$R^{30}$OC(O)$R^{31}$; $R^{30}$ is —CH$_2$—, —CH(CH$_3$)—; and $R^{31}$ is methyl, ethyl, propyl, isopropyl, 2-ethylpropyl, butyl, tert-butyl, pentyl, isobutyl, isopentyl, cyclopropyl, cyclobutyl, cyclopentyl, cyclohexyl, cyclohexylmethyl, piperidinyl, phenyl, or 4-fluorophenyl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is —$R^{30}$OC(O)$R^{31}$; $R^{30}$ is —CH$_2$—, —CH(CH$_3$)—; and $R^{31}$ is methyl, ethyl, propyl, isopropyl, 2-ethylpropyl, butyl, tert-butyl, pentyl, isobutyl, cyclohexyl, cyclohexylmethyl, piperidinyl, phenyl, or 4-fluorophenyl.

In some embodiments of a compound of Formula (II), M is hydrogen, —CN, —C(O)—$R^4$, optionally substituted alkynyl; $R^4$ is optionally substituted $C_1$-$C_6$ alkyl; $R^{30}$ is —CH$_2$—, —CH(CH$_3$)—, —C(CH$_3$)$_2$—, or optionally substituted 1,1'-cyclopropylene; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is —$R^{30}$OC(O)O$R^{31}$; $R^{30}$ is —CH$_2$—, —CH(CH$_3$)—; and $R^{31}$ is optionally substituted $C_1$-$C_{12}$ alkyl, optionally substituted alkoxyalkyl, optionally substituted $C_3$-$C_8$ cycloalkyl, optionally substituted $C_3$-$C_8$ heterocycloalkyl, optionally substituted aryl, or optionally substituted alkylcycloalkyl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is —$R^{30}$OC(O)O$R^{31}$; $R^{30}$ is —CH$_2$—, —CH(CH$_3$)—; and $R^{31}$ is optionally substituted $C_1$-$C_{12}$ alkyl, optionally substituted $C_3$-$C_8$ cycloalkyl, optionally substituted $C_3$-$C_8$ heterocycloalkyl, or optionally substituted alkylcycloalkyl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is —$R^{30}OC(O)OR^{31}$; $R^{30}$ is —$CH_2$—, —$CH(CH_3)$—; and $R^{31}$ is $C_1$-$C_{12}$ alkyl, $C_3$-$C_8$ cycloalkyl, $C_3$-$C_8$ heterocycloalkyl, or alkylcycloalkyl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is —$R^{30}OC(O)OR^{31}$; $R^{30}$ is —$CH_2$—, —$CH(CH_3)$—; and $R^{31}$ is methyl, ethyl, propyl, isopropyl, 2-ethylpropyl, butyl, tert-butyl, pentyl, isobutyl, isopentyl, cyclopropyl, cyclobutyl, cyclopentyl, cyclohexyl, cyclohexylmethyl, or tetrahydropyranyl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is —$R^{30}OC(O)OR^{31}$; $R^{30}$ is —$CH_2$—, —$CH(CH_3)$—; and $R^{31}$ is methyl, ethyl, propyl, isopropyl, butyl, cyclohexyl, cyclohexylmethyl, or tetrahydropyranyl.

In some embodiments of a compound of Formula (II), M is hydrogen, —CN, —$SO_2$—$N(R^4R^5)$, —$N(R^4)$—C(O)—N($R^4R^5$), —$N(R^4)$—$SO_2$—$R^5$, —C(O)—$R^4$, —C(O)—N($R^4R^5$), optionally substituted alkynyl, heteroaryl, or heterocycloalkyl; $R^3$ is $R^{31}$, —$R^{30}OC(O)R^{31}$, or —$R^{30}OC(O)OR^{31}$; $R^{30}$ is —$CH_2$—, —$CH(CH_3)$—, —$C(CH_3)_2$—, or optionally substituted 1,1'-cyclopropylene; and $R^{31}$ is optionally substituted $C_1$-$C_{12}$ alkyl, optionally substituted $C_3$-$C_8$ cycloalkyl, optionally substituted $C_3$-$C_8$ heterocycloalkyl, or optionally substituted aryl.

In some embodiments of a compound of Formula (II), M is hydrogen, —CN, —$SO_2$—$N(R^4R^5)$, —$N(R^4)$—C(O)—N($R^4R^5$), —$N(R^4)$—$SO_2$—$R^5$, —C(O)—$R^4$, —C(O)—N($R^4R^5$), optionally substituted alkynyl, heteroaryl, or heterocycloalkyl; each $R^4$ and $R^5$ are independently hydrogen or optionally substituted $C_1$-$C_6$ alkyl; $R^3$ is $R^{31}$, —$R^{30}OC(O)R^{31}$, or —$R^{30}OC(O)OR^{31}$; $R^{30}$ is —$CH_2$—, —$CH(CH_3)$—, —$C(CH_3)_2$—, or optionally substituted 1,1'-cyclopropylene; and $R^{31}$ is optionally substituted $C_1$-$C_{12}$ alkyl, optionally substituted $C_3$-$C_8$ cycloalkyl, optionally substituted $C_3$-$C_8$ heterocycloalkyl, or optionally substituted aryl.

In some embodiments of a compound of Formula (II), M is hydrogen, —CN, —$SO_2$—$N(R^4R^5)$, —$N(R^4)$—C(O)—N($R^4R^5$), —$N(R^4)$—$SO_2$—$R^5$, —C(O)—$R^4$, —C(O)—N($R^4R^5$), optionally substituted alkynyl, heteroaryl, or heterocycloalkyl; each $R^4$ and $R^5$ are independently hydrogen or optionally substituted $C_1$-$C_6$ alkyl; $R^3$ is $R^{31}$, —$R^{30}OC(O)R^{31}$, or —$R^{30}OC(O)OR^{31}$; $R^{30}$ is —$CH_2$—; and $R^{31}$ is optionally substituted $C_1$-$C_{12}$ alkyl, optionally substituted $C_3$-$C_8$ cycloalkyl, optionally substituted $C_3$-$C_8$ heterocycloalkyl, or optionally substituted aryl.

In some embodiments of a compound of Formula (II), M is hydrogen, —CN, —$SO_2$—$N(R^4R^5)$, —$N(R^4)$—C(O)—N($R^4R^5$), —$N(R^4)$—$SO_2$—$R^5$, —C(O)—$R^4$, —C(O)—N($R^4R^5$), optionally substituted alkynyl, heteroaryl, or heterocycloalkyl; each $R^4$ and $R^5$ are independently hydrogen or $C_1$-$C_6$ alkyl; $R^3$ is $R^{31}$, —$R^{30}OC(O)R^{31}$, or —$R^{30}OC(O)OR^{31}$; $R^{30}$ is —$CH_2$—; and $R^{31}$ is $C_1$-$C_{12}$ alkyl, $C_3$-$C_8$ cycloalkyl, $C_3$-$C_8$ heterocycloalkyl, or aryl.

In some embodiments of a compound of Formula (II), M is hydrogen, —CN, —$SO_2$—$N(R^4R^5)$, —$N(R^4)$—C(O)—N($R^4R^5$), —$N(R^4)$—$SO_2$—$R^5$, —C(O)—$R^4$, —C(O)—N($R^4R^5$), optionally substituted alkynyl, heteroaryl, or heterocycloalkyl; each $R^4$ and $R^5$ are independently hydrogen or $C_1$-$C_6$ alkyl; $R^3$ is $R^{31}$, —$R^{30}OC(O)R^{31}$, or —$R^{30}OC(O)OR^{31}$; $R^{30}$ is —$CH(CH_3)$—; and $R^{31}$ is $C_1$-$C_{12}$ alkyl, $C_3$-$C_8$ cycloalkyl, $C_3$-$C_8$ heterocycloalkyl, or aryl.

In some embodiments of a compound of Formula (II), M is hydrogen, —CN, —$SO_2$—$N(R^4R^5)$, —$N(R^4)$—C(O)—N($R^4R^5$), —$N(R^4)$—$SO_2$—$R^5$, —C(O)—$R^4$, —C(O)—N($R^4R^5$), optionally substituted alkynyl, heteroaryl, or heterocycloalkyl; each $R^4$ and $R^5$ are independently hydrogen or optionally substituted $C_1$-$C_6$ alkyl; $R^3$ is $R^{31}$, —$R^{30}OC(O)R^{31}$, or —$R^{30}OC(O)OR^{31}$; $R^{30}$ is —$C(CH_3)_2$—; and $R^{31}$ is optionally substituted $C_1$-$C_{12}$ alkyl, optionally substituted $C_3$-$C_8$ cycloalkyl, optionally substituted $C_3$-$C_8$ heterocycloalkyl, or optionally substituted aryl.

In some embodiments of a compound of Formula (II), M is hydrogen, —CN, —$SO_2$—$N(R^4R^5)$, —$N(R^4)$—C(O)—N($R^4R^5$), —$N(R^4)$—$SO_2$—$R^5$, —C(O)—$R^4$, —C(O)—N($R^4R^5$), optionally substituted alkynyl, heteroaryl, or heterocycloalkyl; each R and $R^5$ are independently hydrogen or $C_1$-$C_6$ alkyl; $R^3$ is $R^{31}$, —$R^{30}OC(O)R^{31}$, or —$R^{30}OC(O)OR^{31}$; $R^{30}$ is —$C(CH_3)_2$—; and $R^{31}$ is $C_1$-$C_{12}$ alkyl, $C_3$-$C_8$ cycloalkyl, $C_3$-$C_8$ heterocycloalkyl, or aryl.

In some embodiments of a compound of Formula (II), M is hydrogen, —CN, —C(O)—$R^4$, optionally substituted alkynyl; $R^3$ is $R^{31}$, —$R^{30}OC(O)R^{31}$, or —$R^{30}OC(O)OR^{31}$; $R^{30}$ is —$CH_2$—, —$CH(CH_3)$—, —$C(CH_3)_2$—, or optionally substituted 1,1'-cyclopropylene; and $R^{31}$ is optionally substituted $C_1$-$C_{12}$ alkyl, optionally substituted $C_3$-$C_8$ cycloalkyl, optionally substituted $C_3$-$C_8$ heterocycloalkyl, or optionally substituted aryl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is $R^{31}$, —$R^{30}OC(O)R^{31}$, or —$R^{30}OC(O)OR^{31}$; $R^{30}$ is —$CH_2$—, —$CH(CH_3)$—, —$C(CH_3)_2$—, or optionally substituted 1,1'-cyclopropylene; and $R^{31}$ is optionally substituted $C_1$-$C_{12}$ alkyl, optionally substituted $C_3$-$C_8$ cycloalkyl, optionally substituted $C_3$-$C_8$ heterocycloalkyl, or optionally substituted aryl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is $R^{31}$, —$R^{30}OC(O)R^{31}$, or —$R^{30}OC(O)OR^3$; $R^{30}$ is —$CH_2$—; and $R^{31}$ is optionally substituted $C_1$-$C_{12}$ alkyl, optionally substituted $C_3$-$C_8$ cycloalkyl, optionally substituted $C_3$-$C_8$ heterocycloalkyl, or optionally substituted aryl.

In some embodiments of a compound of Formula (II), M is hydrogen, —CN, —C(O)—$R^4$, optionally substituted alkynyl; $R^4$ is $C_1$-$C_6$ alkyl; $R^3$ is $R^{31}$, —$R^{30}OC(O)R^{31}$, or —$R^{30}OC(O)OR^{31}$; $R^{30}$ is —$CH_2$—; and $R^{31}$ is $C_1$-$C_{12}$ alkyl, $C_3$-$C_8$ cycloalkyl, $C_3$-$C_8$ heterocycloalkyl, or aryl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is $R^{31}$, —$R^{30}OC(O)R^{31}$, or —$R^{30}OC(O)OR^3$; $R^{30}$ is —$CH(CH_3)$—; and $R^{31}$ is optionally substituted $C_1$-$C_{12}$ alkyl, optionally substituted $C_3$-$C_8$ cycloalkyl, optionally substituted $C_3$-$C_8$ heterocycloalkyl, or optionally substituted aryl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is $R^{31}$, —$R^{30}OC(O)R^{31}$, or —$R^{30}OC(O)OR^{31}$; $R^{30}$ is —CH($CH_3$)—; and $R^{31}$ is $C_1$-$C_{12}$ alkyl, $C_3$-$C_8$ cycloalkyl, $C_3$-$C_8$ heterocycloalkyl, or aryl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is $R^{31}$, —$R^{30}OC(O)R^{31}$, or —$R^{30}OC(O)OR^{31}$; $R^{30}$ is —C($CH_3$)$_2$—; and $R^{31}$ is optionally substituted $C_1$-$C_{12}$ alkyl, optionally substituted $C_3$-$C_8$ cycloalkyl, optionally substituted $C_3$-$C_8$ heterocycloalkyl, or optionally substituted aryl.

In some embodiments of a compound of Formula (II), M is hydrogen, —CN, —C(O)—$R^4$, optionally substituted alkynyl; $R^4$ is optionally substituted $C_1$-$C_6$ alkyl; $R^3$ is $R^{31}$, —$R^{30}OC(O)R^{31}$, or —$R^{30}OC(O)OR^{31}$; $R^{30}$ is —C($CH_3$)$_2$—; and $R^{31}$ is $C_1$-$C_{12}$ alkyl, $C_3$-$C_8$ cycloalkyl, $C_3$-$C_8$ heterocycloalkyl, or aryl.

In some embodiments of a compound of Formula (II), M is hydrogen; $R^3$ is $R^{31}$, —$R^{30}OC(O)R^{31}$ or —$R^{30}OC(O)OR^{31}$; $R^{30}$ is —$CH_2$—, —CH($CH_3$)—; and $R^{31}$ is $C_1$-$C_{12}$ alkyl.

In some embodiments of a compound of Formula (II), M is hydrogen; $R^3$ is $R^{31}$, —$R^{30}OC(O)R^{31}$ or —$R^{30}OC(O)OR^{31}$; $R^{30}$ is —$CH_2$—, —CH($CH_3$)—; and $R^{31}$ is methyl, ethyl, propyl, isopropyl, 2-ethylpropyl, butyl, tert-butyl, or isobutyl.

In some embodiments of a compound of Formula (II), M is —CN; $R^3$ is $R^{31}$, —$R^{30}OC(O)R^{31}$ or —$R^{30}OC(O)OR^{31}$; $R^{30}$ is —$CH_2$—, —CH($CH_3$)—; and $R^{31}$ is $C_1$-$C_{12}$ alkyl.

In some embodiments of a compound of Formula (II), M is —CN; $R^3$ is $R^{31}$, —$R^{30}OC(O)R^{31}$ or —$R^{30}OC(O)OR^{31}$; $R^{30}$ is —$CH_2$—, —CH($CH_3$)—; and $R^{31}$ is methyl, ethyl, propyl, isopropyl, 2-ethylpropyl, butyl, tert-butyl, or isobutyl.

In some embodiments of a compound of Formula (II), M is alkynyl; $R^3$ is $R^{31}$, —$R^{30}OC(O)R^{31}$ or —$R^{30}OC(O)OR^{31}$; $R^{30}$ is —$CH_2$—, —CH($CH_3$)—; and $R^{31}$ is $C_1$-$C_{12}$ alkyl.

In some embodiments of a compound of Formula (II), M is alkynyl; $R^3$ is $R^{31}$, —$R^{30}OC(O)R^{31}$ or —$R^{30}OC(O)OR^{31}$; $R^{30}$ is —$CH_2$—, —CH($CH_3$)—; and $R^{31}$ is methyl, ethyl, propyl, isopropyl, 2-ethylpropyl, butyl, tert-butyl, or isobutyl.

In some embodiments of a compound of Formula (II), M is —C(O)—$R^4$; R is $C_1$-$C_6$ alkyl; $R^3$ is $R^{31}$, —$R^{30}OC(O)R^{31}$ or —$R^{30}OC(O)OR^{31}$; $R^{30}$ is —$CH_2$—, —CH($CH_3$)—; and $R^{31}$ is $C_1$-$C_{12}$ alkyl.

In some embodiments of a compound of Formula (II), M is —C(O)—$R^4$; R is methyl; $R^3$ is $R^{31}$, —$R^{30}OC(O)R^{31}$ or —$R^{30}OC(O)OR^{31}$; $R^{30}$ is —$CH_2$—, —CH($CH_3$)—; and $R^{31}$ is $C_1$-$C_{12}$ alkyl.

In some embodiments of a compound of Formula (II), M is —C(O)—$R^4$; R is $C_1$-$C_6$ alkyl; $R^3$ is $R^{31}$, —$R^{30}OC(O)R^{31}$ or —$R^{30}OC(O)OR^{31}$; $R^{30}$ is —$CH_2$—, —CH($CH_3$)—; and $R^{31}$ is methyl, ethyl, propyl, isopropyl, 2-ethylpropyl, butyl, tert-butyl, or isobutyl.

In some embodiments of a compound of Formula (II), M is —C(O)—$R^4$; R is methyl; $R^3$ is $R^{31}$, —$R^{30}OC(O)R^{31}$ or —$R^{30}OC(O)OR^{31}$; $R^{30}$ is —$CH_2$—, —CH($CH_3$)—; and $R^{31}$ is methyl, ethyl, propyl, isopropyl, 2-ethylpropyl, butyl, tert-butyl, or isobutyl.

In some embodiments of a compound of Formula (II), M is —N($R^4$)—$SO_2$—$R^5$, —C(O)—N($R^4R^5$), heteroaryl; each $R^4$ or $R^5$ is independently hydrogen or $C_1$-$C_6$ alkyl; $R^3$ is $R^{31}$, —$R^{30}OC(O)R^{31}$ or —$R^{30}OC(O)OR^{31}$; $R^{30}$ is —$CH_2$—, —CH($CH_3$)—; and $R^{31}$ is $C_1$-$C_{12}$ alkyl.

In some embodiments of a compound of Formula (II), M is —N($R^4$)—$SO_2$—$R^5$, —C(O)—N($R^4R^5$), heteroaryl; each $R^4$ or $R^5$ is independently hydrogen or methyl; $R^3$ is $R^{31}$, —$R^{30}OC(O)R^{31}$ or —$R^{30}OC(O)OR^{31}$; $R^{30}$ is —$CH_2$—, —CH($CH_3$)—; and $R^{31}$ is $C_1$-$C_{12}$ alkyl.

In some embodiments of a compound of Formula (II), M is —N($R^4$)—$SO_2$—$R^5$, —C(O)—N($R^4R^5$), heteroaryl; each $R^4$ or $R^5$ is independently hydrogen or $C_1$-$C_6$ alkyl; $R^3$ is $R^{31}$, —$R^{30}OC(O)R^{31}$ or —$R^{30}OC(O)OR^{31}$; $R^{30}$ is —$CH_2$—, —CH($CH_3$)—; and $R^{31}$ is methyl, ethyl, propyl, isopropyl, 2-ethylpropyl, butyl, tert-butyl, or isobutyl.

In some embodiments of a compound of Formula (II), M is —N($R^4$)—$SO_2$—$R^5$, —C(O)—N($R^4R^5$), heteroaryl; each $R^4$ or $R^5$ is independently hydrogen or methyl; $R^3$ is $R^{31}$, —$R^{30}OC(O)R^{31}$ or —$R^{30}OC(O)OR^{31}$; $R^{30}$ is —$CH_2$—, —CH($CH_3$)—; and $R^{31}$ is methyl, ethyl, propyl, isopropyl, 2-ethylpropyl, butyl, tert-butyl, or isobutyl.

In some embodiments of a compound of Formula (II), M is hydrogen; $R^3$ is $R^{31}$; and $R^{31}$ is $C_4$-$C_{12}$ alkyl.

In some embodiments of a compound of Formula (II), M is hydrogen; $R^3$ is $R^{31}$; and $R^{31}$ is 2-ethylpropyl, butyl, tert-butyl, or isobutyl.

In some embodiments of a compound of Formula (II), M is —CN; $R^3$ is $R^{31}$; and $R^{31}$ is $C_4$-$C_{12}$ alkyl.

In some embodiments of a compound of Formula (II), M is —CN; $R^3$ is $R^{31}$; and $R^{31}$ is 2-ethylpropyl, butyl, tert-butyl, or isobutyl.

In some embodiments of a compound of Formula (II), M is alkynyl; $R^3$ is $R^{31}$; and $R^{31}$ is $C_4$-$C_{12}$ alkyl.

In some embodiments of a compound of Formula (II), M is alkynyl; $R^3$ is $R^{31}$; and $R^{31}$ is 2-ethylpropyl, butyl, tert-butyl, or isobutyl.

In some embodiments of a compound of Formula (II), M is —C(O)—$R^4$; $R^4$ is $C_1$-$C_6$ alkyl; $R^3$ is $R^{31}$; and $R^{31}$ is $C_4$-$C_{12}$ alkyl.

In some embodiments of a compound of Formula (II), M is —C(O)—$R^4$; $R^4$ is methyl; $R^3$ is $R^{31}$; and $R^{31}$ is $C_4$-$C_{12}$ alkyl.

In some embodiments of a compound of Formula (II), M is —C(O)—$R^4$; $R^4$ is $C_1$-$C_6$ alkyl; $R^3$ is $R^{31}$; and $R^{31}$ is 2-ethylpropyl, butyl, tert-butyl, or isobutyl.

In some embodiments of a compound of Formula (II), M is —C(O)—$R^4$; $R^4$ is methyl; $R^3$ is $R^{31}$; and $R^{31}$ is 2-ethylpropyl, butyl, tert-butyl, or isobutyl.

In some embodiments of a compound of Formula (II), M is —N($R^4$)—$SO_2$—$R^5$, —C(O)—N($R^4R^5$), heteroaryl; each $R^4$ or $R^5$ is independently hydrogen or $C_1$-$C_6$ alkyl; $R^3$ is $R^{31}$; and $R^{31}$ is $C_4$-$C_{12}$ alkyl.

In some embodiments of a compound of Formula (II), M is —N($R^4$)—$SO_2$—$R^5$, —C(O)—N($R^4R^5$), heteroaryl; each $R^4$ or $R^5$ is independently hydrogen or methyl; $R^3$ is $R^{31}$; and $R^{31}$ is $C_4$-$C_{12}$ alkyl.

In some embodiments of a compound of Formula (II), M is —N($R^4$)—$SO_2$—$R^5$, —C(O)—N($R^4R^5$), heteroaryl; each $R^4$ or $R^5$ is independently hydrogen or $C_1$-$C_6$ alkyl; $R^3$ is $R^{31}$; and $R^{31}$ is 2-ethylpropyl, butyl, tert-butyl, or isobutyl.

In some embodiments of a compound of Formula (II), M is —N($R^4$)—$SO_2$—$R^5$, —C(O)—N($R^4R^5$), heteroaryl; each $R^4$ or $R^5$ is independently hydrogen or methyl; $R^3$ is $R^{31}$; and $R^{31}$ is 2-ethylpropyl, butyl, tert-butyl, or isobutyl.

In some embodiments of a compound of Formula (II), M is hydrogen; $R^3$ is —$R^{30}OC(O)OR^{31}$ or —$R^{30}OC(O)R^{31}$; $R^{30}$ is —$CH_2$—; and $R^{31}$ is $C_1$-$C_{12}$ alkyl or aryl.

In some embodiments of a compound of Formula (II), M is hydrogen; $R^3$ is —$R^{30}OC(O)OR^{31}$ or —$R^{30}OC(O)R^{31}$; $R^{30}$ is —$CH_2$—; and $R^{31}$ is methyl, ethyl, propyl, isopropyl, 2-ethylpropyl, butyl, tert-butyl, isobutyl, or phenyl.

In some embodiments of a compound of Formula (II), M is —CN; $R^3$ is —$R^{30}$OC(O)O$R^{31}$ or —$R^{30}$OC(O)$R^{31}$; $R^{30}$ is —CH$_2$—; and $R^{31}$ is $C_1$-$C_{12}$ alkyl or aryl.

In some embodiments of a compound of Formula (II), M is —CN; $R^3$ is —$R^{30}$OC(O)O$R^{31}$ or —$R^{30}$OC(O)$R^{31}$; $R^{30}$ is —CH$_2$—; and $R^{31}$ is methyl, ethyl, propyl, isopropyl, 2-ethylpropyl, butyl, tert-butyl, isobutyl, or phenyl.

In some embodiments of a compound of Formula (II), M is alkynyl; $R^3$ is —$R^{30}$OC(O)O$R^{31}$ or —$R^{30}$OC(O)$R^{31}$; $R^{30}$ is —CH$_2$—; and $R^{31}$ is $C_1$-$C_{12}$ alkyl or aryl.

In some embodiments of a compound of Formula (II), M is alkynyl; $R^3$ is —$R^{30}$OC(O)O$R^{31}$ or —$R^{30}$OC(O)$R^{31}$; $R^{30}$ is —CH$_2$—; and $R^{31}$ is methyl, ethyl, propyl, isopropyl, 2-ethylpropyl, butyl, tert-butyl, isobutyl, or phenyl.

In some embodiments of a compound of Formula (II), M is —C(O)—$R^4$; $R^4$ is $C_1$-$C_6$ alkyl; $R^3$ is —$R^{30}$OC(O)O$R^{31}$ or —$R^{30}$OC(O)$R^{31}$; $R^{30}$ is —CH$_2$—; and $R^{31}$ is $C_1$-$C_{12}$ alkyl or aryl.

In some embodiments of a compound of Formula (II), M is —C(O)—$R^4$; $R^4$ is methyl; $R^3$ is —$R^{30}$OC(O)O$R^{31}$ or —$R^{30}$OC(O)$R^{31}$; $R^{30}$ is —CH$_2$—; and $R^{31}$ is $C_1$-$C_{12}$ alkyl or aryl.

In some embodiments of a compound of Formula (II), M is —C(O)—$R^4$; $R^4$ is $C_1$-$C_6$ alkyl; $R^3$ is —$R^{30}$OC(O)O$R^{31}$ or —$R^{30}$OC(O)$R^{31}$; $R^{30}$ is —CH$_2$—; and $R^{31}$ is methyl, ethyl, propyl, isopropyl, 2-ethylpropyl, butyl, tert-butyl, isobutyl, or phenyl.

In some embodiments of a compound of Formula (II), M is —C(O)—$R^4$; $R^4$ is methyl; $R^3$ is —$R^{30}$OC(O)O$R^{31}$ or —$R^{30}$OC(O)$R^{31}$; $R^{30}$ is —CH$_2$—; and $R^{31}$ is methyl, ethyl, propyl, isopropyl, 2-ethylpropyl, butyl, tert-butyl, isobutyl, or phenyl.

In some embodiments of a compound of Formula (II), M is —N($R^4$)—SO$_2$—$R^5$, —C(O)—N($R^4R^5$), heteroaryl; each $R^4$ or $R^5$ is independently hydrogen or $C_1$-$C_6$ alkyl; $R^3$ is —$R^{30}$OC(O)O$R^{31}$ or —$R^{30}$OC(O)$R^{31}$; $R^{30}$ is —CH$_2$—; and $R^{31}$ is $C_1$-$C_{12}$ alkyl or aryl.

In some embodiments of a compound of Formula (II), M is —N($R^4$)—SO$_2$—$R^5$, —C(O)—N($R^4R^5$), heteroaryl; each $R^4$ or $R^5$ is independently hydrogen or methyl; $R^3$ is —$R^{30}$OC(O)O$R^{31}$ or —$R^{30}$OC(O)$R^{31}$; $R^{30}$ is —CH$_2$—; and $R^{31}$ is $C_1$-$C_{12}$ alkyl or aryl.

In some embodiments of a compound of Formula (II), M is —N($R^4$)—SO$_2$—$R^5$, —C(O)—N($R^4R^5$), heteroaryl; each $R^4$ or $R^5$ is independently hydrogen or $C_1$-$C_6$ alkyl; $R^3$ is —$R^{30}$OC(O)O$R^{31}$ or —$R^{30}$OC(O)$R^{31}$; $R^{30}$ is —CH$_2$—; and $R^{31}$ is methyl, ethyl, propyl, isopropyl, 2-ethylpropyl, butyl, tert-butyl, isobutyl, or phenyl.

In some embodiments of a compound of Formula (II), M is —N($R^4$)—SO$_2$—$R^5$, —C(O)—N($R^4R^5$), heteroaryl; each $R^4$ or $R^5$ is independently hydrogen or methyl; $R^3$ is —$R^{30}$OC(O)O$R^{31}$ or —$R^{30}$OC(O)$R^{31}$; $R^{30}$ is —CH$_2$—; and $R^{31}$ is methyl, ethyl, propyl, isopropyl, 2-ethylpropyl, butyl, tert-butyl, isobutyl, or phenyl.

In some embodiments of a compound of Formula (II), M is hydrogen, —CN, —SO$_2$—N($R^4R^5$), —N($R^4$)—C(O)—N($R^4R^5$), —N($R^4$)—SO$_2$—$R^5$, —C(O)—$R^4$, —C(O)—N($R^4R^5$), optionally substituted alkynyl, heteroaryl, or heterocycloalkyl; $R^3$ is —$R^{30}$OC(O)$R^{31}$; $R^{30}$ is —CH$_2$—, —CH(CH$_3$)—, —C(CH$_3$)$_2$—, or optionally substituted 1,1'-cyclopropylene; and $R^{31}$ is optionally substituted $C_1$-$C_{12}$ alkyl.

In some embodiments of a compound of Formula (II), M is hydrogen, —CN, —SO$_2$—N($R^4R^5$), —N($R^4$)—C(O)—N($R^4R^5$), —N($R^4$)—SO$_2$—$R^5$, —C(O)—$R^4$, —C(O)—N($R^4R^5$), optionally substituted alkynyl, heteroaryl, or heterocycloalkyl; $R^3$ is —$R^{30}$OC(O)$R^{31}$; $R^{30}$ is —CH$_2$—; and $R^{31}$ is optionally substituted $C_1$-$C_{12}$ alkyl.

In some embodiments of a compound of Formula (II), M is hydrogen, —CN, —SO$_2$—N($R^4R^5$), —N($R^4$)—C(O)—N($R^4R^5$), —N($R^4$)—SO$_2$—$R^5$, —C(O)—$R^4$, —C(O)—N($R^4R^5$), optionally substituted alkynyl, heteroaryl, or heterocycloalkyl; $R^3$ is —$R^{30}$OC(O)$R^{31}$; $R^{30}$ is —CH(CH$_3$)—; and $R^{31}$ is optionally substituted $C_1$-$C_{12}$ alkyl.

In some embodiments of a compound of Formula (II), M is hydrogen, —CN, —SO$_2$—N($R^4R^5$), —N($R^4$)—C(O)—N($R^4R^5$), —N($R^4$)—SO$_2$—$R^5$, —C(O)—$R^4$, —C(O)—N($R^4R^5$), optionally substituted alkynyl, heteroaryl, or heterocycloalkyl; $R^3$ is —$R^{30}$OC(O)$R^{31}$; $R^{30}$ is —CH$_2$—; and $R^{31}$ is $C_1$-$C_{12}$ alkyl.

In some embodiments of a compound of Formula (II), M is hydrogen, —CN, —SO$_2$—N($R^4R^5$), —N($R^4$)—C(O)—N($R^4R^5$), —N($R^4$)—SO$_2$—$R^5$, —C(O)—$R^4$, —C(O)—N($R^4R^5$), optionally substituted alkynyl, heteroaryl, or heterocycloalkyl; $R^3$ is —$R^{30}$OC(O)$R^{31}$; $R^{30}$ is —CH(CH$_3$)—; and $R^{31}$ is $C_1$-$C_{12}$ alkyl.

In some embodiments of a compound of Formula (II), M is hydrogen, —CN, —SO$_2$—N($R^4R^5$), —N($R^4$)—C(O)—N($R^4R^5$), —N($R^4$)—SO$_2$—$R^5$, —C(O)—$R^4$, —C(O)—N($R^4R^5$), optionally substituted alkynyl, heteroaryl, or heterocycloalkyl; each R and R are independently hydrogen or $C_1$-$C_6$ alkyl; $R^3$ is —$R^{30}$OC(O)$R^{31}$; $R^{30}$ is —CH$_2$—; and $R^{31}$ is $C_1$-$C_{12}$ alkyl.

In some embodiments of a compound of Formula (II), M is hydrogen, —CN, —SO$_2$—N($R^4R^5$), —N($R^4$)—C(O)—N($R^4R^5$), —N($R^4$)—SO$_2$—$R^5$, —C(O)—$R^4$, —C(O)—N($R^4R^5$), optionally substituted alkynyl, heteroaryl, or heterocycloalkyl; each $R^4$ and $R^5$ are independently hydrogen or $C_1$-$C_6$ alkyl; $R^3$ is —$R^{30}$OC(O)$R^{31}$; $R^{30}$ is —CH(CH$_3$)—; and $R^{31}$ is $C_1$-$C_{12}$ alkyl.

In some embodiments of a compound of Formula (II), M is hydrogen, —CN, —C(O)—$R^4$, or optionally substituted alkynyl; $R^3$ is —$R^{30}$OC(O)$R^{31}$; $R^{30}$ is —CH$_2$—, —CH(CH$_3$)—, —C(CH$_3$)$_2$—, or optionally substituted 1,1'-cyclopropylene; and $R^{31}$ is optionally substituted $C_1$-$C_{12}$ alkyl.

In some embodiments of a compound of Formula (II), M is hydrogen, —CN, —C(O)—$R^4$, or alkynyl; $R^3$ is —$R^{30}$OC(O)$R^{31}$; $R^{30}$ is —CH$_2$—, —CH(CH$_3$)—, —C(CH$_3$)$_2$—, or optionally substituted 1,1'-cyclopropylene; and $R^{31}$ is optionally substituted $C_1$-$C_{12}$ alkyl.

In some embodiments of a compound of Formula (II), M is hydrogen, —CN, —C(O)—$R^4$, or alkynyl; $R^3$ is —$R^{30}$OC(O)$R^{31}$; $R^{30}$ is —CH$_2$—; and $R^{31}$ is optionally substituted $C_1$-$C_{12}$ alkyl.

In some embodiments of a compound of Formula (II), M is hydrogen, —CN, —C(O)—$R^4$, or alkynyl; $R^3$ is —$R^{30}$OC(O)$R^{31}$; $R^{30}$ is —CH(CH$_3$)—; and $R^{31}$ is optionally substituted $C_1$-$C_{12}$ alkyl.

In some embodiments of a compound of Formula (II), M is hydrogen, —CN, —C(O)—$R^4$, or alkynyl; $R^3$ is —$R^{30}$OC(O)$R^{31}$; $R^{30}$ is —CH$_2$—; and $R^{31}$ is $C_1$-$C_{12}$ alkyl.

In some embodiments of a compound of Formula (II), M is hydrogen, —CN, —C(O)—$R^4$, or alkynyl; $R^3$ is —$R^{30}$OC(O)$R^{31}$; $R^{30}$ is —CH(CH$_3$)—; and $R^{31}$ is $C_1$-$C_{12}$ alkyl.

In some embodiments of a compound of Formula (II), M is hydrogen, —CN, —C(O)—$R^4$, or alkynyl; $R^4$ is optionally substituted $C_1$-$C_6$ alkyl; $R^3$ is —$R^{30}$OC(O)$R^{31}$; $R^{30}$ is —CH$_2$—; and $R^{31}$ is $C_1$-$C_{12}$ alkyl.

In some embodiments of a compound of Formula (II), M is hydrogen, —CN, —C(O)—$R^4$, or alkynyl; $R^4$ is optionally substituted $C_1$-$C_6$ alkyl; $R^3$ is —$R^{30}$OC(O)$R^{31}$; $R^{30}$ is —CH(CH$_3$)—; and $R^{31}$ is $C_1$-$C_{12}$ alkyl.

In some embodiments of a compound of Formula (II), M is hydrogen, —CN, —C(O)—$R^4$, or alkynyl; $R^4$ is $C_1$-$C_6$ alkyl; $R^3$ is —$R^{30}$OC(O)$R^{31}$; $R^{30}$ is —$CH_2$—; and $R^{31}$ is $C_1$-$C_{12}$ alkyl.

In some embodiments of a compound of Formula (II), M is hydrogen, —CN, —C(O)—$R^4$, or alkynyl; $R^4$ is $C_1$-$C_6$ alkyl; $R^3$ is —$R^{30}$OC(O)$R^{31}$; $R^{30}$ is —CH($CH_3$)—; and $R^{31}$ is $C_1$-$C_{12}$ alkyl.

In some embodiments of a compound of Formula (II), M is hydrogen, —CN, —$SO_2$—N($R^4R^5$), —N($R^4$)—C(O)—N($R^4R^5$), —N($R^4$)—$SO_2$—$R^5$, —C(O)—$R^4$, —C(O)—N($R^4R^5$), optionally substituted alkynyl, heteroaryl, or heterocycloalkyl; $R^3$ is —$R^{30}$OC(O)$R^{31}$; $R^{30}$ is —$CH_2$—, —CH($CH_3$)—, —C($CH_3$)$_2$—, or optionally substituted 1,1'-cyclopropylene; and $R^{31}$ is optionally substituted aryl.

In some embodiments of a compound of Formula (II), M is hydrogen, —CN, —$SO_2$—N($R^4R^5$), —N($R^4$)—C(O)—N($R^4R^5$), —N($R^4$)—$SO_2$—$R^5$, —C(O)—$R^4$, —C(O)—N($R^4R^5$), optionally substituted alkynyl, heteroaryl, or heterocycloalkyl; $R^3$ is —$R^{30}$OC(O)$R^{31}$; $R^{30}$ is —$CH_2$—; and $R^{31}$ is optionally substituted aryl.

In some embodiments of a compound of Formula (II), M is hydrogen, —CN, —$SO_2$—N($R^4R^5$), —N($R^4$)—C(O)—N($R^4R^5$), —N($R^4$)—$SO_2$—$R^5$, —C(O)—$R^4$, —C(O)—N($R^4R^5$), optionally substituted alkynyl, heteroaryl, or heterocycloalkyl; $R^3$ is —$R^{30}$OC(O)$R^{31}$; $R^{30}$ is —CH($CH_3$)—; and $R^{31}$ is optionally substituted aryl.

In some embodiments of a compound of Formula (II), M is hydrogen, —CN, —$SO_2$—N($R^4R^5$), —N($R^4$)—C(O)—N($R^4R^5$), —N($R^4$)—$SO_2$—$R^5$, —C(O)—$R^4$, —C(O)—N($R^4R^5$), optionally substituted alkynyl, heteroaryl, or heterocycloalkyl; $R^3$ is —$R^{30}$OC(O)$R^{31}$; $R^{30}$ is —$CH_2$—; and $R^{31}$ is aryl.

In some embodiments of a compound of Formula (II), M is hydrogen, —CN, —$SO_2$—N($R^4R^5$), —N($R^4$)—C(O)—N($R^4R^5$), —N($R^4$)—$SO_2$—$R^5$, —C(O)—$R^4$, —C(O)—N($R^4R^5$), optionally substituted alkynyl, heteroaryl, or heterocycloalkyl; $R^3$ is —$R^{30}$OC(O)$R^{31}$; $R^{30}$ is —CH($CH_3$)—; and $R^{31}$ is aryl.

In some embodiments of a compound of Formula (II), M is hydrogen, —CN, —$SO_2$—N($R^4R^5$), —N($R^4$)—C(O)—N($R^4R^5$), —N($R^4$)—$SO_2$—$R^5$, —C(O)—$R^4$, —C(O)—N($R^4R^5$), optionally substituted alkynyl, heteroaryl, or heterocycloalkyl; each $R^4$ and $R^5$ are independently hydrogen or $C_1$-$C_6$ alkyl; $R^3$ is —$R^{30}$OC(O)$R^{31}$; $R^{30}$ is —$CH_2$—; and $R^{31}$ is aryl.

In some embodiments of a compound of Formula (II), M is hydrogen, —CN, —$SO_2$—N($R^4R^5$), —N($R^4$)—C(O)—N($R^4R^5$), —N($R^4$)—$SO_2$—$R^5$, —C(O)—$R^4$, —C(O)—N($R^4R^5$), optionally substituted alkynyl, heteroaryl, or heterocycloalkyl; each $R^4$ and $R^5$ are independently hydrogen or $C_1$-$C_6$ alkyl; $R^3$ is —$R^{30}$OC(O)$R^{31}$; $R^{30}$ is —CH($CH_3$)—; and $R^{31}$ is aryl.

In some embodiments of a compound of Formula (II), M is hydrogen, —CN, —C(O)—$R^4$, optionally substituted alkynyl; $R^3$ is —$R^{30}$OC(O)$R^{31}$; $R^{30}$ is —$CH_2$—, —CH($CH_3$)—, —C($CH_3$)$_2$—, or optionally substituted 1,1'-cyclopropylene; and $R^{31}$ is optionally substituted aryl.

In some embodiments of a compound of Formula (II), M is hydrogen, —CN, —C(O)—$R^4$, optionally substituted alkynyl; $R^3$ is —$R^{30}$OC(O)$R^{31}$; $R^{30}$ is —$CH_2$—; and $R^{31}$ is optionally substituted aryl.

In some embodiments of a compound of Formula (II), M is hydrogen, —CN, —C(O)—$R^4$, optionally substituted alkynyl; $R^3$ is —$R^{30}$OC(O)$R^{31}$; $R^{30}$ is —CH($CH_3$)—; and $R^{31}$ is optionally substituted aryl.

In some embodiments of a compound of Formula (II), M is hydrogen, —CN, —C(O)—$R^4$, optionally substituted alkynyl; $R^3$ is —$R^{30}$OC(O)$R^{31}$; $R^{30}$ is —$CH_2$—; and $R^{31}$ is aryl.

In some embodiments of a compound of Formula (II), M is hydrogen, —CN, —C(O)—$R^4$, optionally substituted alkynyl; $R^3$ is —$R^{30}$OC(O)$R^{31}$; $R^{30}$ is —CH($CH_3$)—; and $R^{31}$ is aryl.

In some embodiments of a compound of Formula (II), M is hydrogen, —CN, —C(O)—$R^4$, optionally substituted alkynyl; $R^4$ is $C_1$-$C_6$ alkyl; $R^3$ is —$R^{30}$OC(O)$R^{31}$; $R^{30}$ is —$CH_2$—; and $R^{31}$ is aryl.

In some embodiments of a compound of Formula (II), M is hydrogen, —CN, —C(O)—$R^4$, optionally substituted alkynyl; $R^4$ is $C_1$-$C_6$ alkyl; $R^3$ is —$R^{30}$OC(O)$R^{31}$; $R^{30}$ is —CH($CH_3$)—; and $R^{31}$ is aryl.

In some embodiments of a compound of Formula (II), M is hydrogen, —CN, —$SO_2$—N($R^4R^5$), —N($R^4$)—C(O)—N($R^4R^5$), —N($R^4$)—$SO_2$—$R^5$, —C(O)—$R^4$, —C(O)—N($R^4R^5$), optionally substituted alkynyl, heteroaryl, or heterocycloalkyl; $R^3$ is —$R^{30}$OC(O)O$R^{31}$; $R^{30}$ is —$CH_2$—, —CH($CH_3$)—, —C($CH_3$)$_2$—, or optionally substituted 1,1'-cyclopropylene; and $R^{31}$ is optionally substituted $C_3$-$C_8$ cycloalkyl.

In some embodiments of a compound of Formula (II), M is hydrogen, —CN, —$SO_2$—N($R^4R^5$), —N($R^4$)—C(O)—N($R^4R^5$), —N($R^4$)—$SO_2$—$R^5$, —C(O)—$R^4$, —C(O)—N($R^4R^5$), optionally substituted alkynyl, heteroaryl, or heterocycloalkyl; $R^3$ is —$R^{30}$OC(O)O$R^{31}$; $R^{30}$ is —$CH_2$—; and $R^{31}$ is optionally substituted $C_3$-$C_8$ cycloalkyl.

In some embodiments of a compound of Formula (II), M is hydrogen, —CN, —$SO_2$—N($R^4R^5$), —N($R^4$)—C(O)—N($R^4R^5$), —N($R^4$)—$SO_2$—$R^5$, —C(O)—$R^4$, —C(O)—N($R^4R^5$), optionally substituted alkynyl, heteroaryl, or heterocycloalkyl; $R^3$ is —$R^{30}$OC(O)O$R^{31}$; $R^{30}$ is —CH($CH_3$)—; and $R^{31}$ is optionally substituted $C_3$-$C_8$ cycloalkyl.

In some embodiments of a compound of Formula (II), M is hydrogen, —CN, —$SO_2$—N($R^4R^5$), —N($R^4$)—C(O)—N($R^4R^5$), —N($R^4$)—$SO_2$—$R^5$, —C(O)—$R^4$, —C(O)—N($R^4R^5$), optionally substituted alkynyl, heteroaryl, or heterocycloalkyl; $R^3$ is —$R^{30}$OC(O)O$R^{31}$; $R^{30}$ is —$CH_2$—; and $R^{31}$ is $C_3$-$C_8$ cycloalkyl.

In some embodiments of a compound of Formula (II), M is hydrogen, —CN, —$SO_2$—N($R^4R^5$), —N($R^4$)—C(O)—N($R^4R^5$), —N($R^4$)—$SO_2$—$R^5$, —C(O)—$R^4$, —C(O)—N($R^4R^5$), optionally substituted alkynyl, heteroaryl, or heterocycloalkyl; $R^3$ is —$R^{30}$OC(O)O$R^{31}$; $R^{30}$ is —CH($CH_3$)—; and $R^{31}$ is $C_3$-$C_8$ cycloalkyl.

In some embodiments of a compound of Formula (II), M is hydrogen, —CN, —$SO_2$—N($R^4R^5$), —N($R^4$)—C(O)—N($R^4R^5$), —N($R^4$)—$SO_2$—$R^5$, —C(O)—$R^4$, —C(O)—N($R^4R^5$), optionally substituted alkynyl, heteroaryl, or heterocycloalkyl; each $R^4$ and $R^5$ are independently H or $C_1$-$C_6$ alkyl; $R^3$ is —$R^{30}$OC(O)O$R^{31}$; $R^{30}$ is —$CH_2$—; and $R^{31}$ is $C_3$-$C_8$ cycloalkyl.

In some embodiments of a compound of Formula (II), M is hydrogen, —CN, —$SO_2$—N($R^4R^5$), —N($R^4$)—C(O)—N($R^4R^5$), —N($R^4$)—$SO_2$—$R^5$, —C(O)—$R^4$, —C(O)—N($R^4R^5$), optionally substituted alkynyl, heteroaryl, or heterocycloalkyl; each $R^4$ and $R^5$ are independently H or $C_1$-$C_6$ alkyl; $R^3$ is —$R^{30}$OC(O)O$R^{31}$; $R^{30}$ is —CH($CH_3$)—; and $R^{31}$ is $C_3$-$C_8$ cycloalkyl.

In some embodiments of a compound of Formula (II), M is hydrogen, —CN, —C(O)—$R^4$, or optionally substituted alkynyl; $R^3$ is —$R^{30}$OC(O)O$R^{31}$; $R^{30}$ is —$CH_2$—, —CH (CH$_3$)—, —C(CH$_3$)$_2$—, or optionally substituted 1,1'-cyclopropylene; and R$^{31}$ is optionally substituted C$_3$-C$_8$ cycloalkyl.

In some embodiments of a compound of Formula (II), M is hydrogen, —CN, —C(O)—R$^4$, or alkynyl; R$^3$ is —R$^{30}$OC(O)OR$^{31}$; R$^{30}$ is —CH$_2$—, —CH(CH$_3$)—, —C(CH$_3$)$_2$—, or optionally substituted 1,1'-cyclopropylene; and R$^{31}$ is optionally substituted C$_3$-C$_8$ cycloalkyl.

In some embodiments of a compound of Formula (II), M is hydrogen, —CN, —C(O)—R$^4$, or alkynyl; R$^3$ is —R$^{30}$OC(O)OR$^{31}$; R$^{30}$ is —CH$_2$—; and R$^{31}$ is optionally substituted C$_3$-C$_8$ cycloalkyl.

In some embodiments of a compound of Formula (II), M is hydrogen, —CN, —C(O)—R$^4$, or alkynyl; R$^3$ is —R$^{30}$OC(O)OR$^{31}$; R$^{30}$ is —CH(CH$_3$)—; and R$^{31}$ is optionally substituted C$_3$-C$_8$ cycloalkyl.

In some embodiments of a compound of Formula (II), M is hydrogen, —CN, —C(O)—R$^4$, or alkynyl; R$^3$ is —R$^{30}$OC(O)OR$^{31}$; R$^{30}$ is —CH$_2$—; and R$^{31}$ is C$_3$-C$_8$ cycloalkyl.

In some embodiments of a compound of Formula (II), M is hydrogen, —CN, —C(O)—R$^4$, or alkynyl; R$^3$ is —R$^{30}$OC(O)OR$^{31}$; R$^{30}$ is —CH(CH$_3$)—; and R$^{31}$ is C$_3$-C$_8$ cycloalkyl.

In some embodiments of a compound of Formula (II), M is hydrogen, —CN, —C(O)—R$^4$, or alkynyl; R$^4$ is optionally substituted C$_1$-C$_6$ alkyl; R$^3$ is —R$^{30}$OC(O)OR$^{31}$; R$^{30}$ is —CH$_2$—; and R$^{31}$ is C$_3$-C$_8$ cycloalkyl.

In some embodiments of a compound of Formula (II), M is hydrogen, —CN, —C(O)—R$^4$, or alkynyl; R$^4$ is optionally substituted C$_1$-C$_6$ alkyl; R$^3$ is —R$^{30}$OC(O)OR$^{31}$; R$^{30}$ is —CH(CH$_3$)—; and R$^{31}$ is C$_3$-C$_8$ cycloalkyl.

In some embodiments of a compound of Formula (II), M is hydrogen, —CN, —C(O)—R$^4$, or alkynyl; R$^4$ is C$_1$-C$_6$ alkyl; R$^3$ is —R$^{30}$OC(O)OR$^{31}$; R$^{30}$ is —CH$_2$—; and R$^{31}$ is C$_3$-C$_8$ cycloalkyl.

In some embodiments of a compound of Formula (II), M is hydrogen, —CN, —C(O)—R$^4$, or alkynyl; R$^4$ is C$_1$-C$_6$ alkyl; R$^3$ is —R$^{30}$OC(O)OR$^{31}$; R$^{30}$ is —CH(CH$_3$)—; and R$^{31}$ is C$_3$-C$_8$ cycloalkyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; R$^3$ is —R$^{30}$OC(O)OR$^{31}$; R$^{30}$ is —CH$_2$—, —CH(CH$_3$)—, —C(CH$_3$)$_2$—, or optionally substituted 1,1'-cyclopropylene; and R$^{31}$ is optionally substituted C$_3$-C$_8$ heterocycloalkyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; R$^3$ is —R$^{30}$OC(O)OR$^{31}$; R$^{30}$ is —CH$_2$—; and R$^{31}$ is optionally substituted C$_3$-C$_8$ heterocycloalkyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; R$^3$ is —R$^{30}$OC(O)OR$^{31}$; R$^{30}$ is —CH(CH$_3$)—; and R$^{31}$ is optionally substituted C$_3$-C$_8$ heterocycloalkyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; R$^3$ is —R$^{30}$OC(O)OR$^{31}$; R$^{30}$ is —CH$_2$—; and R$^{31}$ is C$_3$-C$_8$ heterocycloalkyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; R$^3$ is —R$^{30}$OC(O)OR$^{31}$; R$^{30}$ is —CH(CH$_3$)—; and R$^{31}$ is C$_3$-C$_8$ heterocycloalkyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; each R$^4$ and R$^5$ are independently H or C$_1$-C$_6$ alkyl; R$^3$ is —R$^{30}$OC(O)OR$^{31}$; R$^{30}$ is —CH$_2$—; and R$^{31}$ is C$_3$-C$_8$ heterocycloalkyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; each R$^4$ and R$^5$ are independently H or C$_1$-C$_6$ alkyl; R$^3$ is —R$^{30}$OC(O)OR$^{31}$; R$^{30}$ is —CH(CH$_3$)—; and R$^{31}$ is C$_3$-C$_8$ heterocycloalkyl.

In some embodiments of a compound of Formula (II), M is hydrogen, —CN, —C(O)—R$^4$, or optionally substituted alkynyl; R$^3$ is —R$^{30}$OC(O)OR$^{31}$; R$^{30}$ is —CH$_2$—, —CH(CH$_3$)—, —C(CH$_3$)$_2$—, or optionally substituted 1,1'-cyclopropylene; and R$^{31}$ is optionally substituted C$_3$-C$_8$ heterocycloalkyl.

In some embodiments of a compound of Formula (II), M is hydrogen, —CN, —C(O)—R$^4$, or alkynyl; R$^3$ is —R$^{30}$OC(O)OR$^{31}$; R$^{30}$ is —CH$_2$—, —CH(CH$_3$)—, —C(CH$_3$)$_2$—, or optionally substituted 1,1'-cyclopropylene; and R$^{31}$ is optionally substituted C$_3$-C$_8$ heterocycloalkyl.

In some embodiments of a compound of Formula (II), M is hydrogen, —CN, —C(O)—R$^4$, or alkynyl; R$^3$ is —R$^{30}$OC(O)OR$^{31}$; R$^{30}$ is —CH$_2$—; and R$^{31}$ is optionally substituted C$_3$-C$_8$ heterocycloalkyl.

In some embodiments of a compound of Formula (II), M is hydrogen, —CN, —C(O)—R$^4$, or alkynyl; R$^3$ is —R$^{30}$OC(O)OR$^{31}$; R$^{30}$ is —CH(CH$_3$)—; and R$^{31}$ is optionally substituted C$_3$-C$_8$ heterocycloalkyl.

In some embodiments of a compound of Formula (II), M is hydrogen, —CN, —C(O)—R$^4$, or alkynyl; R$^3$ is —R$^{30}$OC(O)OR$^{31}$; R$^{30}$ is —CH$_2$—; and R$^{31}$ is C$_3$-C$_8$ heterocycloalkyl.

In some embodiments of a compound of Formula (II), M is hydrogen, —CN, —C(O)—R$^4$, or alkynyl; R$^3$ is —R$^{30}$OC(O)OR$^{31}$; R$^{30}$ is —CH(CH$_3$)—; and R$^{31}$ is C$_3$-C$_8$ heterocycloalkyl.

In some embodiments of a compound of Formula (II), M is hydrogen, —CN, —C(O)—R$^4$, or alkynyl; R$^4$ is optionally substituted C$_1$-C$_6$ alkyl; R$^3$ is —R$^{30}$OC(O)OR$^{31}$; R$^{30}$ is —CH$_2$—; and R$^{31}$ is C$_3$-C$_8$ heterocycloalkyl.

In some embodiments of a compound of Formula (II), M is hydrogen, —CN, —C(O)—R$^4$, or alkynyl; R$^4$ is optionally substituted C$_1$-C$_6$ alkyl; R$^3$ is —R$^{30}$OC(O)OR$^{31}$; R$^{30}$ is —CH(CH$_3$)—; and R$^{31}$ is C$_3$-C$_8$ heterocycloalkyl.

In some embodiments of a compound of Formula (II), M is hydrogen, —CN, —C(O)—R$^4$, or alkynyl; R$^4$ is C$_1$-C$_6$ alkyl; R$^3$ is —R$^{30}$OC(O)OR$^{31}$; R$^{30}$ is —CH$_2$—; and R$^{31}$ is C$_3$-C$_8$ heterocycloalkyl.

In some embodiments of a compound of Formula (II), M is hydrogen, —CN, —C(O)—R$^4$, or alkynyl; R$^4$ is C$_1$-C$_6$ alkyl; R$^3$ is —R$^{30}$OC(O)OR$^{31}$; R$^{30}$ is —CH(CH$_3$)—; and R$^{31}$ is C$_3$-C$_8$ heterocycloalkyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; R$^3$ is —R$^{31}$; and R$^{31}$ is optionally substituted C$_4$-C$_{12}$ alkyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; each R$^4$ and R$^5$ is independently hydrogen or optionally substituted C$_1$-C$_6$ alkyl; R$^3$ is —R$^{31}$; and R$^{31}$ is optionally substituted C$_4$-C$_{12}$ alkyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; each R$^4$ and R$^5$ is independently hydrogen or C$_1$-C$_6$ alkyl; R$^3$ is —R$^{31}$; and R$^{31}$ is optionally substituted C$_4$-C$_{12}$ alkyl.

In some embodiments of a compound of Formula (II), M is hydrogen, —CN, —SO$_2$—N(R$^4$R$^5$), —N(R$^4$)—C(O)—N(R$^4$R$^5$), —N(R$^4$)—SO$_2$—R$^5$, —C(O)—R$^4$, —C(O)—N(R$^4$R$^5$), optionally substituted alkynyl, heteroaryl, or heterocycloalkyl; each R$^4$ and R$^5$ is independently hydrogen or C$_1$-C$_6$ alkyl; R$^3$ is —R$^{31}$; and R$^{31}$ is C$_4$-C$_{12}$ alkyl.

In some embodiments of a compound of Formula (II), M is hydrogen, —CN, —C(O)—R$^4$, optionally substituted alkynyl; R$^4$ is optionally substituted C$_1$-C$_6$ alkyl; R$^3$ is —R$^{31}$; and R$^{31}$ is optionally substituted C$_4$-C$_{12}$ alkyl.

In some embodiments of a compound of Formula (II), M is hydrogen, —CN, —C(O)—R$^4$, optionally substituted alkynyl; R$^4$ is C$_1$-C$_6$ alkyl; R$^3$ is —R$^{31}$; and R$^{31}$ is optionally substituted C$_4$-C$_{12}$ alkyl.

In some embodiments of a compound of Formula (II), M is hydrogen, —CN, —C(O)—R$^4$, optionally substituted alkynyl; R$^4$ is C$_1$-C$_6$ alkyl; R$^3$ is —R$^{31}$; and R$^{31}$ is C$_4$-C$_{12}$ alkyl.

In some embodiments a compound of Formula (II) is a compound of Formula (IIi) or pharmaceutically acceptable salts, tautomers, or N-oxides thereof:

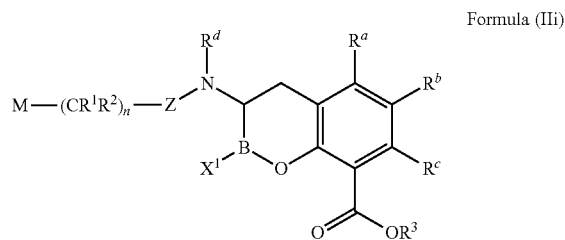

Formula (IIi)

wherein:
M is hydrogen, fluoro, chloro, bromo, —CF$_3$, —CN, —OR$^4$, —SR$^4$, —S(O)—R$^4$, —SO$_2$—R$^4$, —SO$_2$—N(R$^4$R$^5$), —N(R$^4$R$^5$), —N(R$^4$)—C(O)R$^5$, —N(R$^4$)—C(O)—N(R$^4$R$^5$), —N(R$^4$)—SO$_2$—R$^5$, —N(R$^4$)heteroaryl, —C(O)—R$^4$, —C(O)—N(R$^4$R$^5$), —C(O)(C$_1$-C$_3$alkyl)C(O)R$^5$, optionally substituted oxyimino, optionally substituted alkenyl, optionally substituted alkynyl, heteroaryl, or heterocycloalkyl;

each R$^1$ and R$^2$ is independently hydrogen, fluoro, chloro, bromo, optionally substituted C$_1$-C$_6$ alkyl, —CF$_3$, optionally substituted aryl, —OR$^4$, —SR$^4$, or —NR$^4$R$^5$; or R$^1$ and R$^2$ are taken together with the carbon to which they are attached to form an optionally substituted C$_3$-C$_8$ cycloalkyl; or when n is at least 2, two R$^1$ on adjacent carbons are taken together to form a double bond; or two R$^1$ and two R$^2$ on adjacent carbons are taken together to form a triple bond;

each n is independently 0, 1, 2, 3, 4, 5, or 6;

X$^1$ is independently —OR$^4$, or F;

Z is >C=O, >C=S, or >SO$_2$;

R$^3$ is R$^{31}$, —(R$^{30}$)$_q$OR$^{31}$, —(R$^{30}$)$_q$O(R$^{30}$)$_q$OR$^{31}$, —R$^{30}$OC(O)R$^{31}$, —R$^{30}$OC(O)OR$^{31}$, —R$^{30}$OC(O)NHR$^{31}$, —R$^{30}$OC(O)N(R$^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each q is independently 2, 3, 4, 5, or 6;

each R$^{30}$ is independently —CH$_2$—, —CH(CH$_3$)—, —C(CH$_3$)$_2$—, or optionally substituted 1,1'-cyclopropylene;

each R$^{31}$ is independently optionally substituted C$_1$-C$_{12}$ alkyl, optionally substituted C$_1$-C$_{12}$ alkenyl, optionally substituted C$_1$-C$_{12}$ alkynyl, optionally substituted C$_3$-C$_8$ cycloalkyl, optionally substituted C$_3$-C$_8$ heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl; or two R$^{31}$ are taken together with the nitrogen to which they are attached to form a C$_3$-C$_8$ heterocycloalkyl;

R$^a$, R$^b$, and R$^c$ are independently hydrogen, fluoro, chloro, bromo, optionally substituted C$_1$-C$_6$ alkyl, optionally substituted C$_3$-C$_6$ cycloalkyl, optionally substituted heterocycloalkyl, optionally substituted aryl, optionally substituted heteroaryl, —OR$^4$, —NR$^4$R$^5$, or —SR$^4$, with the proviso that at least one of R$^a$, R$^b$, and R$^c$ is not hydrogen;

R$^d$, R$^4$ and R$^5$ are independently hydrogen, —OH, —CN, —CF$_3$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;

or R$^4$ and R$^5$ taken together form an optionally substituted heterocycle with the nitrogen to which they are attached.

In some embodiments, the compound of Formula (II) is:

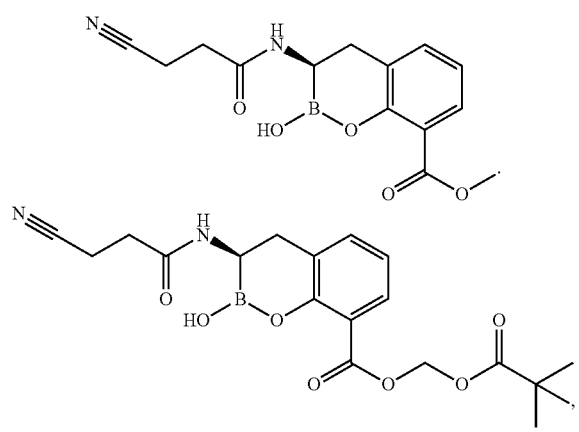

73
-continued
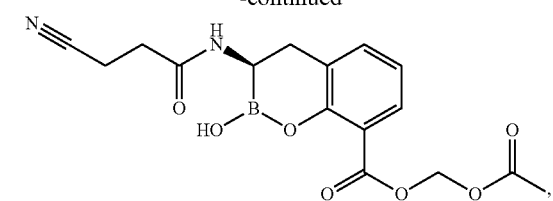
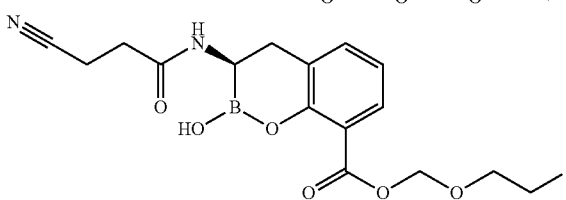
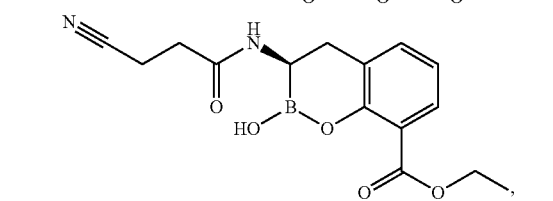
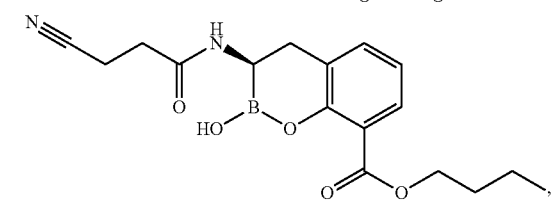
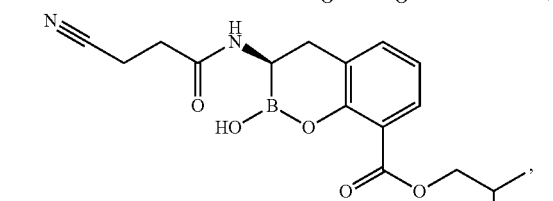
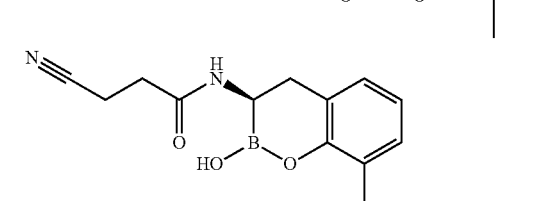
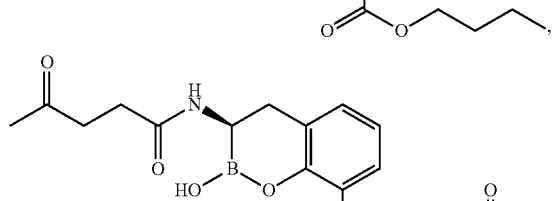
74
-continued
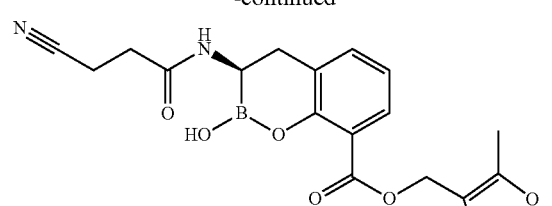
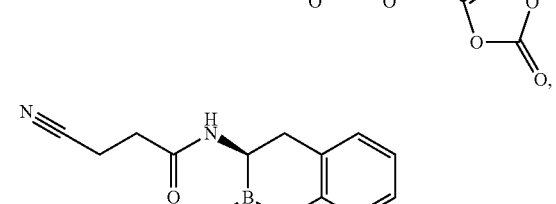
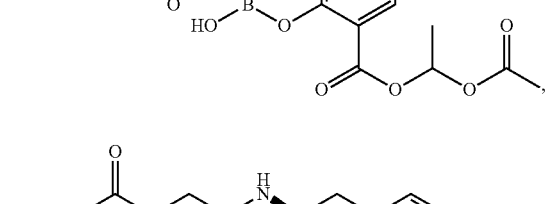
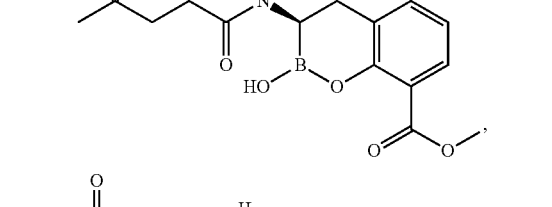
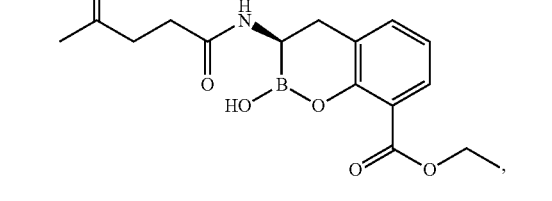
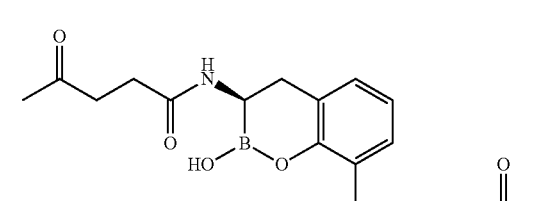
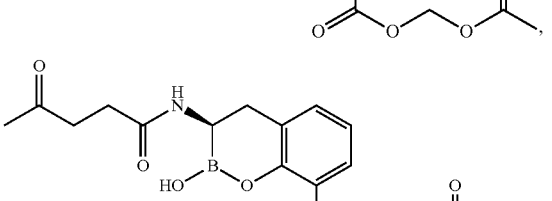

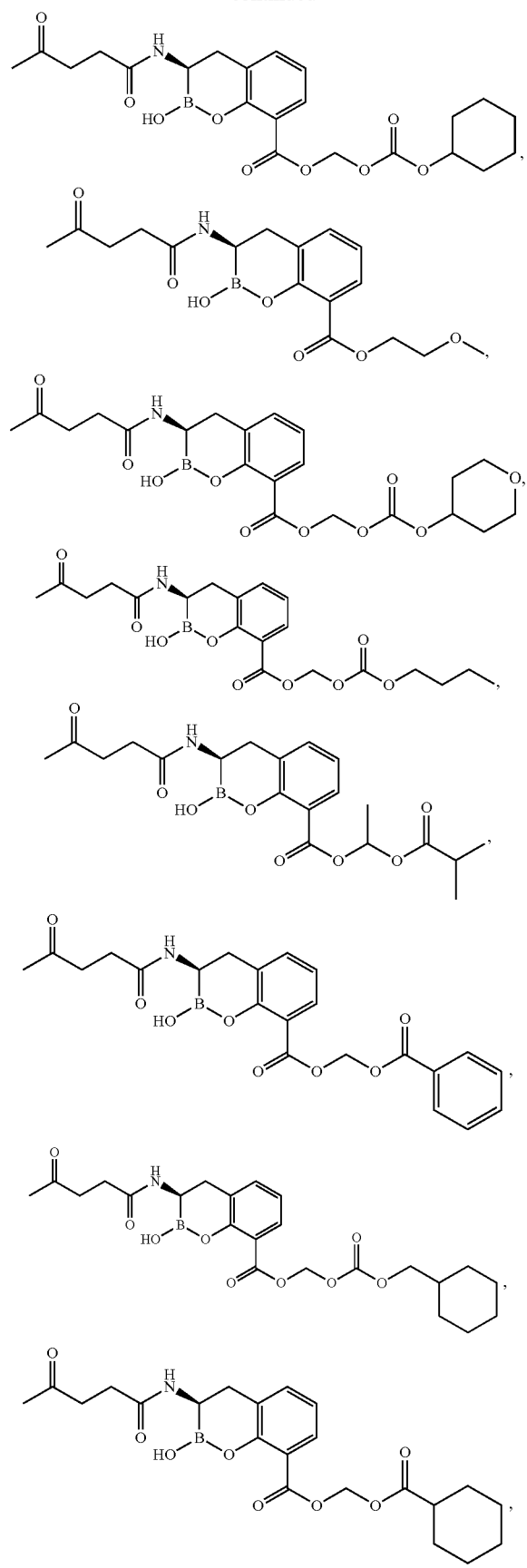
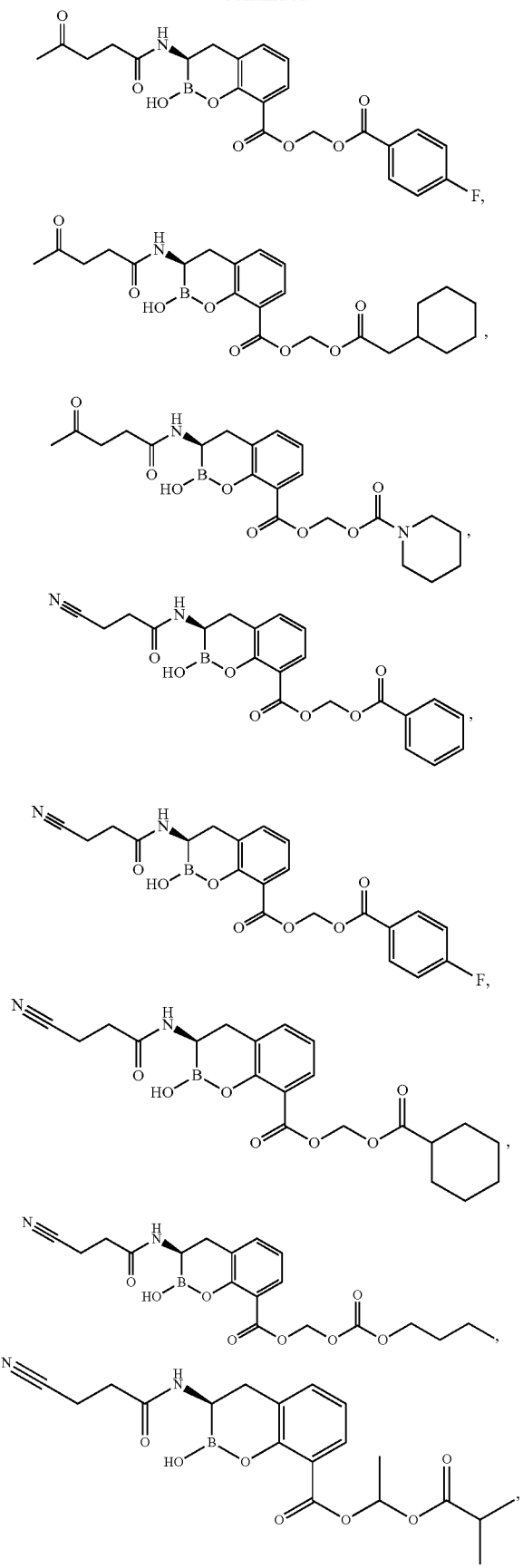

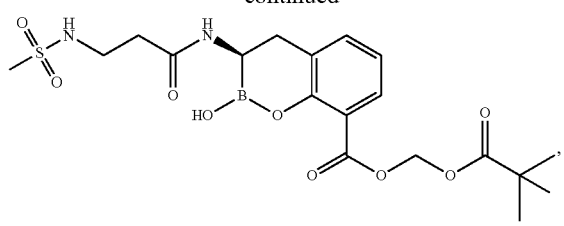
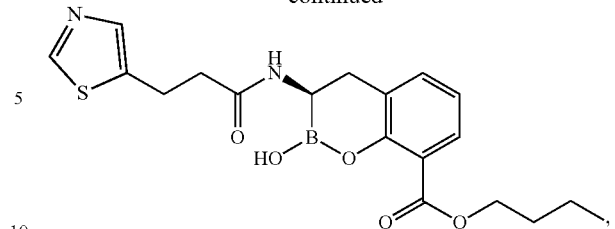

79
-continued
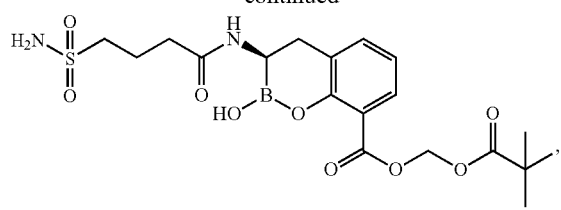
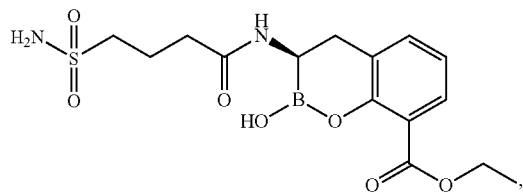
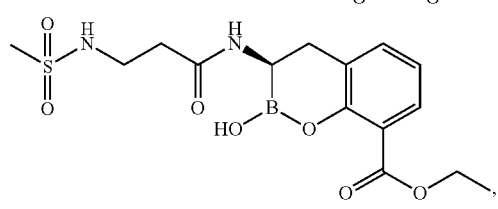
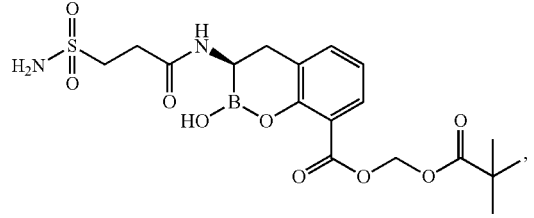
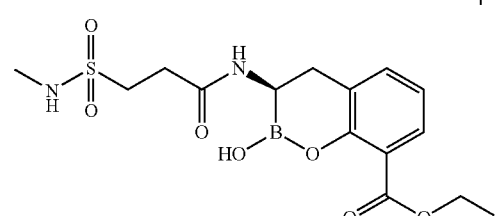
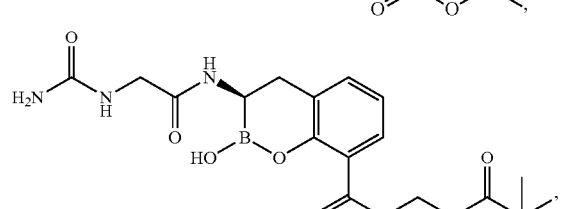
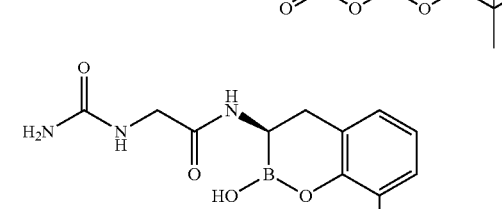
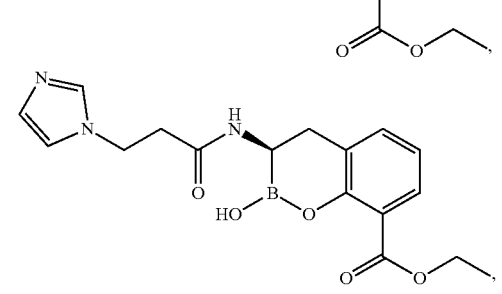
80
-continued
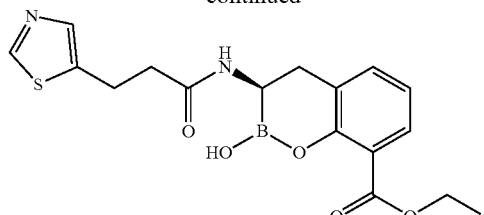
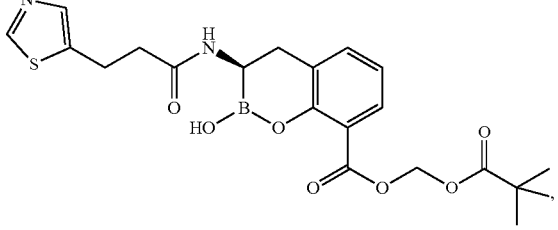
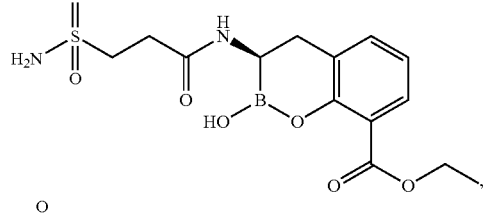
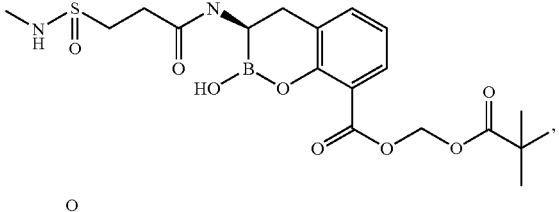
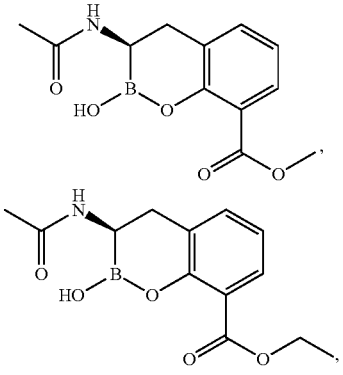

-continued

83
-continued
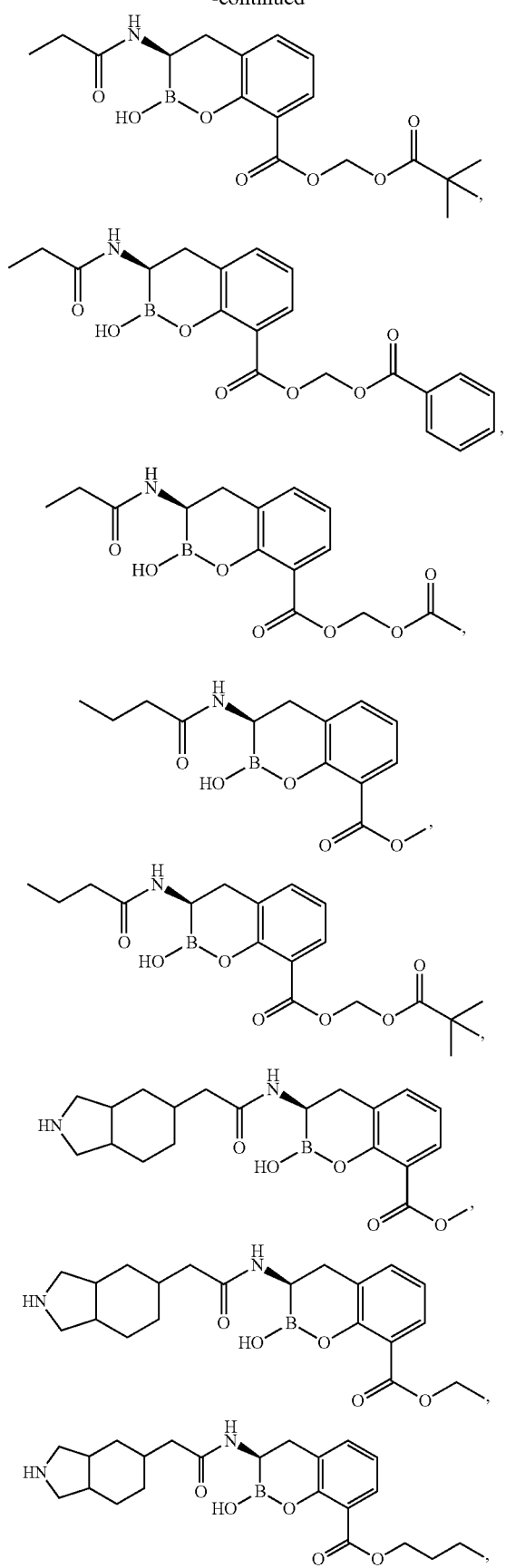
84
-continued
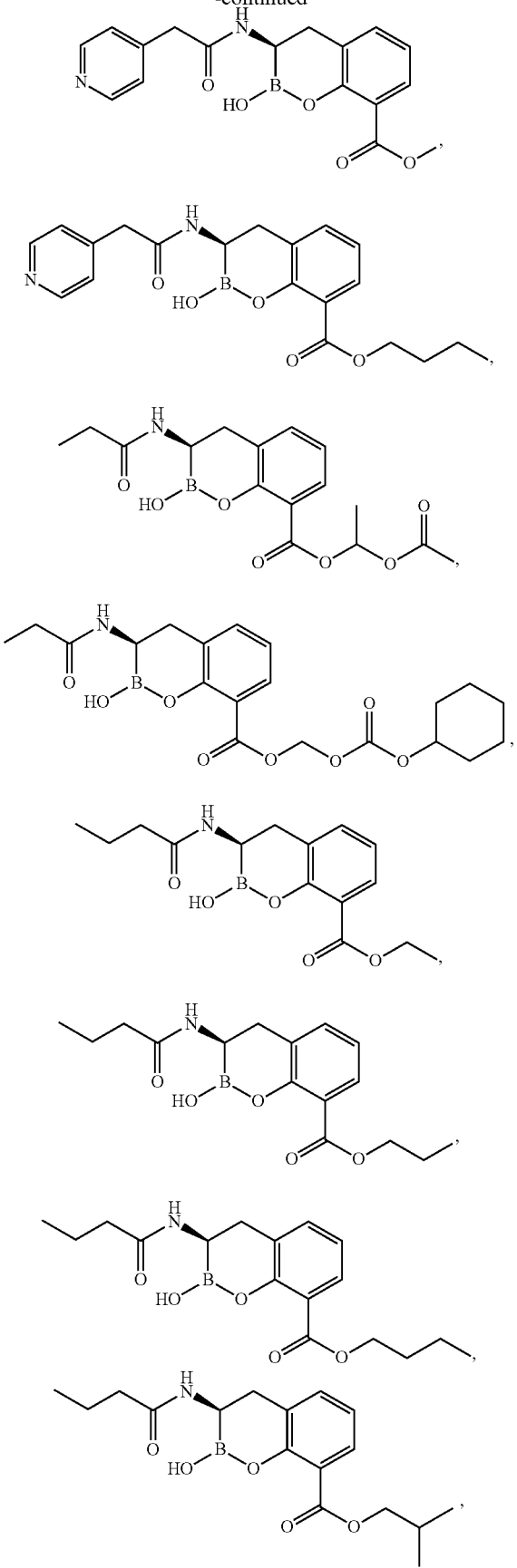

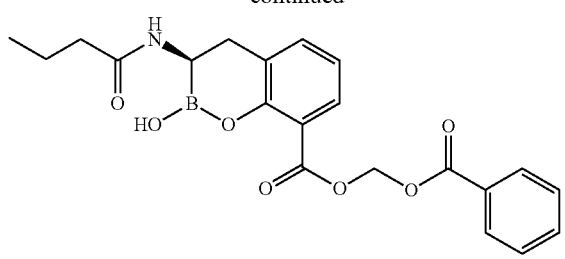
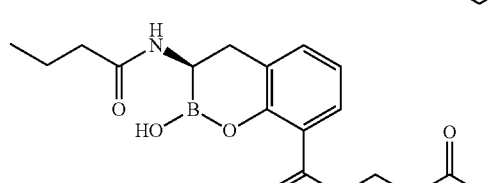
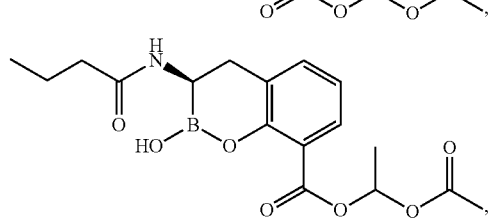
or a pharmaceutically acceptable salt, N-oxide, or isomer thereof.
In some embodiments, the compound of Formula (II) is:
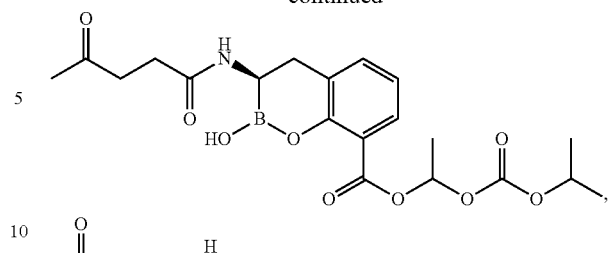
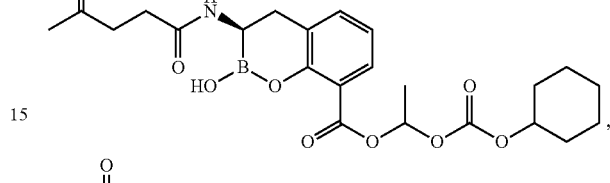
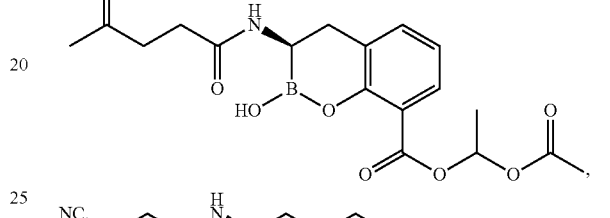
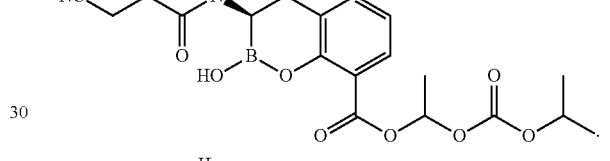
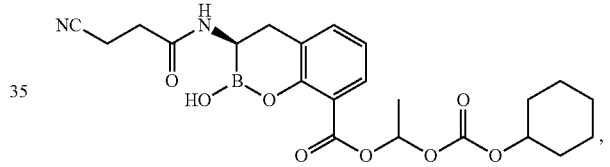
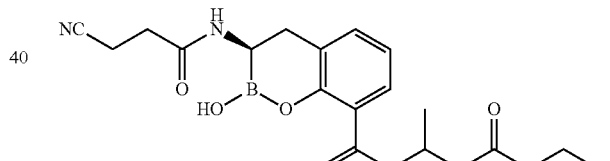
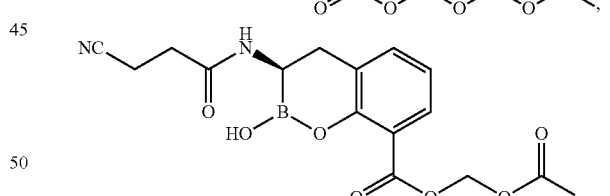
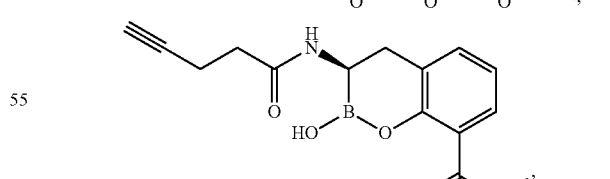
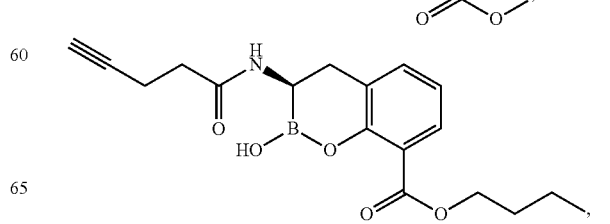

87
-continued
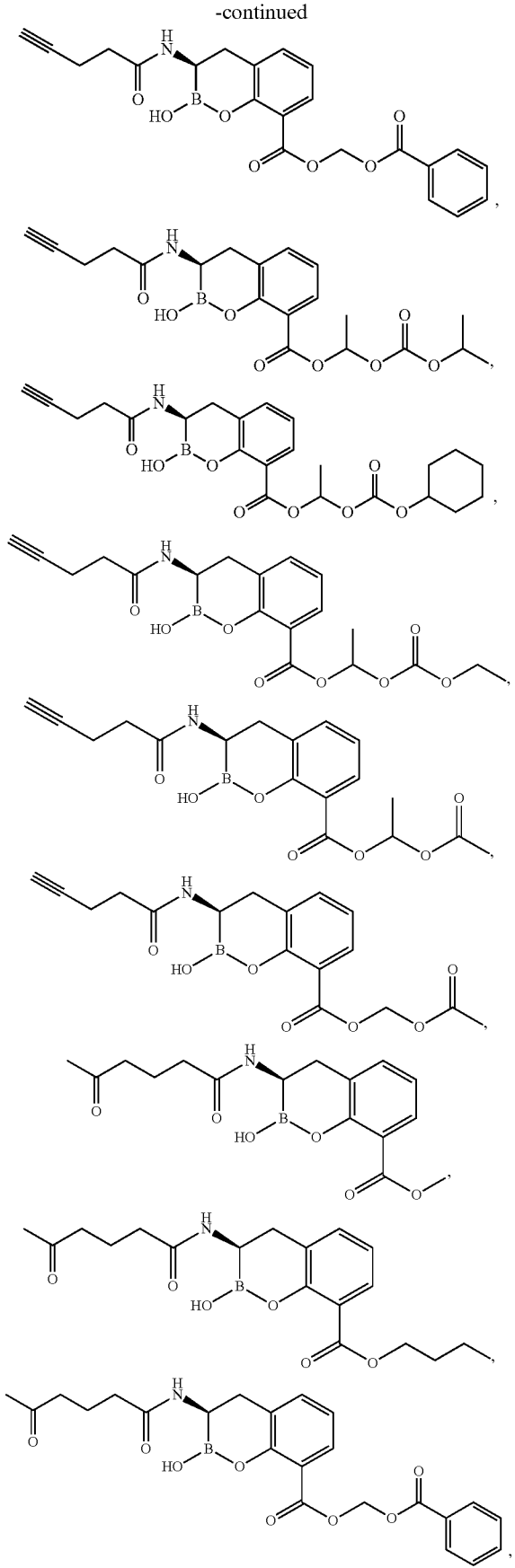
88
-continued
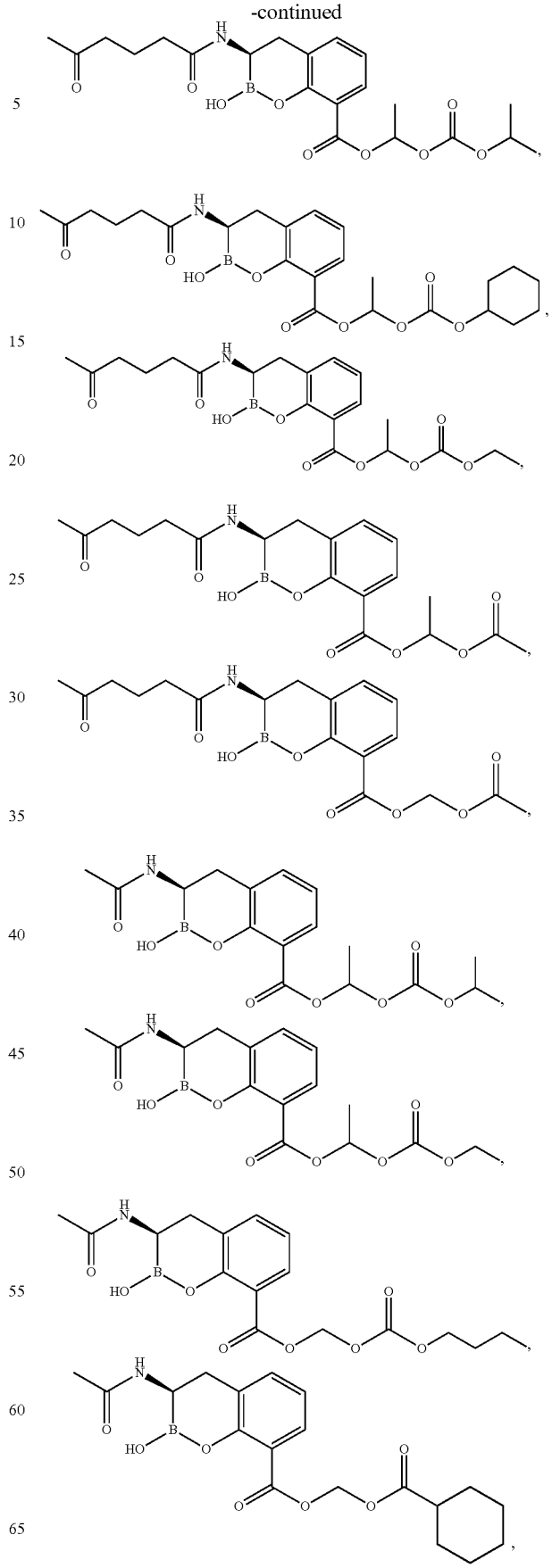

-continued
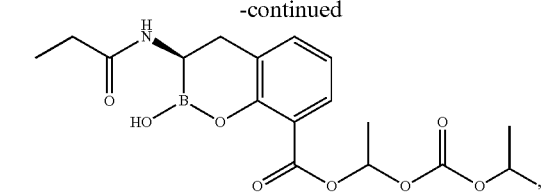
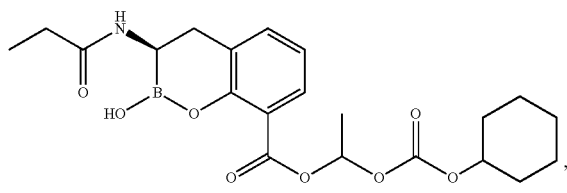
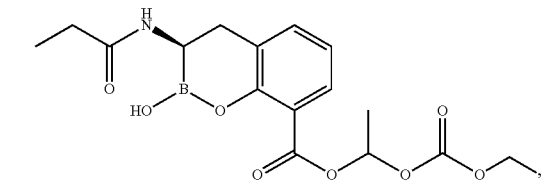
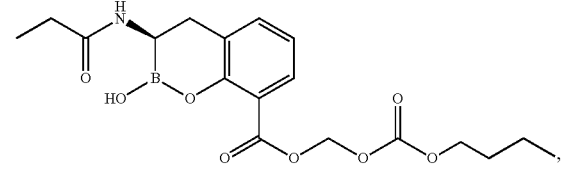
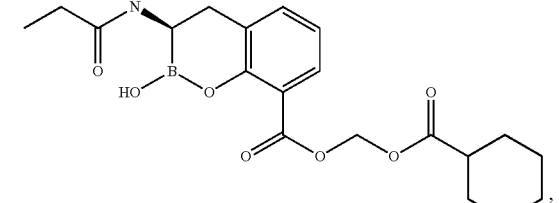
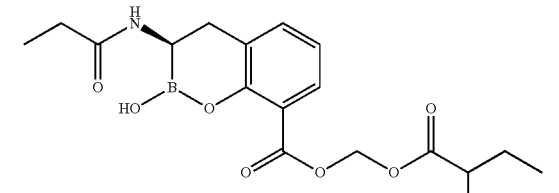
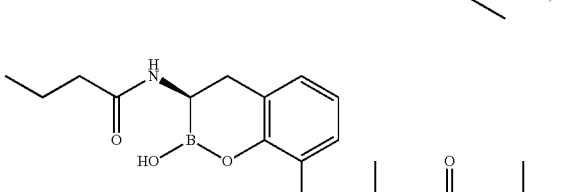
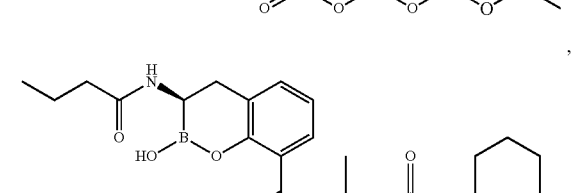
-continued
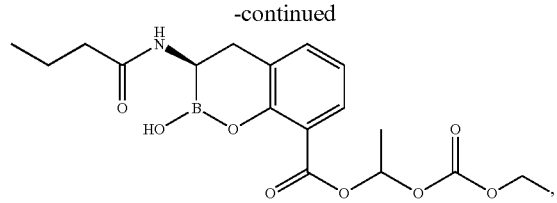
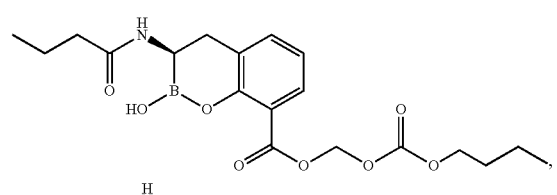
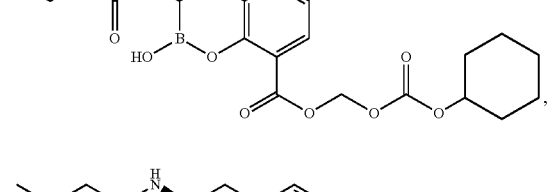
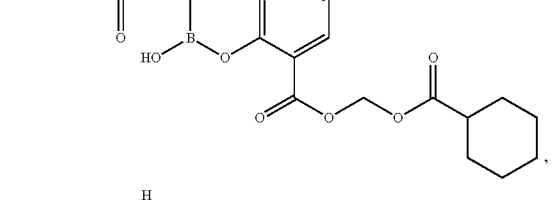
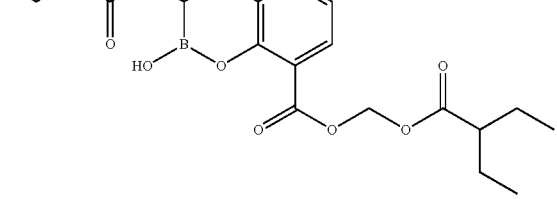
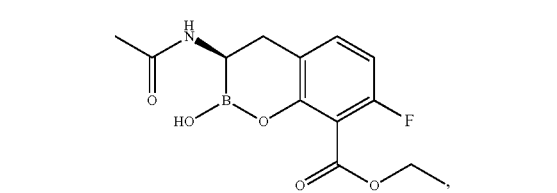
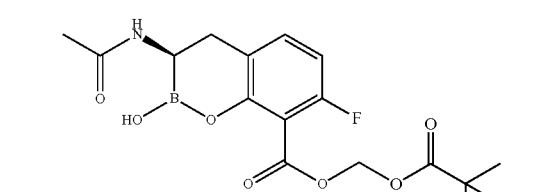
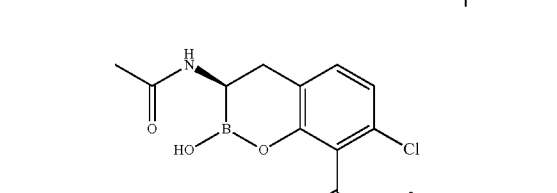

91
-continued
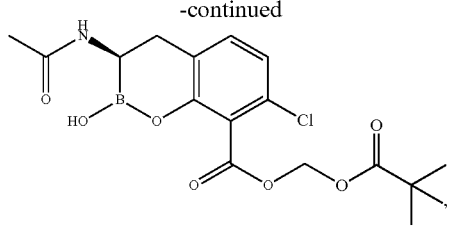
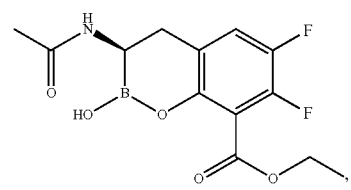
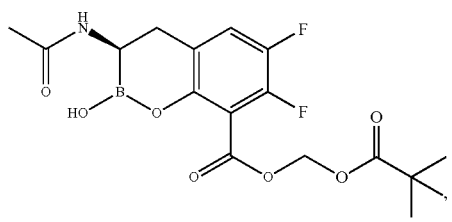
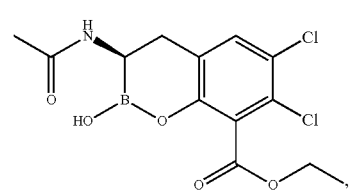
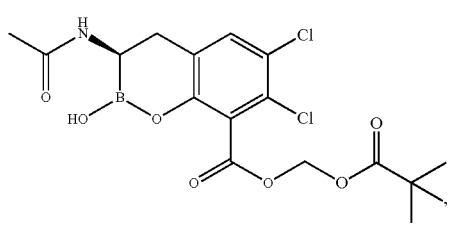
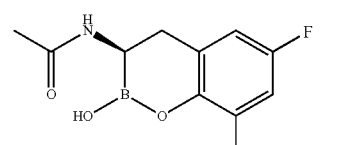
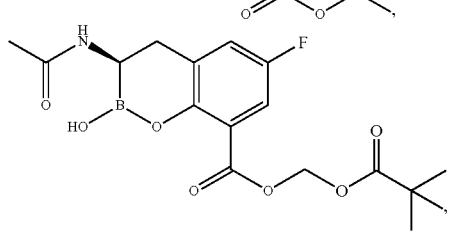
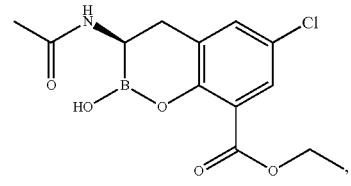
92
-continued
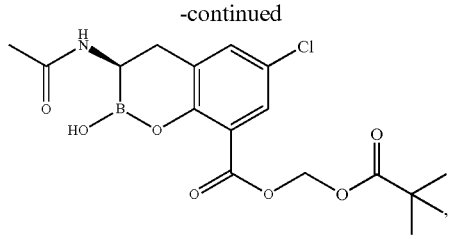
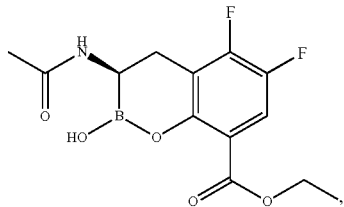
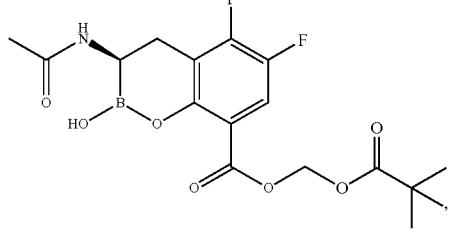
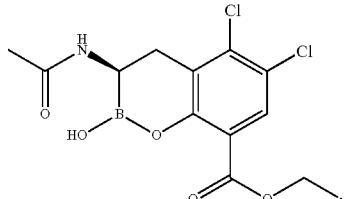
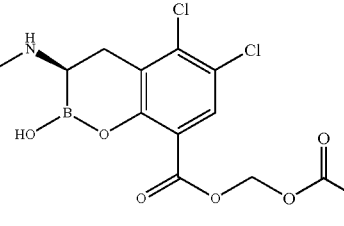
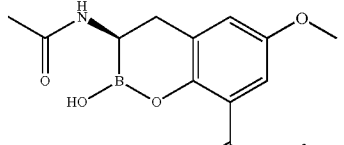
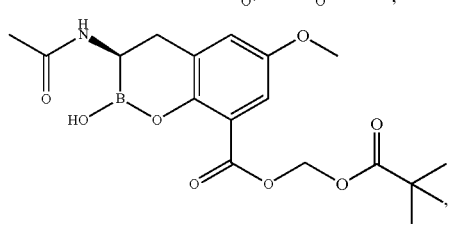
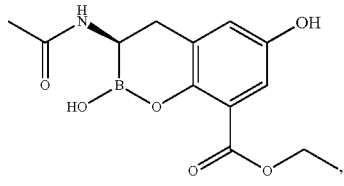

93
-continued
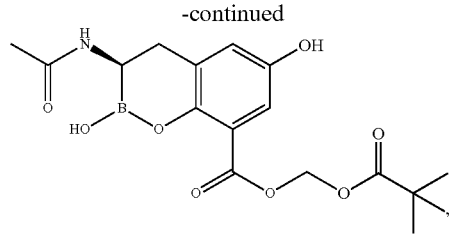
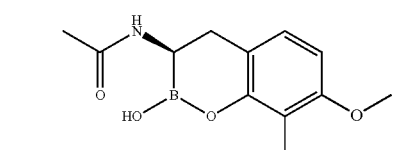
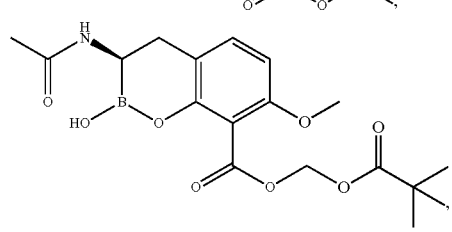
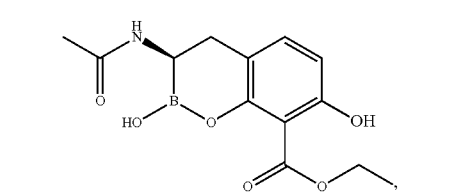
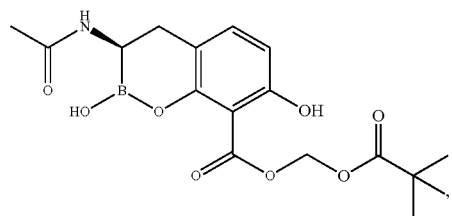
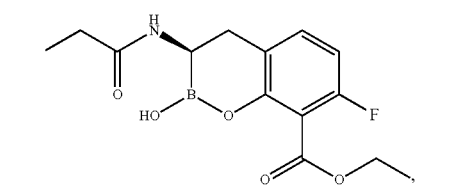
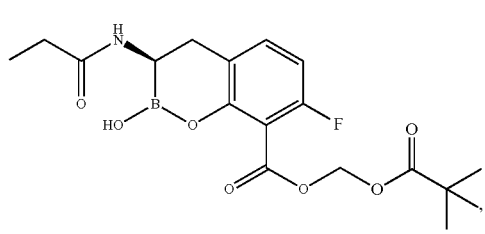
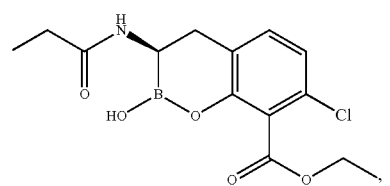
94
-continued
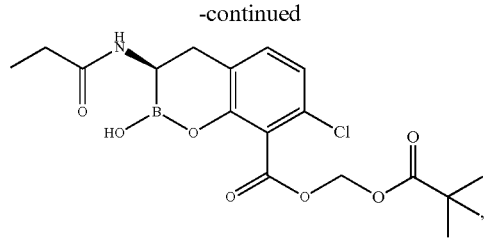
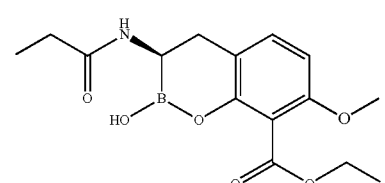
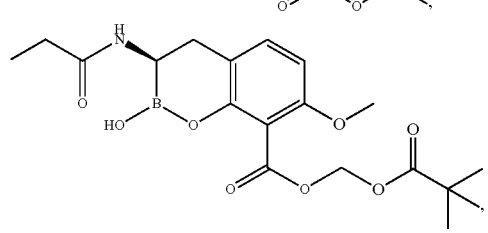
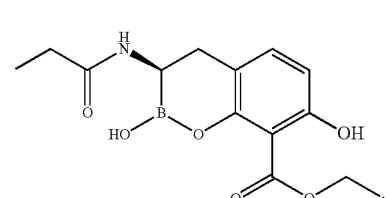
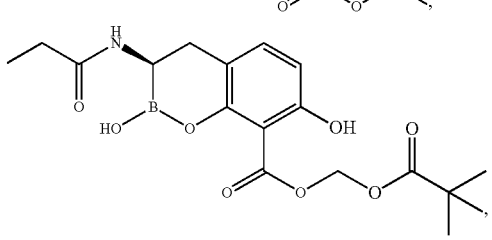
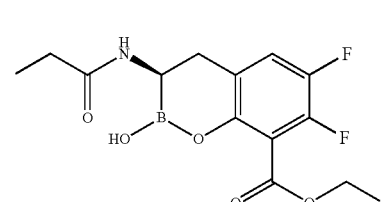
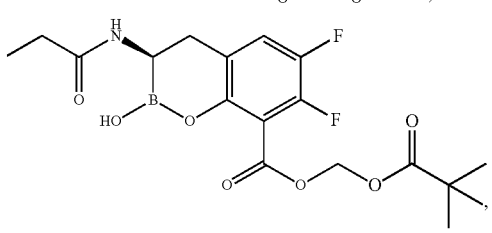
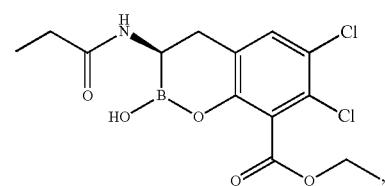

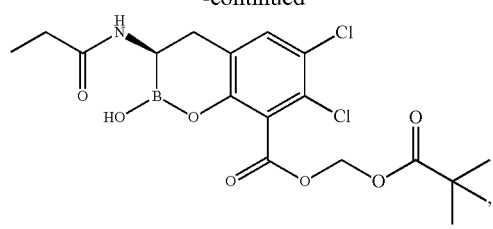
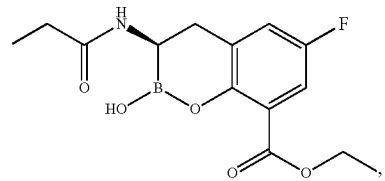
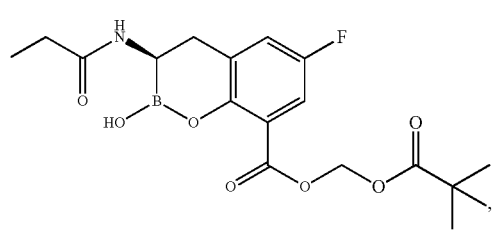
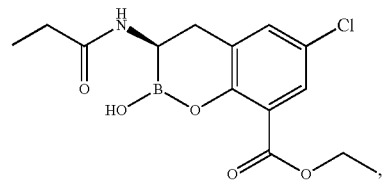
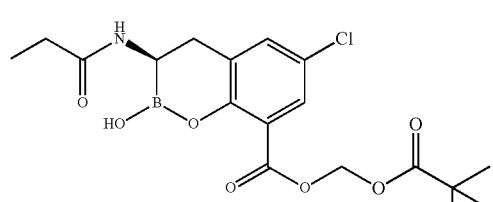
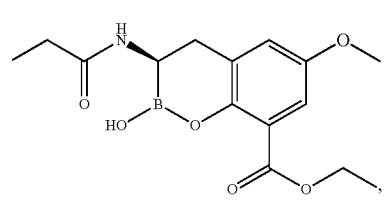
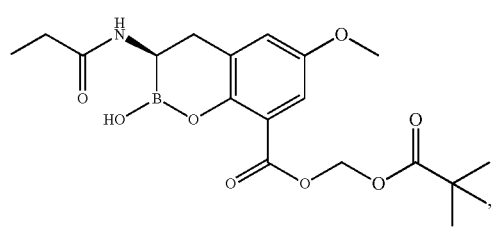
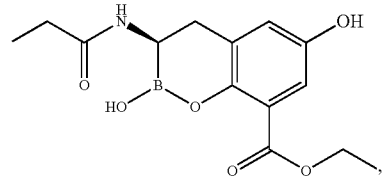
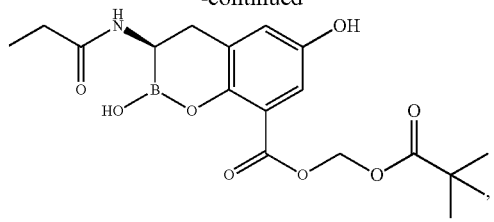
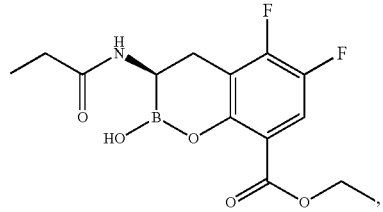
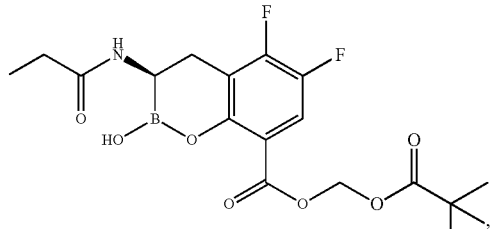
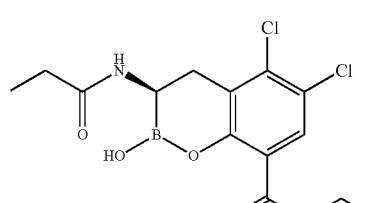
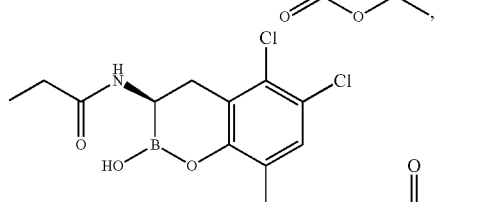
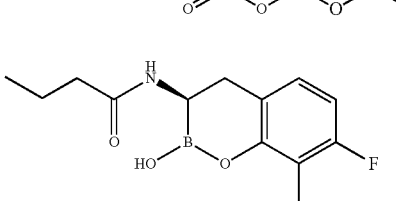
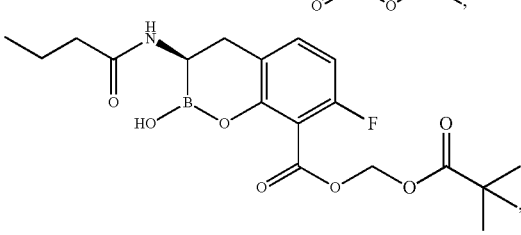
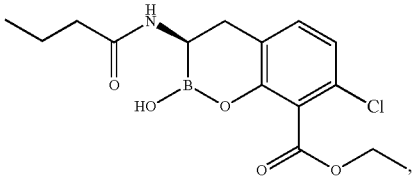

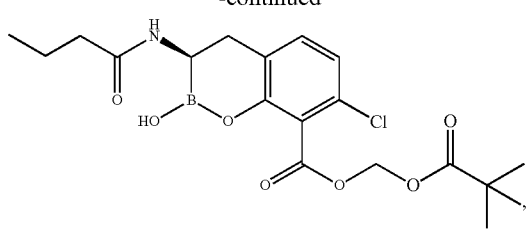
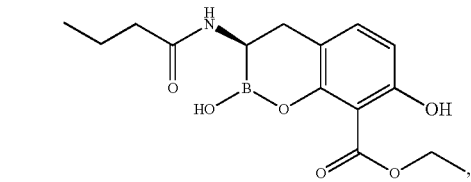
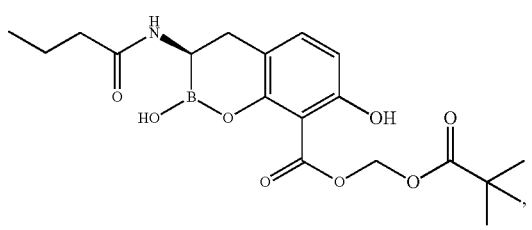
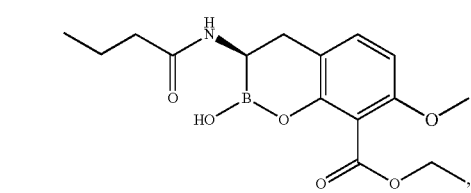
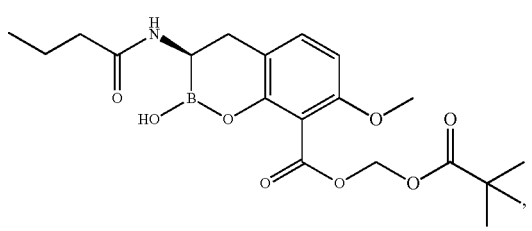
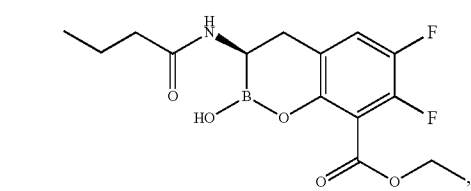
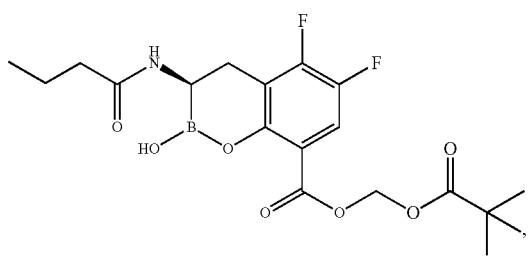
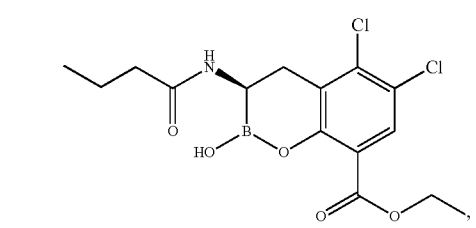

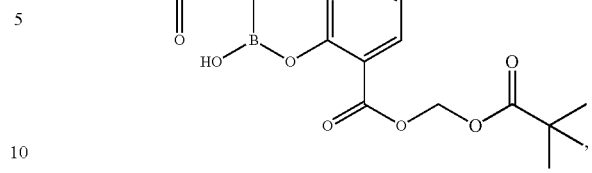
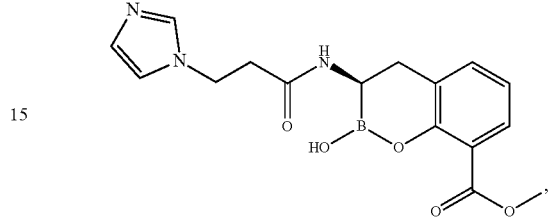
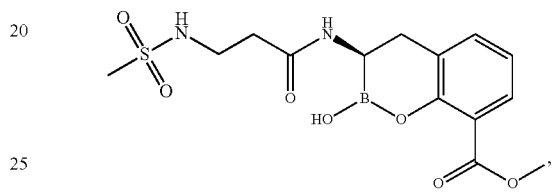
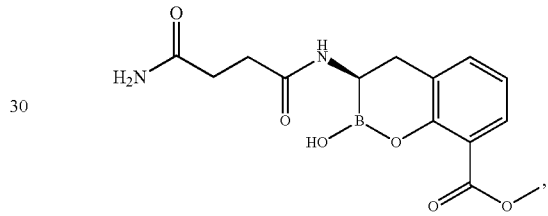
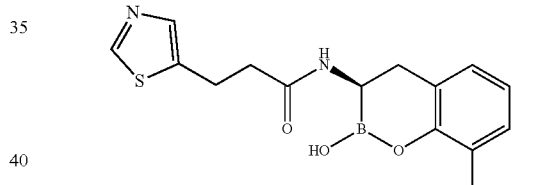
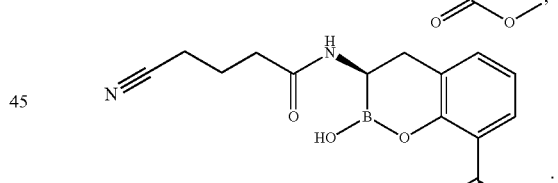

or a pharmaceutically acceptable salt, N-oxide, or isomer thereof.

Preparation of Compounds

Described herein are compounds of Formula (I), Formula (II), or Formula (IX) that inhibit the activity of beta-lactamases, and processes for their preparation. Also described herein are pharmaceutically acceptable salts. Pharmaceutical compositions comprising at least one such compound or a pharmaceutically acceptable salt, and a pharmaceutically acceptable excipient are also provided.

Compounds of Formula (I), Formula (II), or Formula (IX) may be synthesized using standard synthetic reactions known to those of skill in the art or using methods known in the art. The reactions can be employed in a linear sequence to provide the compounds or they may be used to synthesize fragments which are subsequently joined by the methods known in the art.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents can be synthesized using techniques and materials known to those of skill in the art, such as described, for example, in March, Advanced Organic Chemistry 4th Ed., (Wiley 1992); Carey and Sundberg, Advanced Organic Chemistry 4th Ed., Vols. A and B (Plenum 2000, 2001); Green and Wuts, Protective Groups in Organic Synthesis 3rd Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). (all of which are incorporated by reference in their entirety). General methods for the preparation of compounds as disclosed herein may be derived from known reactions in the field, and the reactions may be modified by the use of appropriate reagents and conditions, as would be recognized by the skilled person, for the introduction of the various moieties found in the formulas as provided herein.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared as a single isomer or a mixture of isomers.

Further Forms of Compounds Disclosed Herein

Isomers

In some embodiments, due to the oxophilic nature of the boron atom, the compounds described herein may convert to or exist in equilibrium with alternate forms, particularly in milieu that contain water (aqueous solution, plasma, etc.). Accordingly, the compounds described herein may associate into intramolecular dimers, trimers, and related combinations.

The compounds of Formula (I) and (II) are present in a closed, cyclic form as shown in the structures above, or an open, acyclic form of Formula (I-1) and (II-1), or mixtures thereof.

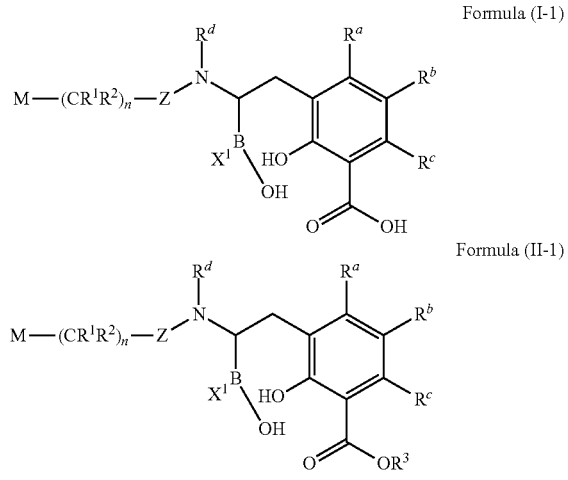

Formula (I-1)

Formula (II-1)

Accordingly, the compounds described herein may exist in an equilibrium between the "closed" cyclic form shown in Formula (I) and (II) and the "open" acyclic form shown in Formula (I-1) and (II-1). In addition the compounds described herein may associate into intramolecular dimers, trimers, and related combinations.

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of the invention and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, N+($C_{1-4}$ alkyl)$_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Pharmaceutical Compositions/Formulations

In another aspect, provided herein are pharmaceutical compositions comprising a compound of Formula (I), Formula (II), or Formula (IX) as described herein, or a pharmaceutically acceptable salt, N-oxide, or isomer thereof, and a pharmaceutically acceptable excipient. In some embodiments, the pharmaceutical composition further comprises a beta-lactam antibiotic. In certain embodiments, the beta-lactam antibiotic is a penicillin, cephalosporin, carbapenem, monobactam, bridged monobactam, or a combination thereof.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula (I), Formula (II), or Formula (IX) and at least one pharmaceutically acceptable inactive ingredient. In some embodiments, the compounds described herein are administered as pharmaceutical compositions in which a compound of Formula (I), Formula (II), or Formula (IX) is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula (I), Formula (II), or Formula (IX) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combinations thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including a compound of Formula (I), Formula (II), or Formula (IX) are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I), Formula (II), or Formula (IX) as an active ingredient in free-acid or free-base form, or in a pharmaceutically acceptable salt form. In addition, the methods and pharmaceutical compositions described herein include the use of N-oxides (if appropriate), crystalline forms, amorphous phases.

Pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

Combination Treatment

The compounds according to Formula (I), Formula (II), or Formula (IX) may be used in combination with one or more antibiotics in the treatment of bacterial infections. Such antibiotics may be administered, by a route and in an amount commonly used therefore, contemporaneously or sequentially with a compound of Formula (I), (II), or (III). When a compound of Formula (I), Formula (II), or Formula (IX) is used contemporaneously with one or more antibiotic, a pharmaceutical composition in unit dosage form containing such other drugs and the compound of the present invention is preferred. However, the combination therapy may also include therapies in which the compound of Formula (I), Formula (II), or Formula (IX) and one or more antibiotics are administered on different overlapping schedules. It is also contemplated that when used in combination with one or more antibiotics, the antibiotics may be used in lower doses than when each is used singly.

Accordingly, the pharmaceutical compositions of the present invention also include those that contain one or more antibiotics, in addition to a compound according to Formula (I), Formula (II), or Formula (IX). In some embodiments, a pharmaceutical composition comprising a compound of Formula (I), Formula (II), or Formula (IX) further comprises a beta-lactam antibiotic. In certain embodiments, the beta-lactam antibiotic is a penicillin, cephalosporin, carbapenem, monobactam, bridged monobactam, or a combination thereof.

The above combinations include combinations of a compound of Formula (I), Formula (II), or Formula (IX) not only with one antibiotic, but also with two or more antibiotics. Likewise, compounds of Formula (I), Formula (II), or Formula (IX), either in combination with an antibiotic or by themselves, may be used in combination with other drugs that are used in the prevention, treatment, control, amelioration, or reduction of risk of bacterial infections or conditions associated with bacterial infections. Such other drugs may be administered, by a route and in an amount commonly used therefore, contemporaneously or sequentially with a compound of Formula (I), Formula (II), or Formula (IX). When a compound of Formula (I), Formula (II), or Formula (IX) is used contemporaneously with one or more other drugs, a pharmaceutical composition containing such other drugs in addition to the compound of the present invention is preferred. Accordingly, the pharmaceutical compositions of the present invention also include those that also contain one or more other active ingredients, in addition to a compound of Formula (I), Formula (II), or Formula (IX). The weight ratio of the compound of Formula (I), Formula (II), or Formula (IX) to the second active ingredient may be varied and will depend upon the effective dose of each ingredient. Generally, an effective dose of each will be used.

In some embodiments, the compounds according to Formula (I), Formula (II), or Formula (IX) are used in combination with one or more antibiotics in the treatment of bacterial infections. In certain embodiments, the bacterial infection is an upper or lower respiratory tract infection, a urinary tract infection, an intra-abdominal infection, or a skin infection. In some embodiments, the one or more antibiotics are selected from β-lactam antibiotics. β-Lactam antibiotics include, but are not limited to, penicillins, penems, carbapenems, cephalosporins, cephamycins, monobactams, or combinations thereof. Penicillins include, but are not limited to, amoxicillin, ampicillin, azidocillin, azlocillin, bacampicillin, benzathine benzylpenicillin, benzathine phenoxymethylpenicillin, benzylpenicillin (G), carbenicillin, carindacillin, clometocillin, cloxacillin, dicloxacillin, epicillin, flucloxacillin, hetacillin, mecillinam, metampicillin, meticillin, mezlocillin, nafcillin, oxacillin, penamecillin, pheneticillin, phenoxymethylpenicillin (V), piperacillin, pivampicillin, pivmecillinam, procaine benzylpenicillin, propicillin, sulbenicillin, talampicillin, temocillin, ticarcillin. Penems include, but are not limited to, faropenem. Carbapenems include, but are not limited to, biapenem, ertapenem, doripenem, imipenem, meropenem, panipenem. Cephasprins/Cephamycins include, but are not limited to, cefacetrile, cefaclor, cefadroxil, cefalexin, cefaloglycin, cefalonium, cefaloridine, cefalotin, cefamandole, cefapirin, cefatrizine, cefazaflur, cefazedone, cefazolin, cefbuperazone, cefcapene, cefdaloxime, cefdinir, cefditoren, cefepime, cefetamet, cefixime, cefmenoxime, cefmetazole, cefminox, cefodizime, cefonicid, cefoperazone, ceforanide, cefotaxime, cefotetan, cefotiam, cefovecin, cefoxitin, cefozopran, cefpimizole, cefpiramide, cefpirome, cefpodoxime, cefprozil, cefquinome, cefquinome, cefradine, cefroxadine, cefsulodin, ceftaroline fosamil, ceftazidime, cefteram, ceftezole, ceftibuten, ceftiofur, ceftiolene, ceftizoxime, ceftobiprole, ceftriaxone, cefuroxime, cefuzonam, flomoxef, latamoxef, loracarbef. Monobactams include, but are not limited to, aztreonam, carumonam, nocardicin A, tigemonam.

Administration of Pharmaceutical Composition

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In some embodiments, compounds of Formula (I), Formula (II), or Formula (IX) and compositions thereof are administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

Assays for Antibacterial Activity

Assays for the inhibition of beta-lactamase activity are well known in the art. For instance, the ability of a compound to inhibit beta-lactamase activity in a standard enzyme inhibition assay may be used (see, e g, Page, *Biochem J*, 295:295-304 (1993)). Beta-lactamases for use in such assays may be purified from bacterial sources or preferably, are produced by recombinant DNA techniques, since genes and cDNA clones coding for many beta-lactamases are known (see, e g, Cartwright & Waley, *Biochem J* 221:505-12 (1984)).

Alternatively, the sensitivity of bacteria known, or engineered, to produce a beta-lactamase to an inhibitor may be determined. Other bacterial inhibition assays include agar disk diffusion and agar dilution (see, e.g, Traub & Leonhard, *Chemotherapy* 43 159-67 (1997)). Thus, a beta-lactamase may be inhibited by contacting the beta-lactamase enzyme with an effective amount of an inventive compound or by contacting bacteria that produce the beta-lactamase enzymes with an effective amount of such a compound so that the beta-lactamase in the bacteria is contacted with the inhibitor. The contacting may take place in vitro or in vivo. "Contacting" means that the beta-lactamase and the inhibitor are brought together so that the inhibitor can bind to the beta-lactamase. Amounts of a compound effective to inhibit a beta-lactamase may be determined empirically, and making such determinations is within the skill in the art. Inhibition includes both reduction and elimination of beta-lactamase activity.

Methods

The present disclosure also provides methods for inhibiting bacterial growth, by, e.g., reducing bacterial resistance to a β-lactam antibiotic, such methods comprising contacting a bacterial cell culture, or a bacterially infected cell culture, tissue, or organism, with a beta-lactamase inhibitor described herein. Preferably, the bacteria to be inhibited by administration of a beta-lactamase inhibitor of Formula (I), Formula (II), or Formula (IX) are bacteria that are resistant to beta-lactam antibiotics. The term "resistant" is well-understood by those of ordinary skill in the art (see, e g Payne et al., *Antimicrobial Agents and Chemotherapy* 38 767-772 (1994), Hanaki et al., *Antimicrobial Agents and Chemotherapy* 30 1120-1126 (1995)).

These methods are useful for inhibiting bacterial growth in a variety of contexts. In certain embodiments, a compound of Formula (I), Formula (II), or Formula (IX) is administered to an experimental cell culture in vitro to prevent the growth of beta-lactam resistant bacteria. In certain other embodiments, a compound of Formula (I), Formula (II), or Formula (IX) is administered to a mammal, including a human to prevent the growth of beta-lactam resistant bacteria in vivo. The method according to this embodiment comprises administering a therapeutically effective amount of a beta-lactamase inhibitor for a therapeutically effective period of time to a mammal, including a human. Preferably, the beta-lactamase inhibitor is administered in the form of a pharmaceutical composition as described above. In some embodiments, a beta-lactam antibiotic is co-administered with the beta-lactamase inhibitor as described above.

In another aspect provided herein are methods of treating a bacterial infection, which method comprises administering to a subject a pharmaceutical composition comprising a compound of Formula (I), Formula (II), or Formula (IX), or a pharmaceutically acceptable salt thereof, and a pharmaceutically acceptable excipient. In some embodiments, the methods of treating a bacterial infection in a subject comprises administering to the subject a pharmaceutical composition as described herein, optionally in combination with a beta-lactam antibiotic. In some embodiments, the bacterial infection is an upper or lower respiratory tract infection, a urinary tract infection, an intra-abdominal infection, or a skin infection.

In some embodiments, the infection that is treated or prevented comprises a bacteria that includes *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi,*

*Pasteurella multocida, Pasteurella haemolytica, Branhamella catarrhalis, Helicobacter pylori, Campylobacter fetus, Campylobacterjejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroidesfragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus.*

In some embodiments, the infection that is treated or prevented comprises a bacteria that includes *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacterjejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii*, or *Bacteroides splanchnicus.*

EXAMPLES

List of Abbreviations

As used above, and throughout the description of the invention, the following abbreviations, unless otherwise indicated, shall be understood to have the following meanings:

ACN acetonitrile
Bn benzyl
BOC or Boc tert-butyl carbamate
BOP benzotriazol-1-yl-oxytris (dimethylamino) phosphonium
t-Bu tert-butyl
Cbz benzyl carbamate
Cy Cyclohexyl
DBU 1,8-Diazabicyclo[5.4.0]undec-7-ene
DCC dicyclohexylcarbodiimide
DCM dichloromethane ($CH_2Cl_2$)
DIC 1,3-diisopropylcarbodiimide
DEAD diethyl azodicarboxylate
DIAD diisopropyl azodicarboxylate
DIEA diisopropylethylamine
DMAP 4-(N,N-dimethylamino)pyridine
DMP reagent Dess-Martin Periodinane reagent
DMF dimethylformamide
DMA N,N-Dimethylacetamide
DME 1,2-Dimethoxy-ethane
DMSO dimethylsulfoxide
Dppf 1,1'-Bis(diphenylphosphino)ferrocene
EDCI 1-ethyl-3-(3-dimethylaminopropyl) carbodiimide HCl
eq equivalent(s)
Et ethyl
$Et_2O$ diethyl ether
EtOH ethanol
EtOAc ethyl acetate
HOAt 1-hydroxy-7-azabenzotriazole
HOBT 1-hydroxybenztriazole
HOSu N-hydroxysuccinamide
HPLC high performance liquid chromatography
LAH lithium aluminum anhydride
LC liquid chromatography
Me methyl
MeI methyliodide
MeOH methanol
MOMCl methoxymethylchloride
MOM methoxymethyl
MS mass spectroscopy
NMP N-methyl-pyrrolidin-2-one
NMR nuclear magnetic resonance
PyBOP benzotriazole-1-yl-oxytris-pyrrolidino-phosphonium hexafluorophosphate
SPHOS 2-Dicyclohexylphosphino-2',6'-dimethoxybiphenyl
TBD 1,5,7-triazabicyclo[4.4.0]-dec-5-ene
RP-HPLC reverse phase-high pressure liquid chromatography
TBS tert-butyldimethylsilyl
TBSCl tert-butyldimethylsilyl chloride
TBTU O-(Benzotriazol-1-yl)-N,N,N',N'-tetramethyluronium
TEOC 2-Trimethylsilylethyl Carbamate
TFA trifluoroacetic acid
$Tf_2O$ triflate anhydride
TMG 1,1,3,3-Tetramethylguanidine
THF tetrahydrofuran
THP tetrahydropyran
TLC thin layer chromatography
XPHOS 2-Dicyclohexylphosphino-2',4',6'-triisopropylbiphenyl General Examples for the Preparation of Compounds of Formula (I), (II), and (IX)

The starting materials and intermediates for the compounds of this invention may be prepared by the application or adaptation of the methods described below, their obvious chemical equivalents, or, for example, as described in literature such as The Science of Synthesis, Volumes 1-8. Editors E. M. Carreira et al. Thieme publishers (2001-2008). Details of reagent and reaction options are also available by structure and reaction searches using commercial computer search engines such as Scifinder (www.cas.org) or Reaxys (www.reaxys.com).

Certain compounds of the invention (I) (SCHEME 1) are prepared from the corresponding functional-group-protected boronic acid esters (III) by treatment with a Lewis acid such as $BCl_3$, $AlCl_3$, or $BBr_3$ in a solvent such as dichloromethane, at a temperature between −78° C. and room temperature followed by an aqueous quench.

SCHEME 1

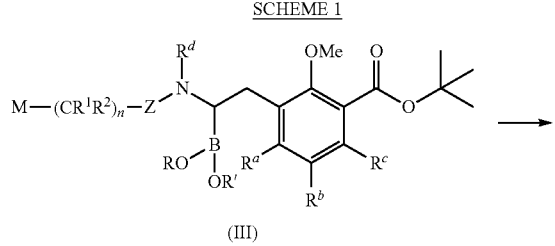

(III)

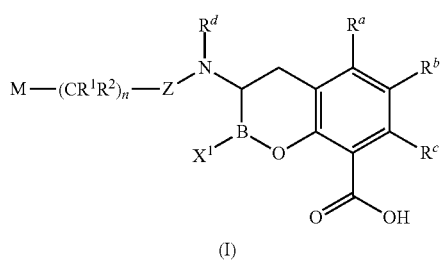

(I)

SCHEME 2

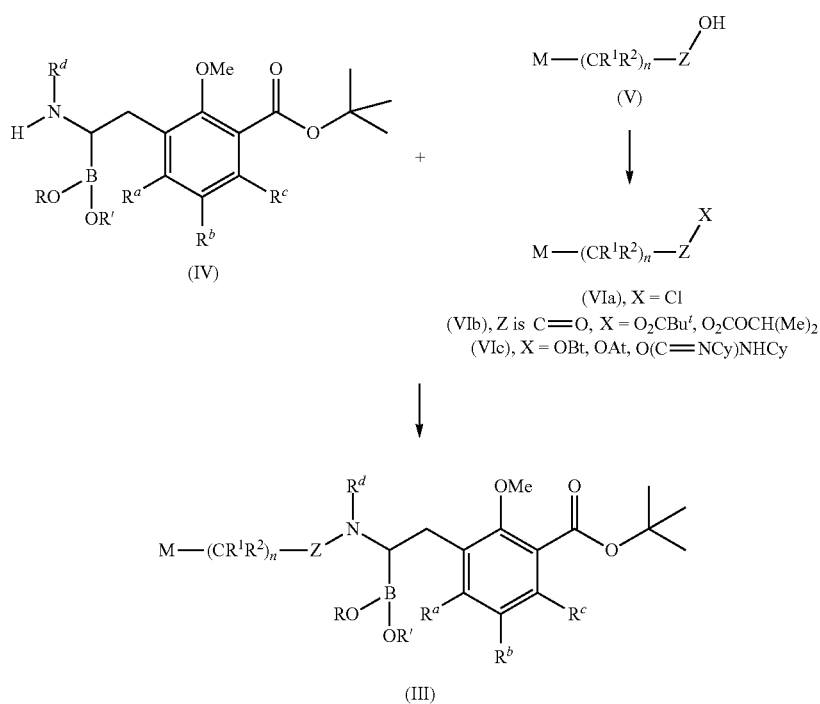

Alternatively, (I) is obtained from (III) by treatment of (III) with aqueous hydrochloric acid (around 3-5 Molar) in dioxane at a temperature between room temperature and 100° C.

The requisite boronic acid esters (III) are obtained (SCHEME 2) by coupling of amine (IV) with carboxylic acid (V). This transformation is effected by first activating the acid functionality as an acid chloride, anhydride or reactive ester (VIa, VIb or VIc), followed by treatment of the activated substrate with (IV) in a solvent such as DMF, DMA, NMP, THF or dichloromethane (or a mixture thereof) at about room temperature, usually in the presence of a non-nucleophilic base such as 4-methyl-morpholine, triethylamine or diisopropylethylamine.

Formation of the acid chloride (VIa) involves treatment of (V) with a chlorinating agent such as thionyl chloride, phosphorous pentachloride or oxalyl chloride, in a solvent such as dichloromethane, in the presence of a catalyst such as DMF, at around room temperature. In certain cases, DMF is also used as a co-solvent. Formation of the anhydride (VIb) (Z is C=O) involves treatment of (V) with a sterically hindered acid chloride or chloroformate, such as trimethylacetyl chloride or isopropylchloroformate, in an inert solvent such as dichloromethane, in the presence of a non-nucleophilic base, such as triethylamine or diisopropylamine at room temperature or below. Formation of the activated ester (VIc) involves treatment of (V) with an activating reagent system such as EDCI, DCC/HOBt, HATU, BOP reagents or TBTU, in a solvent such as DMF, DMA, NMP or dichloromethane at room temperature or below (*International Journal of Pharmaceutical Sciences Review and Research* (2011), 8(1), 108-119).

The requisite acids (V) are commercially available or may be synthesized in a few steps from commercially available starting materials following methods described in the literature [for example, The Science of Synthesis, Volumes 1-8. Editors E. M. Carreira et al. Thieme publishers (2001-2008)]. Details of reagent and reaction options are also available by structure and reaction searches using commercial computer search engines such as Scifinder (www.cas.org) or Reaxys (www.reaxys.com).

Certain compounds of the invention (II) (SCHEME 3) are prepared from the corresponding functional-group-protected boronic acid esters (VII) by treatment with a Lewis acid such as $AlCl_3$, in a solvent such as dichloromethane, at room temperature followed by an aqueous or water/methanol quench.

SCHEME 3

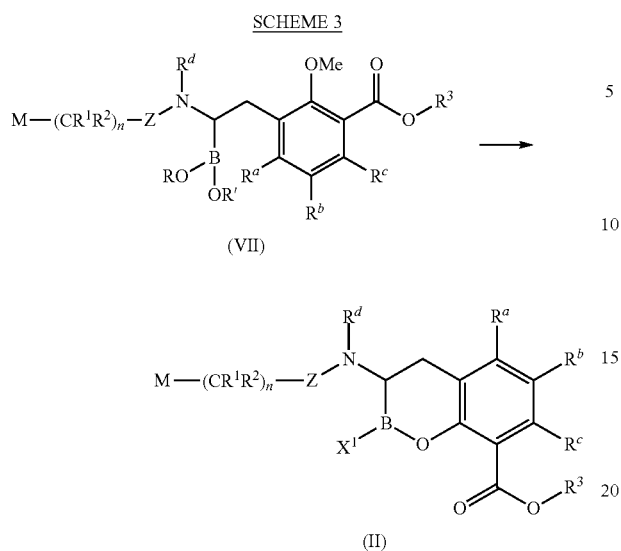

Alternatively, (II) can be obtained by treatment of (I) with hydrochloric acid (around 3-5 Molar in dioxane) in an alcohol solvent such as methanol, ethanol, or n-butanol at a temperature between room temperature and 120° C. (SCHEME 4).

SCHEME 4

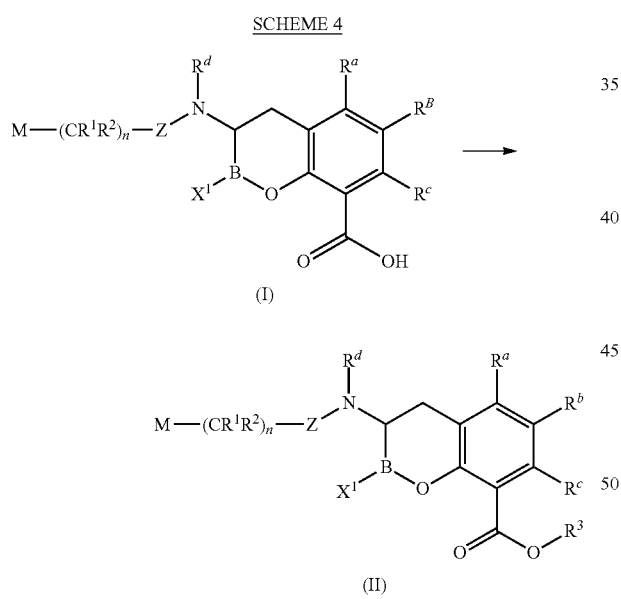

The desired protected carboxylic acid esters (VII) are prepared by treatment of the t-butyl ester (III) with anhydrous acid such as hydrochloric acid (4 Molar) in dioxane at room temperature. The resulting acid (VIII) can be alkylated by addition of an inorganic base such as sodium carbonate or potassium carbonate along with an alkyl halide such as iodoethane, 1-iodobutane, chloromethyl pivalate, or bromomethyl acetate in a solvent such as DMF at room temperature or above. In some cases, sodium iodide can also be added (SCHEME 5).

SCHEME 5

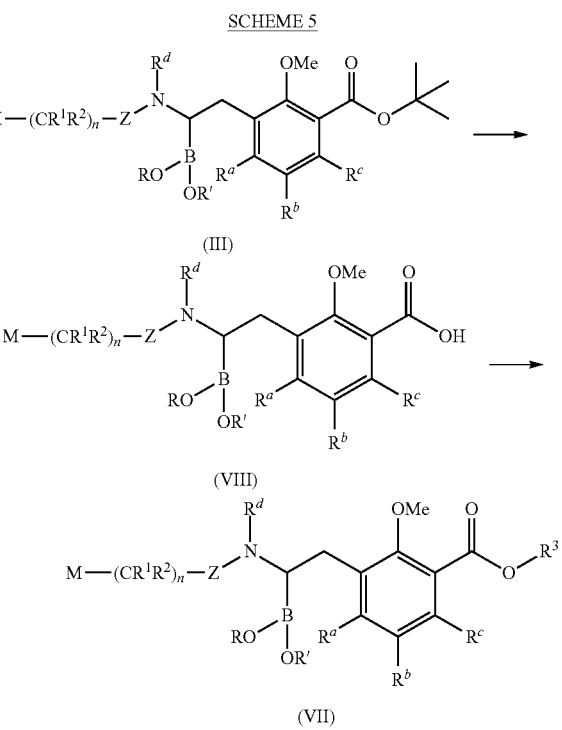

Synthetic Examples

The following preparations of compounds of Formula (I), (IX), or Formula (II) and intermediates are given to enable those of skill in the art to more clearly understand and to practice the present invention. They should not be considered as limiting the scope of the invention, but merely as illustrative and representative thereof.

Example 1

(R)-3-Butyrylamino-2-hydroxy-3,4-dihydro-2H-benzo[e][1,2]oxaborinine-8-carboxylic acid

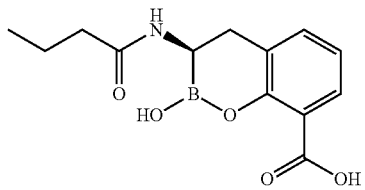 [SMILES: CCCC(=O)N[C@H]1Cc2cccc(C(=O)O)c2OB1O]

Step 1. Synthesis of [(1S)-2-(3-tert-butoxycarbonyl-2-methoxy-phenyl)-1-chloro-ethyl]boronic acid (+) pinanediol ester Method 1: To a cooled (−100° C. external temperature) solution of dichloromethane (2.27 mL, 35 mmol) in THF (44 mL) was added, dropwise down the side of the flask, BuLi (8.88 mL, 2.5 M in hexanes, 22 mmol) over 45 min. After approx. 80% of the BuLi is added, a white precipitate forms. On complete addition, the reaction mixture was stirred 30 min. To this mixture was added, dropwise down the side of the flask, 2-methoxy-3-(2,9,9-trimethyl-3,5-dioxa-4-bora-tricyclo[6.1.1.0 2,6]dec-4-ylmethyl)-benzoic acid tert-butyl ester (8.0 g, 20 mmol) in THF (20 mL) over approximately 30 min. On complete addition, the resulting solution was stirred for 5 min. To this solution was added ZnCl$_2$ (22 mL, 1M in ether), dropwise down the side of the flask, over approximately 12 min. On complete addition, the cold bath was removed and replaced with a −10° C. bath. The reaction mixture was stirred for 1.25 h. To this solution is added ice cold ether (300 mL) and ice cold saturated aqueous NH$_4$Cl (125 mL). The organic phase was washed with brine, dried over magnesium sulfate and concentrated under reduced pressure. The residue was purified by silica chromatography (120 g silica eluted with 2-20% ethyl acetate in hexane) to give the title compound as a colorless oil. This material slowly crystallizes at −10° C.

Method 2: 2-methoxy-3-(2,9,9-trimethyl-3,5-dioxa-4-bora-tricyclo[6.1.1.0 2,6]dec-4-ylmethyl)-benzoic acid tert-butyl ester (2.0 g, 5 mmol) and dichloromethane (1.6 mL, 25 mmol) in THF (20 mL) was stirred at −60° C. for 30 min. To this solution was added LDA (6.5 mmol, 2 M solution from Aldrich) over a period of 10 min. The resulting reaction mixture is stirred at −60° C. for 20 min. ZnCl$_2$ (8.75 mmol, 1M solution in ether) was added at −60° C. slowly. The reaction mixture was stirred at −50 to −60° C. for 30 min. This resulting mixture was warmed up to 0° C. over a period of 1 h, at which time, 10% H$_2$SO$_4$ solution (10 mL) was added and the reaction mixture stirred for 10 min. After phase separation, the organic phase was washed with water and brine. The organic phase was then dried and concentrated in vacuo. The residue was purified by flash silica chromatography (EtOAc/Hexane, 4/1) to give the title compound.

Step 2. Synthesis of 3-[2-Butyrylamino-2-(2,9,9-trimethyl-3,5-dioxa-4-bora-tricyclo[6.1.1.02,6]dec-4-yl)-ethyl]-2-methoxy-benzoic acid tert-butyl ester To a cooled (−25° C.) solution of [(1S)-2-(3-tert-butoxycarbonyl-2-methoxy-phenyl)-1-chloro-ethyl]boronic acid (+) pinanediol ester (0.967 g, 2.15 mmol) in THF (6.5 mL) was added lithium bis-trimethylsilylamide (2.3 mL, 1M in THF) dropwise. On complete addition, the cold bath was removed and stirring continued for 1 h to give a solution of [(1R)-1-[bis(trimethylsilyl)amino]-2-(3-tert-butoxycarbonyl-2-methoxy-phenyl)ethyl]boronic acid (+) pinanediol ester, approximately 0.25M in THF. This solution was used directly in the next operation.

In a separate flask: To a mixture of butyric acid (0.07 mL, 0.79 mmol) and HATU (0.328 g, 0.86 mmol) was added DMA (2.5 mL) followed by N-methylmorpholine (0.10 mL, 0.91 mmol). The resulting solution was stirred for 1.1 h then a solution of [(1R)-1-[bis(trimethylsilyl)amino]-2-(3-tert-butoxycarbonyl-2-methoxy-phenyl)ethyl]boronic acid (+) pinanediol in THF (prepared above) was added. This mixture was stirred for 22 h, quenched with water, and extracted two times with diethyl ether. The combined organic layers were washed with brine, dried over MgSO$_4$, and concentrated. The residue was purified by silica chromatography (30 g silica; eluted with 25-100% EtOAc:Hexane) to give the title compound. ESI-MS m/z 500 (MH)$^+$.

Step 3. (R)-3-Butyrylamino-2-hydroxy-3,4-dihydro-2H-benzo[e][1,2]oxaborinine-8-carboxylic acid Aluminum chloride (0.442 g, 3.31 mmol) was added to a solution of 3-[2-Butyrylamino-2-(2,9,9-trimethyl-3,5-dioxa-4-bora-tricyclo[6.1.1.02,6]dec-4-yl)-ethyl]-2-methoxy-benzoic acid tert-butyl ester (0.207 g, 0.41 mmol) in dichloromethane (10 mL) and the reaction stirred at room temperature for 19 h. The reaction mixture was quenched with water and methanol and extracted two times with hexane. The product remained in the aqueous layer and was purified by reverse phase HPLC. Pure fractions were concentrated by lyophilization to give the title compound as a white solid. ESI-MS m/z 278 (MH)$^+$.

Example 2

(R)-3-(2-Cyano-acetylamino)-2-hydroxy-3,4-dihydro-2H-benzo[e][1,2]oxaborinine-8-carboxylic acid

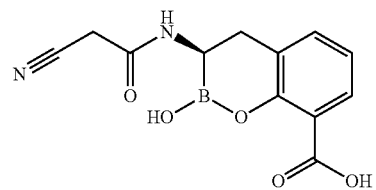 [SMILES: N#CCC(=O)N[C@H]1Cc2cccc(C(=O)O)c2OB1O]

Step 1. Synthesis of 3-[2-(2-Cyano-acetylamino)-2-(2,9,9-trimethyl-3,5-dioxa-4-bora-tricyclo[6.1.1.02,6]dec-4-yl)-ethyl]-2-methoxy-benzoic acid tert-butyl ester Prepared from [(1S)-2-(3-tert-butoxycarbonyl-2-methoxy-phenyl)-1-chloro-ethyl]boronic acid (+) pinanediol ester and cyanoacetic acid following the procedure in Step 2 of Example 1. The crude product was purified by flash chromatography on silica gel (25-100% EtOAc/Hexane). ESI-MS m/z 497 (MH)$^+$.

Step 2. Synthesis of (R)-3-(2-Cyano-acetylamino)-2-hydroxy-3,4-dihydro-2H-benzo[e][1,2]oxaborinine-8-carboxylic acid Prepared from 3-[2-(2-Cyano-acetylamino)-2-(2,9,9-trimethyl-3,5-dioxa-4-bora-tricyclo[6.1.1.02,6]dec-4-yl)-ethyl]-2-methoxy-benzoic acid tert-butyl ester following the procedure described in Step 3 of Example 1. The crude product was purified by reverse phase preparative HPLC and dried using lyophilization. ESI-MS m/z 275 (MH)$^+$.

Example 3

(R)-3-(2,2-Dihydroxy-propionylamino)-2-hydroxy-3,4-dihydro-2H-benzo[e][1,2]oxaborinine-8-carboxylic acid

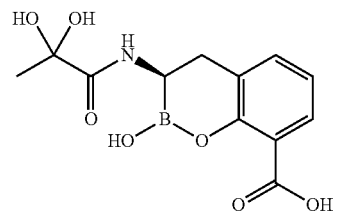 [SMILES: CC(O)(O)C(=O)N[C@H]1Cc2cccc(C(=O)O)c2OB1O]

Step 1. Synthesis of 3-[2-(2,2-Difluoro-propionylamino)-2-(2,9,9-trimethyl-3,5-dioxa-4-bora-tricyclo[6.1.1.02,6]dec-4-yl)-ethyl]-2-methoxy-benzoic acid tert-butyl ester Prepared from [(1S)-2-(3-tert-butoxycarbonyl-2-methoxy-phenyl)-1-chloro-ethyl]boronic acid (+) pinanediol ester and 2,2-difluoropropionic acid following the procedure in Step 2 of Example 1. The crude product was purified by flash chromatography on silica gel (10-100% EtOAc/Hexane). ESI-MS m/z 522 (MH)$^+$.

Step 2. Synthesis of (R)-3-(2,2-Dihydroxy-propionylamino)-2-hydroxy-3,4-dihydro-2H-benzo[e][1,2]oxaborinine-8-carboxylic acid Prepared from 3-[2-(2,2-Difluoro-propionylamino)-2-(2,9,9-trimethyl-3,5-dioxa-4-bora-tricyclo[6.1.1.02,6]dec-4-yl)-ethyl]-2-methoxy-benzoic acid tert-butyl ester following the procedure described in Step 3 of Example 1. The crude product was purified by reverse phase preparative HPLC and dried using lyophilization. ESI-MS m/z 296 (MH)$^+$.

Example 4

(R)-2-Hydroxy-3-(3,3,3-trifluoro-propionylamino)-3,4-dihydro-2H-benzo[e][1,2]oxaborinine-8-carboxylic acid

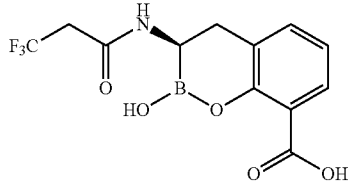

Step 1. Synthesis of 2-Methoxy-3-[2-(3,3,3-trifluoro-propionylamino)-2-(2,9,9-trimethyl-3,5-dioxa-4-bora-tricyclo[6.1.1.02,6]dec-4-yl)-ethyl]-benzoic acid tert-butyl ester Prepared from [(1S)-2-(3-tert-butoxycarbonyl-2-methoxy-phenyl)-1-chloro-ethyl]boronic acid (+) pinanediol ester and 3,3,3-trifluoropropionic acid following the procedure in Step 2 of Example 1. The crude product was purified by flash chromatography on silica gel (10-100% EtOAc/Hexane). ESI-MS m/z 540 (MH)$^+$.

Step 2. Synthesis of (R)-2-Hydroxy-3-(3,3,3-trifluoro-propionylamino)-3,4-dihydro-2H-benzo[e][1,2]oxaborinine-8-carboxylic acid Prepared from 2-Methoxy-3-[2-(3,3,3-trifluoro-propionylamino)-2-(2,9,9-trimethyl-3,5-dioxa-4-bora-tricyclo[6.1.1.02,6]dec-4-yl)-ethyl]-benzoic acid tert-butyl ester following the procedure described in Step 3 of Example 1. The crude product was purified by reverse phase preparative HPLC and dried using lyophilization. ESI-MS m/z 318 (MH)$^+$.

Example 5

(R)-3-(2-Chloro-4,4-difluoro-butyrylamino)-2-hydroxy-3,4-dihydro-2H-benzo[e][1,2]oxaborinine-8-carboxylic acid

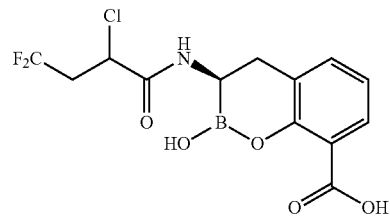

Step 1. Synthesis of 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid tert-butyl ester Prepared from [(1S)-2-(3-tert-butoxycarbonyl-2-methoxy-phenyl)-1-chloro-ethyl]boronic acid (+) pinanediol ester and 4,4,4-trifluorobutyric acid following the procedure in Step 2 of Example 1. The crude product was purified by flash chromatography on silica gel (10-100% EtOAc/Hexane). ESI-MS m/z 554 (MH)$^+$.

Step 2. Synthesis of (R)-3-(2-Chloro-4,4-difluoro-butyrylamino)-2-hydroxy-3,4-dihydro-2H-benzo[e][1,2]oxaborinine-8-carboxylic acid Prepared from 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid tert-butyl ester following the procedure described in Step 3 of Example 1. The crude product was purified by reverse phase preparative HPLC and dried using lyophilization. ESI-MS m/z 348 (MH)$^+$.

Example 6

(R)-2-Hydroxy-3-(3-methyl-butyrylamino)-3,4-dihydro-2H-benzo[e][1,2]oxaborinine-8-carboxylic acid

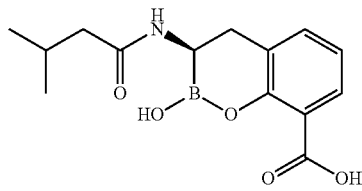 [SMILES: CC(C)CC(=O)N[C@H]1Cc2cccc(C(=O)O)c2OB1O]

Step 1. Synthesis of 2-Methoxy-3-[2-(3-methyl-butyrylamino)-2-(2,9,9-trimethyl-3,5-dioxa-4-bora-tricyclo[6.1.1.02,6]dec-4-yl)-ethyl]-benzoic acid tert-butyl ester Prepared from [(1S)-2-(3-tert-butoxycarbonyl-2-methoxy-phenyl)-1-chloro-ethyl]boronic acid (+) pinanediol ester and isovaleric acid following the procedure in Step 2 of Example 1. The crude product was purified by flash chromatography on silica gel (10-100% EtOAc/Hexane). ESI-MS m/z 514 (MH)⁺.

Step 2. Synthesis of (R)-2-Hydroxy-3-(3-methyl-butyrylamino)-3,4-dihydro-2H-benzo[e][1,2]oxaborinine-8-carboxylic acid Prepared from 2-Methoxy-3-[2-(3-methyl-butyrylamino)-2-(2,9,9-trimethyl-3,5-dioxa-4-bora-tricyclo[6.1.1.0²,⁶]dec-4-yl)-ethyl]-benzoic acid tert-butyl ester following the procedure described in Step 3 of Example 1. The crude product was purified by reverse phase preparative HPLC and dried using lyophilization. ESI-MS m/z 292 (MH)⁺.

Example 7

(R)-2-Hydroxy-3-(4,4,4-trifluoro-butyrylamino)-3,4-dihydro-2H-benzo[e][1,2]oxaborinine-8-carboxylic acid

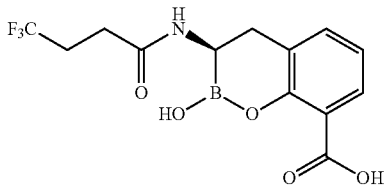

Synthesis of (R)-2-Hydroxy-3-(4,4,4-trifluoro-butyrylamino)-3,4-dihydro-2H-benzo[e][1,2]oxaborinine-8-carboxylic acid To a solution of 2-Methoxy-3-[2-(4,4,4-trifluoro-butyrylamino)-2-(2,9,9-trimethyl-3,5-dioxa-4-bora-tricyclo[6.1.1.0²,⁶]dec-4-yl)-ethyl]-benzoic acid tert-butyl ester (as prepared in Step 1 of Example 5) (0.217 g, 0.392 mmol) in dichloromethane (4.9 mL) was added boron trichloride (1.0M in CH$_2$Cl$_2$, 1.6 mL, 1.60 mmol) at −78° C. The reaction was stirred at −78° C. for 30 min then warmed to 0° C. for 30 min. The reaction was quenched with water and extracted two times with diethyl ether. The product remained in the aqueous layer and was purified by reverse phase preparative HPLC and dried using lyophilization. ESI-MS m/z 332 (MH)⁺.

Example 8

(R)-3-(3-Cyano-propionylamino)-2-hydroxy-3,4-dihydro-2H-benzo[e][1,2]oxaborinine-8-carboxylic acid

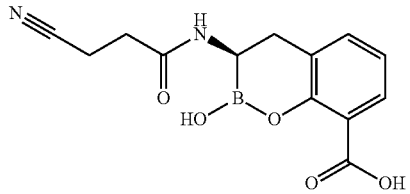 [SMILES: N#CCCC(=O)N[C@H]1Cc2cccc(C(=O)O)c2OB1O]

Step 1. Synthesis of 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid tert-butyl ester Prepared from [(1S)-2-(3-tert-butoxycarbonyl-2-methoxy-phenyl)-1-chloro-ethyl]boronic acid (+) pinanediol ester and 3-cyanopropanoic acid following the procedure in Step 2 of Example 1. The crude product was purified by flash chromatography on silica gel (10-100% EtOAc/Hexane). ESI-MS m/z 511 (MH)⁺.

Step 2. Synthesis of (R)-3-(3-Cyano-propionylamino)-2-hydroxy-3,4-dihydro-2H-benzo[e][1,2]oxaborinine-8-carboxylic acid Prepared from 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid tert-butyl ester following the procedure described in Example 7. The crude product was purified by reverse phase preparative HPLC and dried using lyophilization. ESI-MS m/z 289 (MH)⁺.

Example 9

(R)-2-Hydroxy-3-(4,4,4-trifluoro-3-trifluoromethyl-butyrylamino)-3,4-dihydro-2H-benzo[e][1,2]oxaborinine-8-carboxylic acid

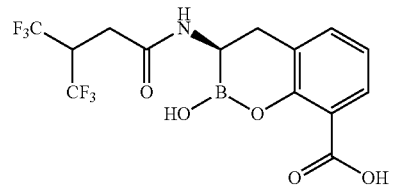 [SMILES: O=C(CC(C(F)(F)F)C(F)(F)F)N[C@H]1Cc2cccc(C(=O)O)c2OB1O]

Step 1. Synthesis of 2-Methoxy-3-[2-(4,4,4-trifluoro-3-trifluoromethyl-butyrylamino)-2-(2,9,9-trimethyl-3,5-dioxa-4-bora-tricyclo[6.1.1.0²,⁶]dec-4-yl)-ethyl]-benzoic acid tert-butyl ester Prepared from [(1S)-2-(3-tert-butoxycarbonyl-2-methoxy-phenyl)-1-chloro-ethyl]boronic acid (+) pinanediol ester and 4,4,4-trifluoro-3-(trifluoromethyl)butyric acid following the procedure in Step 2 of Example 1. The crude product was purified by flash chromatography on silica gel (10-100% EtOAc/Hexane). ESI-MS m/z 622 (MH)⁺.

Step 2. Synthesis of (R)-2-Hydroxy-3-(4,4,4-trifluoro-3-trifluoromethyl-butyrylamino)-3,4-dihydro-2H-benzo[e][1,2]oxaborinine-8-carboxylic acid Prepared from 2-Methoxy-3-[2-(4,4,4-trifluoro-3-trifluoromethyl-butyrylamino)-2-(2,9,9-trimethyl-3,5-dioxa-4-bora-tricyclo[6.1.1.0²,⁶]dec-4-yl)-ethyl]-benzoic acid tert-butyl ester following the procedure described in Example 7. The crude product was purified by reverse phase preparative HPLC and dried using lyophilization. ESI-MS m/z 400 (MH)⁺.

Example 10

(R)-2-Hydroxy-3-(4-oxo-pentanoylamino)-3,4-di-hydro-2H-benzo[e][1,2]oxaborinine-8-carboxylic acid

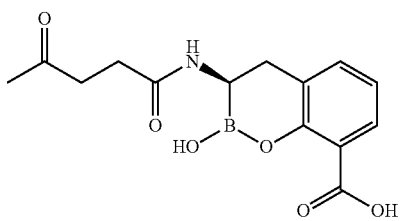 [SMILES: CC(=O)CCC(=O)N[C@H]1Cc2cccc(C(=O)O)c2OB1O]

Step 1. Synthesis of 2-Methoxy-3-[2-(4-oxo-pentanoylamino)-2-(2,9,9-trimethyl-3,5-dioxa-4-bora-tricyclo[6.1.1.02,6]dec-4-yl)-ethyl]-benzoic acid tert-butyl ester Prepared from [(1S)-2-(3-tert-butoxycarbonyl-2-methoxy-phenyl)-1-chloro-ethyl]boronic acid (+) pinanediol ester and levulinic acid following the procedure in Step 2 of Example 1. The crude product was purified by flash chromatography on silica gel (10-100% EtOAc/Hexane). ESI-MS m/z 528 (MH)$^+$.

Step 2. Synthesis of (R)-2-Hydroxy-3-(4-oxo-pentanoylamino)-3,4-dihydro-2H-benzo[e][1,2]oxaborinine-8-carboxylic acid.

Prepared from 2-Methoxy-3-[2-(4-oxo-pentanoylamino)-2-(2,9,9-trimethyl-3,5-dioxa-4-bora-tricyclo[6.1.1.02,6]dec-4-yl)-ethyl]-benzoic acid tert-butyl ester following the procedure described in Example 7. The crude product was purified by reverse phase preparative HPLC and dried using lyophilization. ESI-MS m/z 306 (MH)$^+$.

Example 11

(R)-3-(2,2-Dichloro-propionylamino)-2-hydroxy-3,4-dihydro-2H-benzo[e][1,2]oxaborinine-8-carboxylic acid

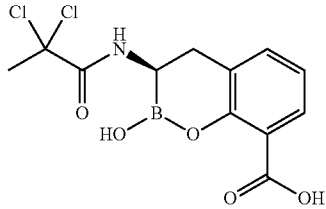 [SMILES: CC(Cl)(Cl)C(=O)N[C@H]1Cc2cccc(C(=O)O)c2OB1O]

Step 1. Synthesis of 3-[2-(2,2-Dichloro-propionylamino)-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 2,2-dichloropropionic acid following the procedure in Step 2 of Example 1. The crude product was purified by flash chromatography on silica gel (10-100% EtOAc/Hexane). ESI-MS m/z 555 (MH)$^+$.

Step 2. Synthesis of (R)-3-(2,2-Dichloro-propionylamino)-2-hydroxy-3,4-dihydro-2H-benzo[e][1,2]oxaborinine-8-carboxylic acid.

Prepared from 3-[2-(2,2-Dichloro-propionylamino)-2-(2,9,9-trimethyl-3,5-dioxa-4-bora-tricyclo[6.1.1.02,6]dec-4-yl)-ethyl]-2-methoxy-benzoic acid tert-butyl ester following the procedure described in Example 7. The crude product was purified by reverse phase preparative HPLC and dried using lyophilization. ESI-MS m/z 333 (MH)$^+$.

Example 12

(R)-3-(3-Chloro-acryloylamino)-2-hydroxy-3,4-dihydro-2H-benzo[e][1,2]oxaborinine-8-carboxylic acid

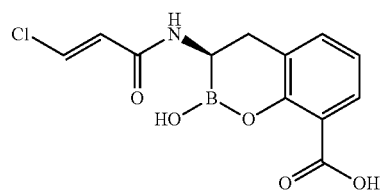 [SMILES: O=C(/C=C/Cl)N[C@H]1Cc2cccc(C(=O)O)c2OB1O]

Step 1. Synthesis of 3-[2-(2,3-Dichloro-propionylamino)-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 2,3-dichloropropionic acid following the procedure in Step 2 of Example 1. The crude product was purified by flash chromatography on silica gel (10-100% EtOAc/Hexane). ESI-MS m/z 555 (MH)$^+$.

Step 2. Synthesis of (R)-3-(3-Chloro-acryloylamino)-2-hydroxy-3,4-dihydro-2H-benzo[e][1,2]oxaborinine-8-carboxylic acid.

Prepared from 3-[2-(2,3-Dichloro-propionylamino)-2-(2,9,9-trimethyl-3,5-dioxa-4-bora-tricyclo[6.1.1.02,6]dec-4-yl)-ethyl]-2-methoxy-benzoic acid tert-butyl ester following the procedure described in Example 7. The crude product was purified by reverse phase preparative HPLC and dried using lyophilization. ESI-MS m/z 296 (MH)$^+$.

Example 13

(R)-2-Hydroxy-3-(5-oxo-hexanoylamino)-3,4-dihydro-2H-benzo[e][1,2]oxaborinine-8-carboxylic acid

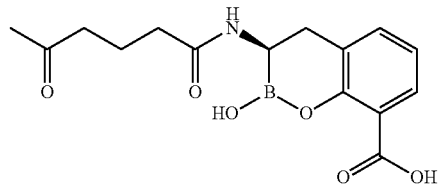 [SMILES: CC(=O)CCCC(=O)N[C@H]1Cc2cccc(C(=O)O)c2OB1O]

Step 1. Synthesis of 2-Methoxy-3-[2-(5-oxo-hexanoylamino)-2-(2,9,9-trimethyl-3,5-dioxa-4-bora-tricyclo[6.1.1.0²,⁶]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 4-acetylbutyric acid following the procedure in Step 2 of Example 1. The crude product was purified by flash chromatography on silica gel (10-100% EtOAc/Hexane). ESI-MS m/z 542 (MH)$^+$.

Step 2. Synthesis of (R)-2-Hydroxy-3-(5-oxo-hexanoylamino)-3,4-dihydro-2H-benzo[e][1,2]oxaborinine-8-carboxylic acid.

Prepared from 2-Methoxy-3-[2-(5-oxo-hexanoylamino)-2-(2,9,9-trimethyl-3,5-dioxa-4-bora-tricyclo[6.1.1.0²,⁶]dec-4-yl)-ethyl]-benzoic acid tert-butyl ester following the procedure described in Step 3 of Example 1. The crude product was purified by reverse phase preparative HPLC and dried using lyophilization. ESI-MS m/z 320 (MH)$^+$.

Example 14

(R)-3-(4-Cyano-butyrylamino)-2-hydroxy-3,4-dihydro-2H-benzo[e][1,2]oxaborinine-8-carboxylic acid

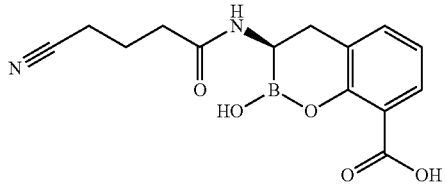 [SMILES: N#CCCCC(=O)N[C@H]1Cc2cccc(C(=O)O)c2OB1O]

Step 1. Synthesis of 3-[2-(4-Cyano-butyrylamino)-2-(2,9,9-trimethyl-3,5-dioxa-4-bora-tricyclo[6.1.1.0²,⁶]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 4-cyanobutanoic acid following the procedure in Step 2 of Example 1. The crude product was purified by flash chromatography on silica gel (10-100% EtOAc/Hexane). ESI-MS m/z 525 (MH)$^+$.

Step 2. Synthesis of (R)-3-(4-Cyano-butyrylamino)-2-hydroxy-3,4-dihydro-2H-benzo[e][1,2]oxaborinine-8-carboxylic acid.

Prepared from 3-[2-(4-Cyano-butyrylamino)-2-(2,9,9-trimethyl-3,5-dioxa-4-bora-tricyclo[6.1.1.0²,⁶]dec-4-yl)-ethyl]-2-methoxy-benzoic acid tert-butyl ester following the procedure described in Step 3 of Example 1. The crude product was purified by reverse phase preparative HPLC and dried using lyophilization. ESI-MS m/z 303 (MH)$^+$.

Example 15

(R)-3-(3-Dimethylcarbamoyl-propionylamino)-2-hydroxy-3,4-dihydro-2H-benzo[e][1,2]oxaborinine-8-carboxylic acid

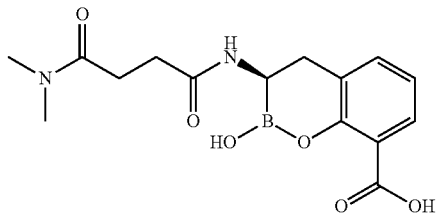 [SMILES: CN(C)C(=O)CCC(=O)N[C@H]1Cc2cccc(C(=O)O)c2OB1O]

Step 1. Synthesis of 3-[2-(3-Dimethylcarbamoyl-propionylamino)-2-(2,9,9-trimethyl-3,5-dioxa-4-bora-tricyclo[6.1.1.0²,⁶]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and N,N-dimethylsuccinamic acid following the procedure in Step 2 of Example 1. The crude product was purified by flash chromatography on silica gel (20-100% EtOAc/Hexane then 15% CH$_3$OH/CH$_2$Cl$_2$). ESI-MS m/z 557 (MH)$^+$.

Step 2. Synthesis of (R)-3-(3-Dimethylcarbamoyl-propionylamino)-2-hydroxy-3,4-dihydro-2H-benzo[e][1,2]oxaborinine-8-carboxylic acid.

Prepared from 3-[2-(3-Dimethylcarbamoyl-propionylamino)-2-(2,9,9-trimethyl-3,5-dioxa-4-bora-tricyclo[6.1.1.0²,⁶]dec-4-yl)-ethyl]-2-methoxy-benzoic acid tert-butyl ester following the procedure described in Step 3 of Example 1. The crude product was purified by reverse phase preparative HPLC and dried using lyophilization. ESI-MS m/z 335 (MH)$^+$.

Example 16

(R)-3-(3-Carbamoyl-propionylamino)-2-hydroxy-3,4-dihydro-2H-benzo[e][1,2]oxaborinine-8-carboxylic acid

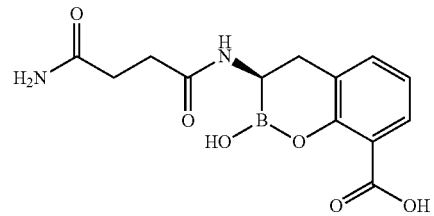

Step 1. Synthesis of 3-[2-(3-Carbamoyl-propionylamino)-2-(2,9,9-trimethyl-3,5-dioxa-4-bora-tricyclo[6.1.1.0²,⁶]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and succinamic acid following the procedure in Step 2 of Example 1. The crude product was purified by flash chromatography on silica gel (20-100% EtOAc/Hexane then 15% CH$_3$OH/CH$_2$Cl$_2$). ESI-MS m/z 529 (MH)$^+$.

Step 2. Synthesis of (R)-3-(3-Carbamoyl-propionylamino)-2-hydroxy-3,4-dihydro-2H-benzo[e][1,2]oxaborinine-8-carboxylic acid.

Prepared from 3-[2-(3-Carbamoyl-propionylamino)-2-(2,9,9-trimethyl-3,5-dioxa-4-bora-tricyclo[6.1.1.0$^{2,6}$]dec-4-yl)-ethyl]-2-methoxy-benzoic acid tert-butyl ester following the procedure described in Step 3 of Example 1. The crude product was purified by reverse phase preparative HPLC and dried using lyophilization. ESI-MS m/z 307 (MH)$^+$.

Example 17

(R)-2-Hydroxy-3-(4-hydroxyimino-pentanoylamino)-3,4-dihydro-2H-benzo[e][1,2]oxaborinine-8-carboxylic acid

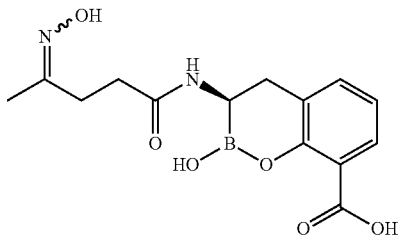

To a solution of (R)-2-hydroxy-3-(4-oxo-pentanoylamino)-3,4-dihydro-2H-benzo[e][1,2]oxaborinine-8-carboxylic acid (20.1 mg, 0.066 mmol, prepared as described in Example 10) in ethanol (1.5 mL) was added sodium acetate (15.0 mg, 0.182 mmol) followed by hydroxylamine hydrochloride (8.2 mg, 0.118 mmol). Solids precipitated within 5 minutes, and the solution was stirred at ambient temperature for 23 h. The solvent was removed in vacuo, water (5 mL) was added and the slurry taken to pH 12 with 1N NaOH to dissolve the solids. The solution was taken to pH 1 with 1N HCl, and the crude product was purified by reverse phase flash chromatography on C$_{18}$ silica gel (100% H$_2$O to 10% IPA/H$_2$O) and dried using lyophilization. ESI-MS m/z 321 (MH)$^+$.

Example 18

(R)-2-Hydroxy-3-(4-methoxyimino-pentanoylamino)-3,4-dihydro-2H-benzo[e][1,2]oxaborinine-8-carboxylic acid

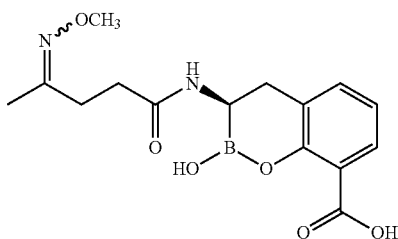

Prepared from (R)-2-hydroxy-3-(4-oxo-pentanoylamino-3,4-dihydro-2H-benzo[e][1,2]oxaborinine-8-carboxylic acid and methoxylamine hydrochloride following the procedure described in Example 17. The crude product was purified by reverse phase flash chromatography on C$_{18}$ silica gel (100% H$_2$O to 10% IPA/H$_2$O) and dried using lyophilization. ESI-MS m/z 335 (MH)$^+$.

Example 19

(R)-2-Hydroxy-3-(3-methylcarbamoyl-propionylamino)-3,4-dihydro-2H-benzo[e][1,2]oxaborinine-8-carboxylic acid

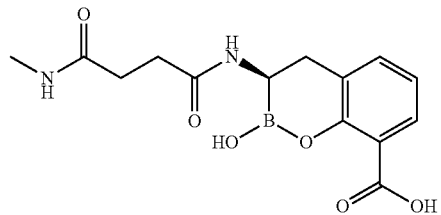 [SMILES: CNC(=O)CCC(=O)N[C@H]1Cc2cccc(C(=O)O)c2OB1O]

Step 1. Synthesis of 2-Methoxy-3-[2-(3-methylcarbamoyl-propionylamino)-2-(2,9,9-trimethyl-3,5-dioxa-4-bora-tricyclo[6.1.1.0$^{2,6}$]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-methylcarbamoylpropionic acid following the procedure in Step 2 of Example 1. The crude product was purified by flash chromatography on silica gel (20-100% EtOAc/Hexane then 10% CH$_3$OH/CH$_2$Cl$_2$). ESI-MS m/z 543 (MH)$^+$.

Step 2. Synthesis of (R)-2-Hydroxy-3-(3-methylcarbamoyl-propionylamino)-3,4-dihydro-2H-benzo[e][1,2]oxaborinine-8-carboxylic acid.

Prepared from 2-Methoxy-3-[2-(3-methylcarbamoyl-propionylamino)-2-(2,9,9-trimethyl-3,5-dioxa-4-bora-tricyclo[6.1.1.0$^{2,6}$]dec-4-yl)-ethyl]-benzoic acid tert-butyl ester following the procedure described in Step 3 of Example 1. The crude product was purified by reverse phase preparative HPLC and dried using lyophilization. ESI-MS m/z 321 (MH)$^+$.

Example 20

(R)-3-(3-Acetylamino-propionylamino)-2-hydroxy-3,4-dihydro-2H-benzo[e][1,2]oxaborinine-8-carboxylic acid

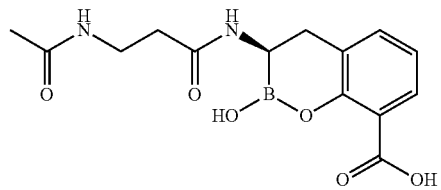 [SMILES: CC(=O)NCCC(=O)N[C@H]1Cc2cccc(C(=O)O)c2OB1O]

Step 1. Synthesis of 3-[2-(3-Acetylamino-propionylamino)-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and N-acetyl-β-alanine following the procedure in Step 2 of Example 1. The crude product was purified by flash chromatography on silica gel (10-100% EtOAc/Hexane then 10% CH$_3$OH/CH$_2$Cl$_2$). ESI-MS m/z 543 (MH)$^+$.

Step 2. Synthesis of (R)-3-(3-Acetylamino-propionylamino)-2-hydroxy-3,4-dihydro-2H-benzo[e][1,2]oxaborinine-8-carboxylic acid.

Prepared from 3-[2-(3-Acetylamino-propionylamino)-2-(2,9,9-trimethyl-3,5-dioxa-4-bora-tricyclo[6.1.1.02,6]dec-4-yl)-ethyl]-2-methoxy-benzoic acid tert-butyl ester following the procedure described in Step 3 of Example 1. The crude product was purified by reverse phase preparative HPLC and dried using lyophilization. ESI-MS m/z 321 (MH)$^+$.

Example 21

(R)-2-Hydroxy-3-(3-methanesulfonyl-propionylamino)-3,4-dihydro-2H-benzo[e][1,2]oxaborinine-8-carboxylic acid

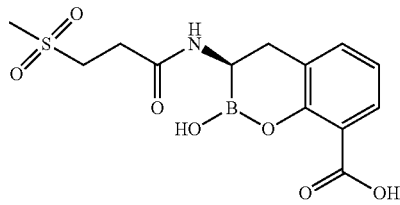 [SMILES: CS(=O)(=O)CCC(=O)N[C@H]1Cc2cccc(C(=O)O)c2OB1O]

Step 1. Synthesis of 3-[2-(3-Methanesulfonyl-propionylamino)-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 3-(methylsulfonyl)propanoic acid following the procedure in Step 2 of Example 1. The crude product was purified by flash chromatography on silica gel (10-100% EtOAc/Hexane). ESI-MS m/z 564 (MH)$^+$.

Step 2. Synthesis of (R)-2-Hydroxy-3-(3-methanesulfonyl-propionylamino)-3,4-dihydro-2H-benzo[e][1,2]oxaborinine-8-carboxylic acid.

Prepared from 3-[2-(3-Methanesulfonyl-propionylamino)-2-(2,9,9-trimethyl-3,5-dioxa-4-bora-tricyclo[6.1.1.02,6]dec-4-yl)-ethyl]-2-methoxy-benzoic acid tert-butyl ester following the procedure described in Step 3 of Example 1. The crude product was purified by reverse phase preparative HPLC and dried using lyophilization. ESI-MS m/z 342 (MH)$^+$.

Example 22

(R)-2-Hydroxy-3-(3-methanesulfonylamino-propionylamino)-3,4-dihydro-2H-benzo[e][1,2]oxaborinine-8-carboxylic acid

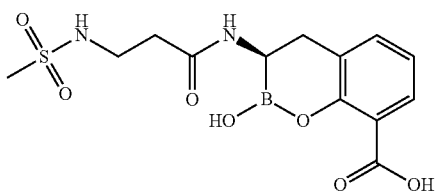 [SMILES: CS(=O)(=O)NCCC(=O)N[C@H]1Cc2cccc(C(=O)O)c2OB1O]

Step 1. Synthesis of 3-[2-(3-Methanesulfonylamino-propionylamino)-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and N-(methylsulfonyl)-β-alanine following the procedure in Step 2 of Example 1. The crude product was purified by flash chromatography on silica gel (10-100% EtOAc/Hexane). ESI-MS m/z 579 (MH)$^+$.

Step 2. Synthesis of (R)-2-Hydroxy-3-(3-methanesulfonylamino-propionylamino)-3,4-dihydro-2H-benzo[e][1,2]oxaborinine-8-carboxylic acid.

Prepared from 3-[2-(3-Methanesulfonylamino-propionylamino)-2-(2,9,9-trimethyl-3,5-dioxa-4-bora-tricyclo[6.1.1.02,6]dec-4-yl)-ethyl]-2-methoxy-benzoic acid tert-butyl ester following the procedure described in Example 7. The crude product was purified by reverse phase preparative HPLC and dried using lyophilization. ESI-MS m/z 357 (MH)$^+$.

Example 23

(R)-2-Hydroxy-3-(3-ureido-propionylamino)-3,4-dihydro-2H-benzo[e][1,2]oxaborinine-8-carboxylic acid

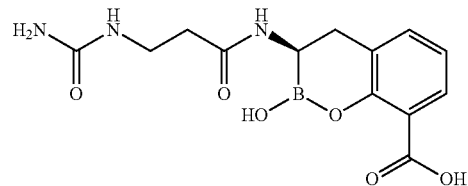 [SMILES: NC(=O)NCCC(=O)N[C@H]1Cc2cccc(C(=O)O)c2OB1O]

Step 1. Synthesis of 2-Methoxy-3-[2-(2,9,9-trimethyl-3,5-dioxa-4-bora-tricyclo[6.1.1.02,6]dec-4-yl)-2-(3-ureido-propionylamino)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-Ureidopropionic acid following the procedure in Step 2 of Example 1. The crude product was purified by flash chromatography on silica gel (10-100% EtOAc/Hexane). ESI-MS m/z 544 (MH)+.

Step 2. Synthesis of (R)-2-Hydroxy-3-(3-ureido-propionylamino)-3,4-dihydro-2H-benzo[e][1,2]oxaborinine-8-carboxylic acid.

Prepared from 2-Methoxy-3-[2-(2,9,9-trimethyl-3,5-dioxa-4-bora-tricyclo[6.1.1.02,6]dec-4-yl)-2-(3-ureido-propionylamino)-ethyl]-benzoic acid tert-butyl ester following the procedure described in Example 7. The crude product was purified by reverse phase preparative HPLC and dried using lyophilization. ESI-MS m/z 322 (MH)+.

Example 24

(R)-3-(4-chloro-4-methylpentanamido)-2-hydroxy-3,4-dihydro-2H-benzo[e][1,2]oxaborinine-8-carboxylic acid

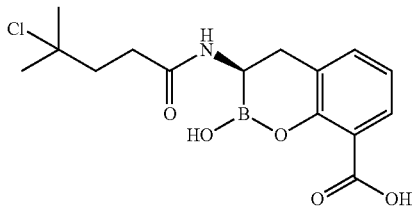

Step 1. Synthesis of 4-Methyl-pent-4-enoic acid ethyl ester.

To a solution of methyltriphenylphosphonium iodide (3.00 g, 7.38 mmol) in THF (25 mL) at room temperature was added LiHMDS (1.0 M solution, 8.4 mL, 8.4 mmol). After 15 min the solution was cooled to −35° C. and ethyl levulinate (1. mL, 7.05 mmol) was added. The cooling bath was removed and the reaction stirred for 40 min then quenched with water and extracted twice with EtOAc. The organic layers were combined, washed with water, brine, dried (Na₂SO₄) and concentrated in vacuo. The crude product was purified using flash chromatography on silica gel (3% EtOAc/Hexane).

Step 2. Synthesis of 4-Methyl-pent-4-enoic acid.

To a solution of 4-methyl-pent-4-enoic acid ethyl ester (530 mg, 3.73 mmol) in EtOH (5 mL) was added 1N NaOH (10 mL). The mixture was stirred for 3 days, concentrated in vacuo to remove the ethanol, and diluted with H₂O and Et₂O. The layers were separated and the organic layer washed once with water. The aqueous layers were combined, acidified to pH 1 with 1N HCl and extracted twice with Et₂O. The organic layers were combined, washed with brine, dried (Na₂SO₄) and concentrated in vacuo. The crude product was used without further purification.

Step 3. Synthesis of 2-Methoxy-3-[2-(4-methyl-pent-4-enoylamino)-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinane-diol ester and 4-methyl-pent-4-enoic acid following the procedure in Step 2 of Example 1. The crude product was purified by flash chromatography on silica gel (20% to 50% EtOAc/Hexane). ESI-MS m/z 526 (MH)+.

Step 4. Synthesis of (R)-3-(4-chloro-4-methylpentanamido)-2-hydroxy-3,4-dihydro-2H-benzo[e][1,2]oxaborinine-8-carboxylic acid.

Prepared from 2-Methoxy-3-[2-(4-methyl-pent-4-enoylamino)-2-(2,9,9-trimethyl-3,5-dioxa-4-bora-tricyclo[6.1.1.02,6]dec-4-yl)-ethyl]-benzoic acid tert-butyl ester following the procedure described in Example 7. The crude product was purified by reverse phase flash chromatography on C₁₈ silica gel (10% to 30% IPA/H₂O) and dried using lyophilization. ESI-MS m/z 340 (MH)+.

Example 25

(R)-3-(2-ethoxyacetamido)-2-hydroxy-3,4-dihydro-2H-benzo[e][1,2]oxaborinine-8-carboxylic acid

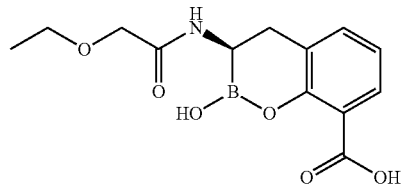 [SMILES: CCOCC(=O)N[C@H]1Cc2cccc(C(=O)O)c2OB1O]

Step 1. Synthesis of 3-[2-(2-Ethoxy-acetylamino)-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinane-diol ester and ethoxyacetic acid following the procedure in Step 2 of Example 1. The crude product was purified by flash chromatography on silica gel (25% to 50% EtOAc/Hexane). ESI-MS m/z 516 (MH)+.

Step 2. Synthesis of (R)-3-(2-ethoxyacetamido)-2-hydroxy-3,4-dihydro-2H-benzo[e][1,2]oxaborinine-8-carboxylic acid.

Prepared from 3-[2-(2-Ethoxy-acetylamino)-2-(2,9,9-trimethyl-3,5-dioxa-4-bora-tricyclo[6.1.1.02,6]dec-4-yl)-ethyl]-2-methoxy-benzoic acid tert-butyl ester following the procedure described in Example 7. The crude product was purified by reverse phase flash chromatography on C₁₈ silica gel (100% H₂O to 8% IPA/H₂O) and dried using lyophilization. ESI-MS m/z 294 (MH)+.

Example 26

(R)-2-Hydroxy-3-(3-methoxy-propionylamino)-3,4-dihydro-2H-benzo[e][1,2]oxaborinine-8-carboxylic acid

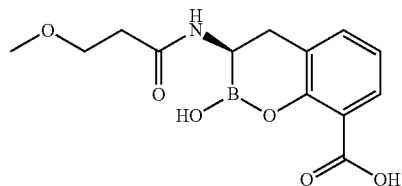 [SMILES: COCCC(=O)N[C@H]1Cc2cccc(C(=O)O)c2OB1O]

Step 1. Synthesis of 2-Methoxy-3-[2-(3-methoxy-propionylamino)-2-(2,9,9-trimethyl-3,5-dioxa-4-bora-tricyclo[6.1.1.0$^{2,6}$]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-Methoxy-propionic acid following the procedure in Step 2 of Example 1. The crude product was purified by flash chromatography on silica gel (25% to 50% EtOAc/Hexane). ESI-MS m/z 516 (MH)$^+$.

Step 2. Synthesis of (R)-2-Hydroxy-3-(3-methoxy-propionylamino)-3,4-dihydro-2H-benzo[e][1,2]oxaborinine-8-carboxylic acid.

Prepared from 2-Methoxy-3-[2-(3-methoxy-propionylamino)-2-(2,9,9-trimethyl-3,5-dioxa-4-bora-tricyclo[6.1.1.0$^{2,6}$]dec-4-yl)-ethyl]-benzoic acid tert-butyl ester following the procedure described in Example 7. The crude product was purified by reverse phase flash chromatography on C$_{18}$ silica gel (100% H$_2$O to 8% IPA/H$_2$O) and dried using lyophilization. ESI-MS m/z 294 (MH)$^+$.

Example 27

(R)-2-Hydroxy-3-[2-(2-methoxy-ethoxy)-acetylamino]-3,4-dihydro-2H-benzo[e][1,2]oxaborinine-8-carboxylic acid

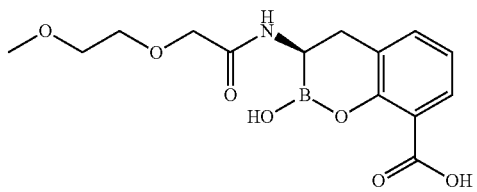 [SMILES: COCCOCC(=O)N[C@H]1Cc2cccc(C(=O)O)c2OB1O]

Step 1. Synthesis of 2-Methoxy-3-[2-[2-(2-methoxy-ethoxy)-acetylamino]-2-(2,9,9-trimethyl-3,5-dioxa-4-bora-tricyclo[6.1.1.0$^{2,6}$]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and (2-Methoxy-ethoxy)-acetic acid following the procedure in Step 2 of Example 1. The crude product was purified by flash chromatography on silica gel (25% to 50% EtOAc/Hexane). ESI-MS m/z 546 (MH)$^+$.

Step 2. Synthesis of (R)-2-Hydroxy-3-[2-(2-methoxy-ethoxy)-acetylamino]-3,4-dihydro-2H-benzo[e][1,2]oxaborinine-8-carboxylic acid.

Prepared from 2-Methoxy-3-[2-[2-(2-methoxy-ethoxy)-acetylamino]-2-(2,9,9-trimethyl-3,5-dioxa-4-bora-tricyclo[6.1.1.0$^{2,6}$]dec-4-yl)-ethyl]-benzoic acid tert-butyl ester following the procedure described in Example 7. The crude product was purified by reverse phase flash chromatography on C$_{18}$ silica gel (100% H$_2$O to 8% IPA/H$_2$O) and dried using lyophilization. ESI-MS m/z 324 (MH)$^+$.

Example 28

(R)-2-Hydroxy-3-(3-pyrazol-1-yl-propionylamino)-3,4-dihydro-2H-benzo[e][1,2]oxaborinine-8-carboxylic acid

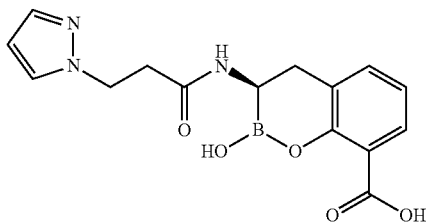 [SMILES: O=C(CCn1cccn1)N[C@H]1Cc2cccc(C(=O)O)c2OB1O]

Step 1. Preparation of 3-Pyrazol-1-yl-propionic acid tert-butyl ester.

To a solution of tert-butylacrylate (5.0 mL, 34.3 mmol) in acetonitrile (12 mL) was added pyrazole (1.55 g, 22.8 mmol) followed by 1,8-diazabicycloundec-7-ene (DBU, 1.7 mL, 11.4 mmol). The solution was stirred for 2 days, diluted with hexane and chromatographed on silica gel (20% EtOAc/Hexane) to afford 4.19 g (94%) of the title product as a colorless oil.

Step 2. Preparation of 3-pyrazol-1-yl-propionic acid hydrochloride.

A solution of 3-pyrazol-1-yl-propionic acid tert-butyl ester (2.0 g, 10.2 mmol) and 80% TFA in dichloromethane was stirred for 2.25 h at which point the reaction was shown to be complete. The solution was concentrated in vacuo, the residue taken up in toluene and concentrated in vacuo. This was repeated twice to afford a viscous oil which was triturated with ethyl ether/hexane to afford 2.28 g of the trifluoroacetate salt as a white solid. This material (700 mg) was dissolved in 5 mL H$_2$O and 5 mL 1N HCl added. The solution was concentrated in vacuo to a film, and this process repeated three times to ensure complete salt exchange. The crude material was dried via azeotroping initially with dioxane/toluene and then a final azeotrope with toluene followed by drying under vacuum overnight.

Step 3. Synthesis of 2-Methoxy-3-[2-(3-pyrazol-1-yl-propionylamino)-2-(2,9,9-trimethyl-3,5-dioxa-4-bora-tricyclo[6.1.1.0$^{2,6}$]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-pyrazol-1-yl-propionic acid hydrochloride following the procedure in Step 2 of Example 1. The crude product was purified by flash chromatography on silica gel (60% to 100% EtOAc:Hexane). ESI-MS m/z 552 (MH)$^+$.

Step 4. Synthesis of (R)-2-hydroxy-3-(3-pyrazol-1-yl-propionylamino)-3,4-dihydro-2H-benzo[e][1,2]oxaborinine-8-carboxylic acid.

Prepared from 2-Methoxy-3-[2-(3-pyrazol-1-yl-propionylamino)-2-(2,9,9-trimethyl-3,5-dioxa-4-bora-tricyclo[6.1.1.0$^{2,6}$]dec-4-yl)-ethyl]-benzoic acid tert-butyl ester following the procedure described in Example 7. The crude product was purified by reverse phase flash chromatography on $C_{18}$ silica gel (100% $H_2O$ to 12% IPA/$H_2O$) and dried using lyophilization. ESI-MS m/z 330 (MH)$^+$.

Example 29

(R)-2-Hydroxy-3-(3-imidazol-1-yl-propionylamino)-3,4-dihydro-2H-benzo[e][1,2]oxaborinine-8-carboxylic acid

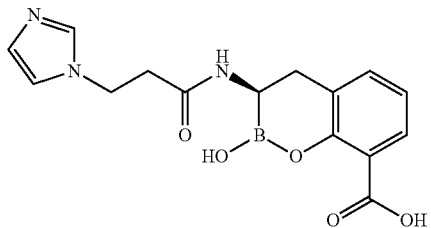

Steps 1 and 2. Preparation of 3-imidazol-1-yl-propionic acid hydrochloride.

Prepared from imidazole and tert-butylacylate following the procedure described in Steps 1 and 2 of Example 28.

Step 3. 2-Methoxy-3-[2-(3-imidazol-1-yl-propionylamino)-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-imidazol-1-yl-propionic acid hydrochloride following the procedure in Step 2 of Example 1. The crude product was purified by flash chromatography on silica gel (2% to 10% $CH_3OH/CH_2Cl_2$). ESI-MS m/z 552 (MH)$^+$.

Step 4. Synthesis of (R)-2-hydroxy-3-(3-pyrazol-1-yl-propionylamino)-3,4-dihydro-2H-benzo[e][1,2]oxaborinine-8-carboxylic acid.

Prepared from 2-Methoxy-3-[2-(3-imidazol-1-yl-propionylamino)-2-(2,9,9-trimethyl-3,5-dioxa-4-bora-tricyclo[6.1.1.02,6]dec-4-yl)-ethyl]-benzoic acid tert-butyl ester following the procedure described in Example 7. The crude product was purified by reverse phase flash chromatography on $C_{18}$ silica gel (100% $H_2O$ to 10% IPA/$H_2O$) and dried using lyophilization. ESI-MS m/z 330 (MH)$^+$.

Example 30

(R)-2-Hydroxy-3-[2-(2-oxo-oxazolidin-3-yl)-acetylamino]-3,4-dihydro-2H-benzo[e][1,2]oxaborinine-8-carboxylic acid

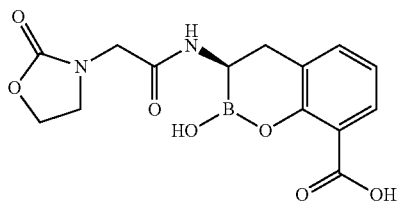 [SMILES: O=C(CN1CCOC1=O)N[C@H]1Cc2cccc(C(=O)O)c2OB1O]

Step 1. Synthesis of 2-Methoxy-3-[2-[2-(2-oxo-oxazolidin-3-yl)-acetylamino]-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and (2-oxo-1,3-oxazolidin-3-yl)acetic acid following the procedure in Step 2 of Example 1. The crude product was purified by flash chromatography on silica gel (10-100% EtOAc/Hexane). ESI-MS m/z 557 (MH)$^+$.

Step 2. Synthesis of (R)-2-Hydroxy-3-[2-(2-oxo-oxazolidin-3-yl)-acetylamino]-3,4-dihydro-2H-benzo[e][1,2]oxaborinine-8-carboxylic acid.

Prepared from 2-Methoxy-3-[2-[2-(2-oxo-oxazolidin-3-yl)-acetylamino]-2-(2,9,9-trimethyl-3,5-dioxa-4-bora-tricyclo[6.1.1.02,6]dec-4-yl)-ethyl]-benzoic acid tert-butyl ester following the procedure described in Step 3 of Example 1. The crude product was purified by reverse phase preparative HPLC and dried using lyophilization. ESI-MS m/z 335 (MH)$^+$.

Example 31

(R)-2-hydroxy-3-(3-(thiazol-2-yl)propanamido)-3,4-dihydro-2H-benzo[e][1,2]oxaborinine-8-carboxylic acid

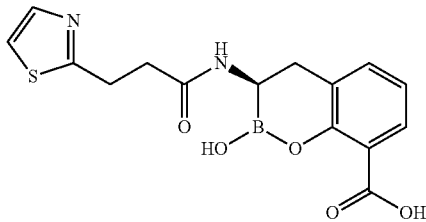 [SMILES: O=C(CCc1nccs1)N[C@H]1Cc2cccc(C(=O)O)c2OB1O]

Step 1. Synthesis of 3-Thiazol-2-yl-acrylic acid benzyl ester.

To a solution of (Benzyloxycarbonylmethyl)triphenylphosphonium bromide (3.92 g, 7.95 mmol) in THF (32 mL) at 0° C. was added LHMDS (1.0 M in THF, 8.4 mL, 8.4 mmol) over 4 min. The solution was stirred for 5 min at 0° C., the cooling bath was removed and stirring continued for 15 min. After recooling to 0° C., thiophene-2-carboxaldehyde (0.7 mL, 7.98 mmol) was added. After stirring for 30 min at 0° C. the cooling bath was removed and the solution stirred for 17 h. The reaction was quenched with water and extracted twice with EtOAc. The organic layers were combined, washed with brine, dried ($Na_2SO_4$) and concentrated in vacuo. To remove remaining residual aldehyde the crude product was dissolved in EtOH (20 mL), and $NaBH_4$ was added. After 10 min $H_2O$ was added and the mixture extracted twice with EtOAc. The organic layers were combined, washed with water, brine, dried ($Na_2SO_4$) and concentrated in vacuo. To the residue was added 20% EtOAc/Hexane and the mixture filtered to remove triphenylphosphine oxide. The filtrate was subjected to flash chromatography (20% to 40% EtOAc/Hexane) to afford the desired product as a mixture of alkene isomers.

Step 2. Synthesis of 3-Thiazol-2-yl-acrylic acid.

To a solution of 3-thiazol-2-yl-acrylic acid benzyl ester (1.71 g, 6.98 mmol) in THF (20 mL) was added 1N NaOH (aq., 9 mL, 9 mmol). The solution was stirred for 5.5 h, diluted with water and concentrated in vacuo to remove THF, and extracted twice with Et$_2$O. The aqueous layer was acidified to pH 1 with 1N HCl and extracted twice with EtOAc. The combined organic layers were washed with water, brine, dried (Na$_2$SO$_4$) and concentrated to afford a crude product which was used without further purification.

Step 3. Synthesis of 3-Thiazol-2-yl-propionic acid.

To a solution of 3-Thiazol-2-yl-acrylic acid (0.95 g, 6.13 mmol) in 10 mL EtOH plus 20 mL EtOAc under argon was added 10% Pd/C. The system was evacuated and purged with H$_2$, and the mixture stirred under 1 atm H$_2$ for 18 h at which time a significant amount of starting material remained. The mixture was filtered through Celite and the solids were washed with EtOAc. The filtrate was concentrated to about one-half volume and then resubjected to the hydrogenation conditions. After 3 h the reaction was deemed complete by LC/MS, the mixture filtered through Celite and the filtrate concentrated to afford a yellow solid which was used without further purification.

Step 4. Synthesis of 2-Methoxy-3-[2-(3-thiazol-2-yl-propionylamino)-2-(2,9,9-trimethyl-3,5-dioxa-4-bora-tricyclo[6.1.1.0²,⁶]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-thiazol-2-yl-propionic acid following the procedure in Step 2 of Example 1. The crude product was purified by flash chromatography on silica gel (60% EtOAc// Hexane to 100% EtOAc). ESI-MS m/z 569 (MH)$^+$.

Step 5. Synthesis of (R)-2-hydroxy-3-(3-(thiazol-2-yl)propanamido)-3,4-dihydro-2H-benzo[e][1,2]oxaborinine-8-carboxylic acid.

Prepared from 2-Methoxy-3-[2-(3-thiazol-2-yl-propionylamino)-2-(2,9,9-trimethyl-3,5-dioxa-4-bora-tricyclo[6.1.1.0²,⁶]dec-4-yl)-ethyl]-benzoic acid tert-butyl ester following the procedure described in Example 7. The crude product was purified by reverse phase flash chromatography on C$_{18}$ silica gel (100% H$_2$O to 9% IPA/H$_2$O) and dried using lyophilization. ESI-MS m/z 347 (MH)$^+$.

Example 32

(R)-2-hydroxy-3-(3-(thiazol-5-yl)propanamido)-3,4-dihydro-2H-benzo[e][1,2]oxaborinine-8-carboxylic acid

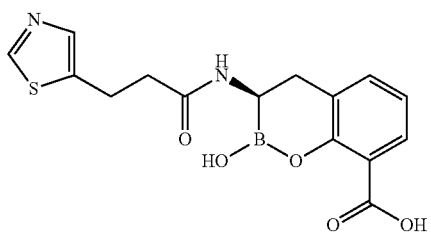 [SMILES: O=C(CCc1cncs1)N[C@H]1Cc2cccc(C(=O)O)c2OB1O]

Steps 1-3. Synthesis of 3-Thiazol-5-yl-propionic acid.

Prepared from thiophene-5-carboxaldehyde following the procedure described in Steps 1 to 3 of Example 31.

Step 4. Synthesis of 2-Methoxy-3-[2-(3-thiazol-5-yl-propionylamino)-2-(2,9,9-trimethyl-3,5-dioxa-4-bora-tricyclo[6.1.1.0²,⁶]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-thiazol-5-yl-propionic acid following the procedure in Step 2 of Example 1. The crude product was purified by flash chromatography on silica gel (60-100% EtOAc/Hexane). ESI-MS m/z 569 (MH)$^+$.

Step 5. Synthesis of (R)-2-hydroxy-3-(3-(thiazol-5-yl)propanamido)-3,4-dihydro-2H-benzo[e][1,2]oxaborinine-8-carboxylic acid.

Prepared from 2-Methoxy-3-[2-(3-thiazol-5-yl-propionylamino)-2-(2,9,9-trimethyl-3,5-dioxa-4-bora-tricyclo[6.1.1.0²,⁶]dec-4-yl)-ethyl]-benzoic acid tert-butyl ester following the procedure described in Example 7. The crude product was purified by reverse phase flash chromatography on C$_{18}$ silica gel (100% H$_2$O to 9% IPA/H$_2$O) and dried using lyophilization. ESI-MS m/z 347 (MH)$^+$.

Example 33

(R)-2-Hydroxy-3-[2-(2-oxo-pyrrolidin-1-yl)-acetylamino]-3,4-dihydro-2H-benzo[e][1,2]oxaborinine-8-carboxylic acid

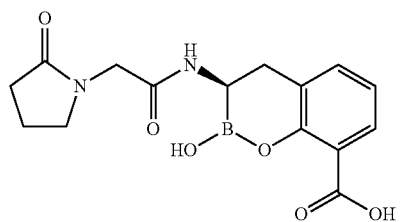 [SMILES: O=C(CN1CCCC1=O)N[C@H]1Cc2cccc(C(=O)O)c2OB1O]

Step 1. Synthesis of 2-Methoxy-3-[2-[2-(2-oxo-pyrrolidin-1-yl)-acetylamino]-2-(2,9,9-trimethyl-3,5-dioxa-4-bora-tricyclo[6.1.1.0²,⁶]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and (2-oxopyrrolidin-1-yl)acetic acid following the procedure in Step 2 of Example 1. The crude product was purified by flash chromatography on silica gel (10-100% EtOAc/Hexane). ESI-MS m/z 555 (MH)$^+$.

Step 2. Synthesis of (R)-2-Hydroxy-3-[2-(2-oxo-pyrrolidin-1-yl)-acetylamino]-3,4-dihydro-2H-benzo[e][1,2]oxaborinine-8-carboxylic acid.

Prepared from 2-Methoxy-3-[2-[2-(2-oxo-pyrrolidin-1-yl)-acetylamino]-2-(2,9,9-trimethyl-3,5-dioxa-4-bora-tricyclo[6.1.1.0²,⁶]dec-4-yl)-ethyl]-benzoic acid tert-butyl ester following the procedure described in Step 3 of Example 1. The crude product was purified by reverse phase preparative HPLC and dried using lyophilization. ESI-MS m/z 333 (MH)⁺.

Example 34

(R)-3-[3-(2,5-Dioxo-pyrrolidin-1-yl)-propionylamino]-2-hydroxy-3,4-dihydro-2H-benzo[e][1,2]oxaborinine-8-carboxylic acid

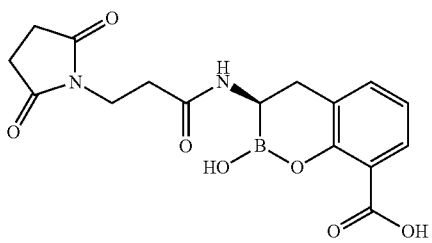 [SMILES: O=C(CCN1C(=O)CCC1=O)N[C@H]1Cc2cccc(C(=O)O)c2OB1O]

Step 1. Synthesis of 3-[2-[3-(2,5-Dioxo-pyrrolidin-1-yl)-propionylamino]-2-(2,9,9-trimethyl-3,5-dioxa-4-bora-tricyclo[6.1.1.0²,⁶]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 3-(2,5-dioxopyrrolidin-1-yl)propanoic acid following the procedure in Step 2 of Example 1. The crude product was purified by flash chromatography on silica gel (10-100% EtOAc/Hexane). ESI-MS m/z 583 (MH)⁺.

Step 2. Synthesis of (R)-3-[3-(2,5-Dioxo-pyrrolidin-1-yl)-propionylamino]-2-hydroxy-3,4-dihydro-2H-benzo[e][1,2]oxaborinine-8-carboxylic acid.

Prepared from 3-[2-[3-(2,5-Dioxo-pyrrolidin-1-yl)-propionylamino]-2-(2,9,9-trimethyl-3,5-dioxa-4-bora-tricyclo[6.1.1.0²,⁶]dec-4-yl)-ethyl]-2-methoxy-benzoic acid tert-butyl ester following the procedure described in Step 3 of Example 1. The crude product was purified by reverse phase preparative HPLC and dried using lyophilization. ESI-MS m/z 361 (MH)⁺.

Example 35

(R)-2-Hydroxy-3-(3-sulfamoyl-propionylamino)-3,4-dihydro-2H-benzo[e][1,2]oxaborinin-8-carboxylic acid

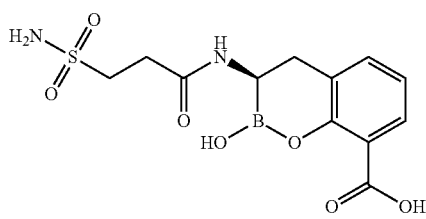 [SMILES: NS(=O)(=O)CCC(=O)N[C@H]1Cc2cccc(C(=O)O)c2OB1O]

Step 1. Synthesis of 2-Methoxy-3-[2-(3-sulfamoyl-propionylamino)-2-(2,9,9-trimethyl-3,5-dioxa-4-bora-tricyclo[6.1.1.0²,⁶]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-sulfamoylpropanoic acid following the procedure in Step 2 of Example 1. The crude product was purified by flash chromatography on silica gel (0-10% CH₃OH/CH₂Cl₂). ESI-MS m/z 565 (MH)⁺.

Step 2. Synthesis of (R)-2-Hydroxy-3-(3-sulfamoyl-propionylamino)-3,4-dihydro-2H-benzo[e][1,2]oxaborinin-8-carboxylic acid.

Prepared from 2-Methoxy-3-[2-(3-sulfamoyl-propionylamino)-2-(2,9,9-trimethyl-3,5-dioxa-4-bora-tricyclo[6.1.1.0²,⁶]dec-4-yl)-ethyl]-benzoic acid tert-butyl ester following the procedure described in Example 7. The crude product was purified by reverse phase preparative HPLC and dried using lyophilization. ESI-MS m/z 343 (MH)⁺.

Example 36

(R)-2-Hydroxy-3-(2-ureido-acetylamino)-3,4-dihydro-2H-benzo[e][1,2]oxaborinin-8-carboxylic acid

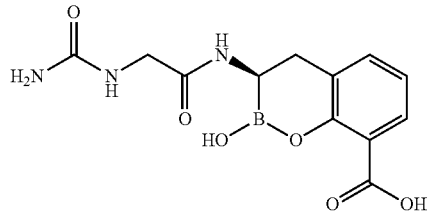

Step 1. Synthesis of 2-Methoxy-3-[2-(2,9,9-trimethyl-3,5-dioxa-4-bora-tricyclo[6.1.1.0²,⁶]dec-4-yl)-2-(2-ureido-acetylamino)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and hydantoic acid following the procedure in Step 2 of Example 1. The crude product was purified by flash chromatography on silica gel (0-10% CH₃OH/CH₂Cl₂). ESI-MS m/z 530 (MH)⁺.

Step 2. Synthesis of (R)-2-Hydroxy-3-(2-ureido-acetylamino)-3,4-dihydro-2H-benzo[e][1,2]oxaborinin-8-carboxylic acid.

Prepared from 2-Methoxy-3-[2-(2,9,9-trimethyl-3,5-dioxa-4-bora-tricyclo[6.1.1.0²,⁶]dec-4-yl)-2-(2-ureido-acetylamino)-ethyl]-benzoic acid tert-butyl ester following the procedure described in Example 7. The crude product was purified by reverse phase preparative HPLC and dried using lyophilization. ESI-MS m/z 308 (MH)⁺.

Example 37

(R)-2-Hydroxy-3-pent-4-ynoylamino-3,4-dihydro-2H-benzo[e][1,2]oxaborinine-8-carboxylic acid

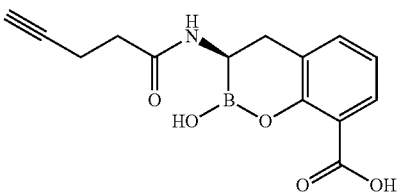 [SMILES: C#CCCC(=O)N[C@H]1Cc2cccc(C(=O)O)c2OB1O]

Step 1. Synthesis of 2-Methoxy-3-[2-pent-4-ynoylamino-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 4-pentynoic acid following the procedure in Step 2 of Example 1. The crude product was purified by flash chromatography on silica gel (10-100% EtOAc/Hexane). ESI-MS m/z 510 (MH)+.

Step 2. Synthesis of (R)-2-Hydroxy-3-pent-4-ynoylamino-3,4-dihydro-2H-benzo[e][1,2]oxaborinine-8-carboxylic acid.

Prepared from 2-Methoxy-3-[2-pent-4-ynoylamino-2-(2,9,9-trimethyl-3,5-dioxa-4-bora-tricyclo[6.1.1.02,6]dec-4-yl)-ethyl]-benzoic acid tert-butyl ester following the procedure described in Example 7. The crude product was purified by reverse phase preparative HPLC and dried using lyophilization. ESI-MS m/z 288 (MH)+.

Example 38

(R)-2-Hydroxy-3-(5,5,5-trifluoro-4-oxo-pentanoylamino)-3,4-dihydro-2H-benzo[e][1,2]oxaborinine-8-carboxylic acid

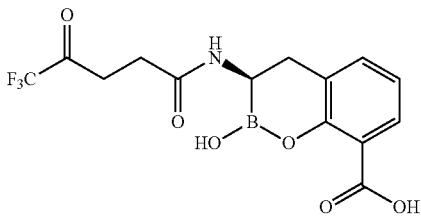 [SMILES: O=C(CCC(=O)C(F)(F)F)N[C@H]1Cc2cccc(C(=O)O)c2OB1O]

Step 1. Synthesis of 2-Methoxy-3-[2-(5,5,5-trifluoro-4-oxo-pentanoylamino)-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 5,5,5-trifluoro-4-oxopentanoic acid following the procedure in Step 2 of Example 1. The crude product was purified by flash chromatography on silica gel (10-100% EtOAc/Hexane). ESI-MS m/z 582 (MH)+.

Step 2. Synthesis of (R)-2-Hydroxy-3-(5,5,5-trifluoro-4-oxo-pentanoylamino)-3,4-dihydro-2H-benzo[e][1,2]oxaborinine-8-carboxylic acid.

Prepared from 2-Methoxy-3-[2-(5,5,5-trifluoro-4-oxo-pentanoylamino)-2-(2,9,9-trimethyl-3,5-dioxa-4-bora-tricyclo[6.1.1.02,6]dec-4-yl)-ethyl]-benzoic acid tert-butyl ester following the procedure described in Example 7. The crude product was purified by reverse phase preparative HPLC and dried using lyophilization. ESI-MS m/z 360 (MH)+.

Example 39

(R)-2-Hydroxy-3-(4-oxo-pent-2-enoylamino)-3,4-dihydro-2H-benzo[e][1,2]oxaborinine-8-carboxylic acid

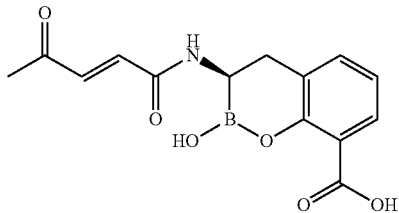 [SMILES: CC(=O)/C=C/C(=O)N[C@H]1Cc2cccc(C(=O)O)c2OB1O]

Step 1. Synthesis of 2-Methoxy-3-[2-(4-oxo-pent-2-enoylamino)-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-acetylacrylic acid following the procedure in Step 2 of Example 1. The crude product was purified by flash chromatography on silica gel (10-100% EtOAc/Hexane). ESI-MS m/z 526 (MH)+.

Step 2. Synthesis of (R)-2-Hydroxy-3-(4-oxo-pent-2-enoylamino)-3,4-dihydro-2H-benzo[e][1,2]oxaborinine-8-carboxylic acid.

Prepared from 2-Methoxy-3-[2-(4-oxo-pent-2-enoylamino)-2-(2,9,9-trimethyl-3,5-dioxa-4-bora-tricyclo[6.1.1.02,6]dec-4-yl)-ethyl]-benzoic acid tert-butyl ester following the procedure described in Example 7. The crude product was purified by reverse phase preparative HPLC and dried using lyophilization. ESI-MS m/z 304 (MH)+.

Example 40

(R)-3-(5,5-Dimethyl-4-oxo-hexanoylamino)-2-hydroxy-3,4-dihydro-2H-benzo[e][1,2]oxaborinine-8-carboxylic acid

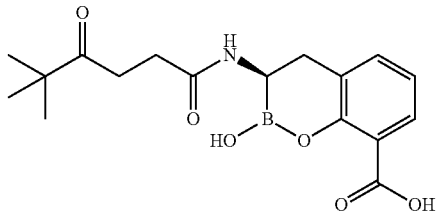 [SMILES: CC(C)(C)C(=O)CCC(=O)N[C@H]1Cc2cccc(C(=O)O)c2OB1O]

Step 1. Synthesis of 3-[2-(5,5-Dimethyl-4-oxo-hexanoylamino)-2-(2,9,9-trimethyl-3,5-dioxa-4-bora-tricyclo[6.1.1.0²,⁶]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 5,5-dimethyl-4-oxohexanoic acid following the procedure in Step 2 of Example 1. The crude product was purified by flash chromatography on silica gel (10-100% EtOAc/Hexane). ESI-MS m/z 570 (MH)$^+$.

Step 2. Synthesis of (R)-3-(5,5-Dimethyl-4-oxo-hexanoylamino)-2-hydroxy-3,4-dihydro-2H-benzo[e][1,2]oxaborinine-8-carboxylic acid.

Prepared from 3-[2-(5,5-Dimethyl-4-oxo-hexanoylamino)-2-(2,9,9-trimethyl-3,5-dioxa-4-bora-tricyclo[6.1.1.0²,⁶]dec-4-yl)-ethyl]-2-methoxy-benzoic acid tert-butyl ester following the procedure described in Example 7. The crude product was purified by reverse phase preparative HPLC and dried using lyophilization. ESI-MS m/z 348 (MH)$^+$.

Example 41

(R)-3-(4,6-Dioxo-heptanoylamino)-2-hydroxy-3,4-dihydro-2H-benzo[e][1,2]oxaborinine-8-carboxylic acid

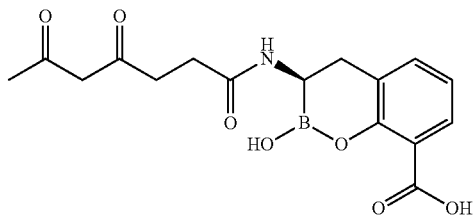 [SMILES: CC(=O)CC(=O)CCC(=O)N[C@H]1Cc2cccc(C(=O)O)c2OB1O]

Step 1. Synthesis of 3-[2-(4,6-Dioxo-heptanoylamino)-2-(2,9,9-trimethyl-3,5-dioxa-4-bora-tricyclo[6.1.1.0²,⁶]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 4,6-dioxoheptanoic acid following the procedure in Step 2 of Example 1. The crude product was purified by flash chromatography on silica gel (0-10% CH$_3$OH/CH$_2$Cl$_2$). ESI-MS m/z 570 (MH)$^+$.

Step 2. Synthesis of (R)-3-(4,6-Dioxo-heptanoylamino)-2-hydroxy-3,4-dihydro-2H-benzo[e][1,2]oxaborinine-8-carboxylic acid.

Prepared from 3-[2-(4,6-Dioxo-heptanoylamino)-2-(2,9,9-trimethyl-3,5-dioxa-4-bora-tricyclo[6.1.1.0²,⁶]dec-4-yl)-ethyl]-2-methoxy-benzoic acid tert-butyl ester following the procedure described in Example 7. The crude product was purified by reverse phase preparative HPLC and dried using lyophilization. ESI-MS m/z 348 (MH)$^+$.

Example 42

(R)-2-Hydroxy-3-(4-oxo-4-phenyl-butyrylamino)-3,4-dihydro-2H-benzo[e][1,2]oxaborinine-8-carboxylic acid

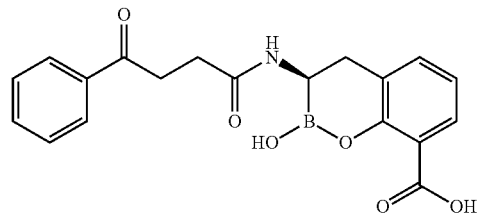 [SMILES: O=C(CCC(=O)c1ccccc1)N[C@H]1Cc2cccc(C(=O)O)c2OB1O]

Step 1. Synthesis of 2-Methoxy-3-[2-(4-oxo-4-phenyl-butyrylamino)-2-(2,9,9-trimethyl-3,5-dioxa-4-bora-tricyclo[6.1.1.0²,⁶]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-benzoylpropionic acid following the procedure in Step 2 of Example 1. The crude product was purified by flash chromatography on silica gel (10-100% EtOAc/Hexane). ESI-MS m/z 590 (MH)$^+$.

Step 2. Synthesis of (R)-2-Hydroxy-3-(4-oxo-4-phenyl-butyrylamino)-3,4-dihydro-2H-benzo[e][1,2]oxaborinine-8-carboxylic acid.

Prepared from 2-Methoxy-3-[2-(4-oxo-4-phenyl-butyrylamino)-2-(2,9,9-trimethyl-3,5-dioxa-4-bora-tricyclo[6.1.1.0²,⁶]dec-4-yl)-ethyl]-benzoic acid tert-butyl ester following the procedure described in Example 7. The crude product was purified by reverse phase preparative HPLC and dried using lyophilization. ESI-MS m/z 368 (MH)$^+$.

Example 43

(R)-3-(3-Cyano-3,3-dimethyl-propionylamino)-2-hydroxy-3,4-dihydro-2H-benzo[e][1,2]oxaborinine-8-carboxylic acid

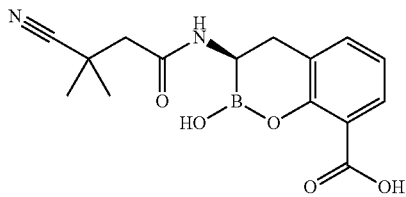

Step 1. Synthesis of 5-Isopropylidene-2,2-dimethyl-[1,3]dioxane-4,6-dione.

To a mixture of 2,2-dimethyl-1,3-dioxane-4,6-dione (3.71 g, 25.7 mmol) and ammonium acetate (3.95 g, 51.2 mmol) in toluene (37 mL) under argon was added acetone (2.0 mL, 27.2 mmol) and glacial acetic acid (3.8 mL, 66.4 mmol). The reaction mixture was heated to 50° C. and stirred for 17 h.

The reaction was cooled to room temperature, quenched with H₂O, and extracted three times with EtOAc. The combined organic layers were washed with brine, dried over MgSO₄, filtered, and concentrated. The crude product was purified by flash chromatography on silica gel (0-50% EtOAc/Hexane) to afford the pure product. ESI-MS m/z 185 (MH)⁺.

Step 2. Synthesis of 2-(2,2-Dimethyl-4,6-dioxo-[1,3]dioxan-5-yl)-2-methyl-propionitrile.

To a solution of 5-Isopropylidene-2,2-dimethyl-[1,3]dioxane-4,6-dione (0.650 g, 3.53 mmol) in ethanol (12 mL) was added potassium cyanide (0.288 g, 4.42 mmol) and tetra-n-butylammonium bromide (0.125 g, 0.388 mmol). The reaction was heated at 80° C. for 3.5 h then cooled to room temperature for 30 min. The reaction mixture was quenched with 1N HCl and extracted three times with EtOAc. The combined organic layers were washed with brine, dried over MgSO₄, filtered, and concentrated. The crude product was carried forward without purification.

Step 3. Synthesis of 3-Cyano-3,3-dimethyl-propionic acid.

A solution of 2-(2,2-Dimethyl-4,6-dioxo-[1,3]dioxan-5-yl)-2-methyl-propionitrile (0.745 g, 3.53 mmol) in N,N-dimethylformamide (10 mL) and H₂O (1.0 mL) was heated at 100° C. for 4 h. The reaction was cooled to room temperature and basified to pH 14 with 10N NaOH. The resulting solution was extracted two times with diethyl ether. The aqueous layer was acidified to pH 1 with 3N HCl and extracted three times with EtOAc. The combined EtOAc layers were washed with brine, dried over MgSO₄, filtered, and concentrated to afford a white solid. ESI-MS m/z 150 (M+Na)⁺.

Step 4. Synthesis of 3-[2-(3-Cyano-3,3-dimethyl-propionylamino)-2-(2,9,9-trimethyl-3,5-dioxa-4-bora-tricyclo[6.1.1.0²,⁶]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 3-cyano-3,3-dimethylpropionic acid following the procedure in Step 2 of Example 1. The crude product was purified by flash chromatography on silica gel (10-100% EtOAc/Hexane). ESI-MS m/z 539 (MH)⁺.

Step 5. Synthesis of (R)-3-(3-Cyano-3,3-dimethyl-propionylamino)-2-hydroxy-3,4-dihydro-2H-benzo[e][1,2]oxaborinine-8-carboxylic acid.

Prepared from 3-[2-(3-Cyano-3,3-dimethyl-propionylamino)-2-(2,9,9-trimethyl-3,5-dioxa-4-bora-tricyclo[6.1.1.0²,⁶]dec-4-yl)-ethyl]-2-methoxy-benzoic acid tert-butyl ester following the procedure described in Example 7. The crude product was purified by reverse phase preparative HPLC and dried using lyophilization. ESI-MS m/z 317 (MH)⁺.

Example 44

(R)-2-Hydroxy-3-(3-oxazol-4-yl-acryloylamino)-3,4-dihydro-2H-benzo[e][1,2]oxaborinine-8-carboxylic acid

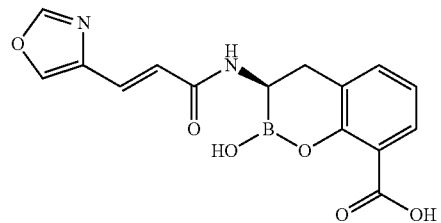 [SMILES: O=C(/C=C/c1cocn1)N[C@H]1Cc2cccc(C(=O)O)c2OB1O]

Step 1. Synthesis of 3-Oxazol-4-yl-acrylic acid.

Prepared following the procedure described in Step 1 and Step 2 of Example 31. The crude product was carried forward without purification.

Step 2. Synthesis of 2-Methoxy-3-[2-(3-oxazol-4-yl-acryloylamino)-2-(2,9,9-trimethyl-3,5-dioxa-4-bora-tricyclo[6.1.1.0²,⁶]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-oxazol-4-yl-acrylic acid following the procedure in Step 2 of Example 1. The crude product was purified by flash chromatography on silica gel (60-100% EtOAc/Hexane). ESI-MS m/z 551 (MH)⁺.

Step 3. Synthesis of (R)-2-Hydroxy-3-(3-oxazol-4-yl-acryloylamino)-3,4-dihydro-2H-benzo[e][1,2]oxaborinine-8-carboxylic acid.

Prepared from 2-Methoxy-3-[2-(3-oxazol-4-yl-acryloylamino)-2-(2,9,9-trimethyl-3,5-dioxa-4-bora-tricyclo[6.1.1.0²,⁶]dec-4-yl)-ethyl]-benzoic acid tert-butyl ester following the procedure described in Example 7. The crude product was purified by reverse phase preparative HPLC and dried using lyophilization. ESI-MS m/z 329 (MH)⁺.

Example 45

(R)-2-Hydroxy-3-(3-oxazol-4-yl-propionylamino)-3,4-dihydro-2H-benzo[e][1,2]oxaborinine-8-carboxylic acid

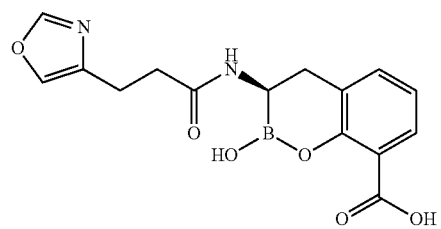 [SMILES: O=C(CCc1cocn1)N[C@H]1Cc2cccc(C(=O)O)c2OB1O]

Synthesis of (R)-2-Hydroxy-3-(3-oxazol-4-yl-propionylamino)-3,4-dihydro-2H-benzo[e][1,2]oxaborinine-8-carboxylic acid.

Prepared from 3-oxazol-4-yl-acrylic acid (Step 1, Example 44) following the procedures described in Steps 3-5 of Example 31. The crude product was purified by reverse phase preparative HPLC and dried using lyophilization. ESI-MS m/z 331 (MH)+.

Example 46

(R)-3-(3-Cyano-propionylamino)-7-fluoro-2-hydroxy-3,4-dihydro-2H-benzo[e][1,2]oxaborinine-8-carboxylic acid

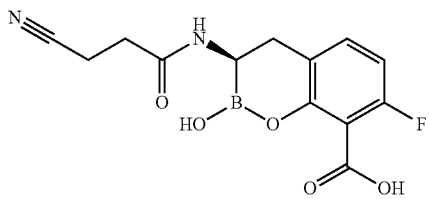 [SMILES: N#CCCC(=O)N[C@H]1Cc2ccc(F)c(C(=O)O)c2OB1O]

Step 1. Synthesis of tert-Butyl-(4-fluoro-2-methoxy-phenoxy)-dimethyl-silane.

To a mixture of 4-fluoro-2-methoxyphenol (5.68 g, 40 mmol), triethylamine (11.2 mL, 80 mmol), and DMAP (0.49 g, 4 mmol) in dichloromethane (100 mL) was added tert-butyldimethylsilyl chloride (7.5 g, 50 mmol) and the reaction mixture was stirred at room temperature overnight. The reaction mixture was quenched with sat. NaHCO$_3$ and layers separated. The organic layer was dried over Na$_2$SO$_4$, filtered, and concentrated. The crude product was purified by flash chromatography on silica gel (2-10% EtOAc/Hexane) to afford the pure product. ESI-MS m/z 257 (MH)+.

Step 2. Synthesis of 3-(tert-Butyl-dimethyl-silanyloxy)-6-fluoro-2-methoxy-benzoic acid tert-butyl ester.

To a solution of diisopropylamine (6.6 mL, 46.8 mmol) in THF (120 mL) at −65° C. under argon was added n-butyllithium (2.5 M in hexanes, 18.2 mL, 46.8 mmol) dropwise. The reaction mixture was stirred at −60° C. to −55° C. for 20 min. tert-Butyl-(4-fluoro-2-methoxy-phenoxy)-dimethyl-silane (10 g, 39 mmol) in THF (15 mL) was added dropwise and the reaction mixture was stirred at −60° C. for 1 h. Di-tert-butyl dicarbonate (28.1 g, 129 mmol) was added and the reaction mixture was allowed to slowly warm to room temperature overnight. The reaction was quenched with water and extracted two times with EtOAc. The combined organic layers were washed with brine, dried over MgSO$_4$, filtered, and concentrated. The crude product was purified by flash chromatography on silica gel (5-50% EtOAc/Hexane) to afford the pure product. ESI-MS m/z 357 (MH)+.

Step 3. Synthesis of 6-Fluoro-3-hydroxy-2-methoxy-benzoic acid tert-butyl ester.

To a solution of 3-(tert-Butyl-dimethyl-silanyloxy)-6-fluoro-2-methoxy-benzoic acid tert-butyl ester (8 g, 22.5 mmol) in THF (150 mL) was added TBAF (1M in THF, 50 mL, 50 mmol) and the reaction mixture was stirred at room temperature for 1.5 h. The reaction was diluted with EtOAc and washed with sat. NaHCO$_3$ and brine, dried over MgSO$_4$, filtered, and concentrated. The crude product was dissolved in dichloromethane (100 mL) and treated with piperidine (27 mL) and stirred at room temperature overnight. The reaction was concentrated then dissolved in dichloromethane, washed with sat. NH$_4$Cl, dried over Na$_2$SO$_4$, filtered, and concentrated. The crude product was purified by flash chromatography on silica gel (5-50% EtOAc/Hexane) to afford the pure product. ESI-MS m/z 243 (MH)+.

Step 4. Synthesis of 6-Fluoro-2-methoxy-3-trifluoromethanesulfonyloxy-benzoic acid tert-butyl ester.

To a solution of 6-Fluoro-3-hydroxy-2-methoxy-benzoic acid tert-butyl ester (1.4 g, 5.8 mmol) in dichloromethane (50 mL) was added triethylamine (2.0 mL, 14.5 mmol), N,N-bis(trifluoromethylsulfonyl)aniline (2.9 g, 8.12 mmol), and DMAP (0.07 g, 0.58 mmol) and the reaction mixture was stirred at room temperature overnight. The reaction was washed with sat. NaHCO$_3$, dried over Na$_2$SO$_4$, filtered, and concentrated. The crude product was purified by flash chromatography on silica gel (5-75% CH$_2$Cl$_2$/Hexane) to afford the pure product. ESI-MS m/z 375 (MH)+.

Step 5. Synthesis of 6-Fluoro-2-methoxy-3-(2,9,9-trimethyl-3,5-dioxa-4-bora-tricyclo[6.1.1.0²,⁶]dec-4-yl)-benzoic acid tert-butyl ester.

A mixture of 6-Fluoro-2-methoxy-3-trifluoromethanesulfonyloxy-benzoic acid tert-butyl ester (3.85 g, 10.3 mmol), bis-(+)-pinanediolatodiborane (5.7 g), potassium acetate (3.1 g), and [1,1'-(bisdiphenylphosphino)ferrocene]dichloropalladium (II) complex with dichloromethane (0.43 g) in DMF (35 mL) was heated at 90° C. to 100° C. overnight. The reaction was quenched with water and extracted two times with EtOAc. The combined organic layers were washed with brine, dried over MgSO$_4$, filtered, and concentrated. The crude product was purified by flash chromatography on silica gel (0-100% CH$_2$Cl$_2$/Hexane) to afford the pure product. ESI-MS m/z 405 (MH)+.

Step 6. Synthesis of 6-Fluoro-2-methoxy-3-(2,9,9-trimethyl-3,5-dioxa-4-bora-tricyclo[6.1.1.0²,⁶]dec-4-ylmethyl)-benzoic acid tert-butyl ester.

To a cooled solution (−78° C.) of chloroiodomethane (3.2 mL) in THF (70 mL) was added under argon i-propylmagnesium chloride lithium chloride (1.3 M in THF, 16.8 mL, 21.8 mmol) over 20 min. The reaction mixture was stirred at −78° C. for 45 min then 6-Fluoro-2-methoxy-3-(2,9,9-trimethyl-3,5-dioxa-4-bora-tricyclo[6.1.1.0²,⁶]dec-4-yl)-benzoic acid tert-butyl ester (2.38 g, 5.89 mmol) in THF (9 mL) was added dropwise. Upon complete addition, the reaction mixture was stirred at −78° C. for 1.5 h. Zinc chloride (1.0M in diethyl ether, 6.4 mL, 6.4 mmol) was added and the reaction was stirred at −78° C. for an additional 15 min before warming to room temperature overnight. The reaction mixture was then cooled back down to −30° C., diluted with diethyl ether, and washed with aqueous NH$_4$Cl, H$_2$O, and brine. The organic layer was dried over MgSO$_4$, filtered, and concentrated. The crude product was purified by flash chromatography on silica gel (5-20% EtOAc/Hexane) to afford the pure product. ESI-MS m/z 419 (MH)+.

Step 7. Synthesis of [(1S)-2-(3-tert-butoxycarbonyl-2-methoxy-4-fluoro-phenyl)-1-chloro-ethyl]boronic acid (+) pinanediol ester.

Prepared from 6-Fluoro-2-methoxy-3-(2,9,9-trimethyl-3,5-dioxa-4-bora-tricyclo[6.1.1.02,6]dec-4-ylmethyl)-benzoic acid tert-butyl ester following the procedure in Step 1 of Example 1. The crude product was purified by flash chromatography on silica gel (40-100% EtOAc/Hexane) and carried to next step.

Step 8. Synthesis of 3-[2-(3-Cyano-propionylamino)-2-(2,9,9-trimethyl-3,5-dioxa-4-bora-tricyclo[6.1.1.02,6]dec-4-yl)-ethyl]-6-fluoro-2-methoxy-benzoic acid tert-butyl ester.

Prepared from [(1S)-2-(3-tert-butoxycarbonyl-2-methoxy-4-fluoro-phenyl)-1-chloro-ethyl]boronic acid (+) pinanediol ester and 3-cyanopropanoic acid following the procedure in Step 2 of Example 1. The crude product was purified by flash chromatography on silica gel (10-100% EtOAc/Hexane). ESI-MS m/z 529 (MH)$^+$.

Step 9. Synthesis of (R)-3-(3-Cyano-propionylamino)-7-fluoro-2-hydroxy-3,4-dihydro-2H-benzo[e][1,2]oxaborinine-8-carboxylic acid.

Prepared from 3-[2-(3-Cyano-propionylamino)-2-(2,9,9-trimethyl-3,5-dioxa-4-bora-tricyclo[6.1.1.02,6]dec-4-yl)-ethyl]-6-fluoro-2-methoxy-benzoic acid tert-butyl ester following the procedure described in Example 7. The crude product was purified by reverse phase preparative HPLC and dried using lyophilization. ESI-MS m/z 307 (MH)$^+$.

Example 47

(R)-7-Fluoro-2-hydroxy-3-(4-oxo-pentanoylamino)-3,4-dihydro-2H-benzo[e][1,2]oxaborinine-8-carboxylic acid

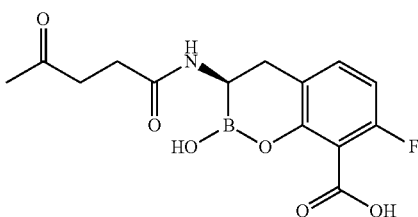 [SMILES: CC(=O)CCC(=O)N[C@H]1Cc2ccc(F)c(C(=O)O)c2OB1O]

Step 1. Synthesis of 6-Fluoro-2-methoxy-3-[2-(4-oxo-pentanoylamino)-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-4-fluoro-phenyl)-1-chloro-ethyl]boronic acid (+) pinanediol ester and levulinic acid following the procedure in Steps 1-8 of Example 46. The crude product was purified by flash chromatography on silica gel (10-100% EtOAc/Hexane). ESI-MS m/z 546 (MH)$^+$.

Step 2. Synthesis of (R)-7-Fluoro-2-hydroxy-3-(4-oxo-pentanoylamino)-3,4-dihydro-2H-benzo[e][1,2]oxaborinine-8-carboxylic acid.

Prepared from 6-Fluoro-2-methoxy-3-[2-(4-oxo-pentanoylamino)-2-(2,9,9-trimethyl-3,5-dioxa-4-bora-tricyclo[6.1.1.02,6]dec-4-yl)-ethyl]-benzoic acid tert-butyl ester following the procedure described in Example 7. The crude product was purified by reverse phase preparative HPLC and dried using lyophilization. ESI-MS m/z 324 (MH)$^+$.

Example 48

(R)-7-Fluoro-2-hydroxy-3-(3-methanesulfonylamino-propionylamino)-3,4-dihydro-2H-benzo[e][1,2]oxaborinine-8-carboxylic acid

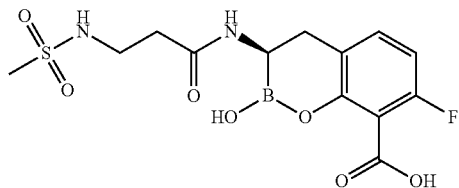 [SMILES: CS(=O)(=O)NCCC(=O)N[C@H]1Cc2ccc(F)c(C(=O)O)c2OB1O]

Step 1. Synthesis of 6-Fluoro-3-[2-(3-methanesulfonylamino-propionylamino)-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-4-fluoro-phenyl)-1-chloro-ethyl]boronic acid (+) pinanediol ester and N-(methylsulfonyl)-3-alanine following the procedure in Steps 1-8 of Example 46. The crude product was purified by flash chromatography on silica gel (10-100% EtOAc/Hexane). ESI-MS m/z 597 (MH)$^+$.

Step 2. Synthesis of (R)-7-Fluoro-2-hydroxy-3-(3-methanesulfonylamino-propionylamino)-3,4-dihydro-2H-benzo[e][1,2]oxaborinine-8-carboxylic acid.

Prepared from 6-Fluoro-3-[2-(3-methanesulfonylamino-propionylamino)-2-(2,9,9-trimethyl-3,5-dioxa-4-bora-tricyclo[6.1.1.02,6]dec-4-yl)-ethyl]-2-methoxy-benzoic acid tert-butyl ester following the procedure described in Example 7. The crude product was purified by reverse phase preparative HPLC and dried using lyophilization. ESI-MS m/z 375 (MH)$^+$.

Example 49

(R)-3-(3-Cyano-propionylamino)-6,7-difluoro-2-hydroxy-3,4-dihydro-2H-benzo[e][1,2]oxaborinine-8-carboxylic acid

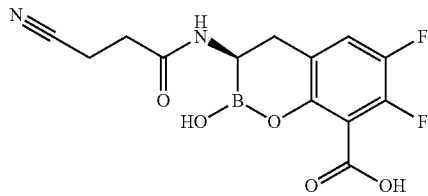 [SMILES: N#CCCC(=O)N[C@H]1Cc2cc(F)c(F)c(C(=O)O)c2OB1O]

Step 1. Synthesis of 2,3-Difluoro-6-hydroxy-benzoic acid tert-butyl ester.

N,N-Dimethylformamide di-tert-butylacetal (10 mL, 42 mmol) was added to a solution of 5,6-difluorosalicylic acid (4 g, 23 mmol) in THF (50 mL) and the reaction heated at reflux for 3.5 h. The reaction mixture was concentrated then dissolved in diethyl ether and washed three times with water. The organic layers was dried over MgSO$_4$, filtered, and concentrated. The crude product was purified by flash chromatography on silica gel (5-50% CH$_2$Cl$_2$/Hexane). ESI-MS m/z 231 (MH)$^+$.

Step 2. Synthesis of 2,3-Difluoro-6-hydroxy-5-iodo-benzoic acid tert-butyl ester.

N-Iodosuccinimide (5 g, 22.2 mmol) was added to a solution of 2,3-Difluoro-6-hydroxy-benzoic acid tert-butyl ester (4.05 g, 17.6 mmol) in DMF (30 mL) and stirred at room temperature for 2 days. The reaction was quenched with water and extracted three times with EtOAc. The combined organic layers were washed with brine, dried over MgSO$_4$, filtered, and concentrated. The crude product was purified by flash chromatography on silica gel (10-50% CH$_2$Cl$_2$/Hexane). ESI-MS m/z 357 (MH)$^+$.

Step 3. Synthesis of 2,3-Difluoro-5-iodo-6-methoxy-benzoic acid tert-butyl ester.

To a solution of 2,3-Difluoro-6-hydroxy-5-iodo-benzoic acid tert-butyl ester (5.96 g, 16.7 mmol) in DMF (50 mL) was added cesium carbonate (12.8 g, 39.3 mmol) and the reaction stirred for 10 min. Iodomethane (2.7 mL, 43.4 mmol) was added and the reaction mixture stirred at room temperature overnight. The reaction was quenched with water and extracted three times with EtOAc. The combined organic layers were washed with brine, dried over MgSO$_4$, filtered, and concentrated. The crude product was purified by flash chromatography on silica gel (10-50% CH$_2$Cl$_2$/Hexane). ESI-MS m/z 393 (M+Na)$^+$.

Step 4. Synthesis of 2,3-Difluoro-6-methoxy-5-(2,9,9-trimethyl-3,5-dioxa-4-bora-tricyclo[6.1.1.0$^{2,6}$]dec-4-ylmethyl)-benzoic acid tert-butyl ester.

To a cooled solution (−45° C.) of 2,3-Difluoro-5-iodo-6-methoxy-benzoic acid tert-butyl ester (6.1 g, 16.5 mmol) in THF (45 mL) was added dropwise i-propylmagnesium chloride lithium chloride (1.3 M in THF, 14 mL, 18.2 mmol) over 15 min followed by stirring for 45 min. 4-Chloromethyl-2,9,9-trimethyl-3,5-dioxa-4-bora-tricyclo[6.1.1.0$^{2,6}$]decane (4.8 g, 21 mmol) in THF (25 mL) was added dropwise over 8 min followed by stirring for 1 h. Zinc chloride (1.0 M in diethyl ether, 18.8 mL, 18.8 mmol) was added dropwise over 6 min and upon complete addition, the cold bath was removed and the reaction stirred at room temperature for 2 h. The reaction was diluted with diethyl ether, washed with aqueous NH$_4$Cl, H$_2$O, and brine, dried over MgSO$_4$, filtered, and concentrated. The crude product was purified by flash chromatography on silica gel (0-15% EtOAc/Hexane). ESI-MS m/z 459 (M+Na)$^+$.

Step 5. Synthesis of [(1S)-2-(3-tert-butoxycarbonyl-2-methoxy-4,5-difluoro-phenyl)-1-chloro-ethyl]boronic acid (+) pinanediol ester.

Prepared from 2,3-Difluoro-6-methoxy-5-(2,9,9-trimethyl-3,5-dioxa-4-bora-tricyclo[6.1.1.0$^{2,6}$]dec-4-ylmethyl)-benzoic acid tert-butyl ester following the procedure in Step 1 of Example 1. The crude product was purified by flash chromatography on silica gel (40-100% EtOAc/Hexane) and carried to next step.

Step 6. Synthesis of 3-[2-(3-Cyano-propionylamino)-2-(2,9,9-trimethyl-3,5-dioxa-4-bora-tricyclo[6.1.1.0$^{2,6}$]dec-4-yl)-ethyl]-5,6-difluoro-2-methoxy-benzoic acid tert-butyl ester.

Prepared from [(1S)-2-(3-tert-butoxycarbonyl-2-methoxy-4,5-difluoro-phenyl)-1-chloro-ethyl]boronic acid (+) pinanediol ester and 3-cyanopropanoic acid following the procedure in Step 2 of Example 1. The crude product was purified by flash chromatography on silica gel (10-100% EtOAc/Hexane). ESI-MS m/z 547 (MH)$^+$.

Step 7. Synthesis of (R)-3-(3-Cyano-propionylamino)-6,7-difluoro-2-hydroxy-3,4-dihydro-2H-benzo[e][1,2]oxaborinine-8-carboxylic acid.

Prepared from 3-[2-(3-Cyano-propionylamino)-2-(2,9,9-trimethyl-3,5-dioxa-4-bora-tricyclo[6.1.1.0$^{2,6}$]dec-4-yl)-ethyl]-5,6-difluoro-2-methoxy-benzoic acid tert-butyl ester following the procedure described in Example 7. The crude product was purified by reverse phase preparative HPLC and dried using lyophilization. ESI-MS m/z 325 (MH)$^+$.

Example 50

(R)-6,7-Difluoro-2-hydroxy-3-(4-oxo-pentanoylamino)-3,4-dihydro-2H-benzo[e][1,2]oxaborinine-8-carboxylic acid

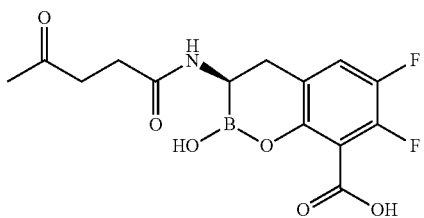 [SMILES: CC(=O)CCC(=O)N[C@H]1Cc2cc(F)c(F)c(C(=O)O)c2OB1O]

Step 1. Synthesis of 2,3-Difluoro-6-methoxy-5-[2-(4-oxo-pentanoylamino)-2-(2,9,9-trimethyl-3,5-dioxa-4-bora-tricyclo[6.1.1.0$^{2,6}$]dec-4-yl)-ethyl]-benzoic acid tert-butyl ester.

Prepared from [(1S)-2-(3-tert-butoxycarbonyl-2-methoxy-4,5-difluoro-phenyl)-1-chloro-ethyl]boronic acid (+) pinanediol ester and levulinic acid following the procedure in Steps 1-6 of Example 49. The crude product was purified by flash chromatography on silica gel (10-100% EtOAc/Hexane). ESI-MS m/z 564 (MH)$^+$.

Step 2. Synthesis of (R)-6,7-Difluoro-2-hydroxy-3-(4-oxo-pentanoylamino)-3,4-dihydro-2H-benzo[e][1,2]oxaborinine-8-carboxylic acid.

Prepared from 2,3-Difluoro-6-methoxy-5-[2-(4-oxo-pentanoylamino)-2-(2,9,9-trimethyl-3,5-dioxa-4-bora-tricyclo[6.1.1.0²,⁶]dec-4-yl)-ethyl]-benzoic acid tert-butyl ester following the procedure described in Example 7. The crude product was purified by reverse phase preparative HPLC and dried using lyophilization. ESI-MS m/z 342 (MH)⁺.

Example 51

(R)-6,7-Difluoro-2-hydroxy-3-(3-methanesulfonylamino-propionylamino)-3,4-dihydro-2H-benzo[e][1,2]oxaborinine-8-carboxylic acid

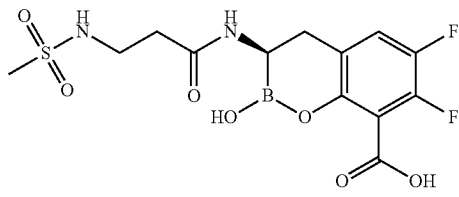 [SMILES: CS(=O)(=O)NCCC(=O)N[C@H]1Cc2cc(F)c(F)c(C(=O)O)c2OB1O]

Step 1. Synthesis of 2,3-Difluoro-5-[2-(3-methanesulfonylamino-propionylamino)-2-(2,9,9-trimethyl-3,5-dioxa-4-bora-tricyclo[6.1.1.0²,⁶]dec-4-yl)-ethyl]-6-methoxy-benzoic acid tert-butyl ester.

Prepared from [(1S)-2-(3-tert-butoxycarbonyl-2-methoxy-4,5-difluoro-phenyl)-1-chloro-ethyl]boronic acid (+) pinanediol ester and N-(methylsulfonyl)-β-alanine following the procedure in Steps 1-6 of Example 49. The crude product was purified by flash chromatography on silica gel (10-100% EtOAc/Hexane). ESI-MS m/z 615 (MH)⁺.

Step 2. Synthesis of (R)-6,7-Difluoro-2-hydroxy-3-(3-methanesulfonylamino-propionylamino)-3,4-dihydro-2H-benzo[e][1,2]oxaborinine-8-carboxylic acid.

Prepared from 2,3-Difluoro-5-[2-(3-methanesulfonylamino-propionylamino)-2-(2,9,9-trimethyl-3,5-dioxa-4-bora-tricyclo[6.1.1.0²,⁶]dec-4-yl)-ethyl]-6-methoxy-benzoic acid tert-butyl ester following the procedure described in Example 7. The crude product was purified by reverse phase preparative HPLC and dried using lyophilization. ESI-MS m/z 393 (MH)⁺.

Example 52

(R)-2-Hydroxy-3-(3-trifluoromethanesulfonylamino-propionylamino)-3,4-dihydro-2H-benzo[e][1,2]oxaborinine-8-carboxylic acid

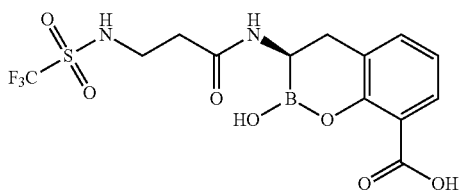 [SMILES: O=C(CCNS(=O)(=O)C(F)(F)F)N[C@H]1Cc2cccc(C(=O)O)c2OB1O]

Step 1. Synthesis of 2-Methoxy-3-[2-(3-trifluoromethanesulfonylamino-propionylamino)-2-(2,9,9-trimethyl-3,5-dioxa-4-bora-tricyclo[6.1.1.0²,⁶]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-trifluoromethanesulfonamidopropanoic acid following the procedure in Step 2 of Example 1. The crude product was purified by flash chromatography on silica gel (10-100% EtOAc/Hexane). ESI-MS m/z 633 (MH)⁺.

Step 2. Synthesis of (R)-2-Hydroxy-3-(3-trifluoromethanesulfonylamino-propionylamino)-3,4-dihydro-2H-benzo[e][1,2]oxaborinine-8-carboxylic acid.

Prepared from 2-Methoxy-3-[2-(3-trifluoromethanesulfonylamino-propionylamino)-2-(2,9,9-trimethyl-3,5-dioxa-4-bora-tricyclo[6.1.1.0²,⁶]dec-4-yl)-ethyl]-benzoic acid tert-butyl ester following the procedure described in Example 7 with substituting boron tribromide for boron trichloride. The crude product was purified by reverse phase preparative HPLC and dried using lyophilization. ESI-MS m/z 411 (MH)⁺.

Example 53

(R)-2-Hydroxy-3-(4-sulfamoyl-butyrylamino)-3,4-dihydro-2H-benzo[e][1,2]oxaborinine-8-carboxylic acid

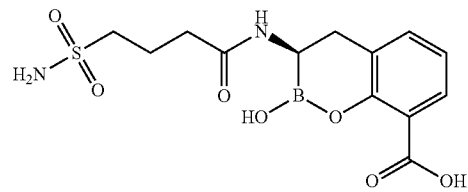 [SMILES: NS(=O)(=O)CCCC(=O)N[C@H]1Cc2cccc(C(=O)O)c2OB1O]

Step 1. Synthesis of 2-Methoxy-3-[2-(4-sulfamoyl-butyrylamino)-2-(2,9,9-trimethyl-3,5-dioxa-4-bora-tricyclo[6.1.1.0²,⁶]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-sulfamoylbutanoic acid following the procedure in Step 2 of Example 1. The crude product was purified by flash chromatography on silica gel (0-10% CH₃OH/CH₂Cl₂). ESI-MS m/z 579 (MH)⁺.

Step 2. Synthesis of (R)-2-Hydroxy-3-(4-sulfamoyl-butyrylamino)-3,4-dihydro-2H-benzo[e][1,2]oxaborinine-8-carboxylic acid.

Prepared from 2-Methoxy-3-[2-(4-sulfamoyl-butyrylamino)-2-(2,9,9-trimethyl-3,5-dioxa-4-bora-tricyclo[6.1.1.0²,⁶]dec-4-yl)-ethyl]-benzoic acid tert-butyl ester following the procedure described in Example 52. The crude product was purified by reverse phase preparative HPLC and dried using lyophilization. ESI-MS m/z 357 (MH)⁺.

Example 54

(R)-2-Hydroxy-3-(3-methylsulfamoyl-propionylamino)-3,4-dihydro-2H-benzo[e][1,2]oxaborinine-8-carboxylic acid

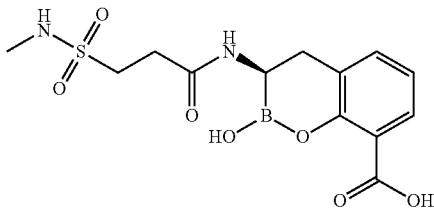 [SMILES: CNS(=O)(=O)CCC(=O)N[C@H]1Cc2cccc(C(=O)O)c2OB1O]

Step 1. Synthesis of 2-Methoxy-3-[2-(3-methylsulfamoyl-propionylamino)-2-(2,9,9-trimethyl-3,5-dioxa-4-bora-tricyclo[6.1.1.0²,⁶]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-(methylsulfamoyl)propanoic acid following the procedure in Step 2 of Example 1. The crude product was purified by flash chromatography on silica gel (5-100% EtOAc/Hexane). ESI-MS m/z 579 (MH)+.

Step 2. Synthesis of (R)-2-Hydroxy-3-(3-methylsulfamoyl-propionylamino)-3,4-dihydro-2H-benzo[e][1,2]oxaborinine-8-carboxylic acid.

Prepared from 2-Methoxy-3-[2-(3-methylsulfamoyl-propionylamino)-2-(2,9,9-trimethyl-3,5-dioxa-4-bora-tricyclo[6.1.1.0²,⁶]dec-4-yl)-ethyl]-benzoic acid tert-butyl ester following the procedure described in Example 52. The crude product was purified by reverse phase preparative HPLC and dried using lyophilization. ESI-MS m/z 357 (MH)+.

Example 55

(R)-3-(3-Dimethylsulfamoyl-propionylamino)-2-hydroxy-3,4-dihydro-2H-benzo[e][1,2]oxaborinine-8-carboxylic acid

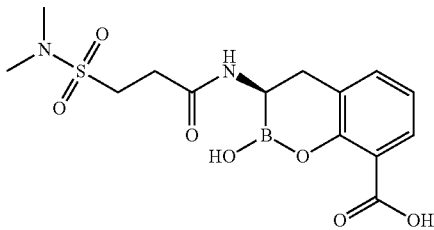 [SMILES: CN(C)S(=O)(=O)CCC(=O)N[C@H]1Cc2cccc(C(=O)O)c2OB1O]

Step 1. Synthesis of 3-[2-(3-Dimethylsulfamoyl-propionylamino)-2-(2,9,9-trimethyl-3,5-dioxa-4-bora-tricyclo[6.1.1.0²,⁶]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 3-(dimethylsulfamoyl)propanoic acid following the procedure in Step 2 of Example 1. The crude product was purified by flash chromatography on silica gel (5-100% EtOAc/Hexane). ESI-MS m/z 593 (MH)+.

Step 2. Synthesis of (R)-3-(3-Dimethylsulfamoyl-propionylamino)-2-hydroxy-3,4-dihydro-2H-benzo[e][1,2]oxaborinine-8-carboxylic acid.

Prepared from 3-[2-(3-Dimethylsulfamoyl-propionylamino)-2-(2,9,9-trimethyl-3,5-dioxa-4-bora-tricyclo[6.1.1.0²,⁶]dec-4-yl)-ethyl]-2-methoxy-benzoic acid tert-butyl ester following the procedure described in Example 52. The crude product was purified by reverse phase preparative HPLC and dried using lyophilization. ESI-MS m/z 371 (MH)+.

Example 56

(R)-2-Hydroxy-3-(2-methoxycarbonylamino-acetylamino)-3,4-dihydro-2H-benzo[e][1,2]oxaborinine-8-carboxylic acid

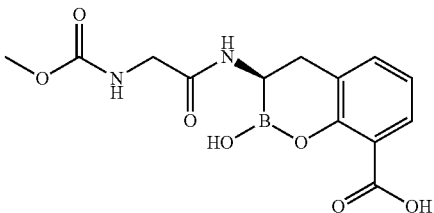 [SMILES: COC(=O)NCC(=O)N[C@H]1Cc2cccc(C(=O)O)c2OB1O]

Step 1. Synthesis of 2-Methoxy-3-[2-(2-methoxycarbonylamino-acetylamino)-2-(2,9,9-trimethyl-3,5-dioxa-4-bora-tricyclo[6.1.1.0²,⁶]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and N-(methoxycarbonyl)glycine following the procedure in Step 2 of Example 1. The crude product was purified by flash chromatography on silica gel (1-3% CH₃OH/CH₂Cl₂). ESI-MS m/z 545 (MH)+.

Step 2. Synthesis of (R)-2-Hydroxy-3-(2-methoxycarbonylamino-acetylamino)-3,4-dihydro-2H-benzo[e][1,2]oxaborinine-8-carboxylic acid.

Prepared from 2-methoxy-3-[2-(2-methoxycarbonylamino-acetylamino)-2-(2,9,9-trimethyl-3,5-dioxa-4-bora-tricyclo[6.1.1.0²,⁶]dec-4-yl)-ethyl]-benzoic acid tert-butyl ester and 1M boron tribromide in dichloromethane following the procedure described in Example 52. The crude product was purified by reverse phase preparative HPLC and dried using lyophilization to give the title compound. ESI-MS m/z 323 (MH)+.

Example 57

(R)-2-Hydroxy-3-(4-methanesulfonylamino-butyrylamino)-3,4-dihydro-2H-benzo[e][1,2]oxaborinine-8-carboxylic acid

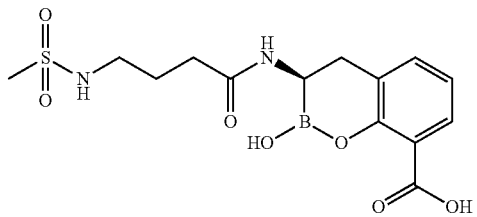 [SMILES: CS(=O)(=O)NCCCC(=O)N[C@H]1Cc2cccc(C(=O)O)c2OB1O]

Step 1. Synthesis of 3-[2-(4-Methanesulfonylamino-butyrylamino)-2-(2,9,9-trimethyl-3,5-dioxa-4-bora-tricyclo[6.1.1.02,6]dec-4-yl)-ethyl]benzoic acid tert-butyl ester.

Prepared from [(1S)-2-(3-tert-butoxycarbonyl-2-methoxy-phenyl)-1-chloro-ethyl]boronic acid (+) pinanediol ester and sodium 4-[(methylsulfonyl)amino]butanoate following the procedure in Step 2 of Example 1. The crude product was purified by flash chromatography on silica gel (1-5% CH$_3$OH/CH$_2$Cl$_2$). ESI-MS m/z 593 (MH)$^+$.

Step 2. Synthesis of (R)-2-Hydroxy-3-(4-methanesulfonylamino-butyrylamino)-3,4-dihydro-2H-benzo[e][1,2]oxaborinine-8-carboxylic acid.

Prepared from 3-[2-(4-methanesulfonylamino-butyrylamino)-2-(2,9,9-trimethyl-3,5-dioxa-4-bora-tricyclo[6.1.1.02,6]dec-4-yl)-ethyl]benzoic acid tert-butyl ester and 1M boron tribromide in dichloromethane following the procedure described in Example 52. The crude product was purified by reverse phase preparative HPLC and dried using lyophilization to give the title compound. ESI-MS m/z 371 (MH)$^+$.

Example 58

(R)-2-Hydroxy-3-(4-methylsulfamoyl-butyrylamino)-3,4-dihydro-2H-benzo[e][1,2]oxaborinine-8-carboxylic acid

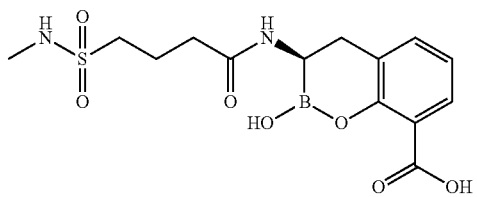 [SMILES: CNS(=O)(=O)CCCC(=O)N[C@H]1Cc2cccc(C(=O)O)c2OB1O]

Step 1. Synthesis of 2-Methoxy-3-[2-(-4-sulfamoyl-butyrylamino)-2-(2,9,9-trimethyl-3,5-dioxa-4-bora-tricyclo[6.1.1.02,6]dec-4-yl)-ethyl]benzoic acid tert-butyl ester.

Prepared from [(1S)-2-(3-tert-butoxycarbonyl-2-methoxy-phenyl)-1-chloro-ethyl]boronic acid (+) pinanediol ester and 3-carboxypropane sulfonamide following the procedure in Step 2 of Example 1. The crude product was purified by flash chromatography on silica gel (1-3% CH$_3$OH/CH$_2$Cl$_2$). ESI-MS m/z 579 (MH)$^+$.

Step 2. Synthesis of 2-Methoxy-3-[2-(4-methylsulfamoyl-butyrylamino)-2-(2,9,9-trimethyl-3,5-dioxa-4-bora-tricyclo[6.1.1.02,6]dec-4-yl)-ethyl]benzoic acid tert-butyl ester.

To 2-methoxy-3-[2-(-4-sulfamoyl-butyrylamino)-2-(2,9,9-trimethyl-3,5-dioxa-4-bora-tricyclo[6.1.1.02,6]dec-4-yl)-ethyl]benzoic acid tert-butyl ester (0.23 g, 0.39 mmol) in anhydrous N,N-dimethylformamide (6 mL) was added potassium carbonate (0.16 g, 1.18 mmol), followed by iodomethane (0.12 mL, 1.96 mmol) and the reaction was stirred at room temperature for 2 h. The reaction was diluted with ethyl acetate, washed with water/brine, dried over sodium sulfate, and concentrated. The crude product was purified using Prep TLC plates (5% CH$_3$OH/CH$_2$Cl$_2$). ESI-MS m/z 593 (MH)$^+$.

Step 3. Synthesis of (R)-2-Hydroxy-3-(4-methylsulfamoyl-butyrylamino)-3,4-dihydro-2H-benzo[e][1,2]oxaborinine-8-carboxylic acid.

Prepared from 2-methoxy-3-[2-(4-methylsulfamoyl-butyrylamino)-2-(2,9,9-trimethyl-3,5-dioxa-4-bora-tricyclo[6.1.1.02,6]dec-4-yl)-ethyl]benzoic acid tert-butyl ester and 1M boron tribromide in dichloromethane following the procedure described in Example 52. The crude product was purified by reverse phase preparative HPLC and dried using lyophilization to give the title compound. ESI-MS m/z 371 (MH)$^+$.

Example 59

(R)-2-Hydroxy-3-(4-methanesulfonyl-butyrylamino)-3,4-dihydro-2H-benzo[e][1,2]oxaborinine-8-carboxylic acid

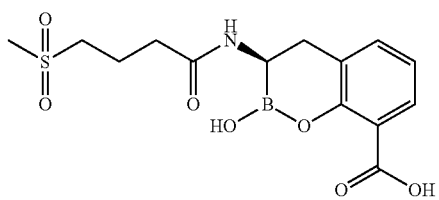 [SMILES: CS(=O)(=O)CCCC(=O)N[C@H]1Cc2cccc(C(=O)O)c2OB1O]

Step 1. Synthesis of 3-[2-(4-Methanesulfonyl-butyrylamino)-2-(2,9,9-trimethyl-3,5-dioxa-4-bora-tricyclo[6.1.1.02,6]dec-4-yl)-ethyl]benzoic acid tert-butyl ester.

Prepared from [(1S)-2-(3-tert-butoxycarbonyl-2-methoxy-phenyl)-1-chloro-ethyl]boronic acid (+) pinanediol ester and 4-methanesulfonylbutanoic acid following the procedure in Step 2 of Example 1. The crude product was purified by flash chromatography on silica gel (100% EtOAc). ESI-MS m/z 578 (MH)$^+$.

Step 2. Synthesis of (R)-2-Hydroxy-3-(4-methane-sulfonyl-butyrylamino)-3,4-dihydro-2H-benzo[e][1,2]oxaborinine-8-carboxylic acid.

Prepared from 3-[2-(4-methanesulfonyl-butyrylamino)-2-(2,9,9-trimethyl-3,5-dioxa-4-bora-tricyclo[6.1.1.02,6]dec-4-yl)-ethyl]benzoic acid tert-butyl ester and 1M boron tribromide in dichloromethane following the procedure described in Example 52. The crude product was purified by reverse phase preparative HPLC and dried using lyophilization to give the title compound ESI-MS m/z 356 (MH)+.

Example 60

(R)-3-(2-Benzoylamino-acetylamino)-2-hydroxy-3,4-dihydro-2H-benzo[e][1,2]oxaborinine-8-carboxylic acid

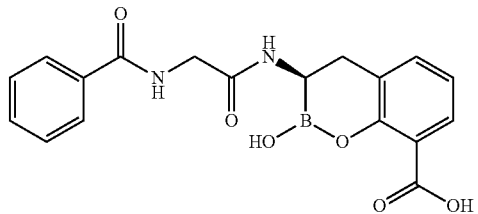 [SMILES: O=C(CNC(=O)c1ccccc1)N[C@H]1Cc2cccc(C(=O)O)c2OB1O]

Step 1. 3-[2-(2-Benzoylamino-acetylamino)-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and hippuric acid following the procedure in Step 2 of Example 1. The crude product was purified by flash chromatography on silica gel (20-70% EtOAc/Hexanes). ESI-MS m/z 591 (MH)+.

Step 2. Synthesis of (R)-3-(2-Benzoylamino-acetylamino)-2-hydroxy-3,4-dihydro-2H-benzo[e][1,2]oxaborinine-8-carboxylic acid.

Prepared from 3-[2-(2-benzoylamino-acetylamino)-2-(2,9,9-trimethyl-3,5-dioxa-4-bora-tricyclo[6.1.1.02,6]dec-4-yl)-ethyl]-2-methoxy-benzoic acid tert-butyl ester and 1M boron tribromide in dichloromethane following the procedure described in Example 52. The crude product was purified by reverse phase preparative HPLC and dried using lyophilization to give the title compound. ESI-MS m/z 369 (MH)+.

Example 61

(R)-3-Acetylamino-2-hydroxy-3,4-dihydro-2H-benzo[e][1,2]oxaborinine-8-carboxylic acid

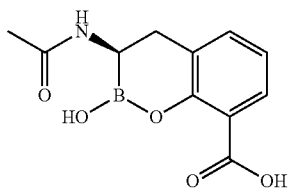 [SMILES: CC(=O)N[C@H]1Cc2cccc(C(=O)O)c2OB1O]

Step 1. Synthesis of 3-[2-Acetylamino-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and acetic acid following the procedure in Step 2 of Example 1. The crude product was purified by flash chromatography on silica gel (10-100% EtOAc/Hexane). ESI-MS m/z 472 (MH)+.

Step 2. Synthesis of (R)-3-Acetylamino-2-hydroxy-3,4-dihydro-2H-benzo[e][1,2]oxaborinine-8-carboxylic acid.

Prepared from 3-[2-Acetylamino-2-(2,9,9-trimethyl-3,5-dioxa-4-bora-tricyclo[6.1.1.02,6]dec-4-yl)-ethyl]-2-methoxy-benzoic acid tert-butyl ester following the procedure described in Step 3 of Example 1. The crude product was purified by reverse phase preparative HPLC and dried using lyophilization. ESI-MS m/z 250 (MH)+.

Example 62

(R)-2-Hydroxy-3-propionylamino-3,4-dihydro-2H-benzo[e][1,2]oxaborinine-8-carboxylic acid

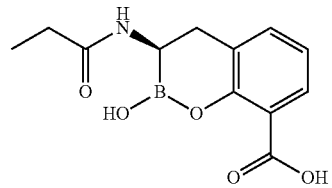 [SMILES: CCC(=O)N[C@H]1Cc2cccc(C(=O)O)c2OB1O]

Step 1. Synthesis of 2-Methoxy-3-[2-propionylamino-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and propionic acid following the procedure in Step 2 of Example 1. The crude product was purified by flash chromatography on silica gel (25-100% EtOAc/Hexane). ESI-MS m/z 486 (MH)+.

Step 2. Synthesis of (R)-2-Hydroxy-3-propionylamino-3,4-dihydro-2H-benzo[e][1,2]oxaborinine-8-carboxylic acid.

Prepared from 2-Methoxy-3-[2-propionylamino-2-(2,9,9-trimethyl-3,5-dioxa-4-bora-tricyclo[6.1.1.02,6]dec-4-yl)-ethyl]-benzoic acid tert-butyl ester following the procedure described in Step 3 of Example 1. The crude product was purified by reverse phase preparative HPLC and dried using lyophilization. ESI-MS m/z 264 (MH)+.

Example 63

(R)-2-Hydroxy-3-(4-hydroxy-pentanoylamino)-3,4-dihydro-2H-benzo[e][1,2]oxaborinine-8-carboxylic acid

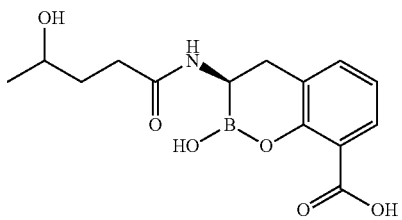

Step 1. Synthesis of 3-[2-(4-Hydroxy-pentanoylamino)-2-(2,9,9-trimethyl-3,5-dioxa-4-bora-tricyclo[6.1.1.02,6]dec-4-yl)-ethyl]-2-methoxy-benzoic acid tert-butyl ester Prepared from [(1S)-2-(3-tert-butoxycarbonyl-2-methoxy-phenyl)-1-chloro-ethyl]boronic acid (+) pinanediol ester and sodium 4-hydroxypentanoate following the procedure in Step 2 of Example 1. The crude product was purified by flash chromatography on silica gel (10-100% EtOAc/Hexane). ESI-MS m/z 530 (MH)+.

Step 2. Synthesis of (R)-2-Hydroxy-3-(4-hydroxy-pentanoylamino)-3,4-dihydro-2H-benzo[e][1,2]oxaborinine-8-carboxylic acid.

Prepared from 3-[2-(4-Hydroxy-pentanoylamino)-2-(2,9,9-trimethyl-3,5-dioxa-4-bora-tricyclo[6.1.1.02,6]dec-4-yl)-ethyl]-2-methoxy-benzoic acid tert-butyl ester following the procedure described in Example 52. The crude product was purified by reverse phase preparative HPLC and dried using lyophilization. ESI-MS m/z 308 (MH)+.

Example 64

(R)-3-(2-2,3-Dihydro-1H-isoindol-5-yl-acetylamino)-2-hydroxy-3,4-dihydro-2H-benzo[e][1,2]oxaborinine-8-carboxylic acid

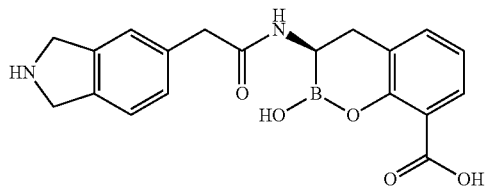 [SMILES: O=C(Cc1ccc2c(c1)CNC2)N[C@H]1Cc2cccc(C(=O)O)c2OB1O]

Step 1. Synthesis of 3-[2-(2-2,3-Dihydro-1H-isoindol-5-yl-acetylamino)-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 5-Carboxymethyl-1,3-dihydro-isoindole-2-carboxylic acid tert-butyl ester following the procedure in Step 2 of Example 1. The crude product was purified by flash chromatography on silica gel (30-100% EtOAc/Hexane). ESI-MS m/z 689 (MH)+.

Step 2. Synthesis of (R)-3-(2-2,3-Dihydro-1H-isoindol-5-yl-acetylamino)-2-hydroxy-3,4-dihydro-2H-benzo[e][1,2]oxaborinine-8-carboxylic acid.

Prepared from 3-[2-(2-2,3-Dihydro-1H-isoindol-5-yl-acetylamino)-2-(2,9,9-trimethyl-3,5-dioxa-4-bora-tricyclo[6.1.1.02,6]dec-4-yl)-ethyl]-2-methoxy-benzoic acid tert-butyl ester following the procedure described in Example 7. The crude product was purified by reverse phase preparative HPLC and dried using lyophilization. ESI-MS m/z 367 (MH)+.

Example 65

(R)-2-Hydroxy-3-(2-pyridin-4-yl-acetylamino)-3,4-dihydro-2H-benzo[e][1,2]oxaborinine-8-carboxylic acid

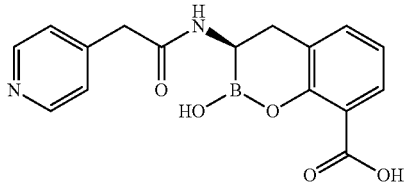 [SMILES: O=C(Cc1ccncc1)N[C@H]1Cc2cccc(C(=O)O)c2OB1O]

Step 1. Synthesis of 2-Methoxy-3-[2-(2-pyridin-4-yl-acetylamino)-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 4-pyridylacetic acid following the procedure in Step 2 of Example 1. The crude product was purified by flash chromatography on silica gel (0-10% CH$_3$OH/CH$_2$Cl$_2$). ESI-MS m/z 549 (MH)+.

Step 2. Synthesis of (R)-2-Hydroxy-3-(2-pyridin-4-yl-acetylamino)-3,4-dihydro-2H-benzo[e][1,2]oxaborinine-8-carboxylic acid.

Prepared from 2-Methoxy-3-[2-(2-pyridin-4-yl-acetylamino)-2-(2,9,9-trimethyl-3,5-dioxa-4-bora-tricyclo[6.1.1.02,6]dec-4-yl)-ethyl]-benzoic acid tert-butyl ester following the procedure described in Example 7. The crude product was purified by reverse phase preparative HPLC and dried using lyophilization. ESI-MS m/z 327 (MH)+.

Example 125

(R)-3-(3-Cyano-propionylamino)-2-hydroxy-3,4-dihydro-2H-benzo[e][1,2]oxaborinine-8-carboxylic acid methyl ester

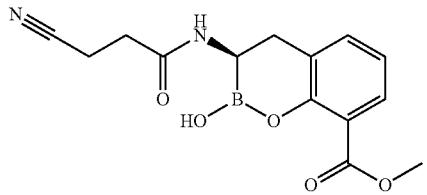 [SMILES: COC(=O)c1cccc2c1OB(O)[C@@H](NC(=O)CCC#N)C2]

Step 1. Synthesis of 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid.

A solution of 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid tert-butyl ester (prepared in Step 1 of Example 8) (1.2 g, 2.35 mmol) and hydrochloric acid (4.0M in 1,4-Dioxane, 18 mL) was stirred at room temperature for 7 h. The reaction mixture was concentrated in vacuo and azeotroped two times with toluene. The crude product was carried forward without purification. ESI-MS m/z 455 (MH)$^+$.

Step 2. Synthesis of 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid methyl ester.

To a solution of 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid (0.280 g, 0.616 mmol) in methanol (3.2 mL) and toluene (3.6 mL) under argon was added trimethylsilyldiazomethane (2.0M in hexanes) in three portions (0.31 mL, 0.23 mL, 0.51 mL, 2.10 mmol total) over 6 h. The reaction was then stirred an additional 17 h at room temperature. The reaction was concentrated in vacuo and the crude product was carried forward without purification. ESI-MS m/z 469 (MH)$^+$.

Step 3. Synthesis of (R)-3-(3-Cyano-propionylamino)-2-hydroxy-3,4-dihydro-2H-benzo[e][1,2]oxaborinine-8-carboxylic acid methyl ester.

Prepared from 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid methyl ester following the procedure described in Step 3 of Example 1. The crude product was purified by reverse phase preparative HPLC and dried using lyophilization. ESI-MS m/z 303 (MH)$^+$.

Example 126

(R)-3-(3-Cyano-propionylamino)-2-hydroxy-3,4-dihydro-2H-benzo[e][1,2]oxaborinine-8-carboxylic acid 2,2-dimethyl-propionyloxymethyl ester

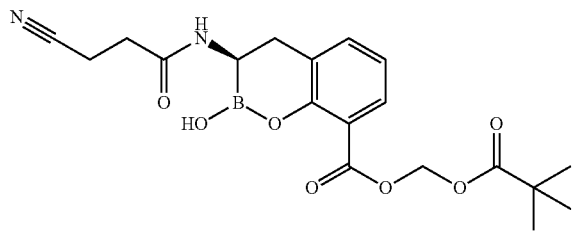 [SMILES: CC(C)(C)C(=O)OCOC(=O)c1cccc2c1OB(O)[C@@H](NC(=O)CCC#N)C2]

Step 1. Synthesis of 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid 2,2-dimethyl-propionyloxymethyl ester.

To a solution of 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid (0.240 g, 0.528 mmol) (prepared in Step 1 of Example 125) in DMF (2.5 mL) under argon was added sodium carbonate (0.113 g, 1.07 mmol) and the reaction was stirred at room temperature for 5 min. Chloromethyl pivalate (0.13 mL, 0.902 mmol) in DMF (0.4 mL) was added followed by sodium iodide (0.042 g, 0.280 mmol) and the reaction stirred at room temperature for 19 h. The reaction was quenched with water and extracted three times with ethyl acetate. The combined organic layers were washed with brine, dried over Na$_2$SO$_4$, filtered, and concentrated. The crude product was purified by flash chromatography on silica gel (10-100% EtOAc/Hexane). ESI-MS m/z 569 (MH)$^+$.

Step 2. Synthesis of (R)-3-(3-Cyano-propionylamino)-2-hydroxy-3,4-dihydro-2H-benzo[e][1,2]oxaborinine-8-carboxylic acid 2,2-dimethyl-propionyloxymethyl ester.

Prepared from 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid 2,2-dimethyl-propionyloxymethyl ester following the procedure described in Step 3 of Example 1. The crude product was purified by reverse phase preparative HPLC and dried using lyophilization. ESI-MS m/z 403 (MH)$^+$.

Example 127

(R)-3-(3-Cyano-propionylamino)-2-hydroxy-3,4-dihydro-2H-benzo[e][1,2]oxaborinine-8-carboxylic acid acetoxymethyl ester

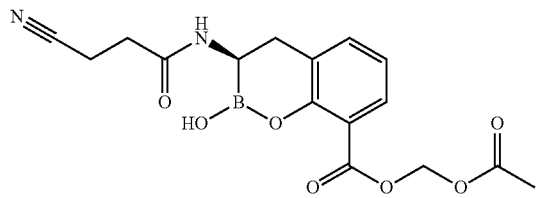 [SMILES: CC(=O)OCOC(=O)c1cccc2c1OB(O)[C@@H](NC(=O)CCC#N)C2]

Step 1. Synthesis of 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid acetoxymethyl ester.

To a mixture of 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid (0.158 g, 0.348 mmol) (prepared in Step 1 of Example 125) and potassium carbonate (0.073 g, 0.528 mmol) under argon was added DMF (1.8 mL). Bromomethyl acetate (0.055 mL, 0.561 mmol) was added and the reaction was stirred at room temperature for 5 h. The reaction was quenched with water and extracted three times with ethyl acetate. The combined organic layers were washed with brine, dried over MgSO$_4$, filtered, and concentrated. The crude product was purified by flash chromatography on silica gel (10-100% EtOAc/Hexane). ESI-MS m/z 527 (MH)$^+$.

Step 2. Synthesis of (R)-3-(3-Cyano-propionylamino)-2-hydroxy-3,4-dihydro-2H-benzo[e][1,2]oxaborinine-8-carboxylic acid acetoxymethyl ester.

Prepared from 3-[2-(3-Cyano-propionylamino)-2-(2,9,9-trimethyl-3,5-dioxa-4-bora-tricyclo[6.1.1.0²,⁶]dec-4-yl)- ethyl]-2-methoxy-benzoic acid acetoxymethyl ester following the procedure described in Example 7. The crude product was purified by reverse phase preparative HPLC and dried using lyophilization. ESI-MS m/z 361 (MH)+.

Example 128

(R)-3-(3-Cyano-propionylamino)-2-hydroxy-3,4-dihydro-2H-benzo[e][1,2]oxaborinine-8-carboxylic acid propyl ester

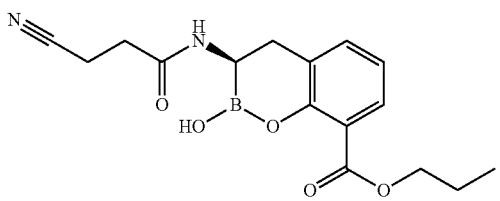 [SMILES: CCCOC(=O)c1cccc2c1OB(O)[C@@H](NC(=O)CCC#N)C2]

Step 1. Synthesis of 3-[2-(3-Cyano-propionylamino)-2-(2,9,9-trimethyl-3,5-dioxa-4-bora-tricyclo[6.1.1.02,6]dec-4-yl)-ethyl]-2-methoxy-benzoic acid propyl ester.

Prepared from 3-[2-(3-Cyano-propionylamino)-2-(2,9,9-trimethyl-3,5-dioxa-4-bora-tricyclo[6.1.1.02,6]dec-4-yl)-ethyl]-2-methoxy-benzoic acid (prepared in Step 1 of Example 125) and 1-iodopropane following the procedure described in Step 1 of Example 127. The crude product was purified by flash chromatography on silica gel (10-100% EtOAc/Hexane). ESI-MS m/z 497 (MH)+.

Step 2. Synthesis of (R)-3-(3-Cyano-propionylamino)-2-hydroxy-3,4-dihydro-2H-benzo[e][1,2]oxaborinine-8-carboxylic acid propyl ester.

Prepared from 3-[2-(3-Cyano-propionylamino)-2-(2,9,9-trimethyl-3,5-dioxa-4-bora-tricyclo[6.1.1.02,6]dec-4-yl)-ethyl]-2-methoxy-benzoic acid propyl ester following the procedure described in Step 3 of Example 1. The crude product was purified by reverse phase preparative HPLC and dried using lyophilization. ESI-MS m/z 331 (MH)+.

Example 129

(R)-3-(3-Cyano-propionylamino)-2-hydroxy-3,4-dihydro-2H-benzo[e][1,2]oxaborinine-8-carboxylic acid ethyl ester

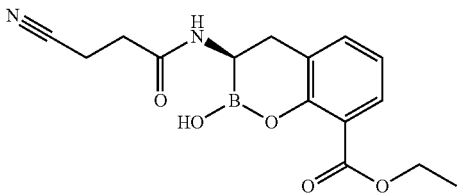 [SMILES: CCOC(=O)c1cccc2c1OB(O)[C@@H](NC(=O)CCC#N)C2]

Step 1. Synthesis of 3-[2-(3-Cyano-propionylamino)-2-(2,9,9-trimethyl-3,5-dioxa-4-bora-tricyclo[6.1.1.02,6]dec-4-yl)-ethyl]-2-methoxy-benzoic acid ethyl ester.

Prepared from 3-[2-(3-Cyano-propionylamino)-2-(2,9,9-trimethyl-3,5-dioxa-4-bora-tricyclo[6.1.1.02,6]dec-4-yl)-ethyl]-2-methoxy-benzoic acid (prepared in Step 1 of Example 125) and iodoethane following the procedure described in Step 1 of Example 127. The crude product was purified by flash chromatography on silica gel (10-100% EtOAc/Hexane). ESI-MS m/z 483 (MH)+.

Step 2. Synthesis of (R)-3-(3-Cyano-propionylamino)-2-hydroxy-3,4-dihydro-2H-benzo[e][1,2]oxaborinine-8-carboxylic acid ethyl ester.

Prepared from 3-[2-(3-Cyano-propionylamino)-2-(2,9,9-trimethyl-3,5-dioxa-4-bora-tricyclo[6.1.1.02,6]dec-4-yl)-ethyl]-2-methoxy-benzoic acid ethyl ester following the procedure described in Step 3 of Example 1. The crude product was purified by reverse phase preparative HPLC and dried using lyophilization. ESI-MS m/z 317 (MH)+.

Example 130

(R)-3-(3-Cyano-propionylamino)-2-hydroxy-3,4-dihydro-2H-benzo[e][1,2]oxaborinine-8-carboxylic acid butyl ester

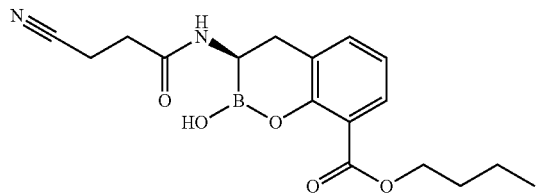 [SMILES: CCCCOC(=O)c1cccc2c1OB(O)[C@@H](NC(=O)CCC#N)C2]

Step 1. Synthesis of 3-[2-(3-Cyano-propionylamino)-2-(2,9,9-trimethyl-3,5-dioxa-4-bora-tricyclo[6.1.1.02,6]dec-4-yl)-ethyl]-2-methoxy-benzoic acid butyl ester Prepared from 3-[2-(3-Cyano-propionylamino)-2-(2,9,9-trimethyl-3,5-dioxa-4-bora-tricyclo[6.1.1.02,6]dec-4-yl)-ethyl]-2-methoxy-benzoic acid (prepared in Step 1 of Example 125) and 1-iodobutane following the procedure described in Step 1 of Example 127. The crude product was purified by flash chromatography on silica gel (10-100% EtOAc/Hexane). ESI-MS m/z 511 (MH)+.

Step 2. Synthesis of (R)-3-(3-Cyano-propionylamino)-2-hydroxy-3,4-dihydro-2H-benzo[e][1,2]oxaborinine-8-carboxylic acid butyl ester.

Prepared from 3-[2-(3-Cyano-propionylamino)-2-(2,9,9-trimethyl-3,5-dioxa-4-bora-tricyclo[6.1.1.02,6]dec-4-yl)-ethyl]-2-methoxy-benzoic acid butyl ester following the procedure described in Step 3 of Example 1. The crude product was purified by reverse phase preparative HPLC and dried using lyophilization. ESI-MS m/z 345 (MH)+.

Example 131

(R)-3-(3-Cyano-propionylamino)-2-hydroxy-3,4-dihydro-2H-benzo[e][1,2]oxaborinine-8-carboxylic acid isobutyl ester

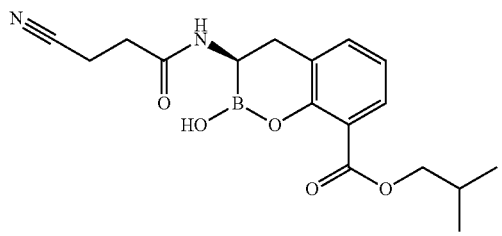 [SMILES: CC(C)COC(=O)c1cccc2c1OB(O)[C@@H](NC(=O)CCC#N)C2]

Step 1. Synthesis of 3-[2-(3-Cyano-propionylamino)-2-(2,9,9-trimethyl-3,5-dioxa-4-bora-tricyclo[6.1.1.02,6]dec-4-yl)-ethyl]-2-methoxy-benzoic acid isobutyl ester.

Prepared from 3-[2-(3-Cyano-propionylamino)-2-(2,9,9-trimethyl-3,5-dioxa-4-bora-tricyclo[6.1.1.02,6]dec-4-yl)-ethyl]-2-methoxy-benzoic acid (prepared in Step 1 of Example 125) and 1-iodo-2-methylpropane following the procedure described in Step 1 of Example 127. The crude product was purified by flash chromatography on silica gel (10-100% EtOAc/Hexane). ESI-MS m/z 511 (MH)+.

Step 2. Synthesis of (R)-3-(3-Cyano-propionylamino)-2-hydroxy-3,4-dihydro-2H-benzo[e][1,2]oxaborinine-8-carboxylic acid isobutyl ester.

Prepared from 3-[2-(3-Cyano-propionylamino)-2-(2,9,9-trimethyl-3,5-dioxa-4-bora-tricyclo[6.1.1.02,6]dec-4-yl)-ethyl]-2-methoxy-benzoic acid isobutyl ester following the procedure described in Step 3 of Example 1. The crude product was purified by reverse phase preparative HPLC and dried using lyophilization. ESI-MS m/z 345 (MH)+.

Example 132

(R)-2-Hydroxy-3-(4-oxo-pentanoylamino)-3,4-dihydro-2H-benzo[e][1,2]oxaborinine-8-carboxylic acid butyl ester

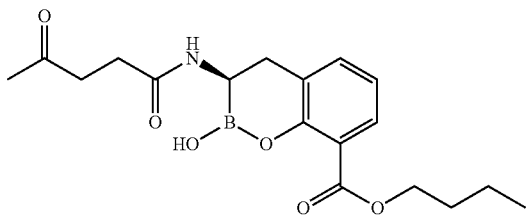 [SMILES: CCCCOC(=O)c1cccc2c1OB(O)[C@@H](NC(=O)CCC(C)=O)C2]

To a solution of (R)-2-Hydroxy-3-(4-oxo-pentanoylamino)-3,4-dihydro-2H-benzo[e][1,2]oxaborinine-8-carboxylic acid (0.39 g, 1.28 mmol) in n-butanol (30 mL) was added 4N HCl in dioxane (6 mL). The solution was stirred at 40° C. for 4.5 h, cooled to room temperature and an additional aliquot of 4N HCl/dioxane was added (4 mL). After stirring for an additional 41 h the solution was concentrated in vacuo, and the crude product was purified by reverse phase flash chromatography on $C_{18}$ silica gel (6% to 35% IPA/$H_2O$) and dried using lyophilization. ESI-MS m/z 384 (M+Na)+.

Example 133

(R)-2-Hydroxy-3-(4-oxo-pentanoylamino)-3,4-dihydro-2H-benzo[e][1,2]oxaborinine-8-carboxylic acid 2,2-dimethyl-propionyloxymethyl ester

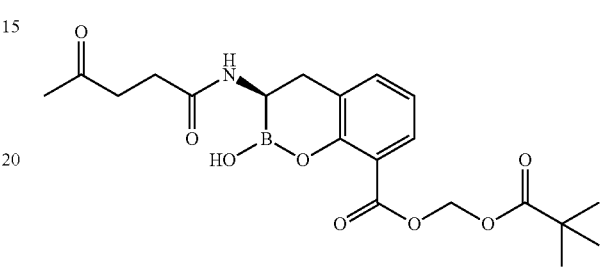

Step 1. Synthesis of 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid.

To a solution of 2-Methoxy-3-[2-(4-oxo-pentanoylamino)-2-(2,9,9-trimethyl-3,5-dioxa-4-bora-tricyclo[6.1.1.02,6]dec-4-yl)-ethyl]-benzoic acid tert-butyl ester (1.57 g, 2.98 mmol, prepared as described in Example 10) in 4N HCl/dioxane (20 mL) was added (+)-pinanediol (510 mg, 3.0 mmol) and the solution stirred for 4 h. An additional 20 mg of (+)-pinanediol was added and the reaction allowed to stir for an additional 1 h. The solution was concentrated in vacuo, the residue dissolved in DCM and concentrated in vacuo. This was repeated once with DCM and once with $Et_2O$ to afford a mixture of diastereomers which was used in the next step without purification.

Step 2. Synthesis of 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid 2,2-dimethyl-propionyloxymethyl ester.

Prepared from 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid (1.20 g, 1.93 mmol) and chloromethyl pivalate following the procedure described in Step 1 of Example 126. The crude material was purified by flash chromatography on silica gel (35%-60% EtOAc/Hexanes). ESI-MS m/z 624 (MH)+.

Step 3. Synthesis of (R)-2-Hydroxy-3-(4-oxo-pentanoylamino)-3,4-dihydro-2H-benzo[e][1,2]oxaborinine-8-carboxylic acid 2,2-dimethyl-propionyloxymethyl ester.

Prepared from 2-Methoxy-3-[2-[3-(2,4,9,9-tetramethyl-3,5-dioxa-tricyclo[6.1.1.02,6]dec-4-yl)-propionylamino]-2-

(2,9,9-trimethyl-3,5-dioxa-4-bora-tricyclo[6.1.1.0 2,6]dec-4-yl)-ethyl]-benzoic acid 2,2-dimethyl-propionyloxymethyl ester following the procedure describe in Step 3 of Example 1. The crude product was purified using by reverse phase flash chromatography on C$_{18}$ silica gel (4% to 30% IPA/H$_2$O) and dried using lyophilization. ESI-MS m/z 420 (MH)$^+$.

Example 134

(R)-2-Hydroxy-3-(4-oxo-pentanoylamino)-3,4-dihydro-2H-benzo[e][1,2]oxaborinine-8-carboxylic acid isobutyl ester

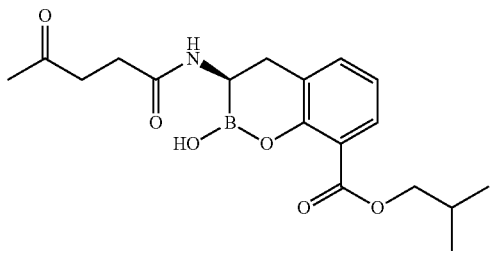 [SMILES: CC(=O)CCC(=O)N[C@H]1Cc2cccc(C(=O)OCC(C)C)c2OB1O]

Prepared from (R)-2-Hydroxy-3-(4-oxo-pentanoylamino)-3,4-dihydro-2H-benzo[e][1,2]oxaborinine-8-carboxylic acid and 2-methyl-1-propanol following the procedure described in Example 132. The crude product was purified by reverse phase flash chromatography on C$_{18}$ silica gel (100% H$_2$O to 25% IPA/H$_2$O) and dried using lyophilization. ESI-MS m/z 384 (M+Na)$^+$.

Example 135

(R)-3-(3-Cyano-propionylamino)-2-hydroxy-3,4-dihydro-2H-benzo[e][1,2]oxaborinine-8-carboxylic acid 5-methyl-2-oxo-[1,3]dioxol-4-ylmethyl ester

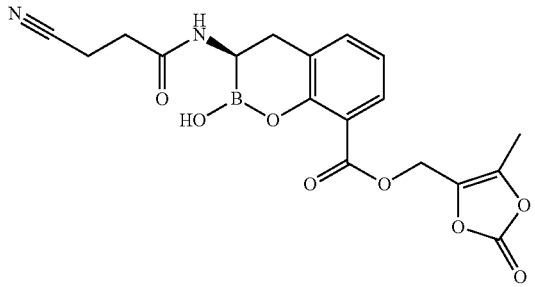 [SMILES: Cc1oc(=O)oc1COC(=O)c1cccc2c1OB(O)[C@@H](NC(=O)CCC#N)C2]

Step 1. Synthesis of 3-[2-(3-Cyano-propionylamino)-2-(2,9,9-trimethyl-3,5-dioxa-4-bora-tricyclo[6.1.1.0 2,6]dec-4-yl)-ethyl]-2-methoxy-benzoic acid 5-methyl-2-oxo-[1,3]dioxol-4-ylmethyl ester.

Prepared from 3-[2-(3-Cyano-propionylamino)-2-(2,9,9-trimethyl-3,5-dioxa-4-bora-tricyclo[6.1.1.0 2,6]dec-4-yl)-ethyl]-2-methoxy-benzoic acid (prepared in Step 1 of Example 125) and 4-bromomethyl-5-methyl-1,3-dioxol-2-one following the procedure described in Step 1 of Example 127. The crude product was purified by flash chromatography on silica gel (10-100% EtOAc/Hexane). ESI-MS m/z 567 (MH)$^+$.

Step 2. Synthesis of (R)-3-(3-Cyano-propionylamino)-2-hydroxy-3,4-dihydro-2H-benzo[e][1,2] oxaborinine-8-carboxylic acid 5-methyl-2-oxo-[1,3] dioxol-4-ylmethyl ester.

Prepared from 3-[2-(3-Cyano-propionylamino)-2-(2,9,9-trimethyl-3,5-dioxa-4-bora-tricyclo[6.1.1.0 2,6]dec-4-yl)-ethyl]-2-methoxy-benzoic acid 5-methyl-2-oxo-[1,3]dioxol-4-ylmethyl ester following the procedure described in Step 3 of Example 1. The crude product was purified by reverse phase preparative HPLC and dried using lyophilization. ESI-MS m/z 401 (MH)$^+$.

Example 136

(R)-3-(3-Cyano-propionylamino)-2-hydroxy-3,4-dihydro-2H-benzo[e][1,2]oxaborinine-8-carboxylic acid 1-acetoxy-ethyl ester

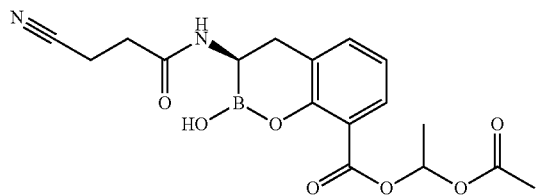 [SMILES: CC(=O)OC(C)OC(=O)c1cccc2c1OB(O)[C@@H](NC(=O)CCC#N)C2]

Step 1. Synthesis of 3-[2-(3-Cyano-propionylamino)-2-(2,9,9-trimethyl-3,5-dioxa-4-bora-tricyclo[6.1.1.0 2,6]dec-4-yl)-ethyl]-2-methoxy-benzoic acid 1-acetoxy-ethyl ester.

Prepared from 3-[2-(3-Cyano-propionylamino)-2-(2,9,9-trimethyl-3,5-dioxa-4-bora-tricyclo[6.1.1.0 2,6]dec-4-yl)-ethyl]-2-methoxy-benzoic acid (prepared in Step 1 of Example 125) and 1-bromoethyl acetate following the procedure described in Step 1 of Example 127. The crude product was purified by flash chromatography on silica gel (10-100% EtOAc/Hexane). ESI-MS m/z 541 (MH)$^+$.

Step 2. Synthesis of (R)-3-(3-Cyano-propionylamino)-2-hydroxy-3,4-dihydro-2H-benzo[e][1,2] oxaborinine-8-carboxylic acid 1-acetoxy-ethyl ester.

Prepared from 3-[2-(3-Cyano-propionylamino)-2-(2,9,9-trimethyl-3,5-dioxa-4-bora-tricyclo[6.1.1.0 2,6]dec-4-yl)-ethyl]-2-methoxy-benzoic acid 1-acetoxy-ethyl ester following the procedure described in Step 3 of Example 1. The crude product was purified by reverse phase preparative HPLC and dried using lyophilization. ESI-MS m/z 375 (MH)$^+$.

Example 137

(R)-2-Hydroxy-3-(4-oxo-pentanoylamino)-3,4-dihydro-2H-benzo[e][1,2]oxaborinine-8-carboxylic acid methyl ester

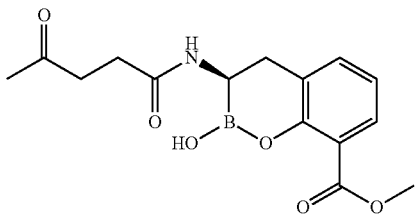 [SMILES: COC(=O)c1cccc2c1OB(O)[C@@H](NC(=O)CCC(C)=O)C2]

Prepared from (R)-2-Hydroxy-3-(4-oxo-pentanoylamino)-3,4-dihydro-2H-benzo[e][1,2]oxaborinine-8-carboxylic acid and methanol following the procedure described in Example 132. The crude product was purified by reverse phase flash chromatography on $C_{18}$ silica gel (1%-12% IPA/$H_2O$) and dried using lyophilization. ESI-MS m/z 320 (MH)$^+$.

Example 138

(R)-2-Hydroxy-3-(4-oxo-pentanoylamino)-3,4-dihydro-2H-benzo[e][1,2]oxaborinine-8-carboxylic acid ethyl ester

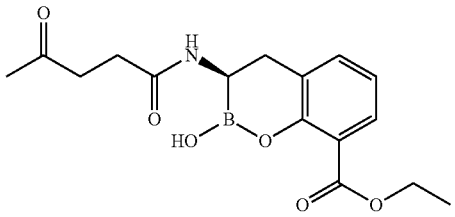 [SMILES: CCOC(=O)c1cccc2c1OB(O)[C@@H](NC(=O)CCC(C)=O)C2]

Prepared from (R)-2-Hydroxy-3-(4-oxo-pentanoylamino)-3,4-dihydro-2H-benzo[e][1,2]oxaborinine-8-carboxylic acid and ethanol following the procedure described in Example 132. The crude product was purified by reverse phase flash chromatography on $C_{18}$ silica gel (1%-12% IPA/$H_2O$) and dried using lyophilization. ESI-MS m/z 334 (MH)$^+$.

Example 139

(R)-2-Hydroxy-3-(4-oxo-pentanoylamino)-3,4-dihydro-2H-benzo[e][1,2]oxaborinine-8-carboxylic acid acetoxymethyl ester

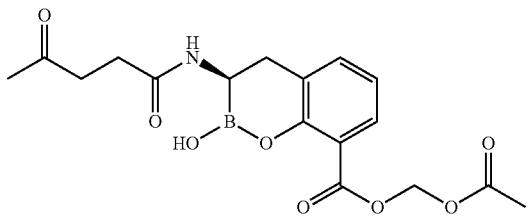

Prepared from 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid and chloromethyl acetate following the procedure described in Steps 1 and 2 of Example 126. The title compound was purified using reverse phase flash chromatography on $C_{18}$ silica gel (3%-20% IPA/$H_2O$) and dried using lyophilization. ESI-MS m/z 378 (MH)$^+$.

Example 140

(R)-2-Hydroxy-3-(4-oxo-pentanoylamino)-3,4-dihydro-2H-benzo[e][1,2]oxaborinine-8-carboxylic acid 2-ethyl-butyryloxymethyl ester

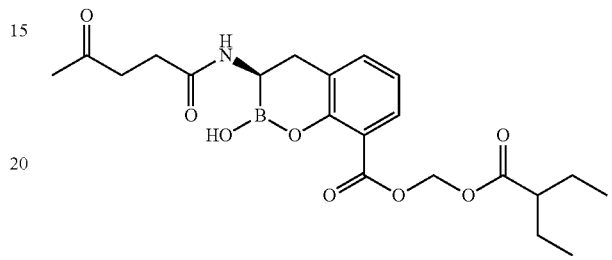

Step 1. Synthesis of 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid 2-ethyl-butyryloxymethyl ester.

Prepared from 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid and chloromethyl 2-ethylbutyrate following the procedure described in Step 1 of Example 126. The crude product was purified using flash chromatography on silica gel (40%-70% EtOAC/Hexane). ESI-MS m/z 752 (MH)$^+$.

Step 2. Synthesis of (R)-2-Hydroxy-3-(4-oxo-pentanoylamino)-3,4-dihydro-2H-benzo[e][1,2]oxaborinine-8-carboxylic acid 2-ethyl-butyryloxymethyl ester.

Prepared from 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid 2-ethyl-butyryloxymethyl ester following the procedure described in Step 3 of Example 1. The title compound was purified using reverse phase flash chromatography on $C_{18}$ silica gel (2%-30% IPA/$H_2O$) and dried using lyophilization. ESI-MS m/z 456 (M+Na)$^+$.

Example 141

(R)-2-Hydroxy-3-(4-oxo-pentanoylamino)-3,4-dihydro-2H-benzo[e][1,2]oxaborinine-8-carboxylic acid 1-ethoxycarbonyloxy-ethyl ester

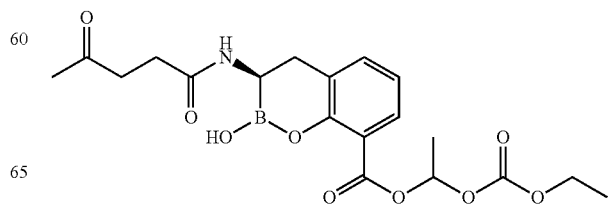

Step 1. Synthesis of 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid 1-ethoxycarbonyloxy-ethyl ester.

Prepared from 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid and 1-chloroethyl ethylcarbonate following the procedure described in Step 1 of Example 126. The crude product was carried forward without purification.

Step 2. Synthesis of (R)-2-Hydroxy-3-(4-oxo-pentanoylamino)-3,4-dihydro-2H-benzo[e][1,2]oxaborinine-8-carboxylic acid 1-ethoxycarbonyloxy-ethyl ester.

Prepared from 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid 1-ethoxycarbonyloxy-ethyl ester following the procedure described in Step 3 of Example 1. The crude product was purified using reverse phase flash chromatography on $C_{18}$ silica gel (2%-25% IPA/$H_2O$) and dried using lyophilization. ESI-MS m/z 444 (M+Na)$^+$.

Example 142

(R)-2-Hydroxy-3-(4-oxo-pentanoylamino)-3,4-dihydro-2H-benzo[e][1,2]oxaborinine-8-carboxylic acid cyclohexyloxycarbonyloxymethyl ester

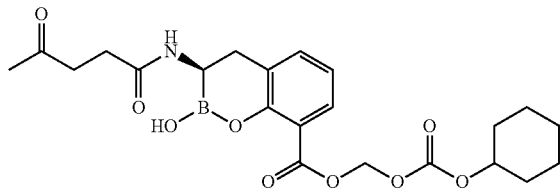 [SMILES: CC(=O)CCC(=O)N[C@H]1Cc2cccc(C(=O)OCOC(=O)OC3CCCCC3)c2OB1O]

Step 1. Synthesis of Chloromethyl cyclohexylcarbonate.

A solution of chloromethyl chloroformate (1.76 mL, 19.8 mmole) and cyclohexanol (2.1 mL, 20 mmol) in DCM (30 mL) at 0° C. was added 4-dimethylaminopyridine (DMAP, 2.54 g, 20.8 mmol). After stirring for 5 min at 0° C. the cooling bath was removed and the mixture stirred at ambient temperature for 23 h. The reaction mass was diluted with DCM and 1M HCl was added. The layers were separated, and the organic layer was washed with brine, dried ($Na_2SO_4$), and concentrated in vacuo. The crude product was purified by flash chromatography on silica gel (3-4% EtOAc/Hexanes).

Step 2. Synthesis of (R)-2-Hydroxy-3-(4-oxo-pentanoylamino)-3,4-dihydro-2H-benzo[e][1,2]oxaborinine-8-carboxylic acid cyclohexyloxycarbonyloxymethyl ester.

To a solution of (R)-2-Hydroxy-3-(4-oxo-pentanoylamino)-3,4-dihydro-2H-benzo[e][1,2]oxaborinine-8-carboxylic acid (prepared as described in Example 10, 20 mg, 0.066 mmol) in DMF (1 mL) was added chloromethyl cyclohexylcarbonate (ca 20 mg), potassium carbonate and sodium iodide. The mixture was stirred at ambient temperature for 18 h then heated to 70° C. and held for 1.25 h. The solution was cooled, combined with a similar reaction mass, diluted with water and extracted with 10% $Et_2O$/Hexane. The aqueous layer was acidified to pH 3-4 with 1N HCl, diluted with a little methanol to afford a less cloudy solution, and then purified using reverse phase flash chromatography on $C_{18}$ silica gel (5%-35% IPA/$H_2O$). ESI-MS m/z 484 (M+Na)$^+$.

Example 143

(R)-2-Hydroxy-3-(4-oxo-pentanoylamino)-3,4-dihydro-2H-benzo[e][1,2]oxaborinine-8-carboxylic acid 2-methoxy-ethyl ester

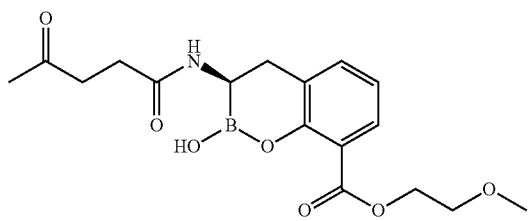

Prepared from (R)-2-Hydroxy-3-(4-oxo-pentanoylamino)-3,4-dihydro-2H-benzo[e][1,2]oxaborinine-8-carboxylic acid and 2-methoxyethanol following the procedure described in Example 132. The crude product was purified by reverse phase flash chromatography on $C_{18}$ silica gel (0-10% IPA/$H_2O$) and dried using lyophilization. ESI-MS m/z 364 (MH)$^+$.

Example 144

(R)-2-Hydroxy-3-(4-oxo-pentanoylamino)-3,4-dihydro-2H-benzo[e][1,2]oxaborinine-8-carboxylic acid tetrahydro-pyran-4-yloxycarbonyloxymethyl ester

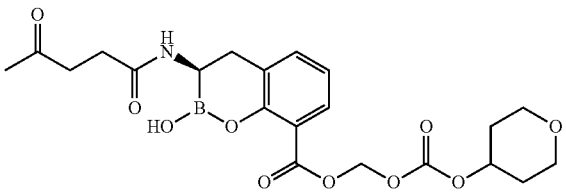 [SMILES: CC(=O)CCC(=O)N[C@H]1Cc2cccc(C(=O)OCOC(=O)OC3CCOCC3)c2OB1O]

Step 1. Synthesis of Carbonic acid chloromethyl ester tetrahydro-pyran-4-yl ester.

Prepared from chloromethyl chloroformate and tetrahydropyran-4-ol following the procedure described in Step 1 of Example 142. The crude product was purified by flash chromatography on silica gel (15%-40% EtOAc/Hexane).

Step 2. Synthesis of 2-Methoxy-3-[2-[3-(2,4,9,9-tetramethyl-3,5-dioxa-tricyclo[6.1.1.0 2,6]dec-4-yl)-propionylamino]-2-(2,9,9-trimethyl-3,5-dioxa-4-bora-tricyclo[6.1.1.0 2,6]dec-4-yl)-ethyl]-benzoic acid tetrahydro-pyran-4-yloxycarbonyloxymethyl ester.

Prepared from 2-Methoxy-3-[2-[3-(2,4,9,9-tetramethyl-3,5-dioxa-tricyclo[6.1.1.0 2,6]dec-4-yl)-propionylamino]-2-(2,9,9-trimethyl-3,5-dioxa-4-bora-tricyclo[6.1.1.0 2,6]dec-4-yl)-ethyl]-benzoic acid and carbonic acid chloromethyl ester tetrahydro-pyran-4-yl ester following the procedure described in Step 1 of Example 126. The crude product was purified by flash chromatography on silica gel (50%-90% EtOAc/Hexane). ESI-MS m/z 782 (MH)+.

Step 3. Synthesis of (R)-2-Hydroxy-3-(4-oxo-pentanoylamino)-3,4-dihydro-2H-benzo[e][1,2]oxaborinine-8-carboxylic acid tetrahydro-pyran-4-yloxycarbonyloxymethyl ester.

Prepared from 2-Methoxy-3-[2-[3-(2,4,9,9-tetramethyl-3,5-dioxa-tricyclo[6.1.1.0 2,6]dec-4-yl)-propionylamino]-2-(2,9,9-trimethyl-3,5-dioxa-4-bora-tricyclo[6.1.1.0 2,6]dec-4-yl)-ethyl]-benzoic acid tetrahydro-pyran-4-yloxycarbonyloxymethyl ester following the procedure described in Step 3 of Example 1. The crude product was purified using reverse phase flash chromatography on $C_{18}$ silica gel (5%-18% IPA/$H_2O$) and dried using lyophilization. ESI-MS m/z 486 (M+Na)+.

Example 145

(R)-2-Hydroxy-3-(4-oxo-pentanoylamino)-3,4-dihydro-2H-benzo[e][1,2]oxaborinine-8-carboxylic acid butoxycarbonyloxymethyl ester

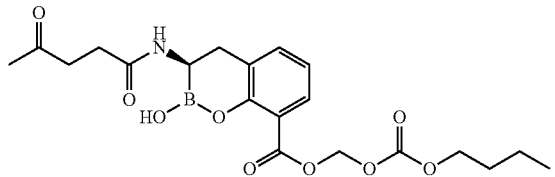 [SMILES: CCCCOC(=O)OCOC(=O)c1cccc2c1OB(O)[C@@H](NC(=O)CCC(C)=O)C2]

Step 1. Synthesis of Carbonic acid butyl ester chloromethyl ester.

Prepared from chloromethyl methylformate and n-butanol following the procedure described in Step 1 of Example 142. The crude product was purified by flash chromatography using silica gel (3-4% EtOAc/Hexane).

Step 2. Synthesis of 2-Methoxy-3-[2-[3-(2,4,9,9-tetramethyl-3,5-dioxa-tricyclo[6.1.1.0 2,6]dec-4-yl)-propionylamino]-2-(2,9,9-trimethyl-3,5-dioxa-4-bora-tricyclo[6.1.1.0 2,6]dec-4-yl)-ethyl]-benzoic acid butoxycarbonyloxymethyl ester.

Prepared from 2-Methoxy-3-[2-[3-(2,4,9,9-tetramethyl-3,5-dioxa-tricyclo[6.1.1.0 2,6]dec-4-yl)-propionylamino]-2-(2,9,9-trimethyl-3,5-dioxa-4-bora-tricyclo[6.1.1.0 2,6]dec-4-yl)-ethyl]-benzoic acid and carbonic acid butyl ester chloromethyl ester following the procedure described in Step 1 of Example 126. The crude product was purified by flash chromatography on silica gel (30%-50% EtOAc/Hexane). ESI-MS m/z 754 (MH)+.

Step 3. Synthesis of (R)-2-Hydroxy-3-(4-oxo-pentanoylamino)-3,4-dihydro-2H-benzo[e][1,2]oxaborinine-8-carboxylic acid butoxycarbonyloxymethyl ester.

Prepared from 2-Methoxy-3-[2-[3-(2,4,9,9-tetramethyl-3,5-dioxa-tricyclo[6.1.1.0 2,6]dec-4-yl)-propionylamino]-2-(2,9,9-trimethyl-3,5-dioxa-4-bora-tricyclo[6.1.1.0 2,6]dec-4-yl)-ethyl]-benzoic acid butoxycarbonyloxymethyl ester following the procedure described in Step 3 of Example 1. The title compound was purified using reverse phase flash chromatography on $C_{18}$ silica gel (8%-35% IPA/$H_2O$) and dried using lyophilization. ESI-MS m/z 458 (M+Na)+.

Example 146

(R)-2-Hydroxy-3-(4-oxo-pentanoylamino)-3,4-dihydro-2H-benzo[e][1,2]oxaborinine-8-carboxylic acid 1-isobutyryloxy-ethyl ester

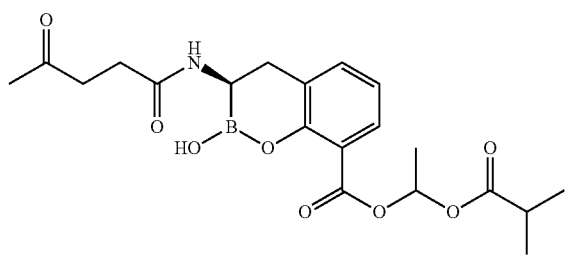 [SMILES: CC(=O)CCC(=O)N[C@H]1Cc2cccc(C(=O)OC(C)OC(=O)C(C)C)c2OB1O]

Step 1. Synthesis of Isobutyric acid 1-chloro-ethyl ester.

To a slurry of isobutyryl chloride (3.55 mL, 33.3 mmol) and $ZnCl_2$ (40 mg) at −10° C. was added acetaldehyde over 3 min. After stirring for 1 h at −10° C. the cooling bath was removed and the mixture stirred for 20 h. The solution was concentrated in vacuo and the crude product purified using flash chromatography on silica gel (2-3% EtOAc/Hexane).

Step 2. Synthesis of 2-Methoxy-3-[2-[3-(2,4,9,9-tetramethyl-3,5-dioxa-tricyclo[6.1.1.0 2,6]dec-4-yl)-propionylamino]-2-(2,9,9-trimethyl-3,5-dioxa-4-bora-tricyclo[6.1.1.0 2,6]dec-4-yl)-ethyl]-benzoic acid 1-isobutyryloxy-ethyl ester.

Prepared from 2-Methoxy-3-[2-[3-(2,4,9,9-tetramethyl-3,5-dioxa-tricyclo[6.1.1.0 2,6]dec-4-yl)-propionylamino]-2-(2,9,9-trimethyl-3,5-dioxa-4-bora-tricyclo[6.1.1.0 2,6]dec-4-yl)-ethyl]-benzoic acid and isobutyric acid 1-chloro-ethyl ester following the procedure described in Step 1 of Example 126. The crude product was purified using flash chromatography on silica gel (30-90% EtOAc/Hexane). ESI-MS m/z 738 (MH)+.

Step 3. Synthesis of (R)-2-Hydroxy-3-(4-oxo-pentanoylamino)-3,4-dihydro-2H-benzo[e][1,2]oxaborinine-8-carboxylic acid 1-isobutyryloxy-ethyl ester.

Prepared from 2-Methoxy-3-[2-[3-(2,4,9,9-tetramethyl-3,5-dioxa-tricyclo[6.1.1.0 2,6]dec-4-yl)-propionylamino]-2-(2,9,9-trimethyl-3,5-dioxa-4-bora-tricyclo[6.1.1.0 2,6]dec- 4-yl)-ethyl]-benzoic acid 1-isobutyryloxy-ethyl ester following the procedure described in Step 3 of Example 1. The title compound was purified using reverse phase flash chromatography on $C_{18}$ silica gel (7%-30% IPA/$H_2O$) and dried using lyophilization. ESI-MS m/z 442 (M+Na)+.

Example 147

(R)-2-Hydroxy-3-(4-oxo-pentanoylamino)-3,4-dihydro-2H-benzo[e][1,2]oxaborinine-8-carboxylic acid benzoyloxymethyl ester

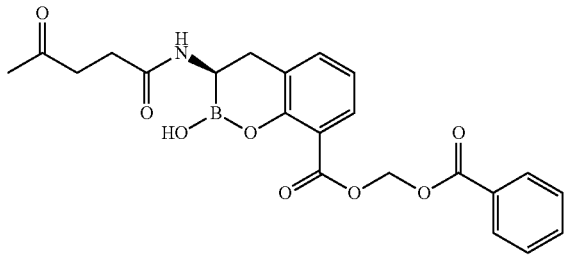 [SMILES: CC(=O)CCC(=O)N[C@H]1Cc2cccc(C(=O)OCOC(=O)c3ccccc3)c2OB1O]

Step 1. Synthesis of 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid benzoyloxymethyl ester.

Prepared from 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid and chloromethylbenzoate following the procedure described in Step 1 of Example 126. The crude product was purified using flash chromatography on silica gel (40-60% EtOAc/Hexane). ESI-MS m/z 758 (MH)+.

Step 2. Synthesis of (R)-2-Hydroxy-3-(4-oxo-pentanoylamino)-3,4-dihydro-2H-benzo[e][1,2]oxaborinine-8-carboxylic acid benzoyloxymethyl ester.

Prepared from 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid benzoyloxymethyl ester following the procedure described in Step 3 of Example 1. The crude product was purified using reverse phase flash chromatography on $C_{18}$ silica gel (10-25% IPA/$H_2O$) and dried using lyophilization. ESI-MS m/z 462 (M+Na)+.

Example 148

(R)-2-Hydroxy-3-(4-oxo-pentanoylamino)-3,4-dihydro-2H-benzo[e][1,2]oxaborinine-8-carboxylic acid cyclohexylmethoxycarbonyloxymethyl ester

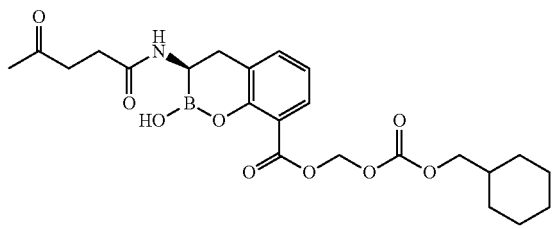 [SMILES: CC(=O)CCC(=O)N[C@H]1Cc2cccc(C(=O)OCOC(=O)OCC3CCCCC3)c2OB1O]

Step 1. Synthesis of Carbonic acid chloromethyl ester cyclohexylmethyl ester.

Prepared from chloromehyl chloroformate and cyclohexylmethanol following the procedure described in Step 1 of Example 142. The crude product was purified by flash chromatography (2-3% EtOAc/Hexane).

Step 2. Synthesis of 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid cyclohexylmethoxycarbonyloxymethyl ester.

Prepared from 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid and carbonic acid chloromethyl ester cyclohexylmethyl ester following the procedure described in Step 1 of Example 126. The crude product was purified using flash chromatography on silica gel (30-85% EtOAc/Hexane). ESI-MS m/z 794 (MH)+.

Step 3. Synthesis of (R)-2-Hydroxy-3-(4-oxo-pentanoylamino)-3,4-dihydro-2H-benzo[e][1,2]oxaborinine-8-carboxylic acid cyclohexylmethoxycarbonyloxymethyl ester.

Prepared from 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid cyclohexylmethoxycarbonyloxymethyl ester following the procedure described in Step 3 of Example 1. The crude product was purified using reverse phase flash chromatography on $C_{18}$ silica gel (20-45% IPA/$H_2O$) and dried using lyophilization. ESI-MS m/z 498 (M+Na)+.

Example 149

(R)-2-Hydroxy-3-(4-oxo-pentanoylamino)-3,4-dihydro-2H-benzo[e][1,2]oxaborinine-8-carboxylic acid cyclohexanecarbonyloxymethyl ester

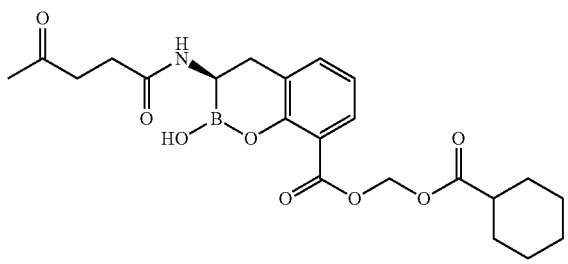 [SMILES: CC(=O)CCC(=O)N[C@H]1Cc2cccc(C(=O)OCOC(=O)C3CCCCC3)c2OB1O]

Step 1. Synthesis of Cyclohexanecarboxylic acid chloromethyl ester.

To a slurry of paraformaldehyde (470 mg, 15.7 mmol) and $ZnCl_2$ (ca. 5 mg) at 0° C. was added cyclohexane carbonyl chloride (2.0 mL, 13.6 mmol). The mixture was heated to 55° C. and stirred for 20 h. After cooling the crude product was purified using flash chromatography (2-3% EtOAc/Hexane).

Step 2. Synthesis of 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid cyclohexanecarbonyloxymethyl ester.

Prepared from 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid and cyclohexanecarboxylic acid chloromethyl ester following the procedure described in Step 1 of Example 126. The crude product was purified using flash chromatography on silica gel (25-65% EtOAc/Hexane). ESI-MS m/z 764 (MH)$^+$.

Step 3. Synthesis of (R)-2-Hydroxy-3-(4-oxo-pentanoylamino)-3,4-dihydro-2H-benzo[e][1,2]oxaborinine-8-carboxylic acid cyclohexanecarbonyloxymethyl ester.

Prepared from 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid cyclohexanecarbonyloxymethyl ester following the procedure described in Step 3 of Example 1. The crude product was purified using reverse phase flash chromatography on $C_{18}$ silica gel (10-40% IPA/$H_2O$) and dried using lyophilization. ESI-MS m/z 468 (M+Na)$^+$.

Example 150

(R)-2-Hydroxy-3-(4-oxo-pentanoylamino)-3,4-dihydro-2H-benzo[e][1,2]oxaborinine-8-carboxylic acid 4-fluoro-benzoyloxymethyl ester

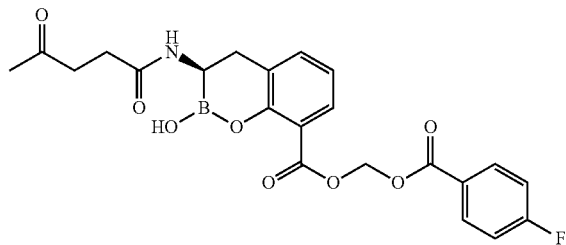 [SMILES: CC(=O)CCC(=O)N[C@H]1Cc2cccc(C(=O)OCOC(=O)c3ccc(F)cc3)c2OB1O]

Step 1. Synthesis of 4-Fluoro-benzoic acid chloromethyl ester.

Prepared from paraformaldehyde and 4-fluorobenzoyl chloride following the procedure described in Step 1 of Example 149.

Step 2. Synthesis of 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid 4-fluoro-benzoyloxymethyl ester.

Prepared from 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid and 4-fluoro-benzoic acid chloromethyl ester following the procedure described in Step 1 of Example 126. The crude product was purified using flash chromatography on silica gel (30-80% EtOAc/Hexane). ESI-MS m/z 776 (MH)$^+$.

Step 3. Synthesis of (R)-2-Hydroxy-3-(4-oxo-pentanoylamino)-3,4-dihydro-2H-benzo[e][1,2]oxaborinine-8-carboxylic acid 4-fluoro-benzoyloxymethyl ester.

Prepared from 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid 4-fluoro-benzoyloxymethyl ester following the procedure described in Step 3 of Example 1. The crude product was purified using reverse phase flash chromatography on $C_{18}$ silica gel (15-35% IPA/$H_2O$) and dried using lyophilization. ESI-MS m/z 480 (M+Na)$^+$.

Example 151

(R)-2-Hydroxy-3-(4-oxo-pentanoylamino)-3,4-dihydro-2H-benzo[e][1,2]oxaborinine-8-carboxylic acid 2-cyclohexyl-acetoxymethyl ester

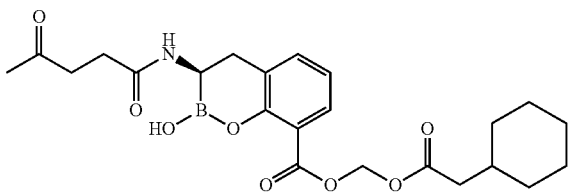 [SMILES: CC(=O)CCC(=O)N[C@H]1Cc2cccc(C(=O)OCOC(=O)CC3(C)CCCCC3)c2OB1O]

Step 1. Synthesis of Cyclohexyl-acetic acid chloromethyl ester.

Prepared from cyclohexyl acetyl chloride and paraformaldehyde following the procedure described in Step 1 of Example 149.

Step 2. Synthesis of 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid 2-cyclohexyl-acetoxymethyl ester.

Prepared from 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid and cyclohexyl-acetic acid chloromethyl ester following the procedure described in Step 1 of Example 126. The crude product was purified using flash chromatography on silica gel (30-80% EtOAc/Hexane). ESI-MS m/z 778 (MH)$^+$.

Step 3. Synthesis of (R)-2-Hydroxy-3-(4-oxo-pentanoylamino)-3,4-dihydro-2H-benzo[e][1,2]oxaborinine-8-carboxylic acid 2-cyclohexyl-acetoxymethyl ester.

Prepared from 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid 2-cyclohexyl-acetoxymethyl ester following the procedure described in Step 3 of Example 1. The crude product was purified using reverse phase flash chromatography on $C_{18}$ silica gel (15-40% IPA/$H_2O$) and dried using lyophilization. ESI-MS m/z 482 (M+Na)$^+$.

Example 152

(R)-Piperidine-1-carboxylic acid 2-hydroxy-3-(4-oxo-pentanoylamino)-3,4-dihydro-2H-benzo[e][1,2]oxaborinine-8-carbonyloxymethyl ester

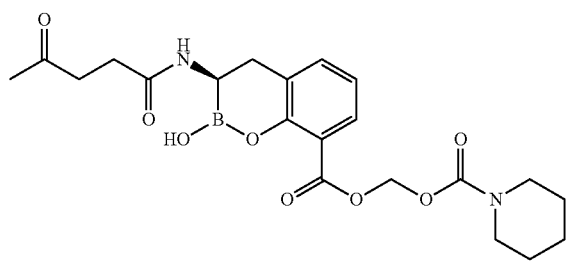 [SMILES: CC(=O)CCC(=O)N[C@H]1Cc2cccc(C(=O)OCOC(=O)N3CCCCC3)c2OB1O]

Step 1. Synthesis of Piperidine-1-carboxylic acid chloromethyl ester.

Prepared from chloromethyl chloroformate and piperidine following the procedure described in Step 1 of Example 149. The crude product was purified by flash chromatography (5-15% EtOAc/Hexane).

Step 2. Synthesis of Piperidine-1-carboxylic acid 2-methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6] dec-4-yl)-ethyl]-benzoyloxymethyl ester.

Prepared from 2-Methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoic acid and piperidine-1-carboxylic acid chloromethyl ester following the procedure described in Step 1 of Example 126. The crude product was purified using flash chromatography on silica gel (30-85% EtOAc/Hexane). ESI-MS m/z 765 (MH)$^+$.

Step 3. Synthesis of (R)-Piperidine-1-carboxylic acid 2-hydroxy-3-(4-oxo-pentanoylamino)-3,4-dihydro-2H-benzo[e][1,2]oxaborinine-8-carbonyloxymethyl ester.

Prepared from piperidine-1-carboxylic acid 2-methoxy-3-[2-[3-(2,4,9,9-tetramethyl-3,5-dioxa-tricyclo[6.1.1.02,6]dec-4-yl)-propionylamino]-2-(2,9,9-trimethyl-3,5-dioxa-4-bora-tricyclo[6.1.1.02,6]dec-4-yl)-ethyl]-benzoyloxymethyl ester following the procedure described in Step 3 of Example 1. The crude product was purified using reverse phase flash chromatography on $C_{18}$ silica gel (20-45% IPA/$H_2O$) and dried using lyophilization. ESI-MS m/z 469 (M+Na)$^+$.

Example 153

(R)-3-(3-Cyano-propionylamino)-2-hydroxy-3,4-dihydro-2H-benzo[e][1,2]oxaborinine-8-carboxylic acid benzoyloxymethyl ester

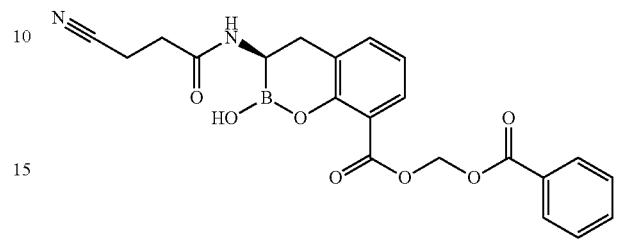

Step 1. Synthesis of 3-[2-(3-Cyano-propionylamino)-2-(2,9,9-trimethyl-3,5-dioxa-4-bora-tricyclo[6.1.1.02,6]dec-4-yl)-ethyl]-2-methoxy-benzoic acid benzoyloxymethyl ester.

Prepared from 3-[2-(3-Cyano-propionylamino)-2-(2,9,9-trimethyl-3,5-dioxa-4-bora-tricyclo[6.1.1.02,6]dec-4-yl)-ethyl]-2-methoxy-benzoic acid (prepared in Step 1 of Example 125) and chloromethyl benzoate following the procedure described in Step 1 of Example 126. The crude product was purified by flash chromatography on silica gel (5-100% EtOAc/Hexane). ESI-MS m/z 589 (MH)$^+$.

Step 2. Synthesis of (R)-3-(3-Cyano-propionylamino)-2-hydroxy-3,4-dihydro-2H-benzo[e][1,2]oxaborinine-8-carboxylic acid benzoyloxymethyl ester.

Prepared from 3-[2-(3-Cyano-propionylamino)-2-(2,9,9-trimethyl-3,5-dioxa-4-bora-tricyclo[6.1.1.02,6]dec-4-yl)-ethyl]-2-methoxy-benzoic acid benzoyloxymethyl ester following the procedure described in Step 3 of Example 1. The crude product was purified by reverse phase preparative HPLC and dried using lyophilization. ESI-MS m/z 423 (MH)$^+$.

Example 154

(R)-3-(3-Cyano-propionylamino)-2-hydroxy-3,4-dihydro-2H-benzo[e][1,2]oxaborinine-8-carboxylic acid 4-fluoro-benzoyloxymethyl ester

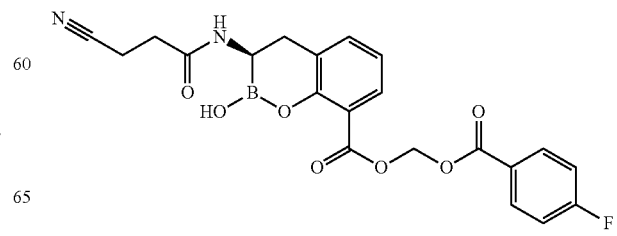

Step 1. Synthesis of 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid 4-fluoro-benzoyloxymethyl ester.

Prepared from 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid (prepared in Step 1 of Example 125) and chloromethyl 4-fluorobenzoate following the procedure described in Step 1 of Example 126. The crude product was purified by flash chromatography on silica gel (5-100% EtOAc/Hexane). ESI-MS m/z 607 (MH)⁺.

Step 2. Synthesis of (R)-3-(3-Cyano-propionylamino)-2-hydroxy-3,4-dihydro-2H-benzo[e][1,2]oxaborinine-8-carboxylic acid 4-fluoro-benzoyloxymethyl ester.

Prepared from 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid 4-fluoro-benzoyloxymethyl ester following the procedure described in Step 3 of Example 1. The crude product was purified by reverse phase preparative HPLC and dried using lyophilization. ESI-MS m/z 441 (MH)⁺.

Example 155

(R)-3-(3-Cyano-propionylamino)-2-hydroxy-3,4-dihydro-2H-benzo[e][1,2]oxaborinine-8-carboxylic acid cyclohexanecarbonyloxymethyl ester

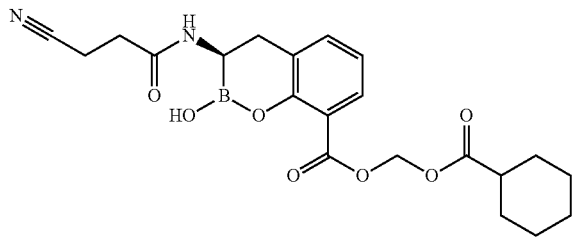 [SMILES: N#CCCC(=O)N[C@H]1Cc2cccc(C(=O)OCOC(=O)C3CCCCC3)c2OB1O]

Step 1. Synthesis of 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid cyclohexanecarbonyloxymethyl ester.

Prepared from 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid (prepared in Step 1 of Example 125) and cyclohexanecarboxylic acid chloromethyl ester following the procedure described in Step 1 of Example 126. The crude product was purified by flash chromatography on silica gel (5-100% EtOAc/Hexane). ESI-MS m/z 595 (MH)⁺.

Step 2. Synthesis of (R)-3-(3-Cyano-propionylamino)-2-hydroxy-3,4-dihydro-2H-benzo[e][1,2]oxaborinine-8-carboxylic acid cyclohexanecarbonyloxymethyl ester.

Prepared from 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid cyclohexanecarbonyloxymethyl ester following the procedure described in Step 3 of Example 1. The crude product was purified by reverse phase preparative HPLC and dried using lyophilization. ESI-MS m/z 429 (MH)⁺.

Example 156

(R)-3-(3-Cyano-propionylamino)-2-hydroxy-3,4-dihydro-2H-benzo[e][1,2]oxaborinine-8-carboxylic acid butoxycarbonyloxymethyl ester

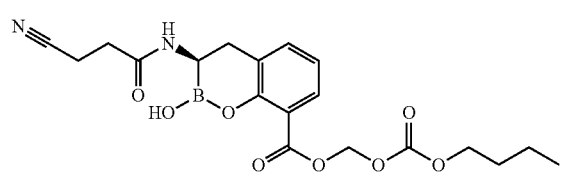 [SMILES: CCCCOC(=O)OCOC(=O)c1cccc2c1OB(O)[C@@H](NC(=O)CCC#N)C2]

Step 1. Synthesis of 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid butoxycarbonyloxymethyl ester.

Prepared from 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid (prepared in Step 1 of Example 125) and carbonic acid butyl ester chloromethyl ester following the procedure described in Step 1 of Example 126. The crude product was purified by flash chromatography on silica gel (5-100% EtOAc/Hexane). ESI-MS m/z 585 (MH)⁺.

Step 2. Synthesis of (R)-3-(3-Cyano-propionylamino)-2-hydroxy-3,4-dihydro-2H-benzo[e][1,2]oxaborinine-8-carboxylic acid butoxycarbonyloxymethyl ester.

Prepared from 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid butoxycarbonyloxymethyl ester following the procedure described in Step 3 of Example 1. The crude product was purified by reverse phase preparative HPLC and dried using lyophilization. ESI-MS m/z 419 (MH)⁺.

Example 157

(R)-3-(3-Cyano-propionylamino)-2-hydroxy-3,4-dihydro-2H-benzo[e][1,2]oxaborinine-8-carboxylic acid 1-isobutyryloxy-ethyl ester

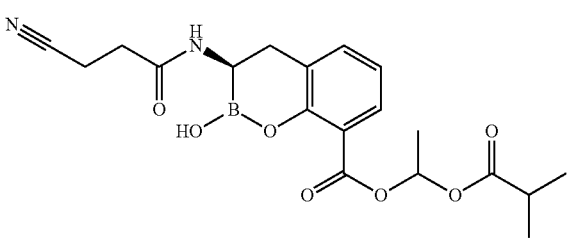 [SMILES: CC(OC(=O)c1cccc2c1OB(O)[C@@H](NC(=O)CCC#N)C2)OC(=O)C(C)C]

Step 1. Synthesis of 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid 1-isobutyryloxy-ethyl ester.

Prepared from 3-[2-(3-Cyano-propionylamino)-2-(2,9,9-trimethyl-3,5-dioxa-4-bora-tricyclo[6.1.1.0²,⁶]dec-4-yl)- ethyl]-2-methoxy-benzoic acid (prepared in Step 1 of Example 125) and isobutyric acid 1-chloro-ethyl ester following the procedure described in Step 1 of Example 126. The crude product was purified by flash chromatography on silica gel (5-100% EtOAc/Hexane). ESI-MS m/z 569 (MH)⁺.

Step 2. Synthesis of (R)-3-(3-Cyano-propionylamino)-2-hydroxy-3,4-dihydro-2H-benzo[e][1,2]oxaborinine-8-carboxylic acid 1-isobutyryloxy-ethyl ester.

Prepared from 3-[2-(3-Cyano-propionylamino)-2-(2,9,9-trimethyl-3,5-dioxa-4-bora-tricyclo[6.1.1.0²,⁶]dec-4-yl)-ethyl]-2-methoxy-benzoic acid 1-isobutyryloxy-ethyl ester following the procedure described in Step 3 of Example 1. The crude product was purified by reverse phase preparative HPLC and dried using lyophilization. ESI-MS m/z 403 (MH)⁺.

Example 158

(R)-2-Hydroxy-3-(3-methanesulfonylamino-propionylamino)-3,4-dihydro-2H-benzo[e][1,2]oxaborinine-8-carboxylic acid 2,2-dimethyl-propionyloxymethyl ester

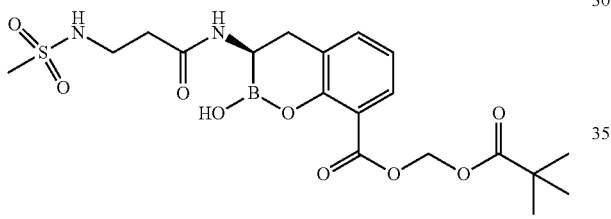

Step 1. Synthesis of 3-[2-(3-Methanesulfonylamino-propionylamino)-2-(2,9,9-trimethyl-3,5-dioxa-4-bora-tricyclo[6.1.1.0²,⁶]dec-4-yl)-ethyl]-2-methoxy-benzoic acid 2,2-dimethyl-propionyloxymethyl ester.

Prepared from 3-[2-(3-Methanesulfonylamino-propionylamino)-2-(2,9,9-trimethyl-3,5-dioxa-4-bora-tricyclo[6.1.1.0²,⁶]dec-4-yl)-ethyl]-2-methoxy-benzoic acid (prepared following the procedure in Step 1 of Example 125) and chloromethyl pivalate following the procedure described in Step 1 of Example 126. The crude product was purified by flash chromatography on silica gel (10-100% EtOAc/Hexane). ESI-MS m/z 637 (MH)⁺.

Step 2. Synthesis of (R)-2-Hydroxy-3-(3-methanesulfonylamino-propionylamino)-3,4-dihydro-2H-benzo[e][1,2]oxaborinine-8-carboxylic acid 2,2-dimethyl-propionyloxymethyl ester.

Prepared from 3-[2-(3-Methanesulfonylamino-propionylamino)-2-(2,9,9-trimethyl-3,5-dioxa-4-bora-tricyclo[6.1.1.0²,⁶]dec-4-yl)-ethyl]-2-methoxy-benzoic acid 2,2-dimethyl-propionyloxymethyl ester following the procedure described in Step 3 of Example 1. The crude product was purified by reverse phase preparative HPLC and dried using lyophilization. ESI-MS m/z 471 (MH)⁺.

Example 159

(R)-2-Hydroxy-3-(3-methanesulfonylamino-propionylamino)-3,4-dihydro-2H-benzo[e][1,2]oxaborinine-8-carboxylic acid butyl ester

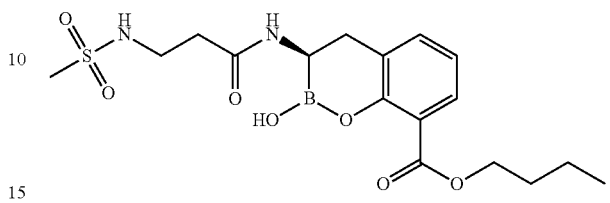

Step 1. Synthesis of 3-[2-(3-Methanesulfonylamino-propionylamino)-2-(2,9,9-trimethyl-3,5-dioxa-4-bora-tricyclo[6.1.1.0²,⁶]dec-4-yl)-ethyl]-2-methoxy-benzoic acid butyl ester.

Prepared from 3-[2-(3-Methanesulfonylamino-propionylamino)-2-(2,9,9-trimethyl-3,5-dioxa-4-bora-tricyclo[6.1.1.0²,⁶]dec-4-yl)-ethyl]-2-methoxy-benzoic acid (prepared following the procedure in Step 1 of Example 125) and 1-iodobutane following the procedure described in Step 1 of Example 126. The crude product was purified by flash chromatography on silica gel (10-100% EtOAc/Hexane). ESI-MS m/z 579 (MH)⁺.

Step 2. Synthesis of (R)-2-Hydroxy-3-(3-methanesulfonylamino-propionylamino)-3,4-dihydro-2H-benzo[e][1,2]oxaborinine-8-carboxylic acid butyl ester.

Prepared from 3-[2-(3-Methanesulfonylamino-propionylamino)-2-(2,9,9-trimethyl-3,5-dioxa-4-bora-tricyclo[6.1.1.0²,⁶]dec-4-yl)-ethyl]-2-methoxy-benzoic acid butyl ester following the procedure described in Step 3 of Example 1. The crude product was purified by reverse phase preparative HPLC and dried using lyophilization. ESI-MS m/z 413 (MH)⁺.

Example 160: (R)-3-(3-Carbamoyl-propionylamino)-2-hydroxy-3,4-dihydro-2H-benzo[e][1,2]oxaborinine-8-carboxylic acid butyl ester

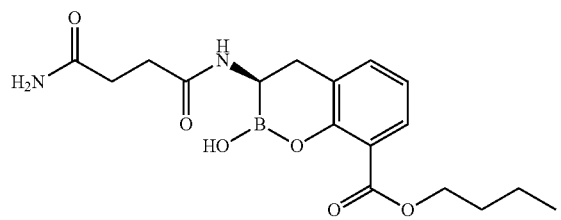 [SMILES: CCCCOC(=O)c1cccc2c1OB(O)[C@@H](NC(=O)CCC(N)=O)C2]

Step 1. Synthesis of 3-[2-(3-Carbamoyl-propionylamino)-2-(2,9,9-trimethyl-3,5-dioxa-4-bora-tricyclo[6.1.1.0²,⁶]dec-4-yl)-ethyl]-2-methoxy-benzoic acid butyl ester.

Prepared from 3-[2-(3-Carbamoyl-propionylamino)-2-(2,9,9-trimethyl-3,5-dioxa-4-bora-tricyclo[6.1.1.0²,⁶]dec-4- yl)-ethyl]-2-methoxy-benzoic acid (prepared following the procedure in Step 1 of Example 125) and 1-iodobutane following the procedure described in Step 1 of Example 126. The crude product was purified by flash chromatography on silica gel (0-10% $CH_3OH/CH_2Cl_2$). ESI-MS m/z 529 $(MH)^+$.

Step 2. Synthesis of (R)-3-(3-Carbamoyl-propionylamino)-2-hydroxy-3,4-dihydro-2H-benzo[e][1,2]oxaborinine-8-carboxylic acid butyl ester.

Prepared from 3-[2-(3-Carbamoyl-propionylamino)-2-(2,9,9-trimethyl-3,5-dioxa-4-bora-tricyclo[6.1.1.0²,⁶]dec-4-yl)-ethyl]-2-methoxy-benzoic acid butyl ester following the procedure described in Step 3 of Example 1. The crude product was purified by reverse phase preparative HPLC and dried using lyophilization. ESI-MS m/z 363 $(MH)^+$.

Example 161

(R)-3-(3-Carbamoyl-propionylamino)-2-hydroxy-3,4-dihydro-2H-benzo[e][1,2]oxaborinine-8-carboxylic acid 2,2-dimethyl-propionyloxymethyl ester

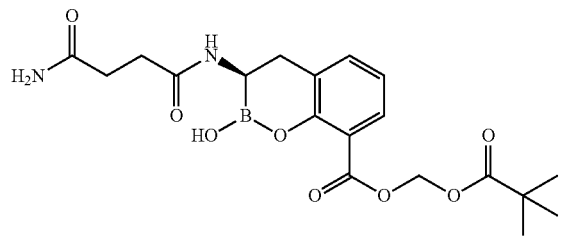 [SMILES: CC(C)(C)C(=O)OCOC(=O)c1cccc2c1OB(O)[C@@H](NC(=O)CCC(N)=O)C2]

Step 1. Synthesis of 3-[2-(3-Carbamoyl-propionylamino)-2-(2,9,9-trimethyl-3,5-dioxa-4-bora-tricyclo[6.1.1.0²,⁶]dec-4-yl)-ethyl]-2-methoxy-benzoic acid 2,2-dimethyl-propionyloxymethyl ester.

Prepared from 3-[2-(3-Carbamoyl-propionylamino)-2-(2,9,9-trimethyl-3,5-dioxa-4-bora-tricyclo[6.1.1.0²,⁶]dec-4-yl)-ethyl]-2-methoxy-benzoic acid (prepared following the procedure in Step 1 of Example 125) and chloromethyl pivalate following the procedure described in Step 1 of Example 126. The crude product was purified by flash chromatography on silica gel (0-10% $CH_3OH/CH_2Cl_2$). ESI-MS m/z 587 $(MH)^+$.

Step 2. Synthesis of (R)-3-(3-Carbamoyl-propionylamino)-2-hydroxy-3,4-dihydro-2H-benzo[e][1,2]oxaborinine-8-carboxylic acid 2,2-dimethyl-propionyloxymethyl ester.

Prepared from 3-[2-(3-Carbamoyl-propionylamino)-2-(2,9,9-trimethyl-3,5-dioxa-4-bora-tricyclo[6.1.1.0²,⁶]dec-4-yl)-ethyl]-2-methoxy-benzoic acid 2,2-dimethyl-propionyloxymethyl ester following the procedure described in Step 3 of Example 1. The crude product was purified by reverse phase preparative HPLC and dried using lyophilization. ESI-MS m/z 421 $(MH)^+$.

Example 162

(R)-2-Hydroxy-3-(3-pyrazol-1-yl-propionylamino)-3,4-dihydro-2H-benzo[e][1,2]oxaborinine-8-carboxylic acid butyl ester

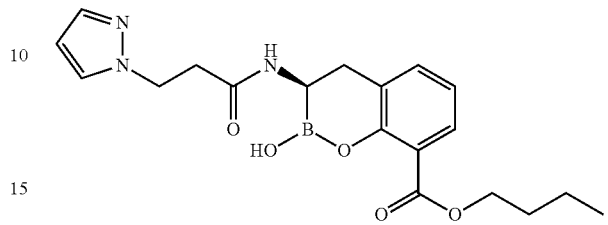

Prepared from (R)-2-Hydroxy-3-(3-pyrazol-1-yl-propionylamino)-3,4-dihydro-2H-benzo[e][1,2]oxaborinine-8-carboxylic acid and n-butanol following the procedure described in Example 132. The crude product was purified by reverse phase flash chromatography on $C_{18}$ silica gel (5-50% $IPA/H_2O$) and dried using lyophilization. ESI-MS m/z 386 $(MH)^+$.

Example 163

(R)-2-Hydroxy-3-(3-imidazol-1-yl-propionylamino)-3,4-dihydro-2H-benzo[e][1,2]oxaborinine-8-carboxylic acid butyl ester

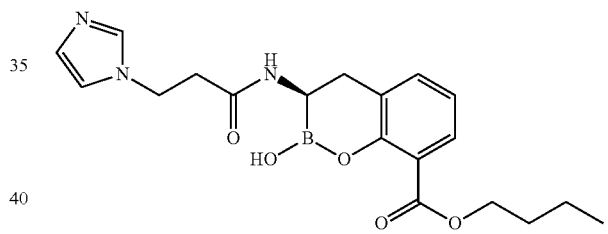

Prepared from (R)-2-Hydroxy-3-(3-imidazol-1-yl-propionylamino)-3,4-dihydro-2H-benzo[e][1,2]oxaborinine-8-carboxylic acid and n-butanol following the procedure described in Example 132. The crude product was purified by reverse phase flash chromatography on $C_{18}$ silica gel (4-25% $IPA/H_2O$) and dried using lyophilization. ESI-MS m/z 386 $(MH)^+$.

Example 164

(R)-2-Hydroxy-3-(3-imidazol-1-yl-propionylamino)-3,4-dihydro-2H-benzo[e][1,2]oxaborinine-8-carboxylic acid 2-methoxy-ethyl ester

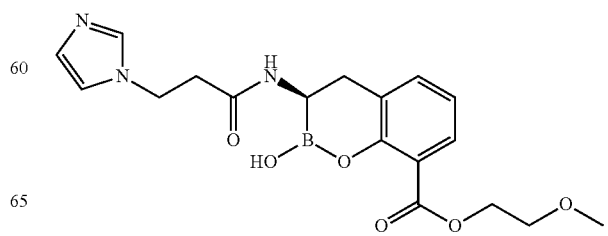

185

Prepared from (R)-2-Hydroxy-3-(3-imidazol-1-yl-propionylamino)-3,4-dihydro-2H-benzo[e][1,2]oxaborinine-8-carboxylic acid and 2-methoxyethanol following the procedure described in Example 132. The crude product was purified by reverse phase flash chromatography on $C_{18}$ silica gel (0-9% IPA/$H_2O$) and dried using lyophilization. ESI-MS m/z 388 (MH)+.

Example 165

(R)-2-Hydroxy-3-(3-thiazol-2-yl-propionylamino)-3,4-dihydro-2H-benzo[e][1,2]oxaborinine-8-carboxylic acid butyl ester

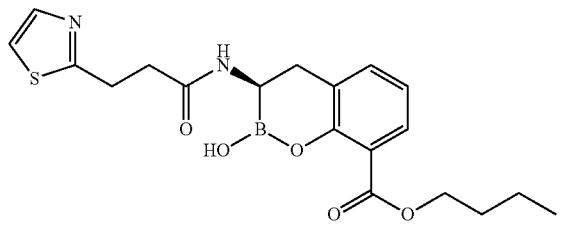 [SMILES: CCCCOC(=O)c1cccc2c1OB(O)[C@@H](NC(=O)CCc1nccs1)C2]

Prepared from (R)-2-hydroxy-3-(3-(thiazol-2-yl)propanamido)-3,4-dihydro-2H-benzo[e][1,2]oxaborinine-8-carboxylic acid and n-butanol following the procedure described in Example 132. The crude product was purified by reverse phase flash chromatography on $C_{18}$ silica gel (8-35% IPA/$H_2O$) and dried using lyophilization. ESI-MS m/z 403 (MH)+.

Example 166

2-Hydroxy-3-(3-thiazol-5-yl-propionylamino)-3,4-dihydro-2H-benzo[e][1,2]oxaborinine-8-carboxylic acid butyl ester

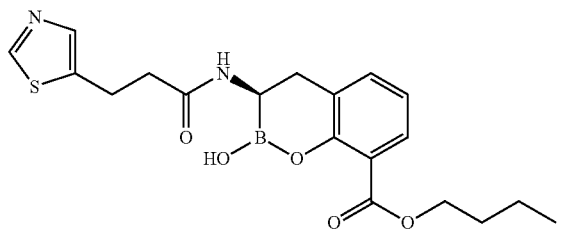 [SMILES: CCCCOC(=O)c1cccc2c1OB(O)[C@@H](NC(=O)CCc1cncs1)C2]

Prepared from (R)-2-hydroxy-3-(3-(thiazol-5-yl)propanamido)-3,4-dihydro-2H-benzo[e][1,2]oxaborinine-8-carboxylic acid and n-butanol following the procedure described in Example 132. The crude product was purified by reverse phase flash chromatography on $C_{18}$ silica gel (10-35% IPA/$H_2O$) and dried using lyophilization. ESI-MS m/z 403 (MH)+.

186

Example 167

(R)-2-Hydroxy-3-(3-thiazol-5-yl-propionylamino)-3,4-dihydro-2H-benzo[e][1,2]oxaborinine-8-carboxylic acid 2-methoxy-ethyl ester

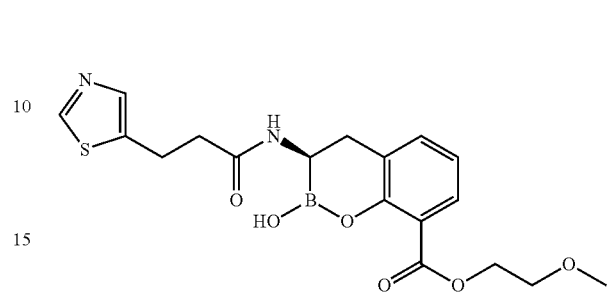

Prepared from (R)-2-hydroxy-3-(3-(thiazol-5-yl)propanamido)-3,4-dihydro-2H-benzo[e][1,2]oxaborinine-8-carboxylic acid and 2-methoxyethanol following the procedure described in Example 132. The crude product was purified by reverse phase flash chromatography on $C_{18}$ silica gel (2-15% IPA/$H_2O$) and dried using lyophilization. ESI-MS m/z 405 (MH)+.

Example 168

(R)-2-Hydroxy-3-(3-imidazol-1-yl-propionylamino)-3,4-dihydro-2H-benzo[e][1,2]oxaborinine-8-carboxylic acid 2,2-dimethyl-propionyloxymethyl ester

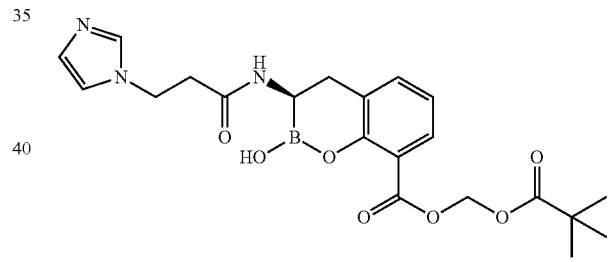

Step 1. Synthesis of 3-[2-(3-Imidazol-1-yl-propionylamino)-2-(2,9,9-trimethyl-3,5-dioxa-4-bora-tricyclo[6.1.1.02,6]dec-4-yl)-ethyl]-2-methoxy-benzoic acid 2,2-dimethyl-propionyloxymethyl ester.

Prepared from 3-[2-(3-Imidazol-1-yl-propionylamino)-2-(2,9,9-trimethyl-3,5-dioxa-4-bora-tricyclo[6.1.1.02,6]dec-4-yl)-ethyl]-2-methoxy-benzoic acid and chloromethyl pivalate following the procedure in Step 1 of Example 126. The crude product was purified by flash chromatography on silica gel (0-10% $CH_3OH$:$CH_2Cl_2$). ESI-MS m/z 610 (MH)+.

Step 2. Synthesis of (R)-2-Hydroxy-3-(3-imidazol-1-yl-propionylamino)-3,4-dihydro-2H-benzo[e][1,2]oxaborinine-8-carboxylic acid 2,2-dimethyl-propionyloxymethyl ester.

Prepared from 3-[2-(3-Imidazol-1-yl-propionylamino)-2-(2,9,9-trimethyl-3,5-dioxa-4-bora-tricyclo[6.1.1.02,6]dec-4-yl)-ethyl]-2-methoxy-benzoic acid 2,2-dimethyl-propionyloxymethyl ester following the procedure in Step 3 of Example 1. The product was purified by reverse phase preparative HPLC and dried using lyophilization. ESI-MS m/z 444 (MH)+.

Example 169

(R)-2-Hydroxy-3,5-oxo-hexanoylamino)-3,4-dihydro-2H-benzo[e][1,2]oxaborinine-8-carboxylic acid 2,2-dimethyl-propionyloxymethyl ester

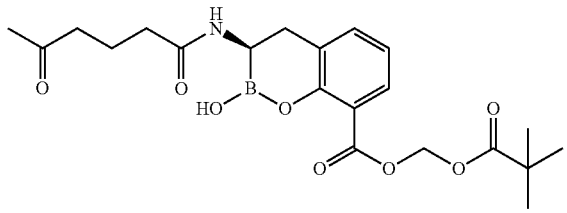 [SMILES: CC(=O)CCCC(=O)N[C@H]1Cc2cccc(C(=O)OCOC(=O)C(C)(C)C)c2OB1O]

Step 1. Synthesis of 2-Methoxy-3-[2-(5-oxo-hexanoylamino)-2-(2,9,9-trimethyl-3,5-dioxa-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 4-acetylbutyric acid following the procedure in Step 2 of Example 1. The crude product was purified by flash chromatography on silica gel (25-100% EtOAc/Hexane). ESI-MS m/z 542 (MH)+.

Step 2. Synthesis of 2-Methoxy-3-[2-(5-oxo-hexanoylamino)-2-(2,2,9-trimethyl-3,5-dioxa-4-bora-tricyclo[6.1.1.02,6]dec-4-yl)-ethyl]-benzoic acid.

Trifluoroacetic acid (1.6 mL) was added to a solution of 2-methoxy-3-[2-(5-oxo-hexanoylamino)-2-(2,9,9-trimethyl-3,5-dioxa-bora-tricyclo[6.1.1.02,6]dec-4-yl)-ethyl]-benzoic acid tert-butyl ester (0.38 g, 0.71 mmol) in dichloromethane (8 mL) and the reaction mixture was stirred at room temperature for 30 min and concentrated. The product was azeotroped with toluene and dried under high vacuum to give an oil. ESI-MS m/z 486 (MH)+.

Step 3. Synthesis of 2-Methoxy-3-[2-(5-oxo-hexanoylamino)-2-(2,2,9-trimethyl-3,5-dioxa-4-bora-tricyclo[6.1.1.02,6]dec-4-yl)-ethyl]-benzoic acid 2,2-dimethyl-propionyloxymethyl ester.

Prepared from 2-methoxy-3-[2-(5-oxo-hexanoylamino)-2-(2,2,9-trimethyl-3,5-dioxa-4-bora-tricyclo[6.1.1.02,6] dec-4-yl)-ethyl]-benzoic acid and chloromethyl pivalate following the procedure described in Step 1 of Example 126. The crude product was purified by flash chromatography on silica gel (10-100% EtOAc/Hexane). ESI-MS m/z 600 (MH)+.

Step 4. Synthesis of (R)-2-Hydroxy-3,5-oxo-hexanoylamino)-3,4-dihydro-2H-benzo[e][1,2]oxaborinine-8-carboxylic acid 2,2-dimethyl-propionyloxymethyl ester.

Prepared from 2-methoxy-3-[2-(5-oxo-hexanoylamino)-2-(2,2,9-trimethyl-3,5-dioxa-4-bora-tricyclo[6.1.1.02,6] dec-4-yl)-ethyl]-benzoic acid 2,2-dimethyl-propionyloxymethyl ester and aluminum chloride following the procedure described in Step 3 of Example 1. The crude product was purified by reverse phase preparative HPLC and dried using lyophilization to give the title compound. ESI-MS m/z 434 (MH)+.

Example 170

(R)-2-Hydroxy-3-(5-oxohexanoylamino)-3,4-dihydro-2H-benzo[e][1,2]oxaborinine-8-carboxylic acid ethyl ester

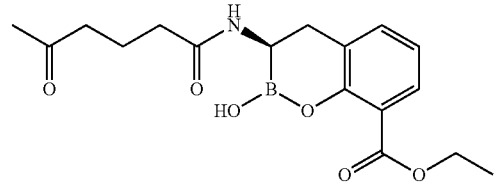 [SMILES: CCOC(=O)c1cccc2c1OB(O)[C@@H](NC(=O)CCCC(C)=O)C2]

Step 1. Synthesis of 2-Hydroxy-3-(5-oxohexanoylamino)-3,4-dihydro-2H-benzo[e][1,2]oxaborinine-8-carboxylic acid.

To 2-methoxy-3-[2-(5-oxo-hexanoylamino)-2-(2,9,9-trimethyl-3,5-dioxa-bora-tricyclo[6.1.1.02,6]dec-4-yl)-ethyl]-benzoic acid tert-butyl ester (0.43 g, 0.8 mmol) in dichloromethane (11 mL) at −78° C. under an atmosphere of argon was added 1M boron tribromide in dichloromethane (2.8 ml, 2.8 mmol) drop wise and the reaction mixture was stirred at this temperature for 1 h and then warmed to 0° C. for 15 min. The reaction was quenched with water and the organics were concentrated off. The crude product was purified by reverse phase preparative HPLC and dried using lyophilization to give the title compound. ESI-MS m/z 320 (MH)+.

Step 2. Synthesis of (R)-2-Hydroxy-3-(5-oxo-hexanoylamino)-3,4-dihydro-2H-benzo[e][1,2]oxaborinine-8-carboxylic acid ethyl ester.

Prepared from 2-hydroxy-3-(5-oxohexanoylamino)-3,4-dihydro-2H-benzo[e][1,2]oxaborinine-8-carboxylic acid and ethanol following the procedure described in Example 132. The crude product was purified by reverse phase preparative HPLC and dried using lyophilization to give the title compound. ESI-MS m/z 348 (MH)+.

Example 171

(R)-2-Hydroxy-3-pent-4-ynoylamino-3,4-dihydro-2H-benzo[e][1,2]oxaborinine-8-carboxylic acid 2,2-dimethyl-propionyloxymethyl ester

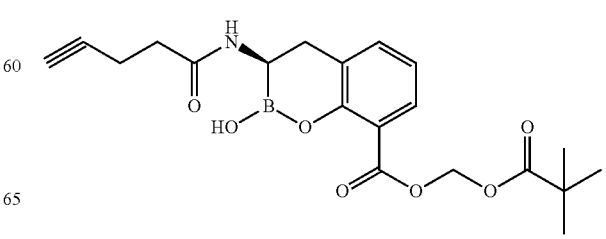

Step 1. Synthesis of 2-Methoxy-3-[2-pent-4-ynoylamino-2-(2,9,9-trimethyl-3,5-dioxa-4-bora-tricyclo[6.1.1.0²,⁶]dec-4-yl-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 4-pentynoic acid following the procedure in Step 2 of Example 1. The crude product was purified by flash chromatography on silica gel (25-100% EtOAc/Hexane). ESI-MS m/z 510 (MH)⁺.

Step 2. Synthesis of 2-Methoxy-3-[2-pent-4-ynoylamino-2-(2,9,9-trimethyl-3,5-dioxa-4-bora-tricyclo[6.1.1.0²,⁶]dec-4-yl-ethyl]-benzoic acid.

Prepared from 2-methoxy-3-[2-pent-4-ynoylamino-2-(2,9,9-trimethyl-3,5-dioxa-4-bora-tricyclo[6.1.1.0²,⁶]dec-4-yl-ethyl]-benzoic acid tert-butyl ester and trifluoroacetic acid following the procedure in Step 2 of Example 169. ESI-MS m/z 454 (MH)⁺.

Step 3. Synthesis of 2-Methoxy-3-[2-pent-4-ynoylamino-2-(2,9,9-trimethyl-3,5-dioxa-4-bora-tricyclo[6.1.1.0²,⁶]dec-4-yl-ethyl]-benzoic acid 2,2-dimethyl-propionyloxymethyl ester.

Prepared from 2-methoxy-3-[2-pent-4-ynoylamino-2-(2,9,9-trimethyl-3,5-dioxa-4-bora-tricyclo[6.1.1.0²,⁶]dec-4-yl-ethyl]-benzoic acid and chloromethyl pivalate following the procedure described in Step 1 of Example 126. The crude product was purified by flash chromatography on silica gel (5-70% EtOAc/Hexane). ESI-MS m/z 568 (MH)⁺.

Step 4. Synthesis of (R)-2-Hydroxy-3-pent-4-ynoylamino-3,4-dihydro-2H-benzo[e][1,2]oxaborinine-8-carboxylic acid 2,2-dimethyl-propionyloxymethyl ester.

Prepared from 2-methoxy-3-[2-pent-4-ynoylamino-2-(2,9,9-trimethyl-3,5-dioxa-4-bora-tricyclo[6.1.1.0²,⁶]dec-4-yl-ethyl]-benzoic acid 2,2-dimethyl-propionyloxymethyl ester and aluminum chloride following the procedure described in Step 3 of Example 1. The crude product was purified by reverse phase preparative HPLC and dried using lyophilization to give the title compound. ESI-MS m/z 402 (MH)⁺.

Example 172

(R)-2-Hydroxy-3-pent-4-ynoylamino-3,4-dihydro-2H-benzo[e][1,2]oxaborinine-8-carboxylic acid ethyl ester

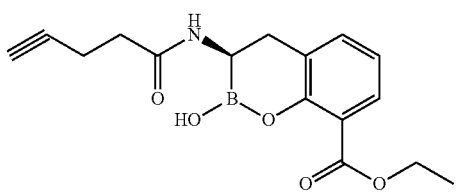 [SMILES: C#CCCC(=O)N[C@H]1Cc2cccc(C(=O)OCC)c2OB1O]

Step 1. Synthesis of 2-Hydroxy-3-pent-4-ynoylamino-3,4-dihydro-2H-benzo[e][1,2]oxaborinine-8-carboxylic acid.

Prepared from 2-methoxy-3-[2-pent-4-ynoylamino-2-(2,9,9-trimethyl-3,5-dioxa-4-bora-tricyclo[6.1.1.0²,⁶]dec-4-yl-ethyl]-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 288 (MH)⁺.

Step 2. Synthesis of (R)-2-Hydroxy-3-pent-4-ynoylamino-3,4-dihydro-2H-benzo[e][1,2]oxaborinine-8-carboxylic acid ethyl ester.

To 2-hydroxy-3-pent-4-ynoylamino-3,4-dihydro-2H-benzo[e][1,2]oxaborinine-8-carboxylic acid was added ethanol (12 mL) and thionyl chloride (0.74 mL) and the reaction mixture was heated at 80° C. for 2 h and quenched with water. The organics were concentrated off and the crude product was purified by reverse phase preparative HPLC and dried using lyophilization to give the title compound. ESI-MS m/z 316 (MH)⁺.

Example 173

(R)-3-(3-Carbamoyl-propionylamino)-2-hydroxy-3,4-dihydro-2H-benzo[e][1,2]oxaborinine-8-carboxylic acid ethyl ester

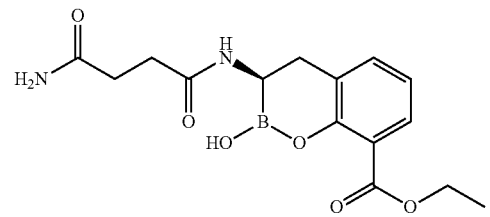 [SMILES: CCOC(=O)c1cccc2c1OB(O)[C@@H](NC(=O)CCC(N)=O)C2]

Step 1. Synthesis of 3-(3-Carbamoyl-propionylamino)-2-hydroxy-3,4-dihydro-2H-benzo[e][1,2]oxaborinine-8-carboxylic acid.

Prepared from 3-[2-(3-carbamoyl-propionylamino)-2-(2,9,9-trimethyl-3,5-dioxa-4-bora-tricyclo[6.1.1.0²,⁶]dec-4-yl)-ethyl]-2-methoxy-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 307 (MH)⁺.

Step 2. Synthesis of (R)-3-(3-Carbamoyl-propionylamino)-2-hydroxy-3,4-dihydro-2H-benzo[e][1,2]oxaborinine-8-carboxylic acid ethyl ester.

Prepared from 3-(3-carbamoyl-propionylamino)-2-hydroxy-3,4-dihydro-2H-benzo[e][1,2]oxaborinine-8-carboxylic acid and ethanol following the procedure described in Example 132. The crude product was purified by reverse phase preparative HPLC and dried using lyophilization to give the title compound. ESI-MS m/z 335 (MH)⁺.

Example 174

(R)-2-Hydroxy-3-(4-sulfamoyl-butyrylamino)-3,4-dihydro-2H-benzo[e][1,2]oxaborinine-8-carboxylic acid 2,2-dimethyl-propionyloxymethyl ester

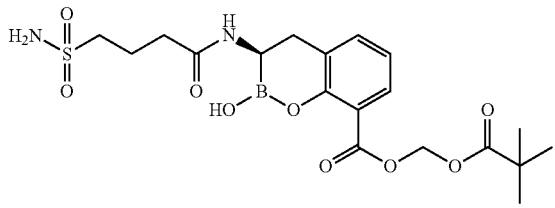 [SMILES: CC(C)(C)C(=O)OCOC(=O)c1cccc2c1OB(O)[C@@H](NC(=O)CCCS(N)(=O)=O)C2]

Step 1. Synthesis of 2-Methoxy-3-[2-(4-sulfamoyl-butyrylamino)-2-(2,9,9-trimethyl-3,5-dioxa-4-bora-tricyclo[6.1.1.02,6]dec-4-yl)-ethyl]benzoic acid tert-butyl ester.

Prepared from [(1S)-2-(3-tert-butoxycarbonyl-2-methoxy-phenyl)-1-chloro-ethyl]boronic acid (+) pinanediol ester and 3-carboxypropane sulfonamide following the procedure in Step 2 of Example 1. The crude product was purified by flash chromatography on silica gel (1-5% $CH_3OH/CH_2Cl_2$). ESI-MS m/z 579 $(MH)^+$.

Step 2. Synthesis of 2-Methoxy-3-[2-(4-sulfamoyl-butyrylamino)-2-(2,9,9-trimethyl-3,5-dioxa-4-bora-tricyclo[6.1.1.02,6]dec-4-yl)-ethyl]benzoic acid.

Prepared from 2-methoxy-3-[2-(4-sulfamoyl-butyrylamino)-2-(2,9,9-trimethyl-3,5-dioxa-4-bora-tricyclo[6.1.1.02,6]dec-4-yl)-ethyl]benzoic acid tert-butyl ester and trifluoroacetic acid following the procedure in Step 2 of Example 169. ESI-MS m/z 423 $(MH)^+$.

Step 3. Synthesis of 2-Methoxy-3-[2-(4-sulfamoyl-butyrylamino)-2-(2,9,9-trimethyl-3,5-dioxa-4-bora-tricyclo[6.1.1.02,6]dec-4-yl)-ethyl]benzoic acid 2,2-dimethyl-propionyloxymethyl ester.

Prepared from 2-methoxy-3-[2-(4-sulfamoyl-butyrylamino)-2-(2,9,9-trimethyl-3,5-dioxa-4-bora-tricyclo[6.1.1.02,6]dec-4-yl)-ethyl]benzoic acid and chloromethyl pivalate following the procedure described in Step 1 of Example 126. The crude product was purified by flash chromatography on silica gel (1-10% EtOAc/Hexane). ESI-MS m/z 637 $(MH)^+$.

Step 4. Synthesis of (R)-2-Hydroxy-3-(4-sulfamoyl-butyrylamino)-3,4-dihydro-2H-benzo[e][1,2]oxaborinine-8-carboxylic acid 2,2-dimethyl-propionyloxymethyl ester.

Prepared from 2-methoxy-3-[2-(4-sulfamoyl-butyrylamino)-2-(2,9,9-trimethyl-3,5-dioxa-4-bora-tricyclo[6.1.1.02,6]dec-4-yl)-ethyl]benzoic acid 2,2-dimethyl-propionyloxymethyl ester and aluminum chloride following the procedure described in Step 3 of Example 1. The crude product was purified by reverse phase preparative HPLC and dried using lyophilization to give the title compound. ESI-MS m/z 471 $(MH)^+$.

Example 175

(R)-2-Hydroxy-3-(4-sulfamoyl-butyrylamino)-3,4-dihydro-2H-benzo[e][1,2]oxaborinine-8-carboxylic acid ethyl ester

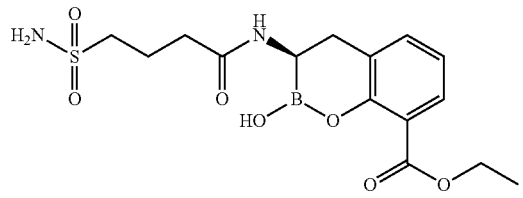 [SMILES: CCOC(=O)c1cccc2c1OB(O)[C@@H](NC(=O)CCCS(N)(=O)=O)C2]

Step 1. Synthesis of 2-Hydroxy-3-(4-sulfamoyl-butyrylamino)-3,4-dihydro-2H-benzo[e][1,2]oxaborinine-8-carboxylic acid.

Prepared from 2-methoxy-3-[2-(4-sulfamoyl-butyrylamino)-2-(2,9,9-trimethyl-3,5-dioxa-4-bora-tricyclo[6.1.1.02,6]dec-4-yl)-ethyl]-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 357 $(MH)^+$.

Step 2. Synthesis of (R)-2-Hydroxy-3-(4-sulfamoyl-butyrylamino)-3,4-dihydro-2H-benzo[e][1,2]oxaborinine-8-carboxylic acid ethyl ester.

Prepared from 2-hydroxy-3-(4-sulfamoyl-butyrylamino)-3,4-dihydro-2H-benzo[e][1,2]oxaborinine-8-carboxylic acid and ethanol following the procedure described in Example 132. The crude product was purified by reverse phase preparative HPLC and dried using lyophilization to give the title compound. ESI-MS m/z 385 $(MH)^+$.

Example 176

(R)-2-Hydroxy-3-(3-methanesulfonylamino-propionylamino)-3,4-dihydro-2H-benzo[e][1,2]oxaborinine-8-carboxylic acid ethyl ester

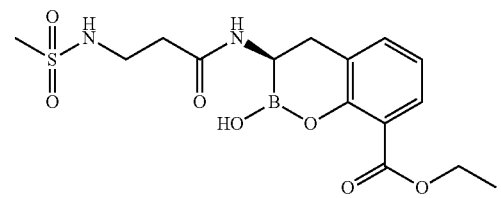 [SMILES: CCOC(=O)c1cccc2c1OB(O)[C@@H](NC(=O)CCNS(C)(=O)=O)C2]

Step 1. Synthesis of 2-Hydroxy-3-(3-methane-sulfonylamino-propionylamino)-3,4-dihydro-2H-benzo[e][1,2]oxaborinine-8-carboxylic acid.

Prepared from 3-[2-(3-methanesulfonylamino-propionylamino)-2-(2,9,9-trimethyl-3,5-dioxa-4-bora-tricyclo[6.1.1.02,6]dec-4-yl)-ethyl]-2-methoxy-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 357 (MH)+.

Step 2. Synthesis of 2-Hydroxy-3-(3-methanesulfonylamino-propionylamino)-3,4-dihydro-2H-benzo[e][1,2]oxaborinine-8-carboxylic acid ethyl ester.

Prepared from 2-Hydroxy-3-(3-methane-sulfonylamino-propionylamino)-3,4-dihydro-2H-benzo[e][1,2]oxaborinine-8-carboxylic acid and ethanol following the procedure described in Example 132. The crude product was purified by reverse phase preparative HPLC and dried using lyophilization to give the title compound. ESI-MS m/z 385 (MH)+.

Example 177

(R)-2-Hydroxy-3-(3-sulfamoyl-propionylamino)-3,4-dihydro-2H-oxa-2-bora-naphthalene-8-carboxylic acid 2,2-dimethyl-propionyloxymethyl ester

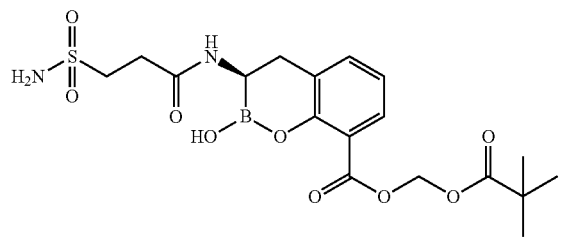 [SMILES: CC(C)(C)C(=O)OCOC(=O)c1cccc2c1OB(O)[C@@H](NC(=O)CCS(N)(=O)=O)C2]

Step 1. Synthesis of 2-Methoxy-3-[2-(3-sulfamoyl-propionylamino)-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-sulfamoylpropanoic acid following the procedure in Step 2 of Example 1. The crude product was purified by flash chromatography on silica gel (1-3% CH₃OH/CH₂Cl₂). ESI-MS m/z 565 (MH)+.

Step 2. Synthesis of 2-Methoxy-3-[2-(3-sulfamoyl-propionylamino)-2-(2,9,9-trimethyl-3,5-dioxa-4-bora-tricyclo[6.1.1.02,6]dec-4-yl)-ethyl]-benzoic acid.

Prepared from 2-methoxy-3-[2-(3-sulfamoyl-propionylamino)-2-(2,9,9-trimethyl-3,5-dioxa-4-bora-tricyclo[6.1.1.02,6]dec-4-yl)-ethyl]-benzoic acid tert-butyl ester and trifluoroacetic acid following the procedure in Step 2 of Example 169. ESI-MS m/z 509 (MH)+.

Step 3. Synthesis of 2-Methoxy-3-[2-(3-sulfamoyl-propionylamino)-2-(2,9,9-trimethyl-3,5-dioxa-4-bora-tricyclo[6.1.1.02,6]dec-4-yl)-ethyl]-benzoic acid 2,2-dimethyl-propionyloxymethyl ester.

Prepared from 2-methoxy-3-[2-(3-sulfamoyl-propionylamino)-2-(2,9,9-trimethyl-3,5-dioxa-4-bora-tricyclo[6.1.1.02,6]dec-4-yl)-ethyl]-benzoic acid and chloromethyl pivalate following the procedure described in Step 1 of Example 126. The crude product was purified using Prep TLC plates (5% CH₃OH/CH₂Cl₂). ESI-MS m/z 623 (MH)+.

Step 4. Synthesis of (R)-2-Hydroxy-3-(3-sulfamoyl-propionylamino)-3,4-dihydro-2H-oxa-2-bora-naphthalene-8-carboxylic acid 2,2-dimethyl-propionyloxymethyl ester.

Prepared from 2-methoxy-3-[2-(3-sulfamoyl-propionylamino)-2-(2,9,9-trimethyl-3,5-dioxa-4-bora-tricyclo[6.1.1.02,6]dec-4-yl)-ethyl]-benzoic acid 2,2-dimethyl-propionyloxymethyl ester and aluminum chloride following the procedure described in Step 3 of Example 1. The crude product was purified by reverse phase preparative HPLC and dried using lyophilization to give the title compound. ESI-MS m/z 457 (MH)+.

Example 178

(R)-2-Hydroxy-3-(3-methylsulfamoyl-propionylamino)-3,4-dihydro-2H-oxa-2-bora-naphthalene-8-carboxylic acid ethyl ester

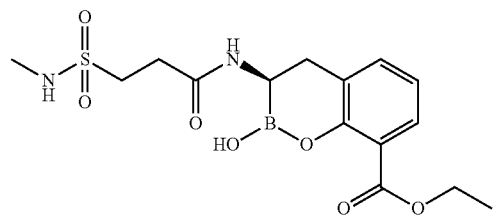 [SMILES: CCOC(=O)c1cccc2c1OB(O)[C@@H](NC(=O)CCS(=O)(=O)NC)C2]

Step 1. Synthesis of 2-Hydroxy-3-(3-methylsulfamoyl-propionylamino)-3,4-dihydro-2H-benzo[e][1,2]oxaborinine-8-carboxylic acid.

Prepared from 2-methoxy-3-[2-(3-methylsulfamoyl-propionylamino)-2-(2,9,9-trimethyl-3,5-dioxa-4-bora-tricyclo[6.1.1.02,6]dec-4-yl)-ethyl]-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 357 (MH)+.

Step 2. Synthesis of (R)-2-Hydroxy-3-(3-methylsulfamoyl-propionylamino)-3,4-dihydro-2H-oxa-2-bora-naphthalene-8-carboxylic acid ethyl ester.

Prepared from 2-hydroxy-3-(3-methylsulfamoyl-propionylamino)-3,4-dihydro-2H-benzo[e][1,2]oxaborinine-8-carboxylic acid and ethanol following the procedure described in Example 132. The crude product was purified by reverse phase preparative HPLC and dried using lyophilization to give the title compound. ESI-MS m/z 385 (MH)+.

Example 179

(R)-2-Hydroxy-3-(2-ureido-acetylamino)-3,4-dihydro-2H-benzo[e][1,2]oxaborinine-8-carboxylic acid 2,2-dimethyl-propionyloxymethyl ester

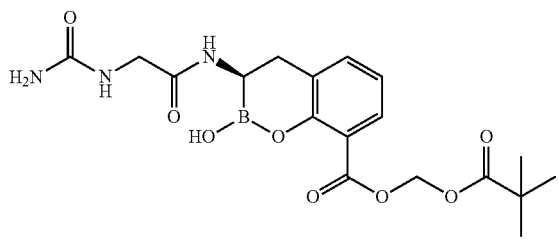 [SMILES: CC(C)(C)C(=O)OCOC(=O)c1cccc2c1OB(O)[C@@H](NC(=O)CNC(N)=O)C2]

Step 1. Synthesis of 2-Methoxy-3-[2-(2,9,9-trimethyl-3,5-dioxa-4-bora-tricyclo[6.1.1.02,6]dec-4-yl-2-(2-ureido-acetylamino)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and hydantoic acid following the procedure in Step 2 of Example 1. The crude product was purified by flash chromatography on silica gel (1-5% $CH_3OH/CH_2Cl_2$). ESI-MS m/z 530 $(MH)^+$.

Step 2. Synthesis of 2-Methoxy-3-[2-(2,9,9-trimethyl-3,5-dioxa-4-bora-tricyclo[6.1.1.02,6]dec-4-yl-2-(2-ureido-acetylamino)-ethyl]-benzoic acid.

Prepared from 2-methoxy-3-[2-(2,9,9-trimethyl-3,5-dioxa-4-bora-tricyclo[6.1.1.02,6]dec-4-yl-2-(2-ureido-acetylamino)-ethyl]-benzoic acid tert-butyl ester and trifluoroacetic acid following the procedure in Step 2 of Example 169. ESI-MS m/z 474 $(MH)^+$.

Step 3. Synthesis of 2-Methoxy-3-[2-(2,9,9-trimethyl-3,5-dioxa-4-bora-tricyclo[6.1.1.02,6]dec-4-yl-2-(2-ureido-acetylamino)-ethyl]-benzoic acid 2,2-dimethyl-propionyloxymethyl ester.

Prepared from 2-methoxy-3-[2-(2,9,9-trimethyl-3,5-dioxa-4-bora-tricyclo[6.1.1.02,6]dec-4-yl-2-(2-ureido-acetylamino)-ethyl]-benzoic acid and chloromethyl pivalate following the procedure described in Step 1 of Example 126. The crude product was purified by flash chromatography on silica gel (1-5% $CH_3OH/CH_2Cl_2$). ESI-MS m/z 588 $(MH)^+$.

Step 4. Synthesis of (R)-2-Hydroxy-3-(2-ureido-acetylamino)-3,4-dihydro-2H-benzo[e][1,2]oxaborinine-8-carboxylic acid 2,2-dimethyl-propionyloxymethyl ester.

Prepared from 2-methoxy-3-[2-(2,9,9-trimethyl-3,5-dioxa-4-bora-tricyclo[6.1.1.02,6]dec-4-yl-2-(2-ureido-acetylamino)-ethyl]-benzoic acid 2,2-dimethyl-propionyloxymethyl ester and aluminum chloride following the procedure described in Step 3 of Example 1. The crude product was purified by reverse phase preparative HPLC and dried using lyophilization to give the title compound. ESI-MS m/z 422 $(MH)^+$.

Example 180

(R)-2-Hydroxy-3-(2-ureido-acetylamino)-3,4-dihydro-2H-benzo[e][1,2]oxaborinine-8-carboxylic acid ethyl ester

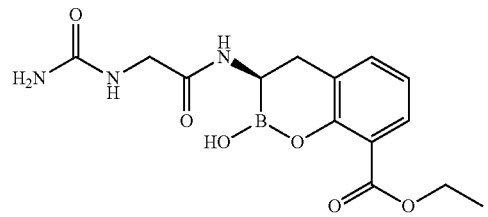 [SMILES: CCOC(=O)c1cccc2c1OB(O)[C@@H](NC(=O)CNC(N)=O)C2]

Step 1. Synthesis of 2-Hydroxy-3-(2-ureido-acetylamino)-3,4-dihydro-2H-benzo[e][1,2]oxaborinine-8-carboxylic acid.

Prepared from 2-methoxy-3-[2-(2,9,9-trimethyl-3,5-dioxa-4-bora-tricyclo[6.1.1.02,6]dec-4-yl-2-(2-ureido-acetylamino)-ethyl]-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 308 $(MH)^+$.

Step 2. Synthesis of (R)-2-Hydroxy-3-(2-ureido-acetylamino)-3,4-dihydro-2H-benzo[e][1,2]oxaborinine-8-carboxylic acid ethyl ester.

Prepared from 2-hydroxy-3-(2-ureido-acetylamino)-3,4-dihydro-2H-benzo[e][1,2]oxaborinine-8-carboxylic acid and ethanol following the procedure described in Example 132. The crude product was purified by reverse phase preparative HPLC and dried using lyophilization to give the title compound. ESI-MS m/z 336 $(MH)^+$.

Example 181

(R)-2-Hydroxy-3-(3-imidazol-1-yl-propionylamino)-3,4-dihydro-2H-benzo[e][1,2]oxaborinine-8-carboxylic acid ethyl ester

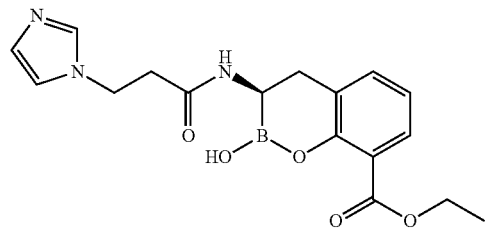 [SMILES: CCOC(=O)c1cccc2c1OB(O)[C@@H](NC(=O)CCn1ccnc1)C2]

Step 1. Synthesis of 3-[2-(3-Imidazol-1-yl-propionylamino-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 3-(1H-imidazol-lyl)propanoic acid following the procedure in Step 2 of Example 1. The crude product was purified by flash chromatography on silica gel (3-8% $CH_3OH/CH_2Cl_2$), followed by Prep TLC plates (8% $CH_3OH/CH_2Cl_2$). ESI-MS m/z 552 (MH)$^+$.

Step 2. Synthesis of 2-Hydroxy-3-(3-imidazol-1-yl-propionylamino)-3,4-dihydro-2H-benzo[e][1,2]oxaborinine-8-carboxylic acid.

Prepared from 3-[2-(3-imidazol-1-yl-propionylamino)-2-(2,9,9-trimethyl-3,5-dioxa-4-bora-tricyclo[6.1.1.02,6]dec-4-yl)-ethyl]-2-methoxy-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 330 (MH)$^+$.

Step 3. Synthesis of (R)-2-Hydroxy-3-(3-imidazol-1-yl-propionylamino)-3,4-dihydro-2H-benzo[e][1,2]oxaborinine-8-carboxylic acid ethyl ester.

Prepared from 2-hydroxy-3-(3-imidazol-1-yl-propionylamino)-3,4-dihydro-2H-benzo[e][1,2]oxaborinine-8-carboxylic acid and ethanol following the procedure described in Example 132. The crude product was purified by reverse phase preparative HPLC and dried using lyophilization to give the title compound. ESI-MS m/z 358 (MH)$^+$.

Example 182

(R)-2-Hydroxy-3-(3-thiazol-5-yl-propionylamino)-3,4-dihydro-2H-benzo[e][1,2]oxaborinine-8-carboxylic acid ethyl ester

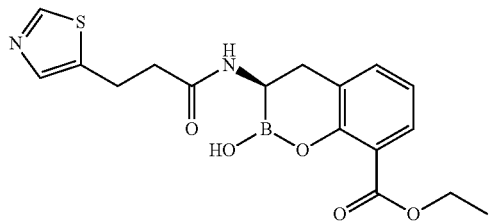 [SMILES: CCOC(=O)c1cccc2c1OB(O)[C@@H](NC(=O)CCc1cncs1)C2]

Step 1. Synthesis 2-Methoxy-3-[2-(3-thiazol-5yl-propionylamino)-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-thiazol-5-yl-propionic acid (prepared in Step 3 of Example 31) following the procedure in Step 2 of Example 1. The crude product was purified by flash chromatography on silica gel (1-3% $CH_3OH/CH_2Cl_2$). ESI-MS m/z 569 (MH)$^+$.

Step 2. Synthesis of 2-Hydroxy-3-(3-thiazol-5-yl-propionylamino)-3,4-dihydro-2H-benzo[e][1,2]oxaborinine-8-carboxylic acid.

Prepared from 2-methoxy-3-[2-(3-thiazol-5yl-propionylamino)-2-(2,9,9-trimethyl-3,5-dioxa-4-bora-tricyclo[6.1.1.02,6]dec-4-yl)-ethyl]-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 347 (MH)$^+$.

Step 3. Synthesis of (R)-2-Hydroxy-3-(3-thiazol-5-yl-propionylamino)-3,4-dihydro-2H-benzo[e][1,2]oxaborinine-8-carboxylic acid ethyl ester.

Prepared from 2-hydroxy-3-(3-thiazol-5-yl-propionylamino)-3,4-dihydro-2H-benzo[e][1,2]oxaborinine-8-carboxylic acid and ethanol following the procedure described in Example 132. The crude product was purified by reverse phase preparative HPLC and dried using lyophilization to give the title compound. ESI-MS m/z 375 (MH)$^+$.

Example 183

(R)-2-Hydroxy-3-(3-thiazol-5-yl-propionylamino)-3,4-dihydro-2H-benzo[e][1,2]oxaborinine-8-carboxylic acid 2,2-dimethyl propionyloxymethyl ester

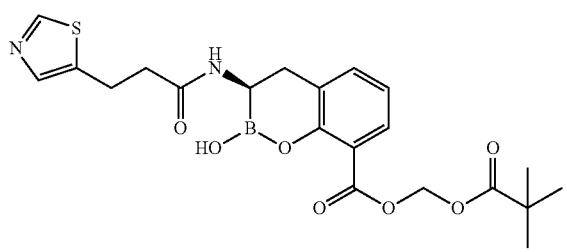 [SMILES: CC(C)(C)C(=O)OCOC(=O)c1cccc2c1OB(O)[C@@H](NC(=O)CCc1cncs1)C2]

Step 1. Synthesis of 2-Methoxy-3-[2-(3-thiazol-5yl-propionylamino)-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-thiazol-5-yl-propionic acid (prepared in Step 3 of Example 31) following the procedure in Step 2 of Example 1. The crude product was purified by flash chromatography on silica gel (1-3% $CH_3OH/CH_2Cl_2$). ESI-MS m/z 569 (MH)$^+$.

Step 2. Synthesis of 2-Methoxy-3-[2-(3-thiazol-5yl-propionylamino)-2-(2,9,9-trimethyl-3,5-dioxa-4-bora-tricyclo[6.1.1.02,6]dec-4-yl)-ethyl]-benzoic acid.

Prepared from 2-methoxy-3-[2-(3-thiazol-5yl-propionylamino)-2-(2,9,9-trimethyl-3,5-dioxa-4-bora-tricyclo[6.1.1.02,6]dec-4-yl)-ethyl]-benzoic acid tert-butyl ester and trifluoroacetic acid following the procedure in Step 2 of Example 169. ESI-MS m/z 513 (MH)$^+$.

Step 3. Synthesis of 2-Methoxy-3-[2-(3-thiazol-5yl-propionylamino)-2-(2,9,9-trimethyl-3,5-dioxa-4-bora-tricyclo[6.1.1.02,6]dec-4-yl)-ethyl]-benzoic acid 2,2-dimethyl propionyloxymethyl ester.

Prepared from 2-methoxy-3-[2-(3-thiazol-5yl-propionylamino)-2-(2,9,9-trimethyl-3,5-dioxa-4-bora-tricyclo

[6.1.1.02,6]dec-4-yl)-ethyl]-benzoic acid and chloromethyl pivalate following the procedure described in Step 1 of Example 126. The crude product was purified using Prep TLC plates (5% CH₃OH/CH₂Cl₂). ESI-MS m/z 627 (MH)⁺.

Step 4. Synthesis of (R)-2-Hydroxy-3-(3-thiazol-5-yl-propionylamino)-3,4-dihydro-2H-benzo[e][1,2]oxaborinine-8-carboxylic acid 2,2-dimethyl propionyloxymethyl ester.

Prepared from 2-methoxy-3-[2-(3-thiazol-5yl-propionylamino)-2-(2,9,9-trimethyl-3,5-dioxa-4-bora-tricyclo[6.1.1.02,6]dec-4-yl)-ethyl]-benzoic acid 2,2-dimethyl propionyloxymethyl ester and aluminum chloride following the procedure described in Step 3 of Example 1. The crude product was purified by reverse phase preparative HPLC and dried using lyophilization to give the title compound. ESI-MS m/z 461 (MH)⁺.

Example 184

(R)-2-Hydroxy-3-(3-sulfamoyl-propionylamino)-3,4-dihydro-2H-oxa-2-bora-naphthalene-8-carboxylic acid ethyl ester

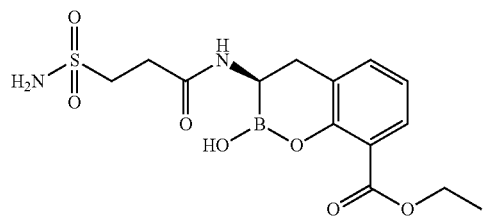 [SMILES: CCOC(=O)c1cccc2c1OB(O)[C@@H](NC(=O)CCS(N)(=O)=O)C2]

Step 1. Synthesis of 2-Hydroxy-3-(3-sulfamoyl-propionylamino)-3,4-dihydro-2H-benzo[e][1,2]oxaborinine-8-carboxylic acid.

Prepared from 2-methoxy-3-[2-(3-sulfamoyl-propionylamino)-2-(2,9,9-trimethyl-3,5-dioxa-4-bora-tricyclo[6.1.1.02,6]dec-4-yl)-ethyl]-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 343 (MH)⁺.

Step 2. Synthesis of (R)-2-Hydroxy-3-(3-sulfamoyl-propionylamino)-3,4-dihydro-2H-oxa-2-bora-naphthalene-8-carboxylic acid ethyl ester.

Prepared from 2-hydroxy-3-(3-sulfamoyl-propionylamino)-3,4-dihydro-2H-benzo[e][1,2]oxaborinine-8-carboxylic acid and ethanol following the procedure described in Example 132. The crude product was purified by reverse phase preparative HPLC and dried using lyophilization to give the title compound. ESI-MS m/z 371 (MH)⁺.

Example 185

(R)-2-Hydroxy-3-(3-methylsulfamoyl-propionylamino)-3,4-dihydro-2H-oxa-2-bora-naphthalene-8-carboxylic acid 2,2-dimethyl-propionyloxymethyl ester

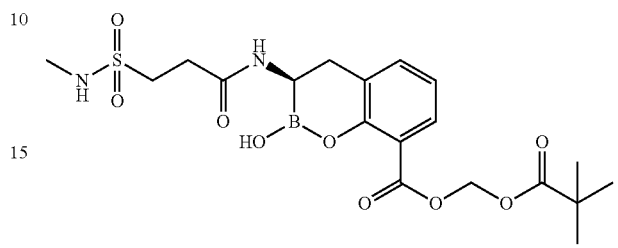

Step 1. Synthesis of 2-Methoxy-3-[2-(3-methylsulfamoyl-propionylamino)-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 3-(methylsulfamoyl)propanoic acid following the procedure in Step 2 of Example 1. The crude product was purified by flash chromatography on silica gel (1-3% CH₃OH/CH₂Cl₂). ESI-MS m/z 579 (MH)⁺.

Step 2. Synthesis of 2-Methoxy-3-[2-(3-methylsulfamoyl-propionylamino)-2-(2,9,9-trimethyl-3,5-dioxa-4-bora-tricyclo[6.1.1.02,6]dec-4-yl)-ethyl]-benzoic acid.

Prepared from 2-methoxy-3-[2-(3-methylsulfamoyl-propionylamino)-2-(2,9,9-trimethyl-3,5-dioxa-4-bora-tricyclo[6.1.1.02,6]dec-4-yl)-ethyl]-benzoic acid tert-butyl ester and trifluoroacetic acid following the procedure in Step 2 of Example 169. ESI-MS m/z 523 (MH)⁺.

Step 3. Synthesis of 2-Methoxy-3-[2-(3-methylsulfamoyl-propionylamino)-2-(2,9,9-trimethyl-3,5-dioxa-4-bora-tricyclo[6.1.1.02,6]dec-4-yl)-ethyl]-benzoic acid 2,2-dimethyl-propionyloxymethyl ester.

Prepared from 2-methoxy-3-[2-(3-methylsulfamoyl-propionylamino)-2-(2,9,9-trimethyl-3,5-dioxa-4-bora-tricyclo[6.1.1.02,6]dec-4-yl)-ethyl]-benzoic acid and chloromethyl pivalate following the procedure described in Step 1 of Example 126. The crude product was purified by flash chromatography on silica gel (1-3% CH₃OH/CH₂Cl₂). ESI-MS m/z 637 (MH)⁺.

Step 4. Synthesis of (R)-2-Hydroxy-3-(3-methylsulfamoyl-propionylamino)-3,4-dihydro-2H-oxa-2-bora-naphthalene-8-carboxylic acid 2,2-dimethyl-propionyloxymethyl ester.

Prepared from 2-methoxy-3-[2-(3-methylsulfamoyl-propionylamino)-2-(2,9,9-trimethyl-3,5-dioxa-4-bora-tricyclo[6.1.1.02,6]dec-4-yl)-ethyl]-benzoic acid 2,2-dimethyl-propionyloxymethyl ester and aluminum chloride following the procedure described in Step 3 of Example 1. The crude product was purified by reverse phase preparative HPLC and dried using lyophilization to give the title compound. ESI-MS m/z 471 (MH)⁺.

Example 186

(R)-2-Hydroxy-3-(2-methoxycarbonylamino-acetylamino)-3,4-dihydro-2H-benzo[e][1,2]oxaborinine-8-carboxylic acid 2,2-dimethyl-propionyloxymethyl ester

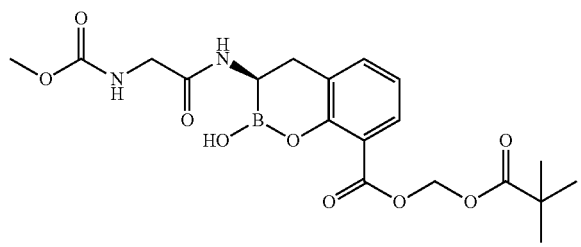 [SMILES: COC(=O)NCC(=O)N[C@H]1Cc2cccc(C(=O)OCOC(=O)C(C)(C)C)c2OB1O]

Step 1. Synthesis of 2-Methoxy-3-[2-(2-methoxycarbonylamino-acetylamino)-2-(2,9,9-trimethyl-3,5-dioxa-4-bora-tricyclo[6.1.1.0²,⁶]dec-4-yl)-ethyl]-benzoic acid.

Prepared from 2-methoxy-3-[2-(2-methoxycarbonylamino-acetylamino)-2-(2,9,9-trimethyl-3,5-dioxa-4-bora-tricyclo[6.1.1.0²,⁶]dec-4-yl)-ethyl]-benzoic acid tert-butyl ester (prepared in Step 1 of Example 56) and trifluoroacetic acid following the procedure in Step 2 of Example 169. ESI-MS m/z 489 (MH)⁺.

Step 2. Synthesis of 2-Methoxy-3-[2-(2-methoxycarbonylamino-acetylamino)-2-(2,9,9-trimethyl-3,5-dioxa-4-bora-tricyclo[6.1.1.0²,⁶]dec-4-yl)-ethyl]-benzoic acid 2,2-dimethyl-propionyloxymethyl ester.

Prepared from 2-methoxy-3-[2-(2-methoxycarbonylamino-acetylamino)-2-(2,9,9-trimethyl-3,5-dioxa-4-bora-tricyclo[6.1.1.0²,⁶]dec-4-yl)-ethyl]-benzoic acid and chloromethyl pivalate following the procedure described in Step 1 of Example 126. The crude product was purified by flash chromatography on silica gel (1-3% CH₃OH/CH₂Cl₂). ESI-MS m/z 603 (MH)⁺.

Step 3. Synthesis of (R)-2-Hydroxy-3-(2-methoxycarbonylamino-acetylamino)-3,4-dihydro-2H-benzo[e][1,2]oxaborinine-8-carboxylic acid 2,2-dimethyl-propionyloxymethyl ester.

Prepared from 2-methoxy-3-[2-(2-methoxycarbonylamino-acetylamino)-2-(2,9,9-trimethyl-3,5-dioxa-4-bora-tricyclo[6.1.1.0²,⁶]dec-4-yl)-ethyl]-benzoic acid 2,2-dimethyl-propionyloxymethyl ester and aluminum chloride following the procedure described in Step 3 of Example 1. The crude product was purified by reverse phase preparative HPLC and dried using lyophilization to give the title compound. ESI-MS m/z 437 (MH)⁺.

Example 187

(R)-2-Hydroxy-3-(2-methoxycarbonylamino-acetylamino)-3,4-dihydro-2H-benzo[e][1,2]oxaborinine-8-carboxylic acid ethyl ester

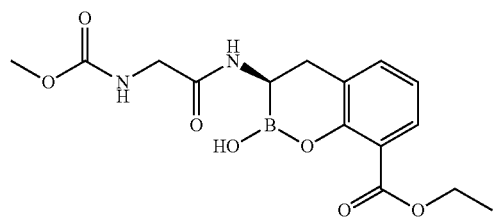 [SMILES: CCOC(=O)c1cccc2c1OB(O)[C@@H](NC(=O)CNC(=O)OC)C2]

Step 1. Synthesis of 2-Hydroxy-3-(2-methoxycarbonylamino-acetylamino)-3,4-dihydro-2H-benzo[e][1,2]oxaborinine-8-carboxylic acid.

Prepared from 2-methoxy-3-[2-(2-methoxycarbonylamino-acetylamino)-2-(2,9,9-trimethyl-3,5-dioxa-4-bora-tricyclo[6.1.1.0²,⁶]dec-4-yl)-ethyl]-benzoic acid tert-butyl ester (prepared in Step 1 of Example 56) and 1M boron tribromide in dichloromethane following the procedure described in Step 1 of Example 170. The crude product was purified by reverse phase preparative HPLC and dried using lyophilization to give the title compound. ESI-MS m/z 323 (MH)⁺.

Step 2. Synthesis of (R)-2-Hydroxy-3-(2-methoxycarbonylamino-acetylamino)-3,4-dihydro-2H-benzo[e][1,2]oxaborinine-8-carboxylic acid ethyl ester.

Prepared from 2-hydroxy-3-(2-methoxycarbonylamino-acetylamino)-3,4-dihydro-2H-benzo[e][1,2]oxaborinine-8-carboxylic acid and ethanol following the procedure described in Example 132. The crude product was purified by reverse phase preparative HPLC and dried using lyophilization to give the title compound. ESI-MS m/z 351 (MH)⁺.

Example 188

(R)-3-Acetylamino-2-hydroxy-3,4-dihydro-2H-benzo[e][1,2]oxaborinine-8-carboxylic acid methyl ester

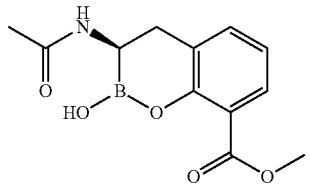 [SMILES: COC(=O)c1cccc2c1OB(O)[C@@H](NC(C)=O)C2]

Step 1. Synthesis of 3-Acetylamino-2-hydroxy-3,4-dihydro-2H-benzo[e][1,2]oxaborinine-8-carboxylic acid.

Prepared from 3-[2-acetylamino-2-(2,9,9-trimethyl-3,5-dioxa-4-bora-tricyclo[6.1.1.0²,⁶]dec-4-yl)-ethyl]-2-methoxy-benzoic acid tert-butyl ester (prepared in Step 1 of Example 61) and 1M boron tribromide in dichloromethane following the procedure described in Step 1 of Example 170. The crude product was purified by reverse phase preparative HPLC and dried using lyophilization to give the title compound. ESI-MS m/z 250 (MH)⁺.

Step 2. Synthesis of (R)-3-Acetylamino-2-hydroxy-3,4-dihydro-2H-benzo[e][1,2]oxaborinine-8-carboxylic acid methyl ester.

Prepared from 3-acetylamino-2-hydroxy-3,4-dihydro-2H-benzo[e][1,2]oxaborinine-8-carboxylic acid and methanol following the procedure described in Example 132. The crude product was purified by reverse phase preparative HPLC and dried using lyophilization to give the title compound. ESI-MS m/z 264 (MH)⁺.

Example 189

(R)-3-Acetylamino-2-hydroxy-3,4-dihydro-2H-benzo[e][1,2]oxaborinine-8-carboxylic acid ethyl ester

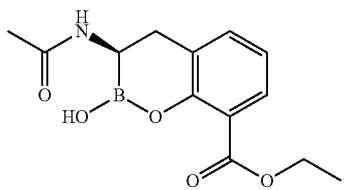 [SMILES: CCOC(=O)c1cccc2c1OB(O)[C@@H](NC(C)=O)C2]

Step 1. Synthesis of 3-[2-Acetylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-acetylamino-2-(2,9,9-trimethyl-3,5-dioxa-4-bora-tricyclo[6.1.1.02,6]dec-4-yl)-ethyl]-2-methoxy-benzoic acid tert-butyl ester (prepared in Step 1 of Example 61) following the procedure described in Step 1 of Example 125. The crude product was carried forward. ESI-MS m/z 416 (MH)⁺.

Step 2. Synthesis of 3-[2-Acetylamino-2-(2,9,9-trimethyl-3,5-dioxa-4-bora-tricyclo[6.1.1.02,6]dec-4-yl)-ethyl]-2-methoxy-benzoic acid ethyl ester.

Prepared from 3-[2-Acetylamino-2-(2,9,9-trimethyl-3,5-dioxa-4-bora-tricyclo[6.1.1.02,6]dec-4-yl)-ethyl]-2-methoxy-benzoic acid and iodoethane following the procedure described in Step 1 of Example 127. The crude product was purified by flash chromatography on silica gel (10-100% EtOAc/Hexane). ESI-MS m/z 444 (MH)⁺.

Step 3. Synthesis of (R)-3-Acetylamino-2-hydroxy-3,4-dihydro-2H-benzo[e][1,2]oxaborinine-8-carboxylic acid ethyl ester.

Prepared from 3-[2-Acetylamino-2-(2,9,9-trimethyl-3,5-dioxa-4-bora-tricyclo[6.1.1.02,6]dec-4-yl)-ethyl]-2-methoxy-benzoic acid ethyl ester following the procedure described in Step 3 of Example 1. The crude product was purified by reverse phase preparative HPLC and dried using lyophilization to give the title compound. ESI-MS m/z 278 (MH)⁺.

Example 190

(R)-3-Acetylamino-2-hydroxy-3,4-dihydro-2H-benzo[e][1,2]oxaborinine-8-carboxylic acid propyl ester

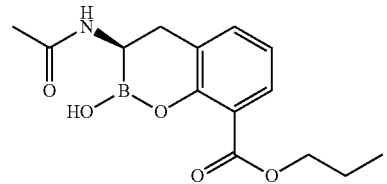 [SMILES: CCCOC(=O)c1cccc2c1OB(O)[C@@H](NC(C)=O)C2]

Step 1. Synthesis of 3-Acetylamino-2-hydroxy-3,4-dihydro-2H-benzo[e][1,2]oxaborinine-8-carboxylic acid.

Prepared from 3-[2-acetylamino-2-(2,9,9-trimethyl-3,5-dioxa-4-bora-tricyclo[6.1.1.02,6]dec-4-yl)-ethyl]-2-methoxy-benzoic acid tert-butyl ester (prepared in Step 1 of Example 61) and 1M boron tribromide in dichloromethane following the procedure described in Step 1 of Example 170. The crude product was purified by reverse phase preparative HPLC and dried using lyophilization to give the title compound. ESI-MS m/z 250 (MH)⁺.

Step 2. Synthesis of 3-Acetylamino-2-hydroxy-3,4-dihydro-2H-benzo[e][1,2]oxaborinine-8-carboxylic acid propyl ester.

Prepared from 3-acetylamino-2-hydroxy-3,4-dihydro-2H-benzo[e][1,2]oxaborinine-8-carboxylic acid and n-propanol following the procedure described in Example 132. The crude product was purified by reverse phase preparative HPLC and dried using lyophilization to give the title compound. ESI-MS m/z 292 (MH)⁺.

Example 191

(R)-3-Acetylamino-2-hydroxy-3,4-dihydro-2H-benzo[e][1,2]oxaborinine-8-carboxylic acid butyl ester

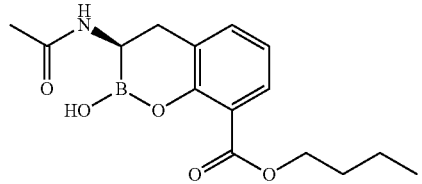 [SMILES: CCCCOC(=O)c1cccc2c1OB(O)[C@@H](NC(C)=O)C2]

Step 1. Synthesis of 3-Acetylamino-2-hydroxy-3,4-dihydro-2H-benzo[e][1,2]oxaborinine-8-carboxylic acid.

Prepared from 3-[2-acetylamino-2-(2,9,9-trimethyl-3,5-dioxa-4-bora-tricyclo[6.1.1.02,6]dec-4-yl)-ethyl]-2-methoxy-benzoic acid tert-butyl ester (prepared in Step 1 of Example 61) and 1M boron tribromide in dichloromethane following the procedure described in Step 1 of Example 170. The crude product was purified by reverse phase preparative HPLC and dried using lyophilization to give the title compound. ESI-MS m/z 250 (MH)⁺.

Step 2. Synthesis of (R)-3-Acetylamino-2-hydroxy-3,4-dihydro-2H-benzo[e][1,2]oxaborinine-8-carboxylic acid butyl ester.

Prepared from 3-acetylamino-2-hydroxy-3,4-dihydro-2H-benzo[e][1,2]oxaborinine-8-carboxylic acid and 1-butanol following the procedure described in Example 132. The crude product was purified by reverse phase preparative HPLC and dried using lyophilization to give the title compound. ESI-MS m/z 306 (MH)+.

Example 192

(R)-3-Acetylamino-2-hydroxy-3,4-dihydro-2H-benzo[e][1,2]oxaborinine-8-carboxylic acid 1-acetoxy-ethyl isobutyl ester

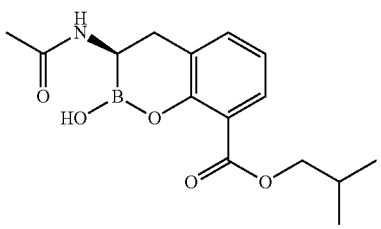 [SMILES: CC(=O)N[C@H]1Cc2cccc(C(=O)OCC(C)C)c2OB1O]

Step 1. Synthesis of 3-Acetylamino-2-hydroxy-3,4-dihydro-2H-benzo[e][1,2]oxaborinine-8-carboxylic acid.

Prepared from 3-[2-acetylamino-2-(2,9,9-trimethyl-3,5-dioxa-4-bora-tricyclo[6.1.1.02,6]dec-4-yl)-ethyl]-2-methoxy-benzoic acid tert-butyl ester (prepared in Step 1 of Example 61) and 1M boron tribromide in dichloromethane following the procedure described in Step 1 of Example 170. The crude product was purified by reverse phase preparative HPLC and dried using lyophilization to give the title compound. ESI-MS m/z 250 (MH)+.

Step 2. Synthesis of 3-Acetylamino-2-hydroxy-3,4-dihydro-2H-benzo[e][1,2]oxaborinine-8-carboxylic acid isobutyl ester Prepared from 3-acetylamino-2-hydroxy-3,4-dihydro-2H-benzo[e][1,2]oxaborinine-8-carboxylic acid. and isobutanol following the procedure described in Example 132. The crude product was purified by reverse phase preparative HPLC and dried using lyophilization to give the title compound. ESI-MS m/z 306 (MH)+.

Example 193

(R)-3-Acetylamino-2-hydroxy-3,4-dihydro-2H-benzo[e][1,2]oxaborinine-8-carboxylic acid 2,2-dimethyl-propionyloxymethyl ester

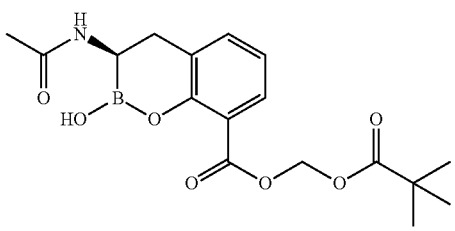 [SMILES: CC(=O)N[C@H]1Cc2cccc(C(=O)OCOC(=O)C(C)(C)C)c2OB1O]

Step 1. Synthesis of 3-[2-Acetylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-acetylamino-2-(2,9,9-trimethyl-3,5-dioxa-4-bora-tricyclo[6.1.1.02,6]dec-4-yl)-ethyl]-2-methoxy-benzoic acid tert-butyl ester (prepared in Step 1 of Example 61) following the procedure described in Step 1 of Example 125. The crude product was carried forward. ESI-MS m/z 416 (MH)+.

Step 2. Synthesis of 3-[2-Acetylamino-2-(2,9,9-trimethyl-3,5-dioxa-4-bora-tricyclo[6.1.1.02,6]dec-4-yl)-ethyl]-2-methoxy-benzoic acid 2,2-dimethyl-propionyloxymethyl ester.

Prepared from 3-[2-Acetylamino-2-(2,9,9-trimethyl-3,5-dioxa-4-bora-tricyclo[6.1.1.02,6]dec-4-yl)-ethyl]-2-methoxy-benzoic acid and chloromethyl pivalate following the procedure described in Step 1 of Example 126. The crude product was purified by flash chromatography on silica gel (10-100% EtOAc/Hexane). ESI-MS m/z 530 (MH)+.

Step 3. Synthesis of (R)-3-Acetylamino-2-hydroxy-3,4-dihydro-2H-benzo[e][1,2]oxaborinine-8-carboxylic acid 2,2-dimethyl-propionyloxymethyl ester.

Prepared from 3-[2-Acetylamino-2-(2,9,9-trimethyl-3,5-dioxa-4-bora-tricyclo[6.1.1.02,6]dec-4-yl)-ethyl]-2-methoxy-benzoic acid 2,2-dimethyl-propionyloxymethyl ester following the procedure described in Step 3 of Example 1. The crude product was purified by reverse phase preparative HPLC and dried using lyophilization to give the title compound. ESI-MS m/z 386 (M+Na)+.

Example 194

(R)-3-Acetylamino-2-hydroxy-3,4-dihydro-2H-benzo[e][1,2]oxaborinine-8-carboxylic acid benzoyloxymethyl ester

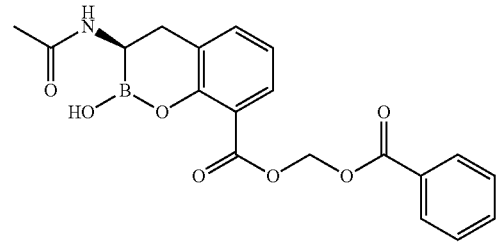 [SMILES: CC(=O)N[C@H]1Cc2cccc(C(=O)OCOC(=O)c3ccccc3)c2OB1O]

Step 1. Synthesis of 3-[2-Acetylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-acetylamino-2-(2,9,9-trimethyl-3,5-dioxa-4-bora-tricyclo[6.1.1.02,6]dec-4-yl)-ethyl]-2-methoxy-benzoic acid tert-butyl ester (prepared in Step 1 of Example 61) following the procedure described in Step 1 of Example 125. The crude product was carried forward. ESI-MS m/z 416 (MH)+.

Step 2. Synthesis of 3-[2-Acetylamino-2-(2,9,9-trimethyl-3,5-dioxa-4-bora-tricyclo[6.1.1.02,6]dec-4-yl)-ethyl]-2-methoxy-benzoic acid benzoyloxymethyl ester.

Prepared from 3-[2-Acetylamino-2-(2,9,9-trimethyl-3,5-dioxa-4-bora-tricyclo[6.1.1.02,6]dec-4-yl)-ethyl]-2-methoxy-benzoic acid and benzoic acid chloromethyl ester following the procedure described in Step 1 of Example 126. The crude product was purified by flash chromatography on silica gel (10-100% EtOAc/Hexane). ESI-MS m/z 550 (MH)+.

Step 3. Synthesis of (R)-3-Acetylamino-2-hydroxy-3,4-dihydro-2H-benzo[e][1,2]oxaborinine-8-carboxylic acid benzoyloxymethyl ester.

Prepared from 3-[2-Acetylamino-2-(2,9,9-trimethyl-3,5-dioxa-4-bora-tricyclo[6.1.1.02,6]dec-4-yl)-ethyl]-2-methoxy-benzoic acid benzoyloxymethyl ester following the procedure described in Step 3 of Example 1. The crude product was purified by reverse phase preparative HPLC and dried using lyophilization to give the title compound. ESI-MS m/z 406 (M+Na)+.

Example 195

(R)-3-Acetylamino-2-hydroxy-3,4-dihydro-2H-benzo[e][1,2]oxaborinine-8-carboxylic acid 2-ethyl-butyryloxymethyl ester

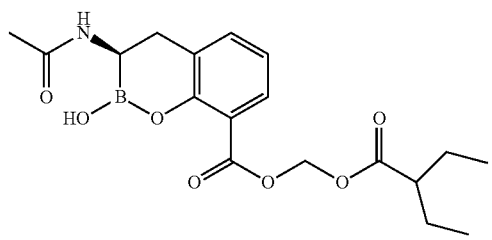 [SMILES: CCC(CC)C(=O)OCOC(=O)c1cccc2c1OB(O)[C@@H](NC(C)=O)C2]

Step 1. Synthesis of 3-[2-Acetylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-acetylamino-2-(2,9,9-trimethyl-3,5-dioxa-4-bora-tricyclo[6.1.1.02,6]dec-4-yl)-ethyl]-2-methoxy-benzoic acid tert-butyl ester (prepared in Step 1 of Example 61) and trifluoroacetic acid following the procedure in Step 2 of Example 169. ESI-MS m/z 416 (MH)+.

Step 2. Synthesis of 3-[2-Acetylamino-2-(2,9,9-trimethyl-3,5-dioxa-4-bora-tricyclo[6.1.1.02,6]dec-4-yl)-ethyl]-2-methoxy-benzoic acid 2-ethyl-butyryloxymethyl ester.

Prepared from 3-[2-acetylamino-2-(2,9,9-trimethyl-3,5-dioxa-4-bora-tricyclo[6.1.1.02,6]dec-4-yl)-ethyl]-2-methoxy-benzoic acid and chloromethyl 2-ethyl butyrate following the procedure described in Step 1 of Example 127. The crude product was purified by flash chromatography on silica gel (70% EtOAc/Hexanes). ESI-MS m/z 544 (MH)+.

Step 3. Synthesis of (R)-3-Acetylamino-2-hydroxy-3,4-dihydro-2H-benzo[e][1,2]oxaborinine-8-carboxylic acid 2-ethyl-butyryloxymethyl ester.

Prepared from 3-[2-acetylamino-2-(2,9,9-trimethyl-3,5-dioxa-4-bora-tricyclo[6.1.1.02,6]dec-4-yl)-ethyl]-2-methoxy-benzoic acid 2-ethyl-butyryloxymethyl ester and aluminum chloride following the procedure described in Step 3 of Example 1. The crude product was purified by reverse phase preparative HPLC and dried using lyophilization to give the title compound. ESI-MS m/z 378 (MH)+.

Example 196

(R)-3-Acetylamino-2-hydroxy-3,4-dihydro-2H-benzo[e][1,2]oxaborinine-8-carboxylic acid 3-oxo-1,3-dihydro-isobenzofuran-1-yl-ester

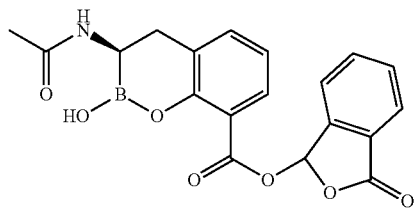 [SMILES: CC(=O)N[C@H]1Cc2cccc(C(=O)OC3OC(=O)c4ccccc43)c2OB1O]

Step 1. Synthesis of 3-[2-Acetylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-acetylamino-2-(2,9,9-trimethyl-3,5-dioxa-4-bora-tricyclo[6.1.1.02,6]dec-4-yl)-ethyl]-2-methoxy-benzoic acid tert-butyl ester (prepared in Step 1 of Example 61) and trifluoroacetic acid following the procedure in Step 2 of Example 169. ESI-MS m/z 416 (MH)+.

Step 2. Synthesis of 3-[2-Acetylamino-2-(2,9,9-trimethyl-3,5-dioxa-4-bora-tricyclo[6.1.1.02,6]dec-4-yl)-ethyl]-2-methoxy-benzoic acid 3-oxo-1,3-dihydroisobenzofuran-1-yl-ester.

To 3-[2-acetylamino-2-(2,9,9-trimethyl-3,5-dioxa-4-bora-tricyclo[6.1.1.02,6]dec-4-yl)-ethyl]-2-methoxy-benzoic acid (0.63 g, 1.51 mmol) in dry N,N-dimethylformamide (10 mL) under an atmosphere of argon was added potassium carbonate (0.62 g, 4.51 mmol), 3-bromophthalide (0.64 g, 3.01 mmol), followed by sodium iodide (0.23 g, 1.51 mmol) and the reaction was stirred at 50° C. overnight. The reaction was diluted with ethyl acetate, washed with water and brine, dried over sodium sulfate, and concentrated. The crude product was purified by flash chromatography on silica gel (100% EtOAc). ESI-MS m/z 548 (MH)+.

Step 4. (R)-3-Acetylamino-2-hydroxy-3,4-dihydro-2H-benzo[e][1,2]oxaborinine-8-carboxylic acid 3-oxo-1,3-dihydro-isobenzofuran-1-yl-ester.

Prepared from of 3-[2-acetylamino-2-(2,9,9-trimethyl-3,5-dioxa-4-bora-tricyclo[6.1.1.02,6]dec-4-yl)-ethyl]-2- methoxy-benzoic acid 3-oxo-1,3-dihydroisobenzofuran-1-yl-ester and aluminum chloride following the procedure described in Step 3 of Example 1. The crude product was purified by reverse phase preparative HPLC and dried using lyophilization to give the title compound. ESI-MS m/z 382 (MH)+.

Example 197

(R)-3-Acetylamino-2-hydroxy-3,4-dihydro-2H-benzo[e][1,2]oxaborinine-8-carboxylic acid cyclohexyloxycarbonyloxymethyl ester

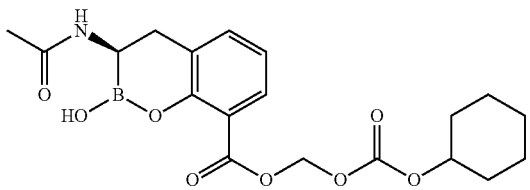 [SMILES: CC(=O)N[C@H]1Cc2cccc(C(=O)OCOC(=O)OC3CCCCC3)c2OB1O]

Step 1. Synthesis of 3-[2-Acetylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-acetylamino-2-(2,9,9-trimethyl-3,5-dioxa-4-bora-tricyclo[6.1.1.02,6]dec-4-yl)-ethyl]-2-methoxy-benzoic acid tert-butyl ester (prepared in Step 1 of Example 61) and trifluoroacetic acid following the procedure in Step 2 of Example 169. ESI-MS m/z 416 (MH)+.

Step 2. Synthesis of 3-[2-Acetylamino-2-(2,9,9-trimethyl-3,5-dioxa-4-bora tricyclo[6.1.1.02,6]dec-4-yl)-ethyl]-2-methoxy-benzoic acid cyclohexyloxycarbonyloxymethyl ester.

Prepared from 3-[2-acetylamino-2-(2,9,9-trimethyl-3,5-dioxa-4-bora-tricyclo[6.1.1.02,6]dec-4-yl)-ethyl]-2-methoxy-benzoic acid and chloromethyl cyclohexyl carbonate following the procedure described in Step 1 of Example 127. The crude product was purified by flash chromatography on silica gel (70% EtOAc/Hexanes). ESI-MS m/z 572 (MH)+.

Step 3. (R)-3-Acetylamino-2-hydroxy-3,4-dihydro-2H-benzo[e][1,2]oxaborinine-8-carboxylic acid. cyclohexyloxycarbonyloxymethyl ester.

Prepared from 3-[2-acetylamino-2-(2,9,9-trimethyl-3,5-dioxa-4-bora tricyclo[6.1.1.02,6]dec-4-yl)-ethyl]-2-methoxy-benzoic acid cyclohexyloxycarbonyloxymethyl ester and aluminum chloride following the procedure described in Step 3 of Example 1. The crude product was purified by reverse phase preparative HPLC and dried using lyophilization to give the title compound. ESI-MS m/z 406 (MH)+.

Example 198

(R)-3-Acetylamino-2-hydroxy-3,4-dihydro-2H-benzo[e][1,2]oxaborinine-8-carboxylic acid acetoxymethyl ester

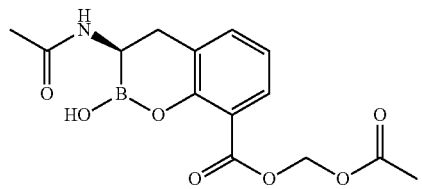 [SMILES: CC(=O)N[C@H]1Cc2cccc(C(=O)OCOC(C)=O)c2OB1O]

Step 1. Synthesis of 3-[2-Acetylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-acetylamino-2-(2,9,9-trimethyl-3,5-dioxa-4-bora-tricyclo[6.1.1.02,6]dec-4-yl)-ethyl]-2-methoxy-benzoic acid tert-butyl ester (prepared in Step 1 of Example 61) and trifluoroacetic acid following the procedure in Step 2 of Example 169. ESI-MS m/z 416 (MH)+.

Step 2. Synthesis of 3-[2-Acetylamino-2-(2,9,9-trimethyl-3,5-dioxa-4-bora tricyclo[6.1.1.02,6]dec-4-yl)-ethyl]-2-methoxy-benzoic acid acetoxymethyl ester.

Prepared from 3-[2-acetylamino-2-(2,9,9-trimethyl-3,5-dioxa-4-bora-tricyclo[6.1.1.02,6]dec-4-yl)-ethyl]-2-methoxy-benzoic acid and bromomethyl acetate following the procedure described in Step 1 of Example 127. The crude product was purified by Prep TLC plates on silica gel (90% EtOAc/Hexanes). ESI-MS m/z 488 (MH)+.

Step 3. Synthesis of (R)-3-Acetylamino-2-hydroxy-3,4-dihydro-2H-benzo[e][1,2]oxaborinine-8-carboxylic acid acetoxymethyl ester.

Prepared from 3-[2-acetylamino-2-(2,9,9-trimethyl-3,5-dioxa-4-bora tricyclo[6.1.1.02,6]dec-4-yl)-ethyl]-2-methoxy-benzoic acid acetoxymethyl ester and aluminum chloride following the procedure described in Step 3 of Example 1. The crude product was purified by reverse phase preparative HPLC and dried using lyophilization to give the title compound. ESI-MS m/z 322 (MH)+.

Example 199

(R)-3-Acetylamino-2-hydroxy-3,4-dihydro-2H-benzo[e][1,2]oxaborinine-8-carboxylic acid 1-acetoxy-ethyl ester

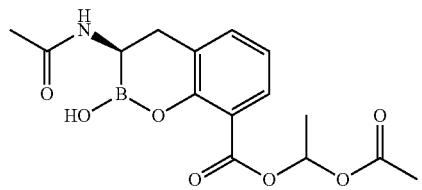 [SMILES: CC(=O)N[C@H]1Cc2cccc(C(=O)OC(C)OC(C)=O)c2OB1O]

Step 1. Synthesis of 3-Acetylamino-2-hydroxy-3,4-dihydro-2H-benzo[e][1,2]oxaborinine-8-carboxylic acid.

Prepared from 3-[2-acetylamino-2-(2,9,9-trimethyl-3,5-dioxa-4-bora-tricyclo[6.1.1.0²,⁶]dec-4-yl)-ethyl]-2-methoxy-benzoic acid tert-butyl ester (prepared in Step 1 of Example 61) and 1M boron tribromide in dichloromethane following the procedure described in Step 1 of Example 170. The crude product was purified by reverse phase preparative HPLC and dried using lyophilization to give the title compound. ESI-MS m/z 250 (MH)⁺.

Step 2. Synthesis of (R)-3-Acetylamino-2-hydroxy-3,4-dihydro-2H-benzo[e][1,2]oxaborinine-8-carboxylic acid 1-acetoxy-ethyl ester.

To 3-acetylamino-2-hydroxy-3,4-dihydro-2H-benzo[e][1,2]oxaborinine-8-carboxylic acid (0.150 g, 0.6 mmol) in acetone (10 mL) under an atmosphere of argon was added potassium carbonate (0.25 g, 1.81 mmol), bromoethyl acetate (0.2 g, 1.2 mmol), followed by sodium iodide (0.09 g, 0.6 mmol) and the reaction was stirred at 50° C. overnight. The reaction was cooled at room temperature, filtered through a pad of celite, washed well with dichloromethane, and concentrated. The crude product was purified by reverse phase preparative HPLC and dried using lyophilization to give the title compound. ESI-MS m/z 336 (MH)⁺.

Example 200

(R)-3-Acetylamino-2-hydroxy-3,4-dihydro-2H-benzo[e][1,2]oxaborinine-8-carboxylic acid 1-cyclohexyloxycarbonyloxyethyl ester

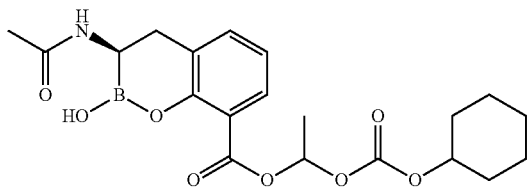 [SMILES: CC(=O)N[C@H]1Cc2cccc(C(=O)OC(C)OC(=O)OC3CCCCC3)c2OB1O]

Step 1. Synthesis of 3-Acetylamino-2-hydroxy-3,4-dihydro-2H-benzo[e][1,2]oxaborinine-8-carboxylic acid.

Prepared from 3-[2-acetylamino-2-(2,9,9-trimethyl-3,5-dioxa-4-bora-tricyclo[6.1.1.0²,⁶]dec-4-yl)-ethyl]-2-methoxy-benzoic acid tert-butyl ester (prepared in Step 1 of Example 61) and 1M boron tribromide in dichloromethane following the procedure described in Step 1 of Example 170. The crude product was purified by reverse phase preparative HPLC and dried using lyophilization to give the title compound. ESI-MS m/z 250 (MH)⁺.

Step 2. Synthesis of (R)-3-Acetylamino-2-hydroxy-3,4-dihydro-2H-benzo[e][1,2]oxaborinine-8-carboxylic acid 1-cyclohexyloxycarbonyloxyethyl ester.

Prepared from 3-acetylamino-2-hydroxy-3,4-dihydro-2H-benzo[e][1,2]oxaborinine-8-carboxylic acid and 1-chloroethyl cyclohexyl carbonate following the procedure described in Step 2 of Example 199. The crude product was purified by reverse phase preparative HPLC and dried using lyophilization to give the title compound. ESI-MS m/z 420 (MH)⁺.

Example 201

(R)-2-Hydroxy-3-propionylamino-3,4-dihydro-2H-benzo[e][1,2]oxaborinine-8-carboxylic acid methyl ester

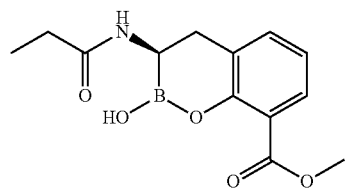 [SMILES: CCC(=O)N[C@H]1Cc2cccc(C(=O)OC)c2OB1O]

Step 1. Synthesis of 2-Methoxy-3-[2-propionylamino-2-(2,9,9-trimethyl-3,5-dioxa-4-bora-tricyclo[6.1.1.0²,⁶]dec-4-yl)-ethyl]-benzoic acid.

Prepared from 2-Methoxy-3-[2-propionylamino-2-(2,9,9-trimethyl-3,5-dioxa-4-bora-tricyclo[6.1.1.0²,⁶]dec-4-yl)-ethyl]-benzoic acid tert-butyl ester (prepared in Step 1 of Example 62) following the procedure described in Step 1 of Example 125. The crude product was carried forward. ESI-MS m/z 430 (MH)⁺.

Step 2. Synthesis of 2-Methoxy-3-[2-propionylamino-2-(2,9,9-trimethyl-3,5-dioxa-4-bora-tricyclo[6.1.1.0²,⁶]dec-4-yl)-ethyl]-benzoic acid methyl ester.

Prepared from 2-Methoxy-3-[2-propionylamino-2-(2,9,9-trimethyl-3,5-dioxa-4-bora-tricyclo[6.1.1.0²,⁶]dec-4-yl)-ethyl]-benzoic acid following the procedure described in Step 2 of Example 125. The crude product was purified by flash chromatography on silica gel (10-100% EtOAc/Hexane). ESI-MS m/z 444 (MH)⁺.

Step 3. Synthesis of (R)-2-Hydroxy-3-propionylamino-3,4-dihydro-2H-benzo[e][1,2]oxaborinine-8-carboxylic acid methyl ester.

Prepared from 2-Methoxy-3-[2-propionylamino-2-(2,9,9-trimethyl-3,5-dioxa-4-bora-tricyclo[6.1.1.0²,⁶]dec-4-yl)-ethyl]-benzoic acid methyl ester following the procedure described in Step 3 of Example 1. The crude product was purified by reverse phase preparative HPLC and dried using lyophilization to give the title compound. ESI-MS m/z 278 (MH)⁺.

Example 202

(R)-2-Hydroxy-3-propionylamino-3,4-dihydro-2H-benzo[e][1,2]oxaborinine-8-carboxylic acid ethyl ester

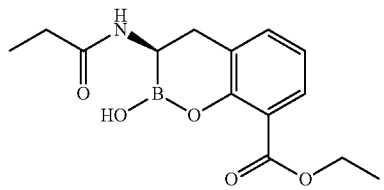 [SMILES: CCOC(=O)c1cccc2c1OB(O)[C@@H](NC(=O)CC)C2]

Step 1. Synthesis of 2-Methoxy-3-[2-propionylamino-2-(2,9,9-trimethyl-3,5-dioxa-4-bora-tricyclo[6.1.1.0²,⁶]dec-4-yl)-ethyl]-benzoic acid.

Prepared from 2-Methoxy-3-[2-propionylamino-2-(2,9,9-trimethyl-3,5-dioxa-4-bora-tricyclo[6.1.1.0²,⁶]dec-4-yl)-ethyl]-benzoic acid tert-butyl ester (prepared in Step 1 of Example 62) following the procedure described in Step 1 of Example 125. The crude product was carried forward. ESI-MS m/z 430 (MH)⁺.

Step 2. Synthesis of 2-Methoxy-3-[2-propionylamino-2-(2,9,9-trimethyl-3,5-dioxa-4-bora-tricyclo[6.1.1.0²,⁶]dec-4-yl)-ethyl]-benzoic acid ethyl ester.

Prepared from 2-Methoxy-3-[2-propionylamino-2-(2,9,9-trimethyl-3,5-dioxa-4-bora-tricyclo[6.1.1.0²,⁶]dec-4-yl)-ethyl]-benzoic acid and iodoethane following the procedure described in Step 1 of Example 127. The crude product was purified by flash chromatography on silica gel (10-100% EtOAc/Hexane). ESI-MS m/z 458 (MH)⁺.

Step 3. Synthesis of (R)-2-Hydroxy-3-propionylamino-3,4-dihydro-2H-benzo[e][1,2]oxaborinine-8-carboxylic acid ethyl ester.

Prepared from 2-Methoxy-3-[2-propionylamino-2-(2,9,9-trimethyl-3,5-dioxa-4-bora-tricyclo[6.1.1.0²,⁶]dec-4-yl)-ethyl]-benzoic acid ethyl ester following the procedure described in Step 3 of Example 1. The crude product was purified by reverse phase preparative HPLC and dried using lyophilization to give the title compound. ESI-MS m/z 292 (MH)⁺.

Example 203

(R)-3-Propionylamino-2-hydroxy-3,4-dihydro-2H-benzo[e][1,2]oxaborinine-8-carboxylic acid propyl ester

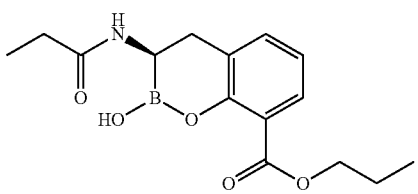 [SMILES: CCCOC(=O)c1cccc2c1OB(O)[C@@H](NC(=O)CC)C2]

Step 1. Synthesis of 3-Propionylamino-2-hydroxy-3,4-dihydro-2H-benzo[e][1,2]oxaborinine-8-carboxylic acid.

Prepared from 3-[2-propionylamino-2-(2,9,9-trimethyl-3,5-dioxa-4-bora-tricyclo[6.1.1.0²,⁶]dec-4-yl)-ethyl]-2-methoxy-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 264 (MH)⁺.

Step 2. Synthesis of (R)-3-Propionylamino-2-hydroxy-3,4-dihydro-2H-benzo[e][1,2]oxaborinine-8-carboxylic acid propyl ester.

Prepared from 3-propionylamino-2-hydroxy-3,4-dihydro-2H-benzo[e][1,2]oxaborinine-8-carboxylic acid and n-propanol following the procedure described in Example 132. The crude product was purified by reverse phase preparative HPLC and dried using lyophilization to give the title compound. ESI-MS m/z 306 (MH)⁺.

Example 204

(R)-2-Hydroxy-3-propionylamino-3,4-dihydro-2H-benzo[e][1,2]oxaborinine-8-carboxylic acid butyl ester

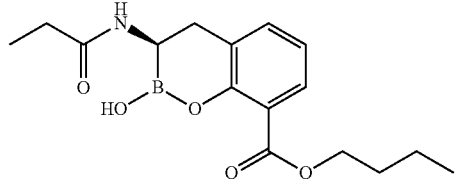 [SMILES: CCCCOC(=O)c1cccc2c1OB(O)[C@@H](NC(=O)CC)C2]

Step 1. Synthesis of 2-Methoxy-3-[2-propionylamino-2-(2,9,9-trimethyl-3,5-dioxa-4-bora-tricyclo[6.1.1.0²,⁶]dec-4-yl)-ethyl]-benzoic acid.

Prepared from 2-Methoxy-3-[2-propionylamino-2-(2,9,9-trimethyl-3,5-dioxa-4-bora-tricyclo[6.1.1.0²,⁶]dec-4-yl)-ethyl]-benzoic acid tert-butyl ester (prepared in Step 1 of Example 62) following the procedure described in Step 1 of Example 125. The crude product was carried forward. ESI-MS m/z 430 (MH)⁺.

Step 2. Synthesis of 2-Methoxy-3-[2-propionylamino-2-(2,9,9-trimethyl-3,5-dioxa-4-bora-tricyclo[6.1.1.0²,⁶]dec-4-yl)-ethyl]-benzoic acid butyl ester.

Prepared from 2-Methoxy-3-[2-propionylamino-2-(2,9,9-trimethyl-3,5-dioxa-4-bora-tricyclo[6.1.1.0²,⁶]dec-4-yl)-ethyl]-benzoic acid and 1-iodobutane following the procedure described in Step 1 of Example 127. The crude product was purified by flash chromatography on silica gel (10-100% EtOAc/Hexane). ESI-MS m/z 458 (MH)⁺.

Step 3. Synthesis of (R)-2-Hydroxy-3-propionylamino-3,4-dihydro-2H-benzo[e][1,2]oxaborinine-8-carboxylic acid butyl ester.

Prepared from 2-Methoxy-3-[2-propionylamino-2-(2,9,9-trimethyl-3,5-dioxa-4-bora-tricyclo[6.1.1.0²,⁶]dec-4-yl)- ethyl]-benzoic acid butyl ester following the procedure described in Step 3 of Example 1. The crude product was purified by reverse phase preparative HPLC and dried using lyophilization to give the title compound. ESI-MS m/z 320 (MH)$^+$.

Example 205

(R)-3-Propionylamino-2-hydroxy-3,4-dihydro-2H-benzo[e][1,2]oxaborinine-8-carboxylic acid isobutyl ester

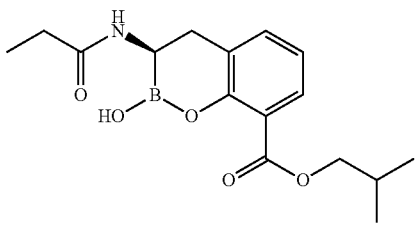 [SMILES: CCC(=O)N[C@H]1Cc2cccc(C(=O)OCC(C)C)c2OB1O]

Step 1. Synthesis of 3-Propionylamino-2-hydroxy-3,4-dihydro-2H-benzo[e][1,2]oxaborinine-8-carboxylic acid.

Prepared from 3-[2-propionylamino-2-(2,9,9-trimethyl-3,5-dioxa-4-bora-tricyclo[6.1.1.02,6]dec-4-yl)-ethyl]-2-methoxy-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 264 (MH)$^+$.

Step 2. Synthesis of 3-Propionylamino-2-hydroxy-3,4-dihydro-2H-benzo[e][1,2]oxaborinine-8-carboxylic acid isobutyl ester.

Prepared from 3-propionylamino-2-hydroxy-3,4-dihydro-2H-benzo[e][1,2]oxaborinine-8-carboxylic acid and isobutanol following the procedure described in Example 132. The crude product was purified by reverse phase preparative HPLC and dried using lyophilization to give the title compound. ESI-MS m/z 320 (MH)$^+$.

Example 206

(R)-2-Hydroxy-3-propionylamino-3,4-dihydro-2H-benzo[e][1,2]oxaborinine-8-carboxylic acid 2,2-dimethyl-propionyloxymethyl ester

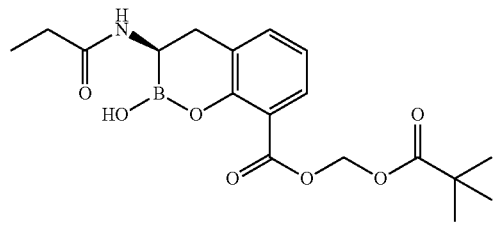 [SMILES: CCC(=O)N[C@H]1Cc2cccc(C(=O)OCOC(=O)C(C)(C)C)c2OB1O]

Step 1. Synthesis of 2-Methoxy-3-[2-propionylamino-2-(2,9,9-trimethyl-3,5-dioxa-4-bora-tricyclo[6.1.1.02,6]dec-4-yl)-ethyl]-benzoic acid.

Prepared from 2-Methoxy-3-[2-propionylamino-2-(2,9,9-trimethyl-3,5-dioxa-4-bora-tricyclo[6.1.1.02,6]dec-4-yl)-ethyl]-benzoic acid tert-butyl ester (prepared in Step 1 of Example 62) following the procedure described in Step 1 of Example 125. The crude product was carried forward. ESI-MS m/z 430 (MH)$^+$.

Step 2. Synthesis of 2-Methoxy-3-[2-propionylamino-2-(2,9,9-trimethyl-3,5-dioxa-4-bora-tricyclo[6.1.1.02,6]dec-4-yl)-ethyl]-benzoic acid 2,2-dimethyl-propionyloxymethyl ester.

Prepared from 2-Methoxy-3-[2-propionylamino-2-(2,9,9-trimethyl-3,5-dioxa-4-bora-tricyclo[6.1.1.02,6]dec-4-yl)-ethyl]-benzoic acid and chloromethyl pivalate following the procedure described in Step 1 of Example 127. The crude product was purified by flash chromatography on silica gel (10-100% EtOAc/Hexane). ESI-MS m/z 544 (MH)$^+$.

Step 3. Synthesis of (R)-2-Hydroxy-3-propionylamino-3,4-dihydro-2H-benzo[e][1,2]oxaborinine-8-carboxylic acid 2,2-dimethyl-propionyloxymethyl ester.

Prepared from 2-Methoxy-3-[2-propionylamino-2-(2,9,9-trimethyl-3,5-dioxa-4-bora-tricyclo[6.1.1.02,6]dec-4-yl)-ethyl]-benzoic acid 2,2-dimethyl-propionyloxymethyl ester following the procedure described in Step 3 of Example 1. The crude product was purified by reverse phase preparative HPLC and dried using lyophilization to give the title compound. ESI-MS m/z 400 (M+Na)$^+$.

Example 207

(R)-3-Propionylamino-2-hydroxy-3,4-dihydro-2H-benzo[e][1,2]oxaborinine-8-carboxylic acid benzoyloxymethyl ester

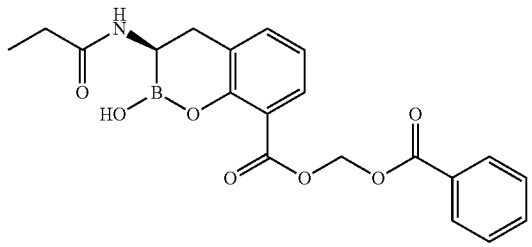 [SMILES: CCC(=O)N[C@H]1Cc2cccc(C(=O)OCOC(=O)c3ccccc3)c2OB1O]

Step 1. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-propionylamino-2-(2,9,9-trimethyl-3,5-dioxa-4-bora-tricyclo[6.1.1.02,6]dec-4-yl)-ethyl]-2-methoxy-benzoic acid tert-butyl ester and trifluoroacetic acid following the procedure in Step 2 of Example 169. ESI-MS m/z 430 (MH)$^+$.

Step 2. Synthesis of 3-[2-Propionylamino-2-(2,9,9-trimethyl-3,5-dioxa-4-bora tricyclo[6.1.1.0 2,6]dec-4-yl)-ethyl]-2-methoxy-benzoic acid benzoyloxymethyl ester.

Prepared from 3-[2-propionylamino-2-(2,9,9-trimethyl-3,5-dioxa-4-bora-tricyclo[6.1.1.0 2,6]dec-4-yl)-ethyl]-2-methoxy-benzoic acid and benzoic acid chloromethyl ester following the procedure described in Step 1 of Example 127. The crude product was purified by Prep TLC plates on silica gel (70% EtOAc/Hexane). ESI-MS m/z 564 (MH)+.

Step 3. Synthesis of (R)-3-Propionylamino-2-hydroxy-3,4-dihydro-2H-benzo[e][1,2]oxaborinine-8-carboxylic acid benzoyloxymethyl ester.

Prepared from 3-[2-propionylamino-2-(2,9,9-trimethyl-3,5-dioxa-4-bora tricyclo[6.1.1.0 2,6]dec-4-yl)-ethyl]-2-methoxy-benzoic acid benzoyloxymethyl ester and aluminum chloride following the procedure described in Step 3 of Example 1. The crude product was purified by reverse phase preparative HPLC and dried using lyophilization to give the title compound. ESI-MS m/z 398 (MH)+.

Example 208

(R)-3-Propionylamino-2-hydroxy-3,4-dihydro-2H-benzo[e][1,2]oxaborinine-8-carboxylic acid acetoxymethyl ester

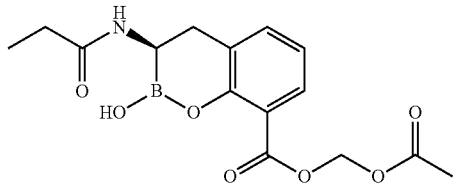 [SMILES: CCC(=O)N[C@H]1Cc2cccc(C(=O)OCOC(C)=O)c2OB1O]

Step 1. Synthesis of 3-[2-Propionylamino-2-(2,9,9-trimethyl-3,5-dioxa-4-bora-tricyclo[6.1.1.0 2,6]dec-4-yl)-ethyl]-2-methoxy-benzoic acid.

Prepared from 3-[2-propionylamino-2-(2,9,9-trimethyl-3,5-dioxa-4-bora-tricyclo[6.1.1.0 2,6]dec-4-yl)-ethyl]-2-methoxy-benzoic acid tert-butyl ester and trifluoroacetic acid following the procedure in Step 2 of Example 169. ESI-MS m/z 430 (MH)+.

Step 2. Synthesis of 3-[2-Propionylamino-2-(2,9,9-trimethyl-3,5-dioxa-4-bora tricyclo[6.1.1.0 2,6]dec-4-yl)-ethyl]-2-methoxy-benzoic acid acetoxymethyl ester.

Prepared from 3-[2-propionylamino-2-(2,9,9-trimethyl-3,5-dioxa-4-bora-tricyclo[6.1.1.0 2,6]dec-4-yl)-ethyl]-2-methoxy-benzoic acid and bromomethyl acetate following the procedure described in Step 1 of Example 127. The crude product was purified by Prep TLC plates on silica gel (90% EtOAc/Hexane). ESI-MS m/z 502 (MH)+.

Step 3. Synthesis of (R)-3-Propionylamino-2-hydroxy-3,4-dihydro-2H-benzo[e][1,2]oxaborinine-8-carboxylic acid acetoxymethyl ester.

Prepared from 3-[2-propionylamino-2-(2,9,9-trimethyl-3,5-dioxa-4-bora tricyclo[6.1.1.0 2,6]dec-4-yl)-ethyl]-2-methoxy-benzoic acid acetoxymethyl ester and aluminum chloride following the procedure described in Step 3 of Example 1. The crude product was purified by reverse phase preparative HPLC and dried using lyophilization to give the title compound. ESI-MS m/z 336 (MH)+.

Example 209

(R)-3-Butyrylamino-2-hydroxy-3,4-dihydro-2H-benzo[e][1,2]oxaborinine-8-carboxylic acid methyl ester

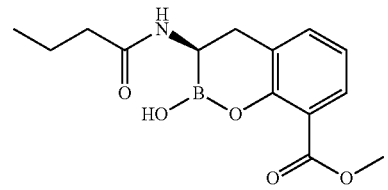 [SMILES: CCCC(=O)N[C@H]1Cc2cccc(C(=O)OC)c2OB1O]

Step 1. Synthesis of 3-[2-Butyrylamino-2-(2,9,9-trimethyl-3,5-dioxa-4-bora-tricyclo[6.1.1.0 2,6]dec-4-yl)-ethyl]-2-methoxy-benzoic acid.

Prepared from 3-[2-Butyrylamino-2-(2,9,9-trimethyl-3,5-dioxa-4-bora-tricyclo[6.1.1.0 2,6]dec-4-yl)-ethyl]-2-methoxy-benzoic acid tert-butyl ester (prepared in Step 2 of Example 1) following the procedure described in Step 1 of Example 125. The crude product was carried forward. ESI-MS m/z 444 (MH)+.

Step 2. Synthesis of 3-[2-Butyrylamino-2-(2,9,9-trimethyl-3,5-dioxa-4-bora-tricyclo[6.1.1.0 2,6]dec-4-yl)-ethyl]-2-methoxy-benzoic acid methyl ester.

Prepared from 3-[2-Butyrylamino-2-(2,9,9-trimethyl-3,5-dioxa-4-bora-tricyclo[6.1.1.0 2,6]dec-4-yl)-ethyl]-2-methoxy-benzoic acid following the procedure described in Step 2 of Example 125. The crude product was purified by flash chromatography on silica gel (10-100% EtOAc/Hexane). ESI-MS m/z 458 (MH)+.

Step 3. Synthesis of (R)-3-Butyrylamino-2-hydroxy-3,4-dihydro-2H-benzo[e][1,2]oxaborinine-8-carboxylic acid methyl ester.

Prepared from 3-[2-Butyrylamino-2-(2,9,9-trimethyl-3,5-dioxa-4-bora-tricyclo[6.1.1.0 2,6]dec-4-yl)-ethyl]-2-methoxy-benzoic acid methyl ester following the procedure described in Step 3 of Example 1. The crude product was purified by reverse phase preparative HPLC and dried using lyophilization to give the title compound. ESI-MS m/z 292 (MH)+.

Example 210

(R)-3-Butyrylamino-2-hydroxy-3,4-dihydro-2H-benzo[e][1,2]oxaborinine-8-carboxylic acid 2,2-dimethyl-propionyloxymethyl ester

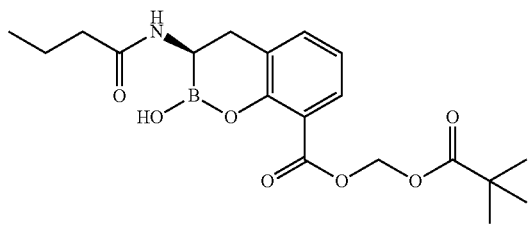 [SMILES: CCCC(=O)N[C@H]1Cc2cccc(C(=O)OCOC(=O)C(C)(C)C)c2OB1O]

Step 1. Synthesis of 3-[2-Butyrylamino-2-(2,9,9-trimethyl-3,5-dioxa-4-bora-tricyclo[6.1.1.0²,⁶]dec-4-yl)-ethyl]-2-methoxy-benzoic acid.

Prepared from 3-[2-Butyrylamino-2-(2,9,9-trimethyl-3,5-dioxa-4-bora-tricyclo[6.1.1.0²,⁶]dec-4-yl)-ethyl]-2-methoxy-benzoic acid tert-butyl ester (prepared in Step 2 of Example 1) following the procedure described in Step 1 of Example 125. The crude product was carried forward. ESI-MS m/z 444 (MH)⁺.

Step 2. Synthesis of 3-[2-Butyrylamino-2-(2,9,9-trimethyl-3,5-dioxa-4-bora-tricyclo[6.1.1.0²,⁶]dec-4-yl)-ethyl]-2-methoxy-benzoic acid 2,2-dimethyl-propionyloxymethyl ester.

Prepared from 3-[2-Butyrylamino-2-(2,9,9-trimethyl-3,5-dioxa-4-bora-tricyclo[6.1.1.0²,⁶]dec-4-yl)-ethyl]-2-methoxy-benzoic acid and chloromethyl pivalate following the procedure described in Step 1 of Example 127. The crude product was purified by flash chromatography on silica gel (10-100% EtOAc/Hexane). ESI-MS m/z 558 (MH)⁺.

Step 3. Synthesis of (R)-3-Butyrylamino-2-hydroxy-3,4-dihydro-2H-benzo[e][1,2]oxaborinine-8-carboxylic acid 2,2-dimethyl-propionyloxymethyl ester.

Prepared from 3-[2-Butyrylamino-2-(2,9,9-trimethyl-3,5-dioxa-4-bora-tricyclo[6.1.1.0²,⁶]dec-4-yl)-ethyl]-2-methoxy-benzoic acid 2,2-dimethyl-propionyloxymethyl ester following the procedure described in Step 3 of Example 1. The crude product was purified by reverse phase preparative HPLC and dried using lyophilization to give the title compound. ESI-MS m/z 414 (M+Na)⁺.

Example 211

(R)-3-(2-2,3-Dihydro-1H-isoindol-5-yl-acetylamino)-2-hydroxy-3,4-dihydro-2H-benzo[e][1,2]oxaborinine-8-carboxylic acid methyl ester

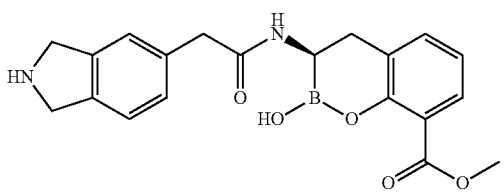 [SMILES: COC(=O)c1cccc2c1OB(O)[C@@H](NC(=O)Cc1ccc3c(c1)CNC3)C2]

Step 1. Synthesis of 3-(2-2,3-Dihydro-1H-isoindol-5-yl-acetylamino)-2-hydroxy-3,4-dihydro-2H-benzo[e][1,2]oxaborinine-8-carboxylic acid.

Prepared from 3-[2-(2-2,3-Dihydro-1H-isoindol-5-yl-acetylamino)-2-(2,9,9-trimethyl-3,5-dioxa-4-bora-tricyclo[6.1.1.0²,⁶]dec-4-yl)-ethyl]-2-methoxy-benzoic acid tert-butyl ester (prepared in Step 1 of Example 64) following the procedure described in Example 7. The crude product was purified by reverse phase preparative HPLC and dried using lyophilization to give the title compound. ESI-MS m/z 367 (MH)⁺.

Step 2. Synthesis of (R)-3-(2-2,3-Dihydro-1H-isoindol-5-yl-acetylamino)-2-hydroxy-3,4-dihydro-2H-benzo[e][1,2]oxaborinine-8-carboxylic acid methyl ester.

Prepared from 3-(2-2,3-Dihydro-1H-isoindol-5-yl-acetylamino)-2-hydroxy-3,4-dihydro-2H-benzo[e][1,2]oxaborinine-8-carboxylic acid and methanol following the procedure described in Example 132. The crude product was purified by reverse phase preparative HPLC and dried using lyophilization to give the title compound. ESI-MS m/z 381 (MH)⁺.

Example 212

(R)-3-(2-2,3-Dihydro-1H-isoindol-5-yl-acetylamino)-2-hydroxy-3,4-dihydro-2H-benzo[e][1,2]oxaborinine-8-carboxylic acid ethyl ester

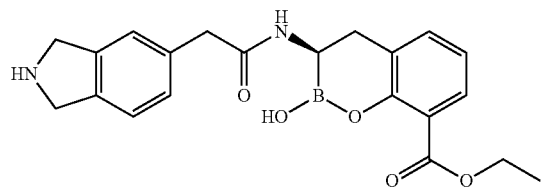 [SMILES: CCOC(=O)c1cccc2c1OB(O)[C@@H](NC(=O)Cc1ccc3c(c1)CNC3)C2]

Step 1. Synthesis of 3-(2-2,3-Dihydro-1H-isoindol-5-yl-acetylamino)-2-hydroxy-3,4-dihydro-2H-benzo[e][1,2]oxaborinine-8-carboxylic acid.

Prepared from 3-[2-(2-2,3-Dihydro-1H-isoindol-5-yl-acetylamino)-2-(2,9,9-trimethyl-3,5-dioxa-4-bora-tricyclo[6.1.1.0²,⁶]dec-4-yl)-ethyl]-2-methoxy-benzoic acid tert-butyl ester (prepared in Step 1 of Example 64) following the procedure described in Example 7. The crude product was purified by reverse phase preparative HPLC and dried using lyophilization to give the title compound. ESI-MS m/z 367 (MH)⁺.

Step 2. Synthesis of (R)-3-(2-2,3-Dihydro-1H-isoindol-5-yl-acetylamino)-2-hydroxy-3,4-dihydro-2H-benzo[e][1,2]oxaborinine-8-carboxylic acid ethyl ester.

Prepared from 3-(2-2,3-Dihydro-1H-isoindol-5-yl-acetylamino)-2-hydroxy-3,4-dihydro-2H-benzo[e][1,2]oxaborinine-8-carboxylic acid and ethanol following the procedure described in Example 132. The crude product was purified by reverse phase preparative HPLC and dried using lyophilization to give the title compound. ESI-MS m/z 395 (MH)⁺.

Example 213

(R)-3-(2-2,3-Dihydro-1H-isoindol-5-yl-acetylamino)-2-hydroxy-3,4-dihydro-2H-benzo[e][1,2]oxaborinine-8-carboxylic acid butyl ester

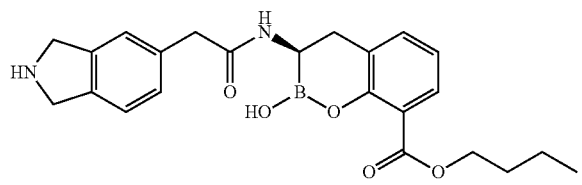 [SMILES: CCCCOC(=O)c1cccc2c1OB(O)[C@@H](NC(=O)Cc1ccc3c(c1)CNC3)C2]

Step 1. Synthesis of 3-(2-2,3-Dihydro-1H-isoindol-5-yl-acetylamino)-2-hydroxy-3,4-dihydro-2H-benzo[e][1,2]oxaborinine-8-carboxylic acid.

Prepared from 3-[2-(2-2,3-Dihydro-1H-isoindol-5-yl-acetylamino)-2-(2,9,9-trimethyl-3,5-dioxa-4-bora-tricyclo[6.1.1.02,6]dec-4-yl)-ethyl]-2-methoxy-benzoic acid tert-butyl ester (prepared in Step 1 of Example 64) following the procedure described in Example 7. The crude product was purified by reverse phase preparative HPLC and dried using lyophilization to give the title compound. ESI-MS m/z 367 (MH)+.

Step 2. Synthesis of (R)-3-(2-2,3-Dihydro-1H-isoindol-5-yl-acetylamino)-2-hydroxy-3,4-dihydro-2H-benzo[e][1,2]oxaborinine-8-carboxylic acid butyl ester.

Prepared from 3-(2-2,3-Dihydro-1H-isoindol-5-yl-acetylamino)-2-hydroxy-3,4-dihydro-2H-benzo[e][1,2]oxaborinine-8-carboxylic acid and n-butanol following the procedure described in Example 132. The crude product was purified by reverse phase preparative HPLC and dried using lyophilization to give the title compound. ESI-MS m/z 423 (MH)+.

Example 214

(R)-2-Hydroxy-3-(2-pyridin-4-yl-acetylamino)-3,4-dihydro-2H-benzo[e][1,2]oxaborinine-8-carboxylic acid methyl ester

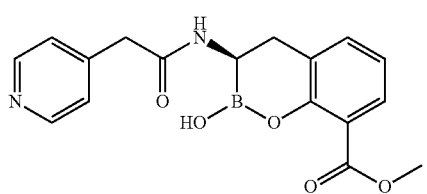 [SMILES: COC(=O)c1cccc2c1OB(O)[C@@H](NC(=O)Cc1ccncc1)C2]

Step 1. Synthesis of 2-Hydroxy-3-(2-pyridin-4-yl-acetylamino)-3,4-dihydro-2H-benzo[e][1,2]oxaborinine-8-carboxylic acid.

Prepared from 2-Methoxy-3-[2-(2-pyridin-4-yl-acetylamino)-2-(2,9,9-trimethyl-3,5-dioxa-4-bora-tricyclo[6.1.1.02,6]dec-4-yl)-ethyl]-benzoic acid tert-butyl ester (prepared in Step 1 of Example 65) following the procedure described in Example 7. The crude product was purified by reverse phase preparative HPLC and dried using lyophilization to give the title compound. ESI-MS m/z 327 (MH)+.

Step 2. Synthesis of (R)-2-Hydroxy-3-(2-pyridin-4-yl-acetylamino)-3,4-dihydro-2H-benzo[e][1,2]oxaborinine-8-carboxylic acid methyl ester.

Prepared from 2-Hydroxy-3-(2-pyridin-4-yl-acetylamino)-3,4-dihydro-2H-benzo[e][1,2]oxaborinine-8-carboxylic acid and methanol following the procedure described in Example 132. The crude product was purified by reverse phase preparative HPLC and dried using lyophilization to give the title compound. ESI-MS m/z 341 (MH)+.

Example 215

(R)-2-Hydroxy-3-(2-pyridin-4-yl-acetylamino)-3,4-dihydro-2H-benzo[e][1,2]oxaborinine-8-carboxylic acid butyl ester

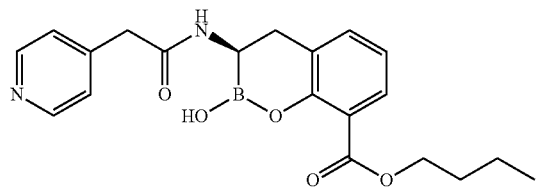 [SMILES: CCCCOC(=O)c1cccc2c1OB(O)[C@@H](NC(=O)Cc1ccncc1)C2]

Step 1. Synthesis of 2-Hydroxy-3-(2-pyridin-4-yl-acetylamino)-3,4-dihydro-2H-benzo[e][1,2]oxaborinine-8-carboxylic acid.

Prepared from 2-Methoxy-3-[2-(2-pyridin-4-yl-acetylamino)-2-(2,9,9-trimethyl-3,5-dioxa-4-bora-tricyclo[6.1.1.02,6]dec-4-yl)-ethyl]-benzoic acid tert-butyl ester (prepared in Step 1 of Example 65) following the procedure described in Example 7. The crude product was purified by reverse phase preparative HPLC and dried using lyophilization to give the title compound. ESI-MS m/z 327 (MH)+.

Step 2. Synthesis of (R)-2-Hydroxy-3-(2-pyridin-4-yl-acetylamino)-3,4-dihydro-2H-benzo[e][1,2]oxaborinine-8-carboxylic acid butyl ester.

Prepared from 2-Hydroxy-3-(2-pyridin-4-yl-acetylamino)-3,4-dihydro-2H-benzo[e][1,2]oxaborinine-8-carboxylic acid and n-butanol following the procedure described in Example 132. The crude product was purified by reverse phase preparative HPLC and dried using lyophilization to give the title compound. ESI-MS m/z 383 (MH)+.

Example 216

(R)-3-Propionylamino-2-hydroxy-3,4-dihydro-2H-benzo[e][1,2]oxaborinine-8-carboxylic acid 1-acetoxyethyl ester

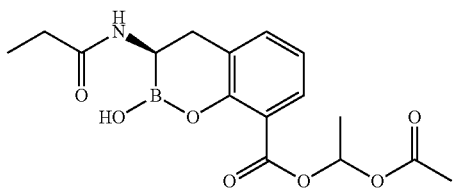 [SMILES: CCC(=O)N[C@H]1Cc2cccc(C(=O)OC(C)OC(C)=O)c2OB1O]

Step 1. Synthesis of 3-Propionylamino-2-hydroxy-3,4-dihydro-2H-benzo[e][1,2]oxaborinine-8-carboxylic acid.

Prepared from 3-[2-propionylamino-2-(2,9,9-trimethyl-3,5-dioxa-4-bora-tricyclo[6.1.1.02,6]dec-4-yl)-ethyl]-2-methoxy-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 264 (MH)+.

Step 2. Synthesis of (R)-3-Propionylamino-2-hydroxy-3,4-dihydro-2H-benzo[e][1,2]oxaborinine-8-carboxylic acid 1-acetoxyethyl ester.

Prepared from 3-propionylamino-2-hydroxy-3,4-dihydro-2H-benzo[e][1,2]oxaborinine-8-carboxylic acid and bromoethyl acetate following the procedure described in Step 1 of Example 127. The crude product was purified by reverse phase preparative HPLC and dried using lyophilization to give the title compound. ESI-MS m/z 350 (MH)+.

Example 217

(R)-3-Propionylamino-2-hydroxy-3,4-dihydro-2H-benzo[e][1,2]oxaborinine-8-carboxylic acid cyclohexyloxycarbonyloxymethyl ester

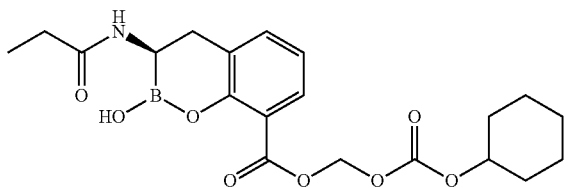 [SMILES: CCC(=O)N[C@H]1Cc2cccc(C(=O)OCOC(=O)OC3CCCCC3)c2OB1O]

Step 1. Synthesis of 3-Propionylamino-2-hydroxy-3,4-dihydro-2H-benzo[e][1,2]oxaborinine-8-carboxylic acid.

Prepared from 3-[2-propionylamino-2-(2,9,9-trimethyl-3,5-dioxa-4-bora-tricyclo[6.1.1.02,6]dec-4-yl)-ethyl]-2-methoxy-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 264 (MH)+.

Step 2. Synthesis of (R)-3-Propionylamino-2-hydroxy-3,4-dihydro-2H-benzo[e][1,2]oxaborinine-8-carboxylic acid cyclohexyloxycarbonyloxymethyl ester.

Prepared from 3-propionylamino-2-hydroxy-3,4-dihydro-2H-benzo[e][1,2]oxaborinine-8-carboxylic acid and chloromethyl cyclohexyl carbonate following the procedure described in Step 1 of Example 127. The crude product was purified by reverse phase preparative HPLC and dried using lyophilization to give the title compound. ESI-MS m/z 420 (MH)+.

Example 218

(R)-3-Butyrylamino-2-hydroxy-3,4-dihydro-2H-benzo[e][1,2]oxaborinine-8-carboxylic acid ethyl ester

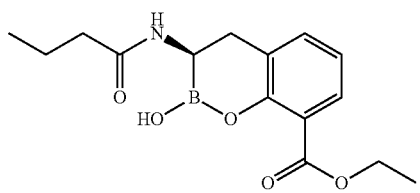 [SMILES: CCCC(=O)N[C@H]1Cc2cccc(C(=O)OCC)c2OB1O]

Step 1. Synthesis of 3-Butyrylamino-2-hydroxy-3,4-dihydro-2H-benzo[e][1,2]oxaborinine-8-carboxylic acid.

Prepared from 3-[2-butyrylamino-2-(2,9,9-trimethyl-3,5-dioxa-4-bora-tricyclo[6.1.1.02,6]dec-4-yl)-ethyl]-2-methoxy-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 278 (MH)+.

Step 2. Synthesis of (R)-3-Butyrylamino-2-hydroxy-3,4-dihydro-2H-benzo[e][1,2]oxaborinine-8-carboxylic acid ethyl ester.

Prepared from 3-butyrylamino-2-hydroxy-3,4-dihydro-2H-benzo[e][1,2]oxaborinine-8-carboxylic acid and ethanol following the procedure described in Example 132. The crude product was purified by reverse phase preparative HPLC and dried using lyophilization to give the title compound. ESI-MS m/z 306 (MH)+.

Example 219

(R)-3-Butyrylamino-2-hydroxy-3,4-dihydro-2H-benzo[e][1,2]oxaborinine-8-carboxylic acid propyl ester

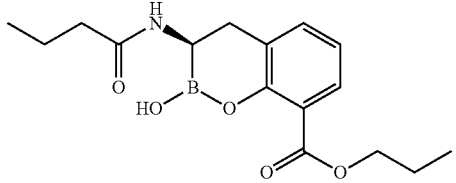 [SMILES: CCCOC(=O)c1cccc2c1OB(O)[C@@H](NC(=O)CCC)C2]

Step 1. Synthesis of 3-Butyrylamino-2-hydroxy-3,4-dihydro-2H-benzo[e][1,2]oxaborinine-8-carboxylic acid.

Prepared from 3-[2-butyrylamino-2-(2,9,9-trimethyl-3,5-dioxa-4-bora-tricyclo[6.1.1.02,6]dec-4-yl)-ethyl]-2-methoxy-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 278 (MH)+.

Step 2. Synthesis of (R)-3-Butyrylamino-2-hydroxy-3,4-dihydro-2H-benzo[e][1,2]oxaborinine-8-carboxylic acid propyl ester.

Prepared from 3-butyrylamino-2-hydroxy-3,4-dihydro-2H-benzo[e][1,2]oxaborinine-8-carboxylic acid and 1-propanol following the procedure described in Example 132. The crude product was purified by reverse phase preparative HPLC and dried using lyophilization to give the title compound. ESI-MS m/z 320 (MH)+.

Example 220

(R)-3-Butyrylamino-2-hydroxy-3,4-dihydro-2H-benzo[e][1,2]oxaborinine-8-carboxylic acid butyl ester

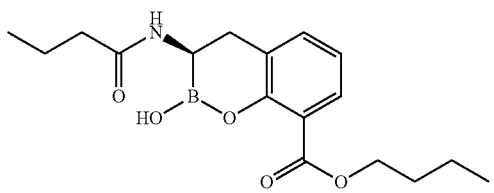 [SMILES: CCCCOC(=O)c1cccc2c1OB(O)[C@@H](NC(=O)CCC)C2]

Step 1. Synthesis of 3-Butyrylamino-2-hydroxy-3,4-dihydro-2H-benzo[e][1,2]oxaborinine-8-carboxylic acid.

Prepared from 3-[2-butyrylamino-2-(2,9,9-trimethyl-3,5-dioxa-4-bora-tricyclo[6.1.1.02,6]dec-4-yl)-ethyl]-2-methoxy-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 278 (MH)+.

Step 2. Synthesis of (R)-3-Butyrylamino-2-hydroxy-3,4-dihydro-2H-benzo[e][1,2]oxaborinine-8-carboxylic acid butyl ester.

Prepared from 3-butyrylamino-2-hydroxy-3,4-dihydro-2H-benzo[e][1,2]oxaborinine-8-carboxylic acid and 1-butanol following the procedure described in Example 132. The crude product was purified by reverse phase preparative HPLC and dried using lyophilization to give the title compound. ESI-MS m/z 334 (MH)+.

Example 221

(R)-3-Butyrylamino-2-hydroxy-3,4-dihydro-2H-benzo[e][1,2]oxaborinine-8-carboxylic acid isobutyl ester

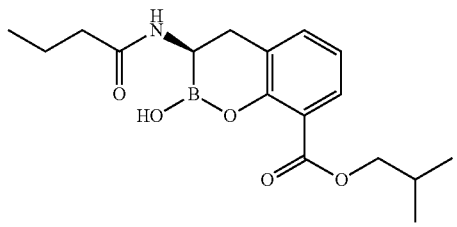 [SMILES: CCCC(=O)N[C@H]1Cc2cccc(C(=O)OCC(C)C)c2OB1O]

Step 1. Synthesis of 3-Butyrylamino-2-hydroxy-3,4-dihydro-2H-benzo[e][1,2]oxaborinine-8-carboxylic acid.

Prepared from 3-[2-butyrylamino-2-(2,9,9-trimethyl-3,5-dioxa-4-bora-tricyclo[6.1.1.02,6]dec-4-yl)-ethyl]-2-methoxy-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 278 (MH)+.

Step 2. Synthesis of (R)-3-Butyrylamino-2-hydroxy-3,4-dihydro-2H-benzo[e][1,2]oxaborinine-8-carboxylic acid butyl ester.

Prepared from 3-butyrylamino-2-hydroxy-3,4-dihydro-2H-benzo[e][1,2]oxaborinine-8-carboxylic acid and isobutanol following the procedure described in Example 132. The crude product was purified by reverse phase preparative HPLC and dried using lyophilization to give the title compound. ESI-MS m/z 334 (MH)+.

Example 222

(R)-3-Butyrylamino-2-hydroxy-3,4-dihydro-2H-benzo[e][1,2]oxaborinine-8-carboxylic acid benzoyloxymethyl ester

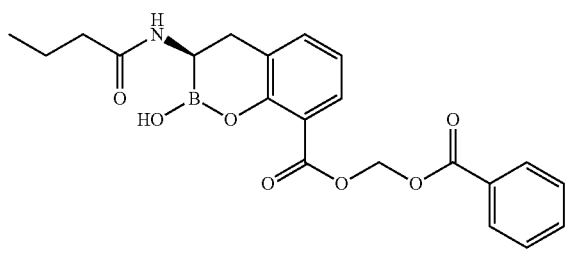 [SMILES: CCCC(=O)N[C@H]1Cc2cccc(C(=O)OCOC(=O)c3ccccc3)c2OB1O]

Step 1. Synthesis of 3-[2-Butyrylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-butyrylamino-2-(2,9,9-trimethyl-3,5-dioxa-4-bora-tricyclo[6.1.1.02,6]dec-4-yl)-ethyl]-2-methoxy-benzoic acid tert-butyl ester and trifluoroacetic acid following the procedure in Step 2 of Example 169. ESI-MS m/z 444 (MH)+.

Step 2. Synthesis of 3-[2-Butyrylamino-2-(2,9,9-trimethyl-3,5-dioxa-4-bora-tricyclo[6.1.1.02,6]dec-4-yl)-ethyl]-2-methoxy-benzoic acid benzoyloxymethyl ester.

Prepared from 3-[2-butyrylamino-2-(2,9,9-trimethyl-3,5-dioxa-4-bora-tricyclo[6.1.1.02,6]dec-4-yl)-ethyl]-2-methoxy-benzoic acid and benzoic acid chloromethyl ester following the procedure described in Step 1 of Example 127. The crude product was purified by Prep TLC plates on silica gel (70% EtOAc/Hexane). ESI-MS m/z 578 (MH)+.

Step 3. Synthesis of (R)-3-Butyrylamino-2-hydroxy-3,4-dihydro-2H-benzo[e][1,2]oxaborinine-8-carboxylic acid benzoyloxymethyl ester.

Prepared from 3-[2-butyrylamino-2-(2,9,9-trimethyl-3,5-dioxa-4-bora tricyclo[6.1.1.02,6]dec-4-yl)-ethyl]-2-methoxy-benzoic acid benzoyloxymethyl ester and aluminum chloride following the procedure described in Step 3 of Example 1. The crude product was purified by reverse phase preparative HPLC and dried using lyophilization to give the title compound. ESI-MS m/z 412 (MH)+.

Example 223

(R)-3-Butyrylamino-2-hydroxy-3,4-dihydro-2H-benzo[e][1,2]oxaborinine-8-carboxylic acid acetoxymethyl ester

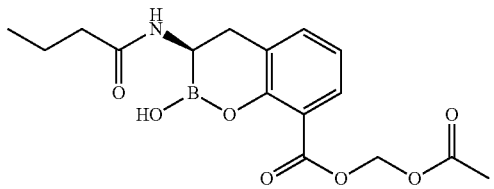 [SMILES: CCCC(=O)N[C@H]1Cc2cccc(C(=O)OCOC(C)=O)c2OB1O]

Step 1. Synthesis of 3-[2-Butyrylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-butyrylamino-2-(2,9,9-trimethyl-3,5-dioxa-4-bora-tricyclo[6.1.1.02,6]dec-4-yl)-ethyl]-2-methoxy-benzoic acid tert-butyl ester and trifluoroacetic acid following the procedure in Step 2 of Example 169. ESI-MS m/z 444 (MH)+.

Step 2. Synthesis of 3-[2-Butyrylamino-2-(2,9,9-trimethyl-3,5-dioxa-4-bora-tricyclo[6.1.1.02,6]dec-4-yl)-ethyl]-2-methoxy-benzoic acid acetoxymethyl ester.

Prepared from 3-[2-butyrylamino-2-(2,9,9-trimethyl-3,5-dioxa-4-bora-tricyclo[6.1.1.02,6]dec-4-yl)-ethyl]-2-methoxy-benzoic acid and bromomethyl acetate following the procedure described in Step 1 of Example 127. The crude product was purified by Prep TLC plates on silica gel (70% EtOAc/Hexane). ESI-MS m/z 516 (MH)+.

Step 3. Synthesis of (R)-3-Butyrylamino-2-hydroxy-3,4-dihydro-2H-benzo[e][1,2]oxaborinine-8-carboxylic acid acetoxymethyl ester.

Prepared from 3-[2-butyrylamino-2-(2,9,9-trimethyl-3,5-dioxa-4-bora tricyclo[6.1.1.02,6]dec-4-yl)-ethyl]-2-methoxy-benzoic acid acetoxymethyl ester and aluminum chloride following the procedure described in Step 3 of Example 1. The crude product was purified by reverse phase preparative HPLC and dried using lyophilization to give the title compound. ESI-MS m/z 350 (MH)+.

Example 224

(R)-3-Butyrylamino-2-hydroxy-3,4-dihydro-2H-benzo[e][1,2]oxaborinine-8-carboxylic acid acetoxy-ethyl ester

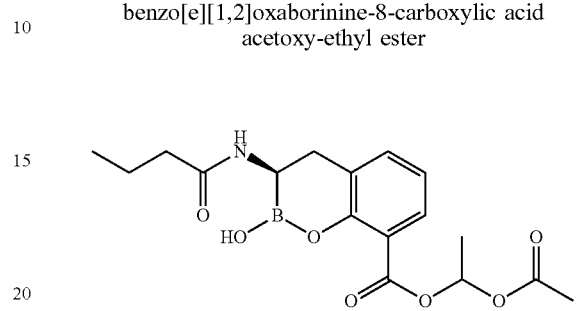

Step 1. Synthesis of 3-Butyrylamino-2-hydroxy-3,4-dihydro-2H-benzo[e][1,2]oxaborinine-8-carboxylic acid.

Prepared from 3-[2-butyrylamino-2-(2,9,9-trimethyl-3,5-dioxa-4-bora-tricyclo[6.1.1.02,6]dec-4-yl)-ethyl]-2-methoxy-benzoic acid tert-butyl ester and 1M boron tribromide in dichloromethane following the procedure described in Step 1 of Example 170. The crude product was purified by reverse phase preparative HPLC and dried using lyophilization to give the title compound. ESI-MS m/z 278 (MH)+.

Step 2. Synthesis of (R)-3-Butyrylamino-2-hydroxy-3,4-dihydro-2H-benzo[e][1,2]oxaborinine-8-carboxylic acid acetoxy-ethyl ester Prepared from 3-butyrylamino-2-hydroxy-3,4-dihydro-2H-benzo[e][1,2]oxaborinine-8-carboxylic acid and bromoethyl acetate following the procedure described in Step 1 of Example 127. The crude product was purified by reverse phase preparative HPLC and dried using lyophilization to give the title compound. ESI-MS m/z 364 (MH)+.

TABLE 1

Examples of compounds (Compounds of Formula (I) or (IX)).

| Example | Structure | MW | ESI-MS (m/z) for [MH]+ |
|---|---|---|---|
| 1 | 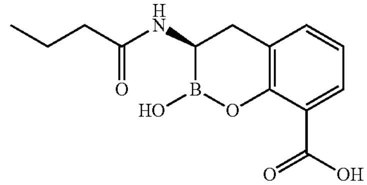 [SMILES: CCCC(=O)N[C@H]1Cc2cccc(C(=O)O)c2OB1O] | 277 | 278 |
| 2 | 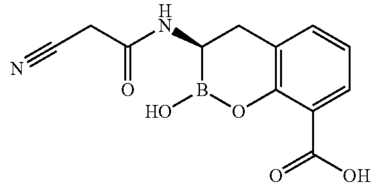 [SMILES: N#CCC(=O)N[C@H]1Cc2cccc(C(=O)O)c2OB1O] | 274 | 275 |

TABLE 1-continued

Examples of compounds (Compounds of Formula (I) or (IX)).

| Example | Structure | MW | ESI-MS (m/z) for [MH]+ |
|---------|-----------|-----|------------------------|
| 3 | 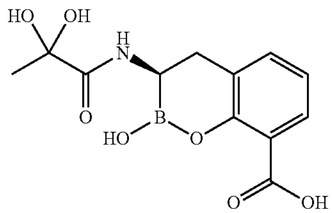 [SMILES: CC(O)(O)C(=O)N[C@H]1Cc2cccc(C(=O)O)c2OB1O] | 295 | 296 |
| 4 | 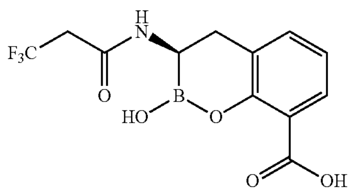 [SMILES: O=C(CC(F)(F)F)N[C@H]1Cc2cccc(C(=O)O)c2OB1O] | 317 | 318 |
| 5 | 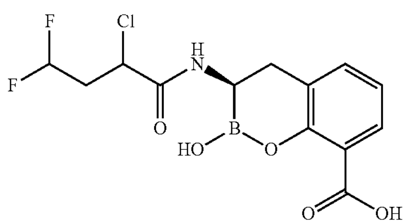 [SMILES: O=C(O)c1cccc2c1OB(O)[C@@H](NC(=O)C(Cl)CC(F)F)C2] | 347 | 348 |
| 6 | 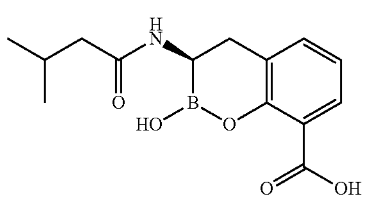 [SMILES: CC(C)CC(=O)N[C@H]1Cc2cccc(C(=O)O)c2OB1O] | 291 | 292 |
| 7 | 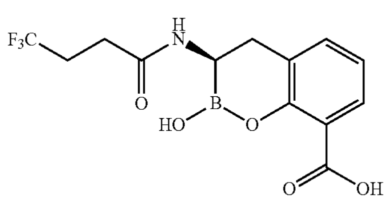 [SMILES: O=C(CCC(F)(F)F)N[C@H]1Cc2cccc(C(=O)O)c2OB1O] | 331 | 332 |
| 8 | 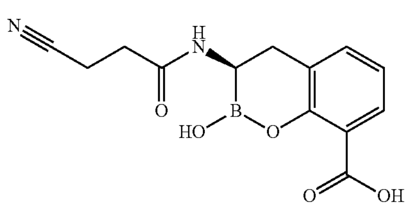 [SMILES: N#CCCC(=O)N[C@H]1Cc2cccc(C(=O)O)c2OB1O] | 288 | 289 |
| 9 | 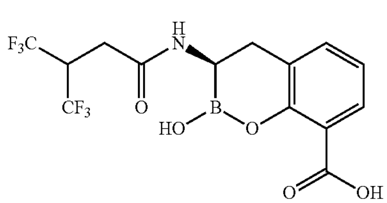 [SMILES: O=C(CC(C(F)(F)F)C(F)(F)F)N[C@H]1Cc2cccc(C(=O)O)c2OB1O] | 399 | 400 |

TABLE 1-continued

Examples of compounds (Compounds of Formula (I) or (IX)).

| Example | Structure | MW | ESI-MS (m/z) for [MH]+ |
|---|---|---|---|
| 10 | 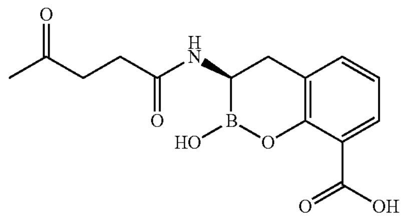 [SMILES: CC(=O)CCC(=O)N[C@H]1Cc2cccc(C(=O)O)c2OB1O] | 305 | 306 |
| 11 | 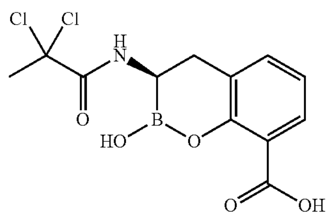 [SMILES: CC(Cl)(Cl)C(=O)N[C@H]1Cc2cccc(C(=O)O)c2OB1O] | 332 | 333 |
| 12 | 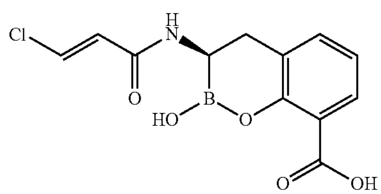 [SMILES: O=C(/C=C/Cl)N[C@H]1Cc2cccc(C(=O)O)c2OB1O] | 295 | 296 |
| 13 | 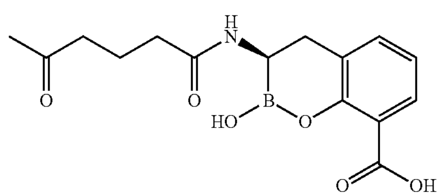 [SMILES: CC(=O)CCCC(=O)N[C@H]1Cc2cccc(C(=O)O)c2OB1O] | 319 | 320 |
| 14 | 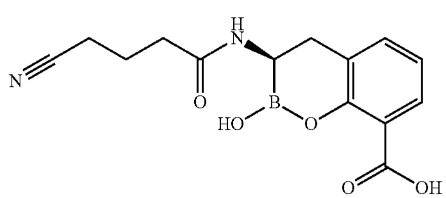 [SMILES: N#CCCCC(=O)N[C@H]1Cc2cccc(C(=O)O)c2OB1O] | 302 | 303 |
| 15 | 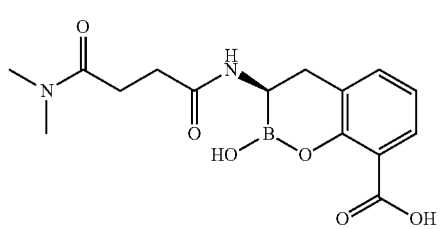 [SMILES: CN(C)C(=O)CCC(=O)N[C@H]1Cc2cccc(C(=O)O)c2OB1O] | 334 | 335 |
| 16 | 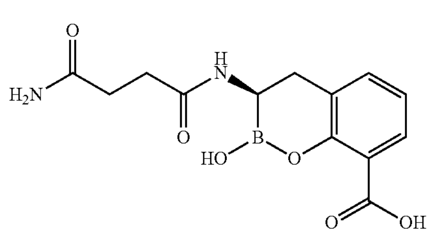 [SMILES: NC(=O)CCC(=O)N[C@H]1Cc2cccc(C(=O)O)c2OB1O] | 306 | 307 |

TABLE 1-continued

Examples of compounds (Compounds of Formula (I) or (IX)).

| Example | Structure | MW | ESI-MS (m/z) for [MH]+ |
|---------|-----------|-----|------------------------|
| 17 | 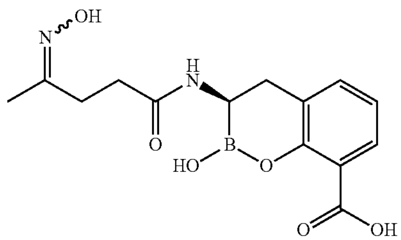 [SMILES: CC(CCC(=O)N[C@H]1Cc2cccc(C(=O)O)c2OB1O)=NO] | 320 | 321 |
| 18 | 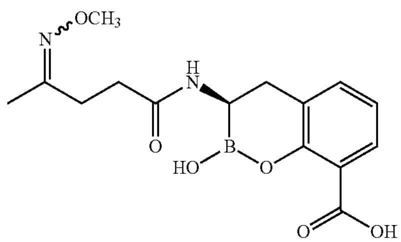 [SMILES: CON=C(C)CCC(=O)N[C@H]1Cc2cccc(C(=O)O)c2OB1O] | 334 | 335 |
| 19 | 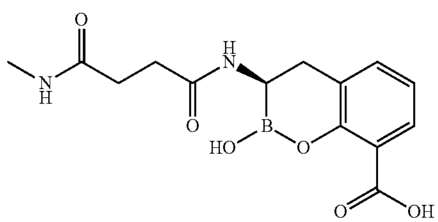 | 320 | 321 |
| 20 | 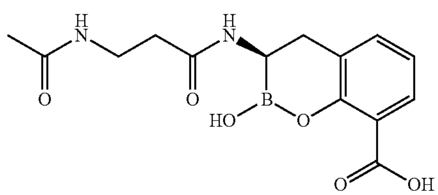 | 320 | 321 |
| 21 | 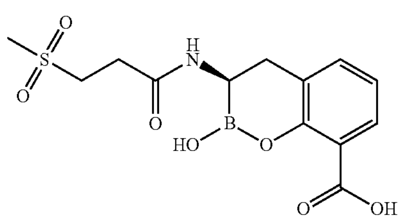 [SMILES: CS(=O)(=O)CCC(=O)N[C@H]1Cc2cccc(C(=O)O)c2OB1O] | 341 | 342 |
| 22 | 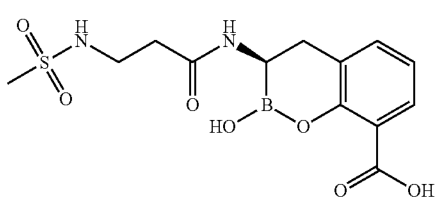 [SMILES: CS(=O)(=O)NCCC(=O)N[C@H]1Cc2cccc(C(=O)O)c2OB1O] | 356 | 357 |
| 23 | 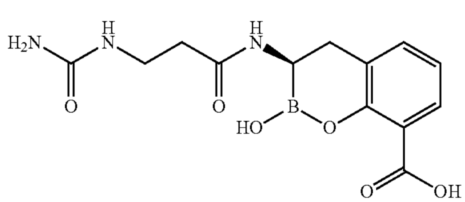 [SMILES: NC(=O)NCCC(=O)N[C@H]1Cc2cccc(C(=O)O)c2OB1O] | 321 | 322 |

TABLE 1-continued

Examples of compounds (Compounds of Formula (I) or (IX)).

| Example | Structure | MW | ESI-MS (m/z) for [MH]+ |
|---|---|---|---|
| 24 | 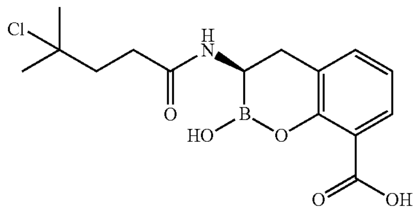 [SMILES: CC(C)(Cl)CCC(=O)N[C@H]1Cc2cccc(C(=O)O)c2OB1O] | 339 | 340 |
| 25 | 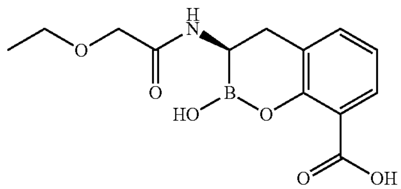 [SMILES: CCOCC(=O)N[C@H]1Cc2cccc(C(=O)O)c2OB1O] | 293 | 294 |
| 26 | 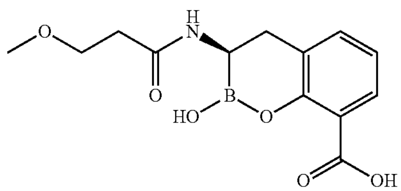 [SMILES: COCCC(=O)N[C@H]1Cc2cccc(C(=O)O)c2OB1O] | 293 | 294 |
| 27 | 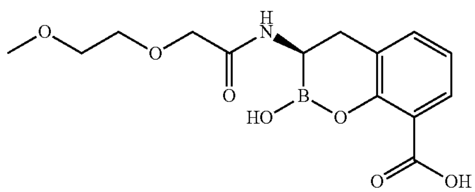 [SMILES: COCCOCC(=O)N[C@H]1Cc2cccc(C(=O)O)c2OB1O] | 323 | 324 |
| 28 | 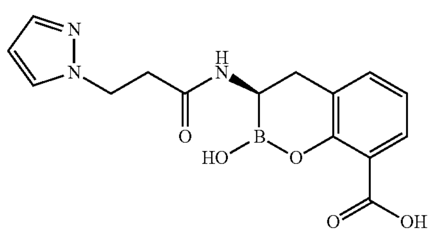 [SMILES: O=C(CCn1cccn1)N[C@H]1Cc2cccc(C(=O)O)c2OB1O] | 329 | 330 |
| 29 | 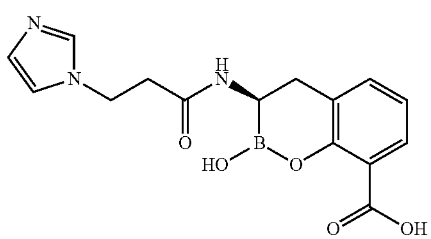 [SMILES: O=C(CCn1ccnc1)N[C@H]1Cc2cccc(C(=O)O)c2OB1O] | 329 | 330 |
| 30 | 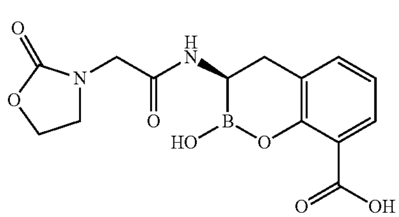 [SMILES: O=C(CN1CCOC1=O)N[C@H]1Cc2cccc(C(=O)O)c2OB1O] | 334 | 335 |

TABLE 1-continued

Examples of compounds (Compounds of Formula (I) or (IX)).

| Example | Structure | MW | ESI-MS (m/z) for [MH]+ |
|---------|-----------|-----|------------------------|
| 31 | 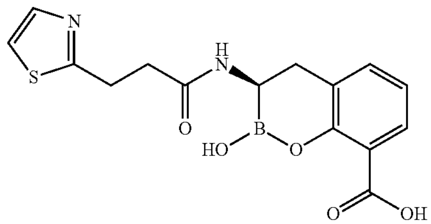 [SMILES: O=C(CCc1nccs1)N[C@H]1Cc2cccc(C(=O)O)c2OB1O] | 346 | 347 |
| 32 | 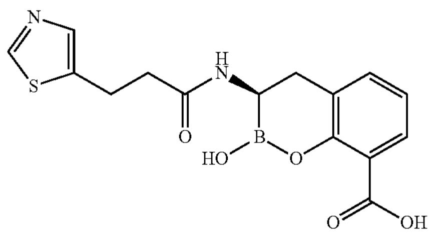 [SMILES: O=C(CCc1cncs1)N[C@H]1Cc2cccc(C(=O)O)c2OB1O] | 346 | 347 |
| 33 | 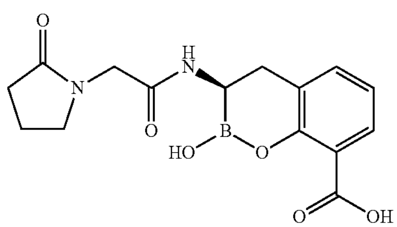 [SMILES: O=C(CN1CCCC1=O)N[C@H]1Cc2cccc(C(=O)O)c2OB1O] | 332 | 333 |
| 34 | 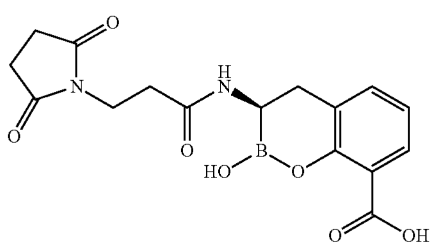 [SMILES: O=C(CCN1C(=O)CCC1=O)N[C@H]1Cc2cccc(C(=O)O)c2OB1O] | 360 | 361 |
| 35 | 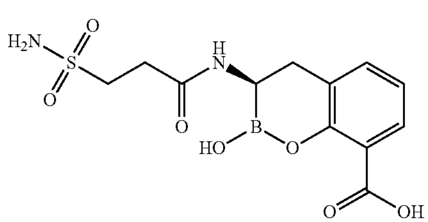 [SMILES: NS(=O)(=O)CCC(=O)N[C@H]1Cc2cccc(C(=O)O)c2OB1O] | 342 | 343 |
| 36 | 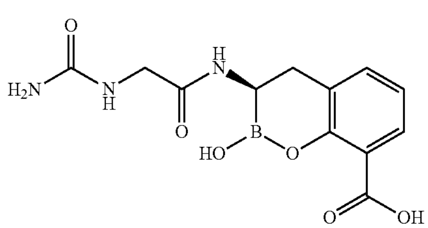 [SMILES: NC(=O)NCC(=O)N[C@H]1Cc2cccc(C(=O)O)c2OB1O] | 307 | 308 |

TABLE 1-continued

Examples of compounds (Compounds of Formula (I) or (IX)).

| Example | Structure | MW | ESI-MS (m/z) for [MH]+ |
|---------|-----------|-----|------------------------|
| 37 | 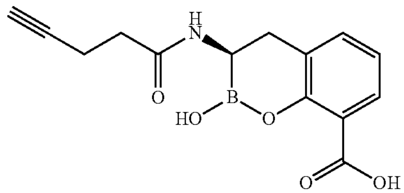 [SMILES: C#CCCC(=O)N[C@H]1Cc2cccc(C(=O)O)c2OB1O] | 287 | 288 |
| 38 | 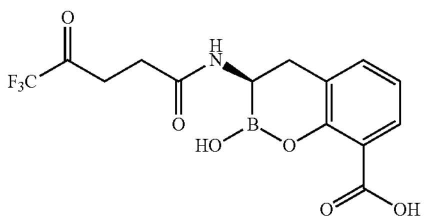 [SMILES: O=C(CCC(=O)C(F)(F)F)N[C@H]1Cc2cccc(C(=O)O)c2OB1O] | 359 | 360 |
| 39 | 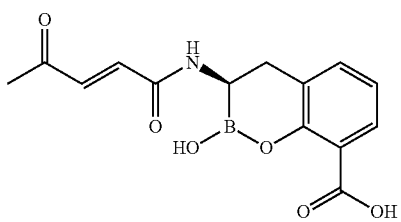 [SMILES: CC(=O)/C=C/C(=O)N[C@H]1Cc2cccc(C(=O)O)c2OB1O] | 303 | 304 |
| 40 | 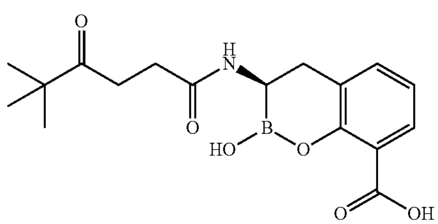 [SMILES: CC(C)(C)C(=O)CCC(=O)N[C@H]1Cc2cccc(C(=O)O)c2OB1O] | 347 | 348 |
| 41 | 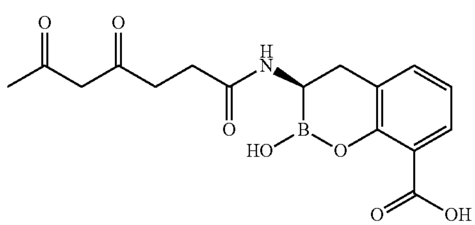 [SMILES: CC(=O)CC(=O)CCC(=O)N[C@H]1Cc2cccc(C(=O)O)c2OB1O] | 347 | 348 |
| 42 | 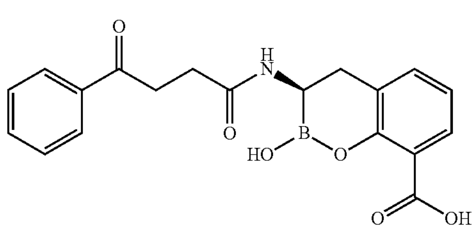 [SMILES: O=C(CCC(=O)c1ccccc1)N[C@H]1Cc2cccc(C(=O)O)c2OB1O] | 367 | 368 |
| 43 | 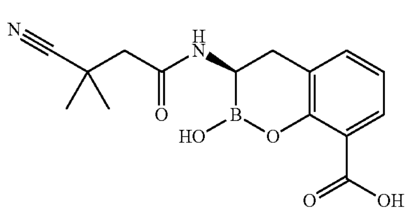 [SMILES: CC(C)(C#N)CC(=O)N[C@H]1Cc2cccc(C(=O)O)c2OB1O] | 316 | 317 |

TABLE 1-continued

Examples of compounds (Compounds of Formula (I) or (IX)).

| Example | Structure | MW | ESI-MS (m/z) for [MH]+ |
|---------|-----------|-----|------------------------|
| 44 | 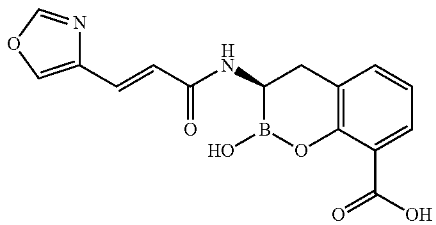 [SMILES: O=C(/C=C/c1cocn1)N[C@H]1Cc2cccc(C(=O)O)c2OB1O] | 328 | 329 |
| 45 | 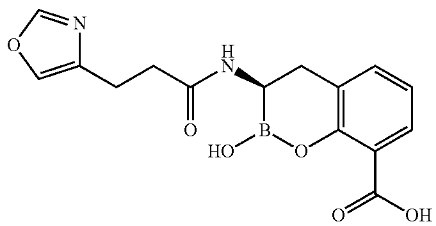 [SMILES: O=C(CCc1cocn1)N[C@H]1Cc2cccc(C(=O)O)c2OB1O] | 330 | 331 |
| 46 | 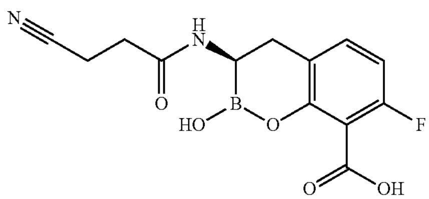 [SMILES: N#CCCC(=O)N[C@H]1Cc2ccc(F)c(C(=O)O)c2OB1O] | 306 | 307 |
| 47 | 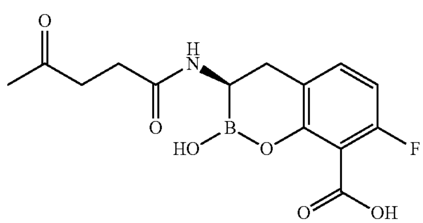 [SMILES: CC(=O)CCC(=O)N[C@H]1Cc2ccc(F)c(C(=O)O)c2OB1O] | 323 | 324 |
| 48 | 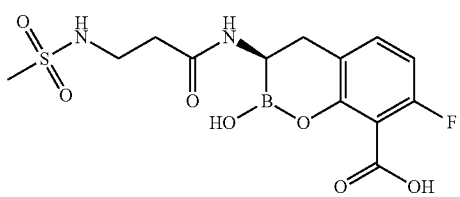 [SMILES: CS(=O)(=O)NCCC(=O)N[C@H]1Cc2ccc(F)c(C(=O)O)c2OB1O] | 374 | 375 |
| 49 | 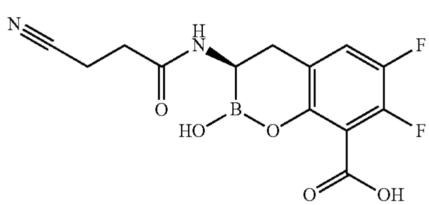 [SMILES: N#CCCC(=O)N[C@H]1Cc2cc(F)c(F)c(C(=O)O)c2OB1O] | 324 | 325 |
| 50 | 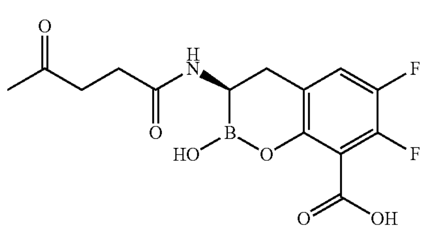 [SMILES: CC(=O)CCC(=O)N[C@H]1Cc2cc(F)c(F)c(C(=O)O)c2OB1O] | 341 | 342 |

TABLE 1-continued

Examples of compounds (Compounds of Formula (I) or (IX)).

| Example | Structure | MW | ESI-MS (m/z) for [MH]+ |
|---|---|---|---|
| 51 | 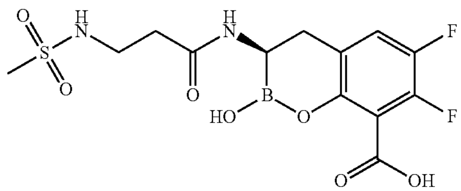 [SMILES: CS(=O)(=O)NCCC(=O)N[C@H]1Cc2cc(F)c(F)c(C(=O)O)c2OB1O] | 392 | 393 |
| 52 | 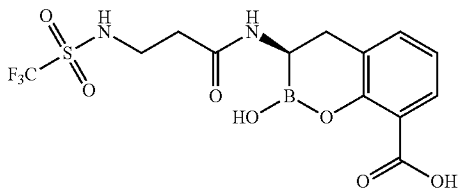 [SMILES: O=C(CCNS(=O)(=O)C(F)(F)F)N[C@H]1Cc2cccc(C(=O)O)c2OB1O] | 410 | 411 |
| 53 | 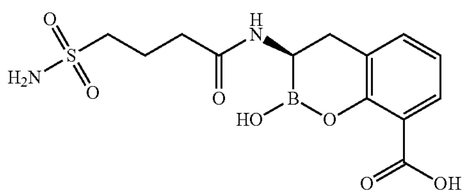 [SMILES: NS(=O)(=O)CCCC(=O)N[C@H]1Cc2cccc(C(=O)O)c2OB1O] | 356 | 357 |
| 54 | 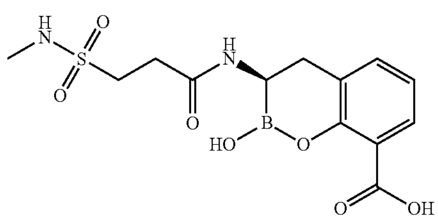 [SMILES: CNS(=O)(=O)CCC(=O)N[C@H]1Cc2cccc(C(=O)O)c2OB1O] | 356 | 357 |
| 55 | 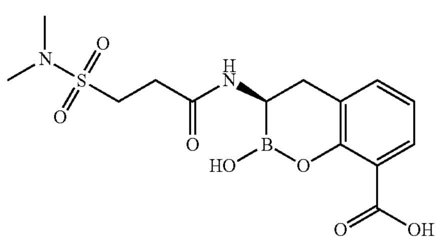 [SMILES: CN(C)S(=O)(=O)CCC(=O)N[C@H]1Cc2cccc(C(=O)O)c2OB1O] | 370 | 371 |
| 56 | 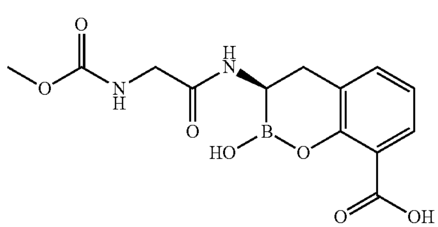 [SMILES: COC(=O)NCC(=O)N[C@H]1Cc2cccc(C(=O)O)c2OB1O] | 322 | 323 |
| 57 | 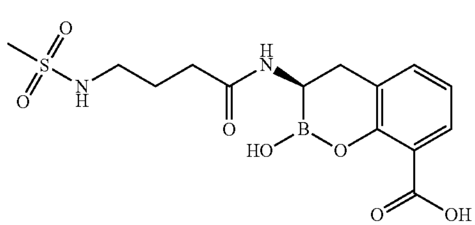 [SMILES: CS(=O)(=O)NCCCC(=O)N[C@H]1Cc2cccc(C(=O)O)c2OB1O] | 370 | 371 |

TABLE 1-continued

Examples of compounds (Compounds of Formula (I) or (IX)).

| Example | Structure | MW | ESI-MS (m/z) for [MH]+ |
|---|---|---|---|
| 58 | 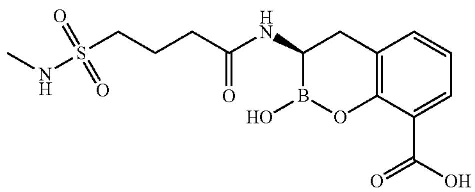 [SMILES: CNS(=O)(=O)CCCC(=O)N[C@H]1Cc2cccc(C(=O)O)c2OB1O] | 370 | 371 |
| 59 | 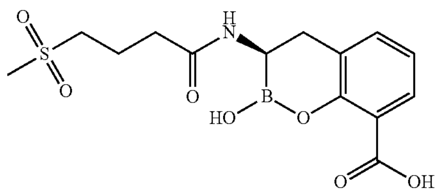 [SMILES: CS(=O)(=O)CCCC(=O)N[C@H]1Cc2cccc(C(=O)O)c2OB1O] | 355 | 356 |
| 60 | 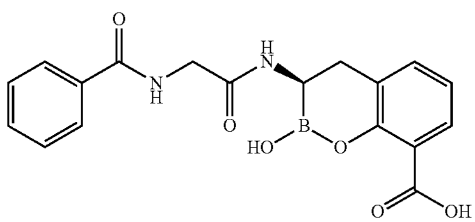 [SMILES: O=C(CNC(=O)c1ccccc1)N[C@H]1Cc2cccc(C(=O)O)c2OB1O] | 368 | 369 |
| 61 | 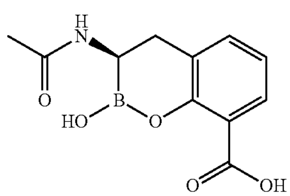 [SMILES: CC(=O)N[C@H]1Cc2cccc(C(=O)O)c2OB1O] | 249 | 250 |
| 62 | 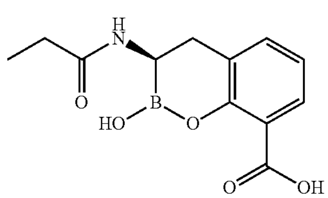 [SMILES: CCC(=O)N[C@H]1Cc2cccc(C(=O)O)c2OB1O] | 263 | 264 |
| 63 | 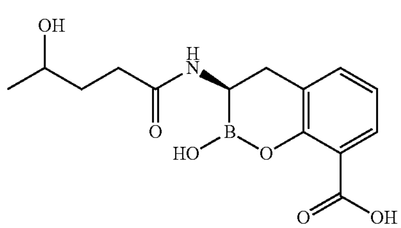 [SMILES: CC(O)CCC(=O)N[C@H]1Cc2cccc(C(=O)O)c2OB1O] | 307 | 308 |
| 64 | 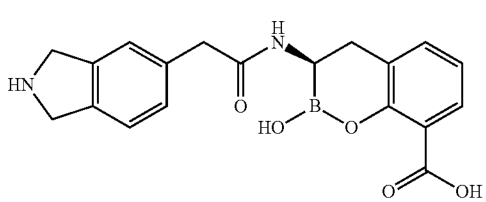 [SMILES: O=C(Cc1ccc2c(c1)CNC2)N[C@H]1Cc2cccc(C(=O)O)c2OB1O] | 366 | 367 |

TABLE 1-continued

Examples of compounds (Compounds of Formula (I) or (IX)).

| Example | Structure | MW | ESI-MS (m/z) for [MH]+ |
|---------|-----------|-----|------------------------|
| 65 | 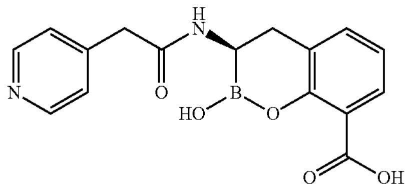 [SMILES: O=C(Cc1ccncc1)N[C@H]1Cc2cccc(C(=O)O)c2OB1O] | 326 | 327 |
| 66 | 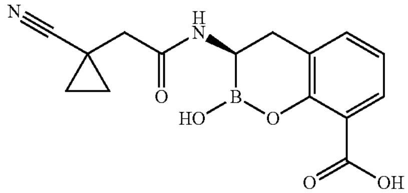 [SMILES: N#CC1(CC(=O)N[C@H]2Cc3cccc(C(=O)O)c3OB2O)CC1] | | |
| 67 | 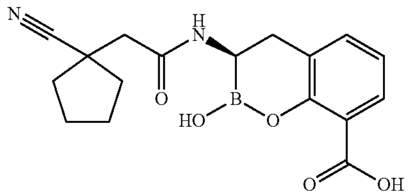 [SMILES: N#CC1(CC(=O)N[C@H]2Cc3cccc(C(=O)O)c3OB2O)CCCC1] | | |
| 68 | 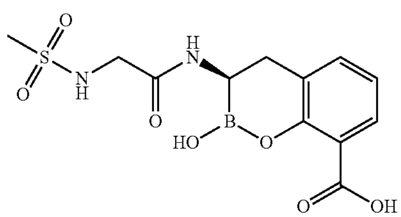 [SMILES: CS(=O)(=O)NCC(=O)N[C@H]1Cc2cccc(C(=O)O)c2OB1O] | | |
| 69 | 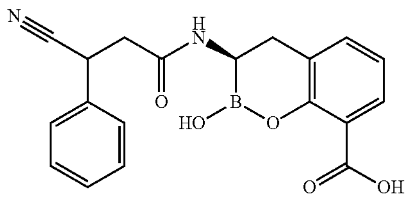 [SMILES: N#CC(CC(=O)N[C@H]1Cc2cccc(C(=O)O)c2OB1O)c1ccccc1] | | |
| 70 | 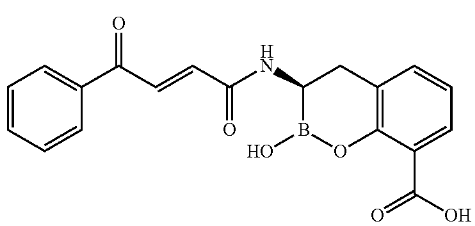 [SMILES: O=C(/C=C/C(=O)c1ccccc1)N[C@H]1Cc2cccc(C(=O)O)c2OB1O] | | |
| 71 | 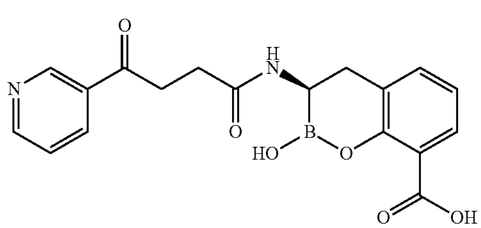 [SMILES: O=C(CCC(=O)c1cccnc1)N[C@H]1Cc2cccc(C(=O)O)c2OB1O] | | |

TABLE 1-continued

Examples of compounds (Compounds of Formula (I) or (IX)).

| Example | Structure | MW | ESI-MS (m/z) for [MH]+ |
|---------|-----------|-----|------------------------|
| 72 | 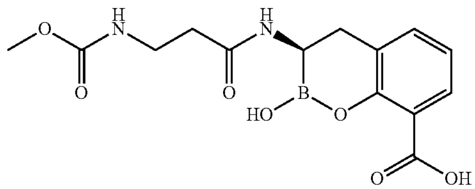 [SMILES: COC(=O)NCCC(=O)N[C@H]1Cc2cccc(C(=O)O)c2OB1O] | | |
| 73 | 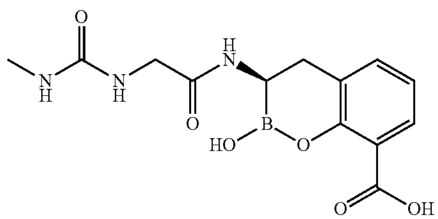 | | |
| 74 | 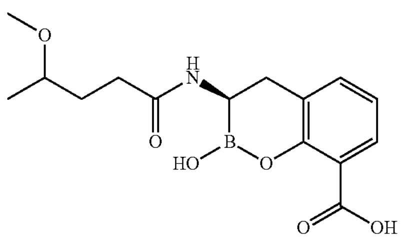 [SMILES: COC(C)CCC(=O)N[C@H]1Cc2cccc(C(=O)O)c2OB1O] | | |
| 75 | 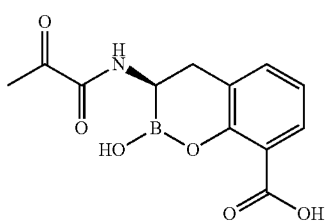 [SMILES: CC(=O)C(=O)N[C@H]1Cc2cccc(C(=O)O)c2OB1O] | | |
| 76 | 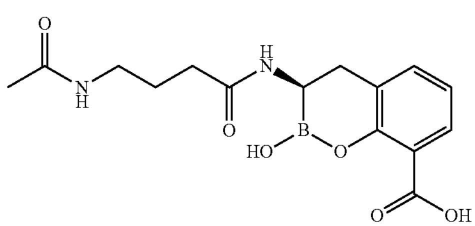 [SMILES: CC(=O)NCCCC(=O)N[C@H]1Cc2cccc(C(=O)O)c2OB1O] | | |
| 77 | 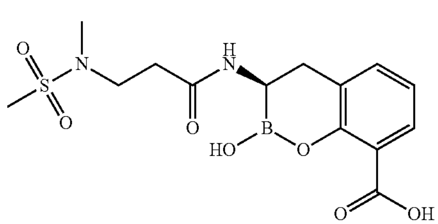 [SMILES: CN(CCC(=O)N[C@H]1Cc2cccc(C(=O)O)c2OB1O)S(C)(=O)=O] | | |
| 78 | 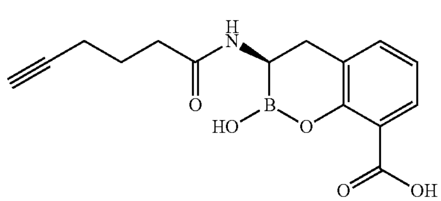 [SMILES: C#CCCCC(=O)N[C@H]1Cc2cccc(C(=O)O)c2OB1O] | | |

TABLE 1-continued

Examples of compounds (Compounds of Formula (I) or (IX)).

| Example | Structure | MW | ESI-MS (m/z) for [MH]+ |
|---|---|---|---|
| 79 | 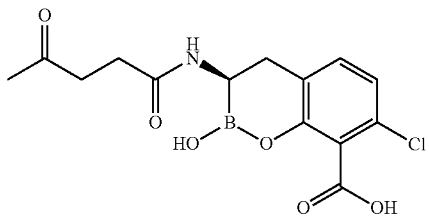 [SMILES: CC(=O)CCC(=O)N[C@H]1Cc2ccc(Cl)c(C(=O)O)c2OB1O] | | |
| 80 | 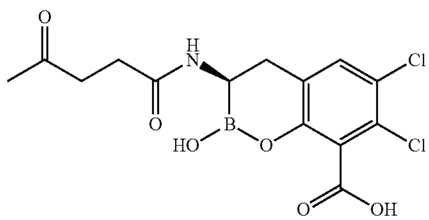 [SMILES: CC(=O)CCC(=O)N[C@H]1Cc2cc(Cl)c(Cl)c(C(=O)O)c2OB1O] | | |
| 81 | 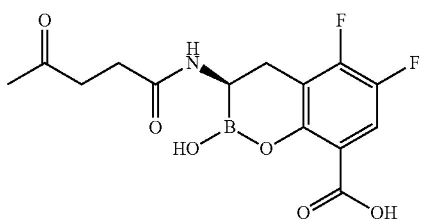 [SMILES: CC(=O)CCC(=O)N[C@H]1Cc2c(F)c(F)cc(C(=O)O)c2OB1O] | | |
| 82 | 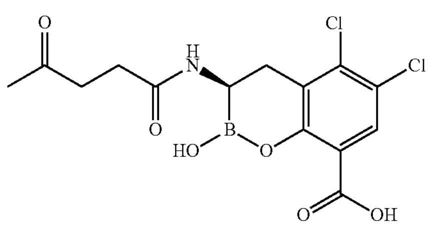 [SMILES: CC(=O)CCC(=O)N[C@H]1Cc2c(Cl)c(Cl)cc(C(=O)O)c2OB1O] | | |
| 83 | 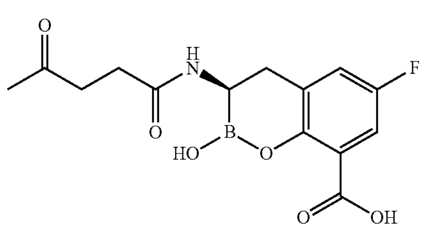 [SMILES: CC(=O)CCC(=O)N[C@H]1Cc2cc(F)cc(C(=O)O)c2OB1O] | | |
| 84 | 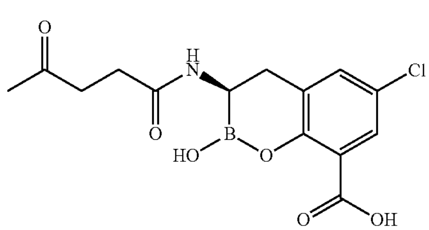 [SMILES: CC(=O)CCC(=O)N[C@H]1Cc2cc(Cl)cc(C(=O)O)c2OB1O] | | |

TABLE 1-continued

Examples of compounds (Compounds of Formula (I) or (IX)).

| Example | Structure | MW | ESI-MS (m/z) for [MH]+ |
|---------|-----------|----|------------------------|
| 85 | 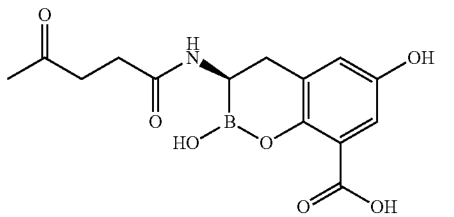 [SMILES: CC(=O)CCC(=O)N[C@H]1Cc2cc(O)cc(C(=O)O)c2OB1O] | | |
| 86 | 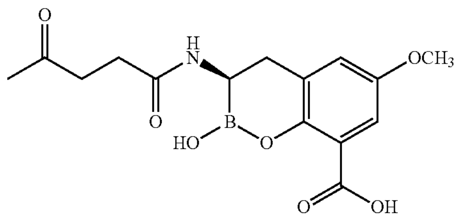 [SMILES: COc1cc2c(c(C(=O)O)c1)OB(O)[C@@H](NC(=O)CCC(C)=O)C2] | | |
| 87 | 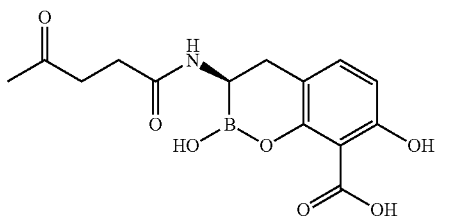 [SMILES: CC(=O)CCC(=O)N[C@H]1Cc2ccc(O)c(C(=O)O)c2OB1O] | | |
| 88 | 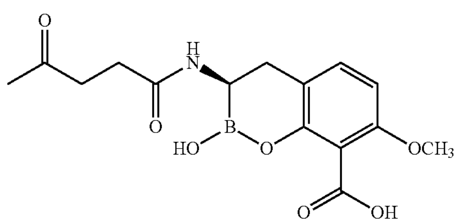 [SMILES: COc1ccc2c(c1C(=O)O)OB(O)[C@@H](NC(=O)CCC(C)=O)C2] | | |
| 89 | 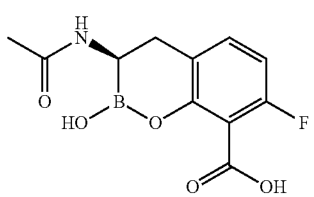 [SMILES: CC(=O)N[C@H]1Cc2ccc(F)c(C(=O)O)c2OB1O] | | |
| 90 | 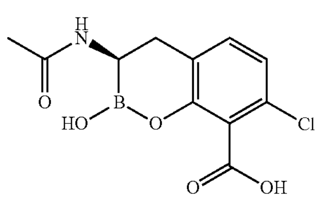 [SMILES: CC(=O)N[C@H]1Cc2ccc(Cl)c(C(=O)O)c2OB1O] | | |
| 91 | 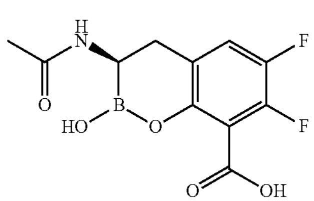 [SMILES: CC(=O)N[C@H]1Cc2cc(F)c(F)c(C(=O)O)c2OB1O] | | |

TABLE 1-continued

Examples of compounds (Compounds of Formula (I) or (IX)).

| Example | Structure | MW | ESI-MS (m/z) for [MH]+ |
|---------|-----------|----|-----------------------|
| 92 | *structure* | | |
| 93 | *structure* | | |
| 94 | *structure* | | |
| 95 | *structure* | | |
| 96 | *structure* | | |
| 97 | *structure* | | |
| 98 | *structure* | | |

TABLE 1-continued

Examples of compounds (Compounds of Formula (I) or (IX)).

| Example | Structure | MW | ESI-MS (m/z) for [MH]+ |
|---------|-----------|----|-----------------------|
| 99 | 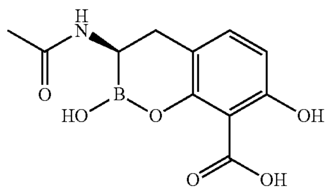 [SMILES: CC(=O)N[C@H]1Cc2ccc(O)c(C(=O)O)c2OB1O] | | |
| 100 | 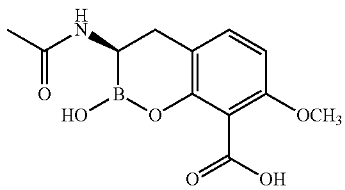 [SMILES: COc1ccc2c(c1C(=O)O)OB(O)[C@@H](NC(C)=O)C2] | | |
| 101 | 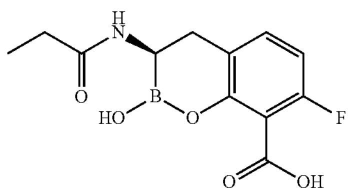 [SMILES: CCC(=O)N[C@H]1Cc2ccc(F)c(C(=O)O)c2OB1O] | | |
| 102 | 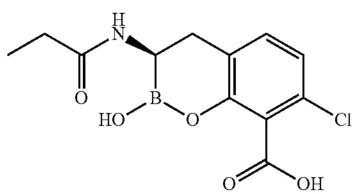 [SMILES: CCC(=O)N[C@H]1Cc2ccc(Cl)c(C(=O)O)c2OB1O] | | |
| 103 | 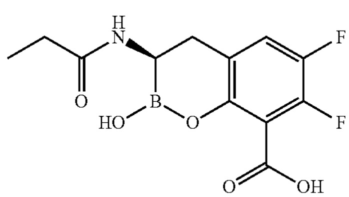 [SMILES: CCC(=O)N[C@H]1Cc2cc(F)c(F)c(C(=O)O)c2OB1O] | | |
| 104 | 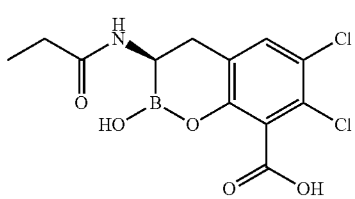 [SMILES: CCC(=O)N[C@H]1Cc2cc(Cl)c(Cl)c(C(=O)O)c2OB1O] | | |
| 105 | 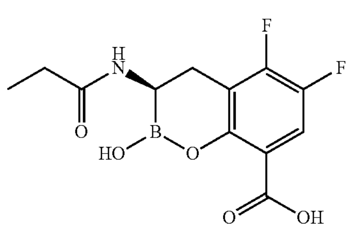 [SMILES: CCC(=O)N[C@H]1Cc2c(F)c(F)cc(C(=O)O)c2OB1O] | | |

TABLE 1-continued

Examples of compounds (Compounds of Formula (I) or (IX)).

| Example | Structure | MW | ESI-MS (m/z) for [MH]+ |
|---------|-----------|----|-----|
| 106 | 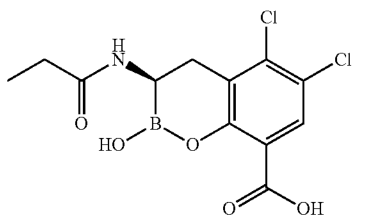 [SMILES: CCC(=O)N[C@H]1Cc2c(Cl)c(Cl)cc(C(=O)O)c2OB1O] | | |
| 107 | 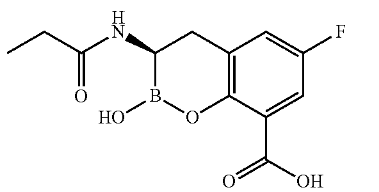 [SMILES: CCC(=O)N[C@H]1Cc2cc(F)cc(C(=O)O)c2OB1O] | | |
| 108 | 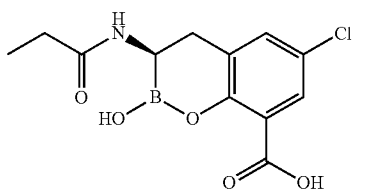 [SMILES: CCC(=O)N[C@H]1Cc2cc(Cl)cc(C(=O)O)c2OB1O] | | |
| 109 | 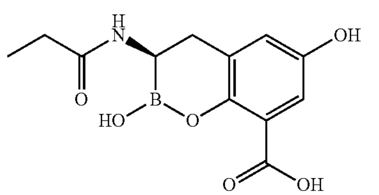 [SMILES: CCC(=O)N[C@H]1Cc2cc(O)cc(C(=O)O)c2OB1O] | | |
| 110 | 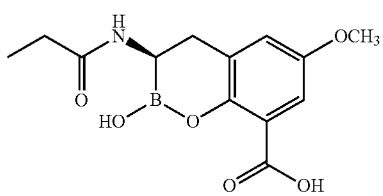 [SMILES: CCC(=O)N[C@H]1Cc2cc(OC)cc(C(=O)O)c2OB1O] | | |
| 111 | 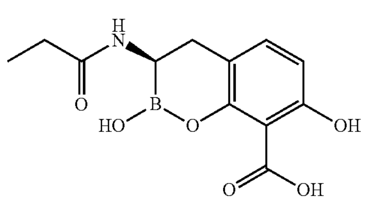 [SMILES: CCC(=O)N[C@H]1Cc2ccc(O)c(C(=O)O)c2OB1O] | | |
| 112 | 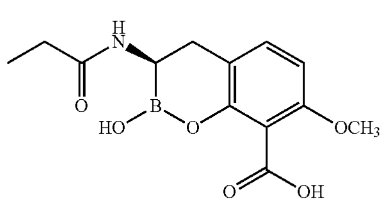 [SMILES: CCC(=O)N[C@H]1Cc2ccc(OC)c(C(=O)O)c2OB1O] | | |

TABLE 1-continued

Examples of compounds (Compounds of Formula (I) or (IX)).

| Example | Structure | MW | ESI-MS (m/z) for [MH]+ |
|---------|-----------|----|-----|
| 113 | 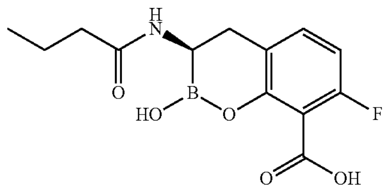 [SMILES: CCCC(=O)N[C@H]1Cc2ccc(F)c(C(=O)O)c2OB1O] | | |
| 114 | 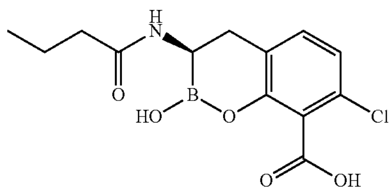 [SMILES: CCCC(=O)N[C@H]1Cc2ccc(Cl)c(C(=O)O)c2OB1O] | | |
| 115 | 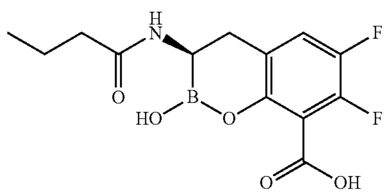 [SMILES: CCCC(=O)N[C@H]1Cc2cc(F)c(F)c(C(=O)O)c2OB1O] | | |
| 116 | 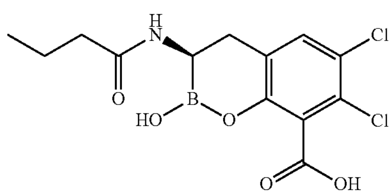 [SMILES: CCCC(=O)N[C@H]1Cc2cc(Cl)c(Cl)c(C(=O)O)c2OB1O] | | |
| 117 | 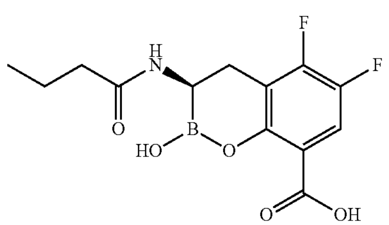 [SMILES: CCCC(=O)N[C@H]1Cc2c(F)c(F)cc(C(=O)O)c2OB1O] | | |
| 118 | 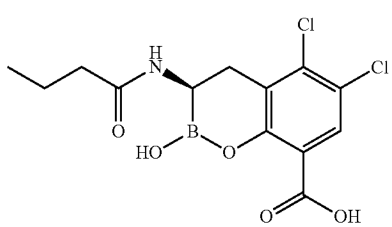 [SMILES: CCCC(=O)N[C@H]1Cc2c(Cl)c(Cl)cc(C(=O)O)c2OB1O] | | |
| 119 | 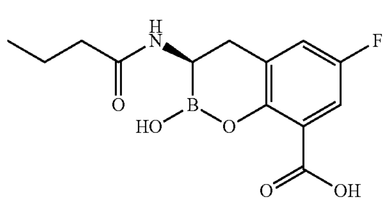 [SMILES: CCCC(=O)N[C@H]1Cc2cc(F)cc(C(=O)O)c2OB1O] | | |

TABLE 1-continued

Examples of compounds (Compounds of Formula (I) or (IX)).

| Example | Structure | MW | ESI-MS (m/z) for [MH]+ |
|---|---|---|---|
| 120 | 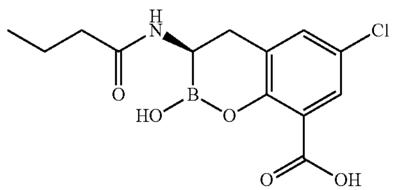 [SMILES: CCCC(=O)N[C@H]1Cc2cc(Cl)cc(C(=O)O)c2OB1O] | | |
| 121 | 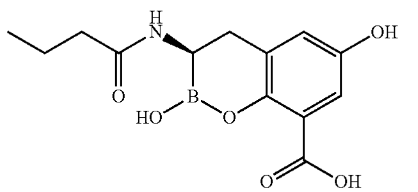 [SMILES: CCCC(=O)N[C@H]1Cc2cc(O)cc(C(=O)O)c2OB1O] | | |
| 122 | 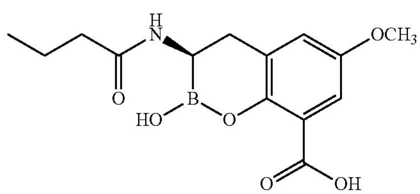 [SMILES: CCCC(=O)N[C@H]1Cc2cc(OC)cc(C(=O)O)c2OB1O] | | |
| 123 | 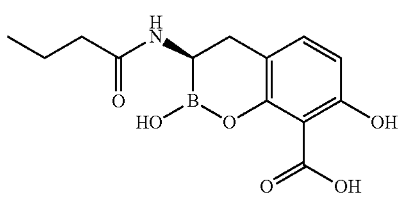 [SMILES: CCCC(=O)N[C@H]1Cc2ccc(O)c(C(=O)O)c2OB1O] | | |
| 124 | 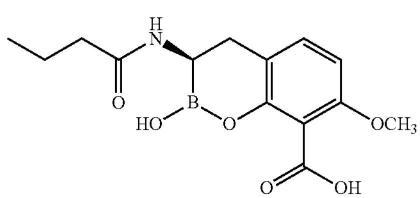 [SMILES: CCCC(=O)N[C@H]1Cc2ccc(OC)c(C(=O)O)c2OB1O] | | |

TABLE 2

Examples of compounds (Compounds of Formula II).

| Example | Structure | MW | ESI-MS (m/z) for [MH]+ |
|---|---|---|---|
| 125 | 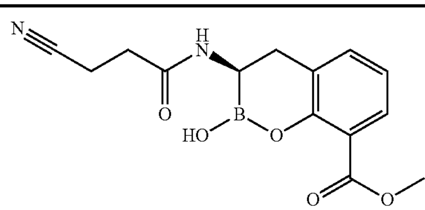 | 302 | 303 |

TABLE 2-continued

Examples of compounds (Compounds of Formula II).

| Example | Structure | MW | ESI-MS (m/z) for [MH]+ |
|---|---|---|---|
| 126 | 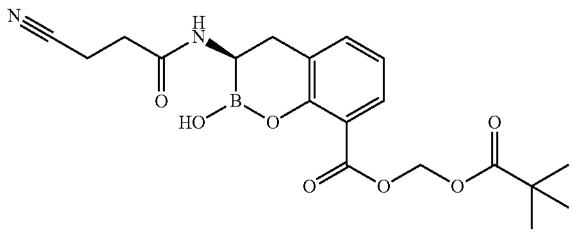 [SMILES: CC(C)(C)C(=O)OCOC(=O)c1cccc2c1OB(O)[C@@H](NC(=O)CCC#N)C2] | 402 | 403 |
| 127 | 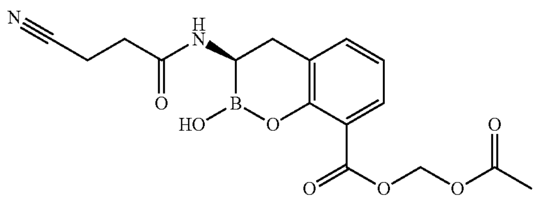 [SMILES: CC(=O)OCOC(=O)c1cccc2c1OB(O)[C@@H](NC(=O)CCC#N)C2] | 360 | 361 |
| 128 | 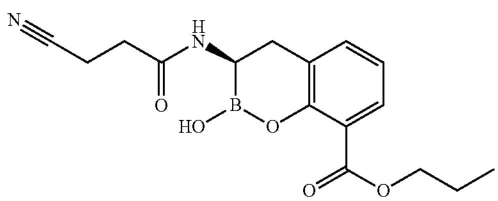 [SMILES: CCCOC(=O)c1cccc2c1OB(O)[C@@H](NC(=O)CCC#N)C2] | 330 | 331 |
| 129 | 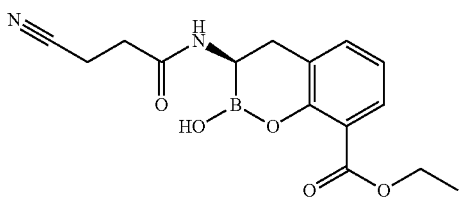 [SMILES: CCOC(=O)c1cccc2c1OB(O)[C@@H](NC(=O)CCC#N)C2] | 316 | 317 |
| 130 | 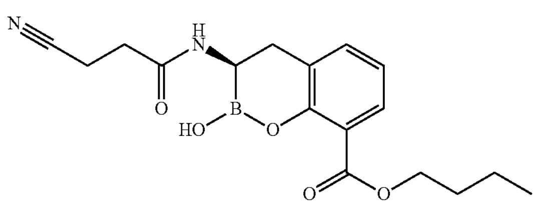 [SMILES: CCCCOC(=O)c1cccc2c1OB(O)[C@@H](NC(=O)CCC#N)C2] | 344 | 345 |
| 131 | 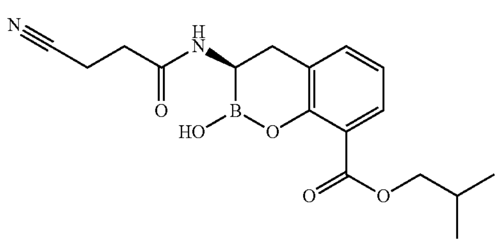 [SMILES: CC(C)COC(=O)c1cccc2c1OB(O)[C@@H](NC(=O)CCC#N)C2] | 344 | 345 |
| 132 | 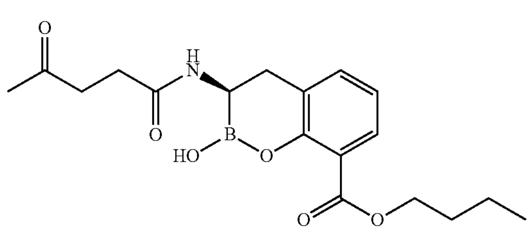 [SMILES: CCCCOC(=O)c1cccc2c1OB(O)[C@@H](NC(=O)CCC(C)=O)C2] | 361 | 384 (+Na) |

TABLE 2-continued

Examples of compounds (Compounds of Formula II).

| Example | Structure | MW | ESI-MS (m/z) for [MH]+ |
|---------|-----------|-----|------------------------|
| 133 | 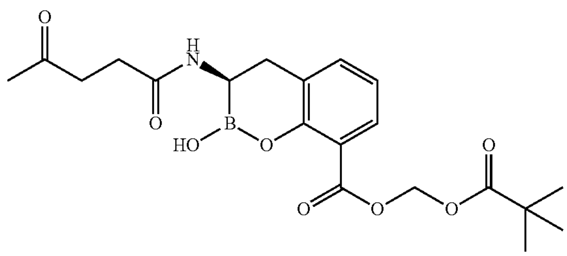 [SMILES: CC(=O)CCC(=O)N[C@H]1Cc2cccc(C(=O)OCOC(=O)C(C)(C)C)c2OB1O] | 419 | 420 |
| 134 | 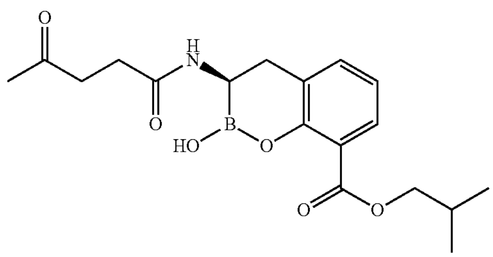 [SMILES: CC(=O)CCC(=O)N[C@H]1Cc2cccc(C(=O)OCC(C)C)c2OB1O] | 361 | 384 (+Na) |
| 135 | 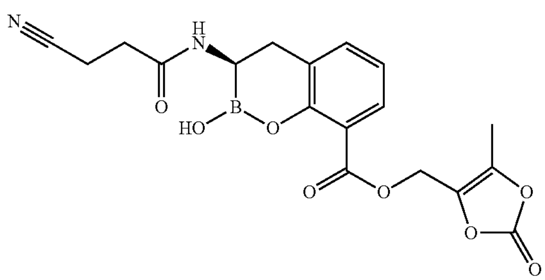 [SMILES: Cc1oc(=O)oc1COC(=O)c1cccc2c1OB(O)[C@@H](NC(=O)CCC#N)C2] | 400 | 401 |
| 136 | 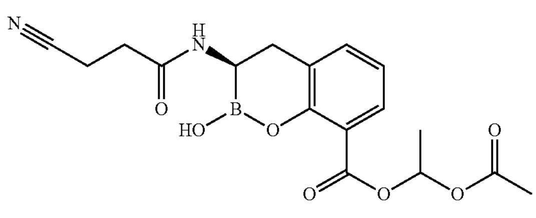 [SMILES: CC(=O)OC(C)OC(=O)c1cccc2c1OB(O)[C@@H](NC(=O)CCC#N)C2] | 374 | 375 |
| 137 | 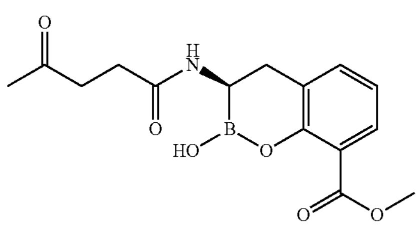 [SMILES: COC(=O)c1cccc2c1OB(O)[C@@H](NC(=O)CCC(C)=O)C2] | 319 | 320 |
| 138 | 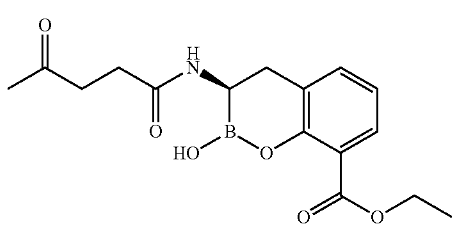 [SMILES: CCOC(=O)c1cccc2c1OB(O)[C@@H](NC(=O)CCC(C)=O)C2] | 333 | 334 |

TABLE 2-continued

Examples of compounds (Compounds of Formula II).

| Example | Structure | MW | ESI-MS (m/z) for [MH]+ |
|---|---|---|---|
| 139 | 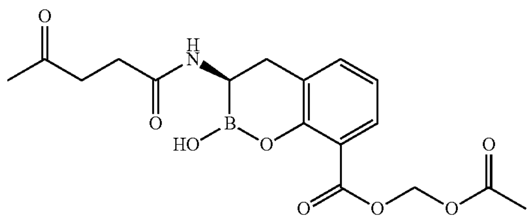 [SMILES: CC(=O)CCC(=O)N[C@H]1Cc2cccc(C(=O)OCOC(C)=O)c2OB1O] | 377 | 378 |
| 140 | 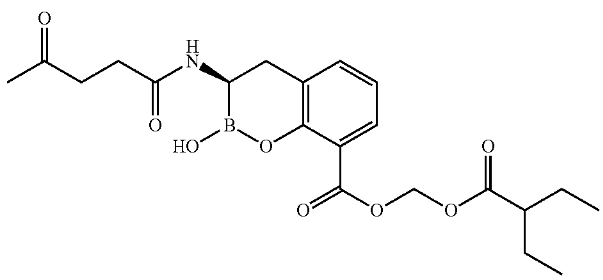 [SMILES: CCC(CC)C(=O)OCOC(=O)c1cccc2c1OB(O)[C@@H](NC(=O)CCC(C)=O)C2] | 433 | 456 (+Na) |
| 141 | 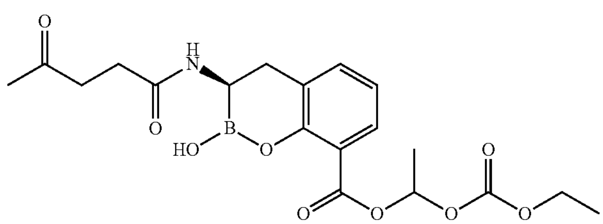 [SMILES: CCOC(=O)OC(C)OC(=O)c1cccc2c1OB(O)[C@@H](NC(=O)CCC(C)=O)C2] | 421 | 444 (+Na) |
| 142 | 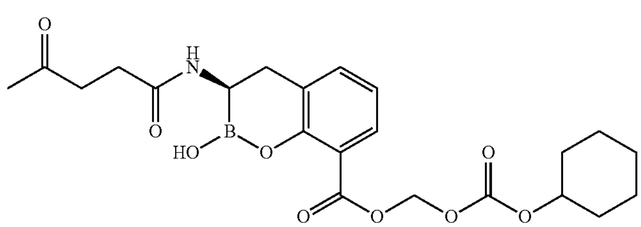 [SMILES: CC(=O)CCC(=O)N[C@H]1Cc2cccc(C(=O)OCOC(=O)OC3CCCCC3)c2OB1O] | 461 | 484 (+Na) |
| 143 | 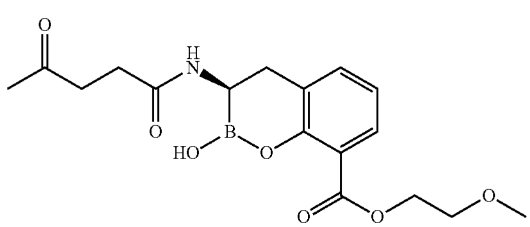 | 363 | 364 |
| 144 | 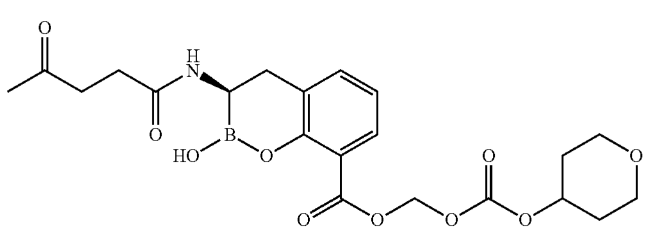 [SMILES: CC(=O)CCC(=O)N[C@H]1Cc2cccc(C(=O)OCOC(=O)OC3CCOCC3)c2OB1O] | 463 | 486 (+Na) |

TABLE 2-continued

Examples of compounds (Compounds of Formula II).

| Example | Structure | MW | ESI-MS (m/z) for [MH]+ |
|---------|-----------|-----|------------------------|
| 145 | 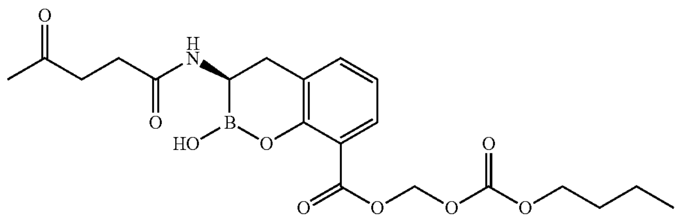 [SMILES: CCCCOC(=O)OCOC(=O)c1cccc2c1OB(O)[C@@H](NC(=O)CCC(C)=O)C2] | 435 | 458 (+Na) |
| 146 | 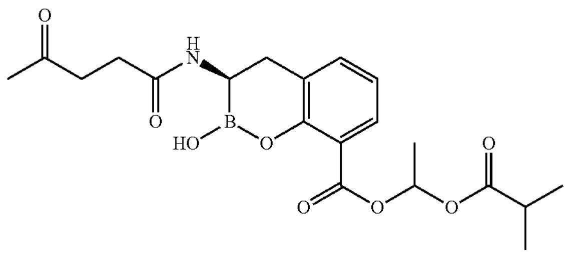 [SMILES: CC(=O)CCC(=O)N[C@H]1Cc2cccc(C(=O)OC(C)OC(=O)C(C)C)c2OB1O] | 419 | 442 (+Na) |
| 147 | 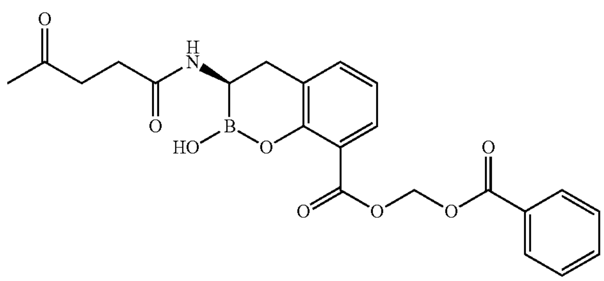 [SMILES: CC(=O)CCC(=O)N[C@H]1Cc2cccc(C(=O)OCOC(=O)c3ccccc3)c2OB1O] | 439 | 462 (+Na) |
| 148 | 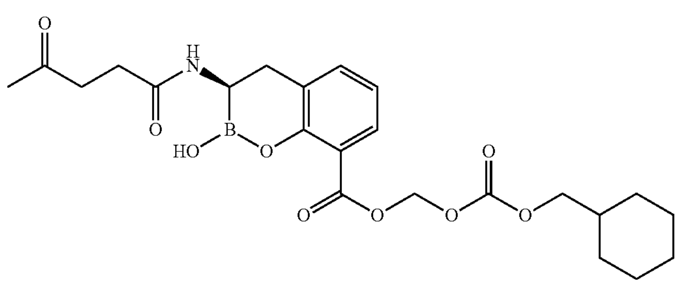 [SMILES: CC(=O)CCC(=O)N[C@H]1Cc2cccc(C(=O)OCOC(=O)OCC3CCCCC3)c2OB1O] | 475 | 498 (+Na) |
| 149 | 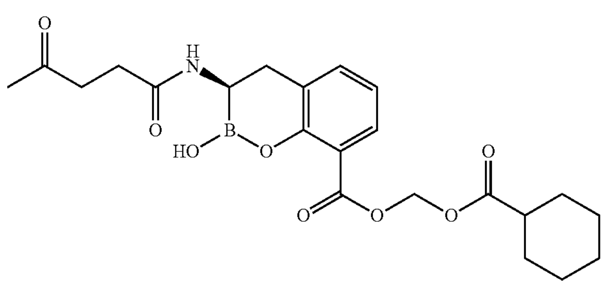 [SMILES: CC(=O)CCC(=O)N[C@H]1Cc2cccc(C(=O)OCOC(=O)C3CCCCC3)c2OB1O] | 445 | 468 (+Na) |

TABLE 2-continued
Examples of compounds (Compounds of Formula II).
| Example | Structure | MW | ESI-MS (m/z) for [MH]+ |
|---|---|---|---|
| 150 | 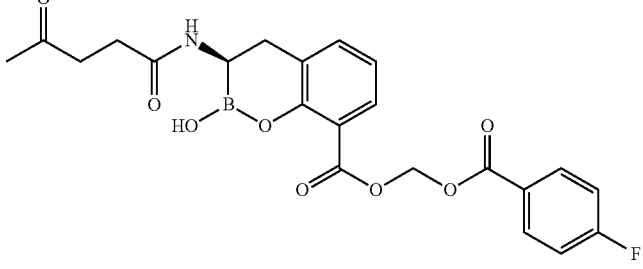 | 457 | 480 (+Na) |
| 151 | 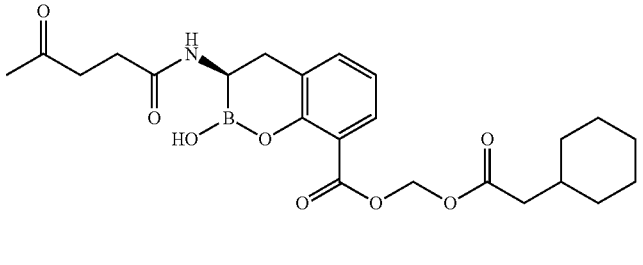 | 459 | 482 (+Na) |
| 152 | 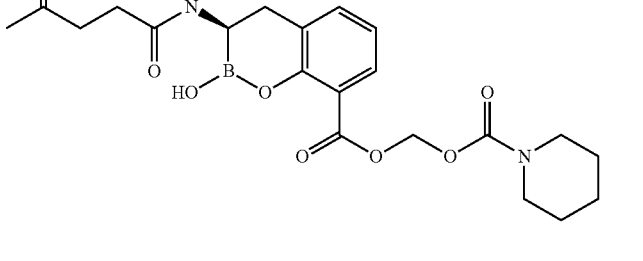 | 446 | 469 (+Na) |
| 153 | 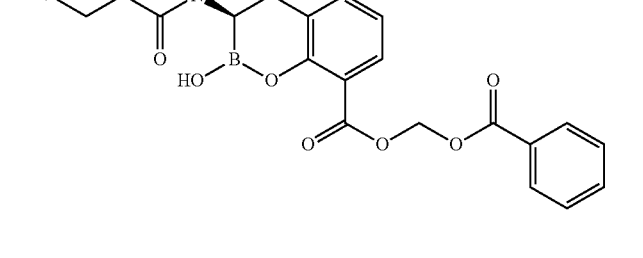 | 422 | 423 |
| 154 | 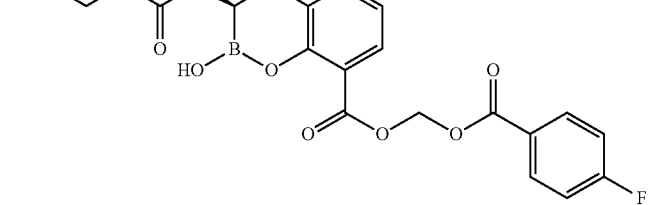 | 440 | 441 |

TABLE 2-continued

Examples of compounds (Compounds of Formula II).

| Example | Structure | MW | ESI-MS (m/z) for [MH]+ |
|---|---|---|---|
| 155 | 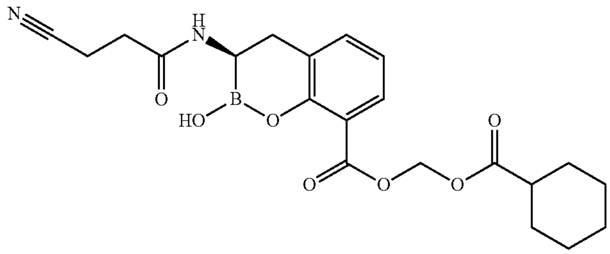 [SMILES: N#CCCC(=O)N[C@H]1Cc2cccc(C(=O)OCOC(=O)C3CCCCC3)c2OB1O] | 428 | 429 |
| 156 | 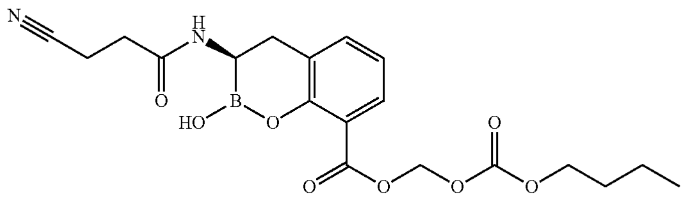 [SMILES: CCCCOC(=O)OCOC(=O)c1cccc2c1OB(O)[C@@H](NC(=O)CCC#N)C2] | 418 | 419 |
| 157 | 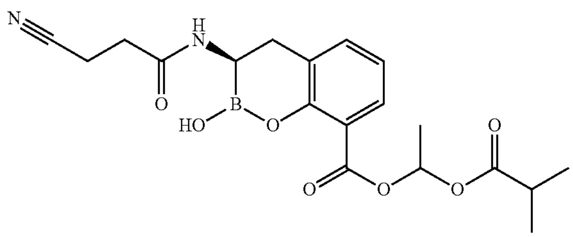 [SMILES: CC(OC(=O)c1cccc2c1OB(O)[C@@H](NC(=O)CCC#N)C2)OC(=O)C(C)C] | 402 | 403 |
| 158 | 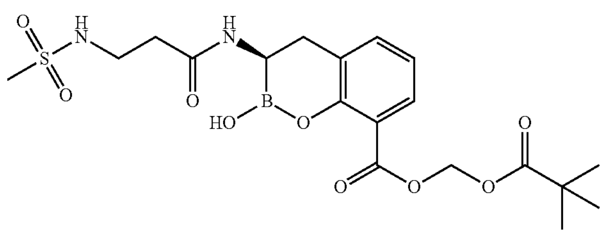 [SMILES: CC(C)(C)C(=O)OCOC(=O)c1cccc2c1OB(O)[C@@H](NC(=O)CCNS(C)(=O)=O)C2] | 470 | 471 |
| 159 | 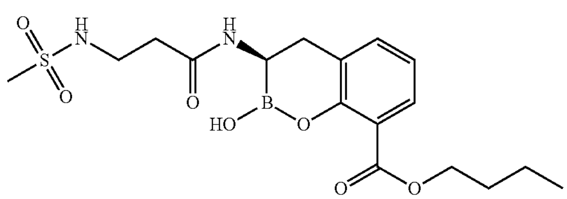 [SMILES: CCCCOC(=O)c1cccc2c1OB(O)[C@@H](NC(=O)CCNS(C)(=O)=O)C2] | 412 | 413 |
| 160 | 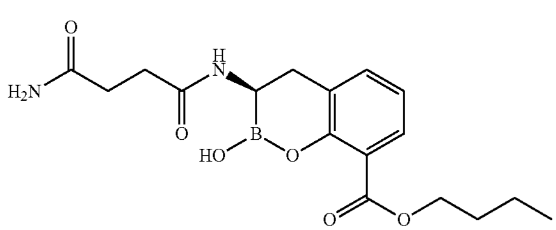 [SMILES: CCCCOC(=O)c1cccc2c1OB(O)[C@@H](NC(=O)CCC(N)=O)C2] | 362 | 363 |

TABLE 2-continued

Examples of compounds (Compounds of Formula II).

| Example | Structure | MW | ESI-MS (m/z) for [MH]+ |
|---|---|---|---|
| 161 | 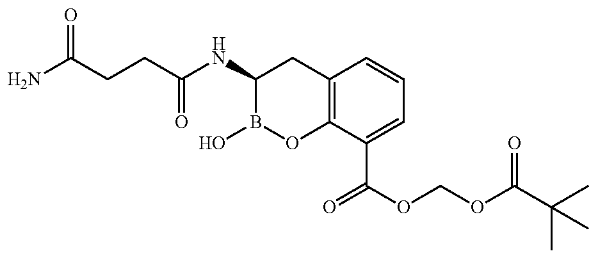 [SMILES: CC(C)(C)C(=O)OCOC(=O)c1cccc2c1OB(O)[C@@H](NC(=O)CCC(N)=O)C2] | 420 | 421 |
| 162 | 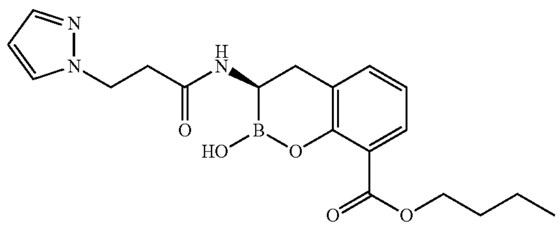 [SMILES: CCCCOC(=O)c1cccc2c1OB(O)[C@@H](NC(=O)CCn1cccn1)C2] | 385 | 386 |
| 163 | 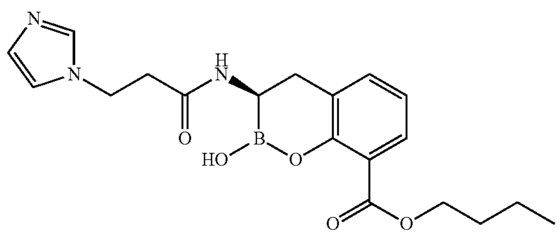 [SMILES: CCCCOC(=O)c1cccc2c1OB(O)[C@@H](NC(=O)CCn1ccnc1)C2] | 385 | 386 |
| 164 | 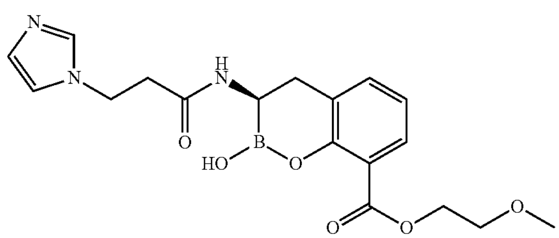 [SMILES: COCCOC(=O)c1cccc2c1OB(O)[C@@H](NC(=O)CCn1ccnc1)C2] | 387 | 388 |
| 165 | 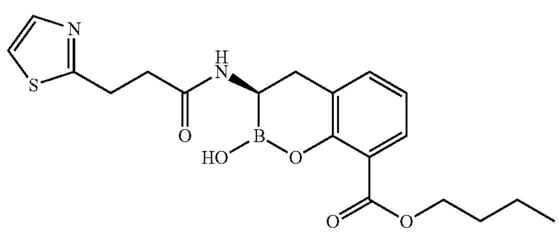 [SMILES: CCCCOC(=O)c1cccc2c1OB(O)[C@@H](NC(=O)CCc1nccs1)C2] | 402 | 403 |
| 166 | 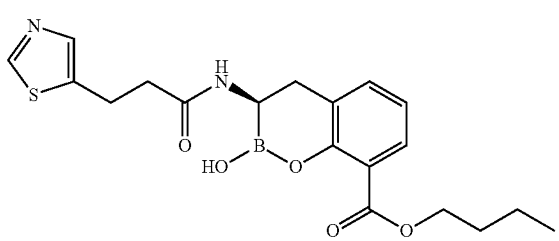 [SMILES: CCCCOC(=O)c1cccc2c1OB(O)[C@@H](NC(=O)CCc1cncs1)C2] | 402 | 403 |

TABLE 2-continued

Examples of compounds (Compounds of Formula II).

| Example | Structure | MW | ESI-MS (m/z) for [MH]+ |
|---------|-----------|-----|------------------------|
| 167 | 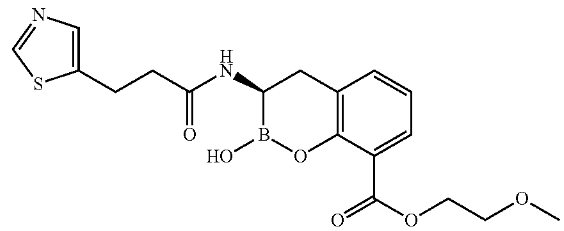 [SMILES: COCCOC(=O)c1cccc2c1OB(O)[C@@H](NC(=O)CCc1cncs1)C2] | 404 | 405 |
| 168 | 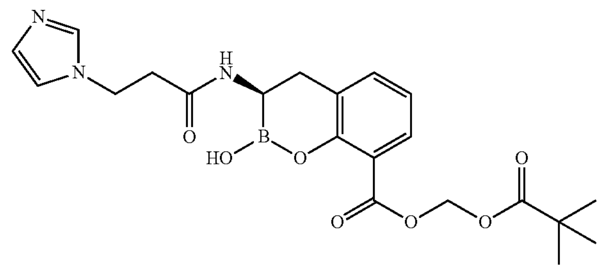 [SMILES: CC(C)(C)C(=O)OCOC(=O)c1cccc2c1OB(O)[C@@H](NC(=O)CCn1ccnc1)C2] | 443 | 444 |
| 169 | 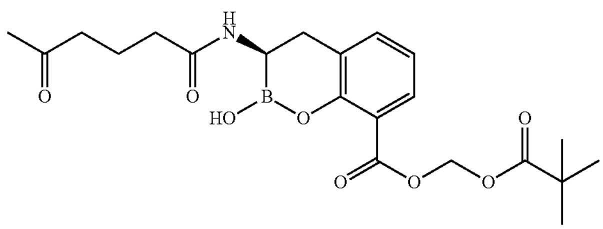 [SMILES: CC(=O)CCCC(=O)N[C@H]1Cc2cccc(C(=O)OCOC(=O)C(C)(C)C)c2OB1O] | 433 | 434 |
| 170 | 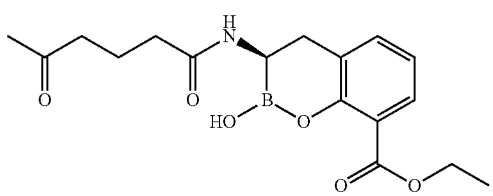 [SMILES: CCOC(=O)c1cccc2c1OB(O)[C@@H](NC(=O)CCCC(C)=O)C2] | 347 | 348 |
| 171 | 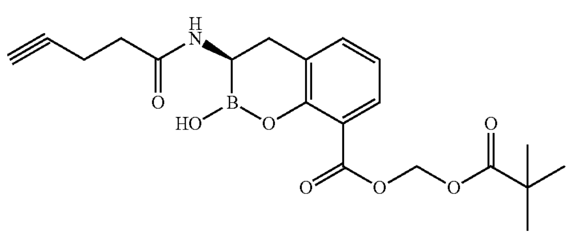 [SMILES: C#CCCC(=O)N[C@H]1Cc2cccc(C(=O)OCOC(=O)C(C)(C)C)c2OB1O] | 401 | 402 |
| 172 | 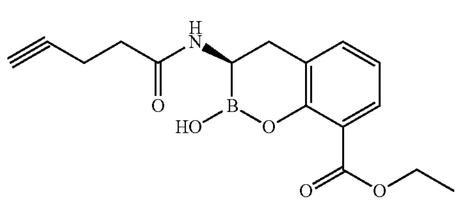 [SMILES: C#CCCC(=O)N[C@H]1Cc2cccc(C(=O)OCC)c2OB1O] | 315 | 316 |

TABLE 2-continued

Examples of compounds (Compounds of Formula II).

| Example | Structure | MW | ESI-MS (m/z) for [MH]+ |
|---------|-----------|-----|------------------------|
| 173 | 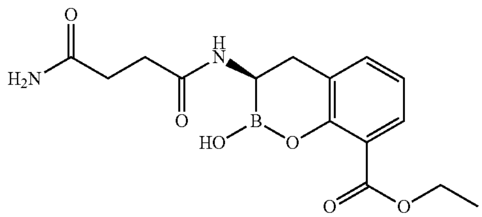 [SMILES: CCOC(=O)c1cccc2c1OB(O)[C@@H](NC(=O)CCC(N)=O)C2] | 334 | 335 |
| 174 | 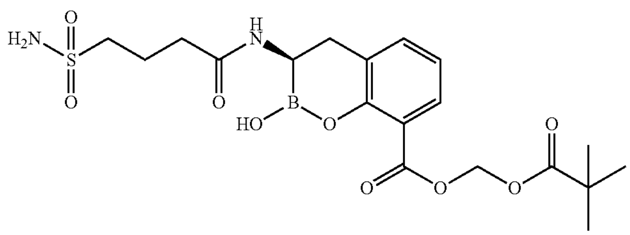 [SMILES: CC(C)(C)C(=O)OCOC(=O)c1cccc2c1OB(O)[C@@H](NC(=O)CCCS(N)(=O)=O)C2] | 470 | 471 |
| 175 | 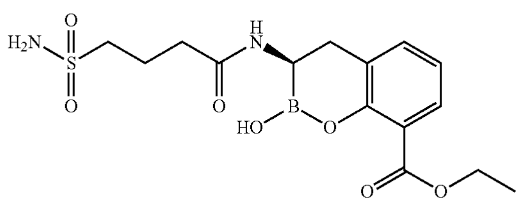 [SMILES: CCOC(=O)c1cccc2c1OB(O)[C@@H](NC(=O)CCCS(N)(=O)=O)C2] | 384 | 385 |
| 176 | 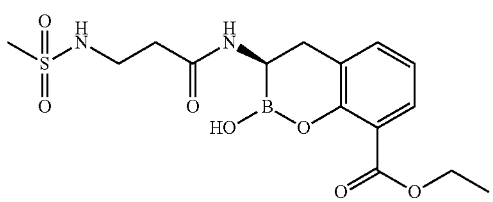 [SMILES: CCOC(=O)c1cccc2c1OB(O)[C@@H](NC(=O)CCNS(C)(=O)=O)C2] | 384 | 385 |
| 177 | 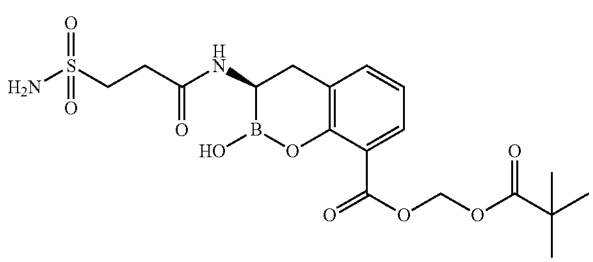 [SMILES: CC(C)(C)C(=O)OCOC(=O)c1cccc2c1OB(O)[C@@H](NC(=O)CCS(N)(=O)=O)C2] | 456 | 457 |
| 178 | 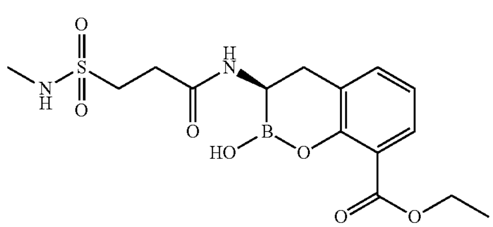 [SMILES: CCOC(=O)c1cccc2c1OB(O)[C@@H](NC(=O)CCS(=O)(=O)NC)C2] | 384 | 385 |

TABLE 2-continued

Examples of compounds (Compounds of Formula II).

| Example | Structure | MW | ESI-MS (m/z) for [MH]+ |
|---|---|---|---|
| 179 | 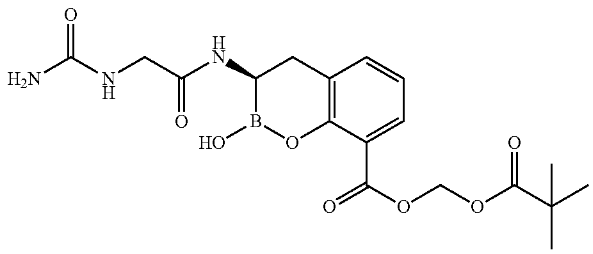 [SMILES: CC(C)(C)C(=O)OCOC(=O)c1cccc2c1OB(O)[C@@H](NC(=O)CNC(N)=O)C2] | 421 | 422 |
| 180 | 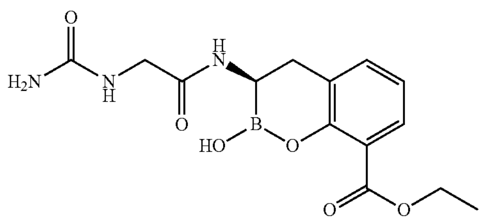 [SMILES: CCOC(=O)c1cccc2c1OB(O)[C@@H](NC(=O)CNC(N)=O)C2] | 335 | 336 |
| 181 | 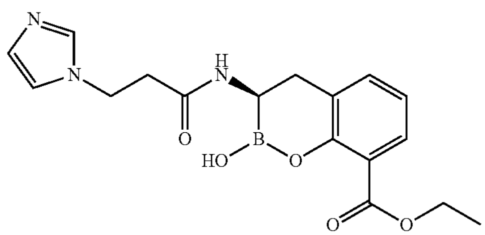 [SMILES: CCOC(=O)c1cccc2c1OB(O)[C@@H](NC(=O)CCn1ccnc1)C2] | 357 | 358 |
| 182 | 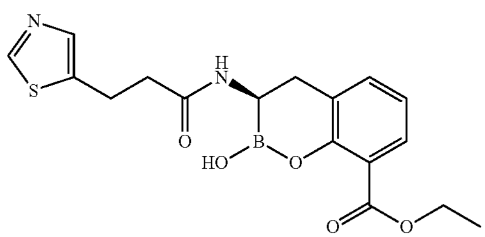 [SMILES: CCOC(=O)c1cccc2c1OB(O)[C@@H](NC(=O)CCc1cncs1)C2] | 374 | 375 |
| 183 | 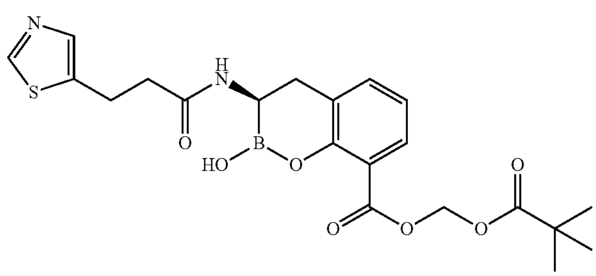 [SMILES: CC(C)(C)C(=O)OCOC(=O)c1cccc2c1OB(O)[C@@H](NC(=O)CCc1cncs1)C2] | 460 | 461 |
| 184 | 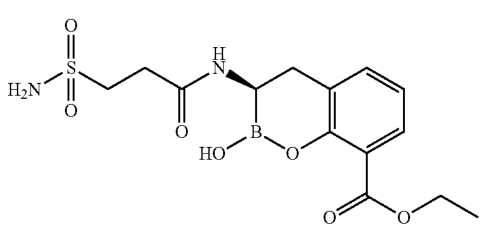 [SMILES: CCOC(=O)c1cccc2c1OB(O)[C@@H](NC(=O)CCS(N)(=O)=O)C2] | 370 | 371 |

TABLE 2-continued

Examples of compounds (Compounds of Formula II).

| Example | Structure | MW | ESI-MS (m/z) for [MH]+ |
|---|---|---|---|
| 185 | 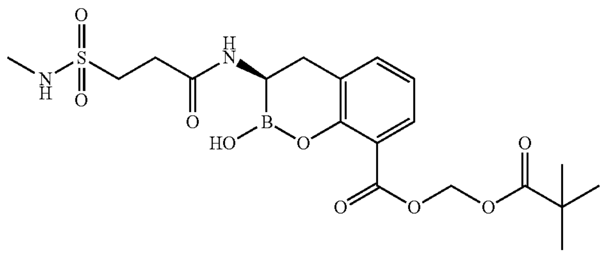 [SMILES: CNS(=O)(=O)CCC(=O)N[C@H]1Cc2cccc(C(=O)OCOC(=O)C(C)(C)C)c2OB1O] | 470 | 471 |
| 186 | 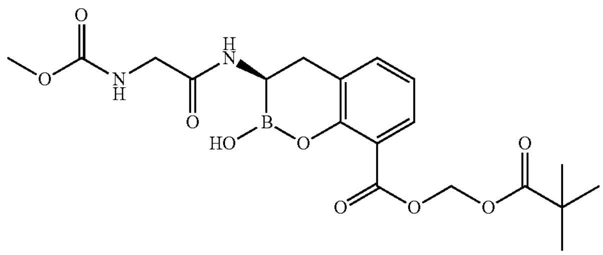 [SMILES: COC(=O)NCC(=O)N[C@H]1Cc2cccc(C(=O)OCOC(=O)C(C)(C)C)c2OB1O] | 436 | 437 |
| 187 | 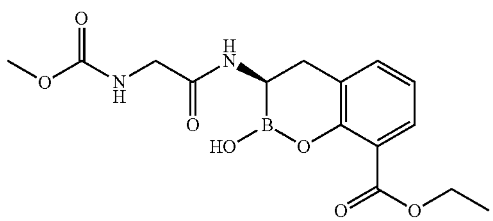 [SMILES: CCOC(=O)c1cccc2c1OB(O)[C@@H](NC(=O)CNC(=O)OC)C2] | 350 | 351 |
| 188 | 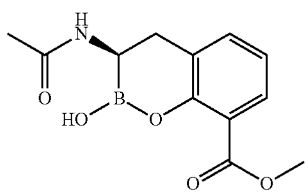 [SMILES: COC(=O)c1cccc2c1OB(O)[C@@H](NC(C)=O)C2] | 263 | 264 |
| 189 | 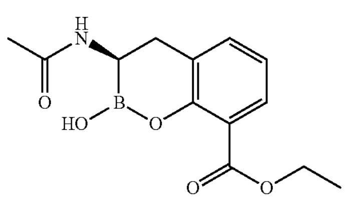 [SMILES: CCOC(=O)c1cccc2c1OB(O)[C@@H](NC(C)=O)C2] | 277 | 278 |
| 190 | 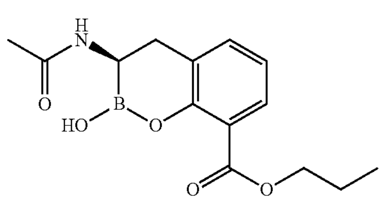 [SMILES: CCCOC(=O)c1cccc2c1OB(O)[C@@H](NC(C)=O)C2] | 291 | 292 |
| 191 | 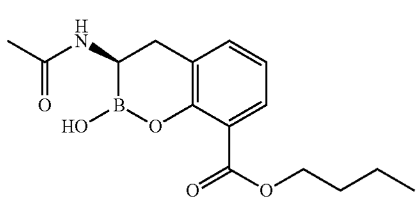 [SMILES: CCCCOC(=O)c1cccc2c1OB(O)[C@@H](NC(C)=O)C2] | 305 | 306 |

TABLE 2-continued

Examples of compounds (Compounds of Formula II).

| Example | Structure | MW | ESI-MS (m/z) for [MH]+ |
|---|---|---|---|
| 192 | 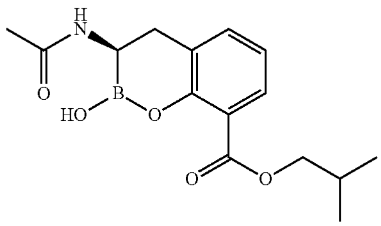 [SMILES: CC(=O)N[C@H]1Cc2cccc(C(=O)OCC(C)C)c2OB1O] | 305 | 306 |
| 193 | 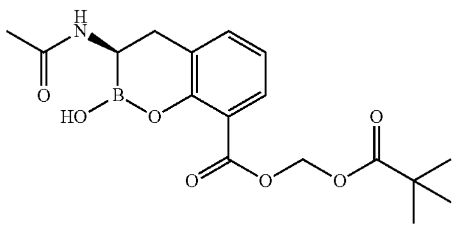 [SMILES: CC(=O)N[C@H]1Cc2cccc(C(=O)OCOC(=O)C(C)(C)C)c2OB1O] | 363 | 386 (+Na) |
| 194 | 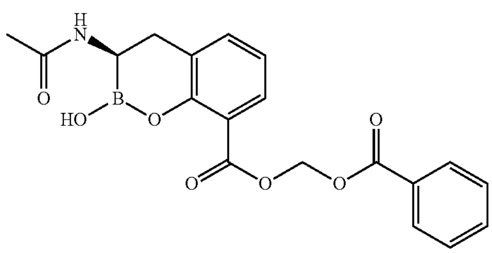 [SMILES: CC(=O)N[C@H]1Cc2cccc(C(=O)OCOC(=O)c3ccccc3)c2OB1O] | 383 | 406 (+Na) |
| 195 | 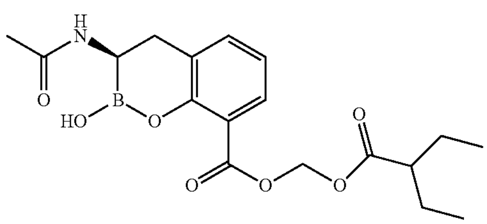 [SMILES: CCC(CC)C(=O)OCOC(=O)c1cccc2c1OB(O)[C@@H](NC(C)=O)C2] | 377 | 378 |
| 196 | 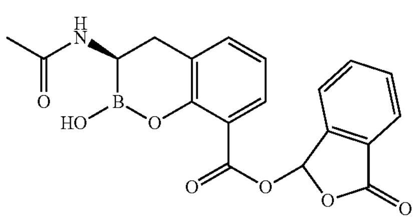 [SMILES: CC(=O)N[C@H]1Cc2cccc(C(=O)OC3OC(=O)c4ccccc43)c2OB1O] | 381 | 382 |
| 197 | 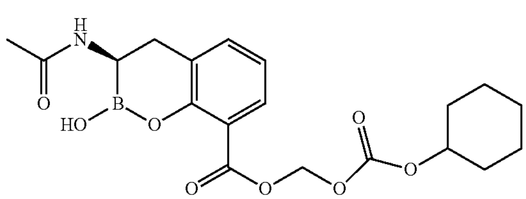 | 405 | 406 |
| 198 | 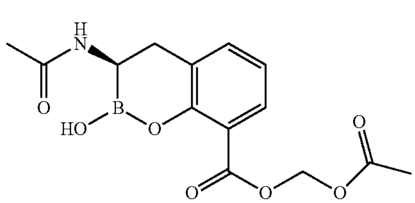 [SMILES: CC(=O)N[C@H]1Cc2cccc(C(=O)OCOC(C)=O)c2OB1O] | 321 | 322 |

TABLE 2-continued

Examples of compounds (Compounds of Formula II).

| Example | Structure | MW | ESI-MS (m/z) for [MH]+ |
|---------|-----------|-----|------------------------|
| 199 | 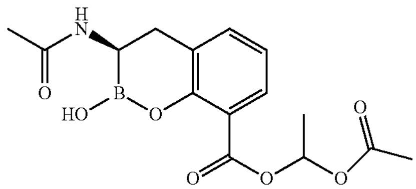 [SMILES: CC(=O)N[C@H]1Cc2cccc(C(=O)OC(C)OC(C)=O)c2OB1O] | 335 | 336 |
| 200 | 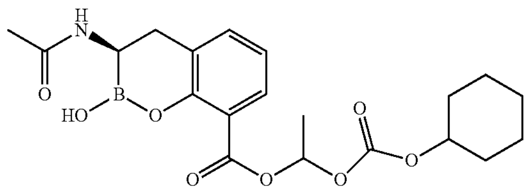 [SMILES: CC(=O)N[C@H]1Cc2cccc(C(=O)OC(C)OC(=O)OC3CCCCC3)c2OB1O] | 419 | 420 |
| 201 | 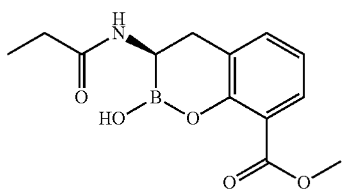 [SMILES: CCC(=O)N[C@H]1Cc2cccc(C(=O)OC)c2OB1O] | 277 | 278 |
| 202 | 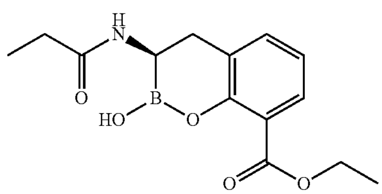 [SMILES: CCOC(=O)c1cccc2c1OB(O)[C@@H](NC(=O)CC)C2] | 291 | 292 |
| 203 | 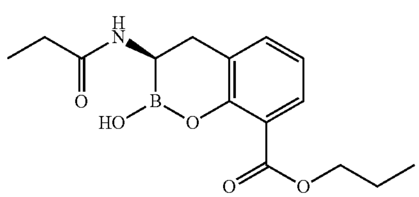 [SMILES: CCCOC(=O)c1cccc2c1OB(O)[C@@H](NC(=O)CC)C2] | 305 | 306 |
| 204 | 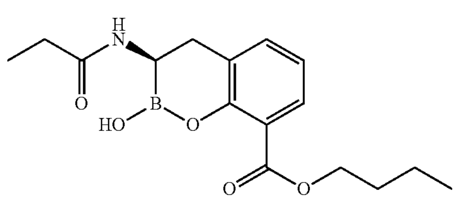 [SMILES: CCCCOC(=O)c1cccc2c1OB(O)[C@@H](NC(=O)CC)C2] | 319 | 320 |
| 205 | 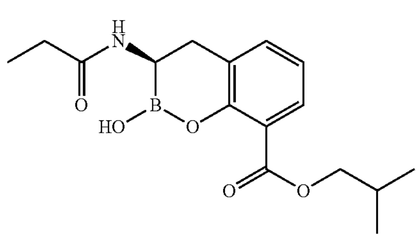 [SMILES: CCC(=O)N[C@H]1Cc2cccc(C(=O)OCC(C)C)c2OB1O] | 319 | 320 |

TABLE 2-continued
Examples of compounds (Compounds of Formula II).
| Example | Structure | MW | ESI-MS (m/z) for [MH]+ |
|---|---|---|---|
| 206 | 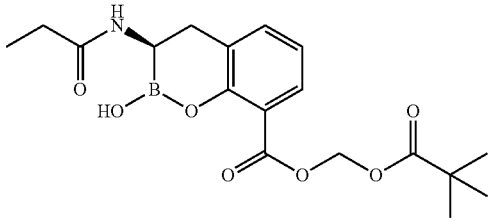 [SMILES: CCC(=O)N[C@H]1Cc2cccc(C(=O)OCOC(=O)C(C)(C)C)c2OB1O] | 377 | 400 (+Na) |
| 207 | 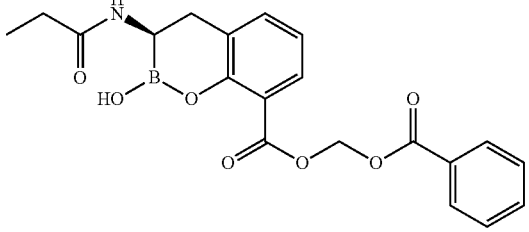 | 397 | 398 |
| 208 | 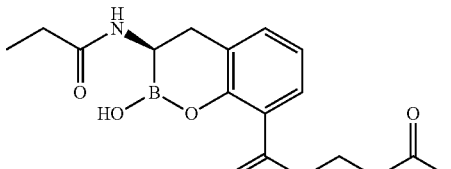 | 335 | 336 |
| 209 | 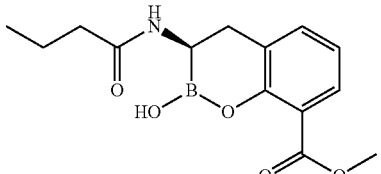 | 291 | 292 |
| 210 | 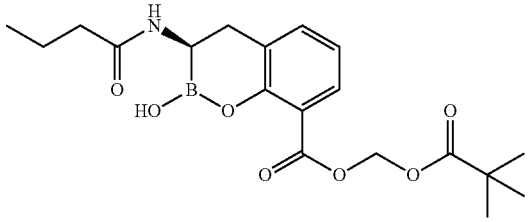 [SMILES: CCCC(=O)N[C@H]1Cc2cccc(C(=O)OCOC(=O)C(C)(C)C)c2OB1O] | 391 | 414 (+Na) |
| 211 | 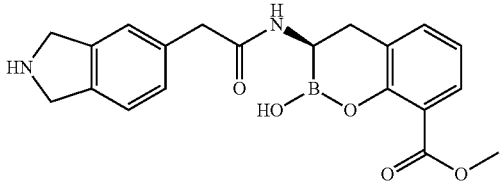 [SMILES: COC(=O)c1cccc2c1OB(O)[C@@H](NC(=O)Cc1ccc3c(c1)CNC3)C2] | 380 | 381 |
| 212 | 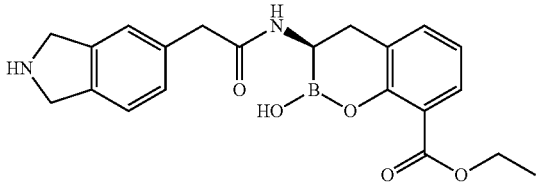 [SMILES: CCOC(=O)c1cccc2c1OB(O)[C@@H](NC(=O)Cc1ccc3c(c1)CNC3)C2] | 394 | 395 |

TABLE 2-continued

Examples of compounds (Compounds of Formula II).

| Example | Structure | MW | ESI-MS (m/z) for [MH]+ |
|---|---|---|---|
| 213 | 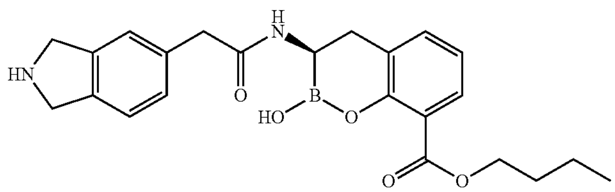 [SMILES: CCCCOC(=O)c1cccc2c1OB(O)[C@@H](NC(=O)Cc1ccc3c(c1)CNC3)C2] | 422 | 423 |
| 214 | 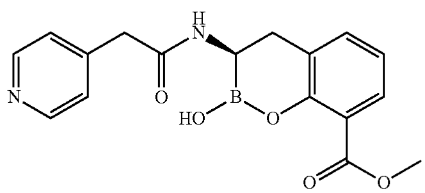 [SMILES: COC(=O)c1cccc2c1OB(O)[C@@H](NC(=O)Cc1ccncc1)C2] | 340 | 341 |
| 215 | 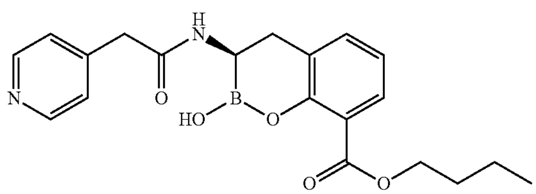 [SMILES: CCCCOC(=O)c1cccc2c1OB(O)[C@@H](NC(=O)Cc1ccncc1)C2] | 382 | 383 |
| 216 | 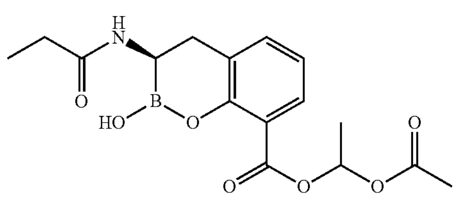 [SMILES: CCC(=O)N[C@H]1Cc2cccc(C(=O)OC(C)OC(C)=O)c2OB1O] | 349 | 350 |
| 217 | 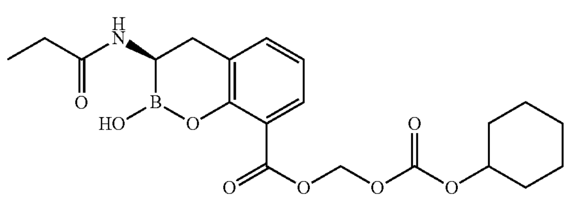 [SMILES: CCC(=O)N[C@H]1Cc2cccc(C(=O)OCOC(=O)OC3CCCCC3)c2OB1O] | 419 | 420 |
| 218 | 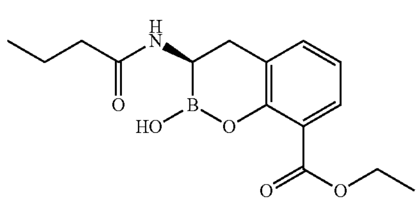 [SMILES: CCCC(=O)N[C@H]1Cc2cccc(C(=O)OCC)c2OB1O] | 305 | 306 |
| 219 | 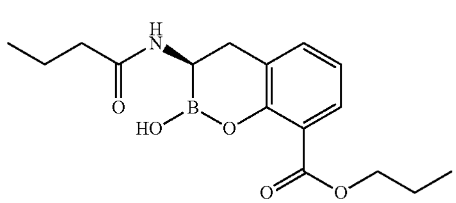 [SMILES: CCCOC(=O)c1cccc2c1OB(O)[C@@H](NC(=O)CCC)C2] | 319 | 320 |

TABLE 2-continued

Examples of compounds (Compounds of Formula II).

| Example | Structure | MW | ESI-MS (m/z) for [MH]+ |
|---|---|---|---|
| 220 | 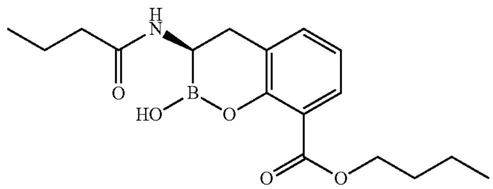 [SMILES: CCCCOC(=O)c1cccc2c1OB(O)[C@@H](NC(=O)CCC)C2] | 333 | 334 |
| 221 | 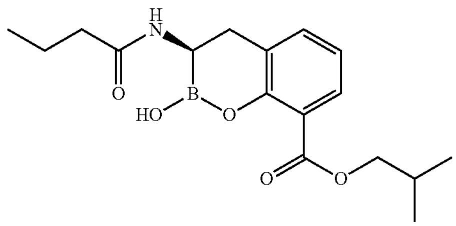 [SMILES: CCCC(=O)N[C@H]1Cc2cccc(C(=O)OCC(C)C)c2OB1O] | 333 | 334 |
| 222 | 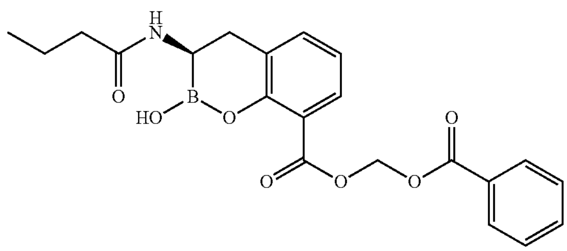 [SMILES: CCCC(=O)N[C@H]1Cc2cccc(C(=O)OCOC(=O)c3ccccc3)c2OB1O] | 411 | 412 |
| 223 | 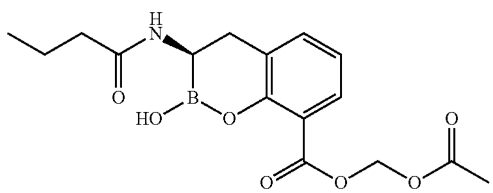 | 349 | 350 |
| 224 | 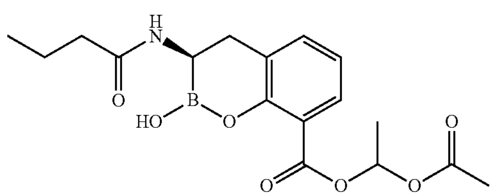 [SMILES: CCCC(=O)N[C@H]1Cc2cccc(C(=O)OC(C)OC(C)=O)c2OB1O] | 363 | 364 |
| 225 | 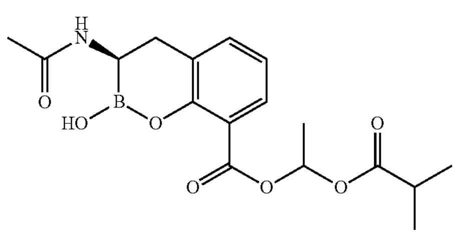 [SMILES: CC(=O)N[C@H]1Cc2cccc(C(=O)OC(C)OC(=O)C(C)C)c2OB1O] | | |
| 226 | 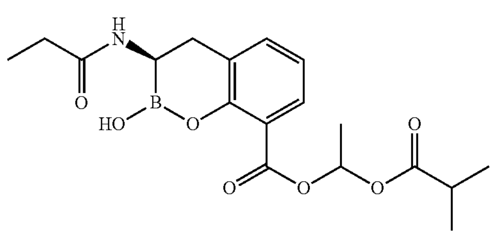 [SMILES: CCC(=O)N[C@H]1Cc2cccc(C(=O)OC(C)OC(=O)C(C)C)c2OB1O] | | |

TABLE 2-continued

Examples of compounds (Compounds of Formula II).

| Example | Structure | ESI-MS MW (m/z) for [MH]+ |
|---|---|---|
| 227 | 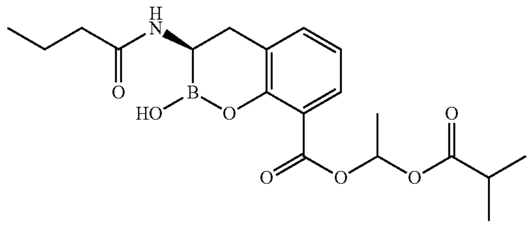 [SMILES: CCCC(=O)N[C@H]1Cc2cccc(C(=O)OC(C)OC(=O)C(C)C)c2OB1O] | |
| 228 | 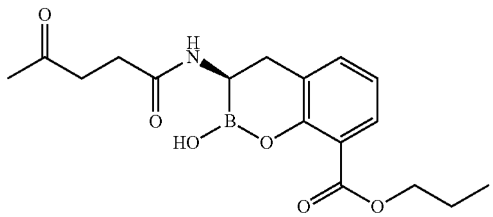 [SMILES: CCCOC(=O)c1cccc2c1OB(O)[C@@H](NC(=O)CCC(C)=O)C2] | |
| 229 | 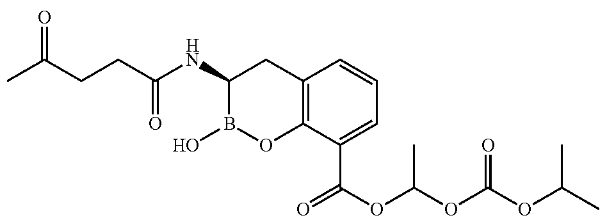 [SMILES: CC(=O)CCC(=O)N[C@H]1Cc2cccc(C(=O)OC(C)OC(=O)OC(C)C)c2OB1O] | |
| 230 | 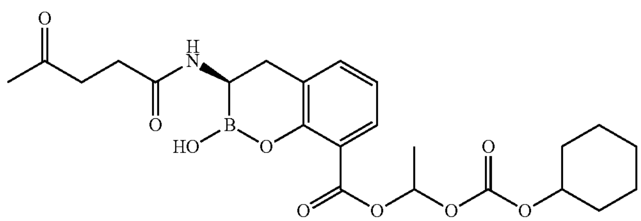 [SMILES: CC(=O)CCC(=O)N[C@H]1Cc2cccc(C(=O)OC(C)OC(=O)OC3CCCCC3)c2OB1O] | |
| 231 | 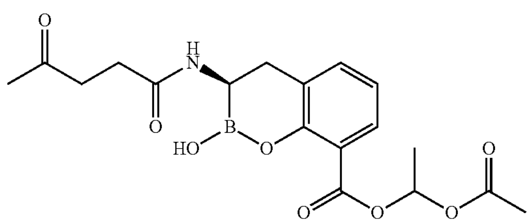 [SMILES: CC(=O)CCC(=O)N[C@H]1Cc2cccc(C(=O)OC(C)OC(C)=O)c2OB1O] | |
| 232 | 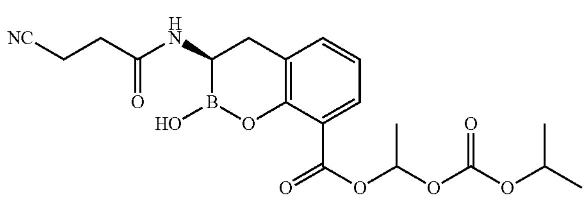 [SMILES: CC(C)OC(=O)OC(C)OC(=O)c1cccc2c1OB(O)[C@@H](NC(=O)CCC#N)C2] | |
| 233 | 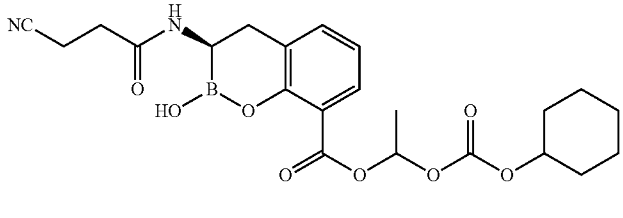 [SMILES: CC(OC(=O)OC1CCCCC1)OC(=O)c1cccc2c1OB(O)[C@@H](NC(=O)CCC#N)C2] | |

TABLE 2-continued

Examples of compounds (Compounds of Formula II).

| Example | Structure | ESI-MS MW (m/z) for [MH]+ |
|---------|-----------|---------------------------|
| 234 | 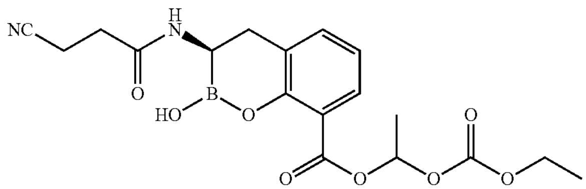 [SMILES: CCOC(=O)OC(C)OC(=O)c1cccc2c1OB(O)[C@@H](NC(=O)CCC#N)C2] | |
| 235 | 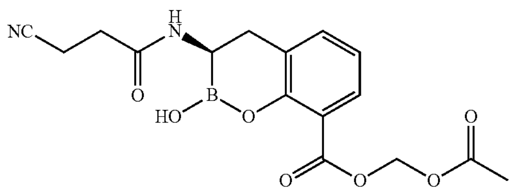 [SMILES: CC(=O)OCOC(=O)c1cccc2c1OB(O)[C@@H](NC(=O)CCC#N)C2] | |
| 236 | 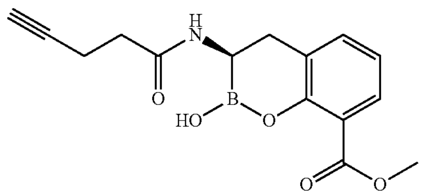 [SMILES: C#CCCC(=O)N[C@H]1Cc2cccc(C(=O)OC)c2OB1O] | |
| 237 | 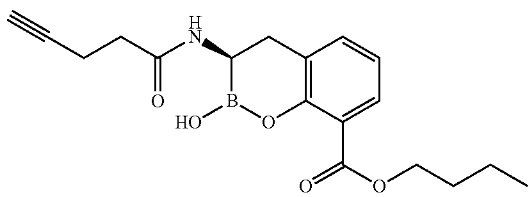 [SMILES: C#CCCC(=O)N[C@H]1Cc2cccc(C(=O)OCCCC)c2OB1O] | |
| 238 | 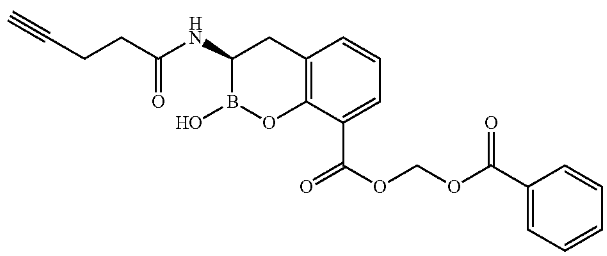 [SMILES: C#CCCC(=O)N[C@H]1Cc2cccc(C(=O)OCOC(=O)c3ccccc3)c2OB1O] | |
| 239 | 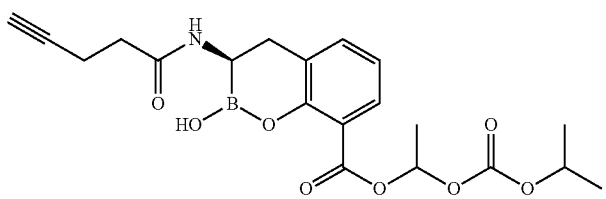 [SMILES: C#CCCC(=O)N[C@H]1Cc2cccc(C(=O)OC(C)OC(=O)OC(C)C)c2OB1O] | |
| 240 | 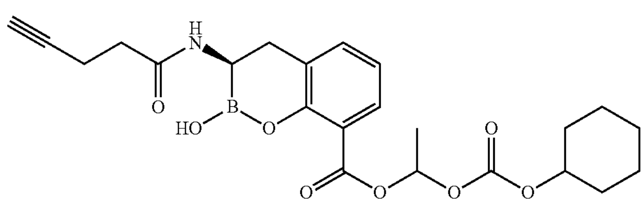 [SMILES: C#CCCC(=O)N[C@H]1Cc2cccc(C(=O)OC(C)OC(=O)OC3CCCCC3)c2OB1O] | |

TABLE 2-continued

Examples of compounds (Compounds of Formula II).

| Example | Structure | ESI-MS MW (m/z) for [MH]+ |
|---------|-----------|---------------------------|
| 241 | 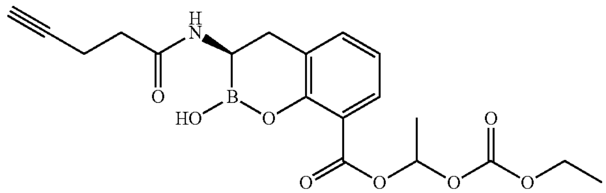 [SMILES: C#CCCC(=O)N[C@H]1Cc2cccc(C(=O)OC(C)OC(=O)OCC)c2OB1O] | |
| 242 | 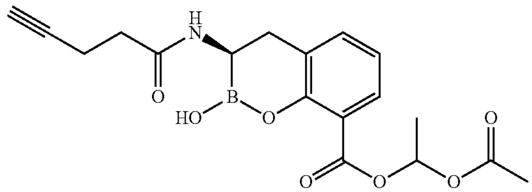 [SMILES: C#CCCC(=O)N[C@H]1Cc2cccc(C(=O)OC(C)OC(C)=O)c2OB1O] | |
| 243 | 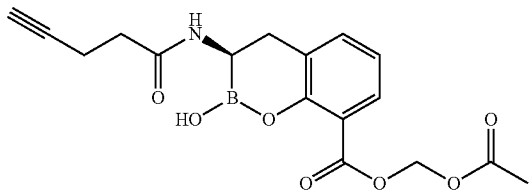 [SMILES: C#CCCC(=O)N[C@H]1Cc2cccc(C(=O)OCOC(C)=O)c2OB1O] | |
| 244 | 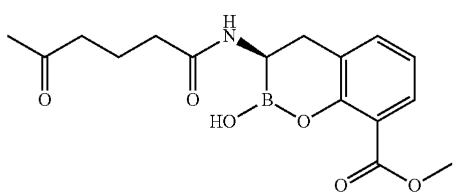 [SMILES: COC(=O)c1cccc2c1OB(O)[C@@H](NC(=O)CCCC(C)=O)C2] | |
| 245 | 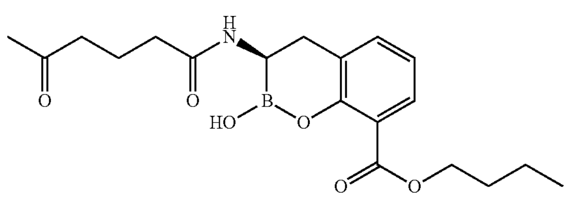 [SMILES: CCCCOC(=O)c1cccc2c1OB(O)[C@@H](NC(=O)CCCC(C)=O)C2] | |
| 246 | 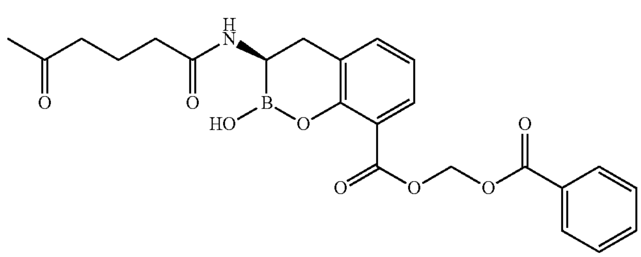 [SMILES: CC(=O)CCCC(=O)N[C@H]1Cc2cccc(C(=O)OCOC(=O)c3ccccc3)c2OB1O] | |
| 247 | 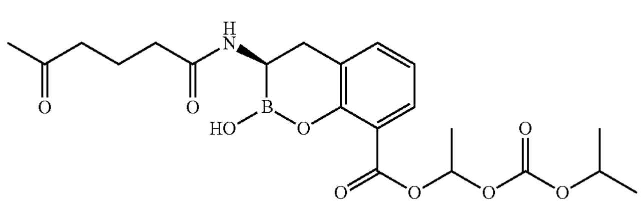 [SMILES: CC(=O)CCCC(=O)N[C@H]1Cc2cccc(C(=O)OC(C)OC(=O)OC(C)C)c2OB1O] | |

TABLE 2-continued
Examples of compounds (Compounds of Formula II).
| Example | Structure | ESI-MS MW (m/z) for [MH]+ |
|---|---|---|
| 248 | 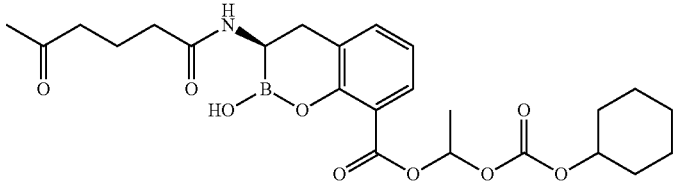 [SMILES: CC(=O)CCCC(=O)N[C@H]1Cc2cccc(C(=O)OC(C)OC(=O)OC3CCCCC3)c2OB1O] | |
| 249 | 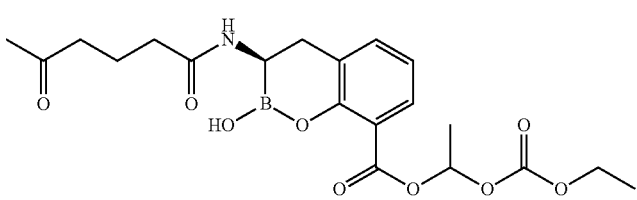 [SMILES: CCOC(=O)OC(C)OC(=O)c1cccc2c1OB(O)[C@@H](NC(=O)CCCC(C)=O)C2] | |
| 250 | 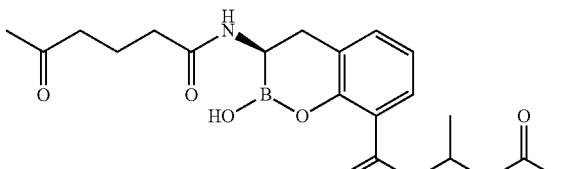 | |
| 251 | 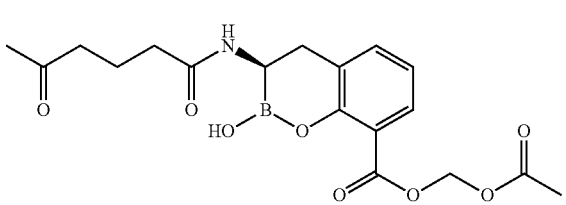 [SMILES: CC(=O)CCCC(=O)N[C@H]1Cc2cccc(C(=O)OCOC(C)=O)c2OB1O] | |
| 252 | 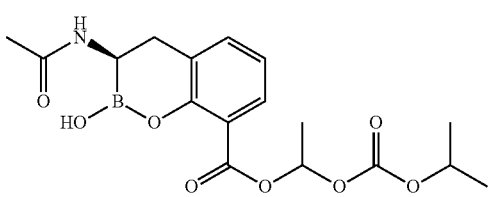 [SMILES: CC(=O)N[C@H]1Cc2cccc(C(=O)OC(C)OC(=O)OC(C)C)c2OB1O] | |
| 253 | 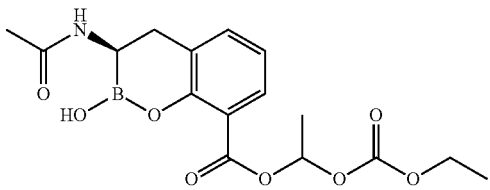 [SMILES: CCOC(=O)OC(C)OC(=O)c1cccc2c1OB(O)[C@@H](NC(C)=O)C2] | |
| 254 | 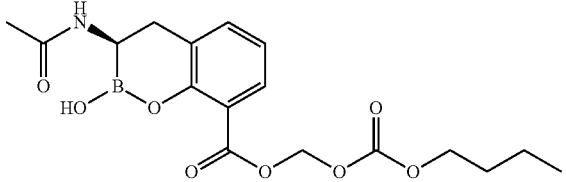 [SMILES: CCCCOC(=O)OCOC(=O)c1cccc2c1OB(O)[C@@H](NC(C)=O)C2] | |

TABLE 2-continued

Examples of compounds (Compounds of Formula II).

| Example | Structure | ESI-MS MW (m/z) for [MH]+ |
|---------|-----------|---------------------------|
| 255 | 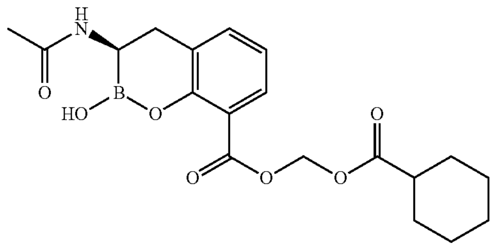 [SMILES: CC(=O)N[C@H]1Cc2cccc(C(=O)OCOC(=O)C3CCCCC3)c2OB1O] | |
| 256 | 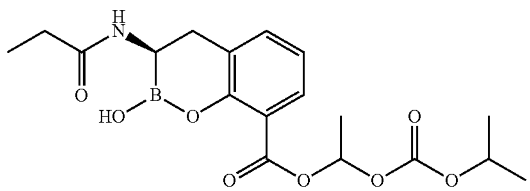 [SMILES: CCC(=O)N[C@H]1Cc2cccc(C(=O)OC(C)OC(=O)OC(C)C)c2OB1O] | |
| 257 | 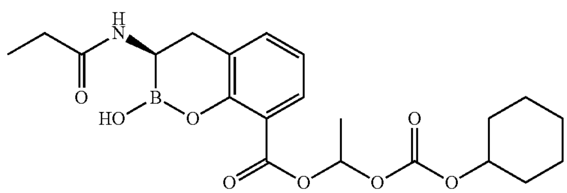 [SMILES: CCC(=O)N[C@H]1Cc2cccc(C(=O)OC(C)OC(=O)OC3CCCCC3)c2OB1O] | |
| 258 | 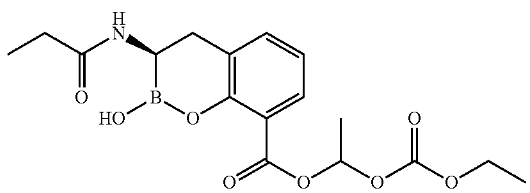 [SMILES: CCOC(=O)OC(C)OC(=O)c1cccc2c1OB(O)[C@@H](NC(=O)CC)C2] | |
| 259 | 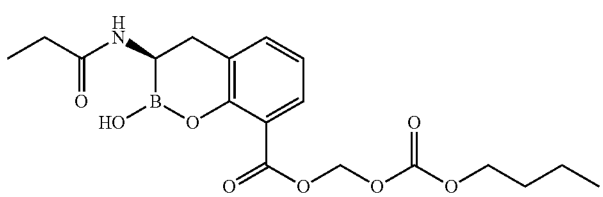 [SMILES: CCCCOC(=O)OCOC(=O)c1cccc2c1OB(O)[C@@H](NC(=O)CC)C2] | |
| 260 | 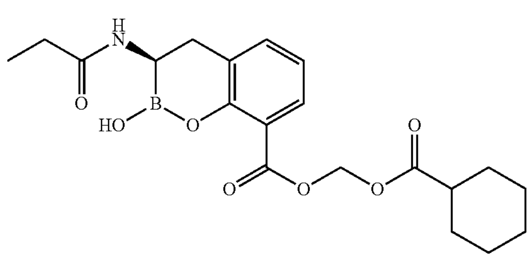 [SMILES: CCC(=O)N[C@H]1Cc2cccc(C(=O)OCOC(=O)C3CCCCC3)c2OB1O] | |
| 261 | 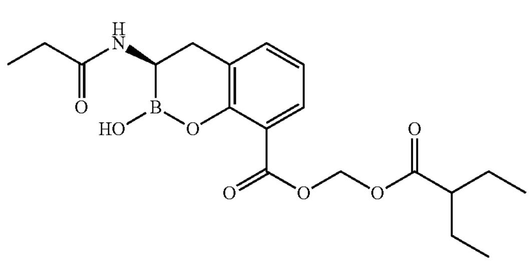 [SMILES: CCC(=O)N[C@H]1Cc2cccc(C(=O)OCOC(=O)C(CC)CC)c2OB1O] | |

TABLE 2-continued

Examples of compounds (Compounds of Formula II).

| Example | Structure | ESI-MS MW (m/z) for [MH]+ |
|---------|-----------|---------------------------|
| 262 | 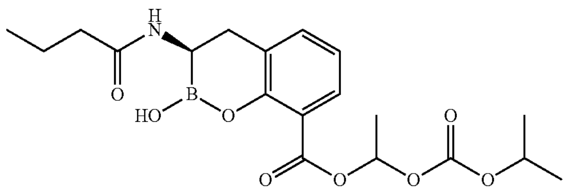 [SMILES: CCCC(=O)N[C@H]1Cc2cccc(C(=O)OC(C)OC(=O)OC(C)C)c2OB1O] | |
| 263 | 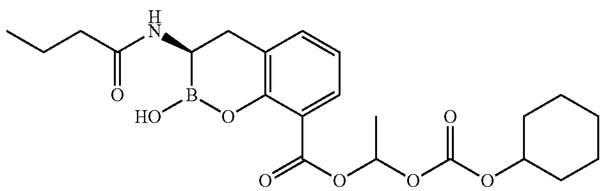 [SMILES: CCCC(=O)N[C@H]1Cc2cccc(C(=O)OC(C)OC(=O)OC3CCCCC3)c2OB1O] | |
| 264 | 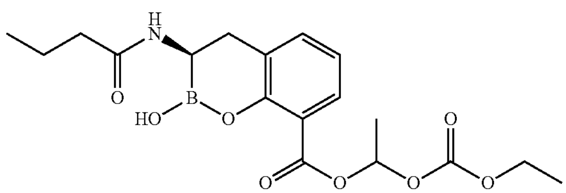 [SMILES: CCCC(=O)N[C@H]1Cc2cccc(C(=O)OC(C)OC(=O)OCC)c2OB1O] | |
| 265 | 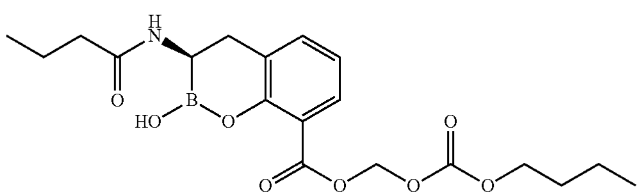 [SMILES: CCCCOC(=O)OCOC(=O)c1cccc2c1OB(O)[C@@H](NC(=O)CCC)C2] | |
| 266 | 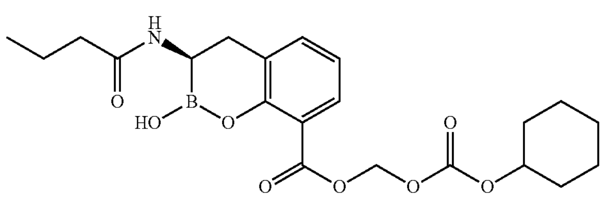 [SMILES: CCCC(=O)N[C@H]1Cc2cccc(C(=O)OCOC(=O)OC3CCCCC3)c2OB1O] | |
| 267 | 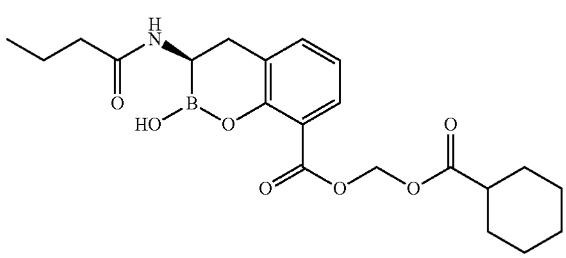 [SMILES: CCCC(=O)N[C@H]1Cc2cccc(C(=O)OCOC(=O)C3CCCCC3)c2OB1O] | |
| 268 | 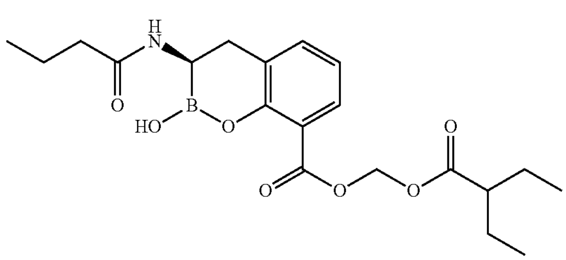 [SMILES: CCCC(=O)N[C@H]1Cc2cccc(C(=O)OCOC(=O)C(CC)CC)c2OB1O] | |

TABLE 2-continued

Examples of compounds (Compounds of Formula II).

| Example | Structure | ESI-MS MW (m/z) for [MH]+ |
|---------|-----------|---------------------------|
| 269 | 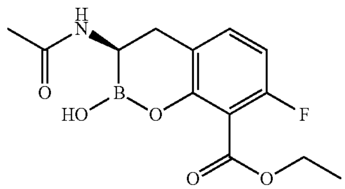 [SMILES: CCOC(=O)c1c(F)ccc2c1OB(O)[C@@H](NC(C)=O)C2] | |
| 270 | 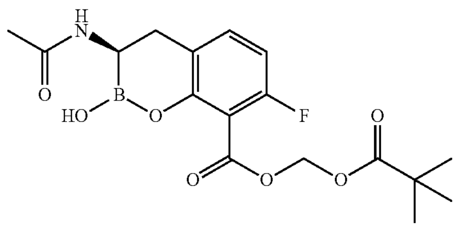 [SMILES: CC(=O)N[C@H]1Cc2ccc(F)c(C(=O)OCOC(=O)C(C)(C)C)c2OB1O] | |
| 271 | 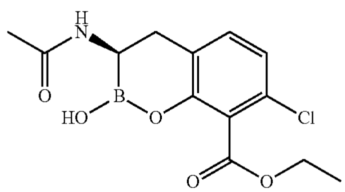 [SMILES: CCOC(=O)c1c(Cl)ccc2c1OB(O)[C@@H](NC(C)=O)C2] | |
| 272 | 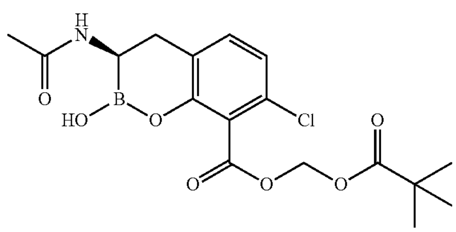 | |
| 273 | 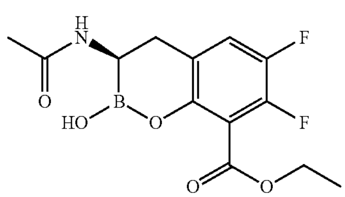 [SMILES: CCOC(=O)c1c(F)c(F)cc2c1OB(O)[C@@H](NC(C)=O)C2] | |
| 274 | 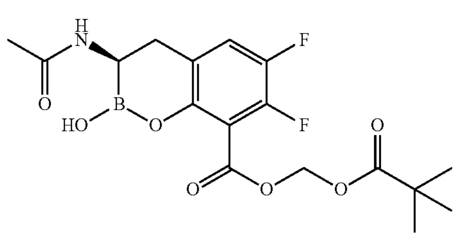 [SMILES: CC(=O)N[C@H]1Cc2cc(F)c(F)c(C(=O)OCOC(=O)C(C)(C)C)c2OB1O] | |
| 275 | 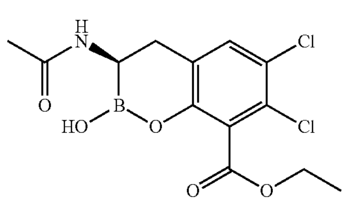 [SMILES: CCOC(=O)c1c(Cl)c(Cl)cc2c1OB(O)[C@@H](NC(C)=O)C2] | |

TABLE 2-continued

Examples of compounds (Compounds of Formula II).

| Example | Structure | MW | ESI-MS (m/z) for [MH]+ |
|---------|-----------|-----|------------------------|
| 276 | 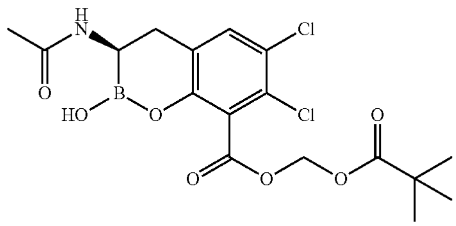 [SMILES: CC(=O)N[C@H]1Cc2cc(Cl)c(Cl)c(C(=O)OCOC(=O)C(C)(C)C)c2OB1O] | | |
| 277 | 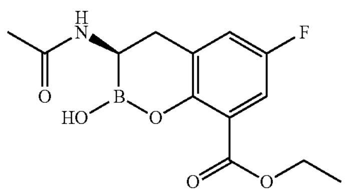 [SMILES: CCOC(=O)c1cc(F)cc2c1OB(O)[C@@H](NC(C)=O)C2] | | |
| 278 | 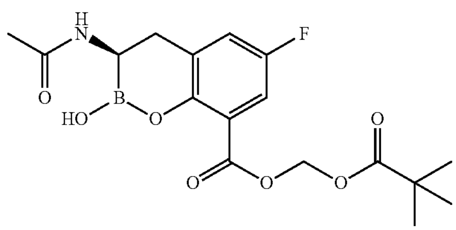 [SMILES: CC(=O)N[C@H]1Cc2cc(F)cc(C(=O)OCOC(=O)C(C)(C)C)c2OB1O] | | |
| 279 | 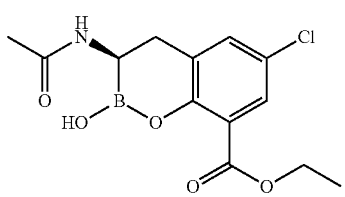 [SMILES: CCOC(=O)c1cc(Cl)cc2c1OB(O)[C@@H](NC(C)=O)C2] | | |
| 280 | 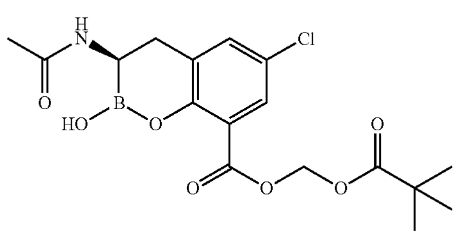 [SMILES: CC(=O)N[C@H]1Cc2cc(Cl)cc(C(=O)OCOC(=O)C(C)(C)C)c2OB1O] | | |
| 281 | 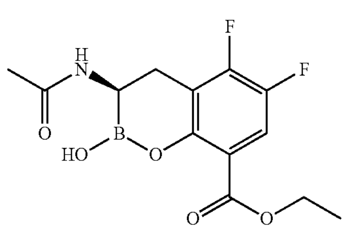 [SMILES: CCOC(=O)c1cc(F)c(F)c2c1OB(O)[C@@H](NC(C)=O)C2] | | |

TABLE 2-continued

Examples of compounds (Compounds of Formula II).

| Example | Structure | ESI-MS MW (m/z) for [MH]+ |
|---------|-----------|---------------------------|
| 282 | 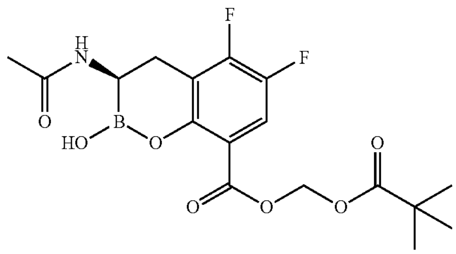 [SMILES: CC(=O)N[C@H]1Cc2c(F)c(F)cc(C(=O)OCOC(=O)C(C)(C)C)c2OB1O] | |
| 283 | 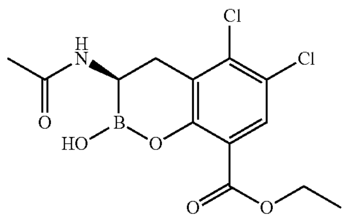 [SMILES: CCOC(=O)c1cc(Cl)c(Cl)c2c1OB(O)[C@@H](NC(C)=O)C2] | |
| 284 | 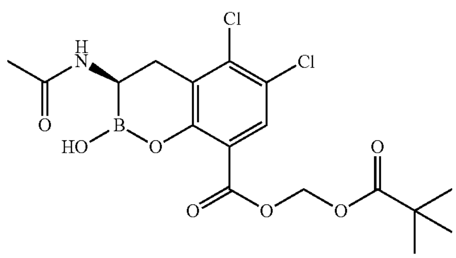 [SMILES: CC(=O)N[C@H]1Cc2c(Cl)c(Cl)cc(C(=O)OCOC(=O)C(C)(C)C)c2OB1O] | |
| 285 | 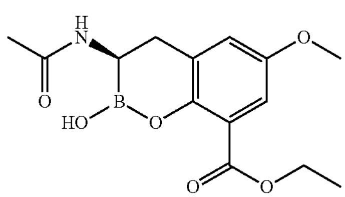 [SMILES: CCOC(=O)c1cc(OC)cc2c1OB(O)[C@@H](NC(C)=O)C2] | |
| 286 | 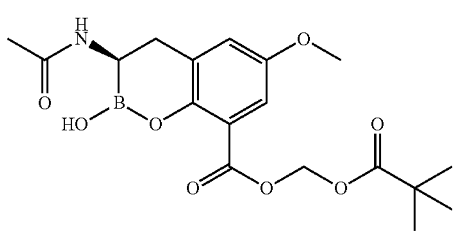 [SMILES: COc1cc2c(c(C(=O)OCOC(=O)C(C)(C)C)c1)OB(O)[C@@H](NC(C)=O)C2] | |
| 287 | 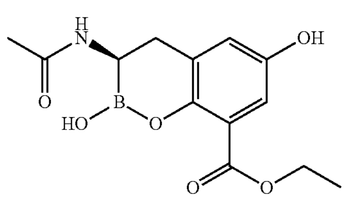 [SMILES: CCOC(=O)c1cc(O)cc2c1OB(O)[C@@H](NC(C)=O)C2] | |

TABLE 2-continued

Examples of compounds (Compounds of Formula II).

| Example | Structure | ESI-MS MW (m/z) for [MH]+ |
|---------|-----------|---------------------------|
| 288 | 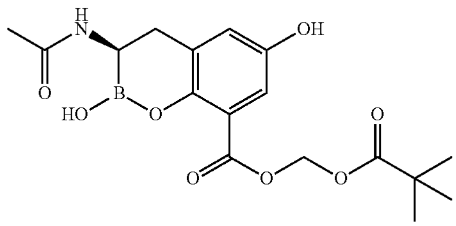 [SMILES: CC(=O)N[C@H]1Cc2cc(O)cc(C(=O)OCOC(=O)C(C)(C)C)c2OB1O] | |
| 289 | 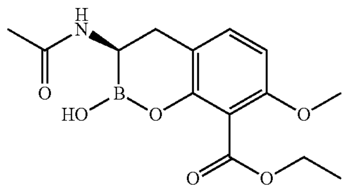 [SMILES: CCOC(=O)c1c(OC)ccc2c1OB(O)[C@@H](NC(C)=O)C2] | |
| 290 | 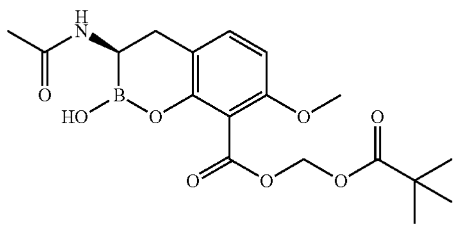 [SMILES: COc1ccc2c(c1C(=O)OCOC(=O)C(C)(C)C)OB(O)[C@@H](NC(C)=O)C2] | |
| 291 | 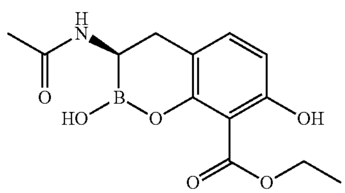 [SMILES: CCOC(=O)c1c(O)ccc2c1OB(O)[C@@H](NC(C)=O)C2] | |
| 292 | 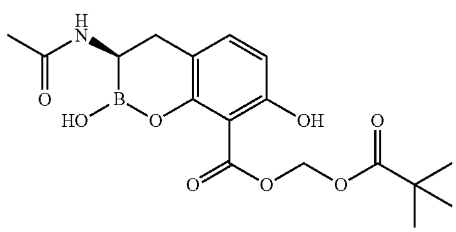 [SMILES: CC(=O)N[C@H]1Cc2ccc(O)c(C(=O)OCOC(=O)C(C)(C)C)c2OB1O] | |
| 293 | 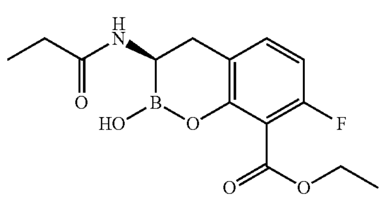 [SMILES: CCOC(=O)c1c(F)ccc2c1OB(O)[C@@H](NC(=O)CC)C2] | |
| 294 | 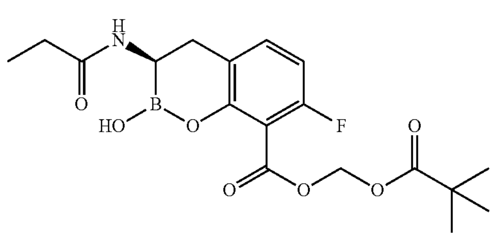 [SMILES: CCC(=O)N[C@H]1Cc2ccc(F)c(C(=O)OCOC(=O)C(C)(C)C)c2OB1O] | |

TABLE 2-continued

Examples of compounds (Compounds of Formula II).

| Example | Structure | MW | ESI-MS (m/z) for [MH]+ |
|---------|-----------|----|-----|
| 295 | 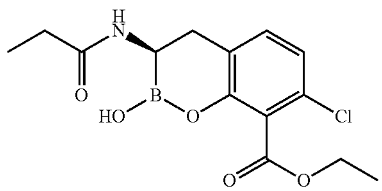 [SMILES: CCOC(=O)c1c(Cl)ccc2c1OB(O)[C@@H](NC(=O)CC)C2] | | |
| 296 | 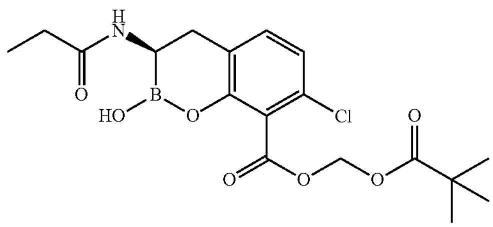 [SMILES: CCC(=O)N[C@H]1Cc2ccc(Cl)c(C(=O)OCOC(=O)C(C)(C)C)c2OB1O] | | |
| 297 | 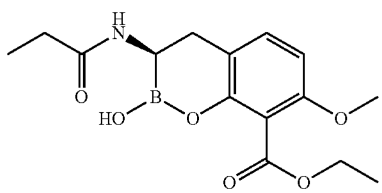 [SMILES: CCOC(=O)c1c(OC)ccc2c1OB(O)[C@@H](NC(=O)CC)C2] | | |
| 298 | 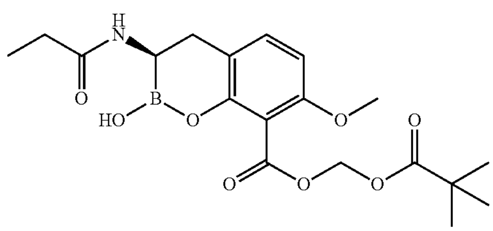 [SMILES: CCC(=O)N[C@H]1Cc2ccc(OC)c(C(=O)OCOC(=O)C(C)(C)C)c2OB1O] | | |
| 299 | 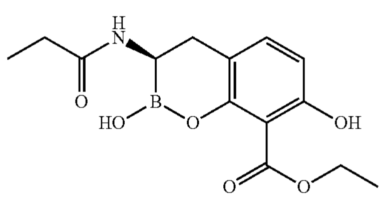 [SMILES: CCOC(=O)c1c(O)ccc2c1OB(O)[C@@H](NC(=O)CC)C2] | | |
| 300 | 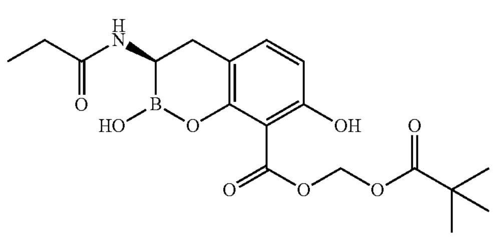 | | |
| 301 | 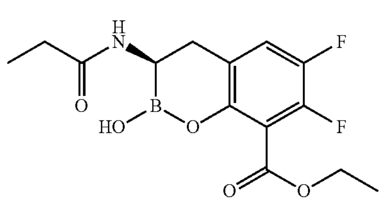 [SMILES: CCOC(=O)c1c(F)c(F)cc2c1OB(O)[C@@H](NC(=O)CC)C2] | | |

TABLE 2-continued

Examples of compounds (Compounds of Formula II).

| Example | Structure | ESI-MS MW (m/z) for [MH]+ |
|---------|-----------|---------------------------|

302

303

304

305

306

307

308

TABLE 2-continued

Examples of compounds (Compounds of Formula II).

| Example | Structure | MW | ESI-MS (m/z) for [MH]+ |
|---------|-----------|----|-----------------------|
| 309 | 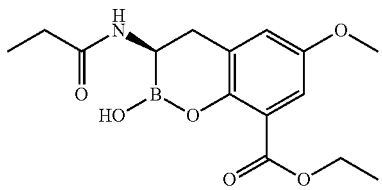 [SMILES: CCOC(=O)c1cc(OC)cc2c1OB(O)[C@@H](NC(=O)CC)C2] | | |
| 310 | 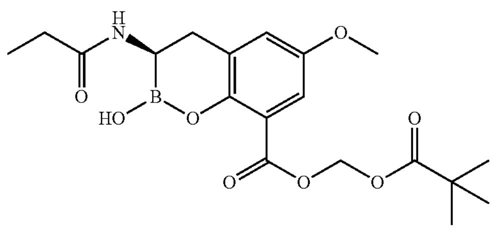 [SMILES: CCC(=O)N[C@H]1Cc2cc(OC)cc(C(=O)OCOC(=O)C(C)(C)C)c2OB1O] | | |
| 311 | 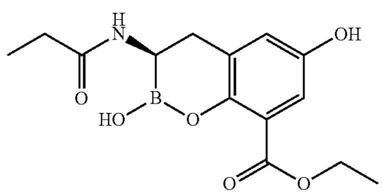 [SMILES: CCOC(=O)c1cc(O)cc2c1OB(O)[C@@H](NC(=O)CC)C2] | | |
| 312 | 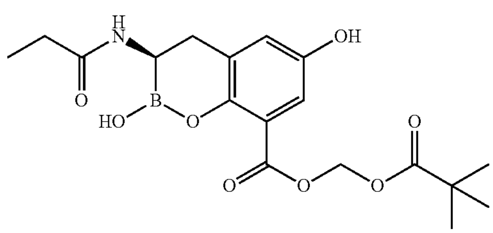 | | |
| 313 | 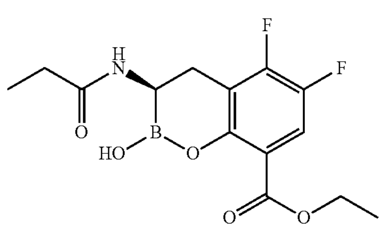 [SMILES: CCOC(=O)c1cc(F)c(F)c2c1OB(O)[C@@H](NC(=O)CC)C2] | | |
| 314 | 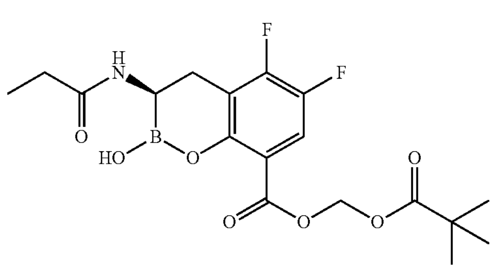 [SMILES: CCC(=O)N[C@H]1Cc2c(F)c(F)cc(C(=O)OCOC(=O)C(C)(C)C)c2OB1O] | | |

TABLE 2-continued

Examples of compounds (Compounds of Formula II).

| Example | Structure | ESI-MS MW (m/z) for [MH]+ |
|---------|-----------|---------------------------|
| 315 | 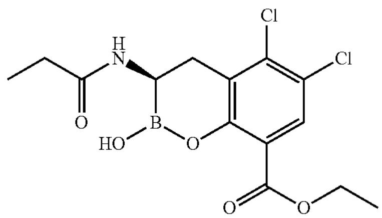 [SMILES: CCOC(=O)c1cc(Cl)c(Cl)c2c1OB(O)[C@@H](NC(=O)CC)C2] | |
| 316 | 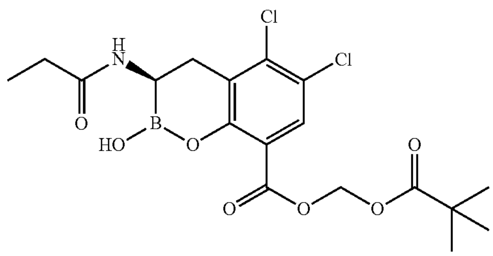 | |
| 317 | 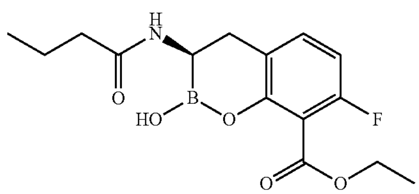 [SMILES: CCCC(=O)N[C@H]1Cc2ccc(F)c(C(=O)OCC)c2OB1O] | |
| 318 | 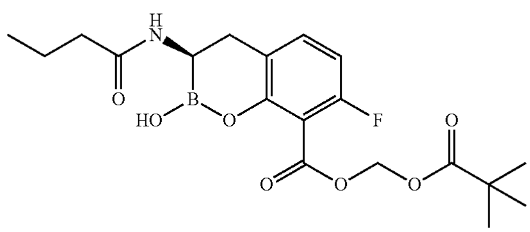 [SMILES: CCCC(=O)N[C@H]1Cc2ccc(F)c(C(=O)OCOC(=O)C(C)(C)C)c2OB1O] | |
| 319 | 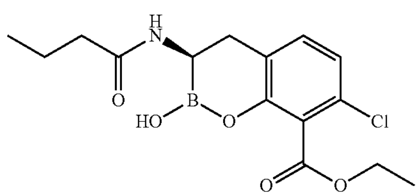 [SMILES: CCCC(=O)N[C@H]1Cc2ccc(Cl)c(C(=O)OCC)c2OB1O] | |
| 320 | 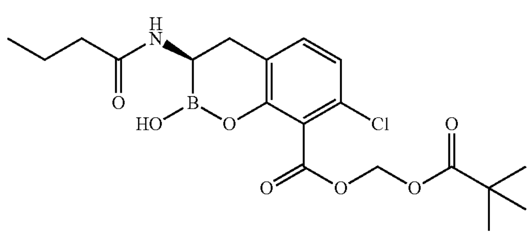 [SMILES: CCCC(=O)N[C@H]1Cc2ccc(Cl)c(C(=O)OCOC(=O)C(C)(C)C)c2OB1O] | |
| 321 | 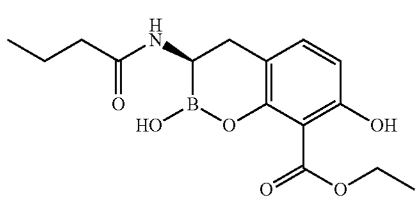 | |

TABLE 2-continued

Examples of compounds (Compounds of Formula II).

| Example | Structure | ESI-MS MW (m/z) for [MH]+ |
|---------|-----------|---------------------------|
| 322 | 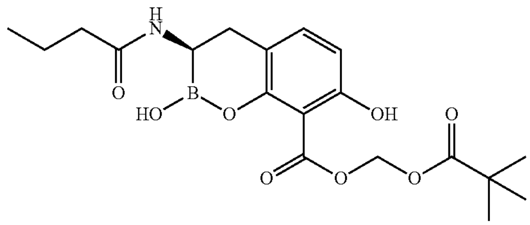 [SMILES: CCCC(=O)N[C@H]1Cc2ccc(O)c(C(=O)OCOC(=O)C(C)(C)C)c2OB1O] | |
| 323 | 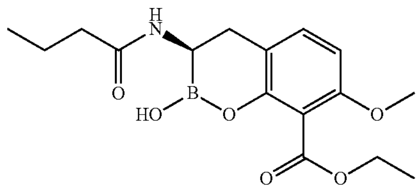 [SMILES: CCCC(=O)N[C@H]1Cc2ccc(OC)c(C(=O)OCC)c2OB1O] | |
| 324 | 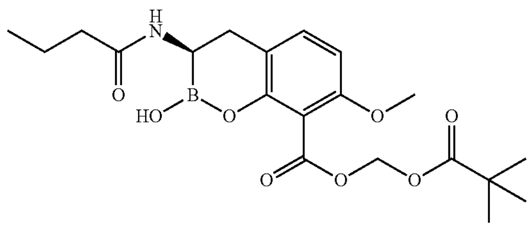 [SMILES: CCCC(=O)N[C@H]1Cc2ccc(OC)c(C(=O)OCOC(=O)C(C)(C)C)c2OB1O] | |
| 325 | 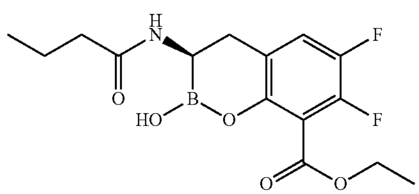 [SMILES: CCCC(=O)N[C@H]1Cc2cc(F)c(F)c(C(=O)OCC)c2OB1O] | |
| 326 | 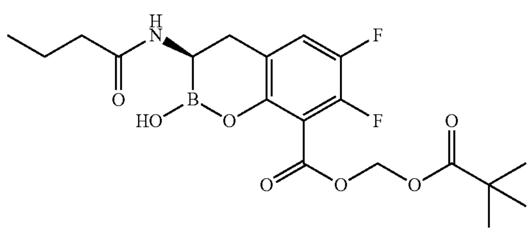 [SMILES: CCCC(=O)N[C@H]1Cc2cc(F)c(F)c(C(=O)OCOC(=O)C(C)(C)C)c2OB1O] | |
| 327 | 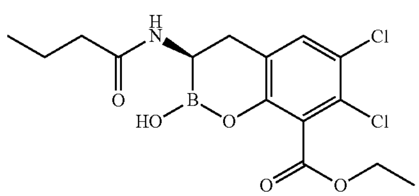 [SMILES: CCCC(=O)N[C@H]1Cc2cc(Cl)c(Cl)c(C(=O)OCC)c2OB1O] | |
| 328 | 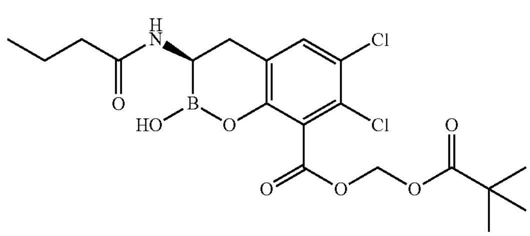 [SMILES: CCCC(=O)N[C@H]1Cc2cc(Cl)c(Cl)c(C(=O)OCOC(=O)C(C)(C)C)c2OB1O] | |

TABLE 2-continued

Examples of compounds (Compounds of Formula II).

| Example | Structure | MW | ESI-MS (m/z) for [MH]+ |
|---|---|---|---|
| 329 | 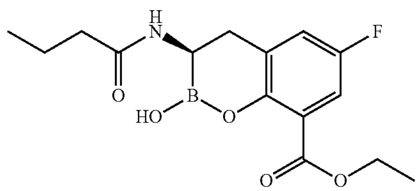 [SMILES: CCCC(=O)N[C@H]1Cc2cc(F)cc(C(=O)OCC)c2OB1O] | | |
| 330 | 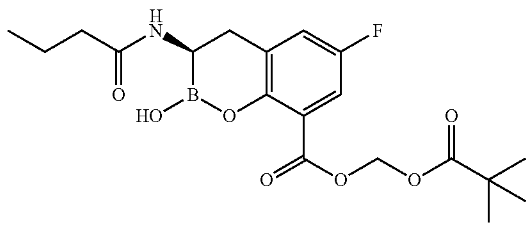 [SMILES: CCCC(=O)N[C@H]1Cc2cc(F)cc(C(=O)OCOC(=O)C(C)(C)C)c2OB1O] | | |
| 331 | 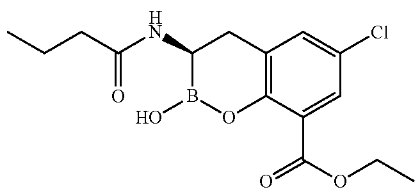 [SMILES: CCCC(=O)N[C@H]1Cc2cc(Cl)cc(C(=O)OCC)c2OB1O] | | |
| 332 | 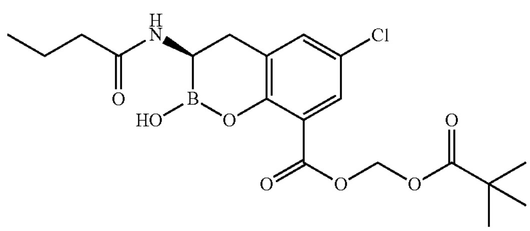 [SMILES: CCCC(=O)N[C@H]1Cc2cc(Cl)cc(C(=O)OCOC(=O)C(C)(C)C)c2OB1O] | | |
| 333 | 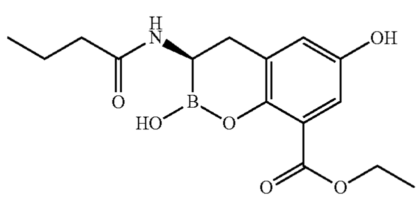 | | |
| 334 | 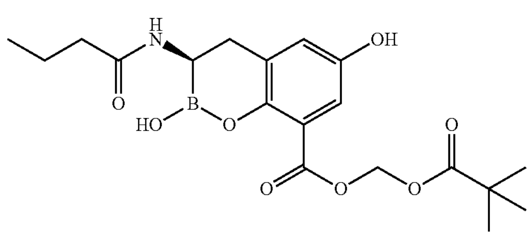 [SMILES: CCCC(=O)N[C@H]1Cc2cc(O)cc(C(=O)OCOC(=O)C(C)(C)C)c2OB1O] | | |
| 335 | 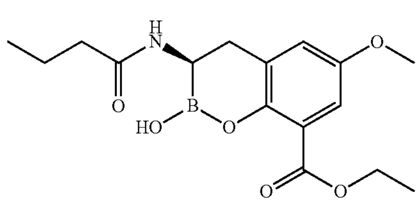 [SMILES: CCCC(=O)N[C@H]1Cc2cc(OC)cc(C(=O)OCC)c2OB1O] | | |

TABLE 2-continued

Examples of compounds (Compounds of Formula II).

| Example | Structure | ESI-MS MW (m/z) for [MH]+ |
|---------|-----------|---------------------------|
| 336 | 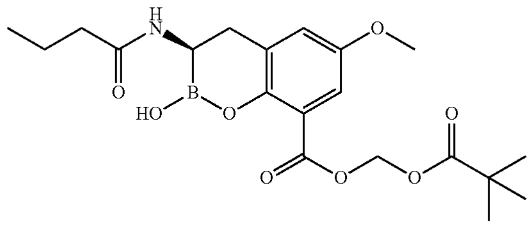 [SMILES: CCCC(=O)N[C@H]1Cc2cc(OC)cc(C(=O)OCOC(=O)C(C)(C)C)c2OB1O] | |
| 337 | 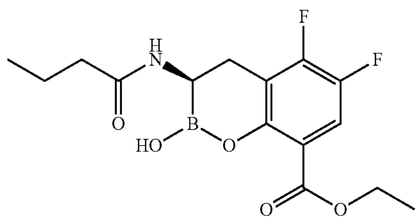 [SMILES: CCCC(=O)N[C@H]1Cc2c(F)c(F)cc(C(=O)OCC)c2OB1O] | |
| 338 | 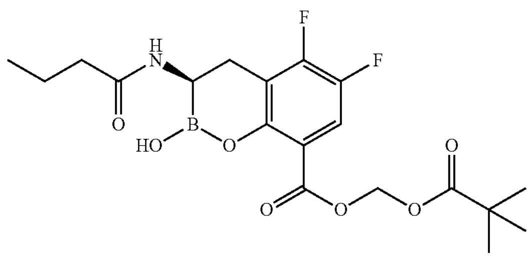 [SMILES: CCCC(=O)N[C@H]1Cc2c(F)c(F)cc(C(=O)OCOC(=O)C(C)(C)C)c2OB1O] | |
| 339 | 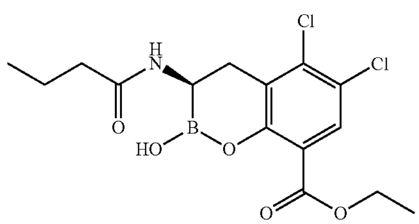 [SMILES: CCCC(=O)N[C@H]1Cc2c(Cl)c(Cl)cc(C(=O)OCC)c2OB1O] | |
| 340 | 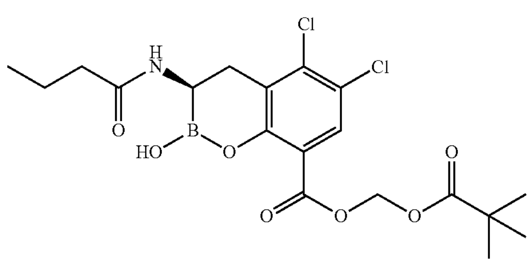 | |
| 341 | 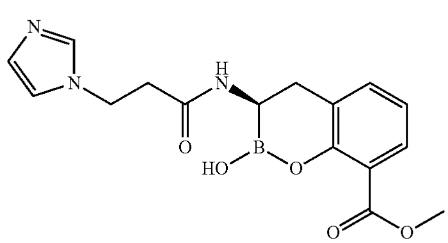 [SMILES: COC(=O)c1cccc2c1OB(O)[C@@H](NC(=O)CCn1ccnc1)C2] | |

TABLE 2-continued

Examples of compounds (Compounds of Formula II).

| Example | Structure | ESI-MS MW (m/z) for [MH]+ |
|---|---|---|
| 342 | 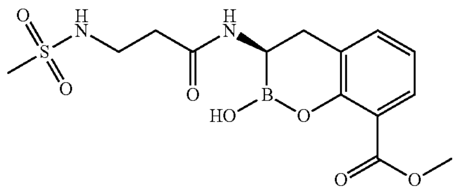 | |
| 343 | 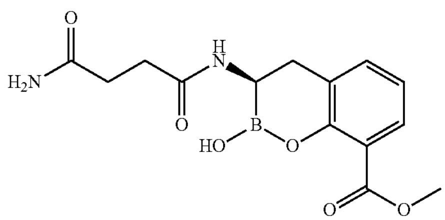 [SMILES: COC(=O)c1cccc2c1OB(O)[C@@H](NC(=O)CCC(N)=O)C2] | |
| 344 | 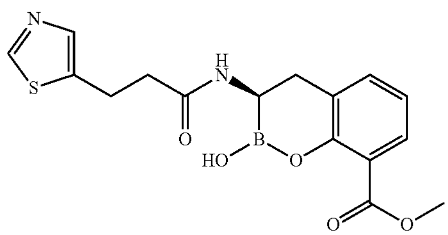 [SMILES: COC(=O)c1cccc2c1OB(O)[C@@H](NC(=O)CCc1cncs1)C2] | |
| 345 | 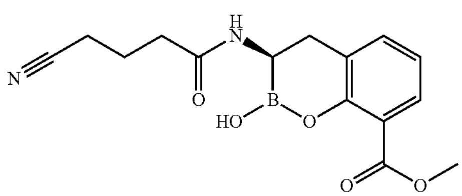 [SMILES: COC(=O)c1cccc2c1OB(O)[C@@H](NC(=O)CCCC#N)C2] | |

Example 346

Parenteral Composition

To prepare a parenteral pharmaceutical composition suitable for administration by injection, 100 mg of a compound of Formula (I), (II), or (IX), or a water soluble pharmaceutically acceptable salt thereof, is dissolved in DMSO and then mixed with 10 ml of 0.9% sterile saline solution. The mixture is incorporated into a dosage unit suitable for administration by injection.

Example 347

Oral Composition

To prepare a pharmaceutical composition for oral delivery, 100 mg of a compound of Formula (I), (II), or (IX), or pharmaceutically acceptable salt thereof, is mixed with 750 mg of starch. The mixture is incorporated into an oral dosage unit for, such as a hard gelatin capsule, which is suitable for oral administration.

Biological Examples

Example I

Experimental Method for β-Lactamase Enzyme Assays

Isolation of β-Lactamases.

For SHV-5, Kpc-2, p99AmpC and OXA-1 β-lactamases, *E. coli* BL21(DE3) bacterial cells carrying expression plasmids (expressed as native untagged proteins) for the individual β-lactamases were grown in 1 L of Superbroth (Teknova Inc. Hollister, Calif.) supplemented with 100 μg/ml kanamycin selection and 1×5052 (0.5% glycerol, 0.05% glucose and 0.2% α-lactose) at 35° C. for 18-20 hours. Cells were harvested by centrifugation (4,000×g, 4° C., 20 min), resuspended in 50 ml of 10 mM HEPES pH 7.5 (1/20 of the initial volume). The cells were lysed by sonication (5 pulses of 45 seconds) at 45 W on ice. The lysates were clarified by centrifugation at 10,000×g for 40 minutes at 4° C. Samples were diluted 5-fold in 50 mM sodium acetate pH 5.0, stored overnight at 4° C., after which they were centrifuged at 10,000×g for 30 minutes to clarify, and filtered through 0.45 µm filters. The samples were loaded onto a 5 ml Capto S sepharose cation exchange column (GE Healthcare) pre-equilibrated with 50 mM sodium acetate pH 5.0. The column was washed with 5 column volumes of 50 mM sodium acetate pH 5.0 to wash out unbound protein and a linear gradient of NaCl (0 to 500 mM) was used to elute the protein (over 16 CV) from the column. Fractions were assayed for β-lactamase activity using Centa (Calbiochem, Gibbstown, N.J.) or Nitrocefin (EMD Millipore chemicals, Darmstadt, Germany) as a reporter β-lactamase substrate for activity in the isolated fractions. Active fractions were pooled, concentrated and further purified by gel filtration chromatography on a Superdex 75 prep grade gel filtration column (GE Healthcare, Piscataway, N.J.) pre-equilibrated in 50 mM Hepes pH 7.5, 150 mM NaCl. Active fractions were pooled, concentrated, and quantitated by BCA protein determination (Thermo Scientific, Rockford, Ill.), dialyzed into PBS and frozen at −80° C. in 20% glycerol until use.

For VIM-2 metallo β-lactamase, the procedure was identical with the following exceptions, first the protein was not pH adjusted to pH 5 with 50 mM sodium acetate. Second, the chromatography step was changed to a 5 ml Q sepharose anion exchange column pre-equilibrated with 50 mM Hepes pH 7.5, and elution of the protein was achieved by a linear gradient of NaCl (0-600 mM). Finally, the VIM-2 purification required a second run ($3^{rd}$ step) on the Q sepharose anion exchange column to achieve acceptable purity (>90%).

β-Lactamase Inhibition.

To determine the level of inhibition of β-lactamase enzymes, compounds were diluted in PBS at pH 7.4 to yield concentrations ranging from 100 to 0.00005 µM in 96-well microtiter plates. An equal volume of diluted enzyme stock was added, and the plates were incubated at 37° C. for 15 min. Nitrocefin was used as substrate for p99 AmpC, VIM-2 and OXA-1 and dispensed into each well at a final concentration of 100 µM. Absorbance at 486 nm was immediately monitored for 10 min using a Biotek Powerwave XS2 microplate spectrophotometer using the GEN5 software package (Biotek Instruments, Winooski Vt.). In an analogous fashion, imipenem was used as substrate for KPC-2 and Cefotaxime was used for SHV-5, while changes in absorbance upon hydrolysis of the β-lactam ring were monitored at 300 nm and 260 nm respectively in UV-transparent 96-well microtiter assay plates. Maximum rates of hydrolysis were compared to those in control wells (without inhibitors), and percentages of enzyme inhibition were calculated for each concentration of inhibitor. The concentration of inhibitor needed to reduce the initial rate of hydrolysis of substrate by 50% ($IC_{50}$) was calculated as the residual activity of β-lactamase at 486 nm using GraFit version 7 kinetics software package (Erithacus Software, Surrey, UK).

Example II

Inhibition of Diverse β-Lactamases by Exemplary Compounds

Using the methodology described above, examples of the current invention were evaluated for their ability to inhibit β-lactamase enzymes from all four Ambler classifications (A through D). The results of these assays are summarized in Table 3 for representative enzymes across different subtypes (note SHV-5 represents an Ambler Class A Extended Spectrum β-Lactamases, KPC-2 exemplifies a Class A carbapenemase, P99 represents chromosomal Class C AmpC, OXA-1 represents a Class D oxacillinase and VIM-2 represents a class B zinc-dependent metallo-β-lactamase also possessing carbapenemase activity), where A represents an $IC_{50}$ of 10-100 µM, B represents an $IC_{50}$ of 1 to 10 µM, C represents an $IC_{50}$ of 0.1 to 1 µM, and D represents an $IC_{50}$ of <0.1 µM. NT=Not tested.

TABLE 3

Inhibition of Diverse β-Lactamases by Exemplary Compounds.

| | Class A | | Class B | Class C | Class D |
|---|---|---|---|---|---|
| EXAMPLE | SHV-5 | KPC-2 | VIM-2 | AmpC | OXA-1 |
| 1 | D | D | B | D | D |
| 2 | D | C | B | D | D |
| 3 | C | C | B | D | D |
| 4 | D | C | B | D | D |
| 5 | D | D | B | D | D |
| 6 | D | D | B | D | D |
| 7 | D | D | B | D | D |
| 8 | D | D | C | D | D |
| 9 | D | C | A | D | C |
| 10 | D | C | C | D | D |
| 11 | D | D | B | D | D |
| 12 | D | D | C | D | D |
| 13 | D | C | C | D | D |
| 14 | D | D | B | D | D |
| 15 | D | D | A | D | D |
| 16 | C | D | C | D | D |
| 17 | D | D | B | D | D |
| 18 | D | D | B | D | D |
| 19 | D | D | B | D | D |
| 20 | D | D | B | D | D |
| 21 | D | D | B | D | D |
| 22 | D | D | B | D | D |
| 23 | C | D | B | D | D |
| 24 | D | D | B | D | D |
| 25 | D | D | B | D | D |
| 26 | C | D | B | D | D |
| 27 | D | D | C | D | D |
| 28 | D | D | B | D | D |
| 29 | D | D | B | D | D |
| 30 | D | D | C | D | D |
| 31 | D | D | B | D | D |
| 32 | D | D | B | D | D |
| 33 | D | D | B | D | D |
| 34 | D | D | B | D | D |
| 35 | D | D | B | D | D |
| 36 | D | C | C | D | D |
| 37 | D | D | B | D | D |
| 38 | D | C | B | D | D |
| 39 | D | D | C | D | D |
| 40 | D | D | B | D | D |
| 41 | D | C | D | D | D |
| 42 | D | D | C | D | D |
| 43 | C | D | C | C | D |
| 44 | D | D | C | D | D |
| 45 | D | D | B | D | D |
| 46 | D | D | C | D | D |
| 47 | D | D | D | D | D |
| 48 | D | D | C | D | D |
| 49 | D | D | B | C | D |
| 50 | D | D | C | C | D |
| 51 | D | D | B | D | D |
| 52 | D | D | B | D | D |
| 53 | D | D | A | D | NT |
| 54 | D | D | B | D | NT |
| 55 | D | D | B | D | NT |
| 56 | D | C | B | D | NT |
| 57 | D | D | B | D | NT |
| 58 | D | D | B | D | NT |
| 59 | D | D | B | D | NT |
| 60 | D | D | A | D | NT |
| 61 | C | D | B | D | C |
| 62 | C | D | B | D | D |
| 63 | NT | NT | NT | NT | NT |
| 64 | D | D | C | D | D |
| 65 | D | D | NT | D | NT |

Example III

In Vitro Antibacterial Assays of β-Lactamase Inhibition

To determine the ability of test compounds to potentiate the inhibition of the growth of bacterial strains that produce beta-lactamase enzymes, classic cell based broth microdilution MIC assays were employed. Six bacteria strains producing beta-lactamase enzymes were used: *E. coli* expressing the Class A Extended Spectrum Beta-Lactamase (ESBL) CTX-M-15, *E. cloacae* expressing the Class C P99, *K. pneumoniae* expressing the Class A carbapenemase KPC-3, *P. aeruginosa* expressing the Class B carbapenemase VIM-2, *K. pneumoniae* expressing the class A carbapenemase KPC-2 and the class B carbapenemase VIM-4, and *S. aureus* producing the Class A penicillinase PC-1. The assay was conducted in Cation Adjusted Mueller Hinton Broth (CAMHB, BD #212322, BD Diagnostic Systems, Sparks, Md.). Bacteria strains were grown for 3-5 hours in CAMBH broth. Test compounds were added to a microtiter plate in 2-fold serial dilutions in CAMHB in a final concentration range of 32 µg/mL to 0.25 µg/ml. An overlay of CAMHB containing a Beta-lactam was added to the compounds at a final static concentration of 4 µg/ml. Ceftazidime (CAZ, Sigma#C3809-1G, Sigma-Aldrich, St. Louis, Mo.) was used as the partner antibiotic for *E. coli* expressing Ambler Class A ESBL CTX-M-15 (MIC alone >128 µg/ml), and *E. cloacae* expressing Class C P99 (MIC alone=128 µg/mL). Meropenem (Mero, USP #1392454, U.S. Pharmacopeia, Rockville, Md.) was used as the partner antibiotic for *K. pneumoniae* expressing Ambler Class A carbapenemase KPC-3 (MIC alone >128 µg/mL), *P. aeruginosa* expressing Class A carbapenemase VIM-2 (MIC alone=16 µg/mL), and *K. pneumoniae* expressing the Ambler Class A carbapenemase KPC-2 and Ambler Class B carbapenemase VIM-4 (MIC alone=64 µg/mL). Piperacillin (Pip, Fisher #ICN15626801, MP Biomedicals, Solon, Ohio) was used as the partner antibiotic for *S. aureus* producing the Class A penicillinase PC-1 (MIC alone=64 µg/ml). Titration of test compounds with MIC readout indicates the concentration of test article needed to sufficiently inhibit beta-lactamase enzyme activity and protect the intrinsic antibacterial activity of the beta-lactam. In addition to the titration of test compounds the MICs of a panel of control beta-lactams is also tested to ensure the strains are behaving consistently from test to test. Once the test compound and antibiotics are added the plates can be inoculated according to CLSI broth microdilution method. After inoculation the plates are incubated for 16-20 hours at 37° C., then the Minimal Inhibitory Concentration (MIC) of the test compound is determined visually.

Using the methodology described above, examples of the current invention were evaluated for their ability to inhibit the growth of β-lactamase-producing bacteria in the presence of a β-lactam antibiotic.

Representative results are shown in Table 4 where A represents an MIC of the fixed β-lactam antibiotic in the presence of >32 µg/mL of a β-lactamase inhibitor of exemplary compounds, B represents the MIC in the presence of between 8 and 32 µg/mL of a β-lactamase inhibitor of exemplary compounds, and C represents the MIC in the presence of ≤4 µg/mL of a β-lactamase inhibitor of exemplary compounds. NT=Not Tested.

TABLE 4

Broad spectrum inhibition of bacterial growth. MIC of example compounds of the invention in the presence of a fixed amount (4 µg/mL) of designated β-lactam antibiotics ceftazidime (CAZ), meropenem (Mero), Piperacillin (Pip).

| | Fixed CAZ | | Fixed Mero | | | |
| | ESBLs (Class A and C) | | Carbapenemases (Classes A and B) | | | Fixed Pip |
| EXAMPLE | *E. coli* ESBL4 CTX-M-15 | *E. cl.* 144200 p99 AmpC | *K. P.* 156319 KPC-3 | *P. aerug.* Ps296 VIM-2 | *K. P.* A-1797 KPC-2 VIM-4 | Penicillinase *S. aureus* MSSA-7 PC-1 |
|---|---|---|---|---|---|---|
| 1 | C | C | C | A | A | C |
| 2 | C | C | C | B | C | C |
| 3 | C | C | C | C | A | C |
| 4 | C | C | C | C | B | C |
| 5 | C | C | C | A | B | C |
| 6 | C | C | C | B | A | C |
| 7 | C | C | C | B | A | NT |
| 8 | C | C | C | C | C | C |
| 9 | B | C | B | A | A | NT |
| 10 | C | C | C | C | C | C |
| 11 | C | C | C | B | A | C |
| 12 | C | C | B | B | A | C |
| 13 | C | C | C | C | C | C |
| 14 | C | C | C | C | B | C |
| 15 | C | C | C | B | A | C |
| 16 | C | C | C | C | B | C |
| 17 | C | C | B | C | B | C |
| 18 | C | C | C | B | A | C |
| 19 | C | C | C | A | B | B |
| 20 | C | C | C | A | B | B |
| 21 | C | C | C | A | B | C |
| 22 | C | C | C | B | B | C |
| 23 | C | C | C | B | B | C |
| 24 | C | C | C | B | B | C |
| 25 | C | C | C | C | B | C |
| 26 | C | C | C | B | B | C |
| 27 | C | C | C | A | B | C |
| 28 | C | C | C | B | B | C |
| 29 | C | C | C | C | A | C |
| 30 | C | C | C | C | C | C |
| 31 | C | C | C | C | B | C |
| 32 | C | C | C | C | B | C |
| 33 | C | C | C | C | C | C |
| 34 | C | C | B | B | B | C |
| 35 | C | C | C | NT | C | NT |
| 36 | C | C | C | NT | C | NT |
| 37 | C | C | C | NT | B | NT |
| 38 | B | C | B | NT | B | NT |
| 39 | C | C | B | NT | B | NT |
| 40 | C | C | B | NT | B | NT |
| 41 | C | C | B | NT | C | NT |
| 42 | C | C | B | NT | B | NT |
| 43 | C | C | C | NT | B | NT |
| 44 | C | C | C | C | B | C |
| 45 | C | C | C | C | B | C |
| 46 | C | C | C | NT | B | NT |
| 47 | C | C | C | NT | C | NT |
| 48 | C | C | C | NT | B | NT |
| 49 | C | C | C | NT | B | NT |
| 50 | C | C | B | NT | B | NT |
| 51 | C | C | C | NT | B | NT |
| 52 | C | C | B | NT | B | NT |
| 53 | C | C | C | NT | B | NT |
| 54 | C | C | C | NT | B | NT |
| 55 | C | C | C | NT | B | NT |
| 56 | C | C | C | NT | B | NT |
| 57 | C | NT | C | NT | B | NT |
| 58 | C | NT | C | NT | B | NT |
| 59 | C | NT | C | NT | B | NT |
| 60 | C | C | B | NT | B | NT |
| 61 | C | C | C | C | B | C |

TABLE 4-continued

Broad spectrum inhibition of bacterial growth. MIC of example compounds of the invention in the presence of a fixed amount (4 μg/mL) of designated β-lactam antibiotics ceftazidime (CAZ), meropenem (Mero), Piperacillin (Pip).

MIC (μg/mL) of exemplary compounds in presence of fixed β-lactams

| | Fixed CAZ | | Fixed Mero | | |
|---|---|---|---|---|---|
| | ESBLs (Class A and C) | | Carbapenemases (Classes A and B) | | Fixed Pip |
| EXAMPLE | E. coli ESBL4 CTX-M-15 | E. cl. 144200 p99 AmpC | K. P. 156319 KPC-3 | P. aerug. Ps296 VIM-2 | K. P. A-1797 KPC-2 VIM-4 | Penicillinase S. aureus MSSA-7 PC-1 |
| 62 | C | C | C | B | B | C |
| 63 | C | C | C | NT | B | NT |
| 64 | C | C | C | C | B | C |
| 65 | C | C | C | NT | C | NT |

Example IV

Absolute Oral Bioavailability Assessments in Sprague-Dawley Rats

An in vivo pharmacokinetics model to measure the plasma levels of carboxylic acid compounds after oral dosing was performed. Male Sprague Dawley rats weighing approximately 250 g at treatment were double cannulated in the jugular and femoral veins for blood sample collection and IV dose administration, respectively. Three rats were utilized per dose group. Test compounds were solubilized sodium acetate/acetic acid buffer (with a final pH of approximately 5.0) for IV administration. Dosing formulations for oral gavage dosing were prepared in 0.5% Tween 80 (polysorbate 80) in sodium acetate/acetic acid buffer (with a final pH of approximately 5.0). Compounds were dosed as a cassette of 2 ester compounds from different corresponding acids. All dosing was conducted at a 3 mg/kg dose level. For IV dosing, 0.5 mL blood samples were drawn at pre-dose, and 0.083, 0.25, 0.5, 1, 2, 4, and 8 h post-dose. For oral dosing, 0.5 mL blood samples were drawn at pre-dose, and 0.25, 0.5, 1, 2, 4, and 8 h post-dose. Blood was collected into tubes containing sodium heparin, centrifuged, and plasma stored frozen prior to bioanalysis.

The absolute bioavailability (% F) shown in table 6 was calculated using the plasma AUC of the acid of Formula (I) after oral dosing of the test compound of Formula (II) ("AUC(oral)") and the plasma AUC of the acid of Formula (I) after intravenous dosing of the acid of Formula (I) ("AUC(IV)") using the formula AUC(oral)/AUC(IV)*100 corrected for any molecular weight difference. The bioanalysis was conducted by a LC-MS/MS methodology with internal standard on a Waters mass spectrometer. LC-MS/MS methods were developed for all test compounds. Duplicate standard curves were run at the beginning and end of the sample run. Calibration curves consisted of standards prepared in blank plasma including a double blank, a single blank containing the internal standard only and a minimum of 5 standards with a lower limit of quantification (LLOQ) of approximately 1 ng/mL. Linearity was assessed by a minimum of 5 standards (with at least one standard at both the bottom and top of the range), back calculated to ±20% of their nominal concentrations.

TABLE 6

Pharmacokinetics of Test Compounds in rat plasma after oral gavage dosing.

| Example # | % F |
|---|---|
| 1 | <5 |
| 8 | <5 |
| 10 | <5 |
| 13 | <5 |
| 16 | <5 |
| 22 | <5 |
| 29 | <5 |
| 32 | <5 |
| 35 | <5 |
| 36 | <5 |
| 53 | <5 |
| 54 | <5 |
| 61 | <5 |
| 62 | <5 |
| 64 | <5 |
| 65 | <5 |
| 125 | 17 |
| 126 | 12 |
| 129 | <5 |
| 130 | 20 |
| 131 | 9 |
| 132 | 24 |
| 133 | 43 |
| 134 | 24 |
| 138 | 8 |
| 144 | 23 |
| 145 | 24 |
| 158 | <5 |
| 161 | <5 |
| 168 | <5 |
| 169 | 33 |
| 170 | 6 |
| 171 | 31 |
| 172 | 10 |
| 173 | <5 |
| 174 | <5 |
| 175 | <5 |
| 176 | <5 |
| 178 | <5 |
| 179 | <5 |
| 180 | <5 |
| 183 | <5 |
| 184 | <5 |
| 185 | <5 |
| 188 | 8 |
| 189 | 25 |
| 191 | 53 |
| 193 | 38 |
| 194 | 52 |
| 195 | 36 |
| 202 | <5 |
| 206 | 63 |
| 210 | 31 |
| 211 | <5 |
| 212 | <5 |
| 213 | <5 |
| 214 | <5 |
| 215 | <5 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A compound of Formula (IX) or Formula (IIi) or pharmaceutically acceptable salts, tautomers, N-oxides, or stereoisomers thereof:
wherein:

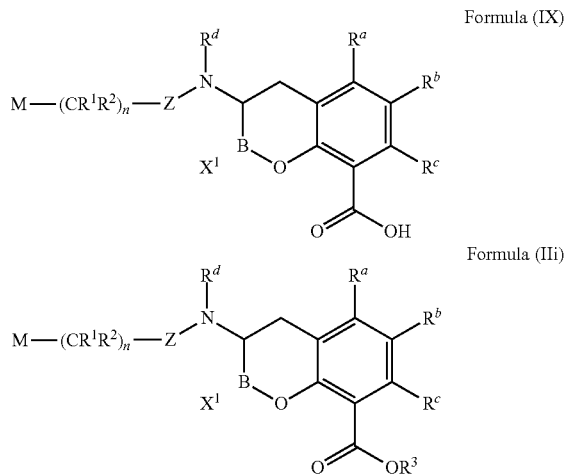

M is hydrogen, fluoro, chloro, bromo, —CF$_3$, —CN, —N(R$^4$R$^5$), —N(R$^4$)C(O)R$^5$, —OR$^4$, —S(O)—R$^4$, —SO$_2$—N(R$^4$R$^5$), —N(R$^4$)—C(O)—O(R$^4$), —N(R$^4$)—C(O)—N(R$^4$R$^5$), —N(R$^4$)—SO$_2$—R$^5$, —N(R$^4$)heteroaryl, —C(O)—R$^4$, —C(O)(C$_1$-C$_3$alkyl)C(O)R$^5$, optionally substituted oxyimino, optionally substituted alkenyl, optionally substituted alkynyl, or heterocycloalkyl;

each R$^1$ and R$^2$ are independently hydrogen, fluoro, chloro, bromo, optionally substituted C$_1$-C$_6$ alkyl, —CF$_3$, substituted aryl, —OR$^4$, —SR$^4$, or —NR$^4$R$^5$;

or R$^1$ and R$^2$ are taken together with the carbon to which they are attached to form an optionally substituted C$_3$-C$_8$ cycloalkyl;

or when n is at least 2, two R$^1$ on adjacent carbons are taken together to form a double bond; or two R$^1$ and two R$^2$ on adjacent carbons are taken together to form a triple bond;

n is 1, 2, 3, 4, 5, or 6;

X$^1$ is —OR$^4$ or F;

Z is >C=O, >C=S, or >SO$_2$;

R$^a$, R$^b$, and R$^c$ are independently hydrogen, fluoro, chloro, bromo, optionally substituted C$_1$-C$_6$ alkyl, optionally substituted C$_3$-C$_6$ cycloalkyl, optionally substituted heterocycloalkyl, optionally substituted aryl, optionally substituted heteroaryl, —OR$^4$, —NR$^4$R$^5$, or —SR$^4$; with the proviso that at least one of R$^a$, R$^b$, or R$^c$ is not hydrogen;

R$^d$, R$^4$, and R$^5$ are each independently hydrogen, —OH, —CN, —CF$_3$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;

or R$^4$ and R$^5$ taken together form an optionally substituted heterocycle with the nitrogen to which they are attached;

R$^3$ is R$^{31}$, —(R$^{30}$)$_q$OR$^{31}$, —(R$^{30}$)$_q$O(R$^{30}$)$_q$OR$^{31}$, —R$^{30}$OC(O)R$^{31}$, —R$^{30}$OC(O)OR$^{31}$, —R$^{30}$OC(O)NHR$^{31}$, —R$^{30}$OC(O)N(R$^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one;

each q is independently 2, 3, 4, 5, or 6;

each R$^{30}$ is independently —CH$_2$—, —CH(CH$_3$)—, —C(CH$_3$)$_2$—, or optionally substituted 1,1'-cyclopropylene; and each R$^{31}$ is independently optionally substituted C$_1$-C$_{12}$ alkyl, optionally substituted C$_1$-C$_{12}$ alkenyl, optionally substituted alkoxyalkyl, optionally substituted C$_1$-C$_{12}$ alkynyl, optionally substituted C$_3$-C$_8$ cycloalkyl, optionally substituted C$_3$-C$_8$ heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl;

or two R$^{31}$ are taken together with the nitrogen to which they are attached to form a C$_3$-C$_8$ heterocycloalkyl.

2. The compound of claim 1, wherein R$^a$, R$^b$, and R$^c$ are independently hydrogen, fluoro, chloro, —OH, or —OCH$_3$; with the proviso that at least one of R$^a$, R$^b$, or R$^c$ is not hydrogen.

3. The compound of claim 1, wherein X$^1$ is —OH.

4. The compound of claim 1, wherein R$^d$ is hydrogen or C$_1$-C$_4$ alkyl.

5. The compound of claim 1, wherein R$^d$ is hydrogen.

6. The compound of claim 1, wherein Z is >C=O.

7. The compound of claim 1, wherein n is 1, 2, or 3.

8. The compound of claim 1, wherein each R$^1$ and R$^2$ are independently hydrogen, fluoro, chloro, optionally substituted C$_1$-C$_6$ alkyl, or —CF$_3$.

9. The compound of claim 1, wherein each R$^1$ and R$^2$ are hydrogen.

10. The compound of claim 1, wherein M is hydrogen, —CF$_3$, —CN, —OR$^4$, or optionally substituted alkynyl.

11. The compound of claim 10, wherein each R$^4$ is independently C$_1$-C$_6$ alkyl.

12. The compound of claim 1, wherein M is hydrogen.

13. The compound of claim 1, wherein R$^3$ is —R$^{31}$; and R$^{31}$ is optionally substituted C$_1$-C$_{12}$ alkyl.

14. The compound of claim 1, wherein R$^3$ is —R$^{30}$OC(O)R$^{31}$ or —R$^{30}$OC(O)OR$^{31}$.

15. The compound of claim 14, wherein each R$^{30}$ is independently —CH$_2$— or —CH(CH$_3$)—; and each R$^{31}$ is independently optionally substituted C$_1$-C$_{12}$ alkyl, aryl, C$_3$-C$_8$ cycloalkyl, or C$_3$-C$_8$ heterocycloalkyl.

16. The compound of claim 1 having the structure:

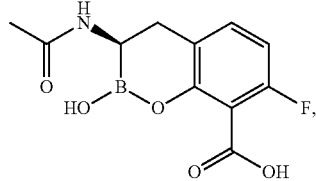

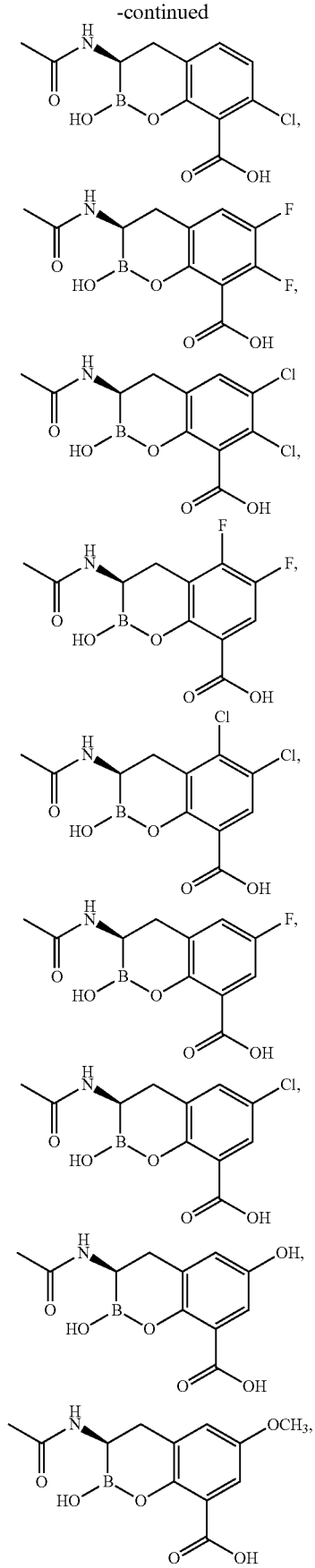
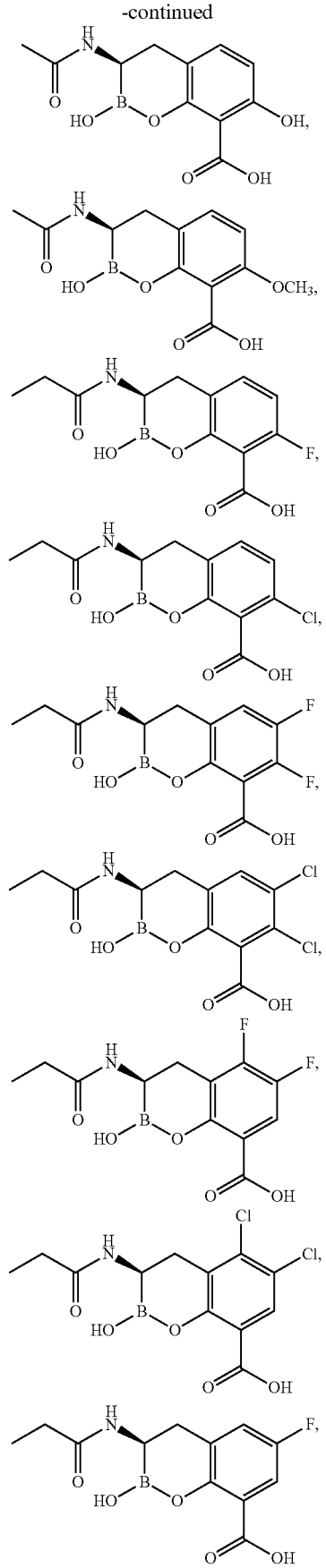

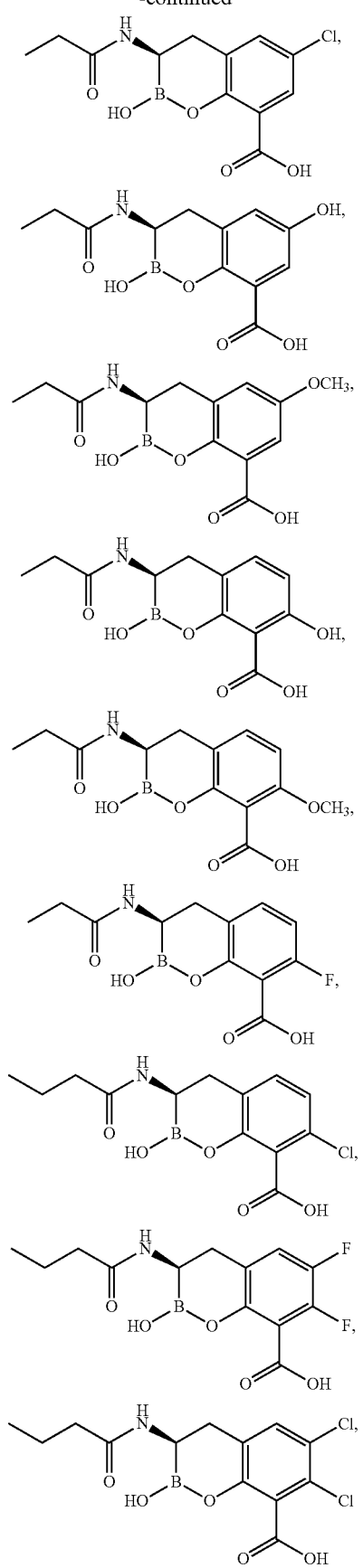
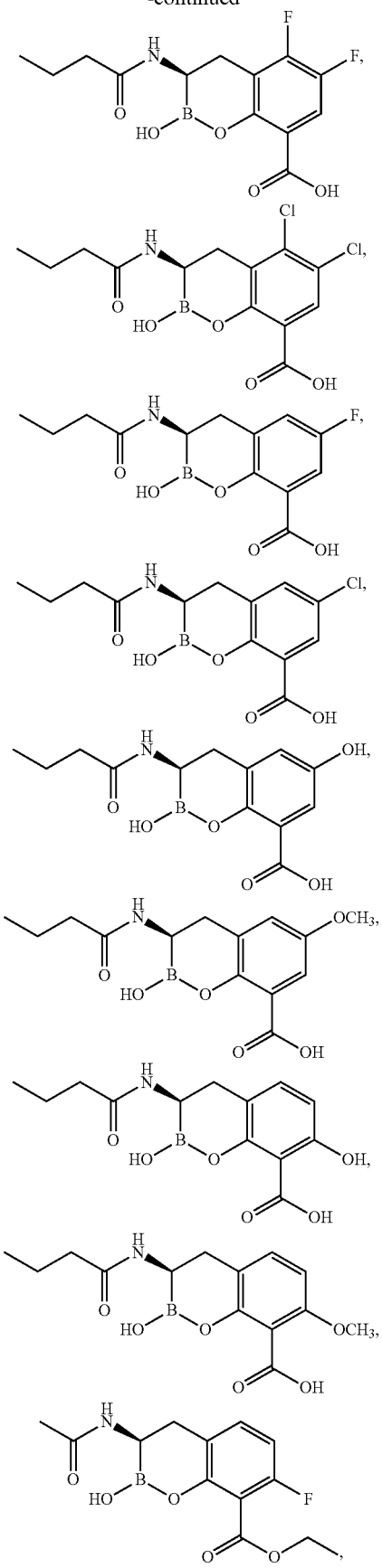

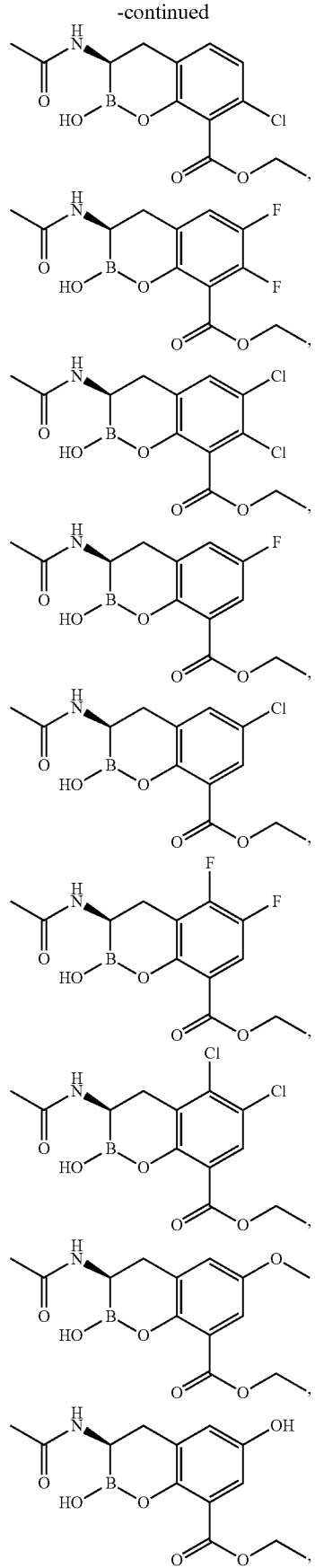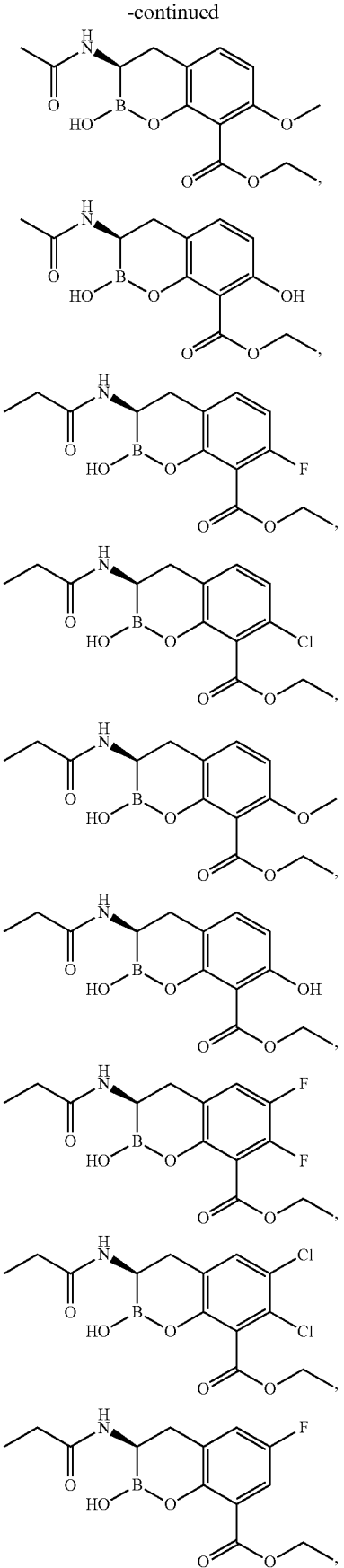

-continued
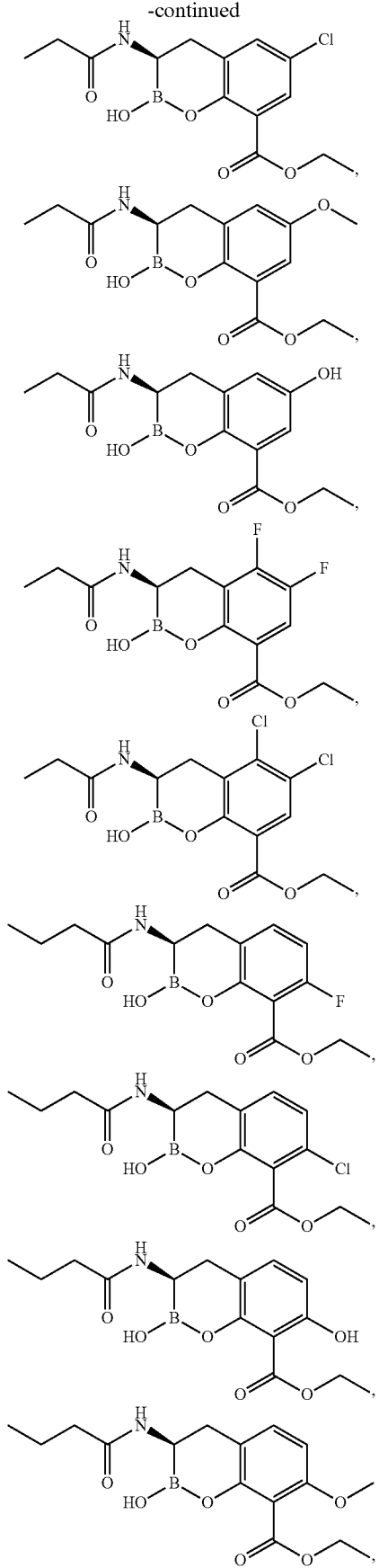
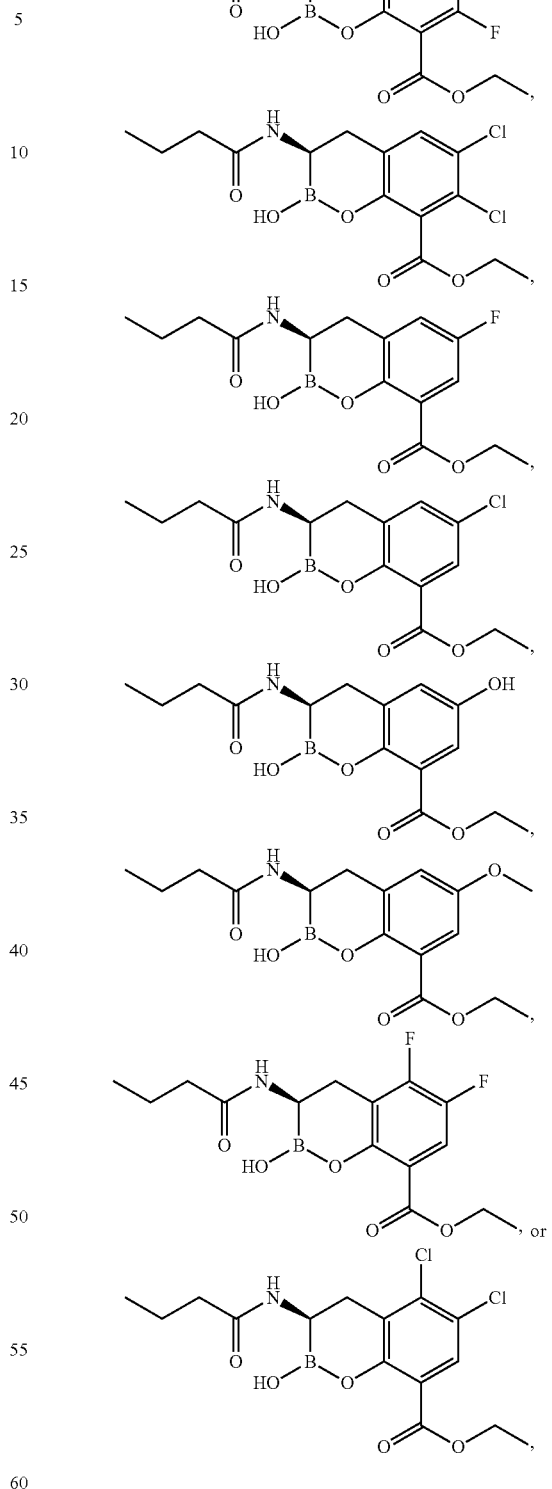
or pharmaceutically acceptable salts, tautomers, N-oxides, or stereoisomers thereof.
17. A pharmaceutical composition comprising a compound of claim 1, or a pharmaceutically acceptable salt, tautomer, N-oxide, or stereoisomer thereof, and a pharmaceutically acceptable excipient.

18. The pharmaceutical composition of claim 17, further comprising a beta-lactam antibiotic.

19. The pharmaceutical composition of claim 18, wherein the beta-lactam antibiotic is a penicillin, cephalosporin, carbapenem, monobactam, bridged monobactam, or a combination thereof.

20. A method of treating a bacterial infection in a subject, comprising administering to the subject a compound of claim 1 optionally in combination with a therapeutically effective amount of a beta-lactam antibiotic.

* * * * *